US010563215B2

(12) United States Patent
Bovet et al.

(10) Patent No.: US 10,563,215 B2
(45) Date of Patent: Feb. 18, 2020

(54) TOBACCO SPECIFIC NITROSAMINE REDUCTION IN PLANTS

(71) Applicant: PHILIP MORRIS PRODUCTS S.A., Neuchatel (CH)

(72) Inventors: Lucien Bovet, Neuchatel (CH); Prisca Campanoni, Vaud (CH)

(73) Assignee: Philip Morris Products S.A., Neuchatel (CH)

( * ) Notice: Subject to any disclaimer, the term of this patent is extended or adjusted under 35 U.S.C. 154(b) by 543 days.

(21) Appl. No.: 14/653,924

(22) PCT Filed: Dec. 19, 2013

(86) PCT No.: PCT/EP2013/077532
§ 371 (c)(1),
(2) Date: Jun. 19, 2015

(87) PCT Pub. No.: WO2014/096283
PCT Pub. Date: Jun. 26, 2014

(65) Prior Publication Data

US 2015/0315603 A1 Nov. 5, 2015

(30) Foreign Application Priority Data

Dec. 21, 2012 (EP) .................................... 12198966

(51) Int. Cl.

| | |
|---|---|
| ***C12N 15/82*** | (2006.01) |
| ***A24B 3/00*** | (2006.01) |
| ***A24B 15/18*** | (2006.01) |
| ***C07K 14/415*** | (2006.01) |
| ***A24B 15/24*** | (2006.01) |

(52) U.S. Cl.
CPC ............ *C12N 15/8243* (2013.01); *A24B 3/00* (2013.01); *A24B 15/18* (2013.01); *A24B 15/245* (2013.01); *C07K 14/415* (2013.01); *C12N 15/8218* (2013.01)

(58) Field of Classification Search
CPC .............. C07K 14/415; C12N 15/8243; C12N 15/8242; A24B 15/245; A24B 3/00
See application file for complete search history.

(56) References Cited

U.S. PATENT DOCUMENTS

| | | | | |
|---|---|---|---|---|
| 5,810,020 | A | 9/1998 | Northway | |
| 6,202,649 | B1 | 3/2001 | Williams | |
| 7,677,253 | B2 * | 3/2010 | Yamada | A24B 15/12 131/297 |
| 2006/0041949 | A1 * | 2/2006 | Xu | C07K 14/415 800/278 |
| 2012/0266327 | A1 * | 10/2012 | Sanz Molinero | C12N 15/8261 800/290 |

FOREIGN PATENT DOCUMENTS

| | | |
|---|---|---|
| EP | 2152891 | 12/2008 |
| JP | 2005-27544 | 2/2005 |
| RU | 2191529 | 10/2002 |
| WO | WO 98/58555 | 12/1988 |
| WO | WO 2006/091194 | 8/2006 |
| WO | WO 2008/070274 | 6/2008 |
| WO | WO 2009/064771 | 5/2009 |
| WO | WO 2009/074325 | 6/2009 |
| WO | WO 2009/091518 | 7/2009 |
| WO | WO 2011/048009 | 4/2011 |
| WO | WO 2011/088180 | 7/2011 |
| WO | WO 2012/028309 | 3/2012 |

OTHER PUBLICATIONS

GenBank polynucleotide sequence AF133209.1, published on May 11, 1999 retrieved from www.ncbi.nlm.nih.gov/nuccore/AF133209.1?report=GenBank.*

De Angeli, A., et al. "The nitrate/proton antiporter AtCLCa mediates nitrate accumulation in plant vacuoles." Nature 442.7105 (2006) : 939-942 (Year: 2006).*

Shi, Hongzhi, et al. "Changes in TSNA contents during tobacco storage and the effect of temperature and nitrate level on TSNA formation." Journal of agricultural and food chemistry 61.47 (2013): 11588-11594. (Year: 2013).*

Ng, P. C., & Henikoff, S. (2001). Predicting deleterious amino acid substitutions. Genome research, 11(5), 863-874. (Year: 2001).*

Kawamura, Yoshifumi, et al. "Determination of Levels of NO-3, NO-2 and NH+ 4 Ions in Leaves of Various Plants by Capillary Electrophoresis." Plant and cell physiology 37.6 (1996): 878-880. (Year: 1996).*

Friedberg, Iddo. "Automated protein function prediction—the genomic challenge." Briefings in bioinformatics 7.3 (2006): 225-242. (Year: 2006).*

(Continued)

*Primary Examiner* — Weihua Fan
(74) *Attorney, Agent, or Firm* — Mueting, Raasch & Gebhardt, P.A.

(57) ABSTRACT

In one aspect, there is provided a mutant, non-naturally occurring or transgenic plant cell comprising: (i) a polynucleotide comprising, consisting or consisting essentially of a sequence encoding a member of the CLC family of chloride channels and having at least 60% sequence identity to SEQ ID NO:1 or SEQ ID NO:2 or SEQ ID NO:3 or SEQ ID NO:4 or SEQ ID NO:10 or SEQ ID NO:11; (ii) a polypeptide encoded by the polynucleotide set forth in (i); (iii) a polypeptide comprising, consisting or consisting essentially of a sequence encoding a member of the CLC family of chloride channels and having at least 60% sequence identity to SEQ ID NO:5 or SEQ ID NO:6 or SEQ ID NO:7 or SEQ ID NO:12 or SEQ ID NO:13 or SEQ ID NO:14; or (iv) a construct, vector or expression vector comprising the isolated polynucleotide set forth in (i); and wherein the expression or activity of the polynucleotide or the polypeptide is modulated as compared to a control plant and wherein the nitrate levels in the mutant, non-naturally occurring or transgenic plant containing the mutant, non-naturally occurring or transgenic plant cell are modulated as compared to the control plant containing the control plant cell.

11 Claims, 6 Drawing Sheets

Specification includes a Sequence Listing.

(56) References Cited

OTHER PUBLICATIONS

Geelen, Danny, et al. "Disruption of putative anion channel gene AtCLC-a in *Arabidopsis* suggests a role in the regulation of nitrate content." The Plant Journal 21.3 (2000): 259-267. (Year: 2000).*
Julio, Emilie, et al. "Reducing the content of nornicotine in tobacco via targeted mutation breeding." Molecular Breeding 21.3 (2008): 369-381. (Year: 2008).*
S. Fischer et al., "Preformed tobacco-specific nitrosamines in tobacco—role of nitrate and influence of tobacco type", Genesis vol. 10 No. 8, pp. 1511-1517, 1989 (Year: 1989).*
Bergsdorf, Eun-Yeong, Anselm A. Zdebik, and Thomas J. Jentsch. "Residues important for nitrate/proton coupling in plant and mammalian CLC transporters." Journal of Biological Chemistry 284.17 (2009): 11184-11193 (Year: 2009).*
Nguyen, Chi Tam, et al. "Characterization of the chloride channel-like, AtCLCg, involved in chloride tolerance in *Arabidopsis thaliana*." Plant and Cell Physiology 57.4 (2015): 764-775. (Year: 2015).*
Barbier-Brygoo, Hélène, et al. "Anion channels/transporters in plants: from molecular bases to regulatory networks." Annual review of plant biology 62 (2011): 25-51 (Year: 2011).*
Nicotiana tabacum CLC-Nt2 protein mRNA with the GenBank Accession No. AF133209.1 (published on May 11, 1999). Retrived from www.ncbi.nlm.nih.gov/nuccore/AF133209.1 (Year: 1999).*
Burton, et al., "Relationship Between Tobacco-Specific Nitrosamines and Nitrite from Different Air-Cured Tobacco Varieties," J. Agric. Food Chem., 1994, 42, 2007- 2011. (Year: 1994).*
Zifarelli et al., "CLC Transport Proteins in Plants,", FEBS Letters, 2010, 584, 2122-2127 (Year: 2010).*
DeAngeli et al., "The Nitrate/Proton Antiporter AtCLCa Mediates Nitrate Accumulation in Plant Vacuoles", *Nature* (2006) 442 (7105):939-42.
GenBank Accession No. L22344.
GenBank Accession No. S78780.
McCallum et at, "Targeted Screening for Induced Mutations", *Nat Biotechnol* 18, 2000: 455-457.
Monachello et al., "Two Anion Transporters AtClCa and AtClCe Fulfil Interconnecting but not Reductant Roles in Nitrate Assimilation Pathways", *New Phytol*. 2009;183(1):88-94.
Smith et al. "Total Silencing by Intron-spliced Hairpin RNAs", *Nature*, 2000, 407, 319-320.
Spetea et al., "Solute Transporters in Plant Thylakoid Membrances", *B. Communicative & Integrative Biology*, 2010; 3(2)122-129.
Stemple, "TILLING-A High-Throughput Harvest for Functional Genomics", *Nat Rev Genet* 5(2): 2004, 145-50.
Stepanov et al, "Tobacco-Specific Nitrosamines in New Tobacco Products", *Nicotine & Tobacco Research* (2006) 2:309-313.
Stepanov et al, "Tobacco-Specific Nitrosamines in Smokeless Tobacco Products Marketed in India", *International Journal of Cancer* (2005);116:16-19.
Stitt & Krapp "The Interaction Between Elevated Carbon Dioxide and Nitrogen Nutrition: The Physiological and Molecular Background", *Plant, Cell and Environment* 22, 583-621 (1999).
Wen et al, "A Novel Approach Obtaining Intron-Containing Hairpin RNA Constructs" *Bioscience, Biotechnology, and Biochemistry*, (2008) 72, 2, 615-617.
Wernsman, et al, "Tobacco", Chapter Seventeen. pp. 669-698 in: *Cultivar Development. Crop Species*. W. H. Fehr (ed.), MacMillan Publishing Co, Inc., New York, N.Y.
Wesley et al. "Construct Design for Efficient, Effective and High-Throughput Gene Silencing in Plants", *The Plant Journal*, 2001, 27, 581-590.
PCT Preliminary Examination Report for PCT/EP2013/077532 dated Jul. 2, 2015 (10 pages).
PCT Search Report and Written Opinion for PCT/EP2013/077532 dated Jun. 26, 2014 (16 pages).
Database UniProt [Online] Nov. 1, 1999 "Subname: Full=CLC-Nt2 protein;", XP002711419, retrieved from EBI Database accession No. Q09XF71 sequence.
Database EMBL [Online] May 11, 1999 "Nicotiana tabacum CLC-Nt2 protein mRNA, complete cds.", XP002711420, retrieved from EBI accession No. EMBL:AF133209 Database accession No. AF133209 sequence.
Office Action issued in Mexico for Application No. MX/a/2015/008084 dated Jun. 14, 2018 (4 pages).
Office Action issued in the Philippines for Application No. 1-2015-501204 (3 pages).
Geelen et al., "Disruption of Putative Anion Channel Gene AtCLC-a in *Arabidopsis* Suggests a Role in the Regulation of Nitrate Content", *The Plant Journal* (2000), 21(3), 259-267.
Shi et al., "Changes in TSNA Contents During Tobacco Storage and the Effect of Temperature and Nitrate Level of TSNA Formation", *Journal of Agricultural and Food Chemistry*, 2013, 61, 11588-11594.
Office Action issued in China for Application No. 201380073174.4 dated Aug. 22, 2018 (22 pages). English translation included.
UniProtKB—Q9XF71 dated Nov. 1, 1999, 4 pages.
Shi Hong-zhi et al., "The relationships between TSNAs and their precursors in different burley tobacco varieties from different regions", Academic Journal Electronic Publishing House, dated Oct. 31, 2012, 7 pages.
Office Action issued in Russia for Application No. 2015126909/10 dated Sep. 27, 2018, 12 pages. English translation included.
Office Action issued in Mexico for Application No. MX/a/2015/008084 dated Feb. 13, 2019 (13 pages). English translation included.
Office Action issued in China for Application No. 201380073174.4 dated Apr. 9, 2019 (14 pages). English translation included.
Shi, Hong-zhi et al., "The Relationships Between TSNAs and Their Precursors in Different Burley Tobacco Varieties from Different Regions", Chinese Tobacco Science, vol. 18, No. 5, pp. 9-15 (2012). English abstract included.
Office Action issued in Japan for Application No. 2015-548608 dated Sep. 11, 2019 (5 pages). English translation included.
Office Action issued in Brazil for Application No. BR112015015016-0 dated Sep. 26, 2019 (7 pages). English translation included.
Burton, et al., "Relationship Between Tobacco-Specific Nitrosamines and Nitrite from Different Air-Cured Tobacco Varieties," *J. Agric. Food Chem*., 1994, 42, 2007-2011.
Zifarelli et al., "CLC Transport Proteins in Plants,", *FEBS Letters*, 2010, 584, 2122-2127.
Office Action issued in Mexico for Application No. MX/a/2015/008084 dated Nov. 8, 2019 (6 pages). English translation included.
Marmagne et al., "Two Members of the Arabidopsis CLC (chloride channel) family, AtCLCe and AtCLCf, are associated with thylakoid and Golgi Membranes, Respectively," *Journal of Experimental Botany*, vol. 58, No. 12, pp. 33853393, 2007 (9 pages).

* cited by examiner

SEQUENCE LISTING

<160> NUMBER OF SEQ ID NOS: 181

<210> SEQ ID NO 1
<211> LENGTH: 4141
<212> TYPE: DNA
<213> ORGANISM: Nicotiana tabacum
<220> FEATURE:
<223> OTHER INFORMATION: DNA sequence of CLC-Nt2 from Nicotiana tabacum;
sequence originating from the ancestor N. sylvestris

<400> SEQUENCE: 1
atggaggagc caactcgatt agtagaagaa gcaacgatta ataacatgga cggacaacag 60
aatgaagaag aaagagatcc agagagcaat tcactgcatc agcctcttct caagagaaac 120
agaacactat catccagtcc atttgccttg gttggagcta aggtctccca catcgaaagt 180
ttggattatg agtaagaaca actaataatc ttatcataga tcaagtatag cttttcttta 240
cttgtgcatt aaaagggcca acagaaattg gatgtcctaa ttgtgtgtgt ctgttttagg 300
atcaacgaga atgatctctt caagcatgac tggagaagga gatctagagt tcaagtatta 360
cagtatgtgt tcttgaaatg gacactggca tttttggtcg gcctgcttac aggagttaca 420
gccaccctca tcaatcttgc aatcgaaaac atggctggtt acaaacttcg agctgttgtg 480
aactatatcg aggatagaag gtaggtgatg ttttccctat gatcaacaat tcataaatgc 540
ttccagaagt cttactactg attcttcaat acgataccac tagctaatga ctaagaacaa 600
gaccaaagat cacttatttg acttgaatta tgttattgat ttattcataa ttgagattgt 660
aacaatggtt acaggtacct tatgggattt gcatattttg cgggtgctaa ttttgtgctc 720

```
actttgatag ctgcccttct ctgcgtgtgc tttgcaccta ctgctgcagg gcctggaatt    780
cctgaaatca aagcttatct caacggtgta gatactccca atatgtatgg agcaaccaca    840
ctttttgtca aggtgcgtca cacacccaat tttatcagtg ctggcaattc agatagcagg    900
cagattataa cgccatcagt atagtattga gattctgtcg aaccagatgt ataaatagat    960
agaatagcag caaataacac atttttatct tagtcgtgat ggcacctaat ccgacccgct   1020
agataagcca aatacaatca acacatattt atggaattca atctcatttg ggaagtgatc   1080
tctatctttc agtaatcaga taggaagtgg tttaagaata aaaagagaat tttagaatcg   1140
aatgcactca tccagcgagg aagatccatc agtggtatct aatttactct tgaacttcca   1200
gcagttcaat cctttggtac cgtcactgta acttgttttt ttcaatcttt gtgactaaca   1260
tggaagggag gaaaatcctg actttcagtg attttcctcg cttacagtga aagtcaggat   1320
atagcttcgg tgagactcag cttatatgtc ttaattgaat atgctatttg ttgactaaca   1380
tggatttgcc ctatcatgaa aatgaaggaa gcgccaaaaa tacatatact taaacagggg   1440
cggacccaag tggtgagaag tgggttcaac tgaacccgct tcgtcaaaaa aatactgtgt   1500
atatgtataa attatggcta aagcaaggta aattttgtat agaaataagc ttatgttagt   1560
tatggacttc tcctgggtcc gctactgtac ttaaaagcac atacgaagag atacacaaac   1620
taagggcaaa ggttcataat ttaaggcagt tgtgtccaga agaacaaatt ttgcttgcat   1680
gttgcagtgt gaatttaaca ataaaagaat tatgatcgca aatttccact tgtaattgta   1740
ctataagatt ctaaattttg agagatttga catgtttgct ttccctttga ctgaatcgta   1800
aaagtgaaag tgaagttcat cagaagtaga ttatgatact taccaacccc tttttccctt   1860
aaacaatctt taatctgttc actcacagat cattggaagc attgcagcag tttctgctag   1920
cttagacctt ggaaaagaag ggccattggt tcacattggc gcttgctttg cttccttact   1980
aggtcaaggt ggtccagata attaccggct caggtggcgt tggctccgtt acttcaacaa   2040
cgatcgggac aggcgagatc ttatcacatg tgggtcatca tcaggtgtgt gtgctgcttt   2100
ccgttctcca gtaggtggtg tcctatttgc tttagaggaa gtggcaacat ggtggagaag   2160
tgcactcctc tggagaactt tcttcagcac ggcagttgtg gtggtgatac tgagggcctt   2220
cattgaatac tgcaaatctg gcaactgtgg actttttgga agaggagggc ttatcatgtt   2280
tgatgtgagt ggtgtcagtg ttagctacca tgttgtggac atcatccctg ttgtagtgat   2340
tggaatcata ggcggacttt tgggaagcct ctacaatcat gtcctccaca aaattctgag   2400
gctctacaat ctgatcaacg agtaagcacc tactcttcca cattcccaac tggatcatca   2460
aacattcagt tggttctcta tattttaaag gcaatgcata tccacacaaa aatgagctta   2520
cttggattag aatcatcttg agacattgat ccaactgtct tgcatctttt taagtttaaa   2580
tcctaattcc tatccaaaca tggccttctt atcacattta actgccaaaa aaaaagggaa   2640
aactatagat gcaaaatcct gactttcaat ctttgatcct tttttatctt gcaggaaggg   2700
aaaactacat aaggttcttc tcgctctgag tgtctccctt ttcacctcca tttgcatgta   2760
tggacttcct tttttggcca aatgcaagcc ttgtgatcca tcacttcccg ggtcttgtcc   2820
tggtactgga gggacaggaa acttcaagca gttcaactgc ccagacggct attacaatga   2880
tcttgctact cttctcctta caaccaacga tgatgcagtc cgaaacattt tctccataaa   2940
cactcccggt gaattccaag ttatgtctct tattatctac ttcgttctgt attgcatatt   3000
gggactcatc acttttggga ttgctgtgcc atctggtctc ttccttccaa tcatcctcat   3060
```

gggttcagct tatggtcgct tgcttgccat tgccatggga tcttatacaa aaattgatcc 3120
agggctgtat gcggttctcg gagcagcttc ccttatggct ggttcaatga gaatgactgt 3180
ttctctttgc gtcatatttc ttgagctaac aaacaatctt ctccttctgc caataacaat 3240
gctggttctt ctaattgcca aaagtgtagg agactgcttc aacctaagta tttatgaaat 3300
aatattggag ctgaaaggtc tacctttcct ggatgccaac ccggagccat ggatgagaaa 3360
tatcactgct ggtgagcttg ctgatgtaaa gccaccagta gttacactct gtggagttga 3420
gaaggtggga cgtatcgtag aggccttgaa gaacaccaca tataacggat tccctgtcgt 3480
cgatgaagga gtagtgccac cggtgggtct gccagttggg gcaactgaat tgcacggtct 3540
tgtcctaaga actcaccttc ttttggttct caagaaaaag tggttccttc atgaaagacg 3600
gaggacagag gagtgggaag tgagagagaa attcacctgg attgatttag ctgagagggg 3660
cggtaagatc gaagatgtgt tagttacaaa ggatgaaatg gagatgtatg tcgatttgca 3720
tcccctgact aacacaaccc cttatactgt ggtagaaagc ttgtcagtgg ctaaggcaat 3780
ggtgcttttc aggcaggtgg ggctccgcca catgctcatt gtacccaaat accaagcagc 3840
aggggtgaga ttataagcaa atttcagtta tttttcttat gcaaatatct ccctcctatc 3900
atagtataaa gatgcacaga aatagtcata tggtaatata agcacttgtt tagaataatt 3960
ataggtggca aagttatttt acattagaag tgataaaagc attacttaca tcacacttgt 4020
gctccttttg taggtatctc ctgtggtggg aatcttgacc aggcaagact tgagagccca 4080
caacattttg agtgtcttcc ctcatctgga gaagtcaaaa agcggtaaaa aggggaactg 4140
a 4141

<210> SEQ ID NO 2
<211> LENGTH: 3781
<212> TYPE: DNA
<213> ORGANISM: Nicotiana tabacum
<220> FEATURE:
<223> OTHER INFORMATION: DNA sequence of CLC-Nt2 from Nicotiana tabacum; sequence originating from the ancestor N. tomentosiformis

<400> SEQUENCE: 2
atggaggagc caactcgatt agtagaagaa gcaacgatta ataacatgga cagacaacag 60
aatgaagaag aaagagatcc agagagcaat tcactgcatc agcctctcct caagagaaac 120
agaacactat catccagtcc atttgccttg gttggagcta aggtctccca tattgaaagt 180
ttagactatg agtaagaaca actaataatc ttatctttag atcaagtata gcttttcttt 240
ataaatgggc caacagaaat tggatgtcct aattttgtgt atctgcttta ggatcaacga 300
gaatgatctc ttcaagcatg actggagaag aagatccaga gttcaagtat tacagtatgt 360
attcttgaaa tggacactgg catttttggt cgggcttctt acaggagtga cagcctccct 420
tatcaatctt gcaatcgaaa acattgctgg ctacaaactt agagctgttg tgaactatat 480
cgaggataga aggttggtga tgttttccct atgatcagca attcataaag gctactataa 540
ttcttcaata tgattccact agctaatgac taagaacaag atcaaagatc acttatttga 600
cttgaattat gttattgatt tgttcataat tgagattgta acaatggtta caggtacctt 660
gtgggatttg catattttgc gggtgctaat tttgtgctca ctttgatagc tgcccttctc 720
tgcgtgtgtt ttgcgcctac tgctgcaggg cctggaattc ctgaaatcaa agcttatctc 780
aacggtgtag atactcccaa catgtacgga gcaaccacac tttttgtcaa ggtgcgtcac 840
gcacccaatt ttatcagtgc tggcaattca ggtagcaggc agattataac gccatcagta 900

```
tagtattgag atcctgttga cctagatgta taaatagaaa gaatagcagc aaataacaca    960
tttttagcct acatatttat ggaattcaat ctcatttggg aagtgatatc tatctttcag   1020
taatcagata ggaagttgtt taagaataaa aagagaattt tatcgaatgc actcatccag   1080
caaggaagat ccatcagtgg tatctaatct actcttgaac ttccagtagt tcaatccttt   1140
ggtactgtca ctgtaacttg ttttctcatc caccattaaa atacaatagc ttccatgaga   1200
ctcagcttat atgtctcaat tgaatatgct atttggtgac taacatgaat ttgccctatc   1260
atgaaaataa atggaagtga caaaaataca tatacttaaa agcacatatg tagagacacg   1320
cagactaagg gcaaaggttc acaattttaa ggcagttgtg tccagaagaa caaatgaaga   1380
attatgatca caaatttcca cttgtaattg tactataaaa tttttaattt tgagagattc   1440
tgacatgttt gctttccctt tgattgaatc gtaaaagtga aagtgaagtt catcagaagt   1500
agattatgat acttaccaac tcctttttcc ccctaaacaa tctttaatct cttcacttac   1560
agatcattgg aagcattgca gcagtttctg ctagcttaga ccttggaaaa gaagggccgt   1620
tggttcacat tggcgcttgt tttgcttcct tactaggtca aggtggtcca gataattacc   1680
ggctcaaatg gcgctggctc cgttacttca acaacgatcg ggacaggcga gatctcatca   1740
catgtgggtc atcatcaggt gtgtgtgctg ctttccgttc tccagtaggt ggtgtcctat   1800
ttgctttaga ggaagtggca acatggtgga gaagtgcact cctctggaga actttcttca   1860
gcacggcagt tgtggtggtg atactgaggg ccttcataga atactgcaaa tctggctact   1920
gtggactttt tggaagagga gggcttatca tgtttgatgt gagtggtgtc agtgttagct   1980
accatgttgt ggacatcatc cctgttgttg tgattggaat cataggcgga cttttgggaa   2040
gcctctacaa ttgtgtcctc cacaaagttc tgaggctcta caatctcatc aacgagtaag   2100
caccaactct tccacattcc caactggatc atcaaacatt cagttggttc tctatattta   2160
aaaggcaatg catatccaca caaaaatgag cttacttgga ttagaatcat cttgagacat   2220
tgatccaact gccttgcatc tttttaagtt tgaatcccaa ttcctatcca aacatggtct   2280
ttttatcaca tttaactgcc aaaaaaagtt actctataga tgtaaaatcc tgactttcaa   2340
actttgatcc tttttttatct tgcaggaagg gaaaactaca taaggttctt ctcgctctga   2400
gcgtctccct tttcacctcc atttgcatgt atggacttcc ttttttggcc aaatgcaagc   2460
cttgtgattc atcacttcaa gggtcttgtc ctggcactgg aggtacagga aacttcaagc   2520
agttcaactg ccctgacggc tattacaatg atctcgctac tcttctcctt acaaccaacg   2580
atgatgcagt ccgaaacatt ttctccataa acactcccgg tgaattccat gttacgtctc   2640
ttattatcta cttcgttctg tattgtatct tgggactcat cacttttggg attgctgtgc   2700
catctggtct cttccttcca atcatcctca tgggttcagc ttatggtcgc ttgcttgcca   2760
ttgccatggg atcttataca aaaattgatc cagggctgta tgccgttctg ggagcagctt   2820
cccttatggc tggttcaatg agaatgactg tttctctttg cgtcatattt cttgagctaa   2880
caaacaatct tctccttctg ccaataacaa tgctggttct tctaattgcc aaaagtgtag   2940
gagactgctt taacctaagt atttatgaaa taatattgga actgaaaggt ctacctttcc   3000
tggatgccaa cccggagcca tggatgagaa atatcactgc tggtgagctt gctgatgtaa   3060
agccaccagt agttacactt tgtggagttg agaaggtggg acgtatcgtc gaggtcttga   3120
agaacaccac atataacgga ttccctgtcg tcgatgaagg agtggtgcca ccggtgggtc   3180
tgccagttgg ggcaactgaa ttgcacggtc ttgtcctaag aactcacctt cttttggttc   3240
tcaagaaaaa gtggttcctt aatgaaagac gaaggacaga ggagtgggaa gtgagagaga   3300
```

aattcacctg gattgattta gctgagaggg gcggtaagat cgaagatgtg gtagttacga 3360
aggatgaaat ggagatgtat gtcgatttgc atcccctgac taacacaacc ccttatactg 3420
tggtagaaag cttgtcagtg gctaaggcaa tggtgctttt caggcaggtg ggctccgcc 3480 acatgctcat tgtacccaaa taccaagcag caggggtgag attataagca aatttcagtt 3540
attattctta tgcaaatatc tccctcctat catagtatta agatgcacag aaatagtcat 3600
atcgtggcaa agttatttta cgttagtaag tgataaaagc attacttaca tcacacttgt 3660
gctccttttg taggtatctc cggtggtggg aatcttgacc aggcaagact tgagagccca 3720
caacattttg agtgtcttcc ctcatctgga gaagtcaaaa agcggtaaaa aggggaactg 3780
a 3781

<210> SEQ ID NO 3
<211> LENGTH: 44278
<212> TYPE: DNA
<213> ORGANISM: Nicotiana tabacum
<220> FEATURE:
<223> OTHER INFORMATION: DNA sequence of NtCLCe from Nicotiana tabacum; sequence originating from the ancestor N. sylvestris; one start codon

<400> SEQUENCE: 3
atgaatcacg gaagttgttg ggtcgtcatc caaattgctg gccttgggct cgacgaccat 60
ctcttcctcc gggacgttcc tctgacggaa acattgaaaa agaacaagat atgtgcgaca 120
gcagcaaagt cgatagtgat agtggcatcc agataggatc tctgctcgag gaagttatcc 180
cacaaggcaa taataccgct ataatctcgg cttgctttgt tggcctcttc accggtatca 240
gtgtcgtgct tttcaacgct gcggtacgtg cgctataggt ctttcatttc tcttttcatg 300
tactattcct ccttacttac ttggcctcag tcaatcagcc ccctgcctac tttaaattat 360
tgtacatttt atcagaggag tgtcctatac atcaaattca cataacttag taaaatatgc 420
tgatattctg aattttaaac ttaccagctt agaacatcca ggttagttca gaaacagata 480
atctaaattg gtctcattta taagtcattt tgttattcaa gacatacaat ttggctcttg 540
ataaaagatt atgcagcgcc cgatgattac ctaatattta tcagcaaccc atgtaattta 600
acaatattgt caccatataa aagagaactg aagagaatgt tcaatttgtg gtcatataac 660
ggatatctcc cttggttagg ttcatgaaat acgtgatctt tgttgggatg gaattccata 720
tcgagctgcc tcagaggagc ccattggagt acattggcaa cgtgtaatct tagtaccagc 780
ttgtggcggt ttggtagtca gctttttgaa tgccttccga gccactctgg aggtttcaac 840
tgaaggaagt tggacatcat ctgttaaatc tgtattggaa ccagttttga agacaatggc 900
cgcttgtgtc acattaggaa ctgggaattc cttaggacca gaaggcccta gtgttgaaat 960
tggcacatct gttgccaagg gagttggagc tctgcttgat aaaggtggtc gtagaaagct 1020
gtcactcaag gctgctggat cagctgctgg aatcgcttct ggtttgttcc ccatattatt 1080
cttggttctg aaccatacat ggtacatttt ccttataatt acatgtagcc tgttgtatgc 1140
tttcctcttt cccgggaagc ctttttgtaa atacaagtgt gtttgcactc aaaccaataa 1200
actgtaaaaa aggtgaactc cttaagcaag caaaagcatt agaaatgtaa actagacata 1260
tttctcagat tgagagtctg agagattaga acacgagtgt ttccattaga gagagaaaag 1320
agacttctag atatttctat tatctctgta agagtgaatc cgttcctata caaaaaatag 1380
gccttcatta aatacaagct tggctgggt actactgggc caaagtaaaa aataaaaaga 1440

```
atcacccact atcaaatggg cctagtctaa caaccccctt caagctggag ggtgacacaa   1500
cccctagctt gcgaatatga aaatgatgag caggcccaag taacactttg gtaagaacat   1560
caaccacttg agaagcactg gagttgtgaa atagactgat caggccattc ccaagcttgc   1620
cacaaacaaa atgacagtcc agcttaatgt gtttagtgcg ttcatggaaa acttggtttt   1680
ttgcaatgtg gacttcctga ttatcacaaa ataaaggaac aggtaaagaa ggagaaactc   1740
caatatcaga caataatttg gtgagccaag acacctctgc aacagcctta ctcatggacc   1800
tatactcagc ttcaattgat gatagtgaga caacaggttg cttctttgat ttccagctca   1860
ccaagctgcc ccccaagaaa aatacaaaaa ccagtgacag acctgcggct gtctgggcaa   1920
gaagcccaat cactgcacaa taaagctgca aagacaagtc tggagagtta ttgcggaaga   1980
ttccaaagtc aaaagtgccc ttgaggtatc ttagcaagtg cagggcagcc tgcatgttag   2040
gaacacaggg agactgcata aactgactca gatgctgaac aacaaaacta aggtcaggcc   2100
ttgtgcgtat caaaaagttt agcttgtgca ttagactcct gtactcttca ggcctgggca   2160
aaggagtgcc aatcttagct tttaacttca cattcaattc aagggggcaa gtgacagaag   2220
agcaattcga ggaatgaaaa tcagccagca aatcatgaat gaactttttc tgatgaagaa   2280
gaaccccaga atcagtgtat aaaacctcaa tgctaaggaa gtaattaaga gagcccatgt   2340
ccttaatctt gaactggtca ctgagaaagg acttcaaagc agccaattca gctagatcac   2400
acctagtcaa tatgatatca ttcacataga caaccaagat gaccaaggaa tccctagaac   2460
ccttggtaaa aatagagaaa tcattcaagg aacgagagaa gccattagag cacaaggctt   2520
gagataattt agcatactat tgtcttgaag ccagtcttaa accataaaga gacttctgga   2580
gtttgcatac taaaggagca gaagaagagt gaggaacagt taggcccggt ggcagcttca   2640
tgaatacctc ctcatcaagg tccccatgta agaagacatt attcacatct agttgaaaga   2700
ggggccagtg ttgtttaaca gctacaacaa taagagtttt gacaatagac atattgacca   2760
caggagaaaa agtttcatta aagtcaatac cctcaacttg agtgacctag ctttatatct   2820
ctcaatactt tcattagccc tatatttaac cttgtatacc cacttacaac tagtaggttt   2880
cttgccagga ggcaattcaa caatgtccca agttctgttg gcatccaagg cctcaaattc   2940
acatctcatg gctgcctgcc attcaggaac agctgcaacc tgagagtaag aataaggctc   3000
aggaacatga agttgactaa gagaaggagc attagaaata gatctggagg gaggaggaga   3060
agaagtggag gtgcagacat aactcttgag atagttggtt ggattgtgtg gcacggaaga   3120
tcttctcaaa gcaggaggag gtacaagaga gttagaataa tgagaaggag aagagatgga   3180
agtgggaaca gagaagattg agaagcagta gaaggagaaa gtgaaggaga tgaaggagag   3240
gaagaagacg gaaaggaaca ttcatcaaaa caagcagaaa agggaaaggg gaagacttga   3300
ggtactacat gagaggattg aaagaaagga aaaatggtgt tcataaaaaa tgacatcttt   3360
tgatacaaaa caggtgttat tctgaagatt aaggcgcttg tagccctttt tggcaaaagg   3420
gtagccaatg aaaacacaag gaagggacct aggatgaaat ttgttttgtg aggggtggtg   3480
acagttgagt aacagaggca cccaaaagct ctaaggtggt gataagtagg gtggaagaat   3540
gaagcaattc atagggactt ttgtgattaa gaagaggaaa aggaaatctg ttaattaaat   3600
atgtggcagt taaaaagcag tcaccccaaa atttaagtgg tagatgagac tgaaacataa   3660
gtgacctagc agtctctagt aaatttctgt gttctctttc tacaatacca ttttattggg   3720
gggtgtgagg acaggaggtt tggtgtacta tccctttttc tgaaaagaaa aggcaaccag   3780
aagaactaga tcccagttcc aaagcattat cactcctaac agtttgaact ttagattgga   3840
```

```
attgggtttc aaccatagca atgaaaacct tgagcaaatc aaaggcattg cggcacccat   3900
taaatgtgtc caagtagccc tagagtagtc atctacaatg gttaaaaaat acctagaacc   3960
attataggta ggagtagaat agggtcacca agtatttatg tgtattagct gaaaaggctg   4020
ggtggagtga atagaactat cagggaagga caacctggtc tgcctcgcta aaggacaaac   4080
cggactagtg aatgaccgtt tggaagacag tttgcaatta agaccagaaa tgcatttcat   4140
tttatagaag ggaatatggc caagtttgta atgccaaaca acatcatctt tattcacatt   4200
atgcaaagca gtactagtat ttacaattgg agtatcatca ggtacagaaa taggagcaga   4260
aactgaatta agcaaacaag aaataaggaa attagaaaga ggtaaaggag atgatgttgg   4320
aggcctggca ttctgaaata gtttgtagag tccattgtcc aatctaccaa gaaccactgg   4380
cttcctcact gaagggccct gtagggtaca agtagccttg gtaaattgta caatatcatc   4440
atcatgggaa agtaatttgt acacaaagat gagattatat tgaaaactag gaatatagag   4500
cacattataa agaatcaagt cagggaacaa ggctaaggaa ccaatattag tgaccttaac   4560
cttataccca ttaggaaggg agacaaggta tggtacagga agtgtttgaa cattaaaaaa   4620
acaaatgttt aagggaggtc atgtggtcag atgcccaggg tctattactc aaactacact   4680
atctatcata gtcagcataa atgcaccata agacaaccct tgtgaggtaa taactcacca   4740
gcaaagttgg tagaagcaag atagttggtt gaagaagtag atgatgctga tgaagacagt   4800
tgagattgtt gaagtaacat tagctgagaa tattggttct tggtaagacc aggaactgga   4860
taggactgtt caggagcaga ggtaccttca ggaccagctg acattgcaga accaccagag   4920
gtatccacct cagcatgggc aacagacctt ctgggaggaa gagatctatt tgacttgaaa   4980
tttggaggaa agccattgag cttatagcac ttatcaatgc tatgtccggg tttcttacaa   5040
tagtagacat gtgaagctca aaagatccct tagaggtagt accggacctt tgaggttcaa   5100
aatttatttt aggagaggga ggaggcctgg atacaccaac actgaaagaa gcagaatttg   5160
aggcatattg agttctagca aaaatttgtc tttgcttctc atcagatagc aaaatcccat   5220
atacattacc aatggaaggt aagggcttca tcatgatgat gttgcttctt gtttggacat   5280
aagtatcatt cagtcccata aagaactggt agaccttttg ttccctgtct tcagcagatt   5340
tacccccaca agtacacatt caaactctcc cggcagacaa agatgcaata tcatcccata   5400
gtcgtttaat tttgttgaaa tatgatgcta tgtccatgga cccttgggaa atatgagcca   5460
gttccttctt tagctcaaag atcctagtac ctctcttcta actcagtcca aatattctta   5520
gcaaactcag agtattcaac actcttggat atttccttgt acatagagtt agtcaaccaa   5580
gagaccacaa ggtcattgca acgttaccac tgtctggcta gaggagaacc ttcaggaggt   5640
ctgtgagaag taccattaat gaaatctagc ttgttacgaa tagacaaggc aactaggaca   5700
ttacgtctcc aattgccata acagcttcca tcaaaaggac cggaaactaa ggaagttccc   5760
agcacgtctg atggatggac atataagggg cgacagggat gggtataatc atcttcatgg   5820
aaaattaggc gtaagggagt agaagaagtc gcatcagcac tggtgttatt atcatttgcc   5880
atttttttca acagattgtc aatcaaccaa cacaatacag atacacatat atagattgtg   5940
agaaagcacg agagaaaaat ctatattatt gatattctat ttaattataa tacaatgagc   6000
cctatttata caatacatat catactccta ttctatgtgg gactaggact aattcatatt   6060
atgtacataa ctatctaaca ctccccctca agccggtgca tacaaatcat atgtaccgaa   6120
cttgttacat atgtaactaa tacaaggacc agtaaggaac ttggtgaaaa tatctgcaaa   6180
```

```
ctgatcattt gacttcacaa actttgtagc aatatctcat gagagtatct tttctctgac   6240
gaaatgacaa ttaatctcaa tgtgtttagt tctctcatga aacaccggat ttgatgctat   6300
atgaatggca gcttggttat cacacatcag ttccatcttg ctgacctcac caaatttcaa   6360
ctaattaagt aaatgtttga tccaaactag ctcacaagtt gtcacagcca ttgctcgata   6420
ttctgcttct gcactagacc gagcaaccac attttgtttc ttgctcttcc aagacaccta   6480
attacctcct actaaaacac aatatccaga cgtagaacat ctgtcaaaag gtgatcctgc   6540
ctagccagca tttgagtacc caacaatttg ctcatggcct cgatcttcaa acaataatct   6600
gttacctgga gctgatttta tatatcgaag aatgcagaca actgcatccc aatgactatc   6660
acaaggagaa tccaagaact gacttaccac actcactgga aaggaaatat caggtctaat   6720
cactgtgagg taatttaatt taccaaccag ccgcctatat ctagcaggat cgctaagcgg   6780
ctccccctgt cctggtagaa gtttagaatt ccgatccata ggagtgtcaa taggtctaca   6840
acgtgtcatt cctgtctcct caagaatgtc taaggcatac ttcctttgtg agataacaat   6900
acatgtgcta gactaagcga cctcaatacc tagaaaatac tttaatctgc ccagatcctt   6960
agtctgaaag tgctgaaaga gatgttgttt caacttagta ataccatctt gatcattgcc   7020
ggtaataaca atattatcaa cataaaccac cagataaata ctaagatttg aagaagaatg   7080
ccgataaaac acagagtgat cagcttcact acgagtcatg ccgaactctt gaataactgt   7140
gctgaactta ccaaaccagg ctcgaggaga ctgttttaga ccatagaggg accgacgcaa   7200
ccgacataca aggccactag actccccctg agcaacaaaa ccaggtggtt gctccatata   7260
aacttcacct caaggtcacc acgaagaaaa gcattcttaa tgtccaactg atagagaggc   7320
caatggagaa caacaaccat ggatagaaaa aggcggactg atgctatttt agccacagga   7380
gagaaagtat cactgtaatc aagcccaaat atctgagtat accctttggc aacaagacga   7440
gccttaagtc gatcaacctg gccatctgga ccaactttga ctgcatacac ccaacgacaa   7500
ccaacaataa atttacccga aggaagagga acaaactccc aagtaccact cgtatgtaaa   7560
gcagacatct cgtcaatcat agcctgtcac caccctagat gagacagtgc ttcacctgga   7620
tggaaataga ggacaaagat gatacaaatg cacaataggg tgatgacaga cgatggtaac   7680
ttaaaccgac ataatgggga ttagcattta gtgtagaccg ttcacctttc cggagtgcaa   7740
tcaattgact aagaggagac aagtccgcag tattagcagg atcaggtgca ggacgtgaat   7800
cagctgggcc tgatgctggg cgcggacgac gatgataagt taggagtggt agagctgtag   7860
aaggttgaac tggactaggc agtggaactg aagctatatg tggtggaact ggagctatag   7920
gtggtggagc tggagctgta ggtgaagatg aatgggagat agtgactgaa tctccaaaag   7980
atggaactgg tagcacctca gatatatcta agtgattacc tggactggtg aagtatgatt   8040
gggtttcaaa gaaggtaaca tcagcagaca taaggtacca cctgaggtca ggagaatagc   8100
atcgatatcc cttttgtgtt ctcgagtaac ccaaaaatac gcacttaaga gcacgaggag   8160
ctaatttatc ttttcttgga gtaaggttat gaacaaaaca cgtgctccca aaggcacggg   8220
gtggaagaga gaacaaaggt aagtggggaa acaagacaga gaatggaact tgattctgga   8280
tagctgaaga tggcatacga ttaataagat agcaagatgt aagaactgca tccccccaaa   8340
aacgcaacgg aacgtgagat tgtatgagta aggtacgagc agtttcaata agatgtctat   8400
tctttctttc agctacccga ttttgttggg atgtgtatgg acaagatgtt ttatgaataa   8460
tcccatgaga gttcataaac tgttgaaatg ggaaagacaa atactctaag gcattatcac   8520
tacgaaatat gcggatagaa accccaaatt gattttgaat ttcagcgtgg aaggtctgga   8580
```

aagtagaaaa caactcagat cgatttttta tcaaaaatat ccaagtgcac ctgtaataat 8640
catcaatgaa actgacaaag tagcggaatc ccaaggtaga actgacctga ctaggacccc 8700
aaacatctga atggactaaa gtaaaaggtg actgactctg ctcgattatc aagacggcga 8760
gggaaatggg agcacgtatg cttaccgagc tgacatgact cacactctag agtggacaag 8820
tgagataaac cagataccat tttttgaagt tttgacaaac tgggatgtcc caaccgttta 8880
tgtaatagat ctggtgaatc agtaacagga caagttgttg aagaaagaca agatgtaagt 8940
ccatgtgatt ttgcaagaat aaggtagtaa aatccattta attcacgccc ggtaccaatg 9000
atccgccctg tactgcgttc ctgtataaaa acaaggtcat caagaaataa aacagagcat 9060
ttaagtgatt tggctaagcg actaacggct atgagattaa aaagactaac gagaacataa 9120
agaactgaat ctaaaggtaa ggaaggaagt ggacttactt ggcttattcc agttgccatg 9180
gtttgagact cgttatccat tgtgactgtt gggagtgatt gagaatatga aatagtaatg 9240
aaaagagatt tgttaccaaa aatatgatca gatgcacctg aatcaatgac ccaagactca 9300
gaggttgaag attgggagac acaagtcaca ctactatctg tttgagcaac ggaagctatc 9360
cctgaagatg tttgtttaca tgttttgaac tgaaggaact caatataatc cggtagagaa 9420
accatccaac tcttcgtagt attggattcc attttgctac aaccaatttc tcaaattctt 9480
gattacaact tgtgtggtta accttggaat gccaaatcag aacacccctt tttttttttt 9540
ggaaaacatt gttcactcgc tggaaaataa aaaaggttgc cggaatttga tgaaacttga 9600
atagaccgac tcggaataat gtcctaagaa ggctgtccaa aaggagtttt gtcagaaact 9660
gaccagaagg aggtccacgc accggcgcgt ggacagatct cgccgaaaaa aaaaatcact 9720
ttggttggcg cgtgatggcg cgtgggtggg gtttttccgg tcgggttttg tggggtttgc 9780
tcccccggag atggagaaca ctgtggtggt gttggtttat gcacaacact ggtaaaaagt 9840
ggttttgatg cgaacagcta ctcaggtcac caaaaaattg cacggtgacg actgatttct 9900
tcccggatgt cgttggaatg acgcacaacg ataattatct caccaatgct ctgataccat 9960
gtgagaaagt acgggagaaa aatctatatt attgatattc tatttaatta taatacaatg 10020
agccctattt ataagactag gattaattca tattatgtac ataactatct aacatagatc 10080
aaataggcat gcaattcaca ataatggtga ataaaatgat acgaagttac ccagctcttt 10140
tcgcgatcga aaaggagaaa atagccttca atcacaaacg agaaagaaga atctccggct 10200
tgacagtaga cgacttcgaa accctagctc gagatgaaaa ccacaaaatc cccaaatcac 10260
attaccaacc aaacaatttg agatcacaaa tgttgaatat gtgagaatcc gactaagaaa 10320
tcaacaaaaa atcaatagaa atggttgaag aataccgact tgaaccctaa atgagtcaga 10380
catcacctag aatgaaatac accttcgaaa ttgacgaaaa caggaccggt tgaaagcgga 10440
gaacgtgcca tagaaggatc tacgctctga taccatgtaa acttgacata cttctcagat 10500
tgagagtctg agagattaga aaacgagtgt ttccattaga aagagagaaa agagacttct 10560
agatatttcg attatctgtg taaaaatgaa tccgttccta tacaaaaatt aggccttcat 10620
taaatacaag attcggccgg gtattactgg cccaaagtaa aatataaaaa gaatcaccca 10680
ctatcaaatg ggcctagtct aacaagaaaa ccaacaaata gtcccccccc cccccccaa 10740
aagataccac tgaaatgaca ccgggtgccc aaaaataaag cagcttactt cttgactttg 10800
agaggaactg caatccttat cggtttgaga ggaactgcaa tcagctataa gtagcttatt 10860
aatttccagt gcctgcattc tgccaagtac tatgatatat ttctgaagct ttgtttcccc 10920
agttcctttt tcagacgttt gctgtcaata aagttgagcc agccaacttg gctcccacaa 10980
gctactaatt ttgtccaagc ttactctatg ggagaagtta aatttcccaa attccttgag 11040
cggaaaatga aaaatggact caaagtgtca tattatgcaa ctatctaaag aaaaatactc 11100
aattgaagtt tagataagaa aagtgaatgt atattgatgt agtctccgtt aggtgagaag 11160
cgtatcactt acccagcaac atatggacct aacattttac tagtgaagtt ttcacattgt 11220
atcaaaagct caacaaacgg aaaggtgact aatcctaaaa tgttatttca catatatggg 11280
cacacggttt gtcaaccttc tcatacgtgc attatttgtt ctctatcttt ctatttcatc 11340
cgatataacc aatcgttatt gtaaattcta taatgcctgt ggttactttt gtctttagtg 11400
acaaatgaca tttaggataa ccatgtagtt attgacttat ttcacttgag gtctcttcca 11460
attatgtagt agtagagtgt tgagatatgg atatgttacc ttctaaaaaa aagagtgtag 11520
agatgcggat agtttgctag ctggcttttg tctcccttca agttgaatta gcaaaagctt 11580
gtctcataag ttggatagct agacaagaaa aactccaaat tactttatgt agagtattct 11640
taagcttgag tcgcgagttg gaaactggaa ttatgtaaaa aaacctggaa ttatttggtt 11700
gagcctgctt tttagttttg tcaatatttc cagtatctaa cccaacatgt ttagagtgat 11760
tcccggagag cctcagtaca aggcatttgc agagtcttta tgagagtcca ggaaggggca 11820
cacattctgt agaggtatag tcttgtcctt attttcaggg ttgaactagt tctttagaag 11880
ttacctaggc ttcctaattt ccaaatttct gccaggtcct tttttggtga agtacttgaa 11940
gtttaataaa tcaaatttta atttctaaca tatcctgaga aatttattca caaattcaac 12000
tggtgacttc tgatgcagaa acataagcaa ctgcttatgg gttcatatgt tcctgcaatt 12060
ttattgttga catggattgg cttcatatgg ttttgttcct gcaattttat cgctgacact 12120
aatcctttca tatggtttta tgtggagtgt taaatagagg ttaagagaca agaagaggct 12180
gaaaaaggtg ggcagttcat ttgttagtag actactctat ttactaagag atatgatgtc 12240
ccatacatta ctcgaattgg ctccgaatcc agattccact tctttgccga gtttccttat 12300
tgtacatagt tcgactcgtc aagggaaatt cacttccttt gactgaataa tgctagtttg 12360
agtagtacct tacattaaat ggaccattta gttctatcta cttgatagaa tagactggtc 12420
atcaactagt tgcaaataca atgacaactt tgccatgttt gcagagtcac ctgatgaaga 12480
agtacctcaa ttagtagaac atttcttgaa tgttctacag tattctctat gcctacatga 12540
ccacatcact tttcctttg cgttgtgaga acttgaactt ggtgagcggg ggttccccag 12600
gaatggcatc ttgatggcag atgaccattc tgtccttgtc ttagctaatg cttcttgcat 12660
tgcctcacta gatttattat acctttaaaa aatgtttgcc attgttctgc cataatagaa 12720
ggatgtaccc agctggtgct tcaaaactaa tgaaatgctt tacaattgtc gagtcctaaa 12780
ggatgatttg tggaatcaga tctcaaacaa ttctttttga ggaagaaaaa taccaaaggt 12840
tttttctgtt tgttggaaga ttaaaaatcc tttaaatggt aaagatttat gaacttaatt 12900
cagcgttttt gtggccattg ctggaaaaga gaaaaaacaa tggcacttct tcgagtttgc 12960
ttatccaaaa aaaagaagaa gagaatgtca cgtaatgcaa tttcatctta ggaaactttg 13020
caggagaaaa gcaagagtga taaaacagaa ctatttgttt tttttaacaa gttgttgtga 13080
cctatttctt gtcattctta tttgctaata agctaatgta ctatagttcc tgtactatgg 13140
tttgttttga cttaatacgg ggatgttcaa tgagcatttt cttgtttttt ctgctttcag 13200
catctgctgc cttacaggaa ttcattttct ggaaatttac ttcttgttct gctaacattt 13260
tcctgttata tcttgtcagt cattttctct ccatggttat actgtttgtg tcactttaaa 13320

-continued

```
ctctccttgt tttctacttt aaaggattta atgctgctgt cgggggctgt ttctttgctg  13380
tggaatctgt gttatggcca tcacctgcag agtcctcctt gtccttaaca aatacgactt  13440
caatggttat tctcagtgct gttatagctt ctgtagtctc agaaattggt cttggctctg  13500
aacctgcatt tgcggtccca ggatatgatt ttcgtacacc tactggtaat tttggacttc  13560
tttctcgagt ttgattctta aatacaattg tacccgtcac ttacagcaac aactacattt  13620
caacagctag ttggggttgg ctacacagat catcactatc catttcaatt catttagtcc  13680
catttctttc gaatattgag tactttggga ttctataata tcaaggttct ttatattttc  13740
tactttgacg tacaaatctc taaatagatt aaagaagact cctagagaca ctggcctaat  13800
gcaaatgtac caccatgaat aaactttaat ctgaaatagc tggtatctta tataaggacc  13860
cttagcttta attgtgttct atattgatct tttgggacaa cttccttcca atattatgtc  13920
ttacttatac agttatactt atccttaagc cttactcttt agagtggtta tccctaattc  13980
aagcttttgt tggcaccata gctagtttgg ttctaagtaa aaagttactc tttagagtgg  14040
taactttttg tcaattttct tagtgaaaat ataacctctg tgacaaatct accaagtata  14100
aatccaattt ggttctatgt catccttgta gtttatccaa gtcaatgctc catcactctt  14160
acaaaggttc atcgtatgac taatcttttt tggagaaagg taacagtttg tattgataat  14220
aagatcagcg ccaggttggt cattagtgct aatagctgta cgtacaactc caaaagagca  14280
aaagacaagc acctgatgta aggtaaatta caagctgcct ataaaatcta tcaggtgtcc  14340
tatctcacta aacatttctt gtttacacca aaaaaataaa acaaggaaag acaatccatc  14400
ttaatcttct gaatggagtt tctttttcct tcaaaacatc tggagttcct tccgttccat  14460
gcaatccacc atatacaagc tgggatgatt ttccatttgt ctttatccat ttcttctacc  14520
aattcccttc caattgatta gaagttccaa tgtggttcta gatatgaccc aattaactcc  14580
caacagataa aagaagatgt gccacggatt tgtagtgatt ctgcaatgta ggaacaagtg  14640
agcattactt tctacttcct gtccacaaag aaaacatctt gagcaaatct ggaaacctct  14700
tctttgtaag ttatcatgtg ttaaacatgc ctttttcacc accaaccaga caaaacatga  14760
tactttggga ggagttttaa ccctccaaat gtgtttccaa ggccacacct cagttgttga  14820
aacattagga tgtagagtcc agtatgctct tttactgaaa atgcaccttt tctattcagc  14880
ttttaaacta ctttatctat ggtctgtgat gtacccttga aaggttcaag agtttggagg  14940
aagatagaaa ctctgtttat ctcccaatca tccaaagatc ttctaaagtt ccagctccat  15000
ccttgtgagc tccagactga cttaccaatg cttggctttg aagacttaga gagaataagt  15060
caggaaaata tctttcaacc ttccttgccc tatccggtga tcttcccaaa aagatgtctg  15120
caacccattg ccaatattga tcttgatatt gctactgaaa gatttctttt ggtggcagga  15180
ttactctcat taacaatgta cttgacaatc tccatacata ctaatgtctc tttaccctct  15240
tgccattaag gttgtaaaga gacttgtcaa attaagaaaa ggtttcctat ggaactgttt  15300
caaggaagga acctcctttc ctttggtcaa gtggagttaa gtcatataat ctaggaagtg  15360
gaggcttggg tatgaaatag ctgcaaatac agaaaaggag catcttattt aaatgatcac  15420
ggaaatgtgc ccaaaacttt aaatatctgc acagcatatg gttgtagcaa aatttgaatc  15480
ttcctgtcaa tggtgctcat gtccagtgaa tacccctgat ggtgaaagtg tcctgaaggg  15540
aagcaggaac ttattggaag aattggcatc taacactcag cttttcggtg ggtcatagcc  15600
cattgaaaat tgagtgccca gatttatata gttttgctct aaactgacga tgcagttgca  15660
```

-continued caacatacga caaactaagg tgggacatca tcttcttcgg aaggaatttt gaggattaag 15720
agatagagtg gttgattcag ttgcaaatga agcttcaagg gttcaatatc atccaggaga 15780
caccggattc tgatagataa aacaacagaa agatgagcac tactttgtta ggcttgttac 15840
aagttgctat cgtctttctt atctcggtac acaatttaga tttgggaact tagttggaaa 15900
agcagagtgg ttgtttttgt gaatagcatc agacaaagct tctgagctgg tacgacagaa 15960
aactcaacag ggagaataga agactgtggt tcacaatttc tgcatgcatc ttgtaggtta 16020
tttggtgggt aaattattta atgttttgaa gggaaggtag aacatgttca taggcttaga 16080
ttcaaatgtt tgtatttttt tggctctttg gtgagagatg ctgaacgtaa atgacatagg 16140
cagctgacta taatttctca gctccttgct ttttaaattg acaggcactg atatgtacat 16200
gtgaacatcc aacacttttg tggtgccgtt ccgatgaata aagaacatta atcacttact 16260
gatcaggagt aatagtttag gagttctaga atttttgtac ataaaatgaa ccaaaaagaa 16320
gatcggaatg agaacatgtt tctttttttg tttttctttt ttcgtgaaaa cttcaataac 16380
acttctgata gaatagctag gtccatttga attcctttgg agacccttac acaaccaatg 16440
aatgacaagt atagcatttc taactccctc ccacacgtat aacccagatt ttagggttta 16500
gatgtggatc tgatttgacc ttattgcctt tttttgtttt tgttcttttt gaagtagaga 16560
gtgaggaggc tcaacaatta attcggctca acgggctaat gattggactt acatgctacg 16620
acaatgttag gagagagaga gagagagaga agcccagagc agttacatga gttaagaaag 16680
agaagtccaa agcgatagaa tatgaagaga gaaagcggtt gtgctaacag gctccctgaa 16740
gtttggctct gagcatccaa ctcaaaacct taaggcaatg agtagagtag cccaggacca 16800
tttaaattgc tgttgaaaac cttacacaac caataaggga acaagtgtaa cattctctta 16860
caaccctacc gtcttataag tcagtgctct aatttagcat aaaatcaaag tgaggcgatc 16920
tacaatgaaa tgaagtaaat aactgataaa tacaaagaat gttaattctc caatatagcc 16980
tgaatgttcc cagaacaaaa taaactagtc tcaggattta tcattaacat gatgttcctc 17040
ttattttgag tgattaggaa ggttaatcaa ggtataaatt ctttctaatt tgtatcgtct 17100
agaattattt atctaacaaa ttttcagatt accggttcaa aagaggaata tattttgcat 17160
acaacgttac cataccttac aaaagggaga tgaacatttt tttattttat tattgtcctt 17220
tttttcaatt agggattatg cagtcttcct ccacgtgata ttactcttag aatcacgttt 17280
ttgtcattgc tattacttaa tgtggtaagt acaaatgtgt tttgaactct ttttggtatg 17340
taatattgag ttaatttttg gtttccattt cagagctgcc gctttatctt ctgctgggca 17400
tcttttgtgg cttagtttca gtggcattat caagttgtac atcatttatg ctgcaaatag 17460
tggaaaatat tcaaacgacc agcggcatgc caaaagcagc ttttcctgtc ctgggtggtc 17520
ttctggttgg gctggtagct ttagcatatc ctgaaatcct ttaccagggt tttgagaatg 17580
ttaatatttt gctagaatct cgcccactag tgaaaggcct ctccgctgat ctgttgctcc 17640
agcttgtagc tgtcaaaata gtaacaactt cattatgtcg agcctctgga ttggttggag 17700
gctactatgc accatctcta ttcatcggtg ctgctactgg aactgcatat gggaaaattg 17760
ttagctacat tatctctcat gctgatccaa tctttcatct ttccatcttg gaagttgcat 17820
ccccacaagc atatggcctg gtatgaattt gtcttttgtt agaagtagca ttacatatct 17880
ggataagtga gttttttatt attgaaaagt aataacagga gagcaagaga atatagcacc 17940
caaatctact tctttcctct cttctattct tctgaaattc aaggtccttt aactcctcca 18000
cggcctgtct agttattgat cctgtagact taattcacat aggtttagga cattcaagtt 18060
tatccaaact tcgtgaaaag gtttctaatt tttttacatt acagtatgag tcgtgtctac 18120
ttgagaaaca tatcactcca tgtttctata gagtctgttt tctcctcagt ttattttgat 18180
atatggggtc ctattaagac agttcaacct tggattttca ttatttttgt tgtttcattg 18240
ataattattc aagatgtact tggattttct taacaagaga tagttctcag ttgtttttg 18300
tgttcctaag tttttgtgct gcaatacaaa attagtttga tgtctctatt tgcatttttc 18360
ccaatgataa tgccttagaa tattttcttc tcggtttcag tagcttatga tttctttaga 18420
aactctctat cagaaatctc aactgagata gatgagagga agaataagca tatcattgag 18480
acggctcgta cccttctcat tcagtcccct gtcaagctta gtttcttggg cgatgcagtt 18540
tcacgtcctt tgattagatt aattggatgc ctcatctgct atccaaaatc agattcaact 18600
ttcgatattg tttcctcgct tacctttata ctctctttcc ctcgagtctt tgggagcaca 18660
tgttttgttc aataacatag ctcctggaaa gtgaccagcg caaccgacaa gcaaggcctt 18720
cttaatatag aaggagggca tatgctattc tagccacgag ggagaaagta atattgtaat 18780
caaacccaaa tatctgagta taacctttgg caatggcgat caatttgatt atatggacca 18840
actttgccta catataccca ccgatagatt tacggggagg tagagaaata agctcccaag 18900
taccactaat atgtaaagca gacatctctt tgatcatagc ctgtccttgt ggacataggg 18960
atagaaattg aggactaaga tgacacaaaa gcataatgct gtgatgataa acgatgataa 19020
ctcaaatcaa tatgatgggg atgggaatta agagtggatt gaatatcttt gcggaatgtg 19080
attggtagac taggaggaga caagtccgca ataggtaaaa gatccagtac atggaatgaa 19140
tcttctggac atgatgttgg actgacgtca atgataagtc aagagtggtg gagttgcaga 19200
acatggaact ggagctgtag gtgacataat cgaagttgta gggggtggag ctatagagga 19260
aggtgaagga gagatagtga ctgaatctcc aaaatatgaa accggtaata cctcaaaaaa 19320
tgtctaagag atcatttgga cctatgaagt atggttgcgt tttaaagaag gtaacatcag 19380
cagacataag gtaccgcgga aagtcaggtg aataacattg atatccttgt tgcgtcctcg 19440
agtaacttag aaatacatat ttgagagcac ggggagctaa cttatctttt ctggagtaag 19500
gttataaaaa aacacatgct cccatagaca cgaggtggaa gagagaaagg tgagtgggga 19560
aacaagacag agtatgaaac ttgattcttg atagttgaag atggcataca attaataaga 19620
caataggatg tgagaactgt atccccacgt aaacacaaca gaacatgaga ttgtacgagt 19680
tgggtatgag cagtctcaat gagataccta ttcttccttt cagctatccc attttattga 19740
gatgtgtatg gacaaaatat ttgatgtatg atcctatgag agttcatgaa ctgctgaaat 19800
ggagaagaca aatactctgg ggcattatca ctatgaaatg tgcggttaga aaccccaaat 19860
tgattttgga tttcagagtg aaaggtctga aaaatagaga ccaactcaga ttgatttttc 19920
atgagaaata tccaagtgga cttggaataa tcatcaatga aactgacaaa gtagcagaat 19980
tccaaggtag aactaactcg acaaggacct caaacatctg aatggactaa agtgaaaggt 20040
gactctattc gattatcaag acaccgagga aaatgagagc gagtatgcct tctgagcgga 20100
tatgactgac gctctagagt ggacaagtga gacaaaccag gtaccatttt ctgaagttct 20160
gataaattgg gatgtcctaa ccgtttatgt aataaatctg gtggatcagt aaaaggacaa 20220
gctgtaaggg gacaaaaata ccaaatattt ccagaagatg gcaaactaca acagaagaag 20280
caactacatt aacaggctca ggatatgtga tgaaatgagg acaaagagtt gatcaagaag 20340
gagattctgg aattctacca gaacttatat agtgaaaatg aaccgtggag gcccagtgca 20400

```
aattttgaag gcatctcctc actaagcata gaagagaaga actagttgga agctccattt  20460
gaagaaatag aggtgcttga agctttgaaa tcatgtgccc ctgataaagc accaggtcca  20520
gacggcttca ccatggcttt ctttcagaaa aattgggata ctcttaaaat ggacatcatg  20580
gccgcactta atcactttca ccagagctgt cacatggtta gggcttgcaa tgccaccttc  20640
atcgccttaa ttccaaagaa aaagggtgct atggagctca gagactacag atctattgac  20700
aaactagtct cgggggaaca aaatgctttc atcaagaaca ggcacatcac tgatgcttcc  20760
ttgattgcca gtgaagtgct ggattggaga atgaaaagtg gaaaaccagg cgtgttgtgc  20820
aaactggaca ttgaaaaggc ttttgatcaa ttaagatggt cttacctcat gagtatcttg  20880
aggcagatgg ctttggggag aaatggataa gatggataaa ctattgcatt tcaactgtca  20940
agaactctgt tttggtgaat agtggcccga ccggtttttt ctcctgccaa aagggcctaa  21000
ggcaggggat ctcctctccc ctttcctatt cattttggcg atggaaggac tcactaaaat  21060
gttggagaag gctaagcaac tacaatggat acaaggcttt caggtgggaa ggaatcctgc  21120
cagctcagtt acagtatccc atctactctt tgcggatgat actcttattt tttgtggtac  21180
tgagagatca caagcacgaa atctcaacct gacgctgatg atcttcgagg cactatcagg  21240
actccacaac aatatgataa agagcatcat ataccctgtg aatgcagtcc ccaacataca  21300
ggagctagca gacatcctat gctgcaaaac agatactttc ccaacatatc ttggacttcc  21360
cttgggagct aaattcaaat caaaagaagt ttggaatgga gtcctagaga agtttgaaaa  21420
gaggcttgcg acttggcgaa tgcaatacct ctccatcggt ggcaagttaa ctttaatcaa  21480
tagtgtactg gacagtcttc ctacatacca catgtctttg ttcccaattc caatctcagt  21540
cctaaagcag atggacaaac tcagaaggaa gttcttacgg gaaggatgca gcaaaacaca  21600
caaatttcca ctagtgaaat gactcaaggt aactcaacca aaattcaaag gaggcttgag  21660
catcagggat ctacaagcac acaacaaagc tatgctctta aaatggctct ggagatatgg  21720
acaggaggaa tctaggctat ggaaggacat catagttgct aaatatggag cacacaatca  21780
ctggtgttcc aagaaaacaa acactcctta tggagttggt ctgtggaaga acatcagcaa  21840
ccactgggat gaattcttcc aaaatgtaac tttcaaagtt gggaatggaa ctcgtattaa  21900
gttttggaag gatagatggc tcggaaatac acctttgaaa gacatgtttc ccggtatgta  21960
tcagattgcc ttgaccaaag actccactgt tgctcaaaat agagacaatg gcacttggtg  22020
cccattttca gaagaaattt gcaggattgg gaggtcaaca gcctactcac aatgttaagc  22080
tccctagaag gtcataatat cgaagatcaa cagcctgaca aacttatttg gggaaattct  22140
gagagaggca agtacacagt caaagaatga tacattcacc tctgtgacca gaatccaata  22200
atagataact agccatggaa acacatctgg agaactgaag tgcctaccaa ggtgacttgc  22260
ttcacatggt tgactctaaa tggggcatgt ctcactcaag acaacttaat caagaggaat  22320
atcatactag ttaatagatg ctacatgtgc caacaacagt cagaaagtgt aaaccaccta  22380
ttcctccact gctcagttgc aaaagacatt tggaacttct tctacactac ctttggtctg  22440
aaatgggtta tgccacaatc aacaaagcaa gcttttgaaa gttggtattt ttggagagtt  22500
gacaaatcca tcaaaaaaat ctggaaaacg gtgccggctg cattttttttg gtgtatttgg  22560
aaagaaagga accgaagatg ttttgatgac atattaactc cactctactc cctcaaggct  22620
gcgtgtttag ttaacttatt tagttttgtg gattttatta gctccctgat agtagcatag  22680
gcttttgtaa atggagctaa ttatcctatc tcttttgtac tctttgcatc ttcttgatgc  22740
cttttaatga atctaattta cttcataaaa aataaaagga caagttgttg aaggaggaaa  22800
```

agatgtgagt ccatgtgatt tagcaaggat aaggtactaa agtccatttg attcacgccc 22860
ggtaccaatg atccatcccg cattgcattc ctgtattaaa acagagtcat caagaaataa 22920
aatagagcaa ataagtgatt ggccaaacga ctagtggata tgagattaaa aggactatcg 22980
ggaacataaa gaactgaatt caaaggtaag gaaggaagtg gactagctta acctattcca 23040
gttgccatgg tttgagaata gttggccatt gtgactgttg gaagtgattg agagtaagaa 23100
atagtagtga aaagagattt gttaccagaa atataatcag atgcaactga atcaataacc 23160
taagagtcgg aaaaagaaac acaagtcatg ttattacctg tttgaacaat agaagttatc 23220
tccgaagagg attatttaca tgttttgtac tgatggaact caatataagc cgataaagaa 23280
accatccgga tattcaaagt attggatcaa cagcttataa gccaaaagca tccgatacga 23340
gtgccattat aatggatcaa gagagatcaa acaacaaatc accaaatatc ataaacaacc 23400
aagaatctcg ctggaatgtg aacaaagatt gaaaaacaac aatgtagctc gccaaaaatg 23460
tgcaaagtga tcgaaaaata ttgaatcgtg agtggagaga aataggagct tcaatcgacc 23520
cacacagtac caaaaaatcc aaaaacggtt gtcggagctc aagaaagttg tcaaaaagta 23580
tattgtatgc ttcgaaagta gccgaaaaag gttggaagtg ggatgtgtca actccgaatt 23640
atgatacgag caccacagaa gatcaatttg tgtcaaaact accgaaaaaa atacttcaca 23700
ccccgacgcg tggagtactc gctcgttgga acccttgctg ccaacgtcgc atgtaggatc 23760
agttttcgaa gaatcttatt ggggtttggt cgccggacga tgtcggatct tgtggtgccg 23820
ttggaattcg cacaaccctg aaggaaaaga aggttacaca aatcagatct gaaagtcacc 23880
gaaaagacac atggcgattg actttttgt ctcagatgtt tctcaccgtc gctctgatac 23940
cagttgttgg gctcaactcg tttgaagata ctcttaacat agtgtgatat tgtccctttt 24000
ggaatgtgag tcatcttagc tcggtaagca tactcgctct tccaactagc ccgaagatac 24060
ttttaacaga gtgtaatatt atctgctttg agccaagctg gcgcggtttt catcaaaaga 24120
cctcatacta ttaaaagatc catacacctt atatgtaggc ttctaagttg ctcggacacg 24180
ggtgcgagta cccgacacag gtgcaaatct agaggtcaga tcctttaaaa tgtaaattct 24240
aagatttggg gatacgaatc ctagtacgga tacgggtgcg aggatccgat taaaaataat 24300
tcaaaaaaat aagaaaataa aaaagtctct aaattatgtg aaattttgtg gaataactac 24360
gtatagcttg taaagtgtgg atttattttt tattctcaag ttgtagataa gtaaatgatt 24420
gatttcctag ataaggtatg ttattttctt caaatttacc ctagtttggt tcgaatttcg 24480
ggaaattgta tcttgtctcg aatttttcct tctgtcctga ttaaactact caaaatcgtc 24540
tgaccagatc cggtacggat cccataccca catccacact agtgtcgtgt ggacaagggt 24600
gcggcaccta aacttccgtg taggagcaat ttaggtaggc tcctaatctt ttcagctatt 24660
aatgtgggac ttttacgcac ctctatcaaa ttccccaata aactaagttt cacgtggtcc 24720
atcatcgcaa tccacgggtc tcttcctcta gttaagtccc acatggccca ttaccatgat 24780
ccacgggtca attttcgtga ttcatcgtgt gccacccaca tcgttagtat tttatggtaac 24840
taaagtacgc aactagcttt tgcttgtgag cgtgtctcca agctcgtaaa ggtaagaaaa 24900
ccgagccgca tattccatca ctctatcatc accatactcg tcccgcgaaa cttgtaagat 24960
aaaggtggct ggttggtcag ttgaactacc tcagagtgac ttggtatagt atttcctttc 25020
ttgtgaatat ttaactcaat tatggactct ctgtgtgata gtcattgaga gccattttct 25080
atatagccgg tgcacacaaa tcatatgtac caagcttgtt atatatgtaa ctaatacgag 25140

```
gaccagtgaa ggactcggtg aaaatatctg caatctggtc attcgacata caaggccaat  25200
agactcccca gcaataaaat caggggggttg ctgataaata gaattggccg aaatgttgcc  25260
agaaaaattt gaaaatagtg agactaagcc gaattctaca ctacaaaata ggttttaaaa  25320
cacaaccaga aaacaaaaac ttttttggaa attactgttc acatcgaaaa aataaaagtt  25380
gtcagaattt gatgtaattt atatggatag gctcgtaatc actggacgag taagttgtcc  25440
tgaagaagtt ttgtcaaaag gtggccggaa tggctcacac atgccggaaa acttattgta  25500
gctcgccgga accctagttc tggcggtgcg tagaggcgtg tgactttctg ccagactgat  25560
tgactgtggt ttgtcgcctg acttttccta acaagatggt agtattggtt ttcgcacaac  25620
aattaccgat gaggagataa cgcaaatcaa tcttgagtcg tcaatcggaa agacgcacgg  25680
tggctgactt tctatttaga tgggactgga atttctggag tttaatcgca caagcgtttt  25740
ggatctgatg gtaatactgg tatgcacagt accactgtag cagtgatgaa ccctcaaaat  25800
aagacaaagt tgccagaaaa ttgcacggcg atgagatctt tcttccggat gtcaccggaa  25860
tgacgcacaa cgataatttc tcactgaagc tctgacacca tgtgagaata cacgggagaa  25920
aaatctattt ttattaacaa tgatacaatg agccctatat ataatacata ttctactcta  25980
ctacatatgg gaatagggca tattttactc ctactacata tgagactagg actatttaca  26040
cataactatc taacaagggc tatatctcag atttatgaga atatctaccc aacgacccag  26100
agagacgagc ctaatcattt tgcagtggca cagactataa caacaaaaaa cctactcata  26160
atggttaaac caactgatta agatgcttac aggactatct tgagaaatgt acatattata  26220
tagatgcttg agttgcgtcc caatcctaaa tagaagcttt tattcgtaag caagaaggga  26280
agcagcttta cttgagccaa tagctttcaa ggtgcatgtt gtcacaccaa ggacatccag  26340
aatttgattt tatagtggga atatcgttta aagataaaaa agatagcgtg cagaagattg  26400
catacattag agatgcaaaa tacggaatac ccatactccc agataatgca gtatgccttt  26460
tgcatgacct actggttgaa tggaagcacc tggtgaattt actaggtgtg ttagtgattt  26520
ctgctgcttc cttcccccttt ctaaactgca tactatctaa aatgttaggg gggcagaagc  26580
ccagtcaatc tgactaggtg atgttagtgg tttccgcttc ttcctcccac ttctaaatgc  26640
gtactttctc aaatttagga gcatagaaac ttaagcagct gcctacctga ggagttgcat  26700
gggaacataa gagaatagac tttacctgtc atattttcca taccttagtt aattacagtg  26760
ttatcctgat aatgatctgt tttctggatc taggctgaat cgagattcaa tcgcttttgg  26820
ttgaaaggat gctgctacag atccttagtt tacatcattt tggttcttat tctataagta  26880
cttcccctat caactacttc cttctttttt cttaggttat ttgcctcttt aggttgtttg  26940
gaaggaaagg aacagtagat gttttgatgg aatagcaact ccaaaccact tccttaaggc  27000
taatatcctg attggccaag tttctccaaa gtccaaaaca cttttttttt ccttcaaaaa  27060
agtacctttt tttttcaaag ttgaggtgtt tggccaagct tttggaagga aaaaaagtgt  27120
ttttgagtag aagcagatgc tcttgagaag cagaagaagt agcttcttcc cggaagcact  27180
tttgagaaaa ataaatttag aaacactttt taaaagcttg gccaaacact aattgctgct  27240
taaaagtatt ttcagattta ttagacaaac acaaactgct tctcaccaaa aatacttttt  27300
tgaaaagtac ttttcaaaca aagcactttt caaaataagt tttttagaag cttggctaaa  27360
caggctataa atgtctttta tttttacagc tggagtaccc taacacctgt aaattcccct  27420
atacattttt ttcgactttg gtagctcatt aaccctagta taggactctt tgttttggag  27480
ctagcaaact cttttgtttt cctatttttg catcttcttg gtgccattta taatatctct  27540
```

tcaccaaaaa aaaaaagttc ccaaactatg actaccttga gttggtcaaa gcataaccaa 27600
agcatgggca caccagtgtt tgcgtgaatt ttatggatgt tccttacctt tatccttctg 27660
tgcttatgta gcatctgtct tggtcaatct tttctgaagt ctatattgta tttctgtgtt 27720
gcaacatgag tttactgtta atcttactgt ttgacctcaa ttttgggttc tttttgattt 27780
tggaagacat cgtttaacag gttggcatgg ctgctactct tgctggtgtc tgtcaggtgc 27840
ctctcactgc ggttttgctt ctctttgaac tgacacagga ttatcggata gttctgcccc 27900
tcttgggagc tgtggggttg tcttcttggg ttacatctgg acaaacaagg aaaagtgtag 27960
tgaaggatag agaaaaacta aaagatgcaa gagcccacat gatgcagcga caaggaactt 28020
ctttctccaa catttctagt ttaacttatt cttcaggttc accttcacag aaagagagta 28080
acctctgcaa acttgagagt tccctctgtc tttatgaatc tgatgatgaa gaaaatgatt 28140
tggcaaggac aattctagtt tcacaggcaa tgagaacacg atatgtgaca gttctaatga 28200
gcaccttgct aatggagacc atatccctca tgctagctga gaagcaatct tgtgcaataa 28260
tagttgatga aaataatttt ctcattggtc tgctgacact tggtgatatc cagaattaca 28320
gcaagttgcc aagaacagag ggcaatttcc aggaggtagc ttcttggtac atttcaatat 28380
tcttaactga tgaaaaaata agggaaattg atctagcatg aaatgaagct aattataagt 28440
tttacacagt agaactggta aaacagggtt ggctggatat ttctttgttg aatttttagg 28500
attatatata ttgttttagt tttgtaggtt gttttctgat gtgctttttg actcggcaga 28560
atcttaagat gaaatggaag gttgtatcat caaatgttaa ataagggaat atgtgacttt 28620
caaagttaag cacggagtat tttggagtca atagttactt cctgaatctt ttaggatgga 28680
ggagacagtt tctataggaa taggaaaagg ggacctgatt tcattatttg tgtgtatata 28740
catttgttat ctgaattcgc attactttct aacaaccaac aaaaggaaag tggacattca 28800
atttgagccg gagggagaaa atttaactag aaaatgacct ggccgtgaaa taaaattatt 28860
gatccgtcct ttaactagtt ttcatggatt gcctccttgc ggatgatttt tccaaccggt 28920
agaactactg ttagtcgtcc aaattctgac cccctactat gaataaaaat gtattagtaa 28980
gtttagtggg taatctcctt gagaaataaa ggaacaggag aaatatttta ttgatatatg 29040
ctaagtgttt tacaatagcc ctatttatat acaatgttta cataaaccta aagccttcta 29100
tataaatgtg ggacactata catgaactaa ctctaacact atccctcaag ctagtgcata 29160
taaattatat atatgcttgt tacatatata attaatttct ctactttttg gtatacttct 29220
tgtatacggg agttatctcc cttttgatta atacaattta ccttatcaaa aaaaaattaa 29280
tacgaggacc agtgagggac ttggtgaaaa tatctgcaag ttgatcattt gacttctcaa 29340
actttgtaac aatatctcct gagaatcttc tctctcgtga agtgacagtc aatctcagtg 29400
tgtttggtcc tctcatggaa cactggattt gatgcaatat gaaggacaac ttgattatca 29460
cacacaagtt ccatctgact gattgctcca aattttaatt atttgagcaa ttgtttgatc 29520
caaactagct cacatggtgc aagagtcatg actcgatatt cggcttctgc gctagatcga 29580
gcaactacat tctgtttctt gcttttccga gagacaaatt acctcctatt aaaacacaat 29640
atccagatac gtaacgtcta tcagaaggtg accctgccca attagcatct gtgcgtccaa 29700
caatatgctc atggcatcga tcttcgaata ttagtcattt gtctggagct gattttatat 29760
aacgaacaat gcgaacaact gcatcccaat gactatcgca aggaaattcc ataaactgac 29820
ttacaacact cacaggaaat aaaatatcag gtctagtaat tatgaggtaa ttcaattttc 29880

```
caaccaggcg cctatatttt gcaggattgc taagaggctc cccoctatcc tggcagaagc  29940
ttagcattcg gattcataag agtatcaata gttctgcagc ccattattca tgtctcctca  30000
agaatgtcta aagcatactt cctttgcgaa ataacaacct gaactagacc gagcgacctc  30060
aatacctaca aagtacttca atctgctaag gtcgttagtc tggaagtgtt gaaagtgatg  30120
ttgtttcaaa ttagtaatac catcctgatc attgcgagta ataacaatat catcaacata  30180
aaccaccaga taaatacaga gattaggagc agaatgccga taaaatacag agtgatcagc  30240
ttcactatta gtcatgccaa attcccgaat aattgtcctg aacttacgaa actaggctcg  30300
acgagattgt tttaaaccat agagacttgc ataagtgaca tacaatacct ctagactccc  30360
cttgagcaac aaaaccaagt ggttgctcca tattaacttt atcctcaaga tcaccatgga  30420
gaaaggcatt ctttatgtcc aactgataaa gaggccaatg atgaacaata gccatggaca  30480
ggaaaaggcg aacagatacg actttagcca cgggagaaaa gtgtcattat tatcaagccc  30540
aaatagctga gtatatcctt ttgcaatcag acgagccttg agccaatcaa cctggccatc  30600
caggtagact ttgactgcat aaacccaacg acaaccaaca gtagacttac ttgaaggaag  30660
agaacaaact cccatgtacc actcactcac atgtaaagca aacatctcgt caatcatagc  30720
ctgtcgccat cctggatgag atagtgcctc acctgtaaac ttaggaatgg aaacagtgga  30780
caaagatgat acaaaatcat aatagggtga tgagatgcgg tgataactta aaccaacata  30840
atggggacta ggattaagtt tggatcatac acccttttcga agtgcaatca gtggactagg  30900
aggagccaag tccgcactag acgtggatga caatgataag tcaagagtgg tggcctcgtg  30960
gttggagatg taggatgagc aactgtagac tcctcagaag tcggtatagg taggagtacc  31020
tgtgatgttg atgtggattt aagaggagga acaatagatt cctcacaagt agatacaggt  31080
aagacctcag atatatcaag atgattagat gaagtaaagt aaggttgaga ctcaaaaaat  31140
gtgacatcga ctgacataag atatctacga agatcaggtg agtagcagcg ataccccttt  31200
tgaacccgag aatagccaag aaagacacac ctgagaacac aaggagctat tttatctttt  31260
tcaggagcta agttatgaac aaatgtactc cttaaaacac taggaggaaa gagtataaag  31320
atgacctagg gaacaatact gagtgtggaa actgattcta gatggaagat gaaggcatcc  31380
gattaattaa gtaacaggtt gtaagaactg catcgtccca aaaacgttgt ggaacatagg  31440
actgaatgag aagtgtgcga gcagttttaa tgagatacct attctttctc tctactaccc  31500
tataatgttg aggagtatac agacatagga taatattttg agaagtcata aactattgaa  31560
actaagagaa tacatatttt aaggcattat cactacgaaa agcgaataaa aacaccaagc  31620
ggagttttaa tttcagcata aaaactctag aatattgaaa acaactcaaa acgatctttc  31680
atttggaaaa tccaaataca tcttgagtaa tcattaatga aactaacaaa atccaaatct  31740
taaggttgtg actctactaa gaccccatat atcataatga actaaagaca aaacagactc  31800
tacacgactc ttagcacgac gtgaaaatgt agctcgaata tatttcccaa gttgacacga  31860
atcacaatct aatgtggaca aaccagacac catcttctga agcttggata aactcggatg  31920
tcctaaacgt ttgtgaatta ggtctagagg atctgtagtt ggacatgttg tagagggatt  31980
gagtgagtta agatagtcaa ggtcttgtga ttcacgccat gtgccaatcg tctgtaccgt  32040
actgcggtcc tgcatagtaa aagaatcatc aataaaatat atatcacaat ggaattcacg  32100
agtcaaatga ctaacagatg cgagattaaa ggacaaccgg ggacataaaa aatagaatct  32160
aaagtgacag aggacatgtg attagcttgt ccaactcctt ttgcttttgt ttagacttca  32220
tttgctaaag tatcattggg aagagattgt gaataaacaa ttatttgaca aaagtgacat  32280
```

attaccactg gggtatcaag ttgcttagtc atactaagaa tgtttgggag agggtggtgg 32340
aagtgagggt aaggaggaca gtgtctctat ccgagaacca gttcggattc atgcatgatc 32400
gttcaactgc ggaagctatc cgtcttatta ggaggctggt ggaacagtac aaggatagga 32460
agaaggattt gcacatgatg tttacctaga gtaagcgtat gacaaggtcc ctaaggaggt 32520
tccttggaga tgtcagaagg ttaaaggtgt tccggtagca tatactaggg tgatgaagga 32580
catgtatgat ggagctaaga ctcgggttag gacaatggaa agagactcta agcattgttt 32640
ggttgttatg gggttacagt aaggatctac gctcaaaccg ttcttatttg ccttggcgat 32700
ggacgcatta acgtaccata ttcagggaga tgtgccatgg tgtatgttat tcgcggatga 32760
tatagttctg attgatgaga cgcgaggcgg tgttaacgag aggttggggg tttggagaca 32820
gacccttgaa tttaaaggtt tcaagttgag caggactaag acagaatact tggaatgtaa 32880
gttcagcgac gtgacggagg aagctgacat ggacgcgagg cttgattcat aagtcatccc 32940
caagagagga agtttcaagt atcttgagtc agttatacag ggagaagatg ggagattga 33000 caaggatgtc acgcaccgta ttaagggcgg ggtggatgaa atggaggtta gcattcggta 33060
tcttttgtca caagaatgtg ccaccaaaac ttaaaggtaa gttctataga gcggtggtta 33120
gaccaaccat gttgtatggg gcagagtgtt ggccagtcaa gaattctcat atctagaaga 33180
tgaaagtagc agaaatgaga atgttgagac ggatatgcgg gcatactacg ttggaagatt 33240
aagaatgaaa atatttgggt gaaggtgggc gtggccccat ggaagttgtg cccaccatta 33300
aagactgcta tctgaaaact aattctttgg gcccaaacat tctggcccaa agtacctcgt 33360
gaataataat attgagctca tgtctgacat gttggaagag gagttactag caaacactta 33420
tacacctatg ttggtaacac aattgaagaa ctacgaaaaa cactcttctg caaaggaaaa 33480
tgagaagaag aagaagaaga agacgaagaa gaaggatgat gcaatgatca ttgaagaaaa 33540
aggagagcag gaggacccat ctaaacttac aaagtctaga ggaagaggag gacccagagt 33600
ttgatgcttc cctctgggta caccaaaaca tcgtcaaact taggcaagga gtttggggta 33660
aacattcagg ggtgtgagaa ggaagctttg gagcttttcg taaaattaca actagaggca 33720
taaaaaaaaa aaaggcaatc caggcatgga ggtgacaacc ttcgaaaaga aagggattca 33780
aagaactgaa agggctggat ttttggagta acttcaagag taatagaaca agaagtaggg 33840
ggttgcatta ttatcaaaga tcaatgaaga ttaacattga agaagtggga aatccaaaaa 33900
gactccaccg agaaggatga tgcaatgatc attgaagaaa aaggagagca tgagaaaaaa 33960
cccgtagaaa ttgacagcac tcacacacaa taagacgaga taataaagta gtgagttggc 34020
caattgaaga agctttacct cttaacttac aaagtctaga ggaagaggag gacccagagt 34080
ttgatgcttc cctctgggta caccaaaaca tcgtcaaact taggcaagga gtttggggta 34140
aactttcagg ggtgtgagaa ggatgttttg gagcttttca taaaattata acaagaggca 34200
tgggaaaaaa aaggaaatcc aggcatgcag gtgacaaaac cttccaaaag aaagggactg 34260
gaagaactga aagggctgga tttttggcgt aacttcaaga gtaataggac aagaagtacg 34320
ggattgcatt attatcaaag atcaatgaag attaacattg tatcatggaa tgtcaggggg 34380
ttaaatcgac atagaaaaag aatgttgatt aggagtttaa ttcataggtg gaaagcagat 34440
gttttctgtt tccaagattc aaaattaaaa ggggacatta gggagtttat aagagaacta 34500
tgggcaaata ggtggtttaa atatgcacag ttggaggcta gtgggcctag agggggtatt 34560
attgtcttat gggatagtaa aattggggag ggggagatca gcagcctgag ctcctattct 34620

```
gttacttgta aatttatagg taaaactcag gagtatactt ggaatttatc cactgtatac  34680
gctccaaatg atagggagga aaggaaagaa gtatggtggg aattagcagg tgccagggga  34740
atttttatgg accttgggta atttctgggg atttcaatac tgtgaggtac ccaccagaga  34800
aaaagaatta cagcaaaatc actagagcaa taaatgaatt ctcataattt attgaagata  34860
tggaactggt ggatctacaa cttgcaggag gaagttacac ttggaggaca ggagatagac  34920
atgtgataac agctagactg gataggttct tggtttttat ggattggaat gagagcatca  34980
gaaacaccaa gcaatcagtt ctccattgaa ttacctctga ccattcccct gtgatgcttc  35040
aatgtggtaa ccggtaccct gtcaaatcct attacaagtt tgagaattgg tggctggaaa  35100
cagagggctt caaagaaagg attaaagtct ggtggagctc ttttgcttgt gaaggaagac  35160
gtgactttat tctggctttc aaacttaaag catcgaagga aaaaattgaa gaaatggagt  35220
aaatctattc aaggaaactt ggagatgcag aaattgagta ttcttagtca acttgcagaa  35280
ctagaagaga cacatgatca aaggagcctt actgaagaag aaatacacac taaatatgca  35340
gtctatggag tttggggaga ttgcaaaaca tgaggaggtg gcttggagac aaagatctag  35400
ggctctttgg ttgaaagaag ggacaaaaac atcaattttt tcctcaaaat tgcaagtgca  35460
cataggaaat acaataacat agaccaactg ttacttgaag gaaaatttgt ggcgaatcca  35520
acatacataa caaataatat tggtacattt tatcaaaaac tatatataaa gattgctaga  35580
ggacaatctt atgttgcaaa gtcttttcga agcttaggaa atttgggata gtgtcaggca  35640
tgtgaaaggg ataaagcacc tggacctgag aactgggagg tgataaacac ggatatgata  35700
gctgcagttc tttgttcatg gaatgtttga ggaaagcttt aatgttacct ttgtggtatt  35760
gattcctaag aagatggaag ctaaggaata gaaggacttt aggcctatta tgataggcaa  35820
tgtgtacaag atcttgatag aaagacttaa gaaattggtg aacaagttgg tgaagggtca  35880
acggatgact tttattaaag gtagacagat aatggatgtt gttctaattg ccaaatgaat  35940
gtgtagatgc aagaacaaag gcgagaaacc tacaatacta tgcaaactag atattgagaa  36000
ggcatatgac catctaaatt ggaactttct attggaatcg ctgatgagga tgggctttgg  36060
tgtaagatgg gtcagctgga tcaaattctg catcagcaca atgaaattct caattttgat  36120
aaatgtttca ccagtaggtt tcttcccttc tcagagggat ttgagacagg gtgatccact  36180
atctcctttt attattcatt agtgctatgg gaggcttaaa tgatatgtta aagactactc  36240
aagataacaa ctgcatacgg ggttttaagg tgaagtccag ggcagacagt actattgaga  36300
tttttcatct tcgatatgca gatgacgcac ttatgttctg tgaggttgac aatgaacaat  36360
tgaaagtgct gaaggtgatc ttcattctgt ttgaagccac atctgtatta caaattaact  36420
ggaatgaaag ctttatctat ctagttaatg aggtaactaa gatccacttt ttggttggaa  36480
tcctagaagg taaaattggg gaattgccta cagttatttg gggatgccat gggggccaag  36540
agcaatttta aggggatttg gactagggtc gtagagatat gtgaaaaaat tttaacaaac  36600
tggaagagtt agtatttatc cttaagggac aaactaatac taatcaattc tatacttgat  36660
gattttccta cttacatgat gttcctcttc tcaatccatg tgaatgttgt gaagagaata  36720
tataccctta gaaggaactt cctatgggga ggaaactatg acaaggaaag atctatttgg  36780
tcaaatggaa gtctctcaca gtcagcaaga agtaagagtg ttttggaatc aagaattgga  36840
gaattcagaa ccaaagtttg atgatgaagt ggctatggag atttactaca gaagaacatt  36900
gtttgtggaa agaggtgatc atggagaagt atggcataga agataaacgg ataacaaagt  36960
ctgtaaatag atcttatgga gttagtcgat ggaaatccat cagggaccta tagcttcagc  37020
```

```
tcttgaataa gtccaaattc tgaataggaa atggattgaa aatatctttt tggaaggata  37080
attggctaac caaggaactt tgaaacaact ctttcttgac atttacattc caaatcaaca  37140
gcataaagca ataatagtag aattatgggc taatcaaggt tggaatctca catacagaag  37200
actatcaaaa gacccggaga ttggcaggtc aacagagttc aaaggcactt tggaacaatt  37260
taaagaggtc tatacttcta tagactattt gacttggcaa gggaagttta ttgttaattc  37320
agcctataag gaattcaact tctcagctaa ctggattggt tgttggccat agaagttgat  37380
ttggaaagtt aaaattcctt atagagttgc ttgtttctct tggcttttgg ctaaagaggc  37440
agttctgacg catgataatc taaccaagag agattaccat ttatgttcaa gatgttattt  37500
atgtgaagag caggcagaga caaccaatcc actttttttt gcattgtaag ttcactgcag  37560
ttatggagga ttttcattag tttaaagggt atcatgtggg ctatgcgtag aagtataacct  37620
gaagttctag catactggaa aaaagaaaga aatctttcca attataaaaa gagatggagg  37680
attatcctag cttgcatctg gtggaccatt tgggaagaaa gaaatcaaag atgcttcaaa  37740
gataaatcag tcatattcag ataattaaaa tgaagtggct agtcttgttt tatttttggt  37800
gttaagtgtt agatagttat gtattatgta taagttgtct agtcccacat tggaacggga  37860
gtaatatgta ctatgtagag tatagctata aataggactt cttgtacttt attgtagaga  37920
atatattaat aatatatttt tcccgtgttg tctcacatgg tatcagagaa accgtgagat  37980
atcagtcgtt gtgaaaaata ccagcggctt cgggaagaaa aaaatcaatc aactgctagg  38040
tatattagtc ttcggcgacc gatccattaa atttctctgg caaagaacca ctcatgggcc  38100
ctcacgcgcc caccgaaaga aatatttccg gcgaggttcc aatttcatgc gcccgcgcgt  38160
gaggcagttt ccggtcaaat tttgacaaag gtcctttttg acagtttgtt caccctgtaa  38220
ttcccagtct atccatcatt tttttattt cgatcacttc gcaatttctc gggcagctac  38280
agtgattttt ccggcagaag cggtgtttcc tttgcctgct tcagcgagat acagttgatt  38340
atttctatta tttgtttcta gacctctctc caatccaacg atgtctttgg aatttgatgt  38400
atttggttct gaaaacacga gttctagaaa gtcaagcttc atgattactt tagagccatt  38460
aatggggagt tcaaactatt tagcttgggt ttcctctgtt gaattgtggt gtaaaggtca  38520
aggtgttcga gatcacttaa tcaaaaaggc tagtgagggc tgtgaaaagg tcaatttaag  38580
cagtttatga cgtctgtata ccactcagca gaataggata gcaaagaaag aatatgcaca  38640
tcattgagac tgctcgcaca cttctcattg agtctcacgt tctgctacat tttctgagcg  38700
atgcagttct aacggcttgt tatttgatta atcggatgcc tttatcttcc atccagaatc  38760
agattctgca gttagtattg ttttctcagt caccccttata ctttttttcgt cctcgtgctt  38820
ttgggagcat gtgtttgttc ataacttagc tcccgaaaaa aataagttag ctcctcgtgc  38880
tctcaagtgt gtcttccttg gatattcccg agtttaaaag tgatattgtt gctactcacc  38940
tgatcgtagg taccttatgt cagttgatgt tgcatttttt gagtctagac cttactttac  39000
ctcttctgac caccttgata tatatatgag gtcttaccta taccgactct tgaggggttt  39060
actatagctc ctcctctaca tactgagcca cagaaatctt actcatacct accattgggg  39120
aatctagtgt tgctcctcct agatccccag ctacaggaac acttttaact tatcgtcgtc  39180
gtccgcgccc agcatcatgt ccagctgatt cacgttctgc acctgctcct actgcggact  39240
agtctcatcc taatctacca attgcacttc ggaaaggtat atagtccaca cttaatccta  39300
atccatatta tgtcggtttg agttatcatc gtgtcatcac ctcattatgc ttttataact  39360
```

```
tctttgtcca ctgtttcaat tcataagttt acaggtgaag cactgtcaca tccaggatgg  39420
caacatgcta tgattgacga gatgtctgct ttacatacga gtagtacttg tgaacttgtt  39480
cctcttcctt caggcaaatc tactgttggt tatcgttggg tttatgccgt caaagttggt  39540
ccagatgacc agattgccaa agggtatagt caaatatttg ggcttggtt acagtgatat  39600
tttctctccc gtggctaaaa taccatcagt tcatctcttt atatccatgg ttgttgttcg  39660
tcattggcat ctctatcagt ttgacattaa gaatgttttt cttcacagtg agattgagga  39720
tgaagtttat atgaattaac cacctaattt tgttgcttag ggggagtcta gtggctttgt  39780
atgttggttg cctcagacgc tctatggtct aaagtaatct cctcgagcct tgtttagtaa  39840
gttgagcaca gttattcggg aatttggcca actcgtagtg aagcttatca ctttgtgctt  39900
tattggcatt ttacttcaaa tctctgtatt tatttggtgg tttatgttga cgatattgtt  39960
attaccggca atgaacagga tggtattact gagttgaagc aacatctctt tcagcacttt  40020
tagactaagg atctgagtag attgaagtat tttttaggta ttgtgattgc tcagtctagc  40080
ttaggttttg ttatttcaca ttggaagtag aaaaacttca atcatttttc tttatttgaa  40140
aggaagaaaa aaaaggtaat atctagacct aaatattaat ctgaagacaa gtgaggcttg  40200
ctcagttggt aaaagcacct ccacctacga tcgttaggtc ctgggttcga gtcaccatgg  40260
aggggaagtg tggaaacact atagatcctc ctaatttggg agggggaaaa aaatattaat  40320
ctgaattgac atgaatctca atgacaatga ccaacgattt cctgcaattc ttttcagtat  40380
ggaatgaata aaaaatcaag ctacaagtct ctattaaacg aaatgcacta acagggatca  40440
ctctcaagaa aggaagtggt tttggttgtt gttattccag gttggataaa tcactttctt  40500
tataaatatc ataaaagaca agggctttct tgcttcagca catgtgggaa atgccggggg  40560
gcttggctgg taccaagctc gagcggtctt tctatctttt tggattgcat gcccaaggca  40620
atgctttttg tagattggga tggattgatc ttcgcagaag tatgctttag acattcttga  40680
ggagacagga atgacggatt gtagacccat tgacacacct atggatccaa atgccacact  40740
tctaccagga tagggggagc ctcttagtga tcctgcaaga tataggcggc tggttggcaa  40800
gttgaattac ctcacagtaa ctagacctta tatatccttt cctgtgagtg ttgtaagtca  40860
gtttatggac tctccttgtg atagtcattg ggatgtggtt ttccgaattc ttcgatataa  40920
aatcagctcc aagcaaagaa ctgttgttcg aggatcgagg cccatgagca gatgttgatt  40980
gggcacgatc accttctaat agacattcta tatctggata ttgtatgtta ataggagtta  41040
atttggtgtc ttggaagatc aagacgtaaa atgtagttga tcggtctagt gcggaagcaa  41100
ataatcgagc aattgttatg gtaacacgtg agctagtttg gatcaaacaa ctgctcaaag  41160
aattgaaatt tggagaaatt gatggaacca gtgtgtaata atcaagcagc tcttcatatt  41220
gcgtcaaatc cggtgttcca tgacagaatt aaacacattg agattgactc tcactttgcc  41280
ggagaaaaga tactctcagg agataccgtt acaaagattg tgaagtcgaa tgatcagctt  41340
agagatattt ttaccaagtc ccttgctggt cctcgtatta gttatatttg tagcaaactc  41400
ggtatatatg atttatatgc accaacttaa gggagagtgt gagatagtta tgtacaacaa  41460
aatacccggt ataatcccac aagtggggta tggagggtag tgtatacgta gagcttaccc  41520
ttaccctgtg aaggtagaga agctgtttcc aaataccctc ggctccagta caaatgaaaa  41580
ggagcagtag caacaagcag taacaacaat gatatagtaa aataactgaa gaaagaaata  41640
acatgtagac atataactcc actaacaaac atgcaaggtt aatactattg ccacgagaat  41700
ggcaaaggaa tgttagatag ttatgtatta tatgtatatt aatagtctag tctcacgttg  41760
```

gaataggagt aatatgtact atgtagagta tagctataac taggacttct tgtaatatat 41820
tgcatagaga tatcaataat atatttttcc tgtgctttct cacgtaaagg aatgtaatgt 41880
acttagaaga tcatgaatct atctttgatg ttttagacac ctcgtgagaa cacaaaggtt 41940
taggaacttt attgtgttct ttgtaattat gggtgactgc caatatgtta ccttttcata 42000
aaaatgatta tttggccatt ggattagttt caacagcctc tctgcccctc cgggtagggg 42060
taaggtctgc gtacatatta ccctctccag accccacttg tgggattata ctgggttgtt 42120
gttgttgttg ttgtggatta gtttcaacaa ttttgatagt tcttttattt gaatcaaact 42180
actcattcac atggattttg tatcgtatca ttgagttaaa aaaattggtt ttgctaattt 42240
atcctcatgt ataacaacta cctatttttc aatatattgg attcaggagc ttgtagtagc 42300
tggagtttgc tcttcaaagg gcaataagtg ccgggtatca tgcacagtga ctccaaatac 42360
agatctcctt tctgctctaa ctcttatgga gaaacatgat ctaagtcagc tacctgttat 42420
actaggggac gtggaggatg aaggcatcca tcctgtgggc attttggaca gagaatgcat 42480
caatgtagct tgcaggtttt tgacattcaa cttttacttc aaagatataa tgctttctgg 42540
aaccattgat gataaaatat gcaagaaact tgtgcagaag tcgcacttta ctatcgatta 42600
ccagataaag ttacttatca agaagtcaaa tatattgaac atatttctct aaaacacttt 42660
gactggactg taagcagaaa cttactaaag taggtcgtaa gaaatggttt gatagggaaa 42720
tcaccatcta cacttaaaag agttgtgtga atttgaattc ttaaagcatg tgaaagttat 42780
aaaaacttgt tattatctaa gcatctgaag cattttggcc atccaaagga tcaaaaatag 42840
gaaataattt catttgtaca atgaactccc tgcacaaatt ctcacactag gtgtattctc 42900
tattcatcac tagcactaca tgtgtcacta cgaatcatat acaataaatc tttgtaacat 42960
aaaagacgac acataatatg gaagtaagcc gagtatacaa gggaagtttc atcattacgg 43020
tgagcttttt ataagataat caagttttac tggaaaaggg caaaaactct cccgtataga 43080
agtataccaa aaagtagaat accttacaaa aatatgattt tctatgaaca acaccctatc 43140
ttctatactt gtagggatct catcggggca ccaaaaagag ataaagggat aagaggcttt 43200
tcctcaaatg tacaaaatcc ttctctattc cttcaaaagc tctcctattt ctctctctgc 43260
acactgtcca cataagttca atggagcaac atccacgccc tgtgtcttct tttccgtctt 43320
ctataggtcc agctgaacat ggcttctttg actgagtgtg gcatcaacgt tgaagaccaa 43380
accatcccag tacttccaac cacaaacgag acactatatg acaatttaga agaagatgat 43440
tcacatcttc tcccgaacat ttacacataa aacaccagct gatacatgta atcttcctct 43500
tcctcaaatt atcagccgtc aggatcaccc gtctcgtagc taactaggtg aagaagcaca 43560
cctttctcga aaacctcagg atccatacag agagatatgg aaaagctgat tcctccatgc 43620
ccagaagctt ctcataataa gacttaacaa agaaacacca ctacttcccc cccccccaa 43680
aaaaaaaaaa tctccataca tcgactttca tgtgtaattc ttgttcgtga aacgacccaa 43740
tcaacctttg gcacaaatct cccagtcttg cgagttcctc ctaaacttca aatcacaatg 43800
aacttctcca ccttgtagcc tccgtgtccc ttggactggc aactcctttg gcatgaaact 43860
ttgtacatat taggagatgt gatactcaaa gtgttgttcc tgcaccaatt gtaccccccaa 43920
aaaacttacc atgctcccat cacctaacat tgaatgatac gttccaaaat cttcgcactc 43980
cttcaagaaa cttttccgta ggccccaccc ataagggagt gtgatttttt ttgctctcca 44040
tcccctctcc aagaatccat tccctaaacc actgcaggac actttaacaa tcactatgtc 44100

```
acttttttcta ctagttctac attgagtgat atcttgatgt cattgaaatg cctctggaaa  44160

atcttcttct catctaaaag aacacttgtt tgccttttga atccccctct aacattttct  44220

atgtttcatt catctttggt ggaacagagc attagcaact agagaacagc tttgctag    44278
```

<210> SEQ ID NO 4
<211> LENGTH: 36700
<212> TYPE: DNA
<213> ORGANISM: Nicotiana tabacum
<220> FEATURE:
<223> OTHER INFORMATION: DNA sequence of NtCLCe from Nicotiana tabacum; sequence originating from the ancestor N. tomentosiformis; one start codon

<400> SEQUENCE: 4

```
atgaatcacg aaagttgttg ggtcgtcatc caaattgctg gccttgggct cgacgaccat     60

ctcttcctcc gggacgttcc tgtgacggaa acattgaaaa agaacaagat atgtgcgaca    120

gcagcaaaga cgatagtgat agtgatagtg gtatccagat aggatctctg ctcgaggaag    180

ttatcccaca aggcaataat accgctataa tctcggcttg ctttgttggc ctcttcaccg    240

gtatcagtgt cgtgcttttc aacgctgcgg taagtgcgct ataggtcttt catttctctt    300

ttcatctact attctccctt acttacttgg cctcagtcaa tcagccccct gcctacttta    360

aattattgta caatttatca gaggagtatc ctatacatca aattcacata acttagtaaa    420

atatgctgac attctgaatt ttaaccttac cagcttagaa catccaggct agttcagaaa    480

cagataatct aaattggcct catttataag tcattttgtt aatcaagaca tacaatttgg    540

ctcttgataa aagattatgc agcgcccgat gataacctaa tatttatcag caacccatat    600

gtcactttct tttgtttaaa tgctctccca tgtaatttaa caatattgtc accatacaaa    660

agagaactga agtgaatgtt ccatttgtgg tcatataacg gatatctccc ttggttaggt    720

tcatgaaata cgtgatcttt gttgggatgg aattccatat cgagctgcct cagaggagcc    780

cattggagta cattggcaac gtgtaatctt agtaccagct tgtggcggtt tggtagtcag    840

ctttttgaat gccttccgag ccactctgga ggtttcaact gaagaaagtt ggacatcatc    900

tgttaaatct gtgttggggc cagttttgaa gacaatggcc gcttgtgtca cattaggaac    960

tgggaattcc ttaggaccag aaggccctag tgttgaaatt ggtacatctg ttgccaaggg   1020

agttggagct ctgcttgata aaggtggtcg tagaaagctg tcactcaagg ctgctggatc   1080

agctgctgga atcgcttctg gtttgttccc catattattc ttggttctga accatacatg   1140

gtacattttc cttataatta catgtagcct gttgtatgct ttcctctttc ctgggaagcc   1200

tttctgtaaa tgcaaatgtg tttgcactca aaccaataaa ctgtaaaaac agtgaacccc   1260

ttgagcaagc aaaagcacta gaaaaccaac aaatagatcc cccccccaag ataccagtga   1320

aatgacaccg ggtgacccaa aaataaagca gcttacatct tgactttgag aggaactgca   1380

atcagctata agtaggttat taatttccag tgcctgcatt ctgcccaagt actatgatat   1440

atttctgaag ctttgtttcc ccagttcctt tttcagacgt ttgctgtcaa taaagttgag   1500

ccagccaact tggttcccac aagctactaa ttttgtccaa gcttactcta tgggagaagt   1560

taaatttccc aaattccttg agcagaaaat gaaaaatgaa ctcaaagtgt catattaggc   1620

aactatctaa agaaaaatac ttaattgaag tttagataag aaaagtgaat atatattgat   1680

gtagtctccg ttaggtgaga agcgcatcac ttacccagca acatatggac ctaaaattta   1740

ctagtgaact tttcacattg tatcaaaagc tcaacaaaca gaaagatgac tagtcctaaa   1800

atgttatttc acatcaacct tatcatacgt gcattatttg ttctctatat ttctatttca   1860
```

```
tccgatataa ccaatcgtca ttgtaaattc tataatgcct gtggttactt ttgtctttag   1920
tgacaaatga catttaggct aaccatgtag ttattgactg atttcgcttg acgtctcttc   1980
caattatgta gtagtagagt gttgagatat ggatatgtta ccttctaaaa aaaaagagtg   2040
ttgagatgcg gatggtttgc tagctggctt ttgtctccct tcaagttgaa ttagcaaaag   2100
caatgtctca taagttggat agctagacaa gaaaaactcc aaattacttt atgtagagta   2160
ttcttaagct tgagtcgcga gttggaaatt ggaattatgt aaaaaaacct ggaattattt   2220
ggttgagcct gctttttatt tttgtcaata tttccagtat ctaacccaac atgtttagag   2280
caattcccag agagcctcaa tacgaggcat ttgcagagtc tttatgagag tccaggaagg   2340
ggcacacact gtagaggtat agtgttgtcc ttattttttt tttttgata aggtaagatt   2400
ttattaaaag gtaccaagat ggtgcaaaat tacaaacatc caaactaata caacaaagca   2460
actacattcc tcctagctcc tctagaaaat tcatatattg ttccatattt ttcattacat   2520
gtcttttaca ccagaaatac aagtttaata agcatctgtt tttaatcctg gatacatgct   2580
gcctttcccc ttcaaagcaa atcctgtttc tttccaacca tattgtccag aacacacata   2640
gaggaattgt tcttcatact atctgttgac tctttgccac tttttgttgt tgccatgtct   2700
ccaacaaact ttacactggc aggcattgcc cacttgacat catatatatt taggaagagc   2760
taccaacact gctttgccac tttgaaatgg atgattagat ggttgactgt ttctgcctct   2820
tcttcacaca tgtaacaccg gttacataga gcaaaacctc tcttctgcaa gttctcctga   2880
gttagaaaag cttcctttgc tccaatccaa ccaaaacggg ctactttaat aagtgctttt   2940
gacttccata ttgctttcca tggccaattt gactgataaa gcccttgtag tttttgtaac   3000
aagctataac aactgctgac tgtgaaaata ccatcattac ttgctgccca gattaatgag   3060
tctctcctgt tttcctccaa tctaacatta ttcaataact gcatcaattg ggaaaattca   3120
tcaacttccc agtcattgag gcccctcttg aagattagct gccagccggt gcttgaatag   3180
aagtctaaca ctcttccatt tttgttaata gagcagctat atagaccagg aaactttgat   3240
ctaagacttc cattttccaa ccacatatca gaccaaaaca gggtattatt accatttcca   3300
agtttcagtt tcacaaactg actatattta ttccaaagat tactaattgt gctccaaact   3360
ccccctttttg aagaagattg aattgaacga ggagcccaca tgtccttcat accatacttg   3420
gcatctatca cctttttcca taatctattc ccatcataat tatatctcca tagccattta   3480
aataaaagac ttttgttatg catctttaga ttcctcactc ctaatccccc tctttctttt   3540
tttttcatca cctcttgcca tttgaccaag tgaaatttct tgttatcatt attaccttcc   3600
cacaaaaatt tattcctcat agtattcaat tttttctcca ctgatgttgg cattttaacg   3660
agagatatta gataagtagg tataccatcc atcacactat tgaccagtgt aagcctacca   3720
ccaagagata aatattgtct tttccatgac accagtttac tgctacatct atccaagacc   3780
ccctgccaca tctttgcatc attctttttt gctccaagtg gtaggcccag ataggtggat   3840
ggtagctgct ccactttaca acccaaaaca tctgccagat catcaataca atgctcggca   3900
ttaatactaa acacattact ctttgccaag ttcactttca atcccgagac agcttcaaaa   3960
gctagtagta ctcctatgag gtgtaagagt tgctcttttt cagcttcaca taatatcaat   4020
gtatcatcag catagagtat gtgtgagaaa tacagttctt ccccctctct ttttctaatt   4080
ttcaatcctc taatccaccc taacttttct gcttttaaaa gcattctgct aaagatttcc   4140
atcaccaaca aaaataaata gggggatatt ggatccccct gtcttaaccc cctctgagaa   4200
```

-continued

```
ttaaagtatc tatgtggact cccattaatt aaaactgaga agctaattga ggatatgcag   4260
aattttatcc acccaatcca tctttcccca aaattcgtat gtttcatcag atttaacaga   4320
catgaccaat ttacatgatc ataagccttt tccacgtcaa gtttgcaggc caccccttta   4380
atcttcctct tgaatagata ttcaagacac tcattagcta ccatagcagc atcaataaat   4440
tgccttcctc ttacaaaggc attctgatta tctaatatca attttcctat caccatcttt   4500
aatctttcag ctatcgactt tgcaattatt ttatagacac tgcccaacaa gctgataggt   4560
ctaaaatctt tcacttccgc tgcccccttt ttcttaggaa taagagcaat gaaaattgag   4620
tttaggctct tagtcttgtc cttattttca gggttgaact agttctttag aagtttccta   4680
ggcttcctaa tttccaaagt tctgccaggt ccttttctag tgaagtactt gaagtttaat   4740
aaatcaaatt ttaatttcta acatatcccg agaaattcat tcacaaattc aactggtgac   4800
ttctgatgca gaaacataag caactgctta tgggttcata tgttcctgca attttattgt   4860
tgacatggat tggcttcata tggttttgtt cctgcaattt tatcgctgac actaatcctt   4920
tcatatggtt ttatgtgggg tggtaaatag aggttaagag acaagaagag gctggaaaag   4980
gtgggcagtt catttgttag tagactactc tatttactaa gagatatgat gtcccataca   5040
ttactcgaat tggctccaaa tacagattcc acttctttgt cgagtttcct tattgtacag   5100
agttcgactc gtcaagggaa attcacttcc tttgactgaa taatgctagt ttgagtagta   5160
ccttaaatta aatggaccat ttaattctat ctacttgata gaatagactg gtcatcaact   5220
agttgcaaat ataatgacaa ctccgccatg tttgcagagt cacctgatga agaagtacct   5280
caattagtag accatttctt gaatgttcta cagtattctc tatgcctaca tgaccacatc   5340
acttttcctt ttgcgttgtg agaacttgaa cttggtgagc gggggttccc caggaatggc   5400
atcttggtgg cagatgacca ttctgtcctt atcttagcta atgcttcttg gattgcctca   5460
ctagatttat tataccttta ataaatgttt gccattgttc tgccataata gagggatgta   5520
cctagctggt gcttcacatc acatagtcca aaactaatga aatgctttac aattgtcgag   5580
tactaaagga tgatttgtgg aatcagatct caaacaattt attttgagga agaaaaatac   5640
caaaggtttt ttctgtttgt tggaagatta aaaatccttt aaaaggtaaa gatttatgaa   5700
cttaattcag catttttgtg gccattgctg aaaaagagaa aacaatggca cttattcgag   5760
tttgcttatc caaaaaaaaa gaagaagaga atgtcacgta atgcaatttc atcttaggaa   5820
actttgcagg agaaaagcaa gagtgataaa acagaactat ttgttttttt gataagttgt   5880
tgtgacctat ttctttgtca ttcttatttg ctaataagct aatgtaccct gtactatggt   5940
tgttttgact taatccgggg atgttcagtg agcattttct tgttttttct gctgtcagca   6000
tctgctgcct tacaggaatt cattttctgg aaatttactt cttgttctgc taacattttc   6060
ctgttatatc ttgtcagtca ttttctctcc atggttatac tgtttgtgtc actttgaaac   6120
tctccttgtt ttctacttta aaggatttaa tgctgctgtc gggggctgtt tctttgctgt   6180
ggaatctgtg ttatggccat cacctgcaga gtcctccttg tacttgacaa atacgacttc   6240
aatggttatt ctcagtgctg ttatagcttc tgtagtctca gaaattggtc ttggctctga   6300
acctgcattt gcagttccag gatatgattt ccgtacacct actggtaatt ttggacttct   6360
ttctcgagtt tgattcttaa atacaattgt acccgtcact tacagcaaca acaactacat   6420
ttcaacagct agttggggtt ggctacacag atcatcacta tccatttcaa tttctttagt   6480
cccatttctt tcgaatattc agtactttgg gattctctat tatcagaggt tctctttatt   6540
ttctactttg acgtacaaat ctctaaatag attaaagaag actcctagag acactggcct   6600
```

aatgcaaatg taccaccatg aataaacctt aatctgaaat agctggtatc gtatataaga 6660
acctttagct ttaattgtgt tctatattga tcttttggga caacttccgt ccaataatat 6720
tatgtcttac ttatacagtt atacttatcc ttaaacttta ctctttagag tggttatccg 6780
tagttcaagc ttttgttggc accatagcta gtttggttct tagtaaaaag ttactcttta 6840
gagtggtaac tttttgtcaa ttttcttagt gaaaatataa cctctgtgac aaatctacca 6900
agtataaatc caatatggtt ctgtgtcata cttgtagttt atccaagtct atgctccatc 6960
actcttacaa aggctcatcg tatgactaat ttttttgag aaaggtaaca gtttgtattg 7020
ataataagat cagcgccagg ttagtcatta gtgctaatag ctgtatgtac aactccaaaa 7080
gagcaaaaga caagcacctg gtgtaacgta aattacaagc tgcctataaa atctatcagg 7140
tctcctacct cactaaacat ttcttgttta caccaaaaaa ataaaacaag gaaagacaat 7200
ccatcttaat cttctgaatg gagtttcttt tgccttcaaa catctcgagt tcctttcgtt 7260
ccatgcaatc caccatatac aagctgggat gcttttccat ttgtctttat ccatttttc 7320
taccaattcc cttccaattg actagaagtt ccaatgtggt tctagatatg acccaattaa 7380
ctcccaacat ataaaagaac atgttccacg gatttgtagt gattctgcaa tgtaggaaca 7440
agtgagcatt actttctact tcctgtccac aaagaaaaca tcttgagcaa atctggaaac 7500
ctcttctttg taagttatca tgtgttaaac atgctttttt accactaacc agacaaaaca 7560
tgatactttg ggaggagttt taaccctcca aatgtgtttc caaggccaca cctcagtcat 7620
tgaaacatta tgatttagag tccagtatgc atcttttact gaaaatgcac ctttgctatt 7680
cagcttccaa actattttat ctatggtctt gttagtttac agctatgtat atagtgtagt 7740
cttgtcccac attggaatag gagtagtatg tccttgtata gtatagctat aaataaggac 7800
ctcttgtatt gtattgaaca tccaatatca ataacatatt ttctcccgtg ctttctcaca 7860
tggtatcaga gcaattgtga gagatttatc gctgcgcata aattccagcg actccgggaa 7920
gagaaatcag tcaccggaag tctttttccg acgactcttt caaggttgtt tgcgtttgct 7980
ttataaatcc aacactacca caagagtaat cactgtccgg cgaccaaacc ccagtaaaaa 8040
tctccggcag cagcctcctc acgccaccag aagctcacgc gccggcgcgt acgaccactt 8100
ccgtccattt tttgaaaaac ttccttcaga acagttgggt cgcctggtaa ttcctatcct 8160
acccctactg ttttcatttc attccgacca ctttgagttt tttccggctg ctacagtact 8220
attccggcag ctatagtact attccgacaa ctacagtaag attccggctg ctacagtatt 8280
tcattattct gtttttgtgt ttccttactc tgtttcagtg gattacaatt gattctttct 8340
cttatttggt aataatttgc aacaatgtct atgggatttg atgtttttgg gtctagaaac 8400
atgagttctg gaagctctag tgttattatt acctcagaac cttaaatggg aggttcaaac 8460
tacttagctt gggcttcatc tgtcgagttg tggtgtagag gccaaggtgt tcaagatcat 8520
ctaatcaaac cgtctagcga aggagatgaa aaggcaataa cactttggac aaaaatcgat 8580
gctcagttat gtagcatctt gtggcgatct attgattcca agttgatgcc cttgtttcgt 8640
ccattcctga catgttattt ggtttgggca aaggcacaca ccttatacac taatgacata 8700
tctcgcttct atgatgtgat atcgcggatg acaaactgaa agaagcaaga attagatatg 8760
tctacttact tgggtcaagt acaagcaatc atgggggaat ttgagaagtt gatgccagtt 8820
tctgctagtg ttgaaaaaca acaagagcag cgacaaaaga tgtttctcgc tcttaccctc 8880
gctgaacttc ctaatgatct tgattcagta cgcgaccata ttttagctag tccgactgtc 8940

-continued

```
ccgacagttg atgaattatt ctctcgatta ctccgccttg ctgtagcacc aagtcaccca   9000
gtgatctcat cacagatact tgattcctct gttcttgcat cccagacaat ggatgttcgg   9060
gcatctcaaa ctatggagca tagacgagga ggaggtcgtt ttggaagatc tagacccaag   9120
tgttcttatt gtcacaaact tggacacact cgtgaaatgt gttattcctt acatggtcgt   9180
ccacccaaaa atgcttacat tgctcagacc gagactccag gtaaccaggg attttcttta   9240
tctaaagaag aatataatga actccttcag tatcgaacaa gtaagcagac atctccacaa   9300
gtagcctcag ttgcttagac tgatacttct tttactggta atttttttgc ttgtgtttcc   9360
cagtctagca ctcttggccc atgggtcatg gactcaggcg cttctgatca catctctggt   9420
aatatatcac ttttgttaaa tattgtatat tcatagtctc ttcccattgt tactttagcc   9480
aatggatgtc aaattacggc aaaaggagtt ggacaagcta atcccttgtc ttctatcacc   9540
ctagattctg ttctttatgt ccctggctgt ctttttcgtc ttgcatctgt tagtcgtttg   9600
actcgtgccc tccattgtgg tatatatttt attgacgatt cttttattat gcaggactgc   9660
agtacgggac agacaattgg tggaggacgt gaatcagaag gcctttacta ccttaactca   9720
cccagtcctt ccacaacatg tctggttaca gatcctccag atctaatcca cagacgttta   9780
ggacatccga gtttatccaa acttcagaag atggtgccta gtttatctag tttgtctaca   9840
ttagattgtg agtcgtgtca gcttgggaaa catacccgag cctccttttc gcgtagtgtt   9900
gagagtcttg catagtctgc cttctcctta gttcattctg atatatgggg tcctagtaga   9960
gtaagttcaa ccttgggatt tcgttatttt gttagtttca ttgatgatta ttcaagatgt  10020
acttggcttt tcttaatgaa agaccgttct gagttatttt ctatattcca gagtttctgt  10080
gctgaaatga aaaaccaatt tggtgtttct attcgcattt ttcgcagtga taatgcctta  10140
gaatatttat cttttcaatt tcagcagttt atgacttctc aaggaattat tcatcagaca  10200
tcttgtcctt ataccccctca acaaaatggg gttgctgaga gaaagaatag gcaccttatt  10260
gagattgctc gcacacttct aattgaatct cgtgttccgt tgcgtttttg gggcgatgca  10320
gtgctcacaa cttgttattt gattaatcgg atgccttcat ctcccatcaa ggatcagatt  10380
ccacattcag tattgtttcc ccagtcaccc ttatactctc ttccaccccg tatttttgga  10440
agcacgtgtt ttgttcataa cttagcccct gggaaagata agttagctct tcgtgctctc  10500
aagtgtgtct tccttggtta ttctcgtgtt cagaagggat atcgttatta ttctccagat  10560
cttcgtaggt accttatgtc agctgacgtc acattttttg agtctaaacc tttctttact  10620
tttgctgacc accatgatat atctgaggtc ttacctatac cgacctttga ggagtttact  10680
atagctcctc ctccaccttc gaccacagag gtttcatcca taccagccgt tgaggagtct  10740
agtgttgttc ctcgtagttc cccagccaca ggaacaccac tcttgactta tcatcatcgt  10800
tcgcgcccta catcgggccc aactggttct cgtcctgcac ctgacccttc tcctgctgcg  10860
gaccctgctc ctagtacact gattgcactt cggaaaggta tacgaaccat acttaaccct  10920
aatcctcatt atgtcggttt gagttatcat cgtctgtcat ttccccatta tgcttttata  10980
tcttctttga actcggtttc catccctaag tctacaggtg aaacgttgtc tcacccagga  11040
tggcgacagg ctatgagtga cgagatgtct gctttacata caagtggtac ttgggagctt  11100
gttcctcttc cctcaggtaa atctactgtt ggttgtcgtt gggtttatgc agtcaaagtt  11160
ggtcccgatg gccagattga tcgacttaag gcccgtcttg ttgccaaagg atatactcag  11220
atatttgggc tcgattacag tgataccttc tctcccgtgg ctaaagtggc ttcagtccgt  11280
ctttttctat ccatggctgc ggttcgtcat tggcccctct atcagctgaa cactaagaat  11340
```

```
gcctttttc acggtgatct tgaggatgag gtttatatag agcaaccacc tggttttgtt  11400
gctcaggagg gggtctcgtg gccttgtatg tcgcttgcgt cggtcacttt atggtctaaa  11460
gcagtctcct agagcctggt ttggtaagtt cagcacggtt atccaggagt ttggcatgac  11520
tcgtagtgaa gctgatcact ctgtgtttta tcggcaccct gttgacattc cgatggatcc  11580
gaattctaaa cttatgccag gacaggggga gccgcttagc gatcctgcaa gctataggcg  11640
gctggttgga aaattaaatt atctcacagt gactagaccc gatatttctt atcctgtaag  11700
tgttgtgagt cgatttatga attctccctg tgatagtcat tgggttgcag ttgtccgcat  11760
tattcggtat ataaaatcgg ctccaggcaa agggttactg tttgaggatc aaggtcatga  11820
gcagatcgtt ggatactcag atgctgattg ggcaggatca ccttctgata gacgttctac  11880
gtctggatgt tgtgttttag taggaggcaa tttggtgtct tggaagagca agaaacagaa  11940
tgtagttgct cggtctagtg cagaagcaga atatcgagca atggctatgg caacatatga  12000
gctagtctcg accaaacaat tgctcaagga gttgaaattt ggtgaaatca atcggatgga  12060
acttgtgtgc gataatcaag ctgcccttca tattgcatca aatccggtgt tccatgagag  12120
aactaaacac attgagattg attgtcactt cgtcagagaa aagatacttt caggagagat  12180
tgctacaaag tttgtgaggt cgaatgatca acttgcagat attttcacca agtctctcac  12240
tggtcctcgt attggttata tatgtaacaa gctcggtaca tatgatttgt atgcaccggc  12300
ttgagggga gtgttagttt acagctatgt atatagtgta gtcttgtctc acattggaat  12360
aggagtagta tgtccttgta tagtatagct ataaataaga cagtactaac gtccctttg  12420
ccgggggttc tgcatcttta aatagatgca cgtggttcca tagcagaccg tgttgatcac  12480
agatcgtgct gcatcctctt cccagcggac tcggtgagcc cctcttgtat tgtattgaac  12540
atccaatatc aataacatat tttctctcgt gctttctcac aggtctgtga tgtacccttg  12600
aaaggttcaa gagtttggag gaagatagaa actctgttta tctcccaatc atccaaagat  12660
cttctaaagt tccagttcca tccttgtgag ctccagactg acttaccaat gcttggcttt  12720
gaagacttag agagaataag tcaggaaaaa tctttcaacc ttccttgccc tatccggtga  12780
tcttcccaaa aagatgtctt caacccattg ccaacattga tcctgatatt gctactgaaa  12840
gatttctttt ggtggcagga ttactctcat taacaatgta cttgacaatc tccatacata  12900
cgaatgtctc tttaccctct tgccattaag gttgtaaaga gacttgtcaa attaagaaga  12960
ggtttcctat ggaactgttt caaggaagga acctcctttc ctttggtcaa gtggagttaa  13020
gtcatataat ctaggaagtg gagacttggg tataaaatag ctgcaactac agaaaaggag  13080
catcttattt aaatgatcac gcaaatgtgc ccaaaacttt aaatatctgc ggagcatatg  13140
gttgtagcaa aatttgaatc ttccggtcaa tgttgctcat gtccagtgaa taccctgat  13200
ggtgaaagtg tcctgaaggg aagcaggaac ttattggagg aattggcatt taacactcag  13260
catttcgtta ggtcatagcc cgctgaaaat tgagtgccca gatttatata gttttgctct  13320
aaactgacga tgcagttgca caacatacga caaactaagg tgggacatct tcttcggaag  13380
gaattttgag gattaagaga tagagtggtt gattcagttg caaatgaagc ttcaagggtt  13440
caatatcatc caggagacac cggattctga tagataaaac aacagaaaga tgaacactac  13500
tttgttaggc ttgttacaag ttgctatcgt ctttcttatc tcggcacaca atttagattt  13560
gggaacttat ttggaaaata gagtggttgt ttttgtgaat agcatcagac aaagcttctg  13620
agctggtacg acagaaaact caacagggag aataaaagac tgtggttcac gatttctgca  13680
```

```
tgcatcttgt aggttatttg gtgggtaaaa tatttaatgt tttgaaggga aggtagaaca  13740
tgttcatagg cttagattca aatgtttgta tttttttggc tctttggtga gagatgctga  13800
atgtaaatga cataggcagc tgactataat ttctcagctc cttgcttttt aaattggcag  13860
gcactgatat gtacatgtga acatccaaca cttttgtggt gccgttccga tgaataaagc  13920
acattaatca cttactgatc aggagtaata gtttaggagt tctagaattt ttgtacataa  13980
aatgaaccaa aaagaatatc ggaatgagaa catgtttctt tttttgtttc ttctttttcg  14040
tacaaatttc aataacactt ctgatagaat agctaggtcc atttgaattc ctttggagac  14100
ccttacacaa ccaatgaatg gcaagtatag cattttctaa caccctccca catgtataat  14160
ccagtttttta gggtttagat gtggatttga tttgacctta ttgccttttt ttgtttttgt  14220
tctttttgaa gtagagagtg aggaggctca caacgacggg ctacgtagag cgagattaat  14280
tcggctcaac gggctaatga ttggacttac atgctacaac aatgttagga gaaagagaga  14340
gagagagaga gaagcccaga gcagttccac gagttaagaa agagaagtcc aaagcgattg  14400
aatatgaaga gagaaagcgg ttgtgctaac aggctccctc aagtttggct ctgagcatcc  14460
aactcaaaac cttaaggcaa tgagtagagt agcccaggac catttaaact cctgttgaaa  14520
accttacaca accaataagg gaacaagtgt aacattctct tacaacccta ccgtcttata  14580
agtcagggct ctaatttagc ataaaatcaa agtgaggcga tctactatga aatgaagaaa  14640
ataactgata aatataaaga atgttaattc tcccatatag cctgaatgtt cccagaacaa  14700
aataaattag tctcatgatt tatcattaac atgatgttcc tcttattttg agtgattagg  14760
aaggttaatc aaggagtaaa ttctttctaa tttgtatcgt ctagaattat ttgtctaaca  14820
aattttcaga ttaccggtga tcaaaagagg aaaatatttt gcatacaacg ttaccatacc  14880
ttacaaaagg gcgatgaaca ttttttttatt ttattattgt ccttttttttc aattaggggt  14940
tatgcagtct tcctccacgt gatattactc ttagaatcac gtttttgtca ttgctattac  15000
ttactgtggt aagtacaaat gtgttttgaa ctctttttgg tatgtattat tgagttaatt  15060
tttcgtttcc atttcagagc tgccgcttta tcttctgctg ggcatctttt gtggcttagt  15120
ttcagtggca ttatcaagtt gtacatcatt tatgctgcaa atagtggaaa atattcaaat  15180
gaccagcggc atgccaaaag cagcttttcc tgtcctgggc ggtcttctgg ttgggctggt  15240
agctttagca tatcctgaaa tcctttacca gggttttgag aatgttaata ttctgctaga  15300
atctcgccca ctagtgaaag gcctctccgc tgatctgttg ctccagcttg tagctgtcaa  15360
aatagtaaca acttcattat gccgagcctc tggattggtt ggaggctact atgcgccatc  15420
tctattcatc ggtgctgcta ctggaactgc atatgggaaa attgttagct acattatctc  15480
tcatgctgat ccaatctttc atctttccat cttggaagtt gcatccccac aagcttatgg  15540
cctggtatga atttgtcttt tgttagaagt agcattacat atctggataa gtgagttttt  15600
tattattgaa aagtaataac aggagaacaa gagaatatat cacccaaatc tacttctttc  15660
ctctcttcta ttcttctgaa attcaaggtc ctttaactcc tccacagtct gtctagttat  15720
tgatcctgta gacttaattc acataggttt aggacattcg agtttatcca aacttcatga  15780
aaaggtttct aattttttta cattacatta tgagtcgtgt ctacttgaga aacatatcac  15840
tccatgtttc tatagtctgt tttctcctta gtttattctg atatgtgggg tcctattaag  15900
tcagttcaac cttgtatttt cattattttt gcagtatcat tgataattat tcaagatgta  15960
cttggatttt ctttacaaga gatagttctc agttgttttt tgtgttccta agtttttatg  16020
ctgcaataca aaattggttt gatgtctcta tttgcatttt tcccaatgat aatgccttag  16080
```

aatattttct tttccgtttc agtagcttat tatttcttta ggaactcttt atcagaaatc 16140
tcaactgaga tagatgagag gaagaataag catatcattg gtctcattca gtcccctgtc 16200
aagcttagtt tcttgagcga tgcggtttca cgtcctttta ttagattaat tggatgcctc 16260
atctgctatc caaaatcagt taactttcga tattgtttcc tcgcttacct ttatactctc 16320
tttccctcga gtctttggga gcacatgttt tgttcaataa catagctcct ggaaagtgac 16380
cagcgcaacc gacaaacaag gccttcttaa tgtagaaggt ggacatatgc tattctagcc 16440
acgggaaaga aagtaatatt gtaatcaaac ccaaatatct gagtataacc tttggcaatg 16500
gcgatcaatt tgattatatg gaccaacttt gcctgcatat acccaccgac aaccaataat 16560
agatttaccg ggaggtagag aaacaagctc ccaaatacca ctaatatgta aagcagatat 16620
atctctgatc atagcttgtc cttgtggaca tagggataga aattaaggac aaagatgaca 16680
caaaagcata atgcggtgat gataaacgat gataactcaa atcaatataa tggggatggg 16740
gattgagagt ggatcgaata tctttgcgga atgcgattgg tagactagga ggagagaagt 16800
ctgtggacat gatgttggac tgagatcaat aataagtcaa gaatggtgga gctacagaac 16860
atggaactgg agctgtaggt gacataatcg gagctgtagg aggtggagct atagaggaag 16920
gtgaaggaga gatagcgact gaatctccaa aagatgaaac cggtaatacc tcaaaaaatg 16980
tctaagagat catttggacc tatgaagtat gattgcgttt ttaaaaaggt aacatcataa 17040
ggtcaggtga ataacattga tatccccgtt gcatcctcga gtaacttaga aatatacatt 17100
tgagagcacg gagagctaac ttatcttttc tggagcaagg ttgtaaacaa aacacgtgct 17160
cccaaagaca cgaggtggaa gagagaaagg tgagtgggga aacaagacag aggatgaaac 17220
ttgactcttg atagttgaag atgacataca attaataaga caataggatg tgagatccaa 17280
tgacagttct catgaactgc tgaaatggag aagacaaata ctctggggcg ttatcactac 17340
gaaatgtgca gttagaaacc ccaaattgat tttggatttc agtgtggaag gtctaaaaaa 17400
tagagaacaa ctcagattga tttttcatca agaatatcca agtggacttg gaataatcat 17460
caatgaaact gacaaagtag cggaattcca aggtagaact aacccgacaa ggaccccaaa 17520
catctgaatg gactaaagtg aaaggtaact ctacccgatt atcaggatgt cgagggaaat 17580
gagagtgagt atgccttctg agcggatatg actcacgctc tagagtggac aagtgagaca 17640
aacgaggtac tattttctaa agttctgata aattgggatg tcctaactgt atatgtaata 17700
aatctggtgg atcagtaaaa ggacaagctg taggggggaaa aaaataccaa atatttccag 17760
aagatggcaa actacaacag aagatgcaac tgcattaaca tgctcaggat aggtgatgaa 17820
atcattgagg acaaagagtt gatcaagaag gagattctgg aattttacca gaacttatat 17880
agtgaaaatg aaccctggag gcgcagtgca aatttcgaag acatctcctc actaagcata 17940
gaagagaaga actggttgga agctccattt gtagaaatag aggtgcttga agctttgaaa 18000
tcatgtgccc cttataaagc accaggtcca gaaggcttca ctatggattt ctttcagaaa 18060
aattgggata ctcttaaaac agacatcatg gctgcactta atcattttca ccagagctgt 18120
cacatggtta gggcttgcaa tgccaccttc attgccctaa ttccaaagaa aaatggtgct 18180
atggagctca gagactacag acctattagc ttgacaggta ttgtatacaa attggtttca 18240
aagattttag cagagaggct caagaaggta attgacaaac tagtctcggg ggaacaaaat 18300
gctttcatca agaacaggca gatcactgat gcttccttga ttgccaatga agtgctggat 18360
tggagaatga aaagtggaga accaggcgtg ttgtgcaaac tggacattaa aaaggctttt 18420

-continued gatcaattaa gctggtctta cctcatgagt atcttgaggc agatgggctt tggggagaaa 18480
tggagaagat ggataaacta ttgcatttca actgtcaagt actctgtttt ggtgaatagg 18540
gacccaatcg gtttttctc cccccaaaag ggcctaaggc agggggatcc cctctccccc 18600
ttcctattca ttctggcgat ggaaggactc actaaaatgt tggagaaggc taagcaactg 18660
caatggatac aaggctttca ggtgggaagg aatcctgcca gctcagttac agtatctcat 18720
ctactctttg cggatgatac tcttattttc tgtggtactg agagatcaca agcacgaaat 18780
ctcaacctga cactgatgat cttcgaggca ctatcaggac tccacatcaa tatgataaag 18840
agcatcatat accctgtgaa tgcagtcccc aacatacaag agctagcaga catcctatgc 18900
cgcaaaacag acactttccc aaccacatat cttggacttc ccttgggagc taaattcaaa 18960
tcaaaagaag tttggaatgg agtcctagag aagtttgaaa agaggcttgc gacttggcaa 19020
atgcaatacc tccccatggg tggcaggtta actttaatca atagtgtact ggacagtctt 19080
cccacatacc acatatcttt gttcccaatt ccaatctcag tcctaaagca gatggacaaa 19140
ctcagaagga agttcttatg ggaaggatgc agcaaaacac acaaatttcc actagtgaaa 19200
tggctgaagg taactcaacc aaaattcaaa ggagtcttgg gaatcaggga tgctatgctc 19260
ttaaaatggc tctggagata tggacaggag gaatctaggc tatggaagga catcatattt 19320
gctaaatatg gagcacacaa ccactggtgt tccaagaaaa caaactctcc ttatggagtt 19380
ggtctgtgga agaacatcag caaccactgg gatgaattct tccaaaatgt aactttcaaa 19440
gttgggaatg taactcgtat aagttttgga aggatagatg gcttggaaat acacctttga 19500
aagacatgtt tcccagtatg tatcagattg ccgtgaccaa agactccact gttgctcata 19560
atagaaacaa tgacacttgg tacccacttt tcagaagaaa tttgcaggat tgggaggtca 19620
acaacctact cacaatgtta agctccctag aatgtcataa cattgaagat caacaacctg 19680
acaaacttat ttgggaaaat tctaagagag gcaagtacac agtcaaagaa tgatacattc 19740
acctctgtga ccagaatcca atatataact ggccatggaa acatatctgg agaactaaag 19800
tgcctaccaa gatgacttgc ttcacatgat tgtctctaaa tggggcctgt ctcactcaag 19860
acaacttaat caagaggaac atcatataag ttaatagatg ctacatgtgc caacaacagt 19920
cagaaagtgt aaagcactta ttccttcact gctcagttgc aaaagaaatt tggaacttct 19980
tctacactac ctttggtcta aaatgggtta tgccacaatc aactaagcaa gcttttgaaa 20040
gttggtattt ttggagagtt gataaatcca ttagaaaaat ctggaaaatg gtgtcggccg 20100
caagtttttg gtgtatttgg aaagaaagga actgaagatg ttttgatggc atatcaactc 20160
cactcaaggc tgcgtgttta gttaacttat tttgctggaa ctatctcacc cctgttaata 20220
gtgctgatac ttctgtggat ttcattagcc ccctgatagt agcataggct tttgtaaatg 20280
gagctaatta tcctttctct tttgtactct ttgcatcttc ttgatgcctt ttaatgaatc 20340
taatttactt catcaaaaag aaaatgacaa gttgttgaag gaggaaaaga tgtgagtcca 20400
tgtgatttag caaggataag gtactaaagt ccatttgatt cacgtccggt accaatgatc 20460
cgtctcgtgc tgcattcctg tattaaaaca gagtcatcaa gaaataaaat agagcaaata 20520
agtgattggc caagcgacta gtggatatga gattaaaagg actatgggga acataaaaaa 20580
ctgaattcaa aggtaaggaa ggaagtggac tagcttaacc tattctagtt gccatggttt 20640
gagaatcgtt ggccattgtg actattggaa gtgattgaga gtaagaaata gtagtgaaag 20700
gagatttgtt acccgaaata taattagatg cacctgaatc aatgacccaa aagtcggaag 20760
aagaggaaac acaagtcacg ctattacctg tttgaacaat agagattagt ttggatcaaa 20820
tagttgtata gagaactgaa atttggagaa atcaatcata tagaacttgt atgtgattat 20880
tgttgccctt tatattgcgt caaatcctaa aacacattga gattaactgc cacttatcac 20940
agaaaagata ttctctagag acattgttac aatttcatga agtcaagtaa ttagcttgaa 21000
catatcttca gcaagtccct cgtcagtcct catattagtt acatttgtaa caatgtcggt 21060
acataagact tataagcacc agtttgagga ggagtggtag agagttgatg tacatagtta 21120
aagtagatat acttacactt agtgttatgt aaagagtgga tataaaaagg gatcagcata 21180
agacaattgt cttcgcgcgt cttaacattt ttttcctgtc tttatttctc tcatggtatc 21240
agataaccta tctctatctt ggtttaccca atggttggcc cccatattgt attagccatg 21300
ctccagttga ctaggcttgg acgggcagag gtgttaaatt atcccatatt ggttgaaaga 21360
atgagctatt gtctccttat atggtcttag acaattctcc aactcatgag atattttgtt 21420
ttggctgagt tagccctaag gtttattttt tgtcatattc tttaacctta tggcaatgct 21480
tgtacacgga aaaaccggag tgcaagactt aaattaggag aaggaaacta ttgaaggtga 21540
ggaacttaaa gggttgtgag aatacacggg agaaaaaaat cttaatacta tctagtggcc 21600
ttgtatatca aatgatcagc ttgcaaatat tttcaccaag tccctcactg gtcctcgtat 21660
tagttacata tgtaacaagt tcggtatata tgatttgtat gcaccggctt gaggttatgc 21720
atattctatt cctcctacta tatatgtgac taggaaatat tttactccta ctgcatatgg 21780
gactaggact atttacacat aactatctaa cattcccctc aagccagtgc acacaagtca 21840
tatgtaccga gcttgttaca tatgtaacta atacgaggac cagtgaggga tttagtaaaa 21900
atatctgcaa gctggtcatt cgacatacaa ggccactaga ctccccccga gcaacaaaac 21960
caggtggttg ctgataaaca gaaactggcc gaaaagttgc cggaaaaatt tgaaaatagt 22020
gagactaagc cgaattctac actacaaaat aggttctaaa acaccaccag aaaacaaaaa 22080
cttttctaga aattactctt cacaccggaa aaaataaaag ttgtcagaat ttgatgtaat 22140
ttatatagat aggttcggaa tcactggagg agtaagttgt cccgaagaag ttttgtcaaa 22200
aagtggccgg aatggctcac atgcgccgga aaacttactg tagctcgcag gaaccctagt 22260
tctggcggtg cgtggaggcg cgtgacttaa gattaagatg cttacaggac tatcttgaga 22320
aatatacata ttatatagac gcttgagttg cttcccaatc ctaaatagaa gcttttattc 22380
gtaggcaaga agggaagcag ctttacttga gccaatagct ttcaaggtgc acgttgtcac 22440
accaaggaca tccagaattt gattttatag ggggtgtgag aaagcacggg agaaaatatg 22500
ttattgatat ttggataata aatacaatac aagaggtccc tatttatagc tatacactac 22560
aaggagatat tactcctctt ccaatgtggg acaagaatac actatacata tctgtaaact 22620
aacactcccc ctcaagtcgg tgcatacaca tcatatgtac cgatcttgtt acacatgtag 22680
ctaatacgag aaccaataag agacttagtg aaaatatctg ctagttgatc attcgacttt 22740
acaaactttg taacaatatc tcctgaaagt attttttctc tgacaaagtg acagtcgatc 22800
tcaatgtgtt tagtcctctc atggaacacc ggatttgaca caatatgaag agtagcttgg 22860
ttatcacaca ttagttccat cttgctgatt tctccgaatt ttaactcctt gagcaactgc 22920
ttgacccaaa ataactcaca cgtcgtcata gccatggccc gatattcggc ttcggcgcta 22980
gatcgagcaa ctacattctg tttcttgctc ttccacgaga ccaaattacc tcctactaga 23040
acacaatatc cagacataga acgtctatca aaaggtgatc ttgcccaatc agcatctgtg 23100
tacccaacaa tctgctcgtg gccttgatcc tcgaatagta atcctttgcc cggagctgac 23160

```
tttatatacc gaagaatgcg aacaactgca tcccagtgac tatcacaggg agaatccata  23220
aactgactta caacactcac cggaaaagaa atgtcaggtc tagtcactgt gaggtaattc  23280
aatttgccaa ccaacctcct atatctcgta gggtctctaa gaggctcccc ctgtccaggc  23340
agaagcttag cattcagatc cataggagag tcaataggtc tgcaacccat cattccagtc  23400
tcctcaagaa tgtctaagac atacttccgc tgtgaaataa caatacctga gctagactga  23460
gcgacctcaa tacctaaaaa atacttcaat ctgcccagat ccttagtctg gaagtgctga  23520
aagagatgtt gcttcagatt agtaatacca tcctgatcat tgccagtaat aacaatatca  23580
tcaacataaa tcactagata aatacacaga ttaggagcag aatgccgata aaacacagag  23640
tgatcagcct cactacgagt cataccgaac tcctgaataa ttgtgctgaa cttaccaaac  23700
caagctcgag ggactgtttt caaaccatat agtgacctgc gcaatctgca cacacaacca  23760
ttaaactccc ctaagcaaca aaaccaggtg gttgctccat ataaacttct tcctcaagat  23820
cactgtggag aaaagcattc ttaatgtcta actgataaag aggccaatga cgtacaacag  23880
ccatggacaa aaagagacga acagatgcta ctttagccac gggagagaac atatcactat  23940
aatcaagccc aaaaatctga gtatatcctt ttgcaacaag acgagcctta aaccgatcaa  24000
cctggccatc cggaccgact ttgactgcat aaacccaacg acaaccaaca gtagacttac  24060
ctgcaggaag aggaacaagc tcccaagtgc aactcgcatg taaagcagac atctcgtcaa  24120
tcatagcatg tcgccatcct ggatgagata gtgcctcacc tgtagactta gggatagaaa  24180
cagtggacaa agaagatata aaagcataat gaggtgacga cagacgatga taacttaaac  24240
cgacatagtg gggattagga ttaagtgtgg atcatacacc tttgcggagt gcaattggtt  24300
gactaagagg agacaagtcc gcagtaggtg cagaatctga tgcggggcgt gaatcacctg  24360
ggcctgatgc tggatatgga cgacgatgat aagtcaagag tggtggagct gccgaaggtt  24420
gaactggatt atgtggagga actggagcta taggtggtgg agctacaact ggagctgtag  24480
gtggtggaac tagagtaact gaatctccaa aagatgaaac tggtagtacc tcagaaatat  24540
ctaagtgatg acctgaacct gtgaagtatg attgggtttc aaagaaggta acatcagcag  24600
acataaggta ctgctggagg ttaggagagt agcatcgata ccccttttgt gttctcgaga  24660
aacctagaaa tacgcactta agagcacgag gagctaactt atccgttcct ggaataaggt  24720
tatgcacaaa acaagtgctt ccaaagatac gaggtggaag agagaacaaa ggtaagtggt  24780
aaaacatgac agagaatgga acttggttct ggatagctga tgatgtcata cgattaataa  24840
gatagcaaga tgtaagaact gtatccccca aaaacgcaac ggagcatgag attgtatgag  24900
tagggtacga gcagtttcaa taaaatgtct attctttctt tcagctaccc cattttgttg  24960
agatgtgtac agacaagatg tttgatgaat aatcccatga gatttcataa actgctgaaa  25020
tggggaagac aaatactctc gggcattatc actacgaaat gtgcgaatag aaaccccaaa  25080
ttgattttga atttcagcgt ggaaggtctg gaaaatagaa aacagctcag atcgattttt  25140
tatcaaaaat atccaagtgc acctggaata atcatcaatg aaactgacaa aatagcagaa  25200
tcccaaggtg gaactgaccc gactaggacc ccaaacatct gaatggacta aagtaaaagg  25260
tgactctgct cgattatcaa gacgcctaag gaaatgggag cgagtatgct taccgagctg  25320
acatgactca cactctagag ctgacaagtg agataaacca gataccattt tctgaagttt  25380
tgacaaactg ggatgtccca accgtttatg taataaatct ggtgaatcag taacaggaca  25440
tattgtagat ggaagacaag atgcgagtcc atgtatttag caaggataag gtaataaagt  25500
ccgtttgatt cacgcccggt accaatgatc cgccccgtac tgcgttcttg tataaaaaca  25560
```

tggtcatcaa gaaataaaat aacgcattta agtgatttgg ctaagcgact aacaactatg 25620
agattaaaag gactattgcg aacataaagg actgaatcta aaggtaagga agaaagtggg 25680
cttgcttgac ctattgcagt tgccatggtt tgagacccat tggctattgt gacttttgga 25740
aaagattgag aatacgaaat agtagtgaaa agagatttgt taccagaaat atgatctgat 25800
gcacctgaat caatgaccca agactcagag gatgaagatt gggaaaaaca agtcacgcta 25860
ttacctgttt gaacaacaga agctatctca gaagatgtct gcttacatgc tttgtactaa 25920
aggaactcaa tataatctgc taaagaaacc atccgactat tcaaagcatc ggttcccatg 25980
tcgctacaat ttgtagtagt agggttaact tgaaatagtg gaaataagta actccggtga 26040
gaaaactgaa gaaatagctt gaaaacactg tttacaacag taaaaacaga acactgttct 26100
gcgccggaat ctactgtagc tgacggaaaa actcaaagta gtcggaatga aacgaaaaac 26160
agtaggggta ggatcggaat taccaggcga cccaactatt ctgaaggaag tttttcaaaa 26220
aatggccgga agtggtcgta cgtgtcggcg cgtgagctca cgcgcgtgag cttctggtgg 26280
cgcgtggagg cgcgtgagga ggctgctgcc ggagattttc actggggttt ggtcgccgga 26340
cagtgactac tcttgtggta gtgttggatt ttgcacaaca ctgacggaga taaagcagac 26400
gcaaacagcc ttgaaaaagt cgccggaaaa gacttccggt gactgatttc tcttcctgga 26460
atcgctggaa tttatgcaca gcgataaatc tctcacaatt gctctgatac catgtgagaa 26520
agcatgggag aaaatatgtt attgatattt ggataataaa tacaatacaa gaggtcccta 26580
tttatagcta tacactacaa ggagatatta cttctcttcc aatgtgggac aaaaatacac 26640
tatacatatc tgtaaactaa caaggggaat atcgtttaaa gataaaaaag atagcgtgca 26700
gaagattgca tacattagag atgcaaaata cagaataccc atactcccag ataatgcagt 26760
atgccttttg catgacccac tggttgaatg gaagcacctg gtcaatttac taggtgtgtt 26820
agtgattttt gctgcttcct tcccctttct aaactacata ctatctaaaa tgttaggggg 26880
acagaagccc agtcaatctg actaggtgat gttagtggtt tccgcttctt tctcccactt 26940
ctaaatgcgt actttctcaa atttaggagc atagaaactt aagcagctgc ctacctgagg 27000
aggtgcatgg gaacataaga gaatagactt tacctgtcat attttccata ccttagttaa 27060
ttacagtgtt atcctgataa tgatctgttt tctgtatcta ggctgaatcg agattcaatc 27120
gcttttggct gaaaggatgc tgctacagat ccttagttta catcattgtg gttcttattc 27180
tataagtact tcccctatca actacttcct tcttttttct taggttattt gcctcttagg 27240
ttgtttgcaa ggaaaggaac aatagatgtt ttgatggaat agcaactcca aaccacttcc 27300
ttaaggctaa tatactgttt ggccaagctt cttcaaagtc caaagccctt ttttgtcttc 27360
aaaaaagtat cttttttttcc caaagttgag gtgtttggcc aaacttttgg aaggaaaaaa 27420
aagtgctttt gagtaaagca gaagctcttg agaagtagaa aaagtagttt tttcccggaa 27480
gcattttttt gaaaagcact tttgagaaaa ataaacttag aaacactttt taaaagtttg 27540
gccaaacact aattgctgct taaaagtgtt tttcagattt attagccaaa cacaaactgc 27600
ttctcaccaa aagtactttt ttgaaaaata cttttttgaa aagtgatttt caaacaaagc 27660
acttttcaaa ataagtttat tttagaagct tgtcaaccgg ctataaatgt cttttatttt 27720
tacagctaga gtaccctaac acctgtaaat tcccctagac atttttttcg actttgttag 27780
ctcattaacc ctagtatagg actctttgtt ttggagctag caaactcttt tgttttccta 27840
tttttgcatc ttcttggtgc catttataat atctcttact tcaccaaaaa aaataagttc 27900

-continued

```
ccaaaatatg actaccttga gttggccaaa gcataaccaa agcttgggca caccagtgtt  27960
tgcgtgaatt ttatggatgt tccttacctt tatccttctg tgcttatgta gcatctgtct  28020
tggttaatct tttctgaagt ctatagtgta tttctgtgtt gcaacatgag tttactgtca  28080
atcttactgt ttgacctcaa ttttgggttc tttttgattt tgaaagacat cgtttaacag  28140
gttggcatgg ctgctactct tgctggtgtc tgtcaggtgc ctctcactgc tgttttgctt  28200
ctctttgaac tgacacagaa ttatcggata gttctgcccc tcttgggagc tgtggggttg  28260
tcttcttggg ttacatctgg acaaacaagg aaaagtgtag tgaaggatag agaaagacta  28320
aaagatgcaa gagcccacat gatgcagcga caaggaactt ctttctccaa catttctagt  28380
ttaacttatt cttcaggtgt gaaaccttca cagaaagaga gtaacctatg caaacttgag  28440
agttccctct gtctttatga atctgatgat gaagaaaatg atttggcaag gacaattcta  28500
gtttcacagg caatgagaac acgatatgtg acagttctaa tgagcacctt gctaacggag  28560
accatatccc tcatgctagc tgagaagcaa tcttgtgcaa taatagttga tgaaaataat  28620
tttctcattg gtctgctgac acttagtgat atccagaatt acagcaagtt gccaagagca  28680
gagggcaatt tccaggaggt agcttcttgg tacatttcaa tattcttaac tgatgaaaaa  28740
ataagggaaa ttgatctagc atgaaattaa gctaattata agttttacac tgtagaactg  28800
gtaaaacagg gttggctgga tatttctttg ttgaattttt aggattatat gtattgtttt  28860
agttttgtag gttgttttct gatgtgcttt ttgacttggc agaatcttaa gatgaaatgg  28920
aaggtgttta accaaaaaat agaattttca gtcaaagcct atatttagaa gaaaacgggt  28980
tattgataac caagttttac tttacttccc caacaatcta tttggtaaat agcaaaagta  29040
atgcgtatgt gagaaagcac gggagaaaat atattattga tattagatat tcaatataat  29100
acaagaggtc ctacacatca tatagctata gtctacaaac tacatattac tctcattcca  29160
atgtgggact acacataact aacactcccc ctcaagccgg tgcatacata tcatatgtac  29220
cgagcttgtt acacatgtaa ctaatacgag aaccagtaag agacttagtg aaaatatctg  29280
ctagttgatc atttgacttt acaaactttg taaaaatatc tcctgaaagt atttttttctc  29340
tgacaaagta acagtcgatc tcaatgtgtt tagtcctctc atggaatagc ggatttgacg  29400
caatatgaag agcagcttgg ttatcacaca ccagttccat cttgctgatt tctccaaact  29460
ttaactcctt gagcaactgc ttgacccaaa ctaactctca cgttgccata gccattgccc  29520
gatattcgac gtcggcgcca gatcgagcaa ctacattctg tttcttgctc ttccacgaga  29580
ccaaattacc tcctactaga acacaatatc caggcgtaga acgtctatca aaaggtgatc  29640
ctgcccaatc agcatttgtg tacccaacaa tttgctcgtg gcctcgatcc tcgagtagta  29700
atcctttgct tggagatgac tttatatacc gaagaatgcg aacaactgca tcccagtgac  29760
tatcacaggg agaatccata aactgactta caacactcac cggaaaagaa atgtcaggtc  29820
tagtcactgt gaggtaattc aatttgccaa ccaacctcct atatctcgta gggtctctaa  29880
gaggctcccc gtgtctaggc agaagcttag cattcggatc cataagagag tcaataggtc  29940
tgtaacccat cattccagtc tcctcaaaaa tgtctaaggc ataattccgc tgtgaaataa  30000
caatacctga gctagactga ggcactgagc aacctcaata cctagaaaat acttcaatct  30060
gcccagatcc ttagtctgga agtgctgaaa gagatgttgc ttcagattag taatatcatc  30120
ctgatcattg ccagtaataa caatatcatc aacataaacc actagataaa tacacagatt  30180
aggagtaaag tgccgataaa acacagagag atcagcctca ctacgagtca tggcgaactc  30240
ctgaataatt atgctgaact taccaaacca agctcgaggg gactgtttca aaccatataa  30300
```

tgacctgcac aatctacaca cacaaccatt aaactccccc tgagcaacaa aaccaggtgg 30360
ttactccata taaacttctt cctcaagatc accgtggaga aaagcattct taatgtctaa 30420
ctgataaaga ggccaatgac gtacaacagc catggacaaa aagagacgaa caaatgctat 30480
tttagccacg ggagagaaag tatcactata atcaagccca aaaatctgag tatatccttt 30540
tgcaacaaga cgagccttaa gccgatcaac ctggccatcc gggccgactt tgaccgcata 30600
aacctaatga caaccaacat tagacttacc tgcaggaaga ggaacaagct cccaagtgcc 30660
actcgcatgt aaagcagaca tctcgtcaat catagcatgt cgccatcctg gatgagatag 30720
tgcctcacct gtagacttag ggatagaaac agtggacaaa gaagatataa aagcataatg 30780
aggtgatgac acacgatgat gacttaaacc gacatagtgg ggattaggat tacgtgtgga 30840
tcgtacgcct ttgcggagtg caattggttg actaagagga gacaagatcg tagtaggtgc 30900
agaatctgat gcagggcgtg aatcacttgg gcatgatgtt ggatgtggac gacgatgata 30960
agtcaagagt ggtggagctg cagaaggttg aactggatta tgtggaggaa ctggaggtgg 31020
agctacaact ggagctgtag gtggtggaac tggagctata agtggtggag ctacaactgg 31080
agctggagat gtagaggaag atgaatgaga gatagtgact gaatctccaa aaaataaaat 31140
tggtagtacc tcagaaatat ctaagtgatg acatgaacct gtgaagtatg attgagtttc 31200
aaagaaggta acatcagcgg acataaggta ccgctgaagg tcaagagagt agcatcgata 31260
ccccttttgt gttctcgagt aacctagaaa tacgcactta agagcacgag gagctaactt 31320
atctgttcct ggagtaaggt tatggacaaa acaagtgatt ccaaagatac agggtggaag 31380
agagaacaaa ggtaagtggg gaaacatgac aaagaatgga acttggtttt ggataactga 31440
agatggcata cgattaataa gatagcaaga tataagaact gcatcccccc aaaaacgaaa 31500
cggagcatga gattgtatga gtagggtacg agcaatttca ataagatgtc tattttttct 31560
ttcagctacc ccattttgtt gagatgtgta cagacaagat gtttgatgaa taatcccatg 31620
agatttcata aactgctgaa atggggaaga caaatactct cgggcattat cactaggaaa 31680
tgtgcgaata gaaaccccaa attgattttg aatttttagc gtggaaggtc tggaaaaata 31740
gaaaacaact cagatcgatt ttttatcaaa aatatccaag tgcaccttga ataatcatca 31800
attattcaat aaaactgaca aagtagcaga atcccaaggt ggaactgacc cgactaggac 31860
cccaaacatt tgagaatgga ctaaagtaaa aggtgactct gcttgattat caagacgccg 31920
agggaaatgg aagcgagtat gcttatcgaa ctgacatgac tcacactcta gagctgacaa 31980
gtgagataaa ccagatacca ttttatgaag ttttgacaaa ttgggatgtc ccgaccgttt 32040
atgtaataaa tttggtgtat tagtaacagg acaagttgtt gaaggaagac aagatgtgag 32100
tccgtgtgat ttagcaagga taaggtaata aagtccgttt gattcacgtc cggtaccaat 32160
aattcgtccc gtactgcgtt cctgtataaa aacatggtca tcaagaaata aaacaacgca 32220
tttaagtgat ttggctaagc gactaatagt tatgagatta aaaggactat tgggaacata 32280
aatgactgaa tataaaggta aggaaggaag tgagcttgct tgacttattg ttgttgccat 32340
tgtttgagac ctattggcca ttgtgactct tgaaagagat tgaaaatacg aaatagtagt 32400
gaaaagagat ttgttaccag aaatatgatc tgatgcacct gaatcaatga cccaaaactc 32460
agatgatgaa gattgggaga aacaagtcac gctattacct gtttaaacaa cagaagctat 32520
cacagaagat gtctgcttac atgctttgta ccgaaggaac tcaatataat ctgctaaaga 32580
aaccatccga ctattcaaag tatcggttcc catgtcgcta caatttgtag taataggatg 32640
gatagactcg gaaaattgta aagttatcgg aatttgtcgt aaccaggatc gagcaagctg 32700
tcttgaagaa atggtttcaa aaaatgtccg gaaaggtcac ttttacgccg gaaaaatata 32760
aaaatggtcg aaatttgatt tgaattagat gggtaggctc ggaattgtga ggagagcaga 32820
ctgtcctgaa gaagcttaat gaaaaaatgg ccggaaagtg gccggaaccc tcgccgtaaa 32880
agttgttacc ggcgcgtgaa ggcgcgtggc attttttctg ccagataaat tttcaggggt 32940
tggtcgtcgg agggtgatcc cttgtggtgg tgttggtttt tgcacaatac cgacaggcct 33000
taggtcaccc gaaaatttgc acgatgacta agttctttct tcccggttaa cgctggaatg 33060
acgcacatcg atcttttctc actaatgcta tgataccatg tgagaaagca cgggagaaaa 33120
tatattattg atattagata ctcaatataa tacaagaggt catatttata gctatagtct 33180
acaaagtaca tattactctc attcaaatgt gggactacac ataactaaca acgtaaatta 33240
acaaagagaa ataaggaatg taacaacagt caatccctaa aatcaaggta gaaaactttg 33300
ataaagcaga gaattataga atgtatttca gtagtacttg gaacttgtcc ttacaaataa 33360
aattctttat ccttatatag gggcgtacaa tcataacatt tttcgcactt aattcgaatt 33420
cattatgagc attaattgta ttgattgccc gttatcatag ataaccataa ctgacgtatt 33480
tgtaactata aatgccttat aacggctctg attccccttc cttatttact tctggtttgt 33540
gtatctttcc ttctttttag cctttattca ttcagttctc gcctcttctt tgacaactgt 33600
caagcccgat cctctgttct gtactgtctc gtgggtgttt cccccgtacc ttccttatat 33660
tcttaattct gttaattgag agtgtcactt gtcactatgc cattgttcca cgcgtcatgt 33720
ttcatccacg tgtaatatct tttttccacc aatacagata atccccccact ttctgaatat 33780
tctcaactga atattcgggt aagtttttat ggcgggaatt ctttgccgtc gtttttcgag 33840
tatcatcgtg tcatcttcag aaccgatgtg acgtacgtca cgtctattta atgcctatgc 33900
caggtggctt ctatcgattg gctctgcagt tttttagcgc tttttagggt ttttcagcgg 33960
ctgcgtcagt cacgaagtga cggttccatt atgacgcttc ataatgacta actttaatga 34020
tggtcgtgtc ttcttattaa tacttcattc ctttttgatc tcttggagtc ttccttcttc 34080
agtatccacc acattacttc tttgtatttc tgcatcttct ctttgatatt cctttggaca 34140
atcatgtctt cttctacacc agacccccgt aaggttgtga ttgttgacga acttgatctt 34200
tctactgctc ctactagaag taggagaggt ggtagacttc gtagtcttgg ttcactatct 34260
aatcgtggtt cttcttccca gggtagtgct gctaagccat cttcttctag acctagggct 34320
cctttaaccc ctagatcttc ttctaggaat agagatttaa atgatccagt gcgcgaacct 34380
acagttgcag agattgttcc tcaagaattt tcttttgtaa ctgaccgtga aaccataagg 34440
aatcaaattt cttctatagc ctccctcaat accgctaacc tttatccaag tttaatcagt 34500
aatggtcttc tctcccgggt tcgaagagaa tattactgaa accagatttc ccaattttag 34560
tccctggtgc caaccagaga attactccat accatgttgg tttttccttt gtttacacct 34620
acccttttac tttagggttc aaaccaccta ttgaaccagt aatcattgaa ttctgtcgtt 34680
atttcaacgt gtgtcttggc cagattgacc acatagtatg gagggctgtt catgccttcg 34740
ttatttatca gatttggttt ccatgccttt cacttttcag cacttgcttc atctctactc 34800
ccctaaattg tttcgtgaag tagtttttac tctcgtggct agaagtaaga gagtgttggt 34860
tagccttgaa gacgattggg accgtggctg gtacgctcgt tttgttgctg ctcccactag 34920
tgcattagtg ggtgaagaaa atatgccttt cccggagaaa tggaactttg cacgtaagct 34980
ttcttctcct cttttttttt gtcttaaaaa aactccatgt aatcatatac ccacttcttc 35040
agcaactatg gaagtttttt atgcttgggt agaaaagatg ttaactgctg cgcctatgga 35100
gaaaagatcc tggaaatact tttctcaaag atttggttgg aaagtgaaga cgcacggtac 35160
tttttacctt cattgttttt ccttttctct tccttgtttg ttcaatgatt tctcatcctt 35220 ccctttttttt ttactagggt ttccgattcg tggtattagt cccgcgtctg ttccatcaac 35280
taggctttcc gtgattcttg ttcaggaaag aattttaagt gcttcttctt caaaaaggaa 35340
aactgacgga gcccgtggct ctgatgacga agaagaaaca gaggagggtt ctttggtgcg 35400
aaggtcacgc gtcaggagac gcgtggtttc tgatgatgaa actactcctt ctcatgaccc 35460
tctatctagt tcaatccctt ttagactcac ggatgagcta gagagtaccc ctttagtgat 35520
ttcttatgat gatgctgttg atccccctcc aagttctgtt gatagattgt ttgctcatgg 35580
cttcgagggt gatgaagttt tgggcctgtt tctgaagaat tgccccttgc ttcccttcca 35640
gtttcagttt tcattaaccc ttccgtgtcc ttacctgatg atactcctgt tgttattctc 35700
gtggctgctt ctactccgtc atctattccc gtgactgctt ctcatgcaga ggccaaacct 35760
tctagcagca gaagggcaat gaaaagagtt gttgttgagg ttcctgaagg tgagaactta 35820
ttaagaaaat ccggtcaagc cgacgtgtag ttgaaaccta tgctcggccc cgtagagaag 35880
aagaagttag aaagccatag ctcactcact ttaatgaatg atatcgttca ttcttccttg 35940
aaagtacaag cttaattata tttcctttct tttctctttc ttattcataa ctcttcctcc 36000
ttttttgcag atcaacttga ttggcacaga gcttatgaaa agagtttctc aggcggaccg 36060
gcaagttata gatttgcgca ccgaggctga taactggaag gaacaattcg aaggtcttca 36120
attggaaaaa gaggttccgg cggaagagaa gaatgctttg gaacaacaga tgagagtgat 36180
tgcctctgaa ttagcagttg aaaaagcttc ctcgagccag gttggaaagg ataagtatat 36240
acttgaatcc tcctttgctg aacaactttc caaggcaact gaagaaataa ggagtttgaa 36300
ggaactcctt aatcaaaaag aggtttatgc gagagaattg gttcaaacac ttactcaagt 36360
tcaggaagat ctccgtgcct ctacttataa gattcagttc ttggaaagtt ctctcgcttc 36420
tttgaagaca gcttacgatg cctctgaagc agaaaaagaa gagctgagag ctgagattta 36480
ccagtgggag aaggattatg agattctcga ggataatcta tcgttggatg taagttgggc 36540
tttcttaaac actcgtctcg agactctagt tgaagccaac catgagggtt ttgaccttaa 36600
tgctgagatt gctaaggcta aagaagcaat tgataaaact cagcaacgtc aaatcttttc 36660
ctcacctgaa gacgaaggtc ccgaaggtga tggagattga 36700

<210> SEQ ID NO 5
<211> LENGTH: 786
<212> TYPE: PRT
<213> ORGANISM: Nicotiana tabacum
<220> FEATURE:
<223> OTHER INFORMATION: Protein sequence of CLC-Nt2 from Nicotiana tabacum, translated from SEQ ID NO:1 of PCT/EP2013/077532

<400> SEQUENCE: 5

Met Glu Glu Pro Thr Arg Leu Val Glu Glu Ala Thr Ile Asn Asn Met
1 5 10 15

Asp Gly Gln Gln Asn Glu Glu Glu Arg Asp Pro Glu Ser Asn Ser Leu
20 25 30

His Gln Pro Leu Leu Lys Arg Asn Arg Thr Leu Ser Ser Ser Pro Phe
35 40 45

Ala Leu Val Gly Ala Lys Val Ser His Ile Glu Ser Leu Asp Tyr Glu
50 55 60

-continued

```
Ile Asn Glu Asn Asp Leu Phe Lys His Asp Trp Arg Arg Arg Ser Arg
65                  70                  75                  80

Val Gln Val Leu Gln Tyr Val Phe Leu Lys Trp Thr Leu Ala Phe Leu
                85                  90                  95

Val Gly Leu Leu Thr Gly Val Thr Ala Thr Leu Ile Asn Leu Ala Ile
            100                 105                 110

Glu Asn Met Ala Gly Tyr Lys Leu Arg Ala Val Val Asn Tyr Ile Glu
        115                 120                 125

Asp Arg Arg Tyr Leu Met Gly Phe Ala Tyr Phe Ala Gly Ala Asn Phe
    130                 135                 140

Val Leu Thr Leu Ile Ala Ala Leu Leu Cys Val Cys Phe Ala Pro Thr
145                 150                 155                 160

Ala Ala Gly Pro Gly Ile Pro Glu Ile Lys Ala Tyr Leu Asn Gly Val
                165                 170                 175

Asp Thr Pro Asn Met Tyr Gly Ala Thr Thr Leu Phe Val Lys Ile Ile
            180                 185                 190

Gly Ser Ile Ala Ala Val Ser Ala Ser Leu Asp Leu Gly Lys Glu Gly
        195                 200                 205

Pro Leu Val His Ile Gly Ala Cys Phe Ala Ser Leu Leu Gly Gln Gly
    210                 215                 220

Gly Pro Asp Asn Tyr Arg Leu Arg Trp Arg Trp Leu Arg Tyr Phe Asn
225                 230                 235                 240

Asn Asp Arg Asp Arg Arg Asp Leu Ile Thr Cys Gly Ser Ser Ser Gly
                245                 250                 255

Val Cys Ala Ala Phe Arg Ser Pro Val Gly Gly Val Leu Phe Ala Leu
            260                 265                 270

Glu Glu Val Ala Thr Trp Trp Arg Ser Ala Leu Leu Trp Arg Thr Phe
        275                 280                 285

Phe Ser Thr Ala Val Val Val Val Ile Leu Arg Ala Phe Ile Glu Tyr
    290                 295                 300

Cys Lys Ser Gly Asn Cys Gly Leu Phe Gly Arg Gly Gly Leu Ile Met
305                 310                 315                 320

Phe Asp Val Ser Gly Val Ser Val Ser Tyr His Val Val Asp Ile Ile
                325                 330                 335

Pro Val Val Val Ile Gly Ile Ile Gly Gly Leu Leu Gly Ser Leu Tyr
            340                 345                 350

Asn His Val Leu His Lys Ile Leu Arg Leu Tyr Asn Leu Ile Asn Glu
        355                 360                 365

Lys Gly Lys Leu His Lys Val Leu Leu Ala Leu Ser Val Ser Leu Phe
    370                 375                 380

Thr Ser Ile Cys Met Tyr Gly Leu Pro Phe Leu Ala Lys Cys Lys Pro
385                 390                 395                 400

Cys Asp Pro Ser Leu Pro Gly Ser Cys Pro Gly Thr Gly Gly Thr Gly
                405                 410                 415

Asn Phe Lys Gln Phe Asn Cys Pro Asp Gly Tyr Tyr Asn Asp Leu Ala
            420                 425                 430

Thr Leu Leu Leu Thr Thr Asn Asp Asp Ala Val Arg Asn Ile Phe Ser
        435                 440                 445

Ile Asn Thr Pro Gly Glu Phe Gln Val Met Ser Leu Ile Ile Tyr Phe
    450                 455                 460

Val Leu Tyr Cys Ile Leu Gly Leu Ile Thr Phe Gly Ile Ala Val Pro
465                 470                 475                 480
```

Ser Gly Leu Phe Leu Pro Ile Ile Leu Met Gly Ser Ala Tyr Gly Arg
485 490 495

Leu Leu Ala Ile Ala Met Gly Ser Tyr Thr Lys Ile Asp Pro Gly Leu
500 505 510

Tyr Ala Val Leu Gly Ala Ala Ser Leu Met Ala Gly Ser Met Arg Met
515 520 525

Thr Val Ser Leu Cys Val Ile Phe Leu Glu Leu Thr Asn Asn Leu Leu
530 535 540

Leu Leu Pro Ile Thr Met Leu Val Leu Leu Ile Ala Lys Ser Val Gly
545 550 555 560

Asp Cys Phe Asn Leu Ser Ile Tyr Glu Ile Ile Leu Glu Leu Lys Gly
565 570 575

Leu Pro Phe Leu Asp Ala Asn Pro Glu Pro Trp Met Arg Asn Ile Thr
580 585 590

Ala Gly Glu Leu Ala Asp Val Lys Pro Pro Val Val Thr Leu Cys Gly
595 600 605

Val Glu Lys Val Gly Arg Ile Val Glu Ala Leu Lys Asn Thr Thr Tyr
610 615 620

Asn Gly Phe Pro Val Val Asp Glu Gly Val Val Pro Pro Val Gly Leu
625 630 635 640

Pro Val Gly Ala Thr Glu Leu His Gly Leu Val Leu Arg Thr His Leu
645 650 655

Leu Leu Val Leu Lys Lys Lys Trp Phe Leu His Glu Arg Arg Arg Thr
660 665 670

Glu Glu Trp Glu Val Arg Glu Lys Phe Thr Trp Ile Asp Leu Ala Glu
675 680 685

Arg Gly Gly Lys Ile Glu Asp Val Leu Val Thr Lys Asp Glu Met Glu
690 695 700

Met Tyr Val Asp Leu His Pro Leu Thr Asn Thr Thr Pro Tyr Thr Val
705 710 715 720

Val Glu Ser Leu Ser Val Ala Lys Ala Met Val Leu Phe Arg Gln Val
725 730 735

Gly Leu Arg His Met Leu Ile Val Pro Lys Tyr Gln Ala Ala Gly Val
740 745 750

Ser Pro Val Val Gly Ile Leu Thr Arg Gln Asp Leu Arg Ala His Asn
755 760 765

Ile Leu Ser Val Phe Pro His Leu Glu Lys Ser Lys Ser Gly Lys Lys
770 775 780

Gly Asn
785

<210> SEQ ID NO 6
<211> LENGTH: 786
<212> TYPE: PRT
<213> ORGANISM: Nicotiana tabacum
<220> FEATURE:
<223> OTHER INFORMATION: Protein sequence of CLC-Nt2 from Nicotiana tabacum, translated from SEQ ID NO: 2 of PCT/EP2013/077532

<400> SEQUENCE: 6

Met Glu Glu Pro Thr Arg Leu Val Glu Glu Ala Thr Ile Asn Asn Met
1 5 10 15

Asp Arg Gln Gln Asn Glu Glu Glu Arg Asp Pro Glu Ser Asn Ser Leu
20 25 30

His Gln Pro Leu Leu Lys Arg Asn Arg Thr Leu Ser Ser Ser Pro Phe
35 40 45

```
Ala Leu Val Gly Ala Lys Val Ser His Ile Glu Ser Leu Asp Tyr Glu
    50                  55                  60

Ile Asn Glu Asn Asp Leu Phe Lys His Asp Trp Arg Arg Arg Ser Arg
65                  70                  75                  80

Val Gln Val Leu Gln Tyr Val Phe Leu Lys Trp Thr Leu Ala Phe Leu
                85                  90                  95

Val Gly Leu Leu Thr Gly Val Thr Ala Ser Leu Ile Asn Leu Ala Ile
            100                 105                 110

Glu Asn Ile Ala Gly Tyr Lys Leu Arg Ala Val Val Asn Tyr Ile Glu
        115                 120                 125

Asp Arg Arg Tyr Leu Val Gly Phe Ala Tyr Phe Ala Gly Ala Asn Phe
    130                 135                 140

Val Leu Thr Leu Ile Ala Ala Leu Leu Cys Val Cys Phe Ala Pro Thr
145                 150                 155                 160

Ala Ala Gly Pro Gly Ile Pro Glu Ile Lys Ala Tyr Leu Asn Gly Val
                165                 170                 175

Asp Thr Pro Asn Met Tyr Gly Ala Thr Thr Leu Phe Val Lys Ile Ile
            180                 185                 190

Gly Ser Ile Ala Ala Val Ser Ala Ser Leu Asp Leu Gly Lys Glu Gly
        195                 200                 205

Pro Leu Val His Ile Gly Ala Cys Phe Ala Ser Leu Leu Gly Gln Gly
    210                 215                 220

Gly Pro Asp Asn Tyr Arg Leu Lys Trp Arg Trp Leu Arg Tyr Phe Asn
225                 230                 235                 240

Asn Asp Arg Asp Arg Arg Asp Leu Ile Thr Cys Gly Ser Ser Ser Gly
                245                 250                 255

Val Cys Ala Ala Phe Arg Ser Pro Val Gly Gly Val Leu Phe Ala Leu
            260                 265                 270

Glu Glu Val Ala Thr Trp Trp Arg Ser Ala Leu Leu Trp Arg Thr Phe
        275                 280                 285

Phe Ser Thr Ala Val Val Val Val Ile Leu Arg Ala Phe Ile Glu Tyr
    290                 295                 300

Cys Lys Ser Gly Tyr Cys Gly Leu Phe Gly Arg Gly Gly Leu Ile Met
305                 310                 315                 320

Phe Asp Val Ser Gly Val Ser Val Ser Tyr His Val Val Asp Ile Ile
                325                 330                 335

Pro Val Val Val Ile Gly Ile Ile Gly Gly Leu Leu Gly Ser Leu Tyr
            340                 345                 350

Asn Cys Val Leu His Lys Val Leu Arg Leu Tyr Asn Leu Ile Asn Glu
        355                 360                 365

Lys Gly Lys Leu His Lys Val Leu Leu Ala Leu Ser Val Ser Leu Phe
    370                 375                 380

Thr Ser Ile Cys Met Tyr Gly Leu Pro Phe Leu Ala Lys Cys Lys Pro
385                 390                 395                 400

Cys Asp Ser Ser Leu Gln Gly Ser Cys Pro Gly Thr Gly Gly Thr Gly
                405                 410                 415

Asn Phe Lys Gln Phe Asn Cys Pro Asp Gly Tyr Tyr Asn Asp Leu Ala
            420                 425                 430

Thr Leu Leu Leu Thr Thr Asn Asp Asp Ala Val Arg Asn Ile Phe Ser
        435                 440                 445

Ile Asn Thr Pro Gly Glu Phe His Val Thr Ser Leu Ile Ile Tyr Phe
    450                 455                 460
```

```
Val Leu Tyr Cys Ile Leu Gly Leu Ile Thr Phe Gly Ile Ala Val Pro
465                 470                 475                 480

Ser Gly Leu Phe Leu Pro Ile Ile Leu Met Gly Ser Ala Tyr Gly Arg
                485                 490                 495

Leu Leu Ala Ile Ala Met Gly Ser Tyr Thr Lys Ile Asp Pro Gly Leu
            500                 505                 510

Tyr Ala Val Leu Gly Ala Ala Ser Leu Met Ala Gly Ser Met Arg Met
        515                 520                 525

Thr Val Ser Leu Cys Val Ile Phe Leu Glu Leu Thr Asn Asn Leu Leu
    530                 535                 540

Leu Leu Pro Ile Thr Met Leu Val Leu Leu Ile Ala Lys Ser Val Gly
545                 550                 555                 560

Asp Cys Phe Asn Leu Ser Ile Tyr Glu Ile Ile Leu Glu Leu Lys Gly
                565                 570                 575

Leu Pro Phe Leu Asp Ala Asn Pro Glu Pro Trp Met Arg Asn Ile Thr
            580                 585                 590

Ala Gly Glu Leu Ala Asp Val Lys Pro Pro Val Val Thr Leu Cys Gly
        595                 600                 605

Val Glu Lys Val Gly Arg Ile Val Glu Val Leu Lys Asn Thr Thr Tyr
    610                 615                 620

Asn Gly Phe Pro Val Val Asp Glu Gly Val Val Pro Pro Val Gly Leu
625                 630                 635                 640

Pro Val Gly Ala Thr Glu Leu His Gly Leu Val Leu Arg Thr His Leu
                645                 650                 655

Leu Leu Val Leu Lys Lys Lys Trp Phe Leu Asn Glu Arg Arg Arg Thr
            660                 665                 670

Glu Glu Trp Glu Val Arg Glu Lys Phe Thr Trp Ile Asp Leu Ala Glu
        675                 680                 685

Arg Gly Gly Lys Ile Glu Asp Val Val Val Thr Lys Asp Glu Met Glu
    690                 695                 700

Met Tyr Val Asp Leu His Pro Leu Thr Asn Thr Thr Pro Tyr Thr Val
705                 710                 715                 720

Val Glu Ser Leu Ser Val Ala Lys Ala Met Val Leu Phe Arg Gln Val
                725                 730                 735

Gly Leu Arg His Met Leu Ile Val Pro Lys Tyr Gln Ala Ala Gly Val
            740                 745                 750

Ser Pro Val Val Gly Ile Leu Thr Arg Gln Asp Leu Arg Ala His Asn
        755                 760                 765

Ile Leu Ser Val Phe Pro His Leu Glu Lys Ser Lys Ser Gly Lys Lys
    770                 775                 780

Gly Asn
785
```

<210> SEQ ID NO 7
<211> LENGTH: 665
<212> TYPE: PRT
<213> ORGANISM: Nicotiana tabacum
<220> FEATURE:
<223> OTHER INFORMATION: Protein sequence of NtCLCe from Nicotiana tabacum; sequence originating from the ancestor N. sylvestris; one start codon, translated from SEQ ID NO: 3 of PCT/EP2013/077532

<400> SEQUENCE: 7

```
Met Cys Asp Ser Ser Lys Val Asp Ser Asp Ser Gly Ile Gln Ile Gly
1               5                   10                  15

Ser Leu Leu Glu Glu Val Ile Pro Gln Gly Asn Asn Thr Ala Ile Ile
```

```
            20                  25                  30

Ser Ala Cys Phe Val Gly Leu Phe Thr Gly Ile Ser Val Val Leu Phe
        35                  40                  45

Asn Ala Ala Val His Glu Ile Arg Asp Leu Cys Trp Asp Gly Ile Pro
    50                  55                  60

Tyr Arg Ala Ala Ser Glu Glu Pro Ile Gly Val His Trp Gln Arg Val
65                  70                  75                  80

Ile Leu Val Pro Ala Cys Gly Gly Leu Val Val Ser Phe Leu Asn Ala
                85                  90                  95

Phe Arg Ala Thr Leu Glu Val Ser Thr Glu Gly Ser Trp Thr Ser Ser
            100                 105                 110

Val Lys Ser Val Leu Glu Pro Val Leu Lys Thr Met Ala Ala Cys Val
        115                 120                 125

Thr Leu Gly Thr Gly Asn Ser Leu Gly Pro Glu Gly Pro Ser Val Glu
    130                 135                 140

Ile Gly Thr Ser Val Ala Lys Gly Val Gly Ala Leu Leu Asp Lys Gly
145                 150                 155                 160

Gly Arg Arg Lys Leu Ser Leu Lys Ala Ala Gly Ser Ala Ala Gly Ile
                165                 170                 175

Ala Ser Gly Phe Asn Ala Ala Val Gly Gly Cys Phe Phe Ala Val Glu
            180                 185                 190

Ser Val Leu Trp Pro Ser Pro Ala Glu Ser Ser Leu Ser Leu Thr Asn
        195                 200                 205

Thr Thr Ser Met Val Ile Leu Ser Ala Val Ile Ala Ser Val Val Ser
    210                 215                 220

Glu Ile Gly Leu Gly Ser Glu Pro Ala Phe Ala Val Pro Gly Tyr Asp
225                 230                 235                 240

Phe Arg Thr Pro Thr Glu Leu Pro Leu Tyr Leu Leu Leu Gly Ile Phe
                245                 250                 255

Cys Gly Leu Val Ser Val Ala Leu Ser Ser Cys Thr Ser Phe Met Leu
            260                 265                 270

Gln Ile Val Glu Asn Ile Gln Thr Thr Ser Gly Met Pro Lys Ala Ala
        275                 280                 285

Phe Pro Val Leu Gly Gly Leu Leu Val Gly Leu Val Ala Leu Ala Tyr
    290                 295                 300

Pro Glu Ile Leu Tyr Gln Gly Phe Glu Asn Val Asn Ile Leu Leu Glu
305                 310                 315                 320

Ser Arg Pro Leu Val Lys Gly Leu Ser Ala Asp Leu Leu Leu Gln Leu
                325                 330                 335

Val Ala Val Lys Ile Val Thr Thr Ser Leu Cys Arg Ala Ser Gly Leu
            340                 345                 350

Val Gly Gly Tyr Tyr Ala Pro Ser Leu Phe Ile Gly Ala Ala Thr Gly
        355                 360                 365

Thr Ala Tyr Gly Lys Ile Val Ser Tyr Ile Ile Ser His Ala Asp Pro
    370                 375                 380

Ile Phe His Leu Ser Ile Leu Glu Val Ala Ser Pro Gln Ala Tyr Gly
385                 390                 395                 400

Leu Val Gly Met Ala Ala Thr Leu Ala Gly Val Cys Gln Val Pro Leu
                405                 410                 415

Thr Ala Val Leu Leu Leu Phe Glu Leu Thr Gln Asp Tyr Arg Ile Val
            420                 425                 430

Leu Pro Leu Leu Gly Ala Val Gly Leu Ser Ser Trp Val Thr Ser Gly
        435                 440                 445
```

```
Gln Thr Arg Lys Ser Val Val Lys Asp Arg Glu Lys Leu Lys Asp Ala
    450                 455                 460

Arg Ala His Met Met Gln Arg Gln Gly Thr Ser Phe Ser Asn Ile Ser
465                 470                 475                 480

Ser Leu Thr Tyr Ser Ser Gly Ser Pro Ser Gln Lys Glu Ser Asn Leu
                485                 490                 495

Cys Lys Leu Glu Ser Ser Leu Cys Leu Tyr Glu Ser Asp Asp Glu Glu
            500                 505                 510

Asn Asp Leu Ala Arg Thr Ile Leu Val Ser Gln Ala Met Arg Thr Arg
        515                 520                 525

Tyr Val Thr Val Leu Met Ser Thr Leu Leu Met Glu Thr Ile Ser Leu
    530                 535                 540

Met Leu Ala Glu Lys Gln Ser Cys Ala Ile Ile Val Asp Glu Asn Asn
545                 550                 555                 560

Phe Leu Ile Gly Leu Leu Thr Leu Gly Asp Ile Gln Asn Tyr Ser Lys
                565                 570                 575

Leu Pro Arg Thr Glu Gly Asn Phe Gln Glu Glu Leu Val Val Ala Gly
            580                 585                 590

Val Cys Ser Ser Lys Gly Asn Lys Cys Arg Val Ser Cys Thr Val Thr
        595                 600                 605

Pro Asn Thr Asp Leu Leu Ser Ala Leu Thr Leu Met Glu Lys His Asp
    610                 615                 620

Leu Ser Gln Leu Pro Val Ile Leu Gly Asp Val Glu Asp Glu Gly Ile
625                 630                 635                 640

His Pro Val Gly Ile Leu Asp Arg Glu Cys Ile Asn Val Ala Cys Arg
                645                 650                 655

Ala Leu Ala Thr Arg Glu Gln Leu Cys
            660                 665
```

<210> SEQ ID NO 8
<211> LENGTH: 408
<212> TYPE: DNA
<213> ORGANISM: Artificial sequence
<220> FEATURE:
<223> OTHER INFORMATION: Synthetic sequence: RNAi sequence used to silence CLC-Nt2

<400> SEQUENCE: 8

```
gtcatcatca ggtgtgtgtg ctgctttccg ttctccagta ggtggtgtcc tatttgcttt      60

agaggaagtg gcaacatggt ggagaagtgc actcctctgg agaactttct tcagcacggc     120

agttgtggtg gtgatactga gggccttcat tgaatactgc aaatctggca actgtggact     180

ttttggaaga ggagggctta tcatgtttga tgtgagtggt gtcagtgtta gctaccatgt     240

tgtggacatc atccctgttg tagtgattgg aatcataggc ggacttttgg gaagcctcta     300

caatcatgtc ctccacaaaa ttctgaggct ctacaatctg atcaacgaga agggaaaact     360

acataaggtt cttctcgctc tgagtgtctc ccttttcacc tccatttg                  408
```

<210> SEQ ID NO 9
<211> LENGTH: 282
<212> TYPE: DNA
<213> ORGANISM: Artificial sequence
<220> FEATURE:
<223> OTHER INFORMATION: Synthetic sequence: RNAi sequence used to silence CLCe

<400> SEQUENCE: 9

```
gaaatccttt accagggttt tgagaatgtt aatattctgc tagaatctcg cccactagtg     60

aaaggcctct ccgctgatct gttgctccag cttgtagctg tcaaaatagt aacaacttca    120

ttatgccgag cctctggatt ggttggaggc tactatgcgc catctctatt catcggtgct    180

gctactggaa ctgcatatgg gaaaattgtt agctacatta tctctcatgc tgatccaatc    240

tttcatcttt ccatcttgga agttgcatcc ccacaagctt at                        282
```

```
<210> SEQ ID NO 10
<211> LENGTH: 44432
<212> TYPE: DNA
<213> ORGANISM: Nicotiana tabacum
<220> FEATURE:
<223> OTHER INFORMATION: DNA sequence of NtCLCe from Nicotiana tabacum;
      sequence originating from the ancestor N. sylvestris; two start
      codons

<400> SEQUENCE: 10

atgattagcg gccaaaacac tgtgctgcac aatcctccta attcgctctt caattcctta     60

tctcctcgcc atatctgtat atctttctgt aacgacaaag ctttaaaaaa gtcagtcacg    120

cactccgccc ctcggtttgc tcgtctgtta aacaatgaat cacggaagtt gttgggtcgt    180

catccaaatt gctggccttg ggctcgacga ccatctcttc ctccgggacg ttcctctgac    240

ggaaacattg aaaaagaaca agatatgtgc gacagcagca aagtcgatag tgatagtggc    300

atccagatag gatctctgct cgaggaagtt atcccacaag gcaataatac cgctataatc    360

tcggcttgct ttgttggcct cttcaccggt atcagtgtcg tgcttttcaa cgctgcggta    420

cgtgcgctat aggtctttca tttctctttt catgtactat tcctccttac ttacttggcc    480

tcagtcaatc agccccctgc ctactttaaa ttattgtaca ttttatcaga ggagtgtcct    540

atacatcaaa ttcacataac ttagtaaaat atgctgatat tctgaatttt aaacttacca    600

gcttagaaca tccaggttag ttcagaaaca gataatctaa attggtctca tttataagtc    660

attttgttat tcaagacata caatttggct cttgataaaa gattatgcag cgcccgatga    720

ttacctaata tttatcagca acccatgtaa tttaacaata ttgtcaccat ataaaagaga    780

actgaagaga atgttcaatt tgtggtcata taacggatat ctcccttggt taggttcatg    840

aaatacgtga tctttgttgg gatggaattc catatcgagc tgcctcagag gagcccattg    900

gagtacattg gcaacgtgta atcttagtac cagcttgtgg cggtttggta gtcagctttt    960

tgaatgcctt ccgagccact ctggaggttt caactgaagg aagttggaca tcatctgtta   1020

aatctgtatt ggaaccagtt ttgaagacaa tggccgcttg tgtcacatta ggaactggga   1080

attccttagg accagaaggc cctagtgttg aaattggcac atctgttgcc aagggagttg   1140

gagctctgct tgataaaggt ggtcgtagaa agctgtcact caaggctgct ggatcagctg   1200

ctggaatcgc ttctggtttg ttccccatat tattcttggt tctgaaccat acatggtaca   1260

ttttccttat aattacatgt agcctgttgt atgctttcct ctttcccggg aagccttttt   1320

gtaaatacaa gtgtgtttgc actcaaacca ataaactgta aaaaaggtga actccttaag   1380

caagcaaaag cattagaaat gtaaactaga catatttctc agattgagag tctgagagat   1440

tagaacacga gtgtttccat tagagagaga aaagagactt ctagatattt ctattatctc   1500

tgtaagagtg aatccgttcc tatacaaaaa ataggccttc attaaataca agcttgggct   1560

gggtactact gggccaaagt aaaaaataaa aagaatcacc cactatcaaa tgggcctagt   1620

ctaacaaccc ccttcaagct ggagggtgac acaaccccta gcttgcgaat atgaaaatga   1680

tgagcaggcc caagtaacac tttggtaaga acatcaacca cttgagaagc actggagttg   1740
```

-continued

```
tgaaatagac tgatcaggcc attcccaagc ttgccacaaa caaaatgaca gtccagctta   1800
atgtgtttag tgcgttcatg gaaaacttgg ttttttgcaa tgtggacttc ctgattatca   1860
caaaataaag gaacaggtaa agaaggagaa actccaatat cagacaataa tttggtgagc   1920
caagacacct ctgcaacagc cttactcatg gacctatact cagcttcaat tgatgatagt   1980
gagacaacag gttgcttctt tgatttccag ctcaccaagc tgccccccaa gaaaaataca   2040
aaaaccagtg acagacctgc ggctgtctgg gcaagaagcc caatcactgc acaataaagc   2100
tgcaaagaca agtctggaga gttattgcgg aagattccaa agtcaaaagt gcccttgagg   2160
tatcttagca agtgcagggc agcctgcatg ttaggaacac agggagactg cataaactga   2220
ctcagatgct gaacaacaaa actaaggtca ggccttgtgc gtatcaaaaa gtttagcttg   2280
tgcattagac tcctgtactc ttcaggcctg ggcaaaggag tgccaatctt agcttttaac   2340
ttcacattca attcaagggg gcaagtgaca gaagagcaat tcgaggaatg aaaatcagcc   2400
agcaaatcat gaatgaactt tttctgatga agaagaaccc cagaatcagt gtataaaacc   2460
tcaatgctaa ggaagtaatt aagagagccc atgtccttaa tcttgaactg gtcactgaga   2520
aaggacttca aagcagccaa ttcagctaga tcacacctag tcaatatgat atcattcaca   2580
tagacaacca agatgaccaa ggaatcccta gaacccttgg taaaaataga gaaatcattc   2640
aaggaacgag agaagccatt agagcacaag gcttgagata atttagcata ctattgtctt   2700
gaagccagtc ttaaaccata aagagacttc tggagtttgc atactaaagg agcagaagaa   2760
gagtgaggaa cagttaggcc cggtggcagc ttcatgaata cctcctcatc aaggtcccca   2820
tgtaagaaga cattattcac atctagttga aagaggggcc agtgttgttt aacagctaca   2880
acaataagag ttttgacaat agacatattg accacaggag aaaaagtttc attaaagtca   2940
ataccctcaa cttgagtgac ctagctttat atctctcaat actttcatta gccctatatt   3000
taaccttgta tacccactta caactagtag gtttcttgcc aggaggcaat tcaacaatgt   3060
cccaagttct gttggcatcc aaggcctcaa attcacatct catggctgcc tgccattcag   3120
gaacagctgc aacctgagag taagaataag gctcaggaac atgaagttga ctaagagaag   3180
gagcattaga aatagatctg gagggaggag gagaagaagt ggaggtgcag acataactct   3240
tgagatagtt ggttggattg tgtggcacgg aagatcttct caaagcagga ggaggtacaa   3300
gagagttaga ataatgagaa ggagaagaga tggaagtggg aacagagaag attgagaagc   3360
agtagaagga gaaagtgaag gagatgaagg agaggaagaa gacggaaagg aacattcatc   3420
aaaacaagca gaaaaggaaa aggggaagac ttgaggtact acatgagagg attgaaagaa   3480
aggaaaaatg gtgttcataa aaaatgacat cttttgatac aaaacaggtg ttattctgaa   3540
gattaaggcg cttgtagccc tttttggcaa aagggtagcc aatgaaaaca caaggaaggg   3600
acctaggatg aaatttgttt tgtgaggggt ggtgacagtt gagtaacaga ggcacccaaa   3660
agctctaagg tggtgataag tagggtggaa gaatgaagca attcataggg acttttgtga   3720
ttaagaagag gaaaaggaaa tctgttaatt aaatatgtgg cagttaaaaa gcagtcaccc   3780
caaaatttaa gtggtagatg agactgaaac ataagtgacc tagcagtctc tagtaaattt   3840
ctgtgttctc tttctacaat accattttat tggggggtgt gaggacagga ggtttggtgt   3900
actatccctt tttctgaaaa gaaaaggcaa ccagaagaac tagatcccag ttccaaagca   3960
ttatcactcc taacagtttg aactttagat tggaattggg tttcaaccat agcaatgaaa   4020
accttgagca aatcaaaggc attgcggcac ccattaaatg tgtccaagta gccctagagt   4080
```

agtcatctac aatggttaaa aaatacctag aaccattata ggtaggagta gaatagggtc 4140
accaagtatt tatgtgtatt agctgaaaag gctgggtgga gtgaatagaa ctatcaggga 4200
aggacaacct ggtctgcctc gctaaaggac aaaccggact agtgaatgac cgtttggaag 4260
acagtttgca attaagacca gaaatgcatt tcattttata gaagggaata tggccaagtt 4320
tgtaatgcca aacaacatca tctttattca cattatgcaa agcagtacta gtatttacaa 4380
ttggagtatc atcaggtaca gaaataggag cagaaactga attaagcaaa caagaaataa 4440
ggaaattaga aagaggtaaa ggagatgatg ttggaggcct ggcattctga aatagtttgt 4500
agagtccatt gtccaatcta ccaagaacca ctggcttcct cactgaaggg ccctgtaggg 4560
tacaagtagc cttggtaaat tgtacaatat catcatcatg ggaaagtaat ttgtacacaa 4620
agatgagatt atattgaaaa ctaggaatat agagcacatt ataaagaatc aagtcaggga 4680
acaaggctaa ggaaccaata ttagtgacct taaccttata cccattagga agggagacaa 4740
ggtatggtac aggaagtgtt tgaacattaa aaaaacaaat gtttaaggga ggtcatgtgg 4800
tcagatgccc agggtctatt actcaaacta cactatctat catagtcagc ataaatgcac 4860
cataagacaa cccttgtgag gtaataactc accagcaaag ttggtagaag caagatagtt 4920
ggttgaagaa gtagatgatg ctgatgaaga cagttgagat tgttgaagta acattagctg 4980
agaatattgg ttcttggtaa gaccaggaac tggataggac tgttcaggag cagaggtacc 5040
ttcaggacca gctgacattg cagaaccacc agaggtatcc acctcagcat gggcaacaga 5100
ccttctggga ggaagagatc tatttgactt gaaatttgga ggaaagccat tgagcttata 5160
gcacttatca atgctatgtc cgggtttctt acaatagtag acatgtgaag ctcaaaagat 5220
cccttagagg tagtaccgga cctttgaggt tcaaaattta ttttaggaga gggaggaggc 5280
ctggatacac caacactgaa agaagcagaa tttgaggcat attgagttct agcaaaaatt 5340
tgtctttgct tctcatcaga tagcaaaatc ccatatacat taccaatgga aggtaagggc 5400
ttcatcatga tgatgttgct tcttgtttgg acataagtat cattcagtcc cataaagaac 5460
tggtagacct tttgttccct gtcttcagca gatttacccc cacaagtaca cattcaaact 5520
ctcccggcag acaaagatgc aatatcatcc catagtcgtt taattttgtt gaaatatgat 5580
gctatgtcca tggacccttg ggaaatatga gccagttcct tctttagctc aaagatccta 5640
gtacctctct tctaactcag tccaaatatt cttagcaaac tcagagtatt caacactctt 5700
ggatatttcc ttgtacatag agttagtcaa ccaagagacc acaaggtcat tgcaacgtta 5760
ccactgtctg gctagaggag aaccttcagg aggtctgtga gaagtaccat taatgaaatc 5820
tagcttgtta cgaatagaca aggcaactag gacattacgt ctccaattgc cataacagct 5880
tccatcaaaa ggaccggaaa ctaaggaagt tcccagcacg tctgatggat ggacatataa 5940
ggggcgacag ggatgggtat aatcatcttc atggaaaatt aggcgtaagg gagtagaaga 6000
agtcgcatca gcactggtgt tattatcatt tgccattttt ttcaacagat tgtcaatcaa 6060
ccaacacaat acagatacac atatatagat tgtgagaaag cacgagagaa aaatctatat 6120
tattgatatt ctatttaatt ataatacaat gagccctatt tatacaatac atatcatact 6180
cctattctat gtgggactag gactaattca tattatgtac ataactatct aacactcccc 6240
ctcaagccgg tgcatacaaa tcatatgtac cgaacttgtt acatatgtaa ctaatacaag 6300
gaccagtaag gaacttggtg aaaatatctg caaactgatc atttgacttc acaaactttg 6360
tagcaatatc tcatgagagt atcttttctc tgacgaaatg acaattaatc tcaatgtgtt 6420
tagttctctc atgaaacacc ggatttgatg ctatatgaat ggcagcttgg ttatcacaca 6480

```
tcagttccat cttgctgacc tcaccaaatt tcaactaatt aagtaaatgt ttgatccaaa   6540
ctagctcaca agttgtcaca gccattgctc gatattctgc ttctgcacta gaccgagcaa   6600
ccacattttg tttcttgctc ttccaagaca cctaattacc tcctactaaa acacaatatc   6660
cagacgtaga acatctgtca aaaggtgatc ctgcctagcc agcatttgag tacccaacaa   6720
tttgctcatg gcctcgatct tcaaacaata atctgttacc tggagctgat tttatatatc   6780
gaagaatgca gacaactgca tcccaatgac tatcacaagg agaatccaag aactgactta   6840
ccacactcac tggaaaggaa atatcaggtc taatcactgt gaggtaattt aatttaccaa   6900
ccagccgcct atatctagca ggatcgctaa gcggctcccc ctgtcctggt agaagtttag   6960
aattccgatc cataggagtg tcaataggtc tacaacgtgt cattcctgtc tcctcaagaa   7020
tgtctaaggc atacttcctt tgtgagataa caatacatgt gctagactaa gcgacctcaa   7080
tacctagaaa atactttaat ctgcccagat ccttagtctg aaagtgctga aagagatgtt   7140
gtttcaactt agtaatacca tcttgatcat tgccggtaat aacaatatta tcaacataaa   7200
ccaccagata aatactaaga tttgaagaag aatgccgata aaacacagag tgatcagctt   7260
cactacgagt catgccgaac tcttgaataa ctgtgctgaa cttaccaaac caggctcgag   7320
gagactgttt tagaccatag agggaccgac gcaaccgaca tacaaggcca ctagactccc   7380
cctgagcaac aaaaccaggt ggttgctcca tataaacttc acctcaaggt caccacgaag   7440
aaaagcattc ttaatgtcca actgatagag aggccaatgg agaacaacaa ccatggatag   7500
aaaaaggcgg actgatgcta ttttagccac aggagagaaa gtatcactgt aatcaagccc   7560
aaatatctga gtataccctt tggcaacaag acgagcctta agtcgatcaa cctggccatc   7620
tggaccaact ttgactgcat acacccaacg acaaccaaca ataaatttac ccgaaggaag   7680
aggaacaaac tcccaagtac cactcgtatg taaagcagac atctcgtcaa tcatagcctg   7740
tcaccaccct agatgagaca gtgcttcacc tggatggaaa tagaggacaa agatgataca   7800
aatgcacaat agggtgatga cagacgatgg taacttaaac cgacataatg gggattagca   7860
tttagtgtag accgttcacc tttccggagt gcaatcaatt gactaagagg agacaagtcc   7920
gcagtattag caggatcagg tgcaggacgt gaatcagctg ggcctgatgc tgggcgcgga   7980
cgacgatgat aagttaggag tggtagagct gtagaaggtt gaactggact aggcagtgga   8040
actgaagcta tatgtggtgg aactggagct ataggtggtg gagctggagc tgtaggtgaa   8100
gatgaatggg agatagtgac tgaatctcca aaagatggaa ctggtagcac ctcagatata   8160
tctaagtgat tacctggact ggtgaagtat gattgggttt caaagaaggt aacatcagca   8220
gacataaggt accacctgag gtcaggagaa tagcatcgat atccttttg tgttctcgag   8280
taacccaaaa atacgcactt aagagcacga ggagctaatt tatcttttct tggagtaagg   8340
ttatgaacaa aacacgtgct cccaaaggca cggggtggaa gagagaacaa aggtaagtgg   8400
ggaaacaaga cagagaatgg aacttgattc tggatagctg aagatggcat acgattaata   8460
agatagcaag atgtaagaac tgcatccccc caaaaacgca acggaacgtg agattgtatg   8520
agtaaggtac gagcagtttc aataagatgt ctattctttc tttcagctac ccgattttgt   8580
tgggatgtgt atggacaaga tgttttatga ataatcccat gagagttcat aaactgttga   8640
aatgggaaag acaaatactc taaggcatta tcactacgaa atatgcggat agaaacccca   8700
aattgatttt gaatttcagc gtggaaggtc tggaaagtag aaaacaactc agatcgattt   8760
tttatcaaaa atatccaagt gcacctgtaa taatcatcaa tgaaactgac aaagtagcgg   8820
```

-continued

```
aatcccaagg tagaactgac ctgactagga ccccaaacat ctgaatggac taaagtaaaa   8880
ggtgactgac tctgctcgat tatcaagacg gcgagggaaa tgggagcacg tatgcttacc   8940
gagctgacat gactcacact ctagagtgga caagtgagat aaaccagata ccattttttg   9000
aagttttgac aaactgggat gtcccaaccg tttatgtaat agatctggtg aatcagtaac   9060
aggacaagtt gttgaagaaa gacaagatgt aagtccatgt gattttgcaa gaataaggta   9120
gtaaaatcca tttaattcac gcccggtacc aatgatccgc cctgtactgc gttcctgtat   9180
aaaaacaagg tcatcaagaa ataaaacaga gcatttaagt gatttggcta agcgactaac   9240
ggctatgaga ttaaaaagac taacgagaac ataaagaact gaatctaaag gtaaggaagg   9300
aagtggactt acttggctta ttccagttgc catggtttga gactcgttat ccattgtgac   9360
tgttgggagt gattgagaat atgaaatagt aatgaaaaga gatttgttac caaaaatatg   9420
atcagatgca cctgaatcaa tgacccaaga ctcagaggtt gaagattggg agacacaagt   9480
cacactacta tctgtttgag caacggaagc tatccctgaa gatgtttgtt tacatgtttt   9540
gaactgaagg aactcaatat aatccggtag agaaaccatc caactcttcg tagtattgga   9600
ttccattttg ctacaaccaa tttctcaaat tcttgattac aacttgtgtg gttaaccttg   9660
gaatgccaaa tcagaacacc cctttttttt ttttggaaaa cattgttcac tcgctggaaa   9720
ataaaaaagg ttgccggaat ttgatgaaac ttgaatagac cgactcggaa taatgtccta   9780
agaaggctgt ccaaaaggag ttttgtcaga aactgaccag aaggaggtcc acgcaccggc   9840
gcgtggacag atctcgccga aaaaaaaaat cactttggtt ggcgcgtgat ggcgcgtggg   9900
tggggttttt ccggtcgggt tttgtggggt ttgctccccc ggagatggag aacactgtgg   9960
tggtgttggt ttatgcacaa cactggtaaa aagtggtttt gatgcgaaca gctactcagg  10020
tcaccaaaaa attgcacggt gacgactgat ttcttcccgg atgtcgttgg aatgacgcac  10080
aacgataatt atctcaccaa tgctctgata ccatgtgaga aagtacggga gaaaaatcta  10140
tattattgat attctattta attataatac aatgagccct atttataaga ctaggattaa  10200
ttcatattat gtacataact atctaacata gatcaaatag gcatgcaatt cacaataatg  10260
gtgaataaaa tgatacgaag ttacccagct cttttcgcga tcgaaaagga gaaaatagcc  10320
ttcaatcaca aacgagaaag aagaatctcc ggcttgacag tagacgactt cgaaacccta  10380
gctcgagatg aaaaccacaa aatccccaaa tcacattacc aaccaaacaa tttgagatca  10440
caaatgttga atatgtgaga atccgactaa gaaatcaaca aaaaatcaat agaaatggtt  10500
gaagaatacc gacttgaacc ctaaatgagt cagacatcac ctagaatgaa atacaccttc  10560
gaaattgacg aaaacaggac cggttgaaag cggagaacgt gccatagaag gatctacgct  10620
ctgataccat gtaaacttga catacttctc agattgagag tctgagagat tagaaaacga  10680
gtgtttccat tagaaagaga gaaaagagac ttctagatat ttcgattatc tgtgtaaaaa  10740
tgaatccgtt cctatacaaa aattaggcct tcattaaata caagattcgg ccgggtatta  10800
ctggcccaaa gtaaaatata aaaagaatca cccactatca aatgggccta gtctaacaag  10860
aaaaccaaca aatagtcccc cccccccccc ccaaaagata ccactgaaat gacaccgggt  10920
gcccaaaaat aaagcagctt acttcttgac tttgagagga actgcaatcc ttatcggttt  10980
gagaggaact gcaatcagct ataagtagct tattaatttc cagtgcctgc attctgccaa  11040
gtactatgat atatttctga agctttgttt ccccagttcc tttttcagac gtttgctgtc  11100
aataaagttg agccagccaa cttggctccc acaagctact aattttgtcc aagcttactc  11160
tatgggagaa gttaaatttc ccaaattcct tgagcggaaa atgaaaaatg gactcaaagt  11220
```

```
gtcatattat gcaactatct aaagaaaaat actcaattga agtttagata agaaaagtga  11280
atgtatattg atgtagtctc cgttaggtga gaagcgtatc acttacccag caacatatgg  11340
acctaacatt ttactagtga agttttcaca ttgtatcaaa agctcaacaa acggaaaggt  11400
gactaatcct aaaatgttat ttcacatata tgggcacacg gtttgtcaac cttctcatac  11460
gtgcattatt tgttctctat ctttctattt catccgatat aaccaatcgt tattgtaaat  11520
tctataatgc ctgtggttac ttttgtcttt agtgacaaat gacatttagg ataaccatgt  11580
agttattgac ttatttcact tgaggtctct tccaattatg tagtagtaga gtgttgagat  11640
atggatatgt taccttctaa aaaaaagagt gtagagatgc ggatagtttg ctagctggct  11700
tttgtctccc ttcaagttga attagcaaaa gcttgtctca taagttggat agctagacaa  11760
gaaaaactcc aaattacttt atgtagagta ttcttaagct tgagtcgcga gttggaaact  11820
ggaattatgt aaaaaaacct ggaattattt ggttgagcct gctttttagt tttgtcaata  11880
tttccagtat ctaacccaac atgtttagag tgattcccgg agagcctcag tacaaggcat  11940
ttgcagagtc tttatgagag tccaggaagg ggcacacatt ctgtagaggt atagtcttgt  12000
ccttattttc agggttgaac tagttcttta gaagttacct aggcttccta atttccaaat  12060
ttctgccagg tcctttttg gtgaagtact tgaagtttaa taaatcaaat tttaatttct  12120
aacatatcct gagaaattta ttcacaaatt caactggtga cttctgatgc agaaacataa  12180
gcaactgctt atgggttcat atgttcctgc aattttattg ttgacatgga ttggcttcat  12240
atggttttgt tcctgcaatt ttatcgctga cactaatcct ttcatatggt tttatgtgga  12300
gtgttaaata gaggttaaga gacaagaaga ggctgaaaaa ggtgggcagt tcatttgtta  12360
gtagactact ctatttacta agagatatga tgtcccatac attactcgaa ttggctccga  12420
atccagattc cacttctttg ccgagtttcc ttattgtaca tagttcgact cgtcaaggga  12480
aattcacttc ctttgactga ataatgctag tttgagtagt accttacatt aaatggacca  12540
tttagttcta tctacttgat agaatagact ggtcatcaac tagttgcaaa tacaatgaca  12600
actttgccat gtttgcagag tcacctgatg aagaagtacc tcaattagta gaacatttct  12660
tgaatgttct acagtattct ctatgcctac atgaccacat cacttttcct tttgcgttgt  12720
gagaacttga acttggtgag cgggggttcc ccaggaatgg catcttgatg gcagatgacc  12780
attctgtcct tgtcttagct aatgcttctt gcattgcctc actagattta ttataccttt  12840
aaaaaatgtt tgccattgtt ctgccataat agaaggatgt acccagctgg tgcttcaaaa  12900
ctaatgaaat gctttacaat tgtcgagtcc taaaggatga tttgtggaat cagatctcaa  12960
acaattcttt ttgaggaaga aaaataccaa aggttttttc tgtttgttgg aagattaaaa  13020
atcctttaaa tggtaaagat ttatgaactt aattcagcgt ttttgtggcc attgctggaa  13080
aagagaaaaa acaatggcac ttcttcgagt ttgcttatcc aaaaaaaaga agaagagaat  13140
gtcacgtaat gcaatttcat cttaggaaac tttgcaggag aaaagcaaga gtgataaaac  13200
agaactattt gtttttttta acaagttgtt gtgacctatt tcttgtcatt cttatttgct  13260
aataagctaa tgtactatag ttcctgtact atggtttgtt ttgacttaat acggggatgt  13320
tcaatgagca ttttcttgtt ttttctgctt tcagcatctg ctgccttaca ggaattcatt  13380
ttctggaaat ttacttcttg ttctgctaac attttcctgt tatatcttgt cagtcatttt  13440
ctctccatgg ttatactgtt tgtgtcactt taaactctcc ttgttttcta ctttaaagga  13500
tttaatgctg ctgtcggggg ctgtttcttt gctgtggaat ctgtgttatg gccatcacct  13560
```

gcagagtcct ccttgtcctt aacaaatacg acttcaatgg ttattctcag tgctgttata 13620
gcttctgtag tctcagaaat tggtcttggc tctgaacctg catttgcggt cccaggatat 13680
gattttcgta cacctactgg taattttgga cttctttctc gagtttgatt cttaaataca 13740
attgtacccg tcacttacag caacaactac atttcaacag ctagttgggg ttggctacac 13800
agatcatcac tatccatttc aattcattta gtcccatttc tttcgaatat tgagtacttt 13860
gggattctat aatatcaagg ttctttatat tttctacttt gacgtacaaa tctctaaata 13920
gattaaagaa gactcctaga gacactggcc taatgcaaat gtaccaccat gaataaactt 13980
taatctgaaa tagctggtat cttatataag gacccttagc tttaattgtg ttctatattg 14040
atcttttggg acaacttcct tccaatatta tgtcttactt atacagttat acttatcctt 14100
aagccttact ctttagagtg gttatcccta attcaagctt ttgttggcac catagctagt 14160
ttggttctaa gtaaaaagtt actctttaga gtggtaactt tttgtcaatt ttcttagtga 14220
aaatataacc tctgtgacaa atctaccaag tataaatcca atttggttct atgtcatcct 14280
tgtagtttat ccaagtcaat gctccatcac tcttacaaag gttcatcgta tgactaatct 14340
tttttggaga aaggtaacag tttgtattga taataagatc agcgccaggt tggtcattag 14400
tgctaatagc tgtacgtaca actccaaaag agcaaaagac aagcacctga tgtaaggtaa 14460
attacaagct gcctataaaa tctatcaggt gtcctatctc actaaacatt tcttgtttac 14520
accaaaaaaa taaaacaagg aaagacaatc catcttaatc ttctgaatgg agtttctttt 14580
tccttcaaaa catctggagt tccttccgtt ccatgcaatc caccatatac aagctgggat 14640
gattttccat ttgtctttat ccatttcttc taccaattcc cttccaattg attagaagtt 14700
ccaatgtggt tctagatatg acccaattaa ctcccaacag ataaaagaag atgtgccacg 14760
gatttgtagt gattctgcaa tgtaggaaca agtgagcatt actttctact tcctgtccac 14820
aaagaaaaca tcttgagcaa atctggaaac ctcttctttg taagttatca tgtgttaaac 14880
atgccttttt caccaccaac cagacaaaac atgatacttt gggaggagtt ttaaccctcc 14940
aaatgtgttt ccaaggccac acctcagttg ttgaaacatt aggatgtaga gtccagtatg 15000
ctcttttact gaaaatgcac cttttctatt cagcttttaa actactttat ctatggtctg 15060
tgatgtaccc ttgaaaggtt caagagtttg gaggaagata gaaactctgt ttatctccca 15120
atcatccaaa gatcttctaa agttccagct ccatccttgt gagctccaga ctgacttacc 15180
aatgcttggc tttgaagact tagagagaat aagtcaggaa aatatctttc aaccttcctt 15240
gccctatccg gtgatcttcc caaaaagatg tctgcaaccc attgccaata ttgatcttga 15300
tattgctact gaaagatttc ttttggtggc aggattactc tcattaacaa tgtacttgac 15360
aatctccata catactaatg tctctttacc ctcttgccat taaggttgta aagagacttg 15420
tcaaattaag aaaaggtttc ctatggaact gtttcaagga aggaacctcc tttcctttgg 15480
tcaagtggag ttaagtcata taatctagga agtggaggct tgggtatgaa atagctgcaa 15540
atacagaaaa ggagcatctt atttaaatga tcacggaaat gtgcccaaaa ctttaaatat 15600
ctgcacagca tatggttgta gcaaaatttg aatcttcctg tcaatggtgc tcatgtccag 15660
tgaatacccc tgatggtgaa agtgtcctga agggaagcag gaacttattg gaagaattgg 15720
catctaacac tcagcttttc ggtgggtcat agcccattga aaattgagtg cccagattta 15780
tatagttttg ctctaaactg acgatgcagt tgcacaacat acgacaaact aaggtgggac 15840
atcatcttct tcggaaggaa ttttgaggat taagagatag agtggttgat tcagttgcaa 15900
atgaagcttc aagggttcaa tatcatccag gagacaccgg attctgatag ataaaacaac 15960

```
agaaagatga gcactacttt gttaggcttg ttacaagttg ctatcgtctt tcttatctcg  16020
gtacacaatt tagatttggg aacttagttg gaaaagcaga gtggttgttt ttgtgaatag  16080
catcagacaa agcttctgag ctggtacgac agaaaactca acagggagaa tagaagactg  16140
tggttcacaa tttctgcatg catcttgtag gttatttggt gggtaaatta tttaatgttt  16200
tgaagggaag gtagaacatg ttcataggct tagattcaaa tgtttgtatt tttttggctc  16260
tttggtgaga gatgctgaac gtaaatgaca taggcagctg actataattt ctcagctcct  16320
tgctttttaa attgacaggc actgatatgt acatgtgaac atccaacact tttgtggtgc  16380
cgttccgatg aataaagaac attaatcact tactgatcag gagtaatagt ttaggagttc  16440
tagaattttt gtacataaaa tgaaccaaaa agaagatcgg aatgagaaca tgtttctttt  16500
tttgtttttt ctttttcgtg aaaacttcaa taacacttct gatagaatag ctaggtccat  16560
ttgaattcct ttggagaccc ttacacaacc aatgaatgac aagtatagca tttctaactc  16620
cctcccacac gtataaccca gattttaggg tttagatgtg gatctgattt gaccttattg  16680
cctttttttg tttttgttct ttttgaagta gagagtgagg aggctcaaca attaattcgg  16740
ctcaacgggc taatgattgg acttacatgc tacgacaatg ttaggagaga gagagagaga  16800
gagaagccca gagcagttac atgagttaag aaagagaagt ccaaagcgat agaatatgaa  16860
gagagaaagc ggttgtgcta acaggctccc tgaagtttgg ctctgagcat ccaactcaaa  16920
accttaaggc aatgagtaga gtagcccagg accatttaaa ttgctgttga aaaccttaca  16980
caaccaataa gggaacaagt gtaacattct cttacaaccc taccgtctta taagtcagtg  17040
ctctaattta gcataaaatc aaagtgaggc gatctacaat gaaatgaagt aaataactga  17100
taaatacaaa gaatgttaat tctccaatat agcctgaatg ttcccagaac aaaataaact  17160
agtctcagga tttatcatta acatgatgtt cctcttattt tgagtgatta ggaaggttaa  17220
tcaaggtata aattctttct aatttgtatc gtctagaatt atttatctaa caaattttca  17280
gattaccggt tcaaaagagg aatatatttt gcatacaacg ttaccatacc ttacaaaagg  17340
gagatgaaca ttttttttatt ttattattgt cctttttttc aattagggat tatgcagtct  17400
tcctccacgt gatattactc ttagaatcac gtttttgtca ttgctattac ttaatgtggt  17460
aagtacaaat gtgttttgaa ctctttttgg tatgtaatat tgagttaatt tttggtttcc  17520
atttcagagc tgccgcttta tcttctgctg ggcatctttt gtggcttagt ttcagtggca  17580
ttatcaagtt gtacatcatt tatgctgcaa atagtggaaa atattcaaac gaccagcggc  17640
atgccaaaag cagcttttcc tgtcctgggt ggtcttctgg ttgggctggt agctttagca  17700
tatcctgaaa tcctttacca gggttttgag aatgttaata ttttgctaga atctcgccca  17760
ctagtgaaag gcctctccgc tgatctgttg ctccagcttg tagctgtcaa aatagtaaca  17820
acttcattat gtcgagcctc tggattggtt ggaggctact atgcaccatc tctattcatc  17880
ggtgctgcta ctggaactgc atatgggaaa attgttagct acattatctc tcatgctgat  17940
ccaatctttc atctttccat cttggaagtt gcatccccac aagcatatgg cctggtatga  18000
atttgtcttt tgttagaagt agcattacat atctggataa gtgagttttt tattattgaa  18060
aagtaataac aggagagcaa gagaatatag cacccaaatc tacttctttc ctctcttcta  18120
ttcttctgaa attcaaggtc ctttaactcc tccacggcct gtctagttat tgatcctgta  18180
gacttaattc acataggttt aggacattca agtttatcca aacttcgtga aaaggtttct  18240
aatttttta cattacagta tgagtcgtgt ctacttgaga aacatatcac tccatgtttc  18300
```

```
tatagagtct gttttctcct cagtttattt tgatatatgg ggtcctatta agacagttca  18360
accttggatt ttcattattt ttgttgtttc attgataatt attcaagatg tacttggatt  18420
ttcttaacaa gagatagttc tcagttgttt tttgtgttcc taagtttttg tgctgcaata  18480
caaaattagt ttgatgtctc tatttgcatt tttcccaatg ataatgcctt agaatatttt  18540
cttctcggtt tcagtagctt atgatttctt tagaaactct ctatcagaaa tctcaactga  18600
gatagatgag aggaagaata agcatatcat tgagacggct cgtacccttc tcattcagtc  18660
ccctgtcaag cttagtttct tgggcgatgc agtttcacgt cctttgatta gattaattgg  18720
atgcctcatc tgctatccaa aatcagattc aactttcgat attgtttcct cgcttacctt  18780
tatactctct ttccctcgag tctttgggag cacatgtttt gttcaataac atagctcctg  18840
gaaagtgacc agcgcaaccg acaagcaagg ccttcttaat atagaaggag ggcatatgct  18900
attctagcca cgagggagaa agtaatattg taatcaaacc caaatatctg agtataacct  18960
ttggcaatgg cgatcaattt gattatatgg accaactttg cctacatata cccaccgata  19020
gatttacggg gaggtagaga aataagctcc caagtaccac taatatgtaa agcagacatc  19080
tctttgatca tagcctgtcc ttgtggacat agggatagaa attgaggact aagatgacac  19140
aaaagcataa tgctgtgatg ataaacgatg ataactcaaa tcaatatgat ggggatggga  19200
attaagagtg gattgaatat ctttgcggaa tgtgattggt agactaggag gagacaagtc  19260
cgcaataggt aaaagatcca gtacatggaa tgaatcttct ggacatgatg ttggactgac  19320
gtcaatgata agtcaagagt ggtggagttg cagaacatgg aactggagct gtaggtgaca  19380
taatcgaagt tgtagggggt ggagctatag aggaaggtga aggagagata gtgactgaat  19440
ctccaaaata tgaaaccggt aatacctcaa aaaatgtcta agagatcatt tggacctatg  19500
aagtatggtt gcgttttaaa gaaggtaaca tcagcagaca taaggtaccg cggaaagtca  19560
ggtgaataac attgatatcc ttgttgcgtc ctcgagtaac ttagaaatac atatttgaga  19620
gcacggggag ctaacttatc ttttctggag taaggttata aaaaaacaca tgctcccata  19680
gacacgaggt ggaagagaga aaggtgagtg gggaaacaag acagagtatg aaacttgatt  19740
cttgatagtt gaagatggca tacaattaat aagacaatag gatgtgagaa ctgtatcccc  19800
acgtaaacac aacagaacat gagattgtac gagttgggta tgagcagtct caatgagata  19860
cctattcttc ctttcagcta tcccatttta ttgagatgtg tatggacaaa atatttgatg  19920
tatgatccta tgagagttca tgaactgctg aaatggagaa gacaaatact ctggggcatt  19980
atcactatga aatgtgcggt tagaaacccc aaattgattt tggatttcag agtgaaaggt  20040
ctgaaaaata gagaccaact cagattgatt tttcatgaga aatatccaag tggacttgga  20100
ataatcatca atgaaactga caaagtagca gaattccaag gtagaactaa ctcgacaagg  20160
acctcaaaca tctgaatgga ctaaagtgaa aggtgactct attcgattat caagacaccg  20220
aggaaaatga gagcgagtat gccttctgag cggatatgac tgacgctcta gagtggacaa  20280
gtgagacaaa ccaggtacca ttttctgaag ttctgataaa ttgggatgtc ctaaccgttt  20340
atgtaataaa tctggtggat cagtaaaagg acaagctgta aggggacaaa aataccaaat  20400
atttccagaa gatggcaaac tacaacagaa gaagcaacta cattaacagg ctcaggatat  20460
gtgatgaaat gaggacaaag agttgatcaa gaaggagatt ctggaattct accagaactt  20520
atatagtgaa aatgaaccgt ggaggcccag tgcaaatttt gaaggcatct cctcactaag  20580
catagaagag aagaactagt tggaagctcc atttgaagaa atagaggtgc ttgaagcttt  20640
gaaatcatgt gcccctgata aagcaccagg tccagacggc ttcaccatgg ctttctttca  20700
```

```
gaaaaattgg gatactctta aaatggacat catggccgca cttaatcact ttcaccagag  20760
ctgtcacatg gttagggctt gcaatgccac cttcatcgcc ttaattccaa agaaaaaggg  20820
tgctatggag ctcagagact acagatctat tgacaaacta gtctcggggg aacaaaatgc  20880
tttcatcaag aacaggcaca tcactgatgc ttccttgatt gccagtgaag tgctggattg  20940
gagaatgaaa agtggaaaac caggcgtgtt gtgcaaactg gacattgaaa aggcttttga  21000
tcaattaaga tggtcttacc tcatgagtat cttgaggcag atggctttgg ggagaaatgg  21060
ataagatgga taaactattg catttcaact gtcaagaact ctgttttggt gaatagtggc  21120
ccgaccggtt ttttctcctg ccaaaagggc ctaaggcagg ggatctcctc tcccctttcc  21180
tattcatttt ggcgatggaa ggactcacta aaatgttgga gaaggctaag caactacaat  21240
ggatacaagg ctttcaggtg ggaaggaatc ctgccagctc agttacagta tcccatctac  21300
tctttgcgga tgatactctt attttttgtg gtactgagag atcacaagca cgaaatctca  21360
acctgacgct gatgatcttc gaggcactat caggactcca caacaatatg ataaagagca  21420
tcatataccc tgtgaatgca gtccccaaca tacaggagct agcagacatc ctatgctgca  21480
aaacagatac tttcccaaca tatcttggac ttcccttggg agctaaattc aaatcaaaag  21540
aagtttggaa tggagtccta gagaagtttg aaaagaggct tgcgacttgg cgaatgcaat  21600
acctctccat cggtggcaag ttaactttaa tcaatagtgt actggacagt cttcctacat  21660
accacatgtc tttgttccca attccaatct cagtcctaaa gcagatggac aaactcagaa  21720
ggaagttctt acgggaagga tgcagcaaaa cacacaaatt tccactagtg aaatgactca  21780
aggtaactca accaaaattc aaaggaggct tgagcatcag ggatctacaa gcacacaaca  21840
aagctatgct cttaaaatgg ctctggagat atggacagga ggaatctagg ctatggaagg  21900
acatcatagt tgctaaatat ggagcacaca atcactggtg ttccaagaaa acaaacactc  21960
cttatggagt tggtctgtgg aagaacatca gcaaccactg ggatgaattc ttccaaaatg  22020
taactttcaa agttgggaat ggaactcgta ttaagttttg gaaggataga tggctcggaa  22080
atacaccttt gaaagacatg tttcccggta tgtatcagat tgccttgacc aaagactcca  22140
ctgttgctca aaatagagac aatggcactt ggtgcccatt ttcagaagaa atttgcagga  22200
ttgggaggtc aacagcctac tcacaatgtt aagctcccta gaaggtcata atatcgaaga  22260
tcaacagcct gacaaactta tttggggaaa ttctgagaga ggcaagtaca cagtcaaaga  22320
atgatacatt cacctctgtg accagaatcc aataatagat aactagccat ggaaacacat  22380
ctggagaact gaagtgccta ccaaggtgac ttgcttcaca tggttgactc taaatggggc  22440
atgtctcact caagacaact taatcaagag gaatatcata ctagttaata gatgctacat  22500
gtgccaacaa cagtcagaaa gtgtaaacca cctattcctc cactgctcag ttgcaaaaga  22560
catttggaac ttcttctaca ctacctttgg tctgaaatgg gttatgccac aatcaacaaa  22620
gcaagctttt gaaagttggt atttttggag agttgacaaa tccatcaaaa aaatctggaa  22680
aacggtgccg gctgcatttt tttggtgtat ttggaaagaa aggaaccgaa gatgttttga  22740
tgacatatta actccactct actccctcaa ggctgcgtgt ttagttaact tatttagttt  22800
tgtggatttt attagctccc tgatagtagc ataggctttt gtaaatggag ctaattatcc  22860
tatctctttt gtactctttg catcttcttg atgcctttta atgaatctaa tttacttcat  22920
aaaaaataaa aggacaagtt gttgaaggag gaaaagatgt gagtccatgt gatttagcaa  22980
ggataaggta ctaaagtcca tttgattcac gcccggtacc aatgatccat cccgcattgc  23040
```

```
attcctgtat taaaacagag tcatcaagaa ataaaataga gcaaataagt gattggccaa  23100
acgactagtg gatatgagat taaaaggact atcgggaaca taaagaactg aattcaaagg  23160
taaggaagga agtggactag cttaacctat tccagttgcc atggtttgag aatagttggc  23220
cattgtgact gttggaagtg attgagagta agaaatagta gtgaaaagag atttgttacc  23280
agaaatataa tcagatgcaa ctgaatcaat aacctaagag tcggaaaaag aaacacaagt  23340
catgttatta cctgtttgaa caatagaagt tatctccgaa gaggattatt tacatgtttt  23400
gtactgatgg aactcaatat aagccgataa agaaaccatc cggatattca aagtattgga  23460
tcaacagctt ataagccaaa agcatccgat acgagtgcca ttataatgga tcaagagaga  23520
tcaaacaaca aatcaccaaa tatcataaac aaccaagaat ctcgctggaa tgtgaacaaa  23580
gattgaaaaa caacaatgta gctcgccaaa aatgtgcaaa gtgatcgaaa aatattgaat  23640
cgtgagtgga gagaaatagg agcttcaatc gacccacaca gtaccaaaaa atccaaaaac  23700
ggttgtcgga gctcaagaaa gttgtcaaaa agtatattgt atgcttcgaa agtagccgaa  23760
aaaggttgga agtgggatgt gtcaactccg aattatgata cgagcaccac agaagatcaa  23820
tttgtgtcaa aactaccgaa aaaaatactt cacaccccga cgcgtggagt actcgctcgt  23880
tggaaccctt gctgccaacg tcgcatgtag gatcagtttt cgaagaatct tattggggtt  23940
tggtcgccgg acgatgtcgg atcttgtggt gccgttggaa ttcgcacaac cctgaaggaa  24000
aagaaggtta cacaaatcag atctgaaagt caccgaaaag acacatggcg attgactttt  24060
ttgtctcaga tgtttctcac cgtcgctctg ataccagttg ttgggctcaa ctcgtttgaa  24120
gatactctta acatagtgtg atattgtccc ttttggaatg tgagtcatct tagctcggta  24180
agcatactcg ctcttccaac tagcccgaag atacttttaa cagagtgtaa tattatctgc  24240
tttgagccaa gctggcgcgg ttttcatcaa aagacctcat actattaaaa gatccataca  24300
ccttatatgt aggcttctaa gttgctcgga cacgggtgcg agtacccgac acaggtgcaa  24360
atctagaggt cagatccttt aaaatgtaaa ttctaagatt tggggatacg aatcctagta  24420
cggatacggg tgcgaggatc cgattaaaaa taattcaaaa aaataagaaa ataaaaaagt  24480
ctctaaatta tgtgaaattt tgtggaataa ctacgtatag cttgtaaagt gtggatttat  24540
tttttattct caagttgtag ataagtaaat gattgatttc ctagataagg tatgttattt  24600
tcttcaaatt taccctagtt tggttcgaat ttcgggaaat tgtatcttgt ctcgaatttt  24660
tccttctgtc ctgattaaac tactcaaaat cgtctgacca gatccggtac ggatcccata  24720
cccacatcca cactagtgtc gtgtggacaa gggtgcggca cctaaacttc cgtgtaggag  24780
caatttaggt aggctcctaa tcttttcagc tattaatgtg ggacttttac gcacctctat  24840
caaattcccc aataaactaa gtttcacgtg gtccatcatc gcaatccacg ggtctcttcc  24900
tctagttaag tcccacatgg cccattacca tgatccacgg gtcaattttc gtgattcatc  24960
gtgtgccacc cacatcgtta gtatttatgg taactaaagt acgcaactag cttttgcttg  25020
tgagcgtgtc tccaagctcg taaaggtaag aaaaccgagc cgcatattcc atcactctat  25080
catcaccata ctcgtcccgc gaaacttgta agataaaggt ggctggttgg tcagttgaac  25140
tacctcagag tgacttggta tagtatttcc tttcttgtga atatttaact caattatgga  25200
ctctctgtgt gatagtcatt gagagccatt ttctatatag ccggtgcaca caaatcatat  25260
gtaccaagct tgttatatat gtaactaata cgaggaccag tgaaggactc ggtgaaaata  25320
tctgcaatct ggtcattcga catacaaggc caatagactc cccagcaata aaatcagggg  25380
gttgctgata aatagaattg gccgaaatgt tgccagaaaa atttgaaaat agtgagacta  25440
```

```
agccgaattc tacactacaa aataggtttt aaaacacaac cagaaaacaa aaactttttt  25500
ggaaattact gttcacatcg aaaaaataaa agttgtcaga atttgatgta atttatatgg  25560
ataggctcgt aatcactgga cgagtaagtt gtcctgaaga agttttgtca aaaggtggcc  25620
ggaatggctc acacatgccg gaaaacttat tgtagctcgc cggaacccta gttctggcgg  25680
tgcgtagagg cgtgtgactt tctgccagac tgattgactg tggtttgtcg cctgactttt  25740
cctaacaaga tggtagtatt ggttttcgca caacaattac cgatgaggag ataacgcaaa  25800
tcaatcttga gtcgtcaatc ggaaagacgc acggtggctg actttctatt tagatgggac  25860
tggaatttct ggagtttaat cgcacaagcg ttttggatct gatggtaata ctggtatgca  25920
cagtaccact gtagcagtga tgaaccctca aaataagaca aagttgccag aaaattgcac  25980
ggcgatgaga tctttcttcc ggatgtcacc ggaatgacgc acaacgataa tttctcactg  26040
aagctctgac accatgtgag aatacacggg agaaaaatct atttttatta acaatgatac  26100
aatgagccct atatataata catattctac tctactacat atgggaatag ggcatatttt  26160
actcctacta catatgagac taggactatt tacacataac tatctaacaa gggctatatc  26220
tcagatttat gagaatatct acccaacgac ccagagagac gagcctaatc attttgcagt  26280
ggcacagact ataacaacaa aaaacctact cataatggtt aaaccaactg attaagatgc  26340
ttacaggact atcttgagaa atgtacatat tatatagatg cttgagttgc gtcccaatcc  26400
taaatagaag cttttattcg taagcaagaa gggaagcagc tttacttgag ccaatagctt  26460
tcaaggtgca tgttgtcaca ccaaggacat ccagaatttg attttatagt gggaatatcg  26520
tttaaagata aaaaagatag cgtgcagaag attgcataca ttagagatgc aaaatacgga  26580
atacccatac tcccagataa tgcagtatgc cttttgcatg acctactggt tgaatggaag  26640
cacctggtga atttactagg tgtgttagtg atttctgctg cttccttccc ctttctaaac  26700
tgcatactat ctaaaatgtt agggggcag aagcccagtc aatctgacta ggtgatgtta  26760
gtggtttccg cttcttcctc ccacttctaa atgcgtactt tctcaaattt aggagcatag  26820
aaacttaagc agctgcctac ctgaggagtt gcatgggaac ataagagaat agactttacc  26880
tgtcatattt tccatacctt agttaattac agtgttatcc tgataatgat ctgttttctg  26940
gatctaggct gaatcgagat tcaatcgctt ttggttgaaa ggatgctgct acagatcctt  27000
agtttacatc attttggttc ttattctata agtacttccc ctatcaacta cttccttctt  27060
ttttcttagg ttatttgcct ctttaggttg tttggaagga aaggaacagt agatgttttg  27120
atggaatagc aactccaaac cacttcctta aggctaatat cctgattggc caagtttctc  27180
caaagtccaa aacacttttt ttttccttca aaaaagtacc ttttttttc aaagttgagg  27240
tgtttggcca agcttttgga aggaaaaaaa gtgtttttga gtagaagcag atgctcttga  27300
gaagcagaag aagtagcttc ttcccggaag cacttttgag aaaaataaat ttagaaacac  27360
tttttaaaag cttggccaaa cactaattgc tgcttaaaag tattttcaga tttattagac  27420
aaacacaaac tgcttctcac caaaaatact tttttgaaaa gtacttttca aacaaagcac  27480
ttttcaaaat aagtttttta gaagcttggc taaacaggct ataaatgtct tttattttta  27540
cagctggagt accctaacac ctgtaaattc ccctatacat ttttttcgac tttggtagct  27600
cattaaccct agtataggac tctttgtttt ggagctagca aactcttttg ttttcctatt  27660
tttgcatctt cttggtgcca tttataatat ctcttcacca aaaaaaaaaa gttcccaaac  27720
tatgactacc ttgagttggt caaagcataa ccaaagcatg ggcacaccag tgtttgcgtg  27780
```

aattttatgg atgttcctta cctttatcct tctgtgctta tgtagcatct gtcttggtca 27840
atcttttctg aagtctatat tgtatttctg tgttgcaaca tgagtttact gttaatctta 27900
ctgtttgacc tcaattttgg gttctttttg attttggaag acatcgttta acaggttggc 27960
atggctgcta ctcttgctgg tgtctgtcag gtgcctctca ctgcggtttt gcttctcttt 28020
gaactgacac aggattatcg gatagttctg cccctcttgg gagctgtggg gttgtcttct 28080
tgggttacat ctggacaaac aaggaaaagt gtagtgaagg atagagaaaa actaaaagat 28140
gcaagagccc acatgatgca gcgacaagga acttctttct ccaacatttc tagtttaact 28200
tattcttcag gttcaccttc acagaaagag agtaacctct gcaaacttga gagttccctc 28260
tgtctttatg aatctgatga tgaagaaaat gatttggcaa ggacaattct agtttcacag 28320
gcaatgagaa cacgatatgt gacagttcta atgagcacct tgctaatgga gaccatatcc 28380
ctcatgctag ctgagaagca atcttgtgca ataatagttg atgaaaataa ttttctcatt 28440
ggtctgctga cacttggtga tatccagaat tacagcaagt tgccaagaac agagggcaat 28500
ttccaggagg tagcttcttg gtacatttca atattcttaa ctgatgaaaa aataagggaa 28560
attgatctag catgaaatga agctaattat aagttttaca cagtagaact ggtaaaacag 28620
ggttggctgg atatttcttt gttgaatttt taggattata tatattgttt tagttttgta 28680
ggttgttttc tgatgtgctt tttgactcgg cagaatctta agatgaaatg gaaggttgta 28740
tcatcaaatg ttaaataagg gaatatgtga ctttcaaagt taagcacgga gtattttgga 28800
gtcaatagtt acttcctgaa tcttttagga tggaggagac agtttctata ggaataggaa 28860
aaggggacct gatttcatta tttgtgtgta tatacatttg ttatctgaat tcgcattact 28920
ttctaacaac caacaaaagg aaagtggaca ttcaatttga gccggaggga gaaaatttaa 28980
ctagaaaatg acctggccgt gaaataaaat tattgatccg tcctttaact agtttcatg 29040 gattgcctcc ttgcggatga tttttccaac cggtagaact actgttagtc gtccaaattc 29100
tgacccccta ctatgaataa aaatgtatta gtaagtttag tgggtaatct ccttgagaaa 29160
taaaggaaca ggagaaatat tttattgata tatgctaagt gttttacaat agccctattt 29220
atatacaatg tttacataaa cctaaagcct tctatataaa tgtgggacac tatacatgaa 29280
ctaactctaa cactatccct caagctagtg catataaatt atatatatgc ttgttacata 29340
tataattaat ttctctactt tttggtatac ttcttgtata cgggagttat ctcccttttg 29400
attaatacaa tttaccttat caaaaaaaaa ttaatacgag gaccagtgag ggacttggtg 29460
aaaatatctg caagttgatc atttgacttc tcaaactttg taacaatatc tcctgagaat 29520
cttctctctc gtgaagtgac agtcaatctc agtgtgtttg gtcctctcat ggaacactgg 29580
atttgatgca atatgaagga caacttgatt atcacacaca agttccatct gactgattgc 29640
tccaaatttt aattatttga gcaattgttt gatccaaact agctcacatg gtgcaagagt 29700
catgactcga tattcggctt ctgcgctaga tcgagcaact acattctgtt tcttgctttt 29760
ccgagagaca aattacctcc tattaaaaca caatatccag atacgtaacg tctatcagaa 29820
ggtgaccctg cccaattagc atctgtgcgt ccaacaatat gctcatggca tcgatcttcg 29880
aatattagtc atttgtctgg agctgatttt atataacgaa caatgcgaac aactgcatcc 29940
caatgactat cgcaaggaaa ttccataaac tgacttacaa cactcacagg aaataaaata 30000
tcaggtctag taattatgag gtaattcaat tttccaacca ggcgcctata ttttgcagga 30060
ttgctaagag gctccccccct atcctggcag aagcttagca ttcggattca taagagtatc 30120
aatagttctg cagcccatta ttcatgtctc ctcaagaatg tctaaagcat acttcctttg 30180

```
cgaaataaca acctgaacta gaccgagcga cctcaatacc tacaaagtac ttcaatctgc  30240
taaggtcgtt agtctggaag tgttgaaagt gatgttgttt caaattagta ataccatcct  30300
gatcattgcg agtaataaca atatcatcaa cataaaccac cagataaata cagagattag  30360
gagcagaatg ccgataaaat acagagtgat cagcttcact attagtcatg ccaaattccc  30420
gaataattgt cctgaactta cgaaactagg ctcgacgaga ttgttttaaa ccatagagac  30480
ttgcataagt gacatacaat acctctagac tccccttgag caacaaaacc aagtggttgc  30540
tccatattaa ctttatcctc aagatcacca tggagaaagg cattctttat gtccaactga  30600
taaagaggcc aatgatgaac aatagccatg gacaggaaaa ggcgaacaga tacgacttta  30660
gccacgggag aaaagtgtca ttattatcaa gcccaaatag ctgagtatat ccttttgcaa  30720
tcagacgagc cttgagccaa tcaacctggc catccaggta gactttgact gcataaaccc  30780
aacgacaacc aacagtagac ttacttgaag gaagagaaca aactcccatg taccactcac  30840
tcacatgtaa agcaaacatc tcgtcaatca tagcctgtcg ccatcctgga tgagatagtg  30900
cctcacctgt aaacttagga atggaaacag tggacaaaga tgatacaaaa tcataatagg  30960
gtgatgagat gcggtgataa cttaaaccaa cataatgggg actaggatta agtttggatc  31020
atacaccctt tcgaagtgca atcagtggac taggaggagc caagtccgca ctagacgtgg  31080
atgacaatga taagtcaaga gtggtggcct cgtggttgga gatgtaggat gagcaactgt  31140
agactcctca gaagtcggta taggtaggag tacctgtgat gttgatgtgg atttaagagg  31200
aggaacaata gattcctcac aagtagatac aggtaagacc tcagatatat caagatgatt  31260
agatgaagta aagtaaggtt gagactcaaa aaatgtgaca tcgactgaca taagatatct  31320
acgaagatca ggtgagtagc agcgataccc cttttgaacc cgagaatagc caagaaagac  31380
acacctgaga acacaaggag ctattttatc tttttcagga gctaagttat gaacaaatgt  31440
actccttaaa acactaggag gaaagagtat aaagatgacc tagggaacaa tactgagtgt  31500
ggaaactgat tctagatgga agatgaaggc atccgattaa ttaagtaaca ggttgtaaga  31560
actgcatcgt cccaaaaacg ttgtggaaca taggactgaa tgagaagtgt gcgagcagtt  31620
ttaatgagat acctattctt tctctctact accctataat gttgaggagt atacagacat  31680
aggataatat tttgagaagt cataaactat tgaaactaag agaatacata ttttaaggca  31740
ttatcactac gaaaagcgaa taaaaacacc aagcggagtt ttaatttcag cataaaaact  31800
ctagaatatt gaaaacaact caaaacgatc tttcatttgg aaaatccaaa tacatcttga  31860
gtaatcatta atgaaactaa caaaatccaa atcttaaggt tgtgactcta ctaagacccc  31920
atatatcata atgaactaaa gacaaaacag actctacacg actcttagca cgacgtgaaa  31980
atgtagctcg aatatatttc ccaagttgac acgaatcaca atctaatgtg gacaaaccag  32040
acaccatctt ctgaagcttg gataaactcg gatgtcctaa acgtttgtga attaggtcta  32100
gaggatctgt agttggacat gttgtagagg gattgagtga gttaagatag tcaaggtctt  32160
gtgattcacg ccatgtgcca atcgtctgta ccgtactgcg gtcctgcata gtaaaagaat  32220
catcaataaa atatatatca caatggaatt cacgagtcaa atgactaaca gatgcgagat  32280
taaaggacaa ccggggacat aaaaaataga atctaaagtg acagaggaca tgtgattagc  32340
ttgtccaact ccttttgctt ttgtttagac ttcatttgct aaagtatcat tgggaagaga  32400
ttgtgaataa acaattattt gacaaaagtg acatattacc actggggtat caagttgctt  32460
agtcatacta agaatgtttg ggagagggtg gtggaagtga gggtaaggag gacagtgtct  32520
```

```
ctatccgaga accagttcgg attcatgcat gatcgttcaa ctgcggaagc tatccgtctt  32580
attaggaggc tggtggaaca gtacaaggat aggaagaagg atttgcacat gatgtttacc  32640
tagagtaagc gtatgacaag gtccctaagg aggttccttg gagatgtcag aaggttaaag  32700
gtgttccggt agcatatact agggtgatga aggacatgta tgatggagct aagactcggg  32760
ttaggacaat ggaaagagac tctaagcatt gtttggttgt tatggggtta cagtaaggat  32820
ctacgctcaa accgttctta tttgccttgg cgatggacgc attaacgtac catattcagg  32880
gagatgtgcc atggtgtatg ttattcgcgg atgatatagt tctgattgat gagacgcgag  32940
gcggtgttaa cgagaggttg ggggtttgga gacagaccct tgaatttaaa ggtttcaagt  33000
tgagcaggac taagacagaa tacttggaat gtaagttcag cgacgtgacg gaggaagctg  33060
acatggacgc gaggcttgat tcataagtca tccccaagag aggaagtttc aagtatcttg  33120
agtcagttat acagggagaa gatggggaga ttgacaagga tgtcacgcac cgtattaagg  33180
gcggggtgga tgaaatggag gttagcattc ggtatctttt gtcacaagaa tgtgccacca  33240
aaacttaaag gtaagttcta tagagcggtg gttagaccaa ccatgttgta tggggcagag  33300
tgttggccag tcaagaattc tcatatctag aagatgaaag tagcagaaat gagaatgttg  33360
agacggatat gcgggcatac tacgttggaa gattaagaat gaaaatattt gggtgaaggt  33420
gggcgtggcc ccatggaagt tgtgcccacc attaaagact gctatctgaa aactaattct  33480
ttgggcccaa acattctggc ccaaagtacc tcgtgaataa taatattgag ctcatgtctg  33540
acatgttgga agaggagtta ctagcaaaca cttatacacc tatgttggta acacaattga  33600
agaactacga aaaacactct tctgcaaagg aaaatgagaa gaagaagaag aagaagacga  33660
agaagaagga tgatgcaatg atcattgaag aaaaaggaga gcaggaggac ccatctaaac  33720
ttacaaagtc tagaggaaga ggaggaccca gagtttgatg cttccctctg ggtacaccaa  33780
aacatcgtca aacttaggca aggagtttgg ggtaaacatt caggggtgtg agaaggaagc  33840
tttggagctt ttcgtaaaat tacaactaga ggcataaaaa aaaaaaaggc aatccaggca  33900
tggaggtgac aaccttcgaa aagaaaggga ttcaaagaac tgaaagggct ggattttttgg  33960
agtaacttca agagtaatag aacaagaagt agggggttgc attattatca aagatcaatg  34020
aagattaaca ttgaagaagt gggaaatcca aaaagactcc accgagaagg atgatgcaat  34080
gatcattgaa gaaaaaggag agcatgagaa aaaacccgta gaaattgaca gcactcacac  34140
acaataagac gagataataa agtagtgagt tggccaattg aagaagcttt acctcttaac  34200
ttacaaagtc tagaggaaga ggaggaccca gagtttgatg cttccctctg ggtacaccaa  34260
aacatcgtca aacttaggca aggagtttgg ggtaaacttt caggggtgtg agaaggatgt  34320
tttggagctt ttcataaaat tataacaaga ggcatgggaa aaaaaaggaa atccaggcat  34380
gcaggtgaca aaaccttcca aaagaaaggg actggaagaa ctgaaagggc tggatttttg  34440
gcgtaacttc aagagtaata ggacaagaag tacgggattg cattattatc aaagatcaat  34500
gaagattaac attgtatcat ggaatgtcag ggggttaaat cgacatagaa aaagaatgtt  34560
gattaggagt ttaattcata ggtggaaagc agatgttttc tgtttccaag attcaaaatt  34620
aaaaggggac attagggagt ttataagaga actatgggca aataggtggt ttaaatatgc  34680
acagttggag gctagtgggc ctagaggggg tattattgtc ttatgggata gtaaaattgg  34740
ggagggggag atcagcagcc tgagctccta ttctgttact tgtaaattta taggtaaaac  34800
tcaggagtat acttggaatt tatccactgt atacgctcca aatgataggg aggaaaggaa  34860
agaagtatgg tgggaattag caggtgccag gggaattttt atggaccttg ggtaatttct  34920
```

-continued

```
ggggatttca atactgtgag gtacccacca gagaaaaaga attacagcaa aatcactaga  34980
gcaataaatg aattctcata atttattgaa gatatggaac tggtggatct acaacttgca  35040
ggaggaagtt acacttggag gacaggagat agacatgtga taacagctag actggatagg  35100
ttcttggttt ttatggattg gaatgagagc atcagaaaca ccaagcaatc agttctccat  35160
tgaattacct ctgaccattc ccctgtgatg cttcaatgtg gtaaccggta ccctgtcaaa  35220
tcctattaca agtttgagaa ttggtggctg gaaacagagg gcttcaaaga aaggattaaa  35280
gtctggtgga gctcttttgc ttgtgaagga agacgtgact ttattctggc tttcaaactt  35340
aaagcatcga aggaaaaaat tgaagaaatg gagtaaatct attcaaggaa acttggagat  35400
gcagaaattg agtattctta gtcaacttgc agaactagaa gagacacatg atcaaaggag  35460
ccttactgaa gaagaaatac acactaaata tgcagtctat ggagtttggg gagattgcaa  35520
aacatgagga ggtggcttgg agacaaagat ctagggctct ttggttgaaa gaagggacaa  35580
aaacatcaat tttttcctca aaattgcaag tgcacatagg aaatacaata acatagacca  35640
actgttactt gaaggaaaat ttgtggcgaa tccaacatac ataacaaata atattggtac  35700
attttatcaa aaactatata taaagattgc tagaggacaa tcttatgttg caaagtcttt  35760
tcgaagctta ggaaatttgg gatagtgtca ggcatgtgaa agggataaag cacctggacc  35820
tgagaactgg gaggtgataa acacggatat gatagctgca gttctttgtt catggaatgt  35880
ttgaggaaag ctttaatgtt acctttgtgg tattgattcc taagaagatg gaagctaagg  35940
aatagaagga ctttaggcct attatgatag gcaatgtgta caagatcttg atagaaagac  36000
ttaagaaatt ggtgaacaag ttggtgaagg gtcaacggat gacttttatt aaaggtagac  36060
agataatgga tgttgttcta attgccaaat gaatgtgtag atgcaagaac aaaggcgaga  36120
aacctacaat actatgcaaa ctagatattg agaaggcata tgaccatcta aattggaact  36180
ttctattgga atcgctgatg aggatgggct ttggtgtaag atgggtcagc tggatcaaat  36240
tctgcatcag cacaatgaaa ttctcaattt tgataaatgt ttcaccagta ggtttcttcc  36300
cttctcagag ggatttgaga cagggtgatc cactatctcc ttttattatt cattagtgct  36360
atgggaggct taaatgatat gttaaagact actcaagata acaactgcat acggggtttt  36420
aaggtgaagt ccagggcaga cagtactatt gagatttttc atcttcgata tgcagatgac  36480
gcacttatgt tctgtgaggt tgacaatgaa caattgaaag tgctgaaggt gatcttcatt  36540
ctgtttgaag ccacatctgt attacaaatt aactggaatg aaagctttat ctatctagtt  36600
aatgaggtaa ctaagatcca ctttttggtt ggaatcctag aaggtaaaat tggggaattg  36660
cctacagtta tttggggatg ccatgggggc caagagcaat tttaagggga tttggactag  36720
ggtcgtagag atatgtgaaa aaattttaac aaactggaag agttagtatt tatccttaag  36780
ggacaaacta atactaatca attctatact tgatgatttt cctacttaca tgatgttcct  36840
cttctcaatc catgtgaatg ttgtgaagag aatatatacc cttagaagga acttcctatg  36900
gggaggaaac tatgacaagg aaagatctat ttggtcaaat ggaagtctct cacagtcagc  36960
aagaagtaag agtgttttgg aatcaagaat tggagaattc agaaccaaag tttgatgatg  37020
aagtggctat ggagatttac tacagaagaa cattgtttgt ggaaagaggt gatcatggag  37080
aagtatggca tagaagataa acggataaca aagtctgtaa atagatctta tggagttagt  37140
cgatggaaat ccatcaggga cctatagctt cagctcttga ataagtccaa attctgaata  37200
ggaaatggat tgaaaatatc tttttggaag gataattggc taaccaagga actttgaaac  37260
```

aactctttct tgacatttac attccaaatc aacagcataa agcaataata gtagaattat 37320
gggctaatca aggttggaat ctcacataca gaagactatc aaaagacccg gagattggca 37380
ggtcaacaga gttcaaaggc actttggaac aatttaaaga ggtctatact tctatagact 37440
atttgacttg gcaagggaag tttattgtta attcagccta taaggaattc aacttctcag 37500
ctaactggat tggttgttgg ccatagaagt tgatttggaa agttaaaatt ccttatagag 37560
ttgcttgttt ctcttggctt ttggctaaag aggcagttct gacgcatgat aatctaacca 37620
agagagatta ccatttatgt tcaagatgtt atttatgtga agagcaggca gagacaacca 37680
atccactttt ttttgcattg taagttcact gcagttatgg aggattttca ttagtttaaa 37740
gggtatcatg tgggctatgc gtagaagtat acctgaagtt ctagcatact ggaaaaaaga 37800
aagaaatctt tccaattata aaaagagatg gaggattatc ctagcttgca tctggtggac 37860
catttgggaa gaaagaaatc aaagatgctt caaagataaa tcagtcatat tcagataatt 37920
aaaatgaagt ggctagtctt gttttatttt tggtgttaag tgttagatag ttatgtatta 37980
tgtataagtt gtctagtccc acattggaac gggagtaata tgtactatgt agagtatagc 38040
tataaatagg acttcttgta ctttattgta gagaatatat taataatata tttttcccgt 38100
gttgtctcac atggtatcag agaaaccgtg agatatcagt cgttgtgaaa aataccagcg 38160
gcttcgggaa gaaaaaaatc aatcaactgc taggtatatt agtcttcggc gaccgatcca 38220
ttaaatttct ctggcaaaga accactcatg ggccctcacg cgcccaccga aagaaatatt 38280
tccggcgagg ttccaatttc atgcgcccgc gcgtgaggca gtttccggtc aaattttgac 38340
aaaggtcctt tttgacagtt tgttcaccct gtaattccca gtctatccat cattttttt 38400 atttcgatca cttcgcaatt tctcgggcag ctacagtgat ttttccggca gaagcggtgt 38460
ttcctttgcc tgcttcagcg agatacagtt gattatttct attatttgtt tctagacctc 38520
tctccaatcc aacgatgtct ttggaatttg atgtatttgg ttctgaaaac acgagttcta 38580
gaaagtcaag cttcatgatt actttagagc cattaatggg gagttcaaac tatttagctt 38640
gggtttcctc tgttgaattg tggtgtaaag gtcaaggtgt tcgagatcac ttaatcaaaa 38700
aggctagtga gggctgtgaa aaggtcaatt taagcagttt atgacgtctg tataccactc 38760
agcagaatag gatagcaaag aaagaatatg cacatcattg agactgctcg cacacttctc 38820
attgagtctc acgttctgct acattttctg agcgatgcag ttctaacggc ttgttatttg 38880
attaatcgga tgcctttatc ttccatccag aatcagattc tgcagttagt attgttttct 38940
cagtcaccct tatacttttt tcgtcctcgt gcttttggga gcatgtgttt gttcataact 39000
tagctcccga aaaaaataag ttagctcctc gtgctctcaa gtgtgtcttc cttggatatt 39060
cccgagttta aaagtgatat tgttgctact cacctgatcg taggtacctt atgtcagttg 39120
atgttgcatt ttttgagtct agaccttact ttacctcttc tgaccacctt gatatatata 39180
tgaggtctta cctataccga ctcttgaggg gtttactata gctcctcctc tacatactga 39240
gccacagaaa tcttactcat acctaccatt ggggaatcta gtgttgctcc tcctagatcc 39300
ccagctacag gaacactttt aacttatcgt cgtcgtccgc gcccagcatc atgtccagct 39360
gattcacgtt ctgcacctgc tcctactgcg gactagtctc atcctaatct accaattgca 39420
cttcggaaag gtatatagtc cacacttaat cctaatccat attatgtcgg tttgagttat 39480
catcgtgtca tcacctcatt atgcttttat aacttctttg tccactgttt caattcataa 39540
gtttacaggt gaagcactgt cacatccagg atggcaacat gctatgattg acgagatgtc 39600
tgctttacat acgagtagta cttgtgaact tgttcctctt ccttcaggca aatctactgt 39660
tggttatcgt tgggtttatg ccgtcaaagt tggtccagat gaccagattg ccaaagggta 39720
tagtcaaata tttggggctt ggttacagtg atattttctc tcccgtggct aaaataccat 39780
cagttcatct ctttatatcc atggttgttg ttcgtcattg gcatctctat cagtttgaca 39840
ttaagaatgt ttttcttcac agtgagattg aggatgaagt ttatatgaat taaccaccta 39900
attttgttgc ttagggggag tctagtggct ttgtatgttg gttgcctcag acgctctatg 39960
gtctaaagta atctcctcga gccttgttta gtaagttgag cacagttatt cgggaatttg 40020
gccaactcgt agtgaagctt atcactttgt gctttattgg cattttactt caaatctctg 40080
tatttatttg gtggtttatg ttgacgatat tgttattacc ggcaatgaac aggatggtat 40140
tactgagttg aagcaacatc tctttcagca cttttagact aaggatctga gtagattgaa 40200
gtatttttta ggtattgtga ttgctcagtc tagcttaggt tttgttattt cacattggaa 40260
gtagaaaaac ttcaatcatt tttctttatt tgaaaggaag aaaaaaaagg taatatctag 40320
acctaaatat taatctgaag acaagtgagg cttgctcagt tggtaaaagc acctccacct 40380
acgatcgtta ggtcctgggt tcgagtcacc atggagggga agtgtggaaa cactatagat 40440
cctcctaatt tgggaggggg aaaaaaatat taatctgaat tgacatgaat ctcaatgaca 40500
atgaccaacg atttcctgca attcttttca gtatggaatg aataaaaaat caagctacaa 40560
gtctctatta aacgaaatgc actaacaggg atcactctca agaaaggaag tggttttggt 40620
tgttgttatt ccaggttgga taaatcactt tctttataaa tatcataaaa gacaagggct 40680
ttcttgcttc agcacatgtg ggaaatgccg gggggcttgg ctggtaccaa gctcgagcgg 40740
tctttctatc tttttggatt gcatgcccaa ggcaatgctt tttgtagatt gggatggatt 40800
gatcttcgca gaagtatgct ttagacattc ttgaggagac aggaatgacg gattgtagac 40860
ccattgacac acctatggat ccaaatgcca cacttctacc aggatagggg gagcctctta 40920
gtgatcctgc aagatatagg cggctggttg gcaagttgaa ttacctcaca gtaactagac 40980
cttatatatc ctttcctgtg agtgttgtaa gtcagtttat ggactctcct tgtgatagtc 41040
attgggatgt ggttttccga attcttcgat ataaaatcag ctccaagcaa agaactgttg 41100
ttcgaggatc gaggcccatg agcagatgtt gattgggcac gatcaccttc taatagacat 41160
tctatatctg gatattgtat gttaatagga gttaatttgg tgtcttggaa gatcaagacg 41220
taaaatgtag ttgatcggtc tagtgcggaa gcaaataatc gagcaattgt tatggtaaca 41280
cgtgagctag tttggatcaa acaactgctc aaagaattga aatttggaga aattgatgga 41340
accagtgtgt aataatcaag cagctcttca tattgcgtca aatccggtgt tccatgacag 41400
aattaaacac attgagattg actctcactt tgccggagaa aagatactct caggagatac 41460
cgttacaaag attgtgaagt cgaatgatca gcttagagat atttttacca agtcccttgc 41520
tggtcctcgt attagttata tttgtagcaa actcggtata tatgatttat atgcaccaac 41580
ttaagggaga gtgtgagata gttatgtaca acaaaatacc cggtataatc ccacaagtgg 41640
ggtatggagg gtagtgtata cgtagagctt acccttaccc tgtgaaggta gagaagctgt 41700
ttccaaatac cctcggctcc agtacaaatg aaaaggagca gtagcaacaa gcagtaacaa 41760
caatgatata gtaaaataac tgaagaaaga aataacatgt agacatataa ctccactaac 41820
aaacatgcaa ggttaatact attgccacga gaatggcaaa ggaatgttag atagttatgt 41880
attatatgta tattaatagt ctagtctcac gttggaatag gagtaatatg tactatgtag 41940
agtatagcta taactaggac ttcttgtaat atattgcata gagatatcaa taatatattt 42000
ttcctgtgct ttctcacgta aaggaatgta atgtacttag aagatcatga atctatcttt 42060
gatgttttag acacctcgtg agaacacaaa ggtttaggaa ctttattgtg ttctttgtaa 42120
ttatgggtga ctgccaatat gttacctttt cataaaaatg attatttggc cattggatta 42180
gtttcaacag cctctctgcc cctccgggta ggggtaaggt ctgcgtacat attaccctct 42240
ccagacccca cttgtgggat tatactgggt tgttgttgtt gttgttgtgg attagtttca 42300
acaattttga tagttctttt atttgaatca aactactcat tcacatggat tttgtatcgt 42360
atcattgagt taaaaaaatt ggttttgcta atttatcctc atgtataaca actacctatt 42420
tttcaatata ttggattcag gagcttgtag tagctggagt ttgctcttca aagggcaata 42480
agtgccgggt atcatgcaca gtgactccaa atacagatct cctttctgct ctaactctta 42540
tggagaaaca tgatctaagt cagctacctg ttatactagg ggacgtggag gatgaaggca 42600
tccatcctgt gggcattttg gacagagaat gcatcaatgt agcttgcagg tttttgacat 42660
tcaactttta cttcaaagat ataatgcttt ctggaaccat tgatgataaa atatgcaaga 42720
aacttgtgca gaagtcgcac tttactatcg attaccagat aaagttactt atcaagaagt 42780
caaatatatt gaacatattt ctctaaaaca ctttgactgg actgtaagca gaaacttact 42840
aaagtaggtc gtaagaaatg gtttgatagg gaaatcacca tctacactta aaagagttgt 42900
gtgaatttga attcttaaag catgtgaaag ttataaaaac ttgttattat ctaagcatct 42960
gaagcatttt ggccatccaa aggatcaaaa ataggaaata atttcatttg tacaatgaac 43020
tccctgcaca aattctcaca ctaggtgtat tctctattca tcactagcac tacatgtgtc 43080
actacgaatc atatacaata aatctttgta acataaaaga cgacacataa tatggaagta 43140
agccgagtat acaagggaag tttcatcatt acggtgagct ttttataaga taatcaagtt 43200
ttactggaaa agggcaaaaa ctctcccgta tagaagtata ccaaaaagta gaatacctta 43260
caaaaatatg attttctatg aacaacaccc tatcttctat acttgtaggg atctcatcgg 43320
ggcaccaaaa agagataaag ggataagagg cttttcctca aatgtacaaa atccttctct 43380
attccttcaa aagctctcct atttctctct ctgcacactg tccacataag ttcaatggag 43440
caacatccac gccctgtgtc ttcttttccg tcttctatag gtccagctga acatggcttc 43500
tttgactgag tgtggcatca acgttgaaga ccaaaccatc ccagtacttc caaccacaaa 43560
cgagacacta tatgacaatt tagaagaaga tgattcacat cttctcccga acatttacac 43620
ataaaacacc agctgataca tgtaatcttc ctcttcctca aattatcagc cgtcaggatc 43680
acccgtctcg tagctaacta ggtgaagaag cacacctttc tcgaaaacct caggatccat 43740
acagagagat atggaaaagc tgattcctcc atgcccagaa gcttctcata ataagactta 43800
acaaagaaac accactactt cccccccccc ccaaaaaaaa aaaatctcca tacatcgact 43860
ttcatgtgta attcttgttc gtgaaacgac ccaatcaacc tttggcacaa atctcccagt 43920
cttgcgagtt cctcctaaac ttcaaatcac aatgaacttc tccaccttgt agcctccgtg 43980
tcccttggac tggcaactcc tttggcatga aactttgtac atattaggag atgtgatact 44040
caaagtgttg ttcctgcacc aattgtaccc ccaaaaaact taccatgctc ccatcaccta 44100
acattgaatg atacgttcca aaatcttcgc actccttcaa gaaacttttc cgtaggcccc 44160
acccataagg gagtgtgatt ttttttgctc tccatcccct ctccaagaat ccattcccta 44220
aaccactgca ggacacttta acaatcacta tgtcactttt tctactagtt ctacattgag 44280
tgatatcttg atgtcattga aatgcctctg gaaaatcttc ttctcatcta aaagaacact 44340
tgtttgcctt ttgaatcccc ctctaacatt ttctatgttt cattcatctt tggtggaaca 44400
gagcattagc aactagagaa cagctttgct ag 44432

<210> SEQ ID NO 11
<211> LENGTH: 36854
<212> TYPE: DNA
<213> ORGANISM: Nicotiana tabacum
<220> FEATURE:
<223> OTHER INFORMATION: DNA sequence of NtCLCe from Nicotiana tabacum; sequence originating from the ancestor N. tomentosiformis; two start codons

<400> SEQUENCE: 11
atgattagcg gccaaaacac cgtgctgcac catcctccta attcgctctt caattcctta 60
tctcctcgcc atatctgtgt atctttctgt aacgacaaag ctttaaaaaa gtcagtcacg 120
cactccgccc ctcggtttgc tcgtctgtta aacaatgaat cacgaaagtt gttgggtcgt 180
catccaaatt gctggccttg ggctcgacga ccatctcttc ctccgggacg ttcctgtgac 240
ggaaacattg aaaaagaaca agatatgtgc gacagcagca aagacgatag tgatagtgat 300
agtggtatcc agataggatc tctgctcgag gaagttatcc cacaaggcaa taataccgct 360
ataatctcgg cttgctttgt tggcctcttc accggtatca gtgtcgtgct tttcaacgct 420
gcggtaagtg cgctataggt ctttcatttc tcttttcatc tactattctc ccttacttac 480
ttggcctcag tcaatcagcc ccctgcctac tttaaattat tgtacaattt atcagaggag 540
tatcctatac atcaaattca cataacttag taaaatatgc tgacattctg aattttaacc 600
ttaccagctt agaacatcca ggctagttca gaaacagata atctaaattg gcctcattta 660
taagtcattt tgttaatcaa gacatacaat ttggctcttg ataaaagatt atgcagcgcc 720
cgatgataac ctaatattta tcagcaaccc atatgtcact ttcttttgtt taaatgctct 780
cccatgtaat ttaacaatat tgtcaccata caaaagagaa ctgaagtgaa tgttccattt 840
gtggtcatat aacggatatc tcccttggtt aggttcatga aatacgtgat ctttgttggg 900
atggaattcc atatcgagct gcctcagagg agcccattgg agtacattgg caacgtgtaa 960
tcttagtacc agcttgtggc ggtttggtag tcagcttttt gaatgccttc cgagccactc 1020
tggaggtttc aactgaagaa agttggacat catctgttaa atctgtgttg gggccagttt 1080
tgaagacaat ggccgcttgt gtcacattag gaactgggaa ttccttagga ccagaaggcc 1140
ctagtgttga aattggtaca tctgttgcca agggagttgg agctctgctt gataaaggtg 1200
gtcgtagaaa gctgtcactc aaggctgctg gatcagctgc tggaatcgct tctggtttgt 1260
tccccatatt attcttggtt ctgaaccata catggtacat tttccttata attacatgta 1320
gcctgttgta tgctttcctc tttcctggga agcctttctg taaatgcaaa tgtgtttgca 1380
ctcaaaccaa taaactgtaa aaacagtgaa ccccttgagc aagcaaaagc actagaaaac 1440
caacaaatag atcccccccc caagatacca gtgaaatgac accgggtgac ccaaaaaataa 1500 agcagcttac atcttgactt tgagaggaac tgcaatcagc tataagtagg ttattaattt 1560
ccagtgcctg cattctgccc aagtactatg atatatttct gaagctttgt ttccccagtt 1620
cctttttcag acgtttgctg tcaataaagt tgagccagcc aacttggttc ccacaagcta 1680
ctaattttgt ccaagcttac tctatgggag aagttaaatt tcccaaattc cttgagcaga 1740
aaatgaaaaa tgaactcaaa gtgtcatatt aggcaactat ctaaagaaaa atacttaatt 1800
gaagtttaga taagaaaagt gaatatatat tgatgtagtc tccgttaggt gagaagcgca 1860
tcacttaccc agcaacatat ggacctaaaa tttactagtg aacttttcac attgtatcaa 1920

-continued

```
aagctcaaca aacagaaaga tgactagtcc taaaatgtta tttcacatca accttatcat   1980
acgtgcatta tttgttctct atatttctat ttcatccgat ataaccaatc gtcattgtaa   2040
attctataat gcctgtggtt acttttgtct ttagtgacaa atgacattta ggctaaccat   2100
gtagttattg actgatttcg cttgacgtct cttccaatta tgtagtagta gagtgttgag   2160
atatggatat gttaccttct aaaaaaaaag agtgttgaga tgcggatggt ttgctagctg   2220
gcttttgtct cccttcaagt tgaattagca aaagcaatgt ctcataagtt ggatagctag   2280
acaagaaaaa ctccaaatta ctttatgtag agtattctta agcttgagtc gcgagttgga   2340
aattggaatt atgtaaaaaa acctggaatt atttggttga gcctgctttt tatttttgtc   2400
aatatttcca gtatctaacc caacatgttt agagcaattc ccagagagcc tcaatacgag   2460
gcatttgcag agtctttatg agagtccagg aaggggcaca cactgtagag gtatagtgtt   2520
gtccttattt tttttttttt gataaggtaa gattttatta aaaggtacca agatggtgca   2580
aaattacaaa catccaaact aatacaacaa agcaactaca ttcctcctag ctcctctaga   2640
aaattcatat attgttccat atttttcatt acatgtcttt tacaccagaa atacaagttt   2700
aataagcatc tgtttttaat cctggataca tgctgccttt ccccttcaaa gcaaatcctg   2760
tttctttcca accatattgt ccagaacaca catagaggaa ttgttcttca tactatctgt   2820
tgactctttg ccactttttg ttgttgccat gtctccaaca aactttacac tggcaggcat   2880
tgcccacttg acatcatata tatttaggaa gagctaccaa cactgctttg ccactttgaa   2940
atggatgatt agatggttga ctgtttctgc ctcttcttca cacatgtaac accggttaca   3000
tagagcaaaa cctctcttct gcaagttctc ctgagttaga aaagcttcct ttgctccaat   3060
ccaaccaaaa cgggctactt taataagtgc ttttgacttc catattgctt tccatggcca   3120
atttgactga taaagccctt gtagtttttg taacaagcta taacaactgc tgactgtgaa   3180
aataccatca ttacttgctg cccagattaa tgagtctctc ctgttttcct ccaatctaac   3240
attattcaat aactgcatca attgggaaaa ttcatcaact tcccagtcat tgaggcccct   3300
cttgaagatt agctgccagc cggtgcttga atagaagtct aacactcttc catttttgtt   3360
aatagagcag ctatatagac caggaaactt tgatctaaga cttccatttt ccaaccacat   3420
atcagaccaa aacagggtat tattaccatt tccaagtttc agtttcacaa actgactata   3480
tttattccaa agattactaa ttgtgctcca aactccccct tttgaagaag attgaattga   3540
acgaggagcc cacatgtcct tcataccata cttggcatct atcacctttt tccataatct   3600
attcccatca taattatatc tccatagcca tttaaataaa agacttttgt tatgcatctt   3660
tagattcctc actcctaatc cccctctttc tttttttttc atcacctctt gccatttgac   3720
caagtgaaat ttcttgttat cattattacc ttcccacaaa aatttattcc tcatagtatt   3780
caatttttttc tccactgatg ttggcatttt aacgagagat attagataag taggtatacc   3840
atccatcaca ctattgacca gtgtaagcct accaccaaga gataaatatt gtcttttcca   3900
tgacaccagt ttactgctac atctatccaa gaccccctgc cacatctttg catcattctt   3960
ttttgctcca agtggtaggc ccagataggt ggatggtagc tgctccactt tacaacccaa   4020
aacatctgcc agatcatcaa tacaatgctc ggcattaata ctaaacacat tactctttgc   4080
caagttcact ttcaatcccg agacagcttc aaaagctagt agtactccta tgaggtgtaa   4140
gagttgctct ttttcagctt cacataatat caatgtatca tcagcataga gtatgtgtga   4200
gaaatacagt tcttcccccct ctctttttct aattttcaat cctctaatcc accctaactt   4260
ttctgctttt aaaagcattc tgctaaagat ttccatcacc aacaaaaata aatagggga    4320
```

```
tattggatcc ccctgtctta acccccctctg agaattaaag tatctatgtg gactcccatt   4380
aattaaaact gagaagctaa ttgaggatat gcagaatttt atccacccaa tccatctttc   4440
cccaaaattc gtatgtttca tcagatttaa cagacatgac caatttacat gatcataagc   4500
cttttccacg tcaagtttgc aggccacccc tttaatcttc ctcttgaata gatattcaag   4560
acactcatta gctaccatag cagcatcaat aaattgcctt cctcttacaa aggcattctg   4620
attatctaat atcaattttc ctatcaccat ctttaatctt tcagctatcg actttgcaat   4680
tattttatag acactgccca acaagctgat aggtctaaaa tctttcactt ccgctgcccc   4740
ctttttctta ggaataagag caatgaaaat tgagtttagg ctcttagtct tgtccttatt   4800
ttcagggttg aactagttct ttagaagttt cctaggcttc ctaatttcca aagttctgcc   4860
aggtcctttt ctagtgaagt acttgaagtt taataaatca aattttaatt tctaacatat   4920
cccgagaaat tcattcacaa attcaactgg tgacttctga tgcagaaaca taagcaactg   4980
cttatgggtt catatgttcc tgcaatttta ttgttgacat ggattggctt catatggttt   5040
tgttcctgca attttatcgc tgacactaat cctttcatat ggttttatgt ggggtggtaa   5100
atagaggtta agagacaaga agaggctgga aaaggtgggc agttcatttg ttagtagact   5160
actctattta ctaagagata tgatgtccca tacattactc gaattggctc caaatacaga   5220
ttccacttct ttgtcgagtt tccttattgt acagagttcg actcgtcaag ggaaattcac   5280
ttcctttgac tgaataatgc tagtttgagt agtaccttaa attaaatgga ccatttaatt   5340
ctatctactt gatagaatag actggtcatc aactagttgc aaatataatg acaactccgc   5400
catgtttgca gagtcacctg atgaagaagt acctcaatta gtagaccatt tcttgaatgt   5460
tctacagtat tctctatgcc tacatgacca catcactttt ccttttgcgt tgtgagaact   5520
tgaacttggt gagcgggggt tccccaggaa tggcatcttg gtggcagatg accattctgt   5580
ccttatctta gctaatgctt cttggattgc ctcactagat ttattatacc tttaataaat   5640
gtttgccatt gttctgccat aatagaggga tgtacctagc tggtgcttca catcacatag   5700
tccaaaacta atgaaatgct ttacaattgt cgagtactaa aggatgattt gtggaatcag   5760
atctcaaaca atttattttg aggaagaaaa ataccaaagg ttttttctgt ttgttggaag   5820
attaaaaatc ctttaaaagg taaagattta tgaacttaat tcagcatttt tgtggccatt   5880
gctgaaaaag agaaaacaat ggcacttatt cgagtttgct tatccaaaaa aaaagaagaa   5940
gagaatgtca cgtaatgcaa tttcatctta ggaaactttg caggagaaaa gcaagagtga   6000
taaaacagaa ctatttgttt ttttgataag ttgttgtgac ctatttcttt gtcattctta   6060
tttgctaata agctaatgta ccctgtacta tggttgtttt gacttaatcc ggggatgttc   6120
agtgagcatt ttcttgtttt ttctgctgtc agcatctgct gccttacagg aattcatttt   6180
ctggaaattt acttcttgtt ctgctaacat tttcctgtta tatcttgtca gtcattttct   6240
ctccatggtt atactgtttg tgtcactttg aaactctcct tgttttctac tttaaaggat   6300
ttaatgctgc tgtcgggggc tgtttctttg ctgtggaatc tgtgttatgg ccatcacctg   6360
cagagtcctc cttgtacttg acaaatacga cttcaatggt tattctcagt gctgttatag   6420
cttctgtagt ctcagaaatt ggtcttggct ctgaacctgc atttgcagtt ccaggatatg   6480
atttccgtac acctactggt aattttggac ttctttctcg agtttgattc ttaaatacaa   6540
ttgtacccgt cacttacagc aacaacaact acatttcaac agctagttgg ggttggctac   6600
acagatcatc actatccatt tcaatttctt tagtcccatt tctttcgaat attcagtact   6660
```

```
ttgggattct ctattatcag aggttctctt tattttctac tttgacgtac aaatctctaa   6720
atagattaaa gaagactcct agagacactg gcctaatgca aatgtaccac catgaataaa   6780
ccttaatctg aaatagctgg tatcgtatat aagaaccttt agctttaatt gtgttctata   6840
ttgatctttt gggacaactt ccgtccaata atattatgtc ttacttatac agttatactt   6900
atccttaaac tttactcttt agagtggtta tccgtagttc aagcttttgt tggcaccata   6960
gctagtttgg ttcttagtaa aaagttactc tttagagtgg taactttttg tcaatttttct   7020
tagtgaaaat ataacctctg tgacaaatct accaagtata aatccaatat ggttctgtgt   7080
catacttgta gtttatccaa gtctatgctc catcactctt acaaaggctc atcgtatgac   7140
taattttttt tgagaaaggt aacagtttgt attgataata agatcagcgc caggttagtc   7200
attagtgcta atagctgtat gtacaactcc aaaagagcaa aagacaagca cctggtgtaa   7260
cgtaaattac aagctgccta taaaatctat caggtctcct acctcactaa acatttcttg   7320
tttacaccaa aaaaataaaa caaggaaaga caatccatct taatcttctg aatggagttt   7380
cttttgcctt caaacatctc gagttccttt cgttccatgc aatccaccat atacaagctg   7440
ggatgctttt ccatttgtct ttatccattt tttctaccaa ttcccttcca attgactaga   7500
agttccaatg tggttctaga tatgacccaa ttaactccca acatataaaa gaacatgttc   7560
cacggatttg tagtgattct gcaatgtagg aacaagtgag cattactttc tacttcctgt   7620
ccacaaagaa aacatcttga gcaaatctgg aaacctcttc tttgtaagtt atcatgtgtt   7680
aaacatgctt ttttaccact aaccagacaa aacatgatac tttgggagga gttttaaccc   7740
tccaaatgtg tttccaaggc cacacctcag tcattgaaac attatgattt agagtccagt   7800
atgcatcttt tactgaaaat gcacctttgc tattcagctt ccaaactatt ttatctatgg   7860
tcttgttagt ttacagctat gtatatagtg tagtcttgtc ccacattgga ataggagtag   7920
tatgtccttg tatagtatag ctataaataa ggacctcttg tattgtattg aacatccaat   7980
atcaataaca tattttctcc cgtgctttct cacatggtat cagagcaatt gtgagagatt   8040
tatcgctgcg cataaattcc agcgactccg ggaagagaaa tcagtcaccg gaagtctttt   8100
tccgacgact ctttcaaggt tgtttgcgtt tgctttataa atccaacact accacaagag   8160
taatcactgt ccggcgacca aaccccagta aaaatctccg gcagcagcct cctcacgcca   8220
ccagaagctc acgcgccggc gcgtacgacc acttccgtcc attttttgaa aaacttcctt   8280
cagaacagtt gggtcgcctg gtaattccta tcctacccct actgttttca tttcattccg   8340
accactttga gtttttttccg gctgctacag tactattccg gcagctatag tactattccg   8400
acaactacag taagattccg gctgctacag tatttcatta ttctgttttt gtgtttcctt   8460
actctgtttc agtggattac aattgattct ttctcttatt tggtaataat ttgcaacaat   8520
gtctatggga tttgatgttt ttgggtctag aaacatgagt tctggaagct ctagtgttat   8580
tattacctca gaaccttaaa tgggaggttc aaactactta gcttgggctt catctgtcga   8640
gttgtggtgt agaggccaag gtgttcaaga tcatctaatc aaaccgtcta gcgaaggaga   8700
tgaaaaggca ataacacttt ggacaaaaat cgatgctcag ttatgtagca tcttgtggcg   8760
atctattgat tccaagttga tgcccttgtt tcgtccattc ctgacatgtt atttggtttg   8820
ggcaaaggca cacaccttat acactaatga catatctcgc ttctatgatg tgatatcgcg   8880
gatgacaaac tgaaagaagc aagaattaga tatgtctact tacttgggtc aagtacaagc   8940
aatcatgggg gaatttgaga agttgatgcc agtttctgct agtgttgaaa aacaacaaga   9000
gcagcgacaa aagatgtttc tcgctcttac cctcgctgaa cttcctaatg atcttgattc   9060
```

agtacgcgac catattttag ctagtccgac tgtcccgaca gttgatgaat tattctctcg 9120
attactccgc cttgctgtag caccaagtca cccagtgatc tcatcacaga tacttgattc 9180
ctctgttctt gcatcccaga caatggatgt tcgggcatct caaactatgg agcatagacg 9240
aggaggaggt cgttttggaa gatctagacc caagtgttct tattgtcaca aacttggaca 9300
cactcgtgaa atgtgttatt ccttacatgg tcgtccaccc aaaaatgctt acattgctca 9360
gaccgagact ccaggtaacc agggattttc tttatctaaa gaagaatata atgaactcct 9420
tcagtatcga acaagtaagc agacatctcc acaagtagcc tcagttgctt agactgatac 9480
ttcttttact ggtaattttt ttgcttgtgt ttcccagtct agcactcttg gcccatgggt 9540
catggactca ggcgcttctg atcacatctc tggtaatata tcacttttgt taaatattgt 9600
atattcatag tctcttccca ttgttacttt agccaatgga tgtcaaatta cggcaaaagg 9660
agttggacaa gctaatccct tgtcttctat caccctagat tctgttcttt atgtccctgg 9720
ctgtcttttt cgtcttgcat ctgttagtcg tttgactcgt gccctccatt gtggtatata 9780
ttttattgac gattctttta ttatgcagga ctgcagtacg ggacagacaa ttggtggagg 9840
acgtgaatca gaaggccttt actaccttaa ctcacccagt ccttccacaa catgtctggt 9900
tacagatcct ccagatctaa tccacagacg tttaggacat ccgagtttat ccaaacttca 9960
gaagatggtg cctagtttat ctagtttgtc tacattagat tgtgagtcgt gtcagcttgg 10020
gaaacatacc cgagcctcct tttcgcgtag tgttgagagt cttgcatagt ctgccttctc 10080
cttagttcat tctgatatat ggggtcctag tagagtaagt tcaaccttgg gatttcgtta 10140
ttttgttagt ttcattgatg attattcaag atgtacttgg cttttcttaa tgaaagaccg 10200
ttctgagtta ttttctatat tccagagttt ctgtgctgaa atgaaaaacc aatttggtgt 10260
ttctattcgc atttttcgca gtgataatgc cttagaatat ttatcttttc aatttcagca 10320
gtttatgact tctcaaggaa ttattcatca gacatcttgt ccttataccc ctcaacaaaa 10380
tggggttgct gagagaaaga ataggcacct tattgagatt gctcgcacac ttctaattga 10440
atctcgtgtt ccgttgcgtt tttggggcga tgcagtgctc acaacttgtt atttgattaa 10500
tcggatgcct tcatctccca tcaaggatca gattccacat tcagtattgt ttccccagtc 10560
acccttatac tctcttccac cccgtatttt tggaagcacg tgttttgttc ataacttagc 10620
ccctgggaaa gataagttag ctcttcgtgc tctcaagtgt gtcttccttg gttattctcg 10680
tgttcagaag ggatatcgtt attattctcc agatcttcgt aggtacctta tgtcagctga 10740
cgtcacattt tttgagtcta aacctttctt tacttttgct gaccaccatg atatatctga 10800
ggtcttacct ataccgacct ttgaggagtt tactatagct cctcctccac cttcgaccac 10860
agaggtttca tccataccag ccgttgagga gtctagtgtt gttcctcgta gttccccagc 10920
cacaggaaca ccactcttga cttatcatca tcgttcgcgc cctacatcgg gcccaactgg 10980
ttctcgtcct gcacctgacc cttctcctgc tgcggaccct gctcctagta cactgattgc 11040
acttcggaaa ggtatacgaa ccatacttaa ccctaatcct cattatgtcg gtttgagtta 11100
tcatcgtctg tcatttcccc attatgcttt tatatcttct ttgaactcgg tttccatccc 11160
taagtctaca ggtgaaacgt tgtctcaccc aggatggcga caggctatga gtgacgagat 11220
gtctgcttta catacaagtg gtacttggga gcttgttcct cttccctcag gtaaatctac 11280
tgttggttgt cgttgggttt atgcagtcaa agttggtccc gatggccaga ttgatcgact 11340
taaggcccgt cttgttgcca aaggatatac tcagatattt gggctcgatt acagtgatac 11400

```
cttctctccc gtggctaaag tggcttcagt ccgtcttttt ctatccatgg ctgcggttcg  11460
tcattggccc ctctatcagc tgaacactaa gaatgccttt tttcacggtg atcttgagga  11520
tgaggtttat atagagcaac cacctggttt tgttgctcag gagggggtct cgtggccttg  11580
tatgtcgctt gcgtcggtca ctttatggtc taaagcagtc tcctagagcc tggtttggta  11640
agttcagcac ggttatccag gagtttggca tgactcgtag tgaagctgat cactctgtgt  11700
tttatcggca ccctgttgac attccgatgg atccgaattc taaacttatg ccaggacagg  11760
gggagccgct tagcgatcct gcaagctata ggcggctggt tggaaaatta aattatctca  11820
cagtgactag acccgatatt tcttatcctg taagtgttgt gagtcgattt atgaattctc  11880
cctgtgatag tcattgggtt gcagttgtcc gcattattcg gtatataaaa tcggctccag  11940
gcaaagggtt actgtttgag gatcaaggtc atgagcagat cgttggatac tcagatgctg  12000
attgggcagg atcaccttct gatagacgtt ctacgtctgg atgttgtgtt ttagtaggag  12060
gcaatttggt gtcttggaag agcaagaaac agaatgtagt tgctcggtct agtgcagaag  12120
cagaatatcg agcaatggct atggcaacat atgagctagt ctcgaccaaa caattgctca  12180
aggagttgaa atttggtgaa atcaatcgga tggaacttgt gtgcgataat caagctgccc  12240
ttcatattgc atcaaatccg gtgttccatg agagaactaa acacattgag attgattgtc  12300
acttcgtcag agaaaagata ctttcaggag agattgctac aaagtttgtg aggtcgaatg  12360
atcaacttgc agatattttc accaagtctc tcactggtcc tcgtattggt tatatatgta  12420
acaagctcgg tacatatgat ttgtatgcac cggcttgagg gggagtgtta gtttacagct  12480
atgtatatag tgtagtcttg tctcacattg gaataggagt agtatgtcct tgtatagtat  12540
agctataaat aagacagtac taacgtccct tttgccgggg gttctgcatc tttaaataga  12600
tgcacgtggt tccatagcag accgtgttga tcacagatcg tgctgcatcc tcttcccagc  12660
ggactcggtg agcccctctt gtattgtatt gaacatccaa tatcaataac atattttctc  12720
tcgtgctttc tcacaggtct gtgatgtacc cttgaaaggt tcaagagttt ggaggaagat  12780
agaaactctg tttatctccc aatcatccaa agatcttcta aagttccagt tccatccttg  12840
tgagctccag actgacttac caatgcttgg ctttgaagac ttagagagaa taagtcagga  12900
aaaatctttc aaccttcctt gccctatccg gtgatcttcc caaaaagatg tcttcaaccc  12960
attgccaaca ttgatcctga tattgctact gaaagatttc ttttggtggc aggattactc  13020
tcattaacaa tgtacttgac aatctccata catacgaatg tctctttacc ctcttgccat  13080
taaggttgta aagagacttg tcaaattaag aagaggtttc ctatggaact gtttcaagga  13140
aggaacctcc tttcctttgg tcaagtggag ttaagtcata taatctagga agtggagact  13200
tgggtataaa atagctgcaa ctacagaaaa ggagcatctt atttaaatga tcacgcaaat  13260
gtgcccaaaa ctttaaatat ctgcggagca tatggttgta gcaaaatttg aatcttccgg  13320
tcaatgttgc tcatgtccag tgaataccccc tgatggtgaa agtgtcctga agggaagcag  13380
gaacttattg gaggaattgg catttaacac tcagcatttc gttaggtcat agcccgctga  13440
aaattgagtg cccagattta tatagttttg ctctaaactg acgatgcagt tgcacaacat  13500
acgacaaact aaggtgggac atcttcttcg gaaggaattt tgaggattaa gagatagagt  13560
ggttgattca gttgcaaatg aagcttcaag ggttcaatat catccaggag acaccggatt  13620
ctgatagata aaacaacaga aagatgaaca ctactttgtt aggcttgtta caagttgcta  13680
tcgtctttct tatctcggca cacaatttag atttgggaac ttatttggaa aatagagtgg  13740
ttgtttttgt gaatagcatc agacaaagct tctgagctgg tacgacagaa aactcaacag  13800
```

ggagaataaa agactgtggt tcacgatttc tgcatgcatc ttgtaggtta tttggtgggt 13860
aaaatattta atgttttgaa gggaaggtag aacatgttca taggcttaga ttcaaatgtt 13920
tgtatttttt tggctctttg gtgagagatg ctgaatgtaa atgacatagg cagctgacta 13980
taatttctca gctccttgct ttttaaattg gcaggcactg atatgtacat gtgaacatcc 14040
aacacttttg tggtgccgtt ccgatgaata aagcacatta atcacttact gatcaggagt 14100
aatagtttag gagttctaga atttttgtac ataaaatgaa ccaaaaagaa tatcggaatg 14160
agaacatgtt tcttttttg tttcttcttt ttcgtacaaa tttcaataac acttctgata 14220
gaatagctag gtccatttga attcctttgg agacccttac acaaccaatg aatggcaagt 14280
atagcatttt ctaacaccct cccacatgta taatccagtt tttagggttt agatgtggat 14340
ttgatttgac cttattgcct ttttttgttt ttgttctttt tgaagtagag agtgaggagg 14400
ctcacaacga cgggctacgt agagcgagat taattcggct caacgggcta atgattggac 14460
ttacatgcta caacaatgtt aggagaaaga gagagagaga gagagaagcc cagagcagtt 14520
ccacgagtta agaaagagaa gtccaaagcg attgaatatg aagagagaaa gcggttgtgc 14580
taacaggctc cctcaagttt ggctctgagc atccaactca aaaccttaag gcaatgagta 14640
gagtagccca ggaccattta aactcctgtt gaaaacctta cacaaccaat aagggaacaa 14700
gtgtaacatt ctcttacaac cctaccgtct tataagtcag ggctctaatt tagcataaaa 14760
tcaaagtgag gcgatctact atgaaatgaa gaaaataact gataaatata aagaatgtta 14820
attctcccat atagcctgaa tgttcccaga acaaaataaa ttagtctcat gatttatcat 14880
taacatgatg ttcctcttat tttgagtgat taggaaggtt aatcaaggag taaattcttt 14940
ctaatttgta tcgtctagaa ttatttgtct aacaaatttt cagattaccg gtgatcaaaa 15000
gaggaaaata ttttgcatac aacgttacca taccttacaa aagggcgatg aacatttttt 15060
tattttatta ttgtcctttt tttcaattag gggttatgca gtcttcctcc acgtgatatt 15120
actcttagaa tcacgttttt gtcattgcta ttacttactg tggtaagtac aaatgtgttt 15180
tgaactcttt ttggtatgta ttattgagtt aatttttcgt ttccatttca gagctgccgc 15240
tttatcttct gctgggcatc ttttgtggct tagtttcagt ggcattatca agttgtacat 15300
catttatgct gcaaatagtg gaaaatattc aaatgaccag cggcatgcca aaagcagctt 15360
ttcctgtcct gggcggtctt ctggttgggc tggtagcttt agcatatcct gaaatccttt 15420
accagggttt tgagaatgtt aatattctgc tagaatctcg cccactagtg aaaggcctct 15480
ccgctgatct gttgctccag cttgtagctg tcaaaatagt aacaacttca ttatgccgag 15540
cctctggatt ggttggaggc tactatgcgc catctctatt catcggtgct gctactggaa 15600
ctgcatatgg gaaaattgtt agctacatta tctctcatgc tgatccaatc tttcatcttt 15660
ccatcttgga agttgcatcc ccacaagctt atggcctggt atgaatttgt cttttgttag 15720
aagtagcatt acatatctgg ataagtgagt tttttattat tgaaaagtaa taacaggaga 15780
acaagagaat atatcaccca aatctacttc tttcctctct tctattcttc tgaaattcaa 15840
ggtcctttaa ctcctccaca gtctgtctag ttattgatcc tgtagactta attcacatag 15900
gtttaggaca ttcgagttta tccaaacttc atgaaaaggt ttctaatttt tttacattac 15960
attatgagtc gtgtctactt gagaaacata tcactccatg tttctatagt ctgttttctc 16020
cttagtttat tctgatatgt ggggtcctat taagtcagtt caaccttgta ttttcattat 16080
ttttgcagta tcattgataa ttattcaaga tgtacttgga ttttctttac aagagatagt 16140

```
tctcagttgt tttttgtgtt cctaagtttt tatgctgcaa tacaaaattg gtttgatgtc  16200
tctatttgca tttttcccaa tgataatgcc ttagaatatt ttcttttccg tttcagtagc  16260
ttattatttc tttaggaact ctttatcaga aatctcaact gagatagatg agaggaagaa  16320
taagcatatc attggtctca ttcagtcccc tgtcaagctt agtttcttga gcgatgcggt  16380
ttcacgtcct tttattagat taattggatg cctcatctgc tatccaaaat cagttaactt  16440
tcgatattgt ttcctcgctt acctttatac tctctttccc tcgagtcttt gggagcacat  16500
gttttgttca ataacatagc tcctggaaag tgaccagcgc aaccgacaaa caaggccttc  16560
ttaatgtaga aggtggacat atgctattct agccacggga aagaaagtaa tattgtaatc  16620
aaacccaaat atctgagtat aacctttggc aatggcgatc aatttgatta tatggaccaa  16680
ctttgcctgc atatacccac cgacaaccaa taatagattt accgggaggt agagaaacaa  16740
gctcccaaat accactaata tgtaaagcag atatatctct gatcatagct tgtccttgtg  16800
gacataggga tagaaattaa ggacaaagat gacacaaaag cataatgcgg tgatgataaa  16860
cgatgataac tcaaatcaat ataatgggga tggggattga gagtggatcg aatatctttg  16920
cggaatgcga ttggtagact aggaggagag aagtctgtgg acatgatgtt ggactgagat  16980
caataataag tcaagaatgg tggagctaca gaacatggaa ctggagctgt aggtgacata  17040
atcggagctg taggaggtgg agctatagag gaaggtgaag gagagatagc gactgaatct  17100
ccaaaagatg aaaccggtaa tacctcaaaa aatgtctaag agatcatttg gacctatgaa  17160
gtatgattgc gtttttaaaa aggtaacatc ataaggtcag gtgaataaca ttgatatccc  17220
cgttgcatcc tcgagtaact tagaaatata catttgagag cacggagagc taacttatct  17280
tttctggagc aaggttgtaa acaaaacacg tgctcccaaa gacacgaggt ggaagagaga  17340
aaggtgagtg gggaaacaag acagaggatg aaacttgact cttgatagtt gaagatgaca  17400
tacaattaat aagacaatag gatgtgagat ccaatgacag ttctcatgaa ctgctgaaat  17460
ggagaagaca aatactctgg ggcgttatca ctacgaaatg tgcagttaga aaccccaaat  17520
tgattttgga tttcagtgtg gaaggtctaa aaaatagaga acaactcaga ttgatttttc  17580
atcaagaata tccaagtgga cttggaataa tcatcaatga aactgacaaa gtagcggaat  17640
tccaaggtag aactaacccg acaaggaccc caaacatctg aatggactaa agtgaaaggt  17700
aactctaccc gattatcagg atgtcgaggg aaatgagagt gagtatgcct tctgagcgga  17760
tatgactcac gctctagagt ggacaagtga gacaaacgag gtactatttt ctaaagttct  17820
gataaattgg gatgtcctaa ctgtatatgt aataaatctg gtggatcagt aaaaggacaa  17880
gctgtagggg gaaaaaaata ccaaatattt ccagaagatg gcaaactaca acagaagatg  17940
caactgcatt aacatgctca ggataggtga tgaaatcatt gaggacaaag agttgatcaa  18000
gaaggagatt ctggaatttt accagaactt atatagtgaa aatgaaccct ggaggcgcag  18060
tgcaaatttc gaagacatct cctcactaag catagaagag aagaactggt tggaagctcc  18120
atttgtagaa atagaggtgc ttgaagcttt gaaatcatgt gccccttata aagcaccagg  18180
tccagaaggc ttcactatgg atttctttca gaaaaattgg gatactctta aaacagacat  18240
catggctgca cttaatcatt ttcaccagag ctgtcacatg gttagggctt gcaatgccac  18300
cttcattgcc ctaattccaa agaaaaatgg tgctatggag ctcagagact acagacctat  18360
tagcttgaca ggtattgtat acaaattggt ttcaaagatt ttagcagaga ggctcaagaa  18420
ggtaattgac aaactagtct cgggggaaca aaatgctttc atcaagaaca ggcagatcac  18480
tgatgcttcc ttgattgcca atgaagtgct ggattggaga atgaaaagtg gagaaccagg  18540
```

```
cgtgttgtgc aaactggaca ttaaaaaggc ttttgatcaa ttaagctggt cttacctcat  18600
gagtatcttg aggcagatgg gctttgggga gaaatggaga agatggataa actattgcat  18660
ttcaactgtc aagtactctg ttttggtgaa tagggaccca atcggttttt tctcccccca  18720
aaagggccta aggcaggggg atcccctctc cccc ttccta ttcattctgg cgatggaagg  18780
actcactaaa atgttggaga aggctaagca actgcaatgg atacaaggct ttcaggtggg  18840
aaggaatcct gccagctcag ttacagtatc tcatctactc tttgcggatg atactcttat  18900
tttctgtggt actgagagat cacaagcacg aaatctcaac ctgacactga tgatcttcga  18960
ggcactatca ggactccaca tcaatatgat aaagagcatc atataccctg tgaatgcagt  19020
ccccaacata caagagctag cagacatcct atgccgcaaa acagacactt tcccaaccac  19080
atatcttgga cttcccttgg gagctaaatt caaatcaaaa gaagtttgga atggagtcct  19140
agagaagttt gaaaagaggc ttgcgacttg gcaaatgcaa tacctcccca tgggtggcag  19200
gttaacttta atcaatagtg tactggacag tcttcccaca taccacatat ctttgttccc  19260
aattccaatc tcagtcctaa agcagatgga caaactcaga aggaagttct tatgggaagg  19320
atgcagcaaa acacacaaat ttccactagt gaaatggctg aaggtaactc aaccaaaatt  19380
caaaggagtc ttgggaatca gggatgctat gctcttaaaa tggctctgga gatatggaca  19440
ggaggaatct aggctatgga aggacatcat atttgctaaa tatggagcac acaaccactg  19500
gtgttccaag aaaacaaact ctccttatgg agttggtctg tggaagaaca tcagcaacca  19560
ctgggatgaa ttcttccaaa atgtaacttt caaagttggg aatgtaactc gtataagttt  19620
tggaaggata gatggcttgg aaatacacct ttgaaagaca tgtttcccag tatgtatcag  19680
attgccgtga ccaaagactc cactgttgct cataatagaa acaatgacac ttggtaccca  19740
cttttcagaa gaaatttgca ggattgggag gtcaacaacc tactcacaat gttaagctcc  19800
ctagaatgtc ataacattga agatcaacaa cctgacaaac ttatttggga aaattctaag  19860
agaggcaagt acacagtcaa agaatgatac attcacctct gtgaccagaa tccaatatat  19920
aactggccat ggaaacatat ctggagaact aaagtgccta ccaagatgac ttgcttcaca  19980
tgattgtctc taaatggggc ctgtctcact caagacaact taatcaagag gaacatcata  20040
taagttaata gatgctacat gtgccaacaa cagtcagaaa gtgtaaagca cttattcctt  20100
cactgctcag ttgcaaaaga aatttggaac ttcttctaca ctacctttgg tctaaaatgg  20160
gttatgccac aatcaactaa gcaagctttt gaaagttggt atttttggag agttgataaa  20220
tccattagaa aaatctggaa aatggtgtcg gccgcaagtt tttggtgtat ttggaaagaa  20280
aggaactgaa gatgttttga tggcatatca actccactca aggctgcgtg tttagttaac  20340
ttattttgct ggaactatct cacccctgtt aatagtgctg atacttctgt ggatttcatt  20400
agccccctga tagtagcata ggcttttgta aatggagcta attatccttt ctcttttgta  20460
ctctttgcat cttcttgatg ccttttaatg aatctaattt acttcatcaa aaagaaaatg  20520
acaagttgtt gaaggaggaa aagatgtgag tccatgtgat ttagcaagga taaggtacta  20580
aagtccattt gattcacgtc cggtaccaat gatccgtctc gtgctgcatt cctgtattaa  20640
aacagagtca tcaagaaata aaatagagca aataagtgat tggccaagcg actagtggat  20700
atgagattaa aaggactatg gggaacataa aaaactgaat tcaaaggtaa ggaaggaagt  20760
ggactagctt aacctattct agttgccatg gtttgagaat cgttggccat tgtgactatt  20820
ggaagtgatt gagagtaaga aatagtagtg aaaggagatt tgttacccga aatataatta  20880
```

gatgcacctg aatcaatgac ccaaaagtcg gaagaagagg aaacacaagt cacgctatta 20940
cctgtttgaa caatagagat tagtttggat caaatagttg tatagagaac tgaaatttgg 21000
agaaatcaat catatagaac ttgtatgtga ttattgttgc cctttatatt gcgtcaaatc 21060
ctaaaacaca ttgagattaa ctgccactta tcacagaaaa gatattctct agagacattg 21120
ttacaatttc atgaagtcaa gtaattagct tgaacatatc ttcagcaagt ccctcgtcag 21180
tcctcatatt agttacattt gtaacaatgt cggtacataa gacttataag caccagtttg 21240
aggaggagtg gtagagagtt gatgtacata gttaaagtag atatacttac acttagtgtt 21300
atgtaaagag tggatataaa aagggatcag cataagacaa ttgtcttcgc gcgtcttaac 21360 attttttcc tgtctttatt tctctcatgg tatcagataa cctatctcta tcttggttta 21420
cccaatggtt ggcccccata ttgtattagc catgctccag ttgactaggc ttggacgggc 21480
agaggtgtta aattatccca tattggttga aagaatgagc tattgtctcc ttatatggtc 21540
ttagacaatt ctccaactca tgagatattt tgttttggct gagttagccc taaggtttat 21600
tttttgtcat attctttaac cttatggcaa tgcttgtaca cggaaaaacc ggagtgcaag 21660
acttaaatta ggagaaggaa actattgaag gtgaggaact taaagggttg tgagaataca 21720
cgggagaaaa aaatcttaat actatctagt ggccttgtat atcaaatgat cagcttgcaa 21780
atattttcac caagtccctc actggtcctc gtattagtta catatgtaac aagttcggta 21840
tatatgattt gtatgcaccg gcttgaggtt atgcatattc tattcctcct actatatatg 21900
tgactaggaa atattttact cctactgcat atgggactag gactatttac acataactat 21960
ctaacattcc cctcaagcca gtgcacacaa gtcatatgta ccgagcttgt tacatatgta 22020
actaatacga ggaccagtga gggatttagt aaaaatatct gcaagctggt cattcgacat 22080
acaaggccac tagactcccc ccgagcaaca aaaccaggtg gttgctgata aacagaaact 22140
ggccgaaaag ttgccggaaa aatttgaaaa tagtgagact aagccgaatt ctacactaca 22200
aaataggttc taaaacacca ccagaaaaca aaaacttttc tagaaattac tcttcacacc 22260
ggaaaaaata aaagttgtca gaatttgatg taatttatat agataggttc ggaatcactg 22320
gaggagtaag ttgtcccgaa gaagttttgt caaaaagtgg ccggaatggc tcacatgcgc 22380
cggaaaactt actgtagctc gcaggaaccc tagttctggc ggtgcgtgga ggcgcgtgac 22440
ttaagattaa gatgcttaca ggactatctt gagaaatata catattatat agacgcttga 22500
gttgcttccc aatcctaaat agaagctttt attcgtaggc aagaagggaa gcagctttac 22560
ttgagccaat agctttcaag gtgcacgttg tcacaccaag gacatccaga atttgatttt 22620
atagggggtg tgagaaagca cgggagaaaa tatgttattg atatttggat aataaataca 22680
atacaagagg tccctattta tagctataca ctacaaggag atattactcc tcttccaatg 22740
tgggacaaga atacactata catatctgta aactaacact ccccctcaag tcggtgcata 22800
cacatcatat gtaccgatct tgttacacat gtagctaata cgagaaccaa taagagactt 22860
agtgaaaata tctgctagtt gatcattcga ctttacaaac tttgtaacaa tatctcctga 22920
aagtattttt tctctgacaa agtgacagtc gatctcaatg tgtttagtcc tctcatggaa 22980
caccggattt gacacaatat gaagagtagc ttggttatca cacattagtt ccatcttgct 23040
gatttctccg aattttaact ccttgagcaa ctgcttgacc caaaataact cacacgtcgt 23100
catagccatg gcccgatatt cggcttcggc gctagatcga gcaactacat tctgtttctt 23160
gctcttccac gagaccaaat tacctcctac tagaacacaa tatccagaca tagaacgtct 23220
atcaaaaggt gatcttgccc aatcagcatc tgtgtaccca acaatctgct cgtggccttg 23280

```
atcctcgaat agtaatcctt tgcccggagc tgactttata taccgaagaa tgcgaacaac  23340
tgcatcccag tgactatcac agggagaatc cataaactga cttacaacac tcaccggaaa  23400
agaaatgtca ggtctagtca ctgtgaggta attcaatttg ccaaccaacc tcctatatct  23460
cgtagggtct ctaagaggct ccccctgtcc aggcagaagc ttagcattca gatccatagg  23520
agagtcaata ggtctgcaac ccatcattcc agtctcctca agaatgtcta agacatactt  23580
ccgctgtgaa ataacaatac ctgagctaga ctgagcgacc tcaataccta aaaaatactt  23640
caatctgccc agatccttag tctggaagtg ctgaaagaga tgttgcttca gattagtaat  23700
accatcctga tcattgccag taataacaat atcatcaaca taaatcacta gataaataca  23760
cagattagga gcagaatgcc gataaaacac agagtgatca gcctcactac gagtcatacc  23820
gaactcctga ataattgtgc tgaacttacc aaaccaagct cgaggggact gtttcaaacc  23880
atatagtgac ctgcgcaatc tgcacacaca accattaaac tcccctaagc aacaaaacca  23940
ggtggttgct ccatataaac ttcttcctca agatcactgt ggagaaaagc attcttaatg  24000
tctaactgat aaagaggcca atgacgtaca acagccatgg acaaaaagag acgaacagat  24060
gctactttag ccacgggaga gaacatatca ctataatcaa gcccaaaaat ctgagtatat  24120
ccttttgcaa caagacgagc cttaaaccga tcaacctggc catccggacc gactttgact  24180
gcataaaccc aacgacaacc aacagtagac ttacctgcag gaagaggaac aagctcccaa  24240
gtgcaactcg catgtaaagc agacatctcg tcaatcatag catgtcgcca tcctggatga  24300
gatagtgcct cacctgtaga cttagggata gaaacagtgg acaaagaaga tataaaagca  24360
taatgaggtg acgacagacg atgataactt aaaccgacat agtggggatt aggattaagt  24420
gtggatcata cacctttgcg gagtgcaatt ggttgactaa gaggagacaa gtccgcagta  24480
ggtgcagaat ctgatgcggg gcgtgaatca cctgggcctg atgctggata tggacgacga  24540
tgataagtca agagtggtgg agctgccgaa ggttgaactg gattatgtgg aggaactgga  24600
gctataggtg gtggagctac aactggagct gtaggtggtg gaactagagt aactgaatct  24660
ccaaaagatg aaactggtag tacctcagaa atatctaagt gatgacctga acctgtgaag  24720
tatgattggg tttcaaagaa ggtaacatca gcagacataa ggtactgctg gaggttagga  24780
gagtagcatc gatacccctt ttgtgttctc gagaaaccta gaaatacgca cttaagagca  24840
cgaggagcta acttatccgt tcctggaata aggttatgca caaaacaagt gcttccaaag  24900
atacgaggtg gaagagagaa caaaggtaag tggtaaaaca tgacagagaa tggaacttgg  24960
ttctggatag ctgatgatgt catacgatta ataagatagc aagatgtaag aactgtatcc  25020
cccaaaaacg caacggagca tgagattgta tgagtagggt acgagcagtt tcaataaaat  25080
gtctattctt tctttcagct accccatttt gttgagatgt gtacagacaa gatgtttgat  25140
gaataatccc atgagatttc ataaactgct gaaatgggga agacaaatac tctcgggcat  25200
tatcactacg aaatgtgcga atagaaaccc caaattgatt ttgaatttca gcgtggaagg  25260
tctggaaaat agaaaacagc tcagatcgat tttttatcaa aaatatccaa gtgcacctgg  25320
aataatcatc aatgaaactg acaaaatagc agaatcccaa ggtggaactg acccgactag  25380
gaccccaaac atctgaatgg actaaagtaa aaggtgactc tgctcgatta tcaagacgcc  25440
taaggaaatg ggagcgagta tgcttaccga gctgacatga ctcacactct agagctgaca  25500
agtgagataa accagatacc attttctgaa gttttgacaa actgggatgt cccaaccgtt  25560
tatgtaataa atctggtgaa tcagtaacag gacatattgt agatggaaga caagatgcga  25620
```

gtccatgtat ttagcaagga taaggtaata aagtccgttt gattcacgcc cggtaccaat 25680
gatccgcccc gtactgcgtt cttgtataaa aacatggtca tcaagaaata aaataacgca 25740
tttaagtgat ttggctaagc gactaacaac tatgagatta aaaggactat tgcgaacata 25800
aaggactgaa tctaaaggta aggaagaaag tgggcttgct tgacctattg cagttgccat 25860
ggtttgagac ccattggcta ttgtgacttt tggaaaagat tgagaatacg aaatagtagt 25920
gaaaagagat ttgttaccag aaatatgatc tgatgcacct gaatcaatga cccaagactc 25980
agaggatgaa gattgggaaa aacaagtcac gctattacct gtttgaacaa cagaagctat 26040
ctcagaagat gtctgcttac atgctttgta ctaaaggaac tcaatataat ctgctaaaga 26100
aaccatccga ctattcaaag catcggttcc catgtcgcta caatttgtag tagtagggtt 26160
aacttgaaat agtggaaata agtaactccg gtgagaaaac tgaagaaata gcttgaaaac 26220
actgtttaca acagtaaaaa cagaacactg ttctgcgccg gaatctactg tagctgacgg 26280
aaaaactcaa agtagtcgga atgaaacgaa aaacagtagg ggtaggatcg gaattaccag 26340
gcgacccaac tattctgaag gaagtttttc aaaaaatggc cggaagtggt cgtacgtgtc 26400
ggcgcgtgag ctcacgcgcg tgagcttctg gtggcgcgtg gaggcgcgtg aggaggctgc 26460
tgccggagat tttcactggg gtttggtcgc cggacagtga ctactcttgt ggtagtgttg 26520
gattttgcac aacactgacg gagataaagc agacgcaaac agccttgaaa aagtcgccgg 26580
aaaagacttc cggtgactga tttctcttcc tggaatcgct ggaatttatg cacagcgata 26640
aatctctcac aattgctctg ataccatgtg agaaagcatg ggagaaaata tgttattgat 26700
atttggataa taaatacaat acaagaggtc cctatttata gctatacact acaaggagat 26760
attacttctc ttccaatgtg ggacaaaaat acactataca tatctgtaaa ctaacaaggg 26820
gaatatcgtt taaagataaa aaagatagcg tgcagaagat tgcatacatt agagatgcaa 26880
aatacagaat acccatactc ccagataatg cagtatgcct tttgcatgac ccactggttg 26940
aatggaagca cctggtcaat ttactaggtg tgttagtgat ttttgctgct tccttcccct 27000
ttctaaacta catactatct aaaatgttag ggggacagaa gcccagtcaa tctgactagg 27060
tgatgttagt ggtttccgct tctttctccc acttctaaat gcgtactttc tcaaatttag 27120
gagcatagaa acttaagcag ctgcctacct gaggaggtgc atgggaacat aagagaatag 27180
actttacctg tcatattttc cataccttag ttaattacag tgttatcctg ataatgatct 27240
gttttctgta tctaggctga atcgagattc aatcgctttt ggctgaaagg atgctgctac 27300
agatccttag tttacatcat tgtggttctt attctataag tacttcccct atcaactact 27360
tccttctttt ttcttaggtt atttgcctct taggttgttt gcaaggaaag gaacaataga 27420
tgttttgatg gaatagcaac tccaaaccac ttccttaagg ctaatatact gtttggccaa 27480
gcttcttcaa agtccaaagc ccttttttgt cttcaaaaaa gtatcttttt ttcccaaagt 27540
tgaggtgttt ggccaaactt ttggaaggaa aaaaaagtgc ttttgagtaa agcagaagct 27600
cttgagaagt agaaaaagta gttttttccc ggaagcattt ttttgaaaag cacttttgag 27660
aaaaataaac ttagaaacac tttttaaaag tttggccaaa cactaattgc tgcttaaaag 27720
tgtttttcag atttattagc caaacacaaa ctgcttctca ccaaaagtac ttttttgaaa 27780
aatacttttt tgaaaagtga ttttcaaaca aagcactttt caaaataagt ttattttaga 27840
agcttgtcaa ccggctataa atgtctttta tttttacagc tagagtaccc taacacctgt 27900
aaattcccct agacattttt ttcgactttg ttagctcatt aaccctagta taggactctt 27960
tgttttggag ctagcaaact cttttgtttt cctatttttg catcttcttg gtgccattta 28020
taatatctct tacttcacca aaaaaaataa gttcccaaaa tatgactacc ttgagttggc 28080
caaagcataa ccaaagcttg ggcacaccag tgtttgcgtg aattttatgg atgttcctta 28140
cctttatcct tctgtgctta tgtagcatct gtcttggtta atcttttctg aagtctatag 28200
tgtatttctg tgttgcaaca tgagtttact gtcaatctta ctgtttgacc tcaattttgg 28260
gttctttttg attttgaaag acatcgttta acaggttggc atggctgcta ctcttgctgg 28320
tgtctgtcag gtgcctctca ctgctgtttt gcttctcttt gaactgacac agaattatcg 28380
gatagttctg cccctcttgg gagctgtggg gttgtcttct tgggttacat ctggacaaac 28440
aaggaaaagt gtagtgaagg atagagaaag actaaaagat gcaagagccc acatgatgca 28500
gcgacaagga acttctttct ccaacatttc tagtttaact tattcttcag gtgtgaaacc 28560
ttcacagaaa gagagtaacc tatgcaaact tgagagttcc ctctgtcttt atgaatctga 28620
tgatgaagaa aatgatttgg caaggacaat tctagtttca caggcaatga gaacacgata 28680
tgtgacagtt ctaatgagca ccttgctaac ggagaccata tccctcatgc tagctgagaa 28740
gcaatcttgt gcaataatag ttgatgaaaa taattttctc attggtctgc tgacacttag 28800
tgatatccag aattacagca agttgccaag agcagagggc aatttccagg aggtagcttc 28860
ttggtacatt tcaatattct taactgatga aaaaataagg gaaattgatc tagcatgaaa 28920
ttaagctaat tataagtttt acactgtaga actggtaaaa cagggttggc tggatatttc 28980
tttgttgaat ttttaggatt atatgtattg ttttagtttt gtaggttgtt ttctgatgtg 29040
ctttttgact tggcagaatc ttaagatgaa atggaaggtg tttaaccaaa aaatagaatt 29100
ttcagtcaaa gcctatattt agaagaaaac gggttattga taaccaagtt ttactttact 29160
tccccaacaa tctatttggt aaatagcaaa agtaatgcgt atgtgagaaa gcacgggaga 29220
aaatatatta ttgatattag atattcaata taatacaaga ggtcctacac atcatatagc 29280
tatagtctac aaactacata ttactctcat tccaatgtgg gactacacat aactaacact 29340
ccccctcaag ccggtgcata catatcatat gtaccgagct tgttacacat gtaactaata 29400
cgagaaccag taagagactt agtgaaaata tctgctagtt gatcatttga ctttacaaac 29460
tttgtaaaaa tatctcctga aagtattttt tctctgacaa agtaacagtc gatctcaatg 29520
tgtttagtcc tctcatggaa tagcggattt gacgcaatat gaagagcagc ttggttatca 29580
cacaccagtt ccatcttgct gatttctcca aactttaact ccttgagcaa ctgcttgacc 29640
caaactaact ctcacgttgc catagccatt gcccgatatt cgacgtcggc gccagatcga 29700
gcaactacat tctgtttctt gctcttccac gagaccaaat tacctcctac tagaacacaa 29760
tatccaggcg tagaacgtct atcaaaaggt gatcctgccc aatcagcatt tgtgtaccca 29820
acaatttgct cgtggcctcg atcctcgagt agtaatcctt tgcttggaga tgactttata 29880
taccgaagaa tgcgaacaac tgcatcccag tgactatcac agggagaatc cataaactga 29940
cttacaacac tcaccggaaa agaaatgtca ggtctagtca ctgtgaggta attcaatttg 30000
ccaaccaacc tcctatatct cgtagggtct ctaagaggct ccccgtgtct aggcagaagc 30060
ttagcattcg gatccataag agagtcaata ggtctgtaac ccatcattcc agtctcctca 30120
aaaatgtcta aggcataatt ccgctgtgaa ataacaatac ctgagctaga ctgaggcact 30180
gagcaacctc aatacctaga aaatacttca atctgcccag atccttagtc tggaagtgct 30240
gaaagagatg ttgcttcaga ttagtaatat catcctgatc attgccagta ataacaatat 30300
catcaacata aaccactaga taaatacaca gattaggagt aaagtgccga taaaacacag 30360
agagatcagc ctcactacga gtcatggcga actcctgaat aattatgctg aacttaccaa 30420
accaagctcg aggggactgt ttcaaaccat ataatgacct gcacaatcta cacacacaac 30480
cattaaactc cccctgagca acaaaaccag gtggttactc catataaact tcttcctcaa 30540
gatcaccgtg gagaaaagca ttcttaatgt ctaactgata aagaggccaa tgacgtacaa 30600
cagccatgga caaaaagaga cgaacaaatg ctattttagc cacgggagag aaagtatcac 30660
tataatcaag cccaaaaatc tgagtatatc cttttgcaac aagacgagcc ttaagccgat 30720
caacctggcc atccgggccg actttgaccg cataaaccta atgacaacca acattagact 30780
tacctgcagg aagaggaaca agctcccaag tgccactcgc atgtaaagca gacatctcgt 30840
caatcatagc atgtcgccat cctggatgag atagtgcctc acctgtagac ttagggatag 30900
aaacagtgga caaagaagat ataaaagcat aatgaggtga tgacacacga tgatgactta 30960
aaccgacata gtggggatta ggattacgtg tggatcgtac gcctttgcgg agtgcaattg 31020
gttgactaag aggagacaag atcgtagtag gtgcagaatc tgatgcaggg cgtgaatcac 31080
ttgggcatga tgttggatgt ggacgacgat gataagtcaa gagtggtgga gctgcagaag 31140
gttgaactgg attatgtgga ggaactggag gtggagctac aactggagct gtaggtggtg 31200
gaactggagc tataagtggt ggagctacaa ctggagctgg agatgtagag gaagatgaat 31260
gagagatagt gactgaatct ccaaaaaata aaattggtag tacctcagaa atatctaagt 31320
gatgacatga acctgtgaag tatgattgag tttcaaagaa ggtaacatca gcggacataa 31380
ggtaccgctg aaggtcaaga gagtagcatc gataccccttt ttgtgttctc gagtaaccta 31440
gaaatacgca cttaagagca cgaggagcta acttatctgt tcctggagta aggttatgga 31500
caaaacaagt gattccaaag atacagggtg gaagagagaa caaaggtaag tggggaaaca 31560
tgacaaagaa tggaacttgg ttttggataa ctgaagatgg catacgatta ataagatagc 31620
aagatataag aactgcatcc ccccaaaaac gaaacggagc atgagattgt atgagtaggg 31680
tacgagcaat ttcaataaga tgtctatttt ttctttcagc taccccattt tgttgagatg 31740
tgtacagaca agatgtttga tgaataatcc catgagattt cataaactgc tgaaatgggg 31800
aagacaaata ctctcgggca ttatcactag gaaatgtgcg aatagaaacc ccaaattgat 31860
tttgaatttt tagcgtggaa ggtctggaaa aatagaaaac aactcagatc gattttttat 31920
caaaaatatc caagtgcacc ttgaataatc atcaattatt caataaaact gacaaagtag 31980
cagaatccca aggtggaact gacccgacta ggaccccaaa catttgagaa tggactaaag 32040
taaaaggtga ctctgcttga ttatcaagac gccgagggaa atggaagcga gtatgcttat 32100
cgaactgaca tgactcacac tctagagctg acaagtgaga taaaccagat accattttat 32160
gaagttttga caaattggga tgtcccgacc gtttatgtaa taaatttggt gtattagtaa 32220
caggacaagt tgttgaagga agacaagatg tgagtccgtg tgatttagca aggataaggt 32280
aataaagtcc gtttgattca cgtccggtac caataattcg tcccgtactg cgttcctgta 32340
taaaaacatg gtcatcaaga aataaaacaa cgcatttaag tgatttggct aagcgactaa 32400
tagttatgag attaaaagga ctattgggaa cataaatgac tgaatataaa ggtaaggaag 32460
gaagtgagct tgcttgactt attgttgttg ccattgtttg agacctattg gccattgtga 32520
ctcttgaaag agattgaaaa tacgaaatag tagtgaaaag agatttgtta ccagaaaatat 32580
gatctgatgc acctgaatca atgacccaaa actcagatga tgaagattgg gagaaacaag 32640
tcacgctatt acctgtttaa acaacagaag ctatcacaga agatgtctgc ttacatgctt 32700
tgtaccgaag gaactcaata taatctgcta aagaaaccat ccgactattc aaagtatcgg 32760

```
ttcccatgtc gctacaattt gtagtaatag gatggataga ctcggaaaat tgtaaagtta  32820
tcggaatttg tcgtaaccag gatcgagcaa gctgtcttga agaaatggtt tcaaaaaatg  32880
tccggaaagg tcacttttac gccggaaaaa tataaaaatg gtcgaaattt gatttgaatt  32940
agatgggtag gctcggaatt gtgaggagag cagactgtcc tgaagaagct taatgaaaaa  33000
atggccggaa agtggccgga accctcgccg taaaagttgt taccggcgcg tgaaggcgcg  33060
tggcattttt tctgccagat aaattttcag gggttggtcg tcggagggtg atcccttgtg  33120
gtggtgttgg tttttgcaca ataccgacag gccttaggtc acccgaaaat ttgcacgatg  33180
actaagttct ttcttcccgg ttaacgctgg aatgacgcac atcgatcttt tctcactaat  33240
gctatgatac catgtgagaa agcacgggag aaaatatatt attgatatta gatactcaat  33300
ataatacaag aggtcatatt tatagctata gtctacaaag tacatattac tctcattcaa  33360
atgtgggact acacataact aacaacgtaa attaacaaag agaaataagg aatgtaacaa  33420
cagtcaatcc ctaaaatcaa ggtagaaaac tttgataaag cagagaatta tagaatgtat  33480
ttcagtagta cttggaactt gtccttacaa ataaaattct ttatccttat ataggggcgt  33540
acaatcataa catttttcgc acttaattcg aattcattat gagcattaat tgtattgatt  33600
gcccgttatc atagataacc ataactgacg tatttgtaac tataaatgcc ttataacggc  33660
tctgattccc cttccttatt tacttctggt ttgtgtatct ttccttcttt ttagccttta  33720
ttcattcagt tctcgcctct tctttgacaa ctgtcaagcc cgatcctctg ttctgtactg  33780
tctcgtgggt gtttcccccg taccttcctt atattcttaa ttctgttaat tgagagtgtc  33840
acttgtcact atgccattgt tccacgcgtc atgtttcatc cacgtgtaat atctttttc  33900
caccaataca gataatcccc cactttctga atattctcaa ctgaatattc gggtaagttt  33960
ttatggcggg aattctttgc cgtcgttttt cgagtatcat cgtgtcatct tcagaaccga  34020
tgtgacgtac gtcacgtcta tttaatgcct atgccaggtg gcttctatcg attggctctg  34080
cagtttttta gcgcttttta gggtttttca gcggctgcgt cagtcacgaa gtgacggttc  34140
cattatgacg cttcataatg actaacttta atgatggtcg tgtcttctta ttaatacttc  34200
attccttttt gatctcttgg agtcttcctt cttcagtatc caccacatta cttctttgta  34260
tttctgcatc ttctctttga tattcctttg gacaatcatg tcttcttcta caccagaccc  34320
ccgtaaggtt gtgattgttg acgaacttga tctttctact gctcctacta gaagtaggag  34380
aggtggtaga cttcgtagtc ttggttcact atctaatcgt ggttcttctt cccagggtag  34440
tgctgctaag ccatcttctt ctagacctag ggctccttta accccctagat cttcttctag  34500
gaatagagat ttaaatgatc cagtgcgcga acctacagtt gcagagattg ttcctcaaga  34560
attttctttt gtaactgacc gtgaaaccat aaggaatcaa atttcttcta tagcctccct  34620
caataccgct aacctttatc caagtttaat cagtaatggt cttctctccc gggttcgaag  34680
agaatattac tgaaaccaga tttcccaatt ttagtccctg gtgccaacca gagaattact  34740
ccataccatg ttggtttttc ctttgtttac acctaccctt ttactttagg gttcaaacca  34800
cctattgaac cagtaatcat tgaattctgt cgttatttca acgtgtgtct tggccagatt  34860
gaccacatag tatggagggc tgttcatgcc ttcgttattt atcagatttg gtttccatgc  34920
ctttcacttt tcagcacttg cttcatctct actcccctaa attgtttcgt gaagtagttt  34980
ttactctcgt ggctagaagt aagagagtgt tggttagcct tgaagacgat tgggaccgtg  35040
gctggtacgc tcgttttgtt gctgctccca ctagtgcatt agtgggtgaa gaaaatatgc  35100
```

-continued

```
ctttcccgga gaaatggaac tttgcacgta agctttcttc tcctcttttt ttttgtctta  35160
aaaaaactcc atgtaatcat atacccactt cttcagcaac tatggaagtt ttttatgctt  35220
gggtagaaaa gatgttaact gctgcgccta tggagaaaag atcctggaaa tacttttctc  35280
aaagatttgg ttggaaagtg aagacgcacg gtacttttta ccttcattgt ttttcctttt  35340
ctcttccttg tttgttcaat gatttctcat ccttcccttt ttttttacta gggtttccga  35400
ttcgtggtat tagtcccgcg tctgttccat caactaggct ttccgtgatt cttgttcagg  35460
aaagaatttt aagtgcttct tcttcaaaaa ggaaaactga cggagcccgt ggctctgatg  35520
acgaagaaga aacagaggag ggttctttgg tgcgaaggtc acgcgtcagg agacgcgtgg  35580
tttctgatga tgaaactact ccttctcatg accctctatc tagttcaatc ccttttagac  35640
tcacggatga gctagagagt accccttag tgatttctta tgatgatgct gttgatcccc  35700
ctccaagttc tgttgataga ttgtttgctc atggcttcga gggtgatgaa gttttgggcc  35760
tgtttctgaa gaattgcccc ttgcttccct tccagtttca gttttcatta acccttccgt  35820
gtccttacct gatgatactc ctgttgttat tctcgtggct gcttctactc cgtcatctat  35880
tcccgtgact gcttctcatg cagaggccaa accttctagc agcagaaggg caatgaaaag  35940
agttgttgtt gaggttcctg aaggtgagaa cttattaaga aaatccggtc aagccgacgt  36000
gtagttgaaa cctatgctcg gccccgtaga gaagaagaag ttagaaagcc atagctcact  36060
cactttaatg aatgatatcg ttcattcttc cttgaaagta caagcttaat tatatttcct  36120
ttcttttctc tttcttattc ataactcttc ctcctttttt gcagatcaac ttgattggca  36180
cagagcttat gaaaagagtt tctcaggcgg accggcaagt tatagatttg cgcaccgagg  36240
ctgataactg gaaggaacaa ttcgaaggtc ttcaattgga aaaagaggtt ccggcggaag  36300
agaagaatgc tttggaacaa cagatgagag tgattgcctc tgaattagca gttgaaaaag  36360
cttcctcgag ccaggttgga aaggataagt atatacttga atcctccttt gctgaacaac  36420
tttccaaggc aactgaagaa ataaggagtt tgaaggaact ccttaatcaa aaagaggttt  36480
atgcgagaga attggttcaa acacttactc aagttcagga agatctccgt gcctctactt  36540
ataagattca gttcttggaa agttctctcg cttctttgaa gacagcttac gatgcctctg  36600
aagcagaaaa agaagagctg agagctgaga tttaccagtg ggagaaggat tatgagattc  36660
tcgaggataa tctatcgttg gatgtaagtt gggctttctt aaacactcgt ctcgagactc  36720
tagttgaagc caaccatgag ggttttgacc ttaatgctga gattgctaag gctaaagaag  36780
caattgataa aactcagcaa cgtcaaatct tttcctcacc tgaagacgaa ggtcccgaag  36840
gtgatggaga ttga                                                    36854
```

<210> SEQ ID NO 12
<211> LENGTH: 753
<212> TYPE: PRT
<213> ORGANISM: Nicotiana tabacum
<220> FEATURE:
<223> OTHER INFORMATION: Protein sequence of NtCLCe from Nicotiana tabacum; sequence originating from the ancestor N. sylvestris; two start codons, translated from SEQ ID NO: 10 of PCT/EP2013/077532

<400> SEQUENCE: 12

```
Met Ile Ser Gly Gln Asn Thr Val Leu His Asn Pro Pro Asn Ser Leu
1               5                   10                  15

Phe Asn Ser Leu Ser Pro Arg His Ile Cys Ile Ser Phe Cys Asn Asp
            20                  25                  30

Lys Ala Leu Lys Lys Ser Val Thr His Ser Ala Pro Arg Phe Ala Arg
```

```
        35                  40                  45

Leu Leu Asn Asn Glu Ser Arg Lys Leu Leu Gly Arg His Pro Asn Cys
    50                  55                  60

Trp Pro Trp Ala Arg Arg Pro Ser Leu Pro Pro Gly Arg Ser Ser Asp
65                  70                  75                  80

Gly Asn Ile Glu Lys Glu Gln Asp Met Cys Asp Ser Ser Lys Val Asp
                85                  90                  95

Ser Asp Ser Gly Ile Gln Ile Gly Ser Leu Leu Glu Glu Val Ile Pro
            100                 105                 110

Gln Gly Asn Asn Thr Ala Ile Ile Ser Ala Cys Phe Val Gly Leu Phe
        115                 120                 125

Thr Gly Ile Ser Val Val Leu Phe Asn Ala Ala Val His Glu Ile Arg
    130                 135                 140

Asp Leu Cys Trp Asp Gly Ile Pro Tyr Arg Ala Ala Ser Glu Glu Pro
145                 150                 155                 160

Ile Gly Val His Trp Gln Arg Val Ile Leu Val Pro Ala Cys Gly Gly
                165                 170                 175

Leu Val Val Ser Phe Leu Asn Ala Phe Arg Ala Thr Leu Glu Val Ser
            180                 185                 190

Thr Glu Gly Ser Trp Thr Ser Ser Val Lys Ser Val Leu Glu Pro Val
        195                 200                 205

Leu Lys Thr Met Ala Ala Cys Val Thr Leu Gly Thr Gly Asn Ser Leu
    210                 215                 220

Gly Pro Glu Gly Pro Ser Val Glu Ile Gly Thr Ser Val Ala Lys Gly
225                 230                 235                 240

Val Gly Ala Leu Leu Asp Lys Gly Gly Arg Arg Lys Leu Ser Leu Lys
                245                 250                 255

Ala Ala Gly Ser Ala Ala Gly Ile Ala Ser Gly Phe Asn Ala Ala Val
            260                 265                 270

Gly Gly Cys Phe Phe Ala Val Glu Ser Val Leu Trp Pro Ser Pro Ala
        275                 280                 285

Glu Ser Ser Leu Ser Leu Thr Asn Thr Thr Ser Met Val Ile Leu Ser
    290                 295                 300

Ala Val Ile Ala Ser Val Val Ser Glu Ile Gly Leu Gly Ser Glu Pro
305                 310                 315                 320

Ala Phe Ala Val Pro Gly Tyr Asp Phe Arg Thr Pro Thr Glu Leu Pro
                325                 330                 335

Leu Tyr Leu Leu Leu Gly Ile Phe Cys Gly Leu Val Ser Val Ala Leu
            340                 345                 350

Ser Ser Cys Thr Ser Phe Met Leu Gln Ile Val Glu Asn Ile Gln Thr
        355                 360                 365

Thr Ser Gly Met Pro Lys Ala Ala Phe Pro Val Leu Gly Gly Leu Leu
    370                 375                 380

Val Gly Leu Val Ala Leu Ala Tyr Pro Glu Ile Leu Tyr Gln Gly Phe
385                 390                 395                 400

Glu Asn Val Asn Ile Leu Leu Glu Ser Arg Pro Leu Val Lys Gly Leu
                405                 410                 415

Ser Ala Asp Leu Leu Leu Gln Leu Val Ala Val Lys Ile Val Thr Thr
            420                 425                 430

Ser Leu Cys Arg Ala Ser Gly Leu Val Gly Gly Tyr Tyr Ala Pro Ser
        435                 440                 445

Leu Phe Ile Gly Ala Ala Thr Gly Thr Ala Tyr Gly Lys Ile Val Ser
    450                 455                 460
```

Tyr Ile Ile Ser His Ala Asp Pro Ile Phe His Leu Ser Ile Leu Glu
465 470 475 480

Val Ala Ser Pro Gln Ala Tyr Gly Leu Val Gly Met Ala Ala Thr Leu
485 490 495

Ala Gly Val Cys Gln Val Pro Leu Thr Ala Val Leu Leu Leu Phe Glu
500 505 510

Leu Thr Gln Asp Tyr Arg Ile Val Leu Pro Leu Leu Gly Ala Val Gly
515 520 525

Leu Ser Ser Trp Val Thr Ser Gly Gln Thr Arg Lys Ser Val Val Lys
530 535 540

Asp Arg Glu Lys Leu Lys Asp Ala Arg Ala His Met Met Gln Arg Gln
545 550 555 560

Gly Thr Ser Phe Ser Asn Ile Ser Ser Leu Thr Tyr Ser Ser Gly Ser
565 570 575

Pro Ser Gln Lys Glu Ser Asn Leu Cys Lys Leu Glu Ser Ser Leu Cys
580 585 590

Leu Tyr Glu Ser Asp Asp Glu Glu Asn Asp Leu Ala Arg Thr Ile Leu
595 600 605

Val Ser Gln Ala Met Arg Thr Arg Tyr Val Thr Val Leu Met Ser Thr
610 615 620

Leu Leu Met Glu Thr Ile Ser Leu Met Leu Ala Glu Lys Gln Ser Cys
625 630 635 640

Ala Ile Ile Val Asp Glu Asn Asn Phe Leu Ile Gly Leu Leu Thr Leu
645 650 655

Gly Asp Ile Gln Asn Tyr Ser Lys Leu Pro Arg Thr Glu Gly Asn Phe
660 665 670

Gln Glu Glu Leu Val Val Ala Gly Val Cys Ser Ser Lys Gly Asn Lys
675 680 685

Cys Arg Val Ser Cys Thr Val Thr Pro Asn Thr Asp Leu Leu Ser Ala
690 695 700

Leu Thr Leu Met Glu Lys His Asp Leu Ser Gln Leu Pro Val Ile Leu
705 710 715 720

Gly Asp Val Glu Asp Glu Gly Ile His Pro Val Gly Ile Leu Asp Arg
725 730 735

Glu Cys Ile Asn Val Ala Cys Arg Ala Leu Ala Thr Arg Glu Gln Leu
740 745 750

Cys

<210> SEQ ID NO 13
<211> LENGTH: 818
<212> TYPE: PRT
<213> ORGANISM: Nicotiana tabacum
<220> FEATURE:
<223> OTHER INFORMATION: Protein sequence of NtCLCe from Nicotiana tabacum; sequence originating from the ancestor N. tomentosiformis; one start codon, translated from SEQ ID NO: 4 of PCT/EP2013/077532

<400> SEQUENCE: 13

Met Cys Asp Ser Ser Lys Asp Asp Ser Asp Ser Asp Ser Gly Ile Gln
1 5 10 15

Ile Gly Ser Leu Leu Glu Glu Val Ile Pro Gln Gly Asn Asn Thr Ala
20 25 30

Ile Ile Ser Ala Cys Phe Val Gly Leu Phe Thr Gly Ile Ser Val Val
35 40 45

-continued

```
Leu Phe Asn Ala Ala Val His Glu Ile Arg Asp Leu Cys Trp Asp Gly
    50                  55                  60

Ile Pro Tyr Arg Ala Ala Ser Glu Glu Pro Ile Gly Val His Trp Gln
65                  70                  75                  80

Arg Val Ile Leu Val Pro Ala Cys Gly Gly Leu Val Val Ser Phe Leu
                85                  90                  95

Asn Ala Phe Arg Ala Thr Leu Glu Val Ser Thr Glu Glu Ser Trp Thr
            100                 105                 110

Ser Ser Val Lys Ser Val Leu Gly Pro Val Leu Lys Thr Met Ala Ala
        115                 120                 125

Cys Val Thr Leu Gly Thr Gly Asn Ser Leu Gly Pro Glu Gly Pro Ser
    130                 135                 140

Val Glu Ile Gly Thr Ser Val Ala Lys Gly Val Gly Ala Leu Leu Asp
145                 150                 155                 160

Lys Gly Gly Arg Arg Lys Leu Ser Leu Lys Ala Ala Gly Ser Ala Ala
                165                 170                 175

Gly Ile Ala Ser Gly Phe Asn Ala Ala Val Gly Gly Cys Phe Phe Ala
            180                 185                 190

Val Glu Ser Val Leu Trp Pro Ser Pro Ala Glu Ser Ser Leu Tyr Leu
        195                 200                 205

Thr Asn Thr Thr Ser Met Val Ile Leu Ser Ala Val Ile Ala Ser Val
    210                 215                 220

Val Ser Glu Ile Gly Leu Gly Ser Glu Pro Ala Phe Ala Val Pro Gly
225                 230                 235                 240

Tyr Asp Phe Arg Thr Pro Thr Glu Leu Pro Leu Tyr Leu Leu Leu Gly
                245                 250                 255

Ile Phe Cys Gly Leu Val Ser Val Ala Leu Ser Ser Cys Thr Ser Phe
            260                 265                 270

Met Leu Gln Ile Val Glu Asn Ile Gln Met Thr Ser Gly Met Pro Lys
        275                 280                 285

Ala Ala Phe Pro Val Leu Gly Gly Leu Leu Val Gly Leu Val Ala Leu
    290                 295                 300

Ala Tyr Pro Glu Ile Leu Tyr Gln Gly Phe Glu Asn Val Asn Ile Leu
305                 310                 315                 320

Leu Glu Ser Arg Pro Leu Val Lys Gly Leu Ser Ala Asp Leu Leu Leu
                325                 330                 335

Gln Leu Val Ala Val Lys Ile Val Thr Thr Ser Leu Cys Arg Ala Ser
            340                 345                 350

Gly Leu Val Gly Gly Tyr Tyr Ala Pro Ser Leu Phe Ile Gly Ala Ala
        355                 360                 365

Thr Gly Thr Ala Tyr Gly Lys Ile Val Ser Tyr Ile Ile Ser His Ala
    370                 375                 380

Asp Pro Ile Phe His Leu Ser Ile Leu Glu Val Ala Ser Pro Gln Ala
385                 390                 395                 400

Tyr Gly Leu Val Gly Met Ala Ala Thr Leu Ala Gly Val Cys Gln Val
                405                 410                 415

Pro Leu Thr Ala Val Leu Leu Leu Phe Glu Leu Thr Gln Asn Tyr Arg
            420                 425                 430

Ile Val Leu Pro Leu Leu Gly Ala Val Gly Leu Ser Ser Trp Val Thr
        435                 440                 445

Ser Gly Gln Thr Arg Lys Ser Val Val Lys Asp Arg Glu Arg Leu Lys
    450                 455                 460

Asp Ala Arg Ala His Met Met Gln Arg Gln Gly Thr Ser Phe Ser Asn
```

```
465                 470                 475                 480

Ile Ser Ser Leu Thr Tyr Ser Ser Gly Val Lys Pro Ser Gln Lys Glu
                485                 490                 495

Ser Asn Leu Cys Lys Leu Glu Ser Ser Leu Cys Leu Tyr Glu Ser Asp
            500                 505                 510

Asp Glu Glu Asn Asp Leu Ala Arg Thr Ile Leu Val Ser Gln Ala Met
        515                 520                 525

Arg Thr Arg Tyr Val Thr Val Leu Met Ser Thr Leu Leu Thr Glu Thr
    530                 535                 540

Ile Ser Leu Met Leu Ala Glu Lys Gln Ser Cys Ala Ile Ile Val Asp
545                 550                 555                 560

Glu Asn Asn Phe Leu Ile Gly Leu Leu Thr Leu Ser Asp Ile Gln Asn
                565                 570                 575

Tyr Ser Lys Leu Pro Arg Ala Glu Gly Asn Phe Gln Glu Ile Asn Leu
            580                 585                 590

Ile Gly Thr Glu Leu Met Lys Arg Val Ser Gln Ala Asp Arg Gln Val
        595                 600                 605

Ile Asp Leu Arg Thr Glu Ala Asp Asn Trp Lys Glu Gln Phe Glu Gly
    610                 615                 620

Leu Gln Leu Glu Lys Glu Val Pro Ala Glu Glu Lys Asn Ala Leu Glu
625                 630                 635                 640

Gln Gln Met Arg Val Ile Ala Ser Glu Leu Ala Val Glu Lys Ala Ser
                645                 650                 655

Ser Ser Gln Val Gly Lys Asp Lys Tyr Ile Leu Glu Ser Ser Phe Ala
            660                 665                 670

Glu Gln Leu Ser Lys Ala Thr Glu Glu Ile Arg Ser Leu Lys Glu Leu
        675                 680                 685

Leu Asn Gln Lys Glu Val Tyr Ala Arg Glu Leu Val Gln Thr Leu Thr
    690                 695                 700

Gln Val Gln Glu Asp Leu Arg Ala Ser Thr Tyr Lys Ile Gln Phe Leu
705                 710                 715                 720

Glu Ser Ser Leu Ala Ser Leu Lys Thr Ala Tyr Asp Ala Ser Glu Ala
                725                 730                 735

Glu Lys Glu Glu Leu Arg Ala Glu Ile Tyr Gln Trp Glu Lys Asp Tyr
            740                 745                 750

Glu Ile Leu Glu Asp Asn Leu Ser Leu Asp Val Ser Trp Ala Phe Leu
        755                 760                 765

Asn Thr Arg Leu Glu Thr Leu Val Glu Ala Asn His Glu Gly Phe Asp
    770                 775                 780

Leu Asn Ala Glu Ile Ala Lys Ala Lys Glu Ala Ile Asp Lys Thr Gln
785                 790                 795                 800

Gln Arg Gln Ile Phe Ser Ser Pro Glu Asp Glu Gly Pro Glu Gly Asp
                805                 810                 815

Gly Asp
```

<210> SEQ ID NO 14
<211> LENGTH: 906
<212> TYPE: PRT
<213> ORGANISM: Nicotiana tabacum
<220> FEATURE:
<223> OTHER INFORMATION: Protein sequence of NtCLCe from Nicotiana tabacum; sequence originating from the ancestor N. tomentosiformis; two start codons, translated from SEQ ID NO: 11 of PCT/EP2013/077532

<400> SEQUENCE: 14

```
Met Ile Ser Gly Gln Asn Thr Val Leu His His Pro Pro Asn Ser Leu
1               5                   10                  15

Phe Asn Ser Leu Ser Pro Arg His Ile Cys Val Ser Phe Cys Asn Asp
            20                  25                  30

Lys Ala Leu Lys Lys Ser Val Thr His Ser Ala Pro Arg Phe Ala Arg
        35                  40                  45

Leu Leu Asn Asn Glu Ser Arg Lys Leu Leu Gly Arg His Pro Asn Cys
    50                  55                  60

Trp Pro Trp Ala Arg Arg Pro Ser Leu Pro Pro Gly Arg Ser Cys Asp
65                  70                  75                  80

Gly Asn Ile Glu Lys Glu Gln Asp Met Cys Asp Ser Ser Lys Asp Asp
                85                  90                  95

Ser Asp Ser Asp Ser Gly Ile Gln Ile Gly Ser Leu Leu Glu Glu Val
            100                 105                 110

Ile Pro Gln Gly Asn Asn Thr Ala Ile Ile Ser Ala Cys Phe Val Gly
        115                 120                 125

Leu Phe Thr Gly Ile Ser Val Val Leu Phe Asn Ala Ala Val His Glu
    130                 135                 140

Ile Arg Asp Leu Cys Trp Asp Gly Ile Pro Tyr Arg Ala Ala Ser Glu
145                 150                 155                 160

Glu Pro Ile Gly Val His Trp Gln Arg Val Ile Leu Val Pro Ala Cys
                165                 170                 175

Gly Gly Leu Val Val Ser Phe Leu Asn Ala Phe Arg Ala Thr Leu Glu
            180                 185                 190

Val Ser Thr Glu Glu Ser Trp Thr Ser Ser Val Lys Ser Val Leu Gly
        195                 200                 205

Pro Val Leu Lys Thr Met Ala Ala Cys Val Thr Leu Gly Thr Gly Asn
    210                 215                 220

Ser Leu Gly Pro Glu Gly Pro Ser Val Glu Ile Gly Thr Ser Val Ala
225                 230                 235                 240

Lys Gly Val Gly Ala Leu Leu Asp Lys Gly Gly Arg Arg Lys Leu Ser
                245                 250                 255

Leu Lys Ala Ala Gly Ser Ala Ala Gly Ile Ala Ser Gly Phe Asn Ala
            260                 265                 270

Ala Val Gly Gly Cys Phe Phe Ala Val Glu Ser Val Leu Trp Pro Ser
        275                 280                 285

Pro Ala Glu Ser Ser Leu Tyr Leu Thr Asn Thr Thr Ser Met Val Ile
    290                 295                 300

Leu Ser Ala Val Ile Ala Ser Val Val Ser Glu Ile Gly Leu Gly Ser
305                 310                 315                 320

Glu Pro Ala Phe Ala Val Pro Gly Tyr Asp Phe Arg Thr Pro Thr Glu
                325                 330                 335

Leu Pro Leu Tyr Leu Leu Leu Gly Ile Phe Cys Gly Leu Val Ser Val
            340                 345                 350

Ala Leu Ser Ser Cys Thr Ser Phe Met Leu Gln Ile Val Glu Asn Ile
        355                 360                 365

Gln Met Thr Ser Gly Met Pro Lys Ala Ala Phe Pro Val Leu Gly Gly
    370                 375                 380

Leu Leu Val Gly Leu Val Ala Leu Ala Tyr Pro Glu Ile Leu Tyr Gln
385                 390                 395                 400

Gly Phe Glu Asn Val Asn Ile Leu Leu Glu Ser Arg Pro Leu Val Lys
                405                 410                 415
```

-continued

```
Gly Leu Ser Ala Asp Leu Leu Leu Gln Leu Val Ala Val Lys Ile Val
            420                 425                 430

Thr Thr Ser Leu Cys Arg Ala Ser Gly Leu Val Gly Gly Tyr Tyr Ala
        435                 440                 445

Pro Ser Leu Phe Ile Gly Ala Ala Thr Gly Thr Ala Tyr Gly Lys Ile
    450                 455                 460

Val Ser Tyr Ile Ile Ser His Ala Asp Pro Ile Phe His Leu Ser Ile
465                 470                 475                 480

Leu Glu Val Ala Ser Pro Gln Ala Tyr Gly Leu Val Gly Met Ala Ala
                485                 490                 495

Thr Leu Ala Gly Val Cys Gln Val Pro Leu Thr Ala Val Leu Leu Leu
            500                 505                 510

Phe Glu Leu Thr Gln Asn Tyr Arg Ile Val Leu Pro Leu Leu Gly Ala
        515                 520                 525

Val Gly Leu Ser Ser Trp Val Thr Ser Gly Gln Thr Arg Lys Ser Val
    530                 535                 540

Val Lys Asp Arg Glu Arg Leu Lys Asp Ala Arg Ala His Met Met Gln
545                 550                 555                 560

Arg Gln Gly Thr Ser Phe Ser Asn Ile Ser Ser Leu Thr Tyr Ser Ser
                565                 570                 575

Gly Val Lys Pro Ser Gln Lys Glu Ser Asn Leu Cys Lys Leu Glu Ser
            580                 585                 590

Ser Leu Cys Leu Tyr Glu Ser Asp Asp Glu Glu Asn Asp Leu Ala Arg
        595                 600                 605

Thr Ile Leu Val Ser Gln Ala Met Arg Thr Arg Tyr Val Thr Val Leu
    610                 615                 620

Met Ser Thr Leu Leu Thr Glu Thr Ile Ser Leu Met Leu Ala Glu Lys
625                 630                 635                 640

Gln Ser Cys Ala Ile Ile Val Asp Glu Asn Asn Phe Leu Ile Gly Leu
                645                 650                 655

Leu Thr Leu Ser Asp Ile Gln Asn Tyr Ser Lys Leu Pro Arg Ala Glu
            660                 665                 670

Gly Asn Phe Gln Glu Ile Asn Leu Ile Gly Thr Glu Leu Met Lys Arg
        675                 680                 685

Val Ser Gln Ala Asp Arg Gln Val Ile Asp Leu Arg Thr Glu Ala Asp
    690                 695                 700

Asn Trp Lys Glu Gln Phe Glu Gly Leu Gln Leu Glu Lys Glu Val Pro
705                 710                 715                 720

Ala Glu Glu Lys Asn Ala Leu Glu Gln Gln Met Arg Val Ile Ala Ser
                725                 730                 735

Glu Leu Ala Val Glu Lys Ala Ser Ser Ser Gln Val Gly Lys Asp Lys
            740                 745                 750

Tyr Ile Leu Glu Ser Ser Phe Ala Glu Gln Leu Ser Lys Ala Thr Glu
        755                 760                 765

Glu Ile Arg Ser Leu Lys Glu Leu Leu Asn Gln Lys Glu Val Tyr Ala
    770                 775                 780

Arg Glu Leu Val Gln Thr Leu Thr Gln Val Gln Glu Asp Leu Arg Ala
785                 790                 795                 800

Ser Thr Tyr Lys Ile Gln Phe Leu Glu Ser Ser Leu Ala Ser Leu Lys
                805                 810                 815

Thr Ala Tyr Asp Ala Ser Glu Ala Glu Lys Glu Glu Leu Arg Ala Glu
            820                 825                 830

Ile Tyr Gln Trp Glu Lys Asp Tyr Glu Ile Leu Glu Asp Asn Leu Ser
```

```
        835                 840                 845

Leu Asp Val Ser Trp Ala Phe Leu Asn Thr Arg Leu Glu Thr Leu Val
    850                 855                 860

Glu Ala Asn His Glu Gly Phe Asp Leu Asn Ala Glu Ile Ala Lys Ala
865                 870                 875                 880

Lys Glu Ala Ile Asp Lys Thr Gln Gln Arg Gln Ile Phe Ser Ser Pro
                885                 890                 895

Glu Asp Glu Gly Pro Glu Gly Asp Gly Asp
            900                 905


<210> SEQ ID NO 15
<211> LENGTH: 11
<212> TYPE: DNA
<213> ORGANISM: Nicotiana tabacum

<400> SEQUENCE: 15

ctctgctcga g                                                            11


<210> SEQ ID NO 16
<211> LENGTH: 11
<212> TYPE: DNA
<213> ORGANISM: Nicotiana tabacum

<400> SEQUENCE: 16

aagttatccc a                                                            11


<210> SEQ ID NO 17
<211> LENGTH: 10
<212> TYPE: DNA
<213> ORGANISM: Nicotiana tabacum

<400> SEQUENCE: 17

aatacgtgat                                                              10


<210> SEQ ID NO 18
<211> LENGTH: 10
<212> TYPE: DNA
<213> ORGANISM: Nicotiana tabacum

<400> SEQUENCE: 18

tttgttggga                                                              10


<210> SEQ ID NO 19
<211> LENGTH: 10
<212> TYPE: DNA
<213> ORGANISM: Nicotiana tabacum

<400> SEQUENCE: 19

accagaaggc                                                              10


<210> SEQ ID NO 20
<211> LENGTH: 10
<212> TYPE: DNA
<213> ORGANISM: Nicotiana tabacum

<400> SEQUENCE: 20

ctagtgttga                                                              10


<210> SEQ ID NO 21
<211> LENGTH: 10
<212> TYPE: DNA
<213> ORGANISM: Nicotiana tabacum
```

<400> SEQUENCE: 21
aatcgcttct 10

<210> SEQ ID NO 22
<211> LENGTH: 10
<212> TYPE: DNA
<213> ORGANISM: Nicotiana tabacum

<400> SEQUENCE: 22
tgcgacagca 10

<210> SEQ ID NO 23
<211> LENGTH: 11
<212> TYPE: DNA
<213> ORGANISM: Nicotiana tabacum

<400> SEQUENCE: 23
caaagtcgat a 11

<210> SEQ ID NO 24
<211> LENGTH: 11
<212> TYPE: DNA
<213> ORGANISM: Nicotiana tabacum

<400> SEQUENCE: 24
tataatctcg g 11

<210> SEQ ID NO 25
<211> LENGTH: 10
<212> TYPE: DNA
<213> ORGANISM: Nicotiana tabacum

<400> SEQUENCE: 25
ttgctttgtt 10

<210> SEQ ID NO 26
<211> LENGTH: 10
<212> TYPE: DNA
<213> ORGANISM: Nicotiana tabacum

<400> SEQUENCE: 26
tgaagacaat 10

<210> SEQ ID NO 27
<211> LENGTH: 10
<212> TYPE: DNA
<213> ORGANISM: Nicotiana tabacum

<400> SEQUENCE: 27
gccgcttgtg 10

<210> SEQ ID NO 28
<211> LENGTH: 11
<212> TYPE: DNA
<213> ORGANISM: Nicotiana tabacum

<400> SEQUENCE: 28
gctttgttgg c 11

<210> SEQ ID NO 29
<211> LENGTH: 10
<212> TYPE: DNA

-continued

<213> ORGANISM: Nicotiana tabacum

<400> SEQUENCE: 29
tcttcaccgg 10

<210> SEQ ID NO 30
<211> LENGTH: 10
<212> TYPE: DNA
<213> ORGANISM: Nicotiana tabacum

<400> SEQUENCE: 30
agatatgtgc 10

<210> SEQ ID NO 31
<211> LENGTH: 10
<212> TYPE: DNA
<213> ORGANISM: Nicotiana tabacum

<400> SEQUENCE: 31
acagcagcaa 10

<210> SEQ ID NO 32
<211> LENGTH: 11
<212> TYPE: DNA
<213> ORGANISM: Nicotiana tabacum

<400> SEQUENCE: 32
aatctcggct t 11

<210> SEQ ID NO 33
<211> LENGTH: 11
<212> TYPE: DNA
<213> ORGANISM: Nicotiana tabacum

<400> SEQUENCE: 33
ctttgttggc c 11

<210> SEQ ID NO 34
<211> LENGTH: 11
<212> TYPE: DNA
<213> ORGANISM: Nicotiana tabacum

<400> SEQUENCE: 34
caataatacc g 11

<210> SEQ ID NO 35
<211> LENGTH: 11
<212> TYPE: DNA
<213> ORGANISM: Nicotiana tabacum

<400> SEQUENCE: 35
tataatctcg g 11

<210> SEQ ID NO 36
<211> LENGTH: 10
<212> TYPE: DNA
<213> ORGANISM: Nicotiana tabacum

<400> SEQUENCE: 36
gctggaatcg 10

<210> SEQ ID NO 37
<211> LENGTH: 11

<212> TYPE: DNA
<213> ORGANISM: Nicotiana tabacum

<400> SEQUENCE: 37
ttctggtttg t 11

<210> SEQ ID NO 38
<211> LENGTH: 10
<212> TYPE: DNA
<213> ORGANISM: Nicotiana tabacum

<400> SEQUENCE: 38
ctcttcaccg 10

<210> SEQ ID NO 39
<211> LENGTH: 10
<212> TYPE: DNA
<213> ORGANISM: Nicotiana tabacum

<400> SEQUENCE: 39
tatcagtgtc 10

<210> SEQ ID NO 40
<211> LENGTH: 10
<212> TYPE: DNA
<213> ORGANISM: Nicotiana tabacum

<400> SEQUENCE: 40
ccagcttgtg 10

<210> SEQ ID NO 41
<211> LENGTH: 11
<212> TYPE: DNA
<213> ORGANISM: Nicotiana tabacum

<400> SEQUENCE: 41
cggtttggta g 11

<210> SEQ ID NO 42
<211> LENGTH: 11
<212> TYPE: DNA
<213> ORGANISM: Nicotiana tabacum

<400> SEQUENCE: 42
ccaagggagt t 11

<210> SEQ ID NO 43
<211> LENGTH: 10
<212> TYPE: DNA
<213> ORGANISM: Nicotiana tabacum

<400> SEQUENCE: 43
gagctctgct 10

<210> SEQ ID NO 44
<211> LENGTH: 10
<212> TYPE: DNA
<213> ORGANISM: Nicotiana tabacum

<400> SEQUENCE: 44
agctctgctt 10

<210> SEQ ID NO 45

<211> LENGTH: 11
<212> TYPE: DNA
<213> ORGANISM: Nicotiana tabacum

<400> SEQUENCE: 45
ataaaggtgg t 11

<210> SEQ ID NO 46
<211> LENGTH: 10
<212> TYPE: DNA
<213> ORGANISM: Nicotiana tabacum

<400> SEQUENCE: 46
ctcaaggctg 10

<210> SEQ ID NO 47
<211> LENGTH: 11
<212> TYPE: DNA
<213> ORGANISM: Nicotiana tabacum

<400> SEQUENCE: 47
tggatcagct g 11

<210> SEQ ID NO 48
<211> LENGTH: 11
<212> TYPE: DNA
<213> ORGANISM: Nicotiana tabacum

<400> SEQUENCE: 48
tggatcagct g 11

<210> SEQ ID NO 49
<211> LENGTH: 11
<212> TYPE: DNA
<213> ORGANISM: Nicotiana tabacum

<400> SEQUENCE: 49
tggaatcgct t 11

<210> SEQ ID NO 50
<211> LENGTH: 11
<212> TYPE: DNA
<213> ORGANISM: Nicotiana tabacum

<400> SEQUENCE: 50
gacaatggcc g 11

<210> SEQ ID NO 51
<211> LENGTH: 10
<212> TYPE: DNA
<213> ORGANISM: Nicotiana tabacum

<400> SEQUENCE: 51
ttgtgtcaca 10

<210> SEQ ID NO 52
<211> LENGTH: 11
<212> TYPE: DNA
<213> ORGANISM: Nicotiana tabacum

<400> SEQUENCE: 52
gtgtcacatt a 11

<210> SEQ ID NO 53
<211> LENGTH: 10
<212> TYPE: DNA
<213> ORGANISM: Nicotiana tabacum

<400> SEQUENCE: 53
gaactgggaa 10

<210> SEQ ID NO 54
<211> LENGTH: 11
<212> TYPE: DNA
<213> ORGANISM: Nicotiana tabacum

<400> SEQUENCE: 54
ctggtttgtt c 11

<210> SEQ ID NO 55
<211> LENGTH: 11
<212> TYPE: DNA
<213> ORGANISM: Nicotiana tabacum

<400> SEQUENCE: 55
ccatattatt c 11

<210> SEQ ID NO 56
<211> LENGTH: 11
<212> TYPE: DNA
<213> ORGANISM: Nicotiana tabacum

<400> SEQUENCE: 56
accagcttgt g 11

<210> SEQ ID NO 57
<211> LENGTH: 11
<212> TYPE: DNA
<213> ORGANISM: Nicotiana tabacum

<400> SEQUENCE: 57
cggtttggta g 11

<210> SEQ ID NO 58
<211> LENGTH: 11
<212> TYPE: DNA
<213> ORGANISM: Nicotiana tabacum

<400> SEQUENCE: 58
ggtcgtagaa a 11

<210> SEQ ID NO 59
<211> LENGTH: 11
<212> TYPE: DNA
<213> ORGANISM: Nicotiana tabacum

<400> SEQUENCE: 59
ctgtcactca a 11

<210> SEQ ID NO 60
<211> LENGTH: 11
<212> TYPE: DNA
<213> ORGANISM: Nicotiana tabacum

<400> SEQUENCE: 60
gtatccagat a 11

<210> SEQ ID NO 61
<211> LENGTH: 10
<212> TYPE: DNA
<213> ORGANISM: Nicotiana tabacum

<400> SEQUENCE: 61
gatctctgct 10

<210> SEQ ID NO 62
<211> LENGTH: 10
<212> TYPE: DNA
<213> ORGANISM: Nicotiana tabacum

<400> SEQUENCE: 62
ggagcccatt 10

<210> SEQ ID NO 63
<211> LENGTH: 11
<212> TYPE: DNA
<213> ORGANISM: Nicotiana tabacum

<400> SEQUENCE: 63
gagtacattg g 11

<210> SEQ ID NO 64
<211> LENGTH: 11
<212> TYPE: DNA
<213> ORGANISM: Nicotiana tabacum

<400> SEQUENCE: 64
tcaaggctgc t 11

<210> SEQ ID NO 65
<211> LENGTH: 10
<212> TYPE: DNA
<213> ORGANISM: Nicotiana tabacum

<400> SEQUENCE: 65
gatcagctgc 10

<210> SEQ ID NO 66
<211> LENGTH: 11
<212> TYPE: DNA
<213> ORGANISM: Nicotiana tabacum

<400> SEQUENCE: 66
accagaaggc c 11

<210> SEQ ID NO 67
<211> LENGTH: 12
<212> TYPE: DNA
<213> ORGANISM: Nicotiana tabacum

<400> SEQUENCE: 67
tagtgttgaa at 12

<210> SEQ ID NO 68
<211> LENGTH: 10
<212> TYPE: DNA
<213> ORGANISM: Nicotiana tabacum

<400> SEQUENCE: 68
aacaagatat 10

<210> SEQ ID NO 69
<211> LENGTH: 11
<212> TYPE: DNA
<213> ORGANISM: Nicotiana tabacum

<400> SEQUENCE: 69
tgcgacagca g 11

<210> SEQ ID NO 70
<211> LENGTH: 10
<212> TYPE: DNA
<213> ORGANISM: Nicotiana tabacum

<400> SEQUENCE: 70
atgtgcgaca 10

<210> SEQ ID NO 71
<211> LENGTH: 12
<212> TYPE: DNA
<213> ORGANISM: Nicotiana tabacum

<400> SEQUENCE: 71
cagcaaagac ga 12

<210> SEQ ID NO 72
<211> LENGTH: 11
<212> TYPE: DNA
<213> ORGANISM: Nicotiana tabacum

<400> SEQUENCE: 72
cccttggtta g 11

<210> SEQ ID NO 73
<211> LENGTH: 11
<212> TYPE: DNA
<213> ORGANISM: Nicotiana tabacum

<400> SEQUENCE: 73
ttcatgaaat a 11

<210> SEQ ID NO 74
<211> LENGTH: 10
<212> TYPE: DNA
<213> ORGANISM: Nicotiana tabacum

<400> SEQUENCE: 74
cggtttggta 10

<210> SEQ ID NO 75
<211> LENGTH: 11
<212> TYPE: DNA
<213> ORGANISM: Nicotiana tabacum

<400> SEQUENCE: 75
gacaatggcc g 11

<210> SEQ ID NO 76
<211> LENGTH: 11
<212> TYPE: DNA
<213> ORGANISM: Nicotiana tabacum

<400> SEQUENCE: 76
ttgtgtcaca t 11

<210> SEQ ID NO 77
<211> LENGTH: 11
<212> TYPE: DNA
<213> ORGANISM: Nicotiana tabacum

<400> SEQUENCE: 77
aactgggaat t 11

<210> SEQ ID NO 78
<211> LENGTH: 10
<212> TYPE: DNA
<213> ORGANISM: Nicotiana tabacum

<400> SEQUENCE: 78
cttaggacca 10

<210> SEQ ID NO 79
<211> LENGTH: 11
<212> TYPE: DNA
<213> ORGANISM: Nicotiana tabacum

<400> SEQUENCE: 79
gaatcgcttc t 11

<210> SEQ ID NO 80
<211> LENGTH: 10
<212> TYPE: DNA
<213> ORGANISM: Nicotiana tabacum

<400> SEQUENCE: 80
gtttgttccc 10

<210> SEQ ID NO 81
<211> LENGTH: 11
<212> TYPE: DNA
<213> ORGANISM: Nicotiana tabacum

<400> SEQUENCE: 81
cattgccatg g 11

<210> SEQ ID NO 82
<211> LENGTH: 10
<212> TYPE: DNA
<213> ORGANISM: Nicotiana tabacum

<400> SEQUENCE: 82
atcttataca 10

<210> SEQ ID NO 83
<211> LENGTH: 11
<212> TYPE: DNA
<213> ORGANISM: Nicotiana tabacum

<400> SEQUENCE: 83
attgcatatt g 11

<210> SEQ ID NO 84
<211> LENGTH: 11
<212> TYPE: DNA
<213> ORGANISM: Nicotiana tabacum

<400> SEQUENCE: 84
gactcatcac t 11

<210> SEQ ID NO 85
<211> LENGTH: 10
<212> TYPE: DNA
<213> ORGANISM: Nicotiana tabacum

<400> SEQUENCE: 85
ccttcttttg 10

<210> SEQ ID NO 86
<211> LENGTH: 11
<212> TYPE: DNA
<213> ORGANISM: Nicotiana tabacum

<400> SEQUENCE: 86
ttctcaagaa a 11

<210> SEQ ID NO 87
<211> LENGTH: 11
<212> TYPE: DNA
<213> ORGANISM: Nicotiana tabacum

<400> SEQUENCE: 87
cttcaaccta a 11

<210> SEQ ID NO 88
<211> LENGTH: 10
<212> TYPE: DNA
<213> ORGANISM: Nicotiana tabacum

<400> SEQUENCE: 88
tatttatgaa 10

<210> SEQ ID NO 89
<211> LENGTH: 11
<212> TYPE: DNA
<213> ORGANISM: Nicotiana tabacum

<400> SEQUENCE: 89
gagtagtgcc a 11

<210> SEQ ID NO 90
<211> LENGTH: 10
<212> TYPE: DNA
<213> ORGANISM: Nicotiana tabacum

<400> SEQUENCE: 90
cggtgggtct 10

<210> SEQ ID NO 91
<211> LENGTH: 11
<212> TYPE: DNA
<213> ORGANISM: Nicotiana tabacum

<400> SEQUENCE: 91
ctggtgagct t 11

<210> SEQ ID NO 92
<211> LENGTH: 11
<212> TYPE: DNA
<213> ORGANISM: Nicotiana tabacum

<400> SEQUENCE: 92
ctgatgtaaa g 11

<210> SEQ ID NO 93
<211> LENGTH: 10
<212> TYPE: DNA
<213> ORGANISM: Nicotiana tabacum

<400> SEQUENCE: 93
gatttgcatc 10

<210> SEQ ID NO 94
<211> LENGTH: 10
<212> TYPE: DNA
<213> ORGANISM: Nicotiana tabacum

<400> SEQUENCE: 94
cctgactaac 10

<210> SEQ ID NO 95
<211> LENGTH: 10
<212> TYPE: DNA
<213> ORGANISM: Nicotiana tabacum

<400> SEQUENCE: 95
gtaccttatg 10

<210> SEQ ID NO 96
<211> LENGTH: 10
<212> TYPE: DNA
<213> ORGANISM: Nicotiana tabacum

<400> SEQUENCE: 96
gatttgcata 10

<210> SEQ ID NO 97
<211> LENGTH: 11
<212> TYPE: DNA
<213> ORGANISM: Nicotiana tabacum

<400> SEQUENCE: 97
tttgatagct g 11

<210> SEQ ID NO 98
<211> LENGTH: 11
<212> TYPE: DNA
<213> ORGANISM: Nicotiana tabacum

<400> SEQUENCE: 98
ccttctctgc g 11

<210> SEQ ID NO 99
<211> LENGTH: 11
<212> TYPE: DNA
<213> ORGANISM: Nicotiana tabacum

<400> SEQUENCE: 99
agctgagagg g 11

<210> SEQ ID NO 100
<211> LENGTH: 10
<212> TYPE: DNA
<213> ORGANISM: Nicotiana tabacum

<400> SEQUENCE: 100
cggtaagatc 10

<210> SEQ ID NO 101
<211> LENGTH: 11
<212> TYPE: DNA
<213> ORGANISM: Nicotiana tabacum

<400> SEQUENCE: 101
tcaggcaggt g 11

<210> SEQ ID NO 102
<211> LENGTH: 10
<212> TYPE: DNA
<213> ORGANISM: Nicotiana tabacum

<400> SEQUENCE: 102
ggctccgcca 10

<210> SEQ ID NO 103
<211> LENGTH: 10
<212> TYPE: DNA
<213> ORGANISM: Nicotiana tabacum

<400> SEQUENCE: 103
gtaccttatg 10

<210> SEQ ID NO 104
<211> LENGTH: 10
<212> TYPE: DNA
<213> ORGANISM: Nicotiana tabacum

<400> SEQUENCE: 104
gatttgcata 10

<210> SEQ ID NO 105
<211> LENGTH: 11
<212> TYPE: DNA
<213> ORGANISM: Nicotiana tabacum

<400> SEQUENCE: 105
ctactgctgc a 11

<210> SEQ ID NO 106
<211> LENGTH: 11
<212> TYPE: DNA
<213> ORGANISM: Nicotiana tabacum

<400> SEQUENCE: 106
ggcctggaat t 11

<210> SEQ ID NO 107
<211> LENGTH: 10
<212> TYPE: DNA
<213> ORGANISM: Nicotiana tabacum

<400> SEQUENCE: 107
gattgctgtg 10

<210> SEQ ID NO 108
<211> LENGTH: 11
<212> TYPE: DNA

<213> ORGANISM: Nicotiana tabacum

<400> SEQUENCE: 108
catctggtct c 11

<210> SEQ ID NO 109
<211> LENGTH: 11
<212> TYPE: DNA
<213> ORGANISM: Nicotiana tabacum

<400> SEQUENCE: 109
cggagcagct t 11

<210> SEQ ID NO 110
<211> LENGTH: 10
<212> TYPE: DNA
<213> ORGANISM: Nicotiana tabacum

<400> SEQUENCE: 110
ccttatggct 10

<210> SEQ ID NO 111
<211> LENGTH: 11
<212> TYPE: DNA
<213> ORGANISM: Nicotiana tabacum

<400> SEQUENCE: 111
cagggctgta t 11

<210> SEQ ID NO 112
<211> LENGTH: 10
<212> TYPE: DNA
<213> ORGANISM: Nicotiana tabacum

<400> SEQUENCE: 112
cggttctcgg 10

<210> SEQ ID NO 113
<211> LENGTH: 11
<212> TYPE: DNA
<213> ORGANISM: Nicotiana tabacum

<400> SEQUENCE: 113
ggttctcgga g 11

<210> SEQ ID NO 114
<211> LENGTH: 11
<212> TYPE: DNA
<213> ORGANISM: Nicotiana tabacum

<400> SEQUENCE: 114
agcttccctt a 11

<210> SEQ ID NO 115
<211> LENGTH: 11
<212> TYPE: DNA
<213> ORGANISM: Nicotiana tabacum

<400> SEQUENCE: 115
catcactttt g 11

<210> SEQ ID NO 116
<211> LENGTH: 10

<212> TYPE: DNA
<213> ORGANISM: Nicotiana tabacum

<400> SEQUENCE: 116
gtggggctcc 10

<210> SEQ ID NO 117
<211> LENGTH: 10
<212> TYPE: DNA
<213> ORGANISM: Nicotiana tabacum

<400> SEQUENCE: 117
ccacatgctc 10

<210> SEQ ID NO 118
<211> LENGTH: 11
<212> TYPE: DNA
<213> ORGANISM: Nicotiana tabacum

<400> SEQUENCE: 118
tgcggttctc g 11

<210> SEQ ID NO 119
<211> LENGTH: 10
<212> TYPE: DNA
<213> ORGANISM: Nicotiana tabacum

<400> SEQUENCE: 119
agcagcttcc 10

<210> SEQ ID NO 120
<211> LENGTH: 11
<212> TYPE: DNA
<213> ORGANISM: Nicotiana tabacum

<400> SEQUENCE: 120
atgccaaccc g 11

<210> SEQ ID NO 121
<211> LENGTH: 11
<212> TYPE: DNA
<213> ORGANISM: Nicotiana tabacum

<400> SEQUENCE: 121
agccatggat g 11

<210> SEQ ID NO 122
<211> LENGTH: 11
<212> TYPE: DNA
<213> ORGANISM: Nicotiana tabacum

<400> SEQUENCE: 122
aggagtggga a 11

<210> SEQ ID NO 123
<211> LENGTH: 11
<212> TYPE: DNA
<213> ORGANISM: Nicotiana tabacum

<400> SEQUENCE: 123
tgagagagaa a 11

<210> SEQ ID NO 124

<211> LENGTH: 11
<212> TYPE: DNA
<213> ORGANISM: Nicotiana tabacum

<400> SEQUENCE: 124
cagggctgta t 11

<210> SEQ ID NO 125
<211> LENGTH: 11
<212> TYPE: DNA
<213> ORGANISM: Nicotiana tabacum

<400> SEQUENCE: 125
ccgttctggg a 11

<210> SEQ ID NO 126
<211> LENGTH: 11
<212> TYPE: DNA
<213> ORGANISM: Nicotiana tabacum

<400> SEQUENCE: 126
gcgtcatatt t 11

<210> SEQ ID NO 127
<211> LENGTH: 11
<212> TYPE: DNA
<213> ORGANISM: Nicotiana tabacum

<400> SEQUENCE: 127
ttgagctaac a 11

<210> SEQ ID NO 128
<211> LENGTH: 11
<212> TYPE: DNA
<213> ORGANISM: Nicotiana tabacum

<400> SEQUENCE: 128
gccatggatg a 11

<210> SEQ ID NO 129
<211> LENGTH: 10
<212> TYPE: DNA
<213> ORGANISM: Nicotiana tabacum

<400> SEQUENCE: 129
aaatatcact 10

<210> SEQ ID NO 130
<211> LENGTH: 10
<212> TYPE: DNA
<213> ORGANISM: Nicotiana tabacum

<400> SEQUENCE: 130
caaataccaa 10

<210> SEQ ID NO 131
<211> LENGTH: 11
<212> TYPE: DNA
<213> ORGANISM: Nicotiana tabacum

<400> SEQUENCE: 131
cagcaggggt g 11

<210> SEQ ID NO 132
<211> LENGTH: 10
<212> TYPE: DNA
<213> ORGANISM: Nicotiana tabacum

<400> SEQUENCE: 132
cttatggctg 10

<210> SEQ ID NO 133
<211> LENGTH: 11
<212> TYPE: DNA
<213> ORGANISM: Nicotiana tabacum

<400> SEQUENCE: 133
ttcaatgaga a 11

<210> SEQ ID NO 134
<211> LENGTH: 12
<212> TYPE: DNA
<213> ORGANISM: Nicotiana tabacum

<400> SEQUENCE: 134
cacttcaagg gt 12

<210> SEQ ID NO 135
<211> LENGTH: 11
<212> TYPE: DNA
<213> ORGANISM: Nicotiana tabacum

<400> SEQUENCE: 135
ttgtcctggc a 11

<210> SEQ ID NO 136
<211> LENGTH: 10
<212> TYPE: DNA
<213> ORGANISM: Nicotiana tabacum

<400> SEQUENCE: 136
cattgccatg 10

<210> SEQ ID NO 137
<211> LENGTH: 11
<212> TYPE: DNA
<213> ORGANISM: Nicotiana tabacum

<400> SEQUENCE: 137
gatcttatac a 11

<210> SEQ ID NO 138
<211> LENGTH: 11
<212> TYPE: DNA
<213> ORGANISM: Nicotiana tabacum

<400> SEQUENCE: 138
ttctccttct g 11

<210> SEQ ID NO 139
<211> LENGTH: 12
<212> TYPE: DNA
<213> ORGANISM: Nicotiana tabacum

<400> SEQUENCE: 139
caataacaat gc 12

<210> SEQ ID NO 140
<211> LENGTH: 10
<212> TYPE: DNA
<213> ORGANISM: Nicotiana tabacum

<400> SEQUENCE: 140
gctgagaggg 10

<210> SEQ ID NO 141
<211> LENGTH: 12
<212> TYPE: DNA
<213> ORGANISM: Nicotiana tabacum

<400> SEQUENCE: 141
cggtaagatc ga 12

<210> SEQ ID NO 142
<211> LENGTH: 10
<212> TYPE: DNA
<213> ORGANISM: Nicotiana tabacum

<400> SEQUENCE: 142
tttgggattg 10

<210> SEQ ID NO 143
<211> LENGTH: 11
<212> TYPE: DNA
<213> ORGANISM: Nicotiana tabacum

<400> SEQUENCE: 143
tgtgccatct g 11

<210> SEQ ID NO 144
<211> LENGTH: 12
<212> TYPE: DNA
<213> ORGANISM: Nicotiana tabacum

<400> SEQUENCE: 144
ctccgccaca tg 12

<210> SEQ ID NO 145
<211> LENGTH: 10
<212> TYPE: DNA
<213> ORGANISM: Nicotiana tabacum

<400> SEQUENCE: 145
tcattgtacc 10

<210> SEQ ID NO 146
<211> LENGTH: 11
<212> TYPE: DNA
<213> ORGANISM: Nicotiana tabacum

<400> SEQUENCE: 146
gcatcccctg a 11

<210> SEQ ID NO 147
<211> LENGTH: 11
<212> TYPE: DNA
<213> ORGANISM: Nicotiana tabacum

<400> SEQUENCE: 147
taacacaacc c 11

<210> SEQ ID NO 148
<211> LENGTH: 10
<212> TYPE: DNA
<213> ORGANISM: Nicotiana tabacum

<400> SEQUENCE: 148
caataacaat 10

<210> SEQ ID NO 149
<211> LENGTH: 10
<212> TYPE: DNA
<213> ORGANISM: Nicotiana tabacum

<400> SEQUENCE: 149
ctggttcttc 10

<210> SEQ ID NO 150
<211> LENGTH: 12
<212> TYPE: DNA
<213> ORGANISM: Nicotiana tabacum

<400> SEQUENCE: 150
gccaacccgg ag 12

<210> SEQ ID NO 151
<211> LENGTH: 11
<212> TYPE: DNA
<213> ORGANISM: Nicotiana tabacum

<400> SEQUENCE: 151
catggatgag a 11

<210> SEQ ID NO 152
<211> LENGTH: 11
<212> TYPE: DNA
<213> ORGANISM: Nicotiana tabacum

<400> SEQUENCE: 152
ccttaatgaa a 11

<210> SEQ ID NO 153
<211> LENGTH: 10
<212> TYPE: DNA
<213> ORGANISM: Nicotiana tabacum

<400> SEQUENCE: 153
acgaaggaca 10

<210> SEQ ID NO 154
<211> LENGTH: 11
<212> TYPE: DNA
<213> ORGANISM: Nicotiana tabacum

<400> SEQUENCE: 154
gtgggaagtg a 11

<210> SEQ ID NO 155
<211> LENGTH: 10
<212> TYPE: DNA
<213> ORGANISM: Nicotiana tabacum

<400> SEQUENCE: 155
agagaaattc 10

<210> SEQ ID NO 156
<211> LENGTH: 11
<212> TYPE: DNA
<213> ORGANISM: Nicotiana tabacum

<400> SEQUENCE: 156
tccctgtcgt c 11

<210> SEQ ID NO 157
<211> LENGTH: 11
<212> TYPE: DNA
<213> ORGANISM: Nicotiana tabacum

<400> SEQUENCE: 157
atgaaggagt g 11

<210> SEQ ID NO 158
<211> LENGTH: 11
<212> TYPE: DNA
<213> ORGANISM: Nicotiana tabacum

<400> SEQUENCE: 158
gaactcacct t 11

<210> SEQ ID NO 159
<211> LENGTH: 11
<212> TYPE: DNA
<213> ORGANISM: Nicotiana tabacum

<400> SEQUENCE: 159
ttttggttct c 11

<210> SEQ ID NO 160
<211> LENGTH: 10
<212> TYPE: DNA
<213> ORGANISM: Nicotiana tabacum

<400> SEQUENCE: 160
caggcaggtg 10

<210> SEQ ID NO 161
<211> LENGTH: 11
<212> TYPE: DNA
<213> ORGANISM: Nicotiana tabacum

<400> SEQUENCE: 161
ggctccgcca c 11

<210> SEQ ID NO 162
<211> LENGTH: 10
<212> TYPE: DNA
<213> ORGANISM: Nicotiana tabacum

<400> SEQUENCE: 162
atggctggtt 10

<210> SEQ ID NO 163
<211> LENGTH: 11
<212> TYPE: DNA
<213> ORGANISM: Nicotiana tabacum

<400> SEQUENCE: 163
aatgagaatg a 11

<210> SEQ ID NO 164
<211> LENGTH: 10
<212> TYPE: DNA
<213> ORGANISM: Nicotiana tabacum

<400> SEQUENCE: 164
tggtgagctt 10

<210> SEQ ID NO 165
<211> LENGTH: 11
<212> TYPE: DNA
<213> ORGANISM: Nicotiana tabacum

<400> SEQUENCE: 165
ctgatgtaaa g 11

<210> SEQ ID NO 166
<211> LENGTH: 10
<212> TYPE: DNA
<213> ORGANISM: Nicotiana tabacum

<400> SEQUENCE: 166
aaggacagag 10

<210> SEQ ID NO 167
<211> LENGTH: 11
<212> TYPE: DNA
<213> ORGANISM: Nicotiana tabacum

<400> SEQUENCE: 167
agtgggaagt g 11

<210> SEQ ID NO 168
<211> LENGTH: 21
<212> TYPE: DNA
<213> ORGANISM: Artificial sequence
<220> FEATURE:
<223> OTHER INFORMATION: Synthetic sequence: Forward primer

<400> SEQUENCE: 168
tatctcctcg ccatatctgt a 21

<210> SEQ ID NO 169
<211> LENGTH: 22
<212> TYPE: DNA
<213> ORGANISM: Artificial sequence
<220> FEATURE:
<223> OTHER INFORMATION: Synthetic sequence: Reverse primer

<400> SEQUENCE: 169
gtgcaaacac acttgtattt ac 22

<210> SEQ ID NO 170
<211> LENGTH: 19
<212> TYPE: DNA
<213> ORGANISM: Artificial sequence
<220> FEATURE:
<223> OTHER INFORMATION: Synthetic sequence: Forward primer

<400> SEQUENCE: 170
accatctctt cctccggga 19

<210> SEQ ID NO 171
<211> LENGTH: 23
<212> TYPE: DNA
<213> ORGANISM: Artificial sequence
<220> FEATURE:
<223> OTHER INFORMATION: Synthetic sequence: Reverse primer

<400> SEQUENCE: 171
tataggatac tcctctgata aat 23

<210> SEQ ID NO 172
<211> LENGTH: 23
<212> TYPE: DNA
<213> ORGANISM: Artificial sequence
<220> FEATURE:
<223> OTHER INFORMATION: Synthetic sequence: Forward primer

<400> SEQUENCE: 172
ttgtacaatt tatcagagga gta 23

<210> SEQ ID NO 173
<211> LENGTH: 20
<212> TYPE: DNA
<213> ORGANISM: Artificial sequence
<220> FEATURE:
<223> OTHER INFORMATION: Synthetic sequence: Reverse primer

<400> SEQUENCE: 173
ttggtttgag tgcaaacaca 20

<210> SEQ ID NO 174
<211> LENGTH: 22
<212> TYPE: DNA
<213> ORGANISM: Artificial sequence
<220> FEATURE:
<223> OTHER INFORMATION: Synthetic sequence: Forward primer

<400> SEQUENCE: 174
actatatcga ggatagaagg ta 22

<210> SEQ ID NO 175
<211> LENGTH: 23
<212> TYPE: DNA
<213> ORGANISM: Artificial sequence
<220> FEATURE:
<223> OTHER INFORMATION: Synthetic sequence: Reverse primer

<400> SEQUENCE: 175
tatctattta tacatctggt tcg 23

<210> SEQ ID NO 176
<211> LENGTH: 20
<212> TYPE: DNA
<213> ORGANISM: Artificial sequence
<220> FEATURE:
<223> OTHER INFORMATION: Synthetic sequence: Forward primer

<400> SEQUENCE: 176
cttgtgatcc atcacttccc 20

<210> SEQ ID NO 177
<211> LENGTH: 23
<212> TYPE: DNA
<213> ORGANISM: Artificial sequence
<220> FEATURE:
<223> OTHER INFORMATION: Synthetic sequence: Reverse primer -continued

```
<400> SEQUENCE: 177

tatgactatt tctgtgcatc ttt                                           23


<210> SEQ ID NO 178
<211> LENGTH: 22
<212> TYPE: DNA
<213> ORGANISM: Artificial sequence
<220> FEATURE:
<223> OTHER INFORMATION: Synthetic sequence: Forward primer

<400> SEQUENCE: 178

gccttgtgat tcatcacttc aa                                            22


<210> SEQ ID NO 179
<211> LENGTH: 23
<212> TYPE: DNA
<213> ORGANISM: Artificial sequence
<220> FEATURE:
<223> OTHER INFORMATION: Synthetic sequence: Reverse primer

<400> SEQUENCE: 179

tatgactatt tctgtgcatc tta                                           23


<210> SEQ ID NO 180
<211> LENGTH: 19
<212> TYPE: DNA
<213> ORGANISM: Artificial sequence
<220> FEATURE:
<223> OTHER INFORMATION: Synthetic sequence: Forward primer

<400> SEQUENCE: 180

ggttcttctc gctctgagc                                                19


<210> SEQ ID NO 181
<211> LENGTH: 22
<212> TYPE: DNA
<213> ORGANISM: Artificial sequence
<220> FEATURE:
<223> OTHER INFORMATION: Synthetic sequence: Reverse primer

<400> SEQUENCE: 181

aacgtaaaat aactttgcca cg                                            22
```

TOBACCO SPECIFIC NITROSAMINE REDUCTION IN PLANTS

This application is a U.S. National Stage Application of International Application No. PCT/EP2013/077532, filed Dec. 19, 2013, which was published in English on Jun. 26, 2014 as International Patent Publication WO 2014/096283 A1. International Application No. PCT/EP2013/077532 claims priority to European Application No. 12198966.9 filed Dec. 21, 2012.

FIELD OF THE INVENTION

The present invention discloses novel polynucleotide sequences of genes encoding members of the CLC family of chloride channels from the genus *Nicotiana* and variants, homologues, fragments and mutants thereof. The polypeptide sequences and variants, homologues, fragments and mutants thereof are also disclosed. The modification of the expression of one or more of these genes or the activity of the protein encoded thereby to modulate the levels of tobacco specific nitrosamines (TSNAs) in a plant or component part thereof is also disclosed.

BACKGROUND OF THE INVENTION

Tobacco Specific Nitrosamines (TSNAs) are formed primarily during the curing and processing of tobacco leaves. Tobacco curing is a process of physical and biochemical changes that bring out the aroma and flavor of each variety of tobacco. It is believed that the amount TSNA in cured tobacco leaf is dependent on the accumulation of nitrites, which accumulate during the death of the plant cell and are formed during curing by the reduction of nitrates under conditions approaching an anaerobic (oxygen deficient) environment. The reduction of nitrates to nitrites is believed to occur by the action of bacteria on the surface of the leaf under anaerobic conditions, and this reduction is particularly pronounced under certain conditions. Once nitrites are formed, these compounds are believed to combine with various tobacco alkaloids, including pyridine-containing compounds, to form nitrosamines.

The four principal TSNAs, that is, those typically found to be present in the highest concentrations, are N-nitrosonicotine (NNN), 4-(methylnitrosamino)-1-(3-pyridyl)-1-butanone (NNK), N-nitrosoanabasine (NAB) and N-nitrosoanatabine (NAT). Minor compounds, that is, those typically found at significantly lower levels than the principal TSNAs, include 4-(methylnitrosamino) 4-(3-pyridyl) butanal (NNA), 4-(methylnitrosamino)-1-(3-pyridyl)-1-butanol (NNAL), 4-(methylnitrosamino)4-(3-pyridyl)-1-butanol (iso-NNAL), and 4-(methylnitrosamino)-4-(3-pyridyl)-1-butyric acid (iso-NNAC). At least NNN and NNK have been reported to be carcinogenic when applied to animals in laboratory studies.

Lowering the concentrations of compounds responsible for the nitrosation of alkaloids to TSNAs can result in decreased TSNA levels in cured leaves. A major nitrosating agent in tobacco leaves is nitrite ($NO_2^-$), resulting from the reduction of free nitrate ($NO_3^-$) through an enzymatic reaction possibly catalyzed by bacteria during curing. Fertilizer studies altering nitrate levels in Burley plants resulted in different TSNA levels in cured leaves and smoke. Nitrate is the major source of nitrogen available in the soil. In plants, it is absorbed by root epidermal cells and transported to the whole plant to be first reduced to nitrite which is further reduced to ammonia and then assimilated into amino acids. Unfortunately, nitrogen limitation during Burley growth results in unfavorable agronomic phenotypes such as poor biomass yield and delay in plant maturation and is therefore not a commercially viable approach to reduce TSNA levels. Trying to manipulate nitrate accumulation in tobacco leaf is a major challenge.

WO98/58555 describes the treatment of tobacco leaves before or during flue-curing by microwaving for reducing TSNAs. U.S. Pat. No. 5,810,020 describes a process for removing TSNAs from tobacco by contacting the tobacco material with a trapping sink, wherein the trapping sink comprises a select transition metal complex which is readily nitrosated to form a nitrosyl complex with little kinetic or thermodynamic hindrance. U.S. Pat. No. 6,202,649 describes a method of substantially preventing formation of TSNAs by, among other things, curing tobacco in a controlled environment having a sufficient airflow to substantially prevent an anaerobic condition around the vicinity of the tobacco leaf. The controlled environment is provided by controlling one or more curing parameters, such as airflow, humidity, and temperature. However, methods such as these can add considerable cost and time to the production of tobacco and therefore are less likely to be accepted by the tobacco industry. Thus, a need remains for an effective and relatively inexpensive method for reducing TSNAs.

Molecular based methods for reducing the levels of TSNAs in plants are highly desirable since they do not require expensive, and often complex, methods to achieve the reduced levels of TSNAs. One such molecular based approach is disclosed in WO2011/088180. Compositions and methods are disclosed for inhibiting the expression or function of root-specific nicotine demethylase polypeptides that are involved in the metabolic conversion of nicotine to nornicotine in the roots of tobacco plants. The gene sequence of the CYP82E10 nicotine demethylase gene is disclosed. Reducing the expression of this gene was found to reduce the levels of NNN in cured tobacco leaves. Whilst reduced levels of NNN may be obtained, there is more than one TSNA that has been reported to be carcinogenic which will still remain in the modified plants. Other nicotine demethylase genes include CYP82E4 and CYP82E5 which participate in the conversion of nicotine to nornicotine and are described in WO2006091194, WO2008070274 and WO2009064771.

There is a continuing need in the art to develop molecular based strategies for reducing the levels of TSNAs in cured tobacco leaves. The present invention seeks to address this need.

SUMMARY OF THE INVENTION

The inventors have cloned novel genes encoding various members of the CLC family of chloride channels from plants belonging to the genus *Nicotiana* and denoted as CLC-Nt2 and NtCLCe. Two copies of the orthologous gene originating from two ancestors, *N. tomentosiformis* and *N. sylvestris* exist in *Nicotiana tabacum*, and are denoted herein as CLC-Nt2-t and CLC-Nt2-s or NtCLCe-t and NtCLCe-s, respectively. The polynucleotide sequences of these genes are set forth in SEQ ID NOs: 1-4, 10 and 11 and the polypeptide sequences of these genes are set forth in SEQ ID NOs: 5-7 and 12-14. By reducing the expression of these genes in tobacco plants a reduction in nitrate levels in plants is seen. In particular, a reduction in nitrate levels in green leaves is seen. Total TSNA content after curing of leaves is reduced in these plants. This suggests that reduced levels of nitrate can cause the formation of lower levels of TSNAs in cured plant material—such as cured leaves. The inventors unexpectedly found that a reduction in at least NNK is seen in cured plant material from both NtCLCe-RNAi and CLC-Nt2-RNAi plants. A reduction in total TSNA content was also observed. Reducing the expression of NtCLCe and/or CLC-Nt2 therefore contributes to reducing nitrate levels in tobacco leaves. After curing, at least NNK and optionally other TSNAs, which may include NNN or NAB or NAT or a combination of two or more thereof, can be reduced. In addition, the visual appearance of the plants is not substantially altered which is an important criterion for acceptance by the industry and for maximising plant yields and the like. In addition, the biomass levels are not substantially altered which is another important criterion for acceptance by the industry and for maximising plant yields and the like The present invention may therefore be particularly useful to modulate (eg. increase or decrease) levels of nitrate or total TSNAs in plants, including at least NNK. In particular, the present invention may be particularly useful when combined with other methods that are able to reduce the levels of TSNAs. Thus, it may be desirable in certain embodiments to reduce the expression of the one or more polynucleotides described herein together with reducing the expression of one or more nicotine demethylase genes in a tobacco plant. This combination would be expected to reduce at least NNK and NNN levels in a cured plant material which would be highly desirable since NNK and NNN have both been reported to be carcinogenic when applied to animals in laboratory studies. The tobacco products derived from the tobacco plants described herein may find use in methods for reducing the carcinogenic potential of these tobacco products, and reducing the exposure of humans to carcinogenic nitrosamines. Mutants of the polypeptide sequences described herein that can modulate nitrate content in plants are also described.

Aspects and Embodiments of the Invention

Aspects and embodiments of the present invention are set forth in the accompanying claims.

In a first aspect, there is described a mutant, non-naturally occurring or transgenic plant cell comprising: (i) a polynucleotide comprising, consisting or consisting essentially of a sequence encoding a member of the CLC family of chloride channels and having at least 60% sequence identity to SEQ ID NO:1 or SEQ ID NO:2 or SEQ ID NO:3 or SEQ ID NO:4 or SEQ ID NO:10 or SEQ ID NO:11; (ii) a polypeptide encoded by the polynucleotide set forth in (i); (iii) a polypeptide comprising, consisting or consisting essentially of a sequence encoding a member of the CLC family of chloride channels and having at least 60% sequence identity to SEQ ID NO:5 or SEQ ID NO:6 or SEQ ID NO:7 or SEQ ID NO:12 or SEQ ID NO:13 or SEQ ID NO:14; or (iv) a construct, vector or expression vector comprising the isolated polynucleotide set forth in (i), and wherein the expression or activity of the polynucleotide or the polypeptide is modulated as compared to a control plant containing the control plant cell and wherein the nitrate levels in the mutant, non-naturally occurring or transgenic plant containing the mutant, non-naturally occurring or transgenic plant cell are modulated as compared to the control plant containing the control plant cell. By reducing the expression of the one or more genes in tobacco plants nitrate levels can be reduced. Total TSNA content and/or NNK levels can be reduced in cured plant material.

In one embodiment, said mutant, non-naturally occurring or transgenic plant cell comprises one or more mutations in the disclosed polypeptides and polynucleotides that decreases the level of nitrate in the mutant, non-naturally occurring or transgenic plant containing the mutant, non-naturally occurring or transgenic plant cell as compared to the control plant containing the control plant cell. The mutation(s) can comprise a substitution mutation at position G163 of SEQ ID NO:5. In one embodiment, said mutant, non-naturally occurring or transgenic plant cell comprises one or more mutations in the disclosed polypeptides and polynucleotides that increase the level of nitrate in the mutant, non-naturally occurring or transgenic plant containing the mutant, non-naturally occurring or transgenic plant cell as compared to the control plant containing the control plant cell. The mutation(s) can comprise a substitution mutation at position P143 of SEQ ID NO:13.

In a further aspect, there is described a mutant, non-naturally occurring or transgenic plant or component thereof comprising the plant cell described herein.

In a further aspect, there is described a method for modulating at least the nitrate (for example, 4-(methylnitrosamino)-1-(3-pyridyl)-1-butanone (NNK)) content of a plant or a component thereof, comprising the steps of: (a) modulating the expression or activity of: (i) a polynucleotide comprising, consisting or consisting essentially of a sequence encoding a member of the CLC family of chloride channels and having at least 60% sequence identity to SEQ ID NO:1 or SEQ ID NO:2 or SEQ ID NO:3 or SEQ ID NO:4 or SEQ ID NO:10 or SEQ ID NO:11; (ii) a polypeptide encoded by the polynucleotide set forth in (i); or (iii) a polypeptide comprising, consisting or consisting essentially of a sequence encoding a member of the CLC family of chloride channels and having at least 60% sequence identity to SEQ ID NO:5 or SEQ ID NO:6 or SEQ ID NO:7 or SEQ ID NO:12 or SEQ ID NO:13 or SEQ ID NO:14; (b) measuring at least the nitrate (for example, NNK) content in at least a part of the mutant, non-naturally occurring or transgenic plant obtained in step (a); and (c) identifying a mutant, non-naturally occurring or transgenic plant in which at least the nitrate (for example, NNK) content therein has changed in comparison to a control plant in which the expression or activity of the polynucleotide or polypeptide set forth in (a) has not been modulated.

In a further aspect, there is described a method for modulating at least the nitrate (for example, 4-(methylnitrosamino)-1-(3-pyridyl)-1-butanone (NNK)) content of a plant or a component thereof, comprising the steps of: (a) modulating the expression or activity of: (i) a polynucleotide comprising, consisting or consisting essentially of a sequence encoding a member of the CLC family of chloride channels and having at least 60% sequence identity to SEQ ID NO:1 or SEQ ID NO:2 or SEQ ID NO:3 or SEQ ID NO:10 or SEQ ID NO:11; (ii) a polypeptide encoded by the polynucleotide set forth in (i); or (iii) a polypeptide comprising, consisting or consisting essentially of a sequence encoding a member of the CLC family of chloride channels and having at least 60% sequence identity to SEQ ID NO:5 or SEQ ID NO:6 or SEQ ID NO:7 or SEQ ID NO:12 or SEQ ID NO:13 or SEQ ID NO:14; (b) measuring at least the nitrate (for example, NNK) content in at least a part of the mutant, non-naturally occurring or transgenic plant obtained in step (a); and (c) identifying a mutant, non-naturally occurring or transgenic plant in which at least the nitrate (for example, NNK) content therein has changed in comparison to a control plant in which the expression or activity of the polynucleotide or polypeptide set forth in (a) has not been modulated.

Suitably, the nitrate (for example, NNK) content and/or total TSNA content and/or the nicotine content is modulated in the plant—such as cured plant material.

Suitably, the NNN content is substantially the same as the control plant.

Suitably, the component of the plant is a leaf, suitably, a cured leaf or cured tobacco.

In a further aspect, there is described a plant or a component thereof obtained or obtainable by the methods described herein.

In a further aspect, there is described a mutant, non-naturally occurring or transgenic plant wherein the NNK content is about 110 ng/g or less, optionally, wherein the nitrate content is about 7 mg/g or less. Suitably, the plant is in the form of cured plant material.

In a further aspect, there is described a mutant plant wherein the nitrate content is about 6 mg/g or less and the nicotine content is about 13 mg/g or less.

Suitably, the expression of: (i) a polynucleotide comprising, consisting or consisting essentially of a sequence encoding a member of the CLC family of chloride channels and having at least 60% sequence identity to SEQ ID NO:1 or SEQ ID NO:2 or SEQ ID NO:3 or SEQ ID NO:4 or SEQ ID NO:10 or SEQ ID NO:11; (ii) a polypeptide encoded by the polynucleotide set forth in (i); or (iii) a polypeptide comprising, consisting or consisting essentially of a sequence encoding a member of the CLC family of chloride channels and having at least 60% sequence identity to SEQ ID NO:5 or SEQ ID NO:6 or SEQ ID NO:7 or SEQ ID NO:12 or SEQ ID NO:13 or SEQ ID NO:14 is modulated as compared to a control plant.

In a further aspect, there is described plant material including biomass, seed, stem or leaves from the plant described herein.

In a further aspect, there is described a tobacco product comprising the plant cell, at least a part of the plant or plant material as described herein.

In a further aspect, there is described a method for producing cured plant material—such as leaves—with reduced levels of NNK therein comprising the steps of: (a) providing at least part of a plant or plant material as described herein; (b) optionally harvesting the plant material from the plant; and (c) curing the plant material for a period of time sufficient for at least the levels of NNK therein to be reduced.

In a further aspect, there is described an isolated polynucleotide comprising, consisting or consisting essentially of a sequence encoding a member of the CLC family of chloride channels and having at least 99.1% sequence identity to SEQ ID NO:1 or 97.1% sequence identity to SEQ ID NO:2 or 63% sequence identity to SEQ ID NO:3 or 61% sequence identity to SEQ ID NO:4 or 60% sequence identity to SEQ ID NO:10 or 60% sequence identity to SEQ ID NO:11.

In a further aspect, there is described an isolated polypeptide encoded by the polynucleotide(s) described herein.

In a further aspect, there is described an isolated polypeptide comprising, consisting or consisting essentially of a sequence encoding a member of the CLC family of chloride channels and having at least 99.1% sequence identity to SEQ ID NO:5 or at least 98.1% sequence identity to SEQ ID NO:6 or at least 60% sequence identity to SEQ ID NO:7 or at least 60% sequence identity to SEQ ID NO:12 or at least 60% sequence identity to SEQ ID NO:13 or at least 60% sequence identity to SEQ ID NO:14.

In a further aspect, there is described a construct, vector or expression vector comprising one or more of the isolated polynucleotide(s) described herein.

In a further aspect, there is described a mutant plant cell comprising one or more mutations in: (i) a polynucleotide comprising, consisting or consisting essentially of a sequence encoding a member of the CLC family of chloride channels and having at least 60% sequence identity to SEQ ID NO:1 or SEQ ID NO:2 or SEQ ID NO:3 or SEQ ID NO:4 or SEQ ID NO:10 or SEQ ID NO:11; (ii) a polypeptide encoded by the polynucleotide set forth in (i); or (iii) a polypeptide comprising, consisting or consisting essentially of a sequence encoding a member of the CLC family of chloride channels and having at least 60% sequence identity to SEQ ID NO:5 or SEQ ID NO:6 or SEQ ID NO:7 or SEQ ID NO:12 or SEQ ID NO:13 or SEQ ID NO:14; and wherein said one more mutations modulate the expression or activity of the polynucleotide or the polypeptide as compared to a control plant comprising a control plant cell and wherein the nitrate levels in the mutant plant containing the mutant plant cell are modulated as compared to the control plant.

In a further aspect, there is described a mutant plant cell comprising one or more mutations in: (i) a polynucleotide comprising, consisting or consisting essentially of a sequence encoding a member of the CLC family of chloride channels and having at least 60% sequence identity to SEQ ID NO:1 or SEQ ID NO:2 or SEQ ID NO:3 or SEQ ID NO:4 or SEQ ID NO:10 or SEQ ID NO:11; (ii) a polypeptide encoded by the polynucleotide set forth in (i); or (iii) a polypeptide comprising, consisting or consisting essentially of a sequence encoding a member of the CLC family of chloride channels and having at least 60% sequence identity to SEQ ID NO:5 or SEQ ID NO:6 or SEQ ID NO:7 or SEQ ID NO:12 or SEQ ID NO:13 or SEQ ID NO:14; and wherein said one more mutations modulate the expression or activity of the polynucleotide or the polypeptide as compared to a control plant comprising a control plant cell and wherein the nitrate levels in the mutant plant containing the mutant plant cell are modulated as compared to the control plant.

In a further aspect, there is provided a method for reducing a carcinogenic potential of a tobacco product, said method comprising preparing said tobacco product from a tobacco plant, or plant part or progeny thereof as described herein.

In a further aspect, there is described the use of the construct as described herein in a method for making plants having modulated levels of nitrate and/or NNK and/or total TSNA relative to a control plant.

In a further aspect, there is described the use a polynucleotide or a polypeptide as described herein for modulating levels of nitrate and/or NNK and/or total TSNA in a plant relative to a control plant.

In a further aspect there is described a mutant plant cell comprising one or more mutations that decrease the level of nitrate in the mutant plant containing the mutant plant cell as compared to the control plant containing the control plant cell, wherein said mutation(s) comprises a substitution mutation at position G163 of SEQ ID NO:5.

In a further aspect there is described a mutant plant cell comprising one or more mutations that decrease the level of nitrate in the mutant plant containing the mutant plant cell as compared to the control plant containing the control plant cell, wherein said mutation(s) comprises a substitution mutation at position P143 of SEQ ID NO:13.

In a further aspect, there is disclosed a polypeptide sequence comprising or consisting of the sequence set forth in SEQ ID NO:5 with a substitution mutation at position G163, suitably, G163R. In a further aspect, there is disclosed a polypeptide sequence comprising or consisting of the sequence set forth in SEQ ID NO:13 with a substitution mutation at position P143, suitably, P143L. In a further aspect, mutant polypeptides as described herein are disclosed.

Each of the embodiments discussed above are disclosed as embodiments of each of the aspects of the invention. Combinations of one or of the embodiments are contemplated.

DEFINITIONS

Figure 1:
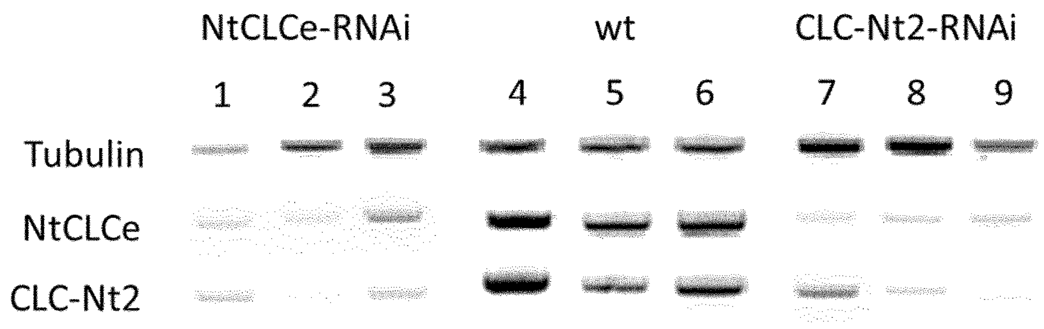
FIG. 1: Semi-quantitative RT-PCR of three representative NtCLCe-RNAi lines (lanes 1, 2 and 3), wt (lanes 4, 5 and 6) and CLC-Nt2-RNAi lines (lanes 7, 8 and 9) showing the expression of tubulin (house-keeping gene), NtCLCe and CLC-Nt2 transcripts.

The technical terms and expressions used within the scope of this application are generally to be given the meaning commonly applied to them in the pertinent art of plant and molecular biology. All of the following term definitions apply to the complete content of this application. The word "comprising" does not exclude other elements or steps, and the indefinite article "a" or "an" does not exclude a plurality. A single step may fulfil the functions of several features recited in the claims. The terms "about", "essentially" and "approximately" in the context of a given numerate value or range refers to a value or range that is within 20%, within 10%, or within 5%, 4%, 3%, 2% or 1% of the given value or range.

The term "isolated" refers to any entity that is taken from its natural milieu, but the term does not connote any degree of purification.

An "expression vector" is a nucleic acid vehicle that comprises a combination of nucleic acid components for enabling the expression of nucleic acid. Suitable expression vectors include episomes capable of extra-chromosomal replication such as circular, double-stranded nucleic acid plasmids; linearized double-stranded nucleic acid plasmids; and other functionally equivalent expression vectors of any origin. An expression vector comprises at least a promoter positioned upstream and operably-linked to a nucleic acid, nucleic acid constructs or nucleic acid conjugate, as defined below.

The term "construct" refers to a double-stranded, recombinant nucleic acid fragment comprising one or more polynucleotides. The construct comprises a "template strand" base-paired with a complementary "sense or coding strand." A given construct can be inserted into a vector in two possible orientations, either in the same (or sense) orientation or in the reverse (or anti-sense) orientation with respect to the orientation of a promoter positioned within a vector—such as an expression vector.

A "vector" refers to a nucleic acid vehicle that comprises a combination of nucleic acid components for enabling the transport of nucleic acid, nucleic acid constructs and nucleic acid conjugates and the like. Suitable vectors include episomes capable of extra-chromosomal replication such as circular, double-stranded nucleic acid plasmids; linearized double-stranded nucleic acid plasmids; and other vectors of any origin.

A "promoter" refers to a nucleic acid element/sequence, typically positioned upstream and operably-linked to a double-stranded DNA fragment. Promoters can be derived entirely from regions proximate to a native gene of interest, or can be composed of different elements derived from different native promoters or synthetic DNA segments.

The terms "homology, identity or similarity" refer to the degree of sequence similarity between two polypeptides or between two nucleic acid molecules compared by sequence alignment. The degree of homology between two discrete nucleic acid sequences being compared is a function of the number of identical, or matching, nucleotides at comparable positions. The percent identity may be determined by visual inspection and mathematical calculation. Alternatively, the percent identity of two nucleic acid sequences may be determined by comparing sequence information using a computer program such as—ClustalW, BLAST, FASTA or Smith-Waterman. Default parameters for these programs can be used.

The term "plant" refers to any plant at any stage of its life cycle or development, and its progenies. In one embodiment, the plant is a "tobacco plant", which refers to a plant belonging to the genus *Nicotiana*. Preferred species of tobacco plant are described herein.

A "plant cell" refers to a structural and physiological unit of a plant. The plant cell may be in the form of a protoplast without a cell wall, an isolated single cell or a cultured cell, or as a part of higher organized unit such as but not limited to, plant tissue, a plant organ, or a whole plant.

The term "plant material" refers to any solid, liquid or gaseous composition, or a combination thereof, obtainable from a plant, including biomass, leaves, stems, roots, flowers or flower parts, fruits, pollen, egg cells, zygotes, seeds, cuttings, secretions, extracts, cell or tissue cultures, or any other parts or products of a plant. In one embodiment, the plant material comprises or consists of biomass, stem, seed or leaves. In another embodiment, the plant material comprises or consists of leaves.

The term "variety" refers to a population of plants that share constant characteristics which separate them from other plants of the same species. While possessing one or more distinctive traits, a variety is further characterized by a very small overall variation between individuals within that variety. A variety is often sold commercially.

The term "line" or "breeding line" as used herein denotes a group of plants that are used during plant breeding. A line is distinguishable from a variety as it displays little variation between individuals for one or more traits of interest, although there may be some variation between individuals for other traits.

The term "modulating" may refer to reducing, inhibiting, increasing or otherwise affecting the expression or activity of a polypeptide. The term may also refer to reducing, inhibiting, increasing or otherwise affecting the activity of a gene encoding a polypeptide which can include, but is not limited to, modulating transcriptional activity.

The term "reduce" or "reduced" as used herein, refers to a reduction of from about 10% to about 99%, or a reduction of at least 10%, at least 20%, at least 25%, at least 30%, at least 40%, at least 50%, at least 60%, at least 70%, at least 75%, at least 80%, at least 90%, at least 95%, at least 98%, at least 99%, or at least 100% or more of a quantity or an activity, such as but not limited to polypeptide activity, transcriptional activity and protein expression.

The term "inhibit" or "inhibited" as used herein, refers to a reduction of from about 98% to about 100%, or a reduction of at least 98%, at least 99%, but particularly of 100%, of a quantity or an activity, such as but not limited to polypeptide activity, transcriptional activity and protein expression.

The term "increase" or "increased" as used herein, refers to an increase of from about 5% to about 99%, or an increase of at least 5%, at least 10%, at least 20%, at least 25%, at least 30%, at least 40%, at least 50%, at least 60%, at least 70%, at least 75%, at least 80%, at least 90%, at least 95%, at least 98%, at least 99%, or at least 100% or more of a quantity or an activity, such as but not limited to polypeptide activity, transcriptional activity and protein expression.

The term "control" in the context of a control plant means a plant or plant cell in which the expression or activity of an enzyme has not been modified (for example, increased or reduced) and so it can provide a comparison with a plant in which the expression or activity of the enzyme has been modified. The control plant may comprise an empty vector. The control plant or plant cell may correspond to a wild-type plant or wild-type plant cell.

DETAILED DESCRIPTION

In one embodiment, there is provided an isolated polynucleotide comprising, consisting or consisting essentially of a polynucleotide sequence having at least 60% sequence identity to any of the sequences described herein, including any of polynucleotides shown in the sequence listing. Suitably, the isolated polynucleotide comprises, consists or consists essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity thereto.

In another embodiment, there is provided an isolated polynucleotide comprising, consisting or consisting essentially of a polynucleotide sequence having at least 60% sequence identity to SEQ ID NO.1 or SEQ ID NO:2 or SEQ ID NO.3 or SEQ ID NO.4 or SEQ ID NO:10 or SEQ ID NO:11. Suitably, the isolated polynucleotide comprises, consists or consist essentially of a sequence having at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO.1 or SEQ ID NO:2 or SEQ ID NO.3 or SEQ ID NO.4 or SEQ ID NO:10 or SEQ ID NO:11.

In another embodiment, there is provided polynucleotides comprising, consisting or consisting essentially of polynucleotides with substantial homology (that is, sequence similarity) or substantial identity to SEQ ID NO.1 or SEQ ID NO:2 or SEQ ID NO.3 or SEQ ID NO.4 or SEQ ID NO:10 or SEQ ID NO:11.

In another embodiment, there is provided polynucleotide variants that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8% or 99.9% sequence identity to the sequence of SEQ ID NO.1 or SEQ ID NO:2 or SEQ ID NO.3 or SEQ ID NO.4 or SEQ ID NO:10 or SEQ ID NO:11.

In another embodiment, there is provided fragments of SEQ ID NO.1 or SEQ ID NO:2 or SEQ ID NO.3 or SEQ ID NO.4 or SEQ ID NO:10 or SEQ ID NO:11 and fragments of SEQ ID NO.1 or SEQ ID NO:2 or SEQ ID NO.3 or SEQ ID NO.4 or SEQ ID NO:10 or SEQ ID NO:11 with substantial homology (that is, sequence similarity) or substantial identity thereto that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO.1 or SEQ ID NO:2 or SEQ ID NO.3 or SEQ ID NO.4 or SEQ ID NO:10 or SEQ ID NO:11.

In another embodiment, there is provided polynucleotides comprising a sufficient or substantial degree of identity or similarity to SEQ ID NO.1 or SEQ ID NO:2 or SEQ ID NO.3 or SEQ ID NO.4 or SEQ ID NO:10 or SEQ ID NO:11 that encode a polypeptide that functions as a member of the CLC family of chloride channels.

In another embodiment, there is provided a polymer of polynucleotides which comprises, consists or consists essentially of a polynucleotide designated herein as SEQ ID NO.1 or SEQ ID NO:2 or SEQ ID NO.3 or SEQ ID NO.4 or SEQ ID NO:10 or SEQ ID NO:11.

Suitably, the polynucleotides described herein encode members of the CLC family of chloride channels. CLCs constitute a family of voltage-gated channels. In plants, chloride channels contribute to a number of plant-specific functions—such as in the regulation of turgor, stomatal movement, nutrient transport and/or metal tolerance and the like. The nitrate/proton antiporter AtCLCa mediates nitrate accumulation in plant vacuoles (see *Nature* (2006) 442 (7105):939-42). In this publication it is shown that AtClCa functions as a $2NO_3^-/1H^+$ exchanger that is able to accumulate nitrate into the vacuole by using electrophysiological approaches. A similar approach can be used to test the nitrate transport activity of CLC-Nt2. "Solute transporters in plant thylakoid membranes: Key players during photosynthesis and light stress by Spetea C, Schoefs B. Communicative & Integrative Biology. 2010; 3(2)122-129 and Monachello et al., *New Phytol.* 2009; 183(1):88-94 disclose that AtClCe is predicted to be involved in nitrite translocation from the stroma into the thylakoid lumen, taking over from the nitrite transporter of the chloroplast envelope. Methods described therein for measuring this activity may be used to measure the activity of NtCLCe.

Combinations of SEQ ID NO.1 or SEQ ID NO:2 or SEQ ID NO.3 or SEQ ID NO.4 or SEQ ID NO:10 or SEQ ID NO:11 are also contemplated. These combinations include various combinations of SEQ ID NO.1, SEQ ID NO:2, SEQ ID NO.3, SEQ ID NO.4, SEQ ID NO:10 and SEQ ID NO:11—including the combination of SEQ ID NO:1 and SEQ ID NO:2; the combination of SEQ ID NO:1 and SEQ ID NO:3; the combination of SEQ ID NO:1 and SEQ ID NO:4; the combination of SEQ ID NO:1 and SEQ ID NO:10; the combination of SEQ ID NO:1 and SEQ ID NO:11; the combination of SEQ ID NO:2 and SEQ ID NO:3; the combination of SEQ ID NO:2 and SEQ ID NO:4; the combination of SEQ ID NO:2 and SEQ ID NO:10; the combination of SEQ ID NO:2 and SEQ ID NO:11; the combination of SEQ ID NO:3 and SEQ ID NO:4, the combination of SEQ ID NO:3 and SEQ ID NO:10; the combination of SEQ ID NO:3 and SEQ ID NO:11; the combination of SEQ ID NO:1, SEQ ID NO:2 and SEQ ID NO:3; the combination of SEQ ID NO:1, SEQ ID NO:2 and SEQ ID NO:4; the combination of SEQ ID NO:1, SEQ ID NO:3 and SEQ ID NO:4; the combination of SEQ ID NO:2, SEQ ID NO:3 and SEQ ID NO:4; the combination of SEQ ID NO:1, SEQ ID NO:2, SEQ ID NO:3 and SEQ ID NO:4; or the combination of SEQ ID NO.1, SEQ ID NO:2 and SEQ ID NO.3; the combination of SEQ ID NO:1, SEQ ID NO:2, SEQ ID NO:3, SEQ ID NO:10 and SEQ ID NO:11; the combination of SEQ ID NO:1, SEQ ID NO:2, SEQ ID NO:4, SEQ ID NO:10 and SEQ ID NO:11; the combination of SEQ ID NO:1, SEQ ID NO:3 SEQ ID NO:4, SEQ ID NO:10 and SEQ ID NO:11; the combination of SEQ ID NO:2, SEQ ID NO:3, SEQ ID NO:4, SEQ ID NO:10 and SEQ ID NO:11; the combination of SEQ ID NO:1, SEQ ID NO:2, SEQ ID NO:3 and SEQ ID NO:4; or the combination of SEQ ID NO.1, SEQ ID NO:2 and SEQ ID NO.3 etc.

A polynucleotide as described herein can include a polymer of nucleotides, which may be unmodified or modified deoxyribonucleic acid (DNA) or ribonucleic acid (RNA). Accordingly, a polynucleotide can be, without limitation, a genomic DNA, complementary DNA (cDNA), mRNA, or antisense RNA or a fragment(s) thereof. Moreover, a polynucleotide can be single-stranded or double-stranded DNA, DNA that is a mixture of single-stranded and double-stranded regions, a hybrid molecule comprising DNA and RNA, or a hybrid molecule with a mixture of single-stranded and double-stranded regions or a fragment(s) thereof. In addition, the polynucleotide can be composed of triple-stranded regions comprising DNA, RNA, or both or a fragment(s) thereof. A polynucleotide can contain one or more modified bases, such as phosphothioates, and can be a peptide nucleic acid. Generally, polynucleotides can be assembled from isolated or cloned fragments of cDNA, genomic DNA, oligonucleotides, or individual nucleotides, or a combination of the foregoing. Although the polynucleotide sequences described herein are shown as DNA sequences, the sequences include their corresponding RNA sequences, and their complementary (for example, completely complementary) DNA or RNA sequences, including the reverse complements thereof.

A polynucleotide as described herein will generally contain phosphodiester bonds, although in some cases, polynucleotide analogues are included that may have alternate backbones, comprising, for example, phosphoramidate, phosphorothioate, phosphorodithioate, or O-methylphophoroamidite linkages; and peptide polynucleotide backbones and linkages. Other analogue polynucleotides include those with positive backbones; non-ionic backbones, and non-ribose backbones. Modifications of the ribose-phosphate backbone may be done for a variety of reasons, for example, to increase the stability and half-life of such molecules in physiological environments or as probes on a biochip. Mixtures of naturally occurring polynucleotides and analogues can be made; alternatively, mixtures of different polynucleotide analogues, and mixtures of naturally occurring polynucleotides and analogues may be made.

A variety of polynucleotide analogues are known, including, for example, phosphoramidate, phosphorothioate, phosphorodithioate, O-methylphophoroamidite linkages and peptide polynucleotide backbones and linkages. Other analogue polynucleotides include those with positive backbones, non-ionic backbones and non-ribose backbones. Polynucleotides containing one or more carbocyclic sugars are also included.

Other analogues include peptide polynucleotides which are peptide polynucleotide analogues. These backbones are substantially non-ionic under neutral conditions, in contrast to the highly charged phosphodiester backbone of naturally occurring polynucleotides. This may result in advantages. First, the peptide polynucleotide backbone may exhibit improved hybridization kinetics. Peptide polynucleotides have larger changes in the melting temperature for mismatched versus perfectly matched base pairs. DNA and RNA typically exhibit a 2-4° C. drop in melting temperature for an internal mismatch. With the non-ionic peptide polynucleotide backbone, the drop is closer to 7-9° C. Similarly, due to their non-ionic nature, hybridization of the bases attached to these backbones is relatively insensitive to salt concentration. In addition, peptide polynucleotides may not be degraded or degraded to a lesser extent by cellular enzymes, and thus may be more stable.

Among the uses of the disclosed polynucleotides, and fragments thereof, is the use of fragments as probes in nucleic acid hybridisation assays or primers for use in nucleic acid amplification assays. Such fragments generally comprise at least about 10, 11, 12, 13, 14, 15, 16, 17, 18, 19 or 20 or more contiguous nucleotides of a DNA sequence. In other embodiments, a DNA fragment comprises at least about 10, 15, 20, 30, 40, 50 or 60 or more contiguous nucleotides of a DNA sequence. Thus, in one aspect, there is also provided a method for detecting a polynucleotide encoding a member of the CLC family of chloride channels comprising the use of the probes or primers or both.

The basic parameters affecting the choice of hybridization conditions and guidance for devising suitable conditions are described by Sambrook, J., E. F. Fritsch, and T. Maniatis (1989, Molecular Cloning: A Laboratory Manual, Cold Spring Harbor Laboratory Press, Cold Spring Harbor, N.Y.). Using knowledge of the genetic code in combination with the amino acid sequences described herein, sets of degenerate oligonucleotides can be prepared. Such oligonucleotides are useful as primers, for example, in polymerase chain reactions (PCR), whereby DNA fragments are isolated and amplified. In certain embodiments, degenerate primers can be used as probes for genetic libraries. Such libraries would include but are not limited to cDNA libraries, genomic libraries, and even electronic express sequence tag or DNA libraries. Homologous sequences identified by this method would then be used as probes to identify homologues of the sequences identified herein. Also of potential use are polynucleotides and oligonucleotides (for example, primers or probes) that hybridize under reduced stringency conditions, typically moderately stringent conditions, and commonly highly stringent conditions to the polynucleotide(s) as described herein. The basic parameters affecting the choice of hybridization conditions and guidance for devising suitable conditions are set forth by Sambrook, J., E. F. Fritsch, and T. Maniatis (1989, Molecular Cloning: A Laboratory Manual, Cold Spring Harbor Laboratory Press, Cold Spring Harbor, N.Y. and can be readily determined by those having ordinary skill in the art based on, for example, the length or base composition of the polynucleotide.

One way of achieving moderately stringent conditions involves the use of a prewashing solution containing 5× Standard Sodium Citrate, 0.5% Sodium Dodecyl Sulphate, 1.0 mM Ethylenediaminetetraacetic acid (pH 8.0), hybridization buffer of about 50% formamide, 6× Standard Sodium Citrate, and a hybridization temperature of about 55° C. (or other similar hybridization solutions, such as one containing about 50% formamide, with a hybridization temperature of about 42° C.), and washing conditions of about 60° C., in 0.5× Standard Sodium Citrate, 0.1% Sodium Dodecyl Sulphate. Generally, highly stringent conditions are defined as hybridization conditions as above, but with washing at approximately 68° C., 0.2× Standard Sodium Citrate, 0.1% Sodium Dodecyl Sulphate. SSPE (1×SSPE is 0.15M sodium chloride, 10 mM sodium phosphate, and 1.25 mM Ethylenediaminetetraacetic acid, pH 7.4) can be substituted for Standard Sodium Citrate (lx Standard Sodium Citrate is 0.15M sodium chloride and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, for example, Sambrook, J., E. F. Fritsch, and T. Maniatis (1989, Molecular Cloning: A Laboratory Manual, Cold Spring Harbor Laboratory Press, Cold Spring Harbor, N.Y.). When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity. The hybridization temperature for hybrids anticipated to be less than 50 base pairs in length should be 5 to 10° C. less than the melting temperature of the hybrid, where melting temperature is determined according to the following equations. For hybrids less than 18 base pairs in length, melting temperature (° C.)=2(number of A+T bases)+4(number of G+C bases). For hybrids above 18 base pairs in length, melting temperature (° C.)=81.5+16.6(log 10 [Na+])+0.41(% G+C)−(600/N), where N is the number of bases in the hybrid, and [Na+] is the concentration of sodium ions in the hybridization buffer ([Na+] for 1× Standard Sodium Citrate=0.165M). Typically, each such hybridizing polynucleotide has a length that is at least 25% (commonly at least 50%, 60%, or 70%, and most commonly at least 80%) of the length of a polynucleotide to which it hybridizes, and has at least 60% sequence identity (for example, at least 70%, 75%, 80%, 85%, 90%, 95%, 96%, 97%, 98%, 99% or 100%) with a polynucleotide to which it hybridizes.

As will be understood by the person skilled in the art, a linear DNA has two possible orientations: the 5'-to-3' direction and the 3'-to-5' direction. For example, if a reference sequence is positioned in the 5'-to-3' direction, and if a second sequence is positioned in the 5'-to-3' direction within the same polynucleotide molecule/strand, then the reference sequence and the second sequence are orientated in the same direction, or have the same orientation. Typically, a promoter sequence and a gene of interest under the regulation of the given promoter are positioned in the same orientation. However, with respect to the reference sequence positioned in the 5'-to-3' direction, if a second sequence is positioned in the 3'-to-5' direction within the same polynucleotide molecule/strand, then the reference sequence and the second sequence are orientated in anti-sense direction, or have anti-sense orientation. Two sequences having anti-sense orientations with respect to each other can be alternatively described as having the same orientation, if the reference sequence (5'-to-3' direction) and the reverse complementary sequence of the reference sequence (reference sequence positioned in the 5'-to-3') are positioned within the same polynucleotide molecule/strand. The sequences set forth herein are shown in the 5'-to-3' direction. Recombinant constructs provided herein can be used to transform plants or plant cells in order to modulate protein expression or activity levels. A recombinant polynucleotide construct can comprise a polynucleotide encoding one or more polynucleotides as described herein, operably linked to a regulatory region suitable for expressing the polypeptide in the plant or plant cell. Thus, a polynucleotide can comprise a coding sequence that encodes the polypeptide as described herein. Plants in which protein expression or activity levels are modulated can include mutant plants, non-naturally occurring plants, transgenic plants, man-made plants or genetically engineered plants. Suitably, the transgenic plant comprises a genome that has been altered by the stable integration of recombinant DNA. Recombinant DNA includes DNA which has been genetically engineered and constructed outside of a cell and includes DNA containing naturally occurring DNA or cDNA or synthetic DNA. A transgenic plant can include a plant regenerated from an originally-transformed plant cell and progeny transgenic plants from later generations or crosses of a transformed plant. Suitably, the transgenic modification alters the expression or activity of the polynucleotide or the polypeptide described herein as compared to a control plant.

The polypeptide encoded by a recombinant polynucleotide can be a native polypeptide, or can be heterologous to the cell. In some cases, the recombinant construct contains a polynucleotide that modulates expression, operably linked to a regulatory region. Examples of suitable regulatory regions are described herein.

Vectors containing recombinant polynucleotide constructs such as those described herein are also provided. Suitable vector backbones include, for example, those routinely used in the art such as plasmids, viruses, artificial chromosomes, bacterial artificial chromosomes, yeast artificial chromosomes, or bacteriophage artificial chromosomes. Suitable expression vectors include, without limitation, plasmids and viral vectors derived from, for example, bacteriophage, baculoviruses, and retroviruses. Numerous vectors and expression systems are commercially available.

The vectors can also include, for example, origins of replication, scaffold attachment regions or markers. A marker gene can confer a selectable phenotype on a plant cell. For example, a marker can confer biocide resistance, such as resistance to an antibiotic (for example, kanamycin, G418, bleomycin, or hygromycin), or an herbicide (for example, glyphosate, chlorsulfuron or phosphinothricin). In addition, an expression vector can include a tag sequence designed to facilitate manipulation or detection (for example, purification or localization) of the expressed polypeptide. Tag sequences, such as luciferase, beta-glucuronidase, green fluorescent protein, glutathione S-transferase, polyhistidine, c-myc or hemagglutinin sequences typically are expressed as a fusion with the encoded polypeptide. Such tags can be inserted anywhere within the polypeptide, including at either the carboxyl or amino terminus.

A plant or plant cell can be transformed by having the recombinant polynucleotide integrated into its genome to become stably transformed. The plant or plant cell described herein can be stably transformed. Stably transformed cells typically retain the introduced polynucleotide with each cell division. A plant or plant cell may also be transiently transformed such that the recombinant polynucleotide is not integrated into its genome. Transiently transformed cells typically lose all or some portion of the introduced recombinant polynucleotide with each cell division such that the introduced recombinant polynucleotide cannot be detected in daughter cells after a sufficient number of cell divisions.

A number of methods are available in the art for transforming a plant cell which are all encompassed herein, including biolistics, gene gun techniques, *Agrobacterium*-mediated transformation, viral vector-mediated transformation and electroporation. The *Agrobacterium* system for integration of foreign DNA into plant chromosomes has been extensively studied, modified, and exploited for plant genetic engineering. Naked recombinant DNA molecules comprising DNA sequences corresponding to the subject purified tobacco protein operably linked, in the sense or antisense orientation, to regulatory sequences are joined to appropriate T-DNA sequences by conventional methods. These are introduced into tobacco protoplasts by polyethylene glycol techniques or by electroporation techniques, both of which are standard. Alternatively, such vectors comprising recombinant DNA molecules encoding the subject purified tobacco protein are introduced into live *Agrobacterium* cells, which then transfer the DNA into the tobacco plant cells. Transformation by naked DNA without accompanying T-DNA vector sequences can be accomplished via fusion of tobacco protoplasts with DNA-containing liposomes or via electroporation. Naked DNA unaccompanied by T-DNA vector sequences can also be used to transform tobacco cells via inert, high velocity microprojectiles.

If a cell or cultured tissue is used as the recipient tissue for transformation, plants can be regenerated from transformed cultures if desired, by techniques known to those skilled in the art.

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a polynucleotide can be modulated in a similar manner. Some suitable regulatory regions initiate transcription only, or predominantly, in certain cell types. Methods for identifying and characterizing regulatory regions in plant genomic DNA are known in the art.

Suitable promoters include tissue-specific promoters recognized by tissue-specific factors present in different tissues or cell types (for example, root-specific promoters, shoot-specific promoters, xylem-specific promoters), or present during different developmental stages, or present in response to different environmental conditions. Suitable promoters include constitutive promoters that can be activated in most cell types without requiring specific inducers. Examples of suitable promoters for controlling RNAi polypeptide production include the cauliflower mosaic virus 35S (CaMV/35S), SSU, OCS, lib4, usp, STLS1, B33, nos or ubiquitin- or phaseolin-promoters. Persons skilled in the art are capable of generating multiple variations of recombinant promoters. Tissue-specific promoters are transcriptional control elements that are only active in particular cells or tissues at specific times during plant development, such as in vegetative tissues or reproductive tissues. Tissue-specific expression can be advantageous, for example, when the expression of polynucleotides in certain tissues is preferred. Examples of tissue-specific promoters under developmental control include promoters that can initiate transcription only (or primarily only) in certain tissues, such as vegetative tissues, for example, roots or leaves, or reproductive tissues, such as fruit, ovules, seeds, pollen, pistols, flowers, or any embryonic tissue. Reproductive tissue-specific promoters may be, for example, anther-specific, ovule-specific, embryo-specific, endosperm-specific, integument-specific, seed and seed coat-specific, pollen-specific, petal-specific, sepal-specific, or combinations thereof.

Suitable leaf-specific promoters include pyruvate, orthophosphate dikinase (PPDK) promoter from C4 plant (maize), cab-m1Ca+2 promoter from maize, the *Arabidopsis thaliana* myb-related gene promoter (Atmyb5), the ribulose biphosphate carboxylase (RBCS) promoters (for example, the tomato RBCS 1, RBCS2 and RBCS3A genes expressed in leaves and light-grown seedlings, RBCS1 and RBCS2 expressed in developing tomato fruits or ribulose bisphosphate carboxylase promoter expressed almost exclusively in mesophyll cells in leaf blades and leaf sheaths at high levels).

Suitable senescence-specific promoters include a tomato promoter active during fruit ripening, senescence and abscission of leaves, a maize promoter of gene encoding a cysteine protease. Suitable anther-specific promoters can be used. Suitable root-preferred promoters known to persons skilled in the art may be selected. Suitable seed-preferred promoters include both seed-specific promoters (those promoters active during seed development such as promoters of seed storage proteins) and seed-germinating promoters (those promoters active during seed germination). Such seed-preferred promoters include, but are not limited to, Cim1 (cytokinin-induced message); cZ19B1 (maize 19 kDa zein); milps (myo-inositol-1-phosphate synthase); mZE40-2, also known as Zm-40; nucic; and celA (cellulose synthase). Gama-zein is an endosperm-specific promoter. Glob-1 is an embryo-specific promoter. For dicots, seed-specific promoters include, but are not limited to, bean beta-phaseolin, napin, β-conglycinin, soybean lectin, cruciferin, and the like. For monocots, seed-specific promoters include, but are not limited to, a maize 15 kDa zein promoter, a 22 kDa zein promoter, a 27 kDa zein promoter, a g-zein promoter, a 27 kDa gamma-zein promoter (such as gzw64A promoter, see Genbank Accession number S78780), a waxy promoter, a shrunken 1 promoter, a shrunken 2 promoter, a globulin 1 promoter (see Genbank Accession number L22344), an Itp2 promoter, cim1 promoter, maize end1 and end2 promoters, nuc1 promoter, Zm40 promoter, eep1 and eep2; led, thioredoxin H promoter; mlip15 promoter, PCNA2 promoter; and the shrunken-2 promoter.

Examples of inducible promoters include promoters responsive to pathogen attack, anaerobic conditions, elevated temperature, light, drought, cold temperature, or high salt concentration. Pathogen-inducible promoters include those from pathogenesis-related proteins (PR proteins), which are induced following infection by a pathogen (for example, PR proteins, SAR proteins, beta-1,3-glucanase, chitinase).

In addition to plant promoters, other suitable promoters may be derived from bacterial origin for example, the octopine synthase promoter, the nopaline synthase promoter and other promoters derived from Ti plasmids), or may be derived from viral promoters (for example, 35S and 19S RNA promoters of cauliflower mosaic virus (CaMV), constitutive promoters of tobacco mosaic virus, cauliflower mosaic virus (CaMV) 19S and 35S promoters, or figwort mosaic virus 35S promoter).

In another aspect, there is provided an isolated polypeptide comprising, consisting or consisting essentially of a polypeptide sequence having at least 60% sequence identity to any of the sequences described herein, including any of the polypeptides shown in the sequence listing. Suitably, the isolated polypeptide comprises, consists or consists essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity thereto.

In one embodiment, there is provided a polypeptide encoded by SEQ ID NO: 1 or SEQ ID NO: 2 or SEQ ID NO: 3 or SEQ ID NO: 4 or SEQ ID NO:10 or SEQ ID NO:11.

In another embodiment, there is provided an isolated polypeptide comprising, consisting or consisting essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% A or 100% sequence identity to SEQ ID NO: 5 or SEQ ID NO: 6 or SEQ ID NO: 7 or SEQ ID NO:12 or SEQ ID NO:13 or SEQ ID NO:14.

In another embodiment, there is provided a polypeptide variant comprising, consisting or consisting essentially of an amino acid sequence encoded by a polynucleotide variant with at least about 66%, 67%, 68%, 69%, 70%, 75%, 80%, 85%, 87%, 88%, 89%, 90%, 91%, 92%, 93%, 94%, 95% 96%, 97%, 98%, 99% 99.1%, 99.2%, 99.3%, 99.4%, 99.5%, 99.6%, 99.7%, 99.8% or 99.9% sequence identity to SEQ ID NO: 1 or SEQ ID NO: 2 or SEQ ID NO: 3 or SEQ ID NO: 4 or SEQ ID NO:10 or SEQ ID NO:11.

In another embodiment, there is provided fragments of the polypeptide of SEQ ID NO: 5 or SEQ ID NO: 6 or SEQ ID NO: 7 or SEQ ID NO:12 or SEQ ID NO:13 or SEQ ID NO:14 and fragments of SEQ ID NO: 5 or SEQ ID NO: 6 or SEQ ID NO: 7 or SEQ ID NO:12 or SEQ ID NO:13 or SEQ ID NO:14 that have at least about 60%, 65%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO: 5 or SEQ ID NO: 6 or SEQ ID NO: 7 or SEQ ID NO:12 or SEQ ID NO:13 or SEQ ID NO:14, respectively. The polypeptide also include sequences comprising a sufficient or substantial degree of identity or similarity to SEQ ID NO: 5 or SEQ ID NO: 6 or SEQ ID NO: 7 or SEQ ID NO:12 or SEQ ID NO:13 or SEQ ID NO:14 to function as a member of the CLC family of chloride channels. The fragments of the polypeptide(s) typically retain some or all of the activity of the full length sequence.

The polypeptides also include mutants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally provided that they still some or all of their function or activity as a member of the CLC family of chloride channels.

The polypeptides may be in linear form or cyclized using known methods.

A polypeptide encoded by SEQ ID NO: 5 or SEQ ID NO: 6 or SEQ ID NO: 7 or SEQ ID NO:12 or SEQ ID NO:13 or SEQ ID NO:14 that has 100% sequence identity thereto or a polypeptide comprising, consisting or consisting essentially of the sequence set forth in SEQ ID NO: 5 or SEQ ID NO: 6 or SEQ ID NO: 7 or SEQ ID NO:12 or SEQ ID NO:13 or SEQ ID NO:14 that has 100% sequence identity thereto is also disclosed.

Various combinations of SEQ ID NO.5 or SEQ ID NO:6 or SEQ ID NO.7 or SEQ ID NO:12 or SEQ ID NO:13 or SEQ ID NO:14 are also contemplated. These combinations include any combinations of SEQ ID NO.5, SEQ ID NO:6, SEQ ID NO.7, SEQ ID NO:12, SEQ ID NO:13 or SEQ ID NO:14—including the combination of SEQ ID NO:5 and SEQ ID NO:6; the combination of SEQ ID NO:5 and SEQ ID NO:7; the combination of SEQ ID NO:6 and SEQ ID NO:7; the combination of SEQ ID NO:5, SEQ ID NO:6 and SEQ ID NO:7; the combination of SEQ ID NO.5, SEQ ID NO:6 and SEQ ID NO.7; the combination of SEQ ID NO:5, SEQ ID NO:6, SEQ ID NO:12, SEQ ID NO:13 and SEQ ID NO:14; the combination of SEQ ID NO:5, SEQ ID NO:7, SEQ ID NO:12, SEQ ID NO:13 and SEQ ID NO:14; the combination of SEQ ID NO:6, SEQ ID NO:7 SEQ ID NO:12, SEQ ID NO:13 and SEQ ID NO:14; the combination of SEQ ID NO:5, SEQ ID NO:6, SEQ ID NO:7 SEQ ID NO:12, SEQ ID NO:13 and SEQ ID NO:14; the combination of SEQ ID NO.5, SEQ ID NO:6 and SEQ ID NO.7, SEQ ID NO:12, SEQ ID NO:13 and SEQ ID NO:14 etc.

Polypeptides include variants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally. A deletion refers to removal of one or more amino acids from a protein. An insertion refers to one or more amino acid residues being introduced into a predetermined site in a polypeptide. Insertions may comprise intra-sequence insertions of single or multiple amino acids. A substitution refers to the replacement of amino acids of the polypeptide with other amino acids having similar properties (such as similar hydrophobicity, hydrophilicity, antigenicity, propensity to form or break a-helical structures or β-sheet structures). Amino acid substitutions are typically of single residues, but may be clustered depending upon functional constraints placed upon the polypeptide and may range from about 1 to about 10 amino acids. The amino acid substitutions are preferably conservative amino acid substitutions as described below. Amino acid substitutions, deletions and/or insertions can be made using peptide synthetic techniques—such as solid phase peptide synthesis or by recombinant DNA manipulation. Methods for the manipulation of DNA sequences to produce substitution, insertion or deletion variants of a protein are well known in the art. The variant may have alterations which produce a silent change and result in a functionally equivalent protein. Deliberate amino acid substitutions may be made on the basis of similarity in polarity, charge, solubility, hydrophobicity, hydrophilicity and the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine. Conservative substitutions may be made, for example according to the Table below. Amino acids in the same block in the second column and preferably in the same line in the third column may be substituted for each other:

| | | |
|---|---|---|
| ALIPHATIC | Non-polar | Gly Ala Pro<br>Ile Leu Val |
| | Polar - uncharged | Cys Ser Thr Met<br>Asn Gly |
| | Polar - charged | Asp Glu<br>Lys Arg |
| AROMATIC | | His Phe TrpTyr |

The polypeptide may be a mature protein or an immature protein or a protein derived from an immature protein. Polypeptides may be in linear form or cyclized using known methods. Polypeptides typically comprise at least 10, at least 20, at least 30, or at least 40 contiguous amino acids.

Mutant polypeptide variants can be used to create mutant, non-naturally occurring or transgenic plants (for example, mutant, non-naturally occurring, transgenic, man-made or genetically engineered plants) comprising one or more mutant polypeptide variants. Suitably, mutant polypeptide variants retain the activity of the unmutated polypeptide. The activity of the mutant polypeptide variant may be higher, lower or about the same as the unmutated polypeptide. Mutations in the nucleotide sequences and polypeptides described herein can include man-made mutations or synthetic mutations or genetically engineered mutations. Mutations in the nucleotide sequences and polypeptides described herein can be mutations that are obtained or obtainable via a process which includes an in vitro or an in vivo manipulation step. Mutations in the nucleotide sequences and polypeptides described herein can be mutations that are obtained or obtainable via a process which includes intervention by man.

Examples of mutations in the polypeptide sequences described herein are shown in Table 1. Accordingly, a further aspect relates to the mutant polypeptides as set forth in Table 1.

The mutation(s) can modulate the activity of the encoded polypeptide. The mutation(s) can modulate the activity of the encoded polypeptide such that the nitrate level in the plant is modulated. The mutation(s) can modulate the activity of the encoded polypeptide such that the nitrate level in the plant is increased or decreased. The mutation(s) can modulate the activity of the encoded polypeptide such that the NNK level in the plant—such as cured plant material—is modulated. The mutation(s) can modulate the activity of the encoded polypeptide such that the NNK level in the plant—such as cured plant material—is increased or decreased. The mutation(s) can modulate the activity of the encoded polypeptide such that the overall TSNA level in the plant—such as cured plant material—is modulated. The mutation(s) can modulate the activity of the encoded polypeptide such that the overall TSNA level in the plant—such as cured plant material—is increased or decreased.

In one embodiment, SEQ ID NO.5 includes one or more mutations at amino acid positions selected from the group consisting of 503, 471, 659, 566, 637, 597, 711, 135, 151, 690, 737, 135, 163, 480, 520, 514, 518, 476, 739, 517, 585 or 677 or a combination of two or more thereof. The type of mutation(s) at this position can be a deletion, an insertion, a substitution or a missense mutation or a combination thereof. The mutation(s) can be a heterozygous or homozygous mutation, suitably, a homozygous mutation. In one embodiment, the mutation(s) is a substitution mutation. In one embodiment, the substitution mutation(s) is selected from the group consisting of G503E, G471 R, V6591, S566N, P637S, A597T, P711L, G135R, A151V, G690D, G737R, G135R, G163R, P480S, S520F, A514T, A518V, G476E, R739S, G517E, E585K or V6771 or a combination of two or more thereof.

In one embodiment, SEQ ID NO.6 includes one or more mutations at amino acid positions selected from the group consisting of 514, 537, 593, 749, 524, 408, 503, 547, 691, 478, 749, 713, 550, 586, 670, 678, 631, 657, 737, 525, 597, 674 or a combination of two or more thereof. The type of mutation(s) at this position can be a deletion, an insertion, a substitution or a missense mutation or a combination thereof. The mutation(s) can be a heterozygous or homozygous mutation, suitably, a homozygous mutation. In one embodiment, the mutation(s) is a substitution mutation. In one embodiment, the substitution mutation(s) is selected from the group consisting of A514T, L537F, R5931, A749T, G524D, 5408F, G503R, P547S, G691D, A478V, A749V, T7131, M5501, P586S, R670K, R678K, D631N, L657F, G737R, S525L, A597T, E674K or a combination of two or more thereof.

In one embodiment, SEQ ID NO:7 includes one or more mutations at amino acid positions selected from the group consisting of 21, 58, 141, 175, 5, 34, 124, 40, 8, 35, 30, 177, 42, 88, 155, 158, 170, 174, 126 or 131 or a combination of two or more thereof. The type of mutation(s) at this position can be a deletion, an insertion, a substitution or a missense mutation or a combination thereof. The mutation(s) can be a heterozygous or homozygous mutation, suitably, a homozygous mutation. In one embodiment, the mutation(s) is a substitution mutation. In one embodiment, the substitution mutation(s) is selected from the group consisting of E21K, L58F, P141S, G175E, S5N, A34V, M1241, L40F, D8N, C35Y, A30V, A177V, G42D, G88D, G155R, D158N, A170V, A174V, A126V or G131R or a combination of two or more thereof.

The sequence shown in SEQ ID NO:12 corresponds to the sequence shown in SEQ ID NO:7 with an extra 88 amino acids at the 5' end. SEQ ID NO:12 can include the same corresponding mutations as SEQ ID NO:7. SEQ ID NO:12 can include one or more mutations at amino acid positions selected from the group consisting of 109, 146, 229, 263, 93, 122, 212, 128, 96, 123, 118, 265, 130, 176, 243, 246, 258, 262, 214, or 219 or a combination of two or more thereof. The type of mutation(s) at this position can be a deletion, an insertion, a substitution or a missense mutation or a combination thereof. The mutation(s) can be a heterozygous or homozygous mutation, suitably, a homozygous mutation. In one embodiment, the mutation(s) is a substitution mutation. In one embodiment, the substitution mutation(s) is selected from the group consisting of E109K, L146F, P229S, G263E, S93N, A122V, M2121, L128F, D96N, C123Y, A118V, A265V, G130D, G176D, G243R, D246N, A258V, A262V, A214V or G219R or a combination of two or more thereof.

In one embodiment, SEQ ID NO:13 includes one or more mutations at amino acid positions selected from the group consisting of 184, 89, 166, 18, 76, 173, 143, 1, 4, 154, 89, 128, 137 or 181 or a combination of two or more thereof. The type of mutation(s) at this position can be a deletion, an insertion, a substitution or a missense mutation or a combination thereof. The mutation(s) can be a heterozygous or homozygous mutation, suitably, a homozygous mutation. In one embodiment, the mutation(s) is a substitution mutation. In one embodiment, the substitution mutation(s) is selected from the group consisting of P184S, G89D, K166N, G18R, G76R, G173R, P143L, Mil, S4N, V1541, G89D, A128V, S137F or G181S or a combination of two or more thereof. The sequence shown in SEQ ID NO:14 corresponds to the sequence shown in SEQ ID NO:13 with an extra 88 amino acids at the 5' end. In one embodiment, SEQ ID NO:14 includes one or more mutations at amino acid positions selected from the group consisting of 272, 177, 254, 106, 164, 261, 231, 89, 92, 242, 177, 269 or 225 or a combination of two or more thereof. The type of mutation(s) at this position can be a deletion, an insertion, a substitution or a missense mutation or a combination thereof. The mutation(s) can be a heterozygous or homozygous mutation, suitably, a homozygous mutation. In one embodiment, the mutation(s) is a substitution mutation. In one embodiment, the substitution mutation(s) is selected from the group consisting of P272S, G177D, K254N, G106R, G164R, G261R, P231L, M891, S92N, V2421, G177D, A269V, S225F or G269S or a combination of two or more thereof.

Suitably, the mutation is a mutation at position G163 of SEQ ID NO:5. Suitably, the mutation is a homozygous mutation at position G163 of SEQ ID NO:5. Suitably, the mutation is a substitution mutation. Suitably, the substitution mutation is G163R. Suitably, the mutation is homozygous substitution mutation at G163R. When a polypeptide comprising this mutation is expressed in a mutant plant the nitrate level in the mutant plant is lower than the control plant during the early and mid-morning. Corresponding mutations can be made in SEQ ID NO:14, which corresponds to the sequence of SEQ ID NO:7 with additional amino acids at the 5' end thereof.

Suitably, the mutation is a mutation at position G163 of SEQ ID NO:5. Suitably, the substitution mutation is G163R. Suitably, the mutation is homozygous substitution mutation at G163R. This mutation can decrease the level of nitrate in a mutant plant containing this mutation. The G163R homozygous mutant tobacco plant has a reduced level of nitrate in the early morning as compared to the control plant. The level of nitrate is reduced from about 11 mg/g in the control plant to about 6 mg/g in the mutant plant. The nitrate level continues to decrease in the mid-morning. The level of nitrate is reduced from about 7 mg/g in the control plant to about 4.5 mg/g in the mutant plant. By the late morning the nitrate level has increased in the mutant plant as compared to the mid-morning and reaches the nitrate level present in the early morning. For the control, the nitrate level in the control plant continues to decrease. By late morning, the level of nitrate increases to about 6 mg/g in the mutant plant and decreases to about 3 mg/g in the control plant. The level of nicotine is somewhat similar during the morning. The level of nicotine varies between about 13 mg/g and about 11 mg/g for the mutant plant and about 9 mg/g and 13 mg/g for the control plant. The nicotine result indicates that the metabolism of the mutant plant is normal. The biomass levels for the mutant and the control plant are also comparable.

Suitably, the mutation is a mutation at position P143 of SEQ ID NO:13. Suitably, the substitution mutation is P143L. Suitably, the mutation is homozygous substitution mutation at P143L. This mutation can increase the level of nitrate in a mutant plant containing this mutation. The P143L homozygous mutant tobacco plant has an increased level of nitrate in the early morning as compared to the control plant. The level of nitrate is increased from about 7 mg/g in the control plant to about 14 mg/g in the mutant plant. The nitrate level decreases in the mid-morning in the mutant plant and increases slightly in the control plant. The level of nitrate in the mutant plant is reduced to about 9 mg/g and the level of nitrate in the control plant increases to about 9 mg/g. By the late morning the nitrate level has continued to decrease in the mutant plant as compared to the mid-morning. For the control, the nitrate level in the control plant decreases. By late morning, the level of nitrate decreases to about 2 mg/g in the mutant plant and decreases to about 4 mg/g in the control plant. The level of nicotine is somewhat similar during the morning for each of the mutant and control plants. The level of nicotine varies between about 20 mg/g and about 24 mg/g for the mutant plant and about 15 mg/g and 17 mg/g for the control plant. The nicotine result indicates that the metabolism of the mutant plant is normal. The biomass levels for the mutant and the control plant are also comparable.

The diurnal regulation of nitrate metabolism is known and has been intensively investigated (see Stitt & Krapp *Plant, Cell and Environment* 22, 583-621 (1999)). In nitrogen replete plants, the level of the transcript for nitrate reductases is high at the end of the night, falls dramatically during the day, and recovers during the night. NIA activity increases three-fold in the first part of the light period, decreases during the second part of the light period and remains low during the night. The increase of NIA activity after illumination is due to an increase of NIA protein.

There is also disclosed a method for modulating the level of nitrate, total TSNA content or NNK in a tobacco plant, or a plant part thereof, said method comprising the steps of: (i) introducing into the genome of said plant one or more mutations within at least one allele of the one or more polynucleotide sequences described herein; and (ii) obtaining a mutant plant in which said mutation modulates the expression of said polynucleotide sequences or the activity of the polypeptide encoded thereby as compared to a control and the tobacco plant or a plant part thereof has a modulated level of nitrate and/or total TSNA content and/or NNK. In certain embodiments, the tobacco plant or plant part thereof is cured plant material.

Processes for preparing mutants are well known in the art and may include mutagenesis using exogenously added chemicals—such as mutagenic, teratogenic, or carcinogenic organic compounds, for example ethyl methanesulfonate (EMS), that produce random mutations in genetic material. By way of further example, the process may include one or more genetic engineering steps—such as one or more of the genetic engineering steps that are described herein or combinations thereof. By way of further example, the process may include one or more plant crossing steps. TILLING may also be used as described elsewherein herein.

A polypeptide may be prepared by culturing transformed or recombinant host cells under culture conditions suitable to express a polypeptide. The resulting expressed polypeptide may then be purified from such culture using known purification processes. The purification of the polypeptide may include an affinity column containing agents which will bind to the polypeptide; one or more column steps over such affinity resins; one or more steps involving hydrophobic interaction chromatography; or immunoaffinity chromatography. Alternatively, the polypeptide may also be expressed in a form that will facilitate purification. For example, it may be expressed as a fusion polypeptide, such as those of maltose binding polypeptide, glutathione-5-transferase or thioredoxin. Kits for expression and purification of fusion polypeptides are commercially available. The polypeptide may be tagged with an epitope and subsequently purified by using a specific antibody directed to such epitope. One or more liquid chromatography steps—such as reverse-phase high performance liquid chromatography can be employed to further purify the polypeptide. Some or all of the foregoing purification steps, in various combinations, can be employed to provide a substantially homogeneous recombinant polypeptide. The polypeptide thus purified may be substantially free of other polypeptides and is defined herein as a "substantially purified polypeptide"; such purified polypeptides include polypeptides, fragments, variants, and the like. Expression, isolation, and purification of the polypeptides and fragments can be accomplished by any suitable technique, including but not limited to the methods described herein.

It is also possible to utilise an affinity column such as a monoclonal antibody generated against polypeptides, to affinity-purify expressed polypeptides. These polypeptides can be removed from an affinity column using conventional techniques, for example, in a high salt elution buffer and then dialyzed into a lower salt buffer for use or by changing pH or other components depending on the affinity matrix utilized, or be competitively removed using the naturally occurring substrate of the affinity moiety.

A polypeptide may also be produced by known conventional chemical synthesis. Methods for constructing the polypeptides or fragments thereof by synthetic means are known to those skilled in the art. The synthetically-constructed polypeptide sequences, by virtue of sharing primary, secondary or tertiary structural or conformational characteristics with native polypeptides may possess biological properties in common therewith, including biological activity.

The term 'non-naturally occurring' as used herein describes an entity (for example, a polynucleotide, a genetic mutation, a polypeptide, a plant, a plant cell and plant material) that is not formed by nature or that does not exist in nature. Such non-naturally occurring entities or artificial entities may be made, synthesized, initiated, modified, intervened, or manipulated by methods described herein or that are known in the art. Such non-naturally occurring entities or artificial entities may be made, synthesized, initiated, modified, intervened, or manipulated by man. Thus, by way of example, a non-naturally occurring plant, a non-naturally occurring plant cell or non-naturally occurring plant material may be made using traditional plant breeding techniques—such as backcrossing—or by genetic manipulation technologies—such as antisense RNA, interfering RNA, meganuclease and the like. By way of further example, a non-naturally occurring plant, a non-naturally occurring plant cell or non-naturally occurring plant material may be made by introgression of or by transferring one or more genetic mutations (for example one or more polymorphisms) from a first plant or plant cell into a second plant or plant cell (which may itself be naturally occurring), such that the resulting plant, plant cell or plant material or the progeny thereof comprises a genetic constitution (for example, a genome, a chromosome or a segment thereof) that is not formed by nature or that does not exist in nature. The resulting plant, plant cell or plant material is thus artificial or non-naturally occurring. Accordingly, an artificial or non-naturally occurring plant or plant cell may be made by modifying a genetic sequence in a first naturally occurring plant or plant cell, even if the resulting genetic sequence occurs naturally in a second plant or plant cell that comprises a different genetic background from the first plant or plant cell. In certain embodiments, a mutation is not a naturally occurring mutation that exists naturally in a nucleotide sequence or a polypeptide—such as a gene or a protein.

Differences in genetic background can be detected by phenotypic differences or by molecular biology techniques known in the art—such as nucleic acid sequencing, presence or absence of genetic markers (for example, microsatellite RNA markers).

Antibodies that are immunoreactive with the polypeptides described herein are also provided. The polypeptides, fragments, variants, fusion polypeptides, and the like, as set forth herein, can be employed as "immunogens" in producing antibodies immunoreactive therewith. Such antibodies may specifically bind to the polypeptide via the antigen-binding sites of the antibody. Specifically binding antibodies are those that will specifically recognize and bind with a polypeptide, homologues, and variants, but not with other molecules. In one embodiment, the antibodies are specific for polypeptides having an amino acid sequence as set forth herein and do not cross-react with other polypeptides.

More specifically, the polypeptides, fragment, variants, fusion polypeptides, and the like contain antigenic determinants or epitopes that elicit the formation of antibodies. These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon polypeptide folding. Epitopes can be identified by any of the methods known in the art. Additionally, epitopes from the polypeptides can be used as research reagents, in assays, and to purify specific binding antibodies from substances such as polyclonal sera or supernatants from cultured hybridomas. Such epitopes or variants thereof can be produced using techniques known in the art such as solid-phase synthesis, chemical or enzymatic cleavage of a polypeptide, or using recombinant DNA technology.

Both polyclonal and monoclonal antibodies to the polypeptides can be prepared by conventional techniques. Hybridoma cell lines that produce monoclonal antibodies specific for the polypeptides are also contemplated herein. Such hybridomas can be produced and identified by conventional techniques. For the production of antibodies, various host animals may be immunized by injection with a polypeptide, fragment, variant, or mutants thereof. Such host animals may include, but are not limited to, rabbits, mice, and rats, to name a few. Various adjutants may be used to increase the immunological response. Depending on the host species, such adjuvants include, but are not limited to, Freund's (complete and incomplete), mineral gels such as aluminium hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. The monoclonal antibodies can be recovered by conventional techniques. Such monoclonal antibodies may be of any immunoglobulin class including IgG, IgM, IgE, IgA, IgD, and any subclass thereof.

The antibodies can also be used in assays to detect the presence of the polypeptides or fragments, either in vitro or in vivo. The antibodies also can be employed in purifying polypeptides or fragments by immunoaffinity chromatography.

Compositions that can modulate the expression or the activity of one or more of the polynucleotides or polypeptides described herein (or any combination thereof as described herein) include, but are not limited to, sequence-specific polynucleotides that can interfere with the transcription of one or more endogenous gene(s); sequence-specific polynucleotides that can interfere with the translation of RNA transcripts (for example, double-stranded RNAs, siRNAs, ribozymes); sequence-specific polypeptides that can interfere with the stability of one or more proteins; sequence-specific polynucleotides that can interfere with the enzymatic activity of one or more proteins or the binding activity of one or more proteins with respect to substrates or regulatory proteins; antibodies that exhibit specificity for one or more proteins; small molecule compounds that can interfere with the stability of one or more proteins or the enzymatic activity of one or more proteins or the binding activity of one or more proteins; zinc finger proteins that bind one or more polynucleotides; and meganucleases that have activity towards one or more polynucleotides. Gene editing technologies, genetic editing technologies and genome editing technologies are well known in the art.

One method of gene editing involves the use of transcription activator-like effector nucleases (TALENs) which induce double-strand breaks which cells can respond to with repair mechanisms. Non-homologous end joining reconnects DNA from either side of a double-strand break where there is very little or no sequence overlap for annealing. This repair mechanism induces errors in the genome via insertion or deletion, or chromosomal rearrangement. Any such errors may render the gene products coded at that location non-functional.

Another method of gene editing involves the use of the bacterial CRISPR/Cas system. Bacteria and archaea exhibit chromosomal elements called clustered regularly interspaced short palindromic repeats (CRISPR) that are part of an adaptive immune system that protects against invading viral and plasmid DNA. In Type II CRISPR systems, CRISPR RNAs (crRNAs) function with trans-activating crRNA (tracrRNA) and CRISPR-associated (Cas) proteins to introduce double-stranded breaks in target DNA. Target cleavage by Cas9 requires base-pairing between the crRNA and tracrRNA as well as base pairing between the crRNA and the target DNA. Target recognition is facilitated by the presence of a short motif called a protospacer-adjacent motif (PAM) that conforms to the sequence NGG. This system can be harnessed for genome editing. Cas9 is normally programmed by a dual RNA consisting of the crRNA and tracrRNA. However, the core components of these RNAs can be combined into a single hybrid 'guide RNA' for Cas9 targeting. The use of a noncoding RNA guide to target DNA for site-specific cleavage promises to be significantly more straightforward than existing technologies—such as TALENs. Using the CRISPR/Cas strategy, retargeting the nuclease complex only requires introduction of a new RNA sequence and there is no need to reengineer the specificity of protein transcription factors. Antisense technology is another well-known method that can be used to modulate the expression of a polypeptide. A polynucleotide of the gene to be repressed is cloned and operably linked to a regulatory region and a transcription termination sequence so that the antisense strand of RNA is transcribed. The recombinant construct is then transformed into plants and the antisense strand of RNA is produced. The polynucleotide need not be the entire sequence of the gene to be repressed, but typically will be substantially complementary to at least a portion of the sense strand of the gene to be repressed.

A polynucleotide may be transcribed into a ribozyme, or catalytic RNA, that affects expression of an mRNA. Ribozymes can be designed to specifically pair with virtually any target RNA and cleave the phosphodiester backbone at a specific location, thereby functionally inactivating the target RNA. Heterologous polynucleotides can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. Hammerhead ribozyme sequences can be embedded in a stable RNA such as a transfer RNA (tRNA) to increase cleavage efficiency in vivo.

In one embodiment, the sequence-specific polynucleotide that can interfere with the translation of RNA transcript(s) is interfering RNA. RNA interference or RNA silencing is an evolutionarily conserved process by which specific mRNAs can be targeted for enzymatic degradation. A double-stranded RNA (double-stranded RNA) is introduced or produced by a cell (for example, double-stranded RNA virus, or interfering RNA polynucleotides) to initiate the interfering RNA pathway. The double-stranded RNA can be converted into multiple small interfering RNA duplexes of 21-23 by length by RNases III, which are double-stranded RNA-specific endonucleases. The small interfering RNAs can be subsequently recognized by RNA-induced silencing complexes that promote the unwinding of small interfering RNA through an ATP-dependent process. The unwound antisense strand of the small interfering RNA guides the activated RNA-induced silencing complexes to the targeted mRNA comprising a sequence complementary to the small interfering RNA anti-sense strand. The targeted mRNA and the anti-sense strand can form an A-form helix, and the major groove of the A-form helix can be recognized by the activated RNA-induced silencing complexes. The target mRNA can be cleaved by activated RNA-induced silencing complexes at a single site defined by the binding site of the 5'-end of the small interfering RNA strand. The activated RNA-induced silencing complexes can be recycled to catalyze another cleavage event.

Interfering RNA expression vectors may comprise interfering RNA constructs encoding interfering RNA polynucleotides that exhibit RNA interference activity by reducing the expression level of mRNAs, pre-mRNAs, or related RNA variants. The expression vectors may comprise a promoter positioned upstream and operably-linked to an Interfering RNA construct, as further described herein. Interfering RNA expression vectors may comprise a suitable minimal core promoter, a Interfering RNA construct of interest, an upstream (5') regulatory region, a downstream (3') regulatory region, including transcription termination and polyadenylation signals, and other sequences known to persons skilled in the art, such as various selection markers.

The polynucleotides can be produced in various forms, including as double stranded structures (that is, a double-stranded RNA molecule comprising an antisense strand and a complementary sense strand), double-stranded hairpin-like structures, or single-stranded structures (that is, a ssRNA molecule comprising just an antisense strand). The structures may comprise a duplex, asymmetric duplex, hairpin or asymmetric hairpin secondary structure, having self-complementary sense and antisense strands. The double stranded interfering RNA can be enzymatically converted to double-stranded small interfering RNAs. One of the strands of the small interfering RNA duplex can anneal to a complementary sequence within the target mRNA and related RNA variants. The small interfering RNA/mRNA duplexes are recognized by RNA-induced silencing complexes that can cleave RNAs at multiple sites in a sequence-dependent manner, resulting in the degradation of the target mRNA and related RNA variants.

The double-stranded RNA molecules may include small interfering RNA molecules assembled from a single oligonucleotide in a stem-loop structure, wherein self-complementary sense and antisense regions of the small interfering RNA molecule are linked by means of a polynucleotide based or non-polynucleotide-based linker(s), as well as circular single-stranded RNA having two or more loop structures and a stem comprising self-complementary sense and antisense strands, wherein the circular RNA can be processed either in vivo or in vitro to generate an active small interfering RNA molecule capable of mediating interfering RNA.

The use of small hairpin RNA molecules is also contemplated. They comprise a specific antisense sequence in addition to the reverse complement (sense) sequence, typically separated by a spacer or loop sequence. Cleavage of the spacer or loop provides a single-stranded RNA molecule and its reverse complement, such that they may anneal to form a double-stranded RNA molecule (optionally with additional processing steps that may result in addition or removal of one, two, three or more nucleotides from the 3' end or the 5' end of either or both strands). The spacer can be of a sufficient length to permit the antisense and sense sequences to anneal and form a double-stranded structure (or stem) prior to cleavage of the spacer (and, optionally, subsequent processing steps that may result in addition or removal of one, two, three, four, or more nucleotides from the 3' end or the 5' end of either or both strands). The spacer sequence is typically an unrelated nucleotide sequence that is situated between two complementary nucleotide sequence regions which, when annealed into a double-stranded polynucleotide, comprise a small hairpin RNA. The spacer sequence generally comprises between about 3 and about 100 nucleotides. Any RNA polynucleotide of interest can be produced by selecting a suitable sequence composition, loop size, and stem length for producing the hairpin duplex. A suitable range for designing stem lengths of a hairpin duplex, includes stem lengths of at least about 10, 11, 12, 13, 14, 15, 16, 17, 18, 19 or 20 nucleotides—such as about 14-30 nucleotides, about 30-50 nucleotides, about 50-100 nucleotides, about 100-150 nucleotides, about 150-200 nucleotides, about 200-300 nucleotides, about 300-400 nucleotides, about 400-500 nucleotides, about 500-600 nucleotides, and about 600-700 nucleotides. A suitable range for designing loop lengths of a hairpin duplex, includes loop lengths of about 4-25 nucleotides, about 25-50 nucleotides, or longer if the stem length of the hair duplex is substantial. In certain embodiments, a double-stranded RNA or ssRNA molecule is between about 15 and about 40 nucleotides in length. In another embodiment, the small interfering RNA molecule is a double-stranded RNA or ssRNA molecule between about 15 and about 35 nucleotides in length. In another embodiment, the small interfering RNA molecule is a double-stranded RNA or ssRNA molecule between about 17 and about 30 nucleotides in length.

In another embodiment, the small interfering RNA molecule is a double-stranded RNA or ssRNA molecule between about 19 and about 25 nucleotides in length. In another embodiment, the small interfering RNA molecule is a double-stranded RNA or ssRNA molecule between about 21 to about 23 nucleotides in length. In certain embodiments, hairpin structures with duplexed regions longer than 21 nucleotides may promote effective small interfering RNA-directed silencing, regardless of loop sequence and length. Exemplary sequences for RNA interference are set forth in SEQ ID NO: 8 or SEQ ID NO: 9.

The target mRNA sequence is typically between about 14 to about 50 nucleotides in length. The target mRNA can, therefore, be scanned for regions between about 14 and about 50 nucleotides in length that preferably meet one or more of the following criteria for a target sequence: an A+T/G+C ratio of between about 2:1 and about 1:2; an AA dinucleotide or a CA dinucleotide at the 5' end of the target sequence; a sequence of at least 10 consecutive nucleotides unique to the target mRNA (that is, the sequence is not present in other mRNA sequences from the same plant); and no "runs" of more than three consecutive guanine (G) nucleotides or more than three consecutive cytosine (C) nucleotides. These criteria can be assessed using various techniques known in the art, for example, computer programs such as BLAST can be used to search publicly available databases to determine whether the selected target sequence is unique to the target mRNA. Alternatively, a target sequence can be selected (and a small interfering RNA sequence designed) using computer software available commercially (for example, OligoEngine, Target Finder and the small interfering RNA Design Tool which are commercially available).

In one embodiment, target mRNA sequences are selected that are between about 14 and about 30 nucleotides in length that meet one or more of the above criteria. In another embodiment, target sequences are selected that are between about 16 and about 30 nucleotides in length that meet one or more of the above criteria. In a further embodiment, target sequences are selected that are between about 19 and about 30 nucleotides in length that meet one or more of the above criteria. In another embodiment, target sequences are selected that are between about 19 and about 25 nucleotides in length that meet one or more of the above criteria.

In an exemplary embodiment, the small interfering RNA molecules comprise a specific antisense sequence that is complementary to at least 12, 13, 14, 15, 16, 17, 18, 19, 20, 21, 22, 23, 24, 25, 26, 27, 28, 29, 30, or more contiguous nucleotides of any one of the polynucleotide sequences described herein.

The specific antisense sequence comprised by the small interfering RNA molecule can be identical or substantially identical to the complement of the target sequence. In one embodiment, the specific antisense sequence comprised by the small interfering RNA molecule is at least about 75%, 80%, 85%, 90%, 95%, 96%, 97%, 98%, 99% or 100% identical to the complement of the target mRNA sequence. Methods of determining sequence identity are known in the art and can be determined, for example, by using the BLASTN program of the University of Wisconsin Computer Group (GCG) software or provided on the NCBI website.

The specific antisense sequence of the small interfering RNA molecules may exhibit variability by differing (for example, by nucleotide substitution, including transition or transversion) at one, two, three, four or more nucleotides from the sequence of the target mRNA. When such nucleotide substitutions are present in the antisense strand of a double-stranded RNA molecule, the complementary nucleotide in the sense strand with which the substitute nucleotide would typically form hydrogen bond base-pairing may or may not be correspondingly substituted. Double-stranded RNA molecules in which one or more nucleotide substitution occurs in the sense sequence, but not in the antisense strand, are also contemplated. When the antisense sequence of an small interfering RNA molecule comprises one or more mismatches between the nucleotide sequence of the small interfering RNA and the target nucleotide sequence, as described above, the mismatches may be found at the 3' terminus, the 5' terminus or in the central portion of the antisense sequence. In another embodiment, the small interfering RNA molecules comprise a specific antisense sequence that is capable of selectively hybridizing under stringent conditions to a portion of a naturally occurring target gene or target mRNA. As known to those of ordinary skill in the art, variations in stringency of hybridization conditions may be achieved by altering the time, temperature or concentration of the solutions used for the hybridization and wash steps. Suitable conditions can also depend in part on the particular nucleotide sequences used, for example the sequence of the target mRNA or gene.

One method for inducing double stranded RNA-silencing in plants is transformation with a gene construct producing hairpin RNA (see Smith et al. (2000) *Nature,* 407, 319-320). Such constructs comprise inverted regions of the target gene sequence, separated by an appropriate spacer. The insertion of a functional plant intron region as a spacer fragment additionally increases the efficiency of the gene silencing induction, due to generation of an intron spliced hairpin RNA (Wesley et al. (2001) *Plant J.,* 27, 581-590). Suitably, the stem length is about 50 nucleotides to about 1 kilobases in length. Methods for producing intron spliced hairpin RNA are well described in the art (see for example, *Bioscience, Biotechnology, and Biochemistry* (2008) 72, 2, 615-617). Interfering RNA molecules having a duplex or double-stranded structure, for example double-stranded RNA or small hairpin RNA, can have blunt ends, or can have 3' or 5' overhangs. As used herein, "overhang" refers to the unpaired nucleotide or nucleotides that protrude from a duplex structure when a 3'-terminus of one RNA strand extends beyond the 5'-terminus of the other strand (3' overhang), or vice versa (5' overhang). The nucleotides comprising the overhang can be ribonucleotides, deoxyribonucleotides or modified versions thereof. In one embodiment, at least one strand of the interfering RNA molecule has a 3' overhang from about 1 to about 6 nucleotides in length. In other embodiments, the 3' overhang is from about 1 to about 5 nucleotides, from about 1 to about 3 nucleotides and from about 2 to about 4 nucleotides in length.

When the interfering RNA molecule comprises a 3' overhang at one end of the molecule, the other end can be blunt-ended or have also an overhang (5' or 3'). When the interfering RNA molecule comprises an overhang at both ends of the molecule, the length of the overhangs may be the same or different. In one embodiment, the interfering RNA molecule comprises 3' overhangs of about 1 to about 3 nucleotides on both ends of the molecule. In a further embodiment, the interfering RNA molecule is a double-stranded RNA having a 3' overhang of 2 nucleotides at both ends of the molecule. In yet another embodiment, the nucleotides comprising the overhang of the interfering RNA are TT dinucleotides or UU dinucleotides.

When determining the percentage identity of the interfering RNA molecule comprising one or more overhangs to the target mRNA sequence, the overhang(s) may or may not be taken into account. For example, the nucleotides from a 3' overhang and up to 2 nucleotides from the 5'- or 3'-terminus of the double strand may be modified without significant loss of activity of the small interfering RNA molecule.

The interfering RNA molecules can comprise one or more 5' or 3'-cap structures. The interfering RNA molecule can comprise a cap structure at the 3'-end of the sense strand, the antisense strand, or both the sense and antisense strands; or at the 5'-end of the sense strand, the antisense strand, or both the sense and antisense strands of the interfering RNA molecule. Alternatively, the interfering RNA molecule can comprise a cap structure at both the 3'-end and 5'-end of the interfering RNA molecule. The term "cap structure" refers to a chemical modification incorporated at either terminus of an oligonucleotide, which protects the molecule from exonuclease degradation, and may also facilitate delivery or localisation within a cell.

Another modification applicable to interfering RNA molecules is the chemical linkage to the interfering RNA molecule of one or more moieties or conjugates which enhance the activity, cellular distribution, cellular uptake, bioavailability or stability of the interfering RNA molecule. The polynucleotides may be synthesized or modified by methods well established in the art. Chemical modifications may include, but are not limited to 2' modifications, introduction of non-natural bases, covalent attachment to a ligand, and replacement of phosphate linkages with thiophosphate linkages. In this embodiment, the integrity of the duplex structure is strengthened by at least one, and typically two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues.

The nucleotides at one or both of the two single strands may be modified to modulate the activation of cellular enzymes, such as, for example, without limitation, certain nucleases. Techniques for reducing or inhibiting the activation of cellular enzymes are known in the art including, but not limited to, 2'-amino modifications, 2'-fluoro modifications, 2'-alkyl modifications, uncharged backbone modifications, morpholino modifications, 2'-O-methyl modifications, and phosphoramidate. Thus, at least one 2'-hydroxyl group of the nucleotides on a double-stranded RNA is replaced by a chemical group. Also, at least one nucleotide may be modified to form a locked nucleotide. Such locked nucleotide contains a methylene or ethylene bridge that connects the 2'-oxygen of ribose with the 4'-carbon of ribose. Introduction of a locked nucleotide into an oligonucleotide improves the affinity for complementary sequences and increases the melting temperature by several degrees.

Ligands may be conjugated to an interfering RNA molecule, for example, to enhance its cellular absorption. In certain embodiments, a hydrophobic ligand is conjugated to the molecule to facilitate direct permeation of the cellular membrane. These approaches have been used to facilitate cell permeation of antisense oligonucleotides. In certain instances, conjugation of a cationic ligand to oligonucleotides often results in improved resistance to nucleases. Representative examples of cationic ligands include propylammonium and dimethylpropylammonium. Anti-sense oligonucleotides can retain their high binding affinity to mRNA when the cationic ligand is dispersed throughout the oligonucleotide.

The molecules and polynucleotides described herein may be prepared using well-known techniques of solid-phase synthesis. Any other means for such synthesis known in the art may additionally or alternatively be employed.

"Targeted Induced Local Lesions In Genomes" (TILLING) is another mutagenesis technology that can be used to generate and/or identify polynucleotides encoding polypeptides with modified expression and/or activity. TILLING also allows selection of plants carrying such mutants. TILLING combines high-density mutagenesis with high-throughput screening methods. Methods for TILLING are well known in the art (see McCallum et al., (2000) *Nat Biotechnol* 18: 455-457 and Stemple (2004) *Nat Rev Genet* 5(2): 145-50).

Various embodiments are directed to expression vectors comprising one or more of the polynucleotides or interfering RNA constructs that comprise one or more polynucleotides described herein.

Various embodiments are directed to expression vectors comprising one or more of the polynucleotides or one or more interfering RNA constructs described herein.

Various embodiments are directed to expression vectors comprising one or more polynucleotides or one or more interfering RNA constructs encoding one or more interfering RNA polynucleotides described herein that are capable of self-annealing to form a hairpin structure, in which the construct comprises (a) one or more of the polynucleotides described herein; (b) a second sequence encoding a spacer element that forms a loop of the hairpin structure; and (c) a third sequence comprising a reverse complementary sequence of the first sequence, positioned in the same orientation as the first sequence, wherein the second sequence is positioned between the first sequence and the third sequence, and the second sequence is operably-linked to the first sequence and to the third sequence.

The disclosed sequences can be utilised for constructing various polynucleotides that do not form hairpin structures. For example, a double-stranded RNA can be formed by (1) transcribing a first strand of the DNA by operably-linking to a first promoter, and (2) transcribing the reverse complementary sequence of the first strand of the DNA fragment by operably-linking to a second promoter. Each strand of the polynucleotide can be transcribed from the same expression vector, or from different expression vectors. The RNA duplex having RNA interference activity can be enzymatically converted to small interfering RNAs to modulate RNA levels.

Thus, various embodiments are directed to expression vectors comprising one or more polynucleotides or interfering RNA constructs described herein encoding interfering RNA polynucleotides capable of self-annealing, in which the construct comprises (a) one or more of the polynucleotides described herein; and (b) a second sequence comprising a complementary (for example, reverse complementary) sequence of the first sequence, positioned in the same orientation as the first sequence.

Various compositions and methods are provided for modulating the endogenous expression levels of one or more of the polypeptides described herein (or any combination thereof as described herein) by promoting co-suppression of gene expression. The phenomenon of co-suppression occurs as a result of introducing multiple copies of a transgene into a plant cell host. Integration of multiple copies of a transgene can result in modulated expression of the transgene and the targeted endogenous gene. The degree of co-suppression is dependent on the degree of sequence identity between the transgene and the targeted endogenous gene. The silencing of both the endogenous gene and the transgene can occur by extensive methylation of the silenced loci (that is, the endogenous promoter and endogenous gene of interest) that can preclude transcription. Alternatively, in some cases, co-suppression of the endogenous gene and the transgene can occur by post transcriptional gene silencing, in which transcripts can be produced but enhanced rates of degradation preclude accumulation of transcripts. The mechanism for co-suppression by post-transcriptional gene silencing is thought to resemble RNA interference, in that RNA seems to be both an important initiator and a target in these processes, and may be mediated at least in part by the same molecular machinery, possibly through RNA-guided degradation of mRNAs.

Co-suppression of nucleic acids can be achieved by integrating multiple copies of the nucleic acid or fragments thereof, as transgenes, into the genome of a plant of interest. The host plant can be transformed with an expression vector comprising a promoter operably-linked to the nucleic acid or fragments thereof. Various embodiments are directed to expression vectors for promoting co-suppression of endogenous genes comprising a promoter operably-linked to a polynucleotide. Various embodiments are directed to methods for modulating the expression level of one or more of the polynucleotide(s) described herein (or any combination thereof as described herein) by integrating multiple copies of the polynucleotide(s) into a (tobacco) plant genome, comprising: transforming a plant cell host with an expression vector that comprises a promoter operably-linked to a polynucleotide.

Various compositions and methods are provided for modulating the endogenous gene expression level by modulating the translation of mRNA. A host (tobacco) plant cell can be transformed with an expression vector comprising: a promoter operably-linked to a polynucleotide, positioned in anti-sense orientation with respect to the promoter to enable the expression of RNA polynucleotides having a sequence complementary to a portion of mRNA.

Various expression vectors for modulating the translation of mRNA may comprise: a promoter operably-linked to a polynucleotide in which the sequence is positioned in anti-sense orientation with respect to the promoter. The lengths of anti-sense RNA polynucleotides can vary, and may be from about 15-20 nucleotides, about 20-30 nucleotides, about 30-50 nucleotides, about 50-75 nucleotides, about 75-100 nucleotides, about 100-150 nucleotides, about 150-200 nucleotides, and about 200-300 nucleotides.

Methods for obtaining mutant polynucleotides and polypeptides are also provided. Any plant of interest, including a plant cell or plant material can be genetically modified by various methods known to induce mutagenesis, including site-directed mutagenesis, oligonucleotide-directed mutagenesis, chemically-induced mutagenesis, irradiation-induced mutagenesis, mutagenesis utilizing modified bases, mutagenesis utilizing gapped duplex DNA, double-strand break mutagenesis, mutagenesis utilizing repair-deficient host strains, mutagenesis by total gene synthesis, DNA shuffling and other equivalent methods.

Alternatively, genes can be targeted for inactivation by introducing transposons (for example, IS elements) into the genomes of plants of interest. These mobile genetic elements can be introduced by sexual cross-fertilization and insertion mutants can be screened for loss in protein activity. The disrupted gene in a parent plant can be introduced into other plants by crossing the parent plant with plant not subjected to transposon-induced mutagenesis by, for example, sexual cross-fertilization. Any standard breeding techniques known to persons skilled in the art can be utilized. In one embodiment, one or more genes can be inactivated by the insertion of one or more transposons. Mutations can result in homozygous disruption of one or more genes, in heterozygous disruption of one or more genes, or a combination of both homozygous and heterozygous disruptions if more than one gene is disrupted. Suitable transposable elements include retrotransposons, retroposons, and SINE-like elements. Such methods are known to persons skilled in the art.

Alternatively, genes can be targeted for inactivation by introducing ribozymes derived from a number of small circular RNAs that are capable of self-cleavage and replication in plants. These RNAs can replicate either alone (viroid RNAs) or with a helper virus (satellite RNAs). Examples of suitable RNAs include those derived from avocado sunblotch viroid and satellite RNAs derived from tobacco ringspot virus, lucerne transient streak virus, velvet tobacco mottle virus, *solanum nodiflorum* mottle virus, and subterranean clover mottle virus. Various target RNA-specific ribozymes are known to persons skilled in the art.

In some embodiments, the expression of a polypeptide is modulated by non-transgenic means, such as creating a mutation in a gene. Methods that introduce a mutation randomly in a gene sequence can include chemical mutagenesis, EMS mutagenesis and radiation mutagenesis. Methods that introduce one or more targeted mutations into a cell include but are not limited to genome editing technology, particularly zinc finger nuclease-mediated mutagenesis, tilling (targeting induced local lesions in genomes), homologous recombination, oligonucleotide-directed mutagenesis, and meganuclease-mediated mutagenesis.

Some non-limiting examples of mutations are deletions, insertions and missense mutations of at least one nucleotide, single nucleotide polymorphisms and a simple sequence repeat. After mutation, screening can be performed to identify mutations that create premature stop codons or otherwise non-functional genes. After mutation, screening can be performed to identify mutations that create functional genes that are capable of being expressed at elevated levels. Screening of mutants can be carried out by sequencing, or by the use of one or more probes or primers specific to the gene or protein. Specific mutations in polynucleotides can also be created that can result in modulated gene expression, modulated stability of mRNA, or modulated stability of protein. Such plants are referred to herein as "non-naturally occurring" or "mutant" plants. Typically, the mutant or non-naturally occurring plants will include at least a portion of foreign or synthetic or man-made nucleic acid (for example, DNA or RNA) that was not present in the plant before it was manipulated. The foreign nucleic acid may be a single nucleotide, two or more nucleotides, two or more contiguous nucleotides or two or more non-contiguous nucleotides—such as at least 10, 20, 30, 40, 50, 100, 200, 300, 400, 500, 600, 700, 800, 900, 1000, 1100, 1200, 1300, 1400 or 1500 or more contiguous or non-contiguous nucleotides.

The mutant or non-naturally occurring plants can have any combination of one or more mutations which results in modulated protein levels. For example, the mutant or non-naturally occurring plants may have a single mutation in a single gene; multiple mutations in a single gene; a single mutation in two or more or three or more genes; or multiple mutations in two or more or three or more genes. By way of further example, the mutant or non-naturally occurring plants may have one or more mutations in a specific portion of the gene(s)—such as in a region of the gene that encodes an active site of the protein or a portion thereof. By way of further example, the mutant or non-naturally occurring plants may have one or more mutations in a region outside of one or more gene(s)—such as in a region upstream or downstream of the gene it regulates provided that they modulate the activity or expression of the gene(s). Upstream elements can include promoters, enhancers or transription factors. Some elements—such as enhancers—can be positioned upstream or downstream of the gene it regulates. The element(s) need not be located near to the gene that it regulates since some elements have been found located several hundred thousand base pairs upstream or downstream of the gene that it regulates. The mutant or non-naturally occurring plants may have one or more mutations located within the first 100 nucleotides of the gene(s), within the first 200 nucleotides of the gene(s), within the first 300 nucleotides of the gene(s), within the first 400 nucleotides of the gene(s), within the first 500 nucleotides of the gene(s), within the first 600 nucleotides of the gene(s), within the first 700 nucleotides of the gene(s), within the first 800 nucleotides of the gene(s), within the first 900 nucleotides of the gene(s), within the first 1000 nucleotides of the gene(s), within the first 1100 nucleotides of the gene(s), within the first 1200 nucleotides of the gene(s), within the first 1300 nucleotides of the gene(s), within the first 1400 nucleotides of the gene(s) or within the first 1500 nucleotides of the gene(s). The mutant or non-naturally occurring plants may have one or more mutations located within the first, second, third, fourth, fifth, sixth, seventh, eighth, ninth, tenth, eleventh, twelfth, thirteenth, fourteenth or fifteenth set of 100 nucleotides of the gene(s) or combinations thereof. Mutant or non-naturally occurring plants (for example, mutant, non-naturally occurring or transgenic plants and the like, as described herein) comprising the mutant polypeptide variants are disclosed.

In one embodiment, seeds from plants are mutagenised and then grown into first generation mutant plants. The first generation plants are then allowed to self-pollinate and seeds from the first generation plant are grown into second generation plants, which are then screened for mutations in their loci. Though the mutagenized plant material can be screened for mutations, an advantage of screening the second generation plants is that all somatic mutations correspond to germline mutations. One of skill in the art would understand that a variety of plant materials, including but not limited to, seeds, pollen, plant tissue or plant cells, may be mutagenised in order to create the mutant plants. However, the type of plant material mutagenised may affect when the plant nucleic acid is screened for mutations. For example, when pollen is subjected to mutagenesis prior to pollination of a non-mutagenized plant the seeds resulting from that pollination are grown into first generation plants. Every cell of the first generation plants will contain mutations created in the pollen; thus these first generation plants may then be screened for mutations instead of waiting until the second generation.

Mutagens that create primarily point mutations and short deletions, insertions, transversions, and or transitions, including chemical mutagens or radiation, may be used to create the mutations. Mutagens include, but are not limited to, ethyl methanesulfonate, methylmethane sulfonate, N-ethyl-N-nitrosurea, triethylmelamine, N-methyl-N-nitrosourea, procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine, nitrosoguanidine, 2-aminopurine, 7,12 dimethyl-benz(a)anthracene, ethylene oxide, hexamethylphosphoramide, bisulfan, diepoxyalkanes (diepoxyoctane, diepoxybutane, and the like), 2-methoxy-6-chloro-9[3-(ethyl-2-chloro-ethyl)aminopropylamino]acridine dihydrochloride and formaldehyde.

Spontaneous mutations in the locus that may not have been directly caused by the mutagen are also contemplated provided that they result in the desired phenotype. Suitable mutagenic agents can also include, for example, ionising radiation—such as X-rays, gamma rays, fast neutron irradiation and UV radiation. Any method of plant nucleic acid preparation known to those of skill in the art may be used to prepare the plant nucleic acid for mutation screening.

Prepared nucleic acid from individual plants, plant cells, or plant material can optionally be pooled in order to expedite screening for mutations in the population of plants originating from the mutagenized plant tissue, cells or material. One or more subsequent generations of plants, plant cells or plant material can be screened. The size of the optionally pooled group is dependent upon the sensitivity of the screening method used.

After the nucleic acid samples are optionally pooled, they can be subjected to polynucleotide-specific amplification techniques, such as Polymerase Chain Reaction. Any one or more primers or probes specific to the gene or the sequences immediately adjacent to the gene may be utilized to amplify the sequences within the optionally pooled nucleic acid sample. Suitably, the one or more primers or probes are designed to amplify the regions of the locus where useful mutations are most likely to arise. Most preferably, the primer is designed to detect mutations within regions of the polynucleotide. Additionally, it is preferable for the primer(s) and probe(s) to avoid known polymorphic sites in order to ease screening for point mutations. To facilitate detection of amplification products, the one or more primers or probes may be labelled using any conventional labelling method. Primer(s) or probe(s) can be designed based upon the sequences described herein using methods that are well understood in the art.

To facilitate detection of amplification products, the primer(s) or probe(s) may be labelled using any conventional labelling method. These can be designed based upon the sequences described herein using methods that are well understood in the art.

Polymorphisms may be identified by means known in the art and some have been described in the literature.

In a further aspect there is provided a method of preparing a mutant plant. The method involves providing at least one cell of a plant comprising a gene encoding a functional polynucleotide described herein (or any combination thereof as described herein). Next, the at least one cell of the plant is treated under conditions effective to modulate the activity of the polynucleotide(s) described herein. The at least one mutant plant cell is then propagated into a mutant plant, where the mutant plant has a modulated level of polypeptide(s) described (or any combination thereof as described herein) as compared to that of a control plant. In one embodiment of this method of making a mutant plant, the treating step involves subjecting the at least one cell to a chemical mutagenising agent as described above and under conditions effective to yield at least one mutant plant cell. In another embodiment of this method, the treating step involves subjecting the at least one cell to a radiation source under conditions effective to yield at least one mutant plant cell. The term "mutant plant" includes mutants plants in which the genotype is modified as compared to a control plant, suitably by means other than genetic engineering or genetic modification.

In certain embodiments, the mutant plant, mutant plant cell or mutant plant material may comprise one or more mutations that have occurred naturally in another plant, plant cell or plant material and confer a desired trait. This mutation can be incorporated (for example, introgressed) into another plant, plant cell or plant material (for example, a plant, plant cell or plant material with a different genetic background to the plant from which the mutation was derived) to confer the trait thereto. Thus by way of example, a mutation that occurred naturally in a first plant may be introduced into a second plant—such as a second plant with a different genetic background to the first plant. The skilled person is therefore able to search for and identify a plant carrying naturally in its genome one or more mutant alleles of the genes described herein which confer a desired trait. The mutant allele(s) that occurs naturally can be transferred to the second plant by various methods including breeding, backcrossing and introgression to produce a lines, varieties or hybrids that have one or more mutations in the genes described herein. Plants showing a desired trait may be screened out of a pool of mutant plants. Suitably, the selection is carried out utilising the knowledge of the nucleotide sequences as described herein. Consequently, it is possible to screen for a genetic trait as compared to a control. Such a screening approach may involve the application of conventional nucleic acid amplification and/or hybridization techniques as discussed herein. Thus, a further aspect of the present invention relates to a method for identifying a mutant plant comprising the steps of: (a) providing a sample comprising nucleic acid from a plant; and (b) determining the nucleic acid sequence of the polynucleotide, wherein a difference in the sequence of the polynucleotide as compared to the polynucleotide sequence of a control plant is indicative that said plant is a mutant plant. In another aspect there is provided a method for identifying a mutant plant which accumulates reduced levels of at least NNK and/or nitrate as compared to a control plant comprising the steps of: (a) providing a sample from a plant to be screened; (b) determining if said sample comprises one or more mutations in one or more of the polynucleotides described herein; and (c) determining the (i) nitrate content; and/or (ii) at least the NNK content of said plant. Suitably at least the NNK and/or nitrate content is determined in green leaves. In another aspect there is provided a method for preparing a mutant plant which has reduced levels of at least NNK and/or nitrate as compared to a control plant comprising the steps of: (a) providing a sample from a first plant; (b) determining if said sample comprises one or more mutations in one or more the polynucleotides described herein that result in reduced levels of at least NNK and/or nitrate; and (c) transferring the one or more mutations into a second plant. Suitably the NNK and/or nitrate content is determined in green leaves. The mutation(s) can be transferred into the second plant using various methods that are known in the art—such as by genetic engineering, genetic manipulation, introgression, plant breeding, backcrossing and the like. In one embodiment, the first plant is a naturally occurring plant. In one embodiment, the second plant has a different genetic background to the first plant. In another aspect there is provided a method for preparing a mutant plant which has reduced levels of at least NNK and/or nitrate as compared to a control plant comprising the steps of: (a) providing a sample from a first plant; (b) determining if said sample comprises one or more mutations in one or more of the polynucleotides described herein that results in reduced levels of at least NNK and/or nitrate; and (c) introgressing the one or more mutations from the first plant into a second plant. Suitably the NNK and/or nitrate content is determined in green leaves. In one embodiment, the step of introgressing comprises plant breeding, optionally including backcrossing and the like. In one embodiment, the first plant is a naturally occurring plant. In one embodiment, the second plant has a different genetic background to the first plant. In one embodiment, the first plant is not a cultivar or an elite cultivar. In one embodiment, the second plant is a cultivar or an elite cultivar. A further aspect relates to a mutant plant (including a cultivar or elite cultivar mutant plant) obtained or obtainable by the methods described herein. In certain embodiments, the "mutant plants" may have one or more mutations localised only to a specific region of the plant—such as within the sequence of the one or more polynucleotide(s) described herein. According to this embodiment, the remaining genomic sequence of the mutant plant will be the same or substantially the same as the plant prior to the mutagenesis.

In certain embodiments, the mutant plants may have one or more mutations localised in more than one region of the plant—such as within the sequence of one or more of the polynucleotides described herein and in one or more further regions of the genome. According to this embodiment, the remaining genomic sequence of the mutant plant will not be the same or will not be substantially the same as the plant prior to the mutagenesis. In certain embodiments, the mutant plants may not have one or more mutations in one or more, two or more, three or more, four or more or five or more exons of the polynucleotide(s) described herein; or may not have one or more mutations in one or more, two or more, three or more, four or more or five or more introns of the polynucleotide(s) described herein; or may not have one or more mutations in a promoter of the polynucleotide(s) described herein; or may not have one or more mutations in the 3' untranslated region of the polynucleotide(s) described herein; or may not have one or more mutations in the 5' untranslated region of the polynucleotide(s) described herein; or may not have one or more mutations in the coding region of the polynucleotide(s) described herein; or may not have one or more mutations in the non-coding region of the polynucleotide(s) described herein; or any combination of two or more, three or more, four or more, five or more; or six or more thereof parts thereof.

In a further aspect there is provided a method of identifying a plant, a plant cell or plant material comprising a mutation in a gene encoding a polynucleotide described herein comprising: (a) subjecting a plant, a plant cell or plant material to mutagenesis; (b) obtaining a nucleic acid sample from said plant, plant cell or plant material or descendants thereof; and (c) determining the nucleic acid sequence of the gene encoding a polynucleotide described herein or a variant or a fragment thereof, wherein a difference in said sequence is indicative of one or more mutations therein. Zinc finger proteins can be used to modulate the expression or the activity of one or more of the polynucleotides described herein. In various embodiments, a genomic DNA sequence comprising a part of or all of the coding sequence of the polynucleotide is modified by zinc finger nuclease-mediated mutagenesis. The genomic DNA sequence is searched for a unique site for zinc finger protein binding. Alternatively, the genomic DNA sequence is searched for two unique sites for zinc finger protein binding wherein both sites are on opposite strands and close together, for example, 1, 2, 3, 4, 5, 6 or more basepairs apart. Accordingly, zinc finger proteins that bind to polynucleotides are provided.

A zinc finger protein may be engineered to recognize a selected target site in a gene. A zinc finger protein can comprise any combination of motifs derived from natural zinc finger DNA-binding domains and non-natural zinc finger DNA-binding domains by truncation or expansion or a process of site-directed mutagenesis coupled to a selection method such as, but not limited to, phage display selection, bacterial two-hybrid selection or bacterial one-hybrid selection. The term "non-natural zinc finger DNA-binding domain" refers to a zinc finger DNA-binding domain that binds a three-base pair sequence within the target nucleic acid and that does not occur in the cell or organism comprising the nucleic acid which is to be modified. Methods for the design of zinc finger protein which binds specific nucleotide sequences which are unique to a target gene are known in the art.

A zinc finger nuclease may be constructed by making a fusion of a first polynucleotide coding for a zinc finger protein that binds to a polynucleotide, and a second polynucleotide coding for a non-specific endonuclease such as, but not limited to, those of a Type IIS endonuclease. A fusion protein between a zinc finger protein and the nuclease may comprise a spacer consisting of two base pairs or alternatively, the spacer can consist of three, four, five, six, seven or more base pairs. In various embodiments, a zinc finger nuclease introduces a double stranded break in a regulatory region, a coding region, or a non-coding region of a genomic DNA sequence of a polynucleotide and leads to a reduction of the level of expression of a polynucleotide, or a reduction in the activity of the protein encoded thereby. Cleavage by zinc finger nucleases frequently results in the deletion of DNA at the cleavage site following DNA repair by non-homologous end joining.

In other embodiments, a zinc finger protein may be selected to bind to a regulatory sequence of a polynucleotide. More specifically, the regulatory sequence may comprise a transcription initiation site, a start codon, a region of an exon, a boundary of an exon-intron, a terminator, or a stop codon. Accordingly, the invention provides a mutant, non-naturally occurring or transgenic plant or plant cells, produced by zinc finger nuclease-mediated mutagenesis in the vicinity of or within one or more polynucleotides described herein, and methods for making such a plant or plant cell by zinc finger nuclease-mediated mutagenesis. Methods for delivering zinc finger protein and zinc finger nuclease to a tobacco plant are similar to those described below for delivery of meganuclease.

In another aspect, methods for producing mutant, non-naturally occurring or transgenic or otherwise genetically-modified plants using meganucleases, such as I-CreI, are described. Naturally occurring meganucleases as well as recombinant meganucleases can be used to specifically cause a double-stranded break at a single site or at relatively few sites in the genomic DNA of a plant to allow for the disruption of one or more polynucleotides described herein. The meganuclease may be an engineered meganuclease with altered DNA-recognition properties. Meganuclease proteins can be delivered into plant cells by a variety of different mechanisms known in the art.

The inventions encompass the use of meganucleases to inactivate a polynucleotide(s) described herein (or any combination thereof as described herein) in a plant cell or plant. Particularly, the invention provides a method for inactivating a polynucleotide in a plant using a meganuclease comprising: a) providing a plant cell comprising a polynucleotide as described herein; (b) introducing a meganuclease or a construct encoding a meganuclease into said plant cell; and (c) allowing the meganuclease to substantially inactivate the polynucleotide(s)

Meganucleases can be used to cleave meganuclease recognition sites within the coding regions of a polynucleotide. Such cleavage frequently results in the deletion of DNA at the meganuclease recognition site following mutagenic DNA repair by non-homologous end joining. Such mutations in the gene coding sequence are typically sufficient to inactivate the gene. This method to modify a plant cell involves, first, the delivery of a meganuclease expression cassette to a plant cell using a suitable transformation method. For highest efficiency, it is desirable to link the meganuclease expression cassette to a selectable marker and select for successfully transformed cells in the presence of a selection agent. This approach will result in the integration of the meganuclease expression cassette into the genome, however, which may not be desirable if the plant is likely to require regulatory approval. In such cases, the meganuclease expression cassette (and linked selectable marker gene) may be segregated away in subsequent plant generations using conventional breeding techniques. Alternatively, plant cells may be initially be transformed with a meganuclease expression cassette lacking a selectable marker and may be grown on media lacking a selection agent. Under such conditions, a fraction of the treated cells will acquire the meganuclease expression cassette and will express the engineered meganuclease transiently without integrating the meganuclease expression cassette into the genome. Because it does not account for transformation efficiency, this latter transformation procedure requires that a greater number of treated cells be screened to obtain the desired genome modification. The above approach can also be applied to modify a plant cell when using a zinc finger protein or zinc finger nuclease.

Following delivery of the meganuclease expression cassette, plant cells are grown, initially, under conditions that are typical for the particular transformation procedure that was used. This may mean growing transformed cells on media at temperatures below 26° C., frequently in the dark. Such standard conditions can be used for a period of time, preferably 1-4 days, to allow the plant cell to recover from the transformation process. At any point following this initial recovery period, growth temperature may be raised to stimulate the activity of the engineered meganuclease to cleave and mutate the meganuclease recognition site.

For certain applications, it may be desirable to precisely remove the polynucleotide from the genome of the plant. Such applications are possible using a pair of engineered meganucleases, each of which cleaves a meganuclease recognition site on either side of the intended deletion. TAL Effector Nucleases (TALENs) that are able to recognize and bind to a gene and introduce a double-strand break into the genome can also be used. Thus, in another aspect, methods for producing mutant, non-naturally occurring or transgenic or otherwise genetically-modified plants as described herein using TAL Effector Nucleases are contemplated.

Plants suitable for use in genetic modification include, but are not limited to, monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genera *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea*. Suitable species may include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), Salix spp. (willow), *Eucalyptus* spp. (*eucalyptus*), *Triticosecale* (tritic wheat times rye), bamboo, *Helianthus annuus* (sunflower), *Carthamus tinctorius* (safflower), *Jatropha curcas* (*jatropha*), *Ricinus communis* (castor), *Elaeis guineensis* (palm), *Linum usitatissimum* (flax), *Brassica juncea, Beta vulgaris* (sugarbeet), *Manihot esculenta* (cassaya), *Lycopersicon esculentum* (tomato), *Lactuca sativa* (lettuce), *Musyclise alca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), Coffe45ycliseca (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Rosa* spp. (rose), *Dianthus caryophyllus* (carnation), *Petunia* spp. (*petunia*), *Poinsettia pulcherrima* (poinsettia), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy), *Panicum virgatum* (switchgrass), Sorghu45yclise45or (*sorghum*, sudangrass), *Miscanthus giganteus* (*miscanthus*), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

Various embodiments are directed to mutant tobacco plants, non-naturally occurring tobacco plants or transgenic tobacco plants modified to modulate gene expression levels thereby producing plants—such as tobacco plant—in which the expression level of a polypeptide is modulated within plant tissues of interest as compared to a control plant. The disclosed compositions and methods can be applied to any species of the genus *Nicotiana*, including *N. rustica* and *N. tabacum* (for example, LA B21, LN KY171, TI 1406, Basma, Galpao, Perique, Beinhart 1000-1, and Petico). Other species include *N. acaulis*, N46yclise4646ta, N46yclise4646ta var. *multiflora*, N46yclise46na, *N. alata, N. amplexicaulis, N. arentsii, N*46yclise4646ta, *N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora*, N46yclise46ma, *N. megalosiphon, N. miersii, N. noctiflora, N. nudicaulis, N. obtusifolia, N. occidentalis, N. occidentalis* subsp. *hesperis, N. otophora, N. paniculata, N. pauciflora, N. petunioides, N. plumbaginifolia, N. quadrivalvis, N. raimondii, N. repanda, N. rosulata, N. rosulata* subsp. *ingulba, N. rotundifolia, N. setchellii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica*, N46yclise46ta, *N. velutina, N. wigandioides*, and *N. x sanderae*.

The use of tobacco cultivars and elite tobacco cultivars is also contemplated herein. The transgenic, non-naturally occurring or mutant plant may therefore be a tobacco variety or elite tobacco cultivar that comprises one or more transgenes, or one or more genetic mutations or a combination thereof. The genetic mutation(s) (for example, one or more polymorphisms) can be mutations that do not exist naturally in the individual tobacco variety or tobacco cultivar (for example, elite tobacco cultivar) or can be genetic mutation(s) that do occur naturally provided that the mutation does not occur naturally in the individual tobacco variety or tobacco cultivar (for example, elite tobacco cultivar).

Particularly useful *Nicotiana tabacum* varieties include Burley type, dark type, flue-cured type, and Oriental type tobaccos. Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF911, DT 538 LC Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KTY14xL8 LC, Little Crittenden, McNair 373, McNair 944, msKY 14xL8, Narrow Leaf Madole, Narrow Leaf Madole LC, NBH 98, N-126, N-777LC, N-7371LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC' Periq'e' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, VA359, AA 37-1, B 13P, Xanthi (Mitchell-Mor), Bel-W3, 79-615, Samsun Holmes NN, KTRDC number 2 Hybrid 49, Burley 21, KY 8959, KY 9, MD 609, PG 01, PG 04, P01, P02, P03, RG 11, RG 8, VA 509, AS44, Banket A1, Basma Drama B84/31, Basma I Zichna ZP4/B, Basma Xanthi BX 2A, Batek, Besuki Jember, 0104, Coker 347, Criollo Misionero, Delcrest, Djebel 81, DVH 405, Galpão Comum, HBO4P, Hicks Broadleaf, Kabakulak Elassona, Kutsage E1, LA BU 21, NC 2326, NC 297, PVH 2110, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, Basma xanthi, GR149, GR153, Petit Havana. Low converter subvarieties of the above, even if not specifically identified herein, are also contemplated.

Embodiments are also directed to compositions and methods for producing mutant plants, non-naturally occurring plants, hybrid plants, or transgenic plants that have been modified to modulate the expression or activity of a polynucleotide(s) described herein (or any combination thereof as described herein). Advantageously, the mutant plants, non-naturally occurring plants, hybrid plants, or transgenic plants that are obtained may be similar or substantially the same in overall appearance to control plants. Various phenotypic characteristics such as degree of maturity, number of leaves per plant, stalk height, leaf insertion angle, leaf size (width and length), internode distance, and lamina-midrib ratio can be assessed by field observations.

One aspect relates to a seed of a mutant plant, a non-naturally occurring plant, a hybrid plant or a transgenic plant described herein. Preferably, the seed is a tobacco seed. A further aspect relates to pollen or an ovule of a mutant plant, a non-naturally occurring plant, a hybrid plant or a transgenic plant that is described herein. In addition, there is provided a mutant plant, a non-naturally occurring plant, a hybrid plant or a transgenic plant as described herein which further comprises a nucleic acid conferring male sterility.

Also provided is a tissue culture of regenerable cells of the mutant plant, non-naturally occurring plant, hybrid plant, or transgenic plant or a part thereof as described herein, which culture regenerates plants capable of expressing all the morphological and physiological characteristics of the parent. The regenerable cells include but are not limited to cells from leaves, pollen, embryos, cotyledons, hypocotyls, roots, root tips, anthers, flowers and a part thereof, ovules, shoots, stems, stalks, pith and capsules or callus or protoplasts derived therefrom.

One object is to provide mutant, transgenic or non-naturally occurring plants or parts thereof that exhibit modulated (eg. reduced) levels of TSNAs in the plant material, for example, in cured leaves. Suitably, mutant, transgenic or non-naturally occurring plants or parts thereof that exhibit modulated (eg. reduced) levels of at least NNK and/or nitrate as compared to a control plant. In certain embodiments, the level of at least NNN will be substantially the same. In certain embodiments, the level of at least NNN, NAB and NAT will be substantially the same. In certain embodiments, the level of at least NNN will be substantially the same and the level of NAB will be reduced as compared to a control plant. In certain embodiments, the level of at least NNN will be substantially the same and the level of NAT will be reduced as compared to a control plant. In certain embodiments, the level of at least NNN will be substantially the same and the level of NAT and NAB will be reduced as compared to a control plant. The nicotine content in the mutant, transgenic or non-naturally occurring plants or parts thereof can be substantially the same as the control or wild type plant or can be lower than the control or wild type plant. Suitably, the mutant, transgenic or non-naturally occurring plants or parts thereof have substantially the same visual appearance as the control plant.

The four principal TSNAs, those typically found to be present in the highest concentrations, are N-nitrosonicotine (NNN), 4-(methylnitrosamino)-1-(3-pyridyl)-1-butanone (NNK), N-nitrosoanabasine (NAB) and N-nitrosoanatabine (NAT). Minor compounds, those typically found at significantly lower levels than the principal TSNAs, include 4-(methylnitrosamino) 4-(3-pyridyl)butanal (NNA), 4-(methylnitrosamino)-1-(3-pyridyl)-1-butanol (NNAL), 4-(methylnitrosamino)4-(3-pyridyl)-1-butanol (iso-NNAL), and 4-(methylnitrosamino)-4-(3-pyridyl)-1-butyric acid (iso-NNAC). At least NNN and NNK have been reported to be carcinogenic when applied to animals in laboratory studies.

Accordingly, there is described herein mutant, transgenic or non-naturally occurring plants or parts thereof or plant cells that have modulated (eg. reduced) levels of at least NNK and/or nitrate as compared to control cells or control plants. In certain embodiments, the level of NNN will be substantially the same. The mutant, transgenic or non-naturally occurring plants or plant cells have been modified to modulate (eg. reduce) the synthesis or activity of one or more of the polypeptides described herein by modulating the expression of one or more of the corresponding polynucleotide sequences described herein. Suitably, the modulated levels of at least NNK and/or nitrate are observed in at least the green leaves, suitably cured leaves. In certain embodiments, the level of total TSNAs in the plant—such as the green leaves, suitably cured leaves or cured tobacco—may be modulated (eg. reduced). In certain embodiments, the level of nicotine in the plant—such as the green leaves, suitably cured leaves or cured tobacco—may be modulated (eg. reduced).

A further aspect, relates to a mutant, non-naturally occurring or transgenic plant or cell, wherein the expression of or the activity of one or more of the polypeptides described herein is modulated (eg. reduced) and a part of the plant (for example, the green leaves, suitably cured leaves or cured tobacco) have reduced levels of nitrate and/or at least NNK of at least 5% therein as compared to a control plant in which the expression or the activity said polypeptide(s) has not been modulated. In certain embodiments, the level of NNN will be substantially the same. In certain embodiments, the level of total TSNAs in the plant—such as the green leaves, suitably cured leaves or cured tobacco—may also be modulated (eg. reduced), for example, by at least about 5%. In certain embodiments, the level of nicotine in the plant—such as the green leaves, suitably cured leaves or cured tobacco—may also be modulated (eg. reduced), for example, by at least about 5%. In certain embodiments, the level of total TSNAs in the plant—such as in green leaves—may also be modulated (eg. reduced), for example, by at least about 5% and the level of nicotine in the plant—such as the green leaves, suitably cured leaves or cured tobacco—may also be modulated (eg. reduced), for example, by at least about 5%.

A still further aspect, relates to a cured plant material—such as cured leaf or cured tobacco-derived or derivable from a mutant, non-naturally occurring or transgenic plant or cell, wherein expression of one or more of the polynucleotides described herein or the activity of the protein encoded thereby is reduced and wherein the nitrate and/or NNK level is reduced by at least 5% as compared to a control plant. In certain embodiments, the level of NNN will be substantially the same.

A still further aspect, relates to mutant, non-naturally occurring or transgenic cured plant material—such as leaf or cured tobacco—which has nitrate and/or NNK levels that are reduced at least 5% as compared to a control plant. In certain embodiments, the level of NNN will be substantially the same. In certain embodiments, the level of total TSNAs in the cured plant material may also be reduced, for example, by at least about 5%. In certain embodiments, the level of nicotine in the cured plant material may also be reduced, for example, by at least about 5%. In certain embodiments, the level of total TSNAs in the cured plant material may also be reduced, for example, by at least about 5% and the level of nicotine in the cured plant material may also be reduced by at least about 5%.

In a still further aspect, there is provided a mutant, non-naturally occurring or transgenic plant or plant cell, wherein expression of one or more of the polypeptides described herein is reduced as compared to a control or a wild-type plant and wherein (i) the nitrate content is about 7 mg/g or less—such as about 6.9 mg/g or less, about 6.8 mg/g or less, about 6.7 mg/g or less, about 6.6 mg/g or less, about 6.5 mg/g or less, about 6.4 mg/g or less, about 6.3 mg/g or less, about 6.2 mg/g or less, about 6.1 mg/g or less, or about 6 mg/g or less; and (ii) the NNK content is about 110 ng/g or less—such as about 109 ng/g or less, about 108 ng/g or less, about 107 ng/g or less, about 106 ng/g or less, about 105 ng/g or less, about 104 ng/g or less, about 103 ng/g or less, about 102 ng/g or less, about 101 ng/g or less, or about 100 ng/g or less. In certain embodiments the level of nicotine is about 30 mg/g or less—such as about 29.9 mg/g or less, about 29.8 mg/g or less, about 29.7 mg/g or less, about 29.6 mg/g or less, about 29.5 mg/g or less, about 29.4 mg/g or less, about 29.3 mg/g or less, about 29.2 mg/g or less, about 29.1 mg/g or less, or about 29 mg/g or less. In certain embodiments, the total TSNA content is about 250 ng/g or less—such as about 240 ng/g or less, about 230 ng/g or less, about 220 ng/g or less, about 210 ng/g or less, about 200 ng/g or less, about 190 ng/g or less, about 180 ng/g or less, about 170 ng/g or less, about 160 ng/g or less, or about 150 ng/g or less.

In a still further aspect, there is provided a mutant, non-naturally occurring or transgenic leaf, wherein expression of one or more of the polypeptides described herein is reduced as compared to a control or a wild-type leaf and wherein (i) the nitrate content is about 7 mg/g or less—such as about 6.9 mg/g or less, about 6.8 mg/g or less, about 6.7 mg/g or less, about 6.6 mg/g or less, about 6.5 mg/g or less, about 6.4 mg/g or less, about 6.3 mg/g or less, about 6.2 mg/g or less, about 6.1 mg/g or less, or about 6 mg/g or less; and (ii) the NNK content is about 110 ng/g or less-such as about 109 ng/g or less, about 108 ng/g or less, about 107 ng/g or less, about 106 ng/g or less, about 105 ng/g or less, about 104 ng/g or less, about 103 ng/g or less, about 102 ng/g or less, about 101 ng/g or less, or about 100 ng/g or less. In certain embodiments the level of nicotine is about 30 mg/g or less—such as about 29.9 mg/g or less, about 29.8 mg/g or less, about 29.7 mg/g or less, about 29.6 mg/g or less, about 29.5 mg/g or less, about 29.4 mg/g or less, about 29.3 mg/g or less, about 29.2 mg/g or less, about 29.1 mg/g or less, or about 29 mg/g or less. In certain embodiments, the total TSNA content is about 250 ng/g or less—such as about 240 ng/g or less, about 230 ng/g or less, about 220 ng/g or less, about 210 ng/g or less, about 200 ng/g or less, about 190 ng/g or less, about 180 ng/g or less, about 170 ng/g or less, about 160 ng/g or less, or about 150 ng/g or less.

In a still further aspect, there is provided mutant, non-naturally occurring or transgenic cured plant material—such as cured leaf or cured tobacco—wherein expression of one or more of the polypeptides described herein is reduced as compared to control or a wild-type cured plant material and wherein: (i) the nitrate content is about 7 mg/g or less—such as about 6.9 mg/g or less, about 6.8 mg/g or less, about 6.7 mg/g or less, about 6.6 mg/g or less, about 6.5 mg/g or less, about 6.4 mg/g or less, about 6.3 mg/g or less, about 6.2 mg/g or less, about 6.1 mg/g or less, or about 6 mg/g or less; and (ii) the NNK content is about 110 ng/g or less—such as about 109 ng/g or less, about 108 ng/g or less, about 107 ng/g or less, about 106 ng/g or less, about 105 ng/g or less, about 104 ng/g or less, about 103 ng/g or less, about 102 ng/g or less, about 101 ng/g or less, or about 100 ng/g or less. In certain embodiments the level of nicotine is about 30 mg/g or less—such as about 29.9 mg/g or less, about 29.8 mg/g or less, about 29.7 mg/g or less, about 29.6 mg/g or less, about 29.5 mg/g or less, about 29.4 mg/g or less, about 29.3 mg/g or less, about 29.2 mg/g or less, about 29.1 mg/g or less, or about 29 mg/g or less. In certain embodiments, the total TSNA content is about 250 ng/g or less—such as about 240 ng/g or less, about 230 ng/g or less, about 220 ng/g or less, about 210 ng/g or less, about 200 ng/g or less, about 190 ng/g or less, about 180 ng/g or less, about 170 ng/g or less, about 160 ng/g or less, or about 150 ng/g or less.

Suitably the visual appearance of said plant or part thereof (for example, leaf) is substantially the same as the control plant. Suitably, the plant is a tobacco plant.

Embodiments are also directed to compositions and methods for producing mutant, non-naturally occurring or transgenic plants that have been modified to modulate the expression or activity of the one or more of the polynucleotides or polypeptides described herein which can result in plants or plant components (for example, leaves—such as green leaves or cured leaves—or tobacco) with modulated levels of nitrate and/or NNK and/or NNN and/or TSNAs and/or nicotine as compared to a control plant.

Advantageously, the mutant, non-naturally occurring or transgenic plants that are obtained according to the methods described herein are similar or substantially the same in visual appearance to the control plants. In one embodiment, the leaf weight of the mutant, non-naturally occurring or transgenic plant is substantially the same as the control plant. In one embodiment, the leaf number of the mutant, non-naturally occurring or transgenic plant is substantially the same as the control plant. In one embodiment, the leaf weight and the leaf number of the mutant, non-naturally occurring or transgenic plant is substantially the same as the control plant. In one embodiment, the stalk height of the mutant, non-naturally occurring or transgenic plants is substantially the same as the control plants at, for example, one, two or three or more months after field transplant or 10, 20, 30 or 36 or more days after topping. For example, the stalk height of the mutant, non-naturally occurring or transgenic plants is not less than the stalk height of the control plants. In another embodiment, the chlorophyll content of the mutant, non-naturally occurring or transgenic plants is substantially the same as the control plants. In another embodiment, the stalk height of the mutant, non-naturally occurring or transgenic plants is substantially the same as the control plants and the chlorophyll content of the mutant, non-naturally occurring or transgenic plants is substantially the same as the control plants. In other embodiments, the size or form or number or colouration of the leaves of the mutant, non-naturally occurring or transgenic plants is substantially the same as the control plants. Suitably, the plant is a tobacco plant.

In another aspect, there is provided a method for modulating (eg. reducing) the amount of nitrate and/or at least NNK in at least a part of a plant (for example, the leaves—such as cured leaves—or in tobacco), comprising the steps of: (i) modulating (eg. reducing) the expression or activity of an one or more of the polypeptides described herein (or any combination thereof as described herein), suitably, wherein the polypeptide(s) is encoded by the corresponding polynucleotide sequence described herein; (ii) measuring the nitrate and/or at least NNK content in at least a part (for example, the leaves—such as cured leaves—or tobacco) of the mutant, non-naturally occurring or transgenic plant obtained in step (i); and (iii) identifying a mutant, non-naturally occurring or transgenic plant in which the nitrate and/or at least NNK content therein has been modulated (eg. reduced) in comparison to a control plant. Suitably, the visual appearance of said mutant, non-naturally occurring or transgenic plant is substantially the same as the control plant. Suitably, the plant is a tobacco plant.

In another aspect, there is provided a method for modulating (eg. reducing) the amount of nitrate and/or at least NNK in at least a part of cured plant material—such as cured leaf—comprising the steps of: (i) modulating (eg. reducing) the expression or activity of an one or more of the polypeptides (or any combination thereof as described herein), suitably, wherein the polypeptide(s) is encoded by the corresponding polynucleotide sequence described herein; (ii) harvesting plant material—such as one or more of the leaves—and curing for a period of time; (iii) measuring the nitrate and/or at least NNK content in at least a part of the cured plant material obtained in step (ii); and (iv) identifying cured plant material in which the nitrate and/or at least NNK content therein has been modulated (eg. reduced) in comparison to a control plant.

The increase in expression as compared to the control plant may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or 100% or more—such as 200% or 300% or more, which includes an increase in transcriptional activity or protein expression or both.

The increase in the activity as compared to a control type plant may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or 100% or more—such as 200% or 300% or more.

The reduction in expression as compared to the control plant may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%, which includes a reduction in transcriptional activity or protein expression or both.

The reduction in activity as compared to a control type plant may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%.

Polynucleotides and recombinant constructs described herein can be used to modulate the expression of the enzymes described herein in a plant species of interest, suitably tobacco.

A number of polynucleotide based methods can be used to increase gene expression in plants. By way of example, a construct, vector or expression vector that is compatible with the plant to be transformed can be prepared which comprises the gene of interest together with an upstream promoter that is capable of overexpressing the gene in the plant. Exemplary promoters are described herein. Following transformation and when grown under suitable conditions, the promoter can drive expression in order to modulate (for example, reduce) the levels of this enzyme in the plant, or in a specific tissue thereof. In one exemplary embodiment, a vector carrying one or more polynucleotides described herein (or any combination thereof as described herein) is generated to overexpress the gene in a plant. The vector carries a suitable promoter—such as the cauliflower mosaic virus CaMV 35S promoter—upstream of the transgene driving its constitutive expression in all tissues of the plant. The vector also carries an antibiotic resistance gene in order to confer selection of the transformed calli and cell lines.

Various embodiments are therefore directed to methods for modulating (for example, reducing) the expression level of one or more polynucleotides described herein (or any combination thereof as described herein) by integrating multiple copies of the polynucleotide into a plant genome, comprising: transforming a plant cell host with an expression vector that comprises a promoter operably-linked to one or more polynucleotides described herein. The polypeptide encoded by a recombinant polynucleotide can be a native polypeptide, or can be heterologous to the cell.

A tobacco plant carrying a mutant allele of one or more polynucleotides described herein (or any combination thereof as described herein) can be used in a plant breeding program to create useful lines, varieties and hybrids. In particular, the mutant allele is introgressed into the commercially important varieties described above. Thus, methods for breeding plants are provided, that comprise crossing a mutant plant, a non-naturally occurring plant or a transgenic plant as described herein with a plant comprising a different genetic identity. The method may further comprise crossing the progeny plant with another plant, and optionally repeating the crossing until a progeny with the desirable genetic traits or genetic background is obtained. One purpose served by such breeding methods is to introduce a desirable genetic trait into other varieties, breeding lines, hybrids or cultivars, particularly those that are of commercial interest. Another purpose is to facilitate stacking of genetic modifications of different genes in a single plant variety, lines, hybrids or cultivars. Intraspecific as well as interspecific matings are contemplated. The progeny plants that arise from such crosses, also referred to as breeding lines, are examples of non-naturally occurring plants of the invention.

In one embodiment, a method is provided for producing a non-naturally occurring tobacco plant comprising: (a) crossing a mutant or transgenic tobacco plant with a second tobacco plant to yield progeny tobacco seed; (b) growing the progeny tobacco seed, under plant growth conditions, to yield the non-naturally occurring tobacco plant. The method may further comprises: (c) crossing the previous generation of non-naturally occurring tobacco plant with itself or another tobacco plant to yield progeny tobacco seed; (d) growing the progeny tobacco seed of step (c) under plant growth conditions, to yield additional non-naturally occurring tobacco plants; and (e) repeating the crossing and growing steps of (c) and (d) multiple times to generate further generations of non-naturally occurring tobacco plants. The method may optionally comprises prior to step (a), a step of providing a parent plant which comprises a genetic identity that is characterized and that is not identical to the mutant or transgenic plant. In some embodiments, depending on the breeding program, the crossing and growing steps are repeated from 0 to 2 times, from 0 to 3 times, from 0 to 4 times, 0 to 5 times, from 0 to 6 times, from 0 to 7 times, from 0 to 8 times, from 0 to 9 times or from 0 to 10 times, in order to generate generations of non-naturally occurring tobacco plants. Backcrossing is an example of such a method wherein a progeny is crossed with one of its parents or another plant genetically similar to its parent, in order to obtain a progeny plant in the next generation that has a genetic identity which is closer to that of one of the parents. Techniques for plant breeding, particularly tobacco plant breeding, are well known and can be used in the methods of the invention. The invention further provides non-naturally occurring tobacco plants produced by these methods. Certain embodiments exclude the step of selecting a plant.

In some embodiments of the methods described herein, lines resulting from breeding and screening for variant genes are evaluated in the field using standard field procedures. Control genotypes including the original unmutagenized parent are included and entries are arranged in the field in a randomized complete block design or other appropriate field design. For tobacco, standard agronomic practices are used, for example, the tobacco is harvested, weighed, and sampled for chemical and other common testing before and during curing. Statistical analyses of the data are performed to confirm the similarity of the selected lines to the parental line. Cytogenetic analyses of the selected plants are optionally performed to confirm the chromosome complement and chromosome pairing relationships.

DNA fingerprinting, single nucleotide polymorphism, microsatellite markers, or similar technologies may be used in a marker-assisted selection (MAS) breeding program to transfer or breed mutant alleles of a gene into other tobaccos, as described herein. For example, a breeder can create segregating populations from hybridizations of a genotype containing a mutant allele with an agronomically desirable genotype. Plants in the F2 or backcross generations can be screened using a marker developed from a genomic sequence or a fragment thereof, using one of the techniques listed herein. Plants identified as possessing the mutant allele can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered.

According to the disclosure, in a breeding program, successful crosses yield F1 plants that are fertile. Selected F1 plants can be crossed with one of the parents, and the first backcross generation plants are self-pollinated to produce a population that is again screened for variant gene expression (for example, the null version of the gene). The process of backcrossing, self-pollination, and screening is repeated, for example, at least 4 times until the final screening produces a plant that is fertile and reasonably similar to the recurrent parent. This plant, if desired, is self-pollinated and the progeny are subsequently screened again to confirm that the plant exhibits variant gene expression. In some embodiments, a plant population in the F2 generation is screened for variant gene expression, for example, a plant is identified that fails to express a polypeptide due to the absence of the gene according to standard methods, for example, by using a PCR method with primers based upon the nucleotide sequence information for the polynucleotide(s) described herein (or any combination thereof as described herein).

Hybrid tobacco varieties can be produced by preventing self-pollination of female parent plants (that is, seed parents)

of a first variety, permitting pollen from male parent plants of a second variety to fertilize the female parent plants, and allowing F1 hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), or transgenic male sterility wherein a transgene inhibits microsporogenesis and/or pollen formation, or self-incompatibility. Female parent plants containing CMS are particularly useful. In embodiments in which the female parent plants are CMS, pollen is harvested from male fertile plants and applied manually to the stigmas of CMS female parent plants, and the resulting F1 seed is harvested.

Varieties and lines described herein can be used to form single-cross tobacco F1 hybrids. In such embodiments, the plants of the parent varieties can be grown as substantially homogeneous adjoining populations to facilitate natural cross-pollination from the male parent plants to the female parent plants. The F1 seed formed on the female parent plants is selectively harvested by conventional means. One also can grow the two parent plant varieties in bulk and harvest a blend of F1 hybrid seed formed on the female parent and seed formed upon the male parent as the result of self-pollination. Alternatively, three-way crosses can be carried out wherein a single-cross F1 hybrid is used as a female parent and is crossed with a different male parent. As another alternative, double-cross hybrids can be created wherein the F1 progeny of two different single-crosses are themselves crossed.

A population of mutant, non-naturally occurring or transgenic plants can be screened or selected for those members of the population that have a desired trait or phenotype. For example, a population of progeny of a single transformation event can be screened for those plants having a desired level of expression or activity of the polypeptide(s) encoded thereby. Physical and biochemical methods can be used to identify expression or activity levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining and enzyme assays also can be used to detect the presence or expression or activity of polypeptides or polynucleotides.

Mutant, non-naturally occurring or transgenic plant cells and plants are described herein comprising one or more recombinant polynucleotides, one or more polynucleotide constructs, one or more double-stranded RNAs, one or more conjugates or one or more vectors/expression vectors.

Without limitation, the plants described herein may be modified for other purposes either before or after the expression or activity has been modulated according to the present invention. One or more of the following genetic modifications can be present in the mutant, non-naturally occurring or transgenic plants. In one embodiment, one or more genes that are involved in the conversion of nitrogenous metabolic intermediates is modified resulting in plants or parts of plants (such as leaves or tobacco) that when cured, produces lower levels of at least one tobacco-specific nitrosamine than control plants or parts thereof. Non-limiting examples of genes that can be modified include genes encoding a nicotine demethylase, such as CYP82E4, CYP82E5 and CYP82E10 which participate in the conversion of nicotine to nornicotine and are described in WO2006091194, WO2008070274, WO2009064771 and PCT/US2011/021088. In another embodiment, one or more genes that are involved in heavy metal uptake or heavy metal transport are modified resulting in plants or parts of plants (such as leaves) having a lower heavy metal content than control plants or parts thereof without the modification(s). Non-limiting examples include genes in the family of multidrug resistance associated proteins, the family of cation diffusion facilitators (CDF), the family of Zrt-, Irt-like proteins (ZIP), the family of cation exchangers (CAX), the family of copper transporters (COPT), the family of heavy-metal P-type ATPases (for example, HMAs, as described in WO2009074325), the family of homologs of natural resistance-associated macrophage proteins (NRAMP), and the family of ATP-binding cassette (ABC) transporters (for example, MRPs, as described in WO2012/028309, which participate in transport of heavy metals, such as cadmium. The term heavy metal as used herein includes transition metals. Examples of other modifications include herbicide tolerance, for example, glyphosate is an active ingredient of many broad spectrum herbicides. Glyphosate resistant transgenic plants have been developed by transferring the aroA gene (a glyphosate EPSP synthetase from *Salmonella typhimurium* and *E. coli*). Sulphonylurea resistant plants have been produced by transforming the mutant ALS (acetolactate synthetase) gene from *Arabidopsis*. OB protein of photosystem II from mutant *Amaranthus hybridus* has been transferred in to plants to produce atrazine resistant transgenic plants; and bromoxynil resistant transgenic plants have been produced by incorporating the bxn gene from the bacterium *Klebsiella pneumoniae*. Another exemplary modification results in plants that are resistant to insects. *Bacillus thuringiensis* (Bt) toxins can provide an effective way of delaying the emergence of Bt-resistant pests, as recently illustrated in broccoli where pyramided cry1Ac and cry1C Bt genes controlled diamondback moths resistant to either single protein and significantly delayed the evolution of resistant insects. Another exemplary modification results in plants that are resistant to diseases caused by pathogens (for example, viruses, bacteria, fungi). Plants expressing the Xa21 gene (resistance to bacterial blight) with plants expressing both a Bt fusion gene and a chitinase gene (resistance to yellow stem borer and tolerance to sheath) have been engineered. Another exemplary modification results in altered reproductive capability, such as male sterility. Another exemplary modification results in plants that are tolerant to abiotic stress (for example, drought, temperature, salinity), and tolerant transgenic plants have been produced by transferring acyl glycerol phosphate enzyme from *Arabidopsis*; genes coding mannitol dehydrogenase and sorbitol dehydrogenase which are involved in synthesis of mannitol and sorbitol improve drought resistance. Another exemplary modification results in plants that produce proteins which may have favourable immunogenic properties for use in humans. For example, plants capable of producing proteins which substantially lack alpha-1,3-linked fucose residues, beta-1,2-linked xylose residues, or both, in its N-glycan may be of use. Other exemplary modifications can result in plants with improved storage proteins and oils, plants with enhanced photosynthetic efficiency, plants with prolonged shelf life, plants with enhanced carbohydrate content, and plants resistant to fungi; plants encoding an enzyme involved in the biosynthesis of alkaloids. Transgenic plants in which the expression of S-adenosyl-L-methionine (SAM) and/or cystathionine gamma-synthase (CGS) has been modulated are also contemplated.

One or more such traits may be introgressed into the mutant, non-naturally occurring or transgenic tobacco plants from another tobacco cultivar or may be directly transformed into it. The introgression of the trait(s) into the mutant, non-naturally occurring or transgenic tobacco plants of the invention maybe achieved by any method of plant breeding known in the art, for example, pedigree breeding, backcrossing, doubled-haploid breeding, and the like (see, Wernsman, E. A, and Rufty, R. C. 1987. Chapter Seventeen. Tobacco. Pages 669-698 In: *Cultivar Development. Crop* Species. W. H. Fehr (ed.), MacMillan Publishing Co, Inc., New York, N.Y. 761 pp.). Molecular biology-based techniques described above, in particular RFLP and microsatelite markers, can be used in such backcrosses to identify the progenies having the highest degree of genetic identity with the recurrent parent. This permits one to accelerate the production of tobacco varieties having at least 90%, preferably at least 95%, more preferably at least 99% genetic identity with the recurrent parent, yet more preferably genetically identical to the recurrent parent, and further comprising the trait(s) introgressed from the donor parent. Such determination of genetic identity can be based on molecular markers known in the art.

The last backcross generation can be selfed to give pure breeding progeny for the nucleic acid(s) being transferred. The resulting plants generally have essentially all of the morphological and physiological characteristics of the mutant, non-naturally occurring or transgenic tobacco plants of the invention, in addition to the transferred trait(s) (for example, one or more single gene traits). The exact backcrossing protocol will depend on the trait being altered to determine an appropriate testing protocol. Although backcrossing methods are simplified when the trait being transferred is a dominant allele, a recessive allele may also be transferred. In this instance, it may be necessary to introduce a test of the progeny to determine if the desired trait has been successfully transferred. Various embodiments provide mutant plants, non-naturally occurring plants or transgenic plants, as well as biomass in which the expression level of a polynucleotide (or any combination thereof as described herein) is modulated to modulate the nitrate and/or at least NNK content therein Parts of such plants, particularly tobacco plants, and more particularly the leaf lamina and midrib of tobacco plants, can be incorporated into or used in making various consumable products including but not limited to aerosol forming materials, aerosol forming devices, smoking articles, smokable articles, smokeless products, and tobacco products. Examples of aerosol forming materials include but are not limited to tobacco compositions, tobaccos, tobacco extract, cut tobacco, cut filler, cured tobacco, expanded tobacco, homogenized tobacco, reconstituted tobacco, and pipe tobaccos. Smoking articles and smokable articles are types of aerosol forming devices. Examples of smoking articles or smokable articles include but are not limited to cigarettes, cigarillos, and cigars. Examples of smokeless products comprise chewing tobaccos, and snuffs. In certain aerosol forming devices, rather than combustion, a tobacco composition or another aerosol forming material is heated by one or more electrical heating elements to produce an aerosol. In another type of heated aerosol forming device, an aerosol is produced by the transfer of heat from a combustible fuel element or heat source to a physically separate aerosol forming material, which may be located within, around or downstream of the heat source. Smokeless tobacco products and various tobacco-containing aerosol forming materials may contain tobacco in any form, including as dried particles, shreds, granules, powders, or a slurry, deposited on, mixed in, surrounded by, or otherwise combined with other ingredients in any format, such as flakes, films, tabs, foams, or beads. As used herein, the term 'smoke' is used to describe a type of aerosol that is produced by smoking articles, such as cigarettes, or by combusting an aerosol forming material.

In one embodiment, there is also provided cured plant material from the mutant, transgenic and non-naturally occurring tobacco plants described herein. Processes of curing green tobacco leaves are known by those having skills in the art and include without limitation air-curing, fire-curing, flue-curing and sun-curing. The process of curing green tobacco leaves depends on the type of tobacco harvested. For example, Virginia flue (bright) tobacco is typically flue-cured, Burley and certain dark strains are usually air-cured, and pipe tobacco, chewing tobacco, and snuff are usually fire-cured.

In another embodiment, there is described tobacco products including tobacco-containing aerosol forming materials comprising plant material—such as leaves, preferably cured leaves—from the mutant tobacco plants, transgenic tobacco plants or non-naturally occurring tobacco plants described herein. The tobacco products described herein can be a blended tobacco product which may further comprise unmodified tobacco.

The amount of NNK in these smokable articles and smokeless products and aerosols thereof may be at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, and 100% lower—such as about 200% or 300% lower—when compared to consumable products derived from non-mutant, non-naturally occurring or non-transgenic counterparts.

The amount of NNN in these smokable articles and smokeless products and aerosols thereof may be at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, and 100% lower—such as about 200% or 300% lower—when compared to consumable products derived from non-mutant, non-naturally occurring or non-transgenic counterparts.

The amount of nitrate in these smokable articles and smokeless products and aerosols thereof may be at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, and 100% lower—such as about 200% or 300% lower—when compared to consumable products derived from non-mutant, non-naturally occurring or non-transgenic counterparts.

The amount of nicotine in these smokable articles and smokeless products and aerosols thereof may be at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, and 100% lower—such as about 200% or 300% lower—when compared to consumable products derived from non-mutant, non-naturally occurring or non-transgenic counterparts. The amount of nicotine in these smokable articles and smokeless products and aerosols thereof may be about the same as compared to consumable products derived from non-mutant, non-naturally occurring or non-transgenic counterparts.

The amount of total TSNAs in these smokable articles and smokeless products and aerosols thereof may be at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, and 100% lower—such as about 200% or 300% lower—when compared to consumable products derived from non-mutant, non-naturally occurring or non-transgenic counterparts.

The mutant, non-naturally occurring or transgenic plants may have other uses in, for example, agriculture. For example, mutant, non-naturally occurring or transgenic plants described herein can be used to make animal feed and human food products.

The invention also provides methods for producing seeds comprising cultivating the mutant plant, non-naturally occurring plant, or transgenic plant described herein, and collecting seeds from the cultivated plants. Seeds from plants described herein can be conditioned and bagged in packaging material by means known in the art to form an article of manufacture. Packaging material such as paper and cloth are well known in the art. A package of seed can have a label, for example, a tag or label secured to the packaging material, a label printed on the package that describes the nature of the seeds therein.

Compositions, methods and kits for genotyping plants for identification, selection, or breeding can comprise a means of detecting the presence of a polynucleotide (or any combination thereof as described herein) in a sample of polynucleotide. Accordingly, a composition is described comprising one of more primers for specifically amplifying at least a portion of one or more of the polynucleotides and optionally one or more probes and optionally one or more reagents for conducting the amplification or detection.

Accordingly, gene specific oligonucleotide primers or probes comprising about 10 or more contiguous polynucleotides corresponding to the polynucleotide(s) described herein are disclosed. Said primers or probes may comprise or consist of about 15, 20, 25, 30, 40, 45 or 50 more contiguous polynucleotides that hybridise (for example, specifically hybridise) to the polynucleotide(s) described herein. In some embodiments, the primers or probes may comprise or consist of about 10 to 50 contiguous nucleotides, about 10 to 40 contiguous nucleotides, about 10 to 30 contiguous nucleotides or about 15 to 30 contiguous nucleotides that may be used in sequence-dependent methods of gene identification (for example, Southern hybridization) or isolation (for example, in situ hybridization of bacterial colonies or bacteriophage plaques) or gene detection (for example, as one or more amplification primers in nucleic acid amplification or detection). The one or more specific primers or probes can be designed and used to amplify or detect a part or all of the polynucleotide(s). By way of specific example, two primers may be used in a polymerase chain reaction protocol to amplify a nucleic acid fragment encoding a nucleic acid—such as DNA or RNA. The polymerase chain reaction may also be performed using one primer that is derived from a nucleic acid sequence and a second primer that hybridises to the sequence upstream or downstream of the nucleic acid sequence—such as a promoter sequence, the 3' end of the mRNA precursor or a sequence derived from a vector. Examples of thermal and isothermal techniques useful for in vitro amplification of polynucleotides are well known in the art. The sample may be or may be derived from a plant, a plant cell or plant material or a tobacco product made or derived from the plant, the plant cell or the plant material as described herein.

In a further aspect, there is also provided a method of detecting a polynucleotide(s) described herein (or any combination thereof as described herein) in a sample comprising the step of: (a) providing a sample comprising, or suspected of comprising, a polynucleotide; (b) contacting said sample with one of more primers or one or more probes for specifically detecting at least a portion of the polynucleotide(s); and (c) detecting the presence of an amplification product, wherein the presence of an amplification product is indicative of the presence of the polynucleotide(s) in the sample. In a further aspect, there is also provided the use of one of more primers or probes for specifically detecting at least a portion of the polynucleotide(s). Kits for detecting at least a portion of the polynucleotide(s) are also provided which comprise one of more primers or probes for specifically detecting at least a portion of the polynucleotide(s). The kit may comprise reagents for polynucleotide amplification—such as PCR—or reagents for probe hybridization-detection technology—such as Southern Blots, Northern Blots, in-situ hybridization, or microarray. The kit may comprise reagents for antibody binding-detection technology such as Western Blots, ELISAs, SELDI mass spectrometry or test strips. The kit may comprise reagents for DNA sequencing. The kit may comprise reagents and instructions for determining nitrate content and/or at least NNK content and/or NNN content and/or nicotine content and/or total TSNA content. Suitably, the kit comprises reagents and instructions for determining nitrate content and/or at least NNK content and/or nicotine content and/or NNN content and/or total TSNA content in plant material, cured plant material or cured leaves.

In some embodiments, a kit may comprise instructions for one or more of the methods described. The kits described may be useful for genetic identity determination, phylogenetic studies, genotyping, haplotyping, pedigree analysis or plant breeding particularly with co-dominant scoring. The present invention also provides a method of genotyping a plant, a plant cell or plant material comprising a polynucleotide as described herein. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. The specific method of genotyping may employ any number of molecular marker analytic techniques including amplification fragment length polymorphisms (AFLPs). AFLPs are the product of allelic differences between amplification fragments caused by nucleotide sequence variability. Thus, the present invention further provides a means to follow segregation of one or more genes or nucleic acids as well as chromosomal sequences genetically linked to these genes or nucleic acids using such techniques as AFLP analysis.

In one embodiment, there is also provided cured plant material from the mutant, transgenic and non-naturally occurring plants described herein. For example, processes of curing tobacco leaves are known by those having skills in the field and include without limitation air-curing, fire-curing, flue-curing and sun-curing. The process of curing green tobacco leaves depends on the type of tobacco harvested. For example, Virginia flue (bright) tobacco is typically flue-cured, Burley and certain dark strains are usually air-cured, and pipe tobacco, chewing tobacco, and snuff are usually fire-cured.

In another embodiment, there is described tobacco products including tobacco products comprising plant material—such as leaves, suitably cured plant material—such as cured leaves—from the mutant, transgenic and non-naturally occurring plants described herein or which are produced by the methods described herein. The tobacco products described herein may further comprise unmodified tobacco.

In another embodiment, there is described tobacco products comprising plant material, preferably leaves—such as cured leaves, from the mutant, transgenic and non-naturally occurring plants described herein. For example, the plant material may be added to the inside or outside of the tobacco product and so upon burning a desirable aroma is released. The tobacco product according to this embodiment may even be an unmodified tobacco or a modified tobacco. The tobacco product according to this embodiment may even be derived from a mutant, transgenic or non-naturally occurring plant which has modifications in one or more genes other than the genes disclosed herein.

The invention is further described in the Examples below, which are provided to describe the invention in further detail. These examples, which set forth a preferred mode presently contemplated for carrying out the invention, are intended to illustrate and not to limit the invention.

EXAMPLES

Example 1: Identification of NtCLCe-s Sequences

For the identification of NtCLCe-s, related transcripts are detected in *N. tabacum* leaves by RT-PCR analyses and the existence of potentially matching EST-contigs (NtCLCe-s: NCBI_43350-v4ctg-in). Data from an Affymetrix custom-made tobacco exon-array (sequence probes from NtPMI-a1g22230e1-st) is used to confirm that NtCLCe-s is equally expressed in roots, green and senescent leaves of *N. tabacum*. Furthermore, cold stress and strong cadmium stress is found not to affect NtCLCe-s expression levels, thereby suggesting that NtCLCe-s is constitutively expressed in tobacco root and leaf organs. Constitutive NtCLCe expression may be correlated with the maintenance of its essential cellular role in plastids which is presumably linked to the nitrogen assimilation pathway. According to WoLFPSORT software, NtCLCe-s is highly predicted to be a plastidial membrane protein. RNAseq studies confirms the presence of the transcript in its ancestor *N. sylvestris.*

Example 2: Identification of NtCLCe-t Sequences

For the identification of NtCLCe-t, related transcripts are detected in *N. tabacum* leaves by RT-PCR analyses and the existence of corresponding EST-contigs. RNAseq studies confirm the presence of the transcript in the ancestor *N. tomentosiformis*, thereby suggesting that the expression of the NtCLCe-t copy is possibly lost in *N. tabacum* after entering the allotetraploid state, possibly due to gene disruption and/or rearrangement.

Example 3: Expression of NtCLCe-s or NtCLCe-t in *N. tabacum* Leaves

Both CLC-Nt2-s and CLC-Nt2-t genes are expressed in *N. tabacum* leaves, as determined by the presence of both transcripts in *N. tabacum* leaves (custom made tobacco exon-array studies validated by RT-PCR) and corresponding EST-contigs (CLC-Nt2-s: MIRA_20760-v4ctg-in; CLC-Nt2-t: NCBI_56794-v4ctg-in). In addition RNAseq studies confirms the presence of the corresponding transcripts in the two ancestors *N. sylvestris* and *N. tomentosiformis.*

When looking more carefully at transcriptomic data from the tobacco exon-array with specific probes for CLC-Nt2-t and CLC-Nt2-s, NtPMIa1g19904e2-st and NtPMIa1g-50210e2-st, respectively, it is seen that both copies are differentially expressed in *N. tabacum*. CLC-Nt2-s is poorly expressed in Burley root (TN90) and CLC-Nt2-t is sensitive to the circadian rhythm. Both genes are expressed in root and leaf of flue-cured tobacco and are insensitive to cadmium treatment.

Example 4: Silencing of CLC-Nt2-t Expression in *N. tabacum*

A DNA fragment (SEQ ID NO: 8) identified in the coding sequence of CLC-Nt2 and flanking an intron (100% identity with CLC-Nt2-s and 97% identity with CLC-Nt2-t) in *N. tabacum* (Hicks broadleaf) is cloned in order to silence both CLC-Nt2 copies in tobacco using a RNAi approach. The corresponding DNA fragment is inserted into the Gateway vector pB7GWIWG2(II) via an entry vector, exactly as detailed by the manufacturer (Invitrogen). This vector contains a promoter for constitutive expression (the cauliflower mosaic virus CaMV 35S promoter) of the transgene in all tissues of the plant and the kan gene for kanamycin antibiotic resistance. The construct is then inserted in to the genome of the Burley tobacco Kentucky 14 (KY14) via *Agrobacterium tumefasciens* using a classical leaf disk procedure. From calli, individual lines are regenerated. The selection of transgenic lines is performed by PCR on isolated genomic DNA from plantlets. RNAi silencing T0 lines are monitored by RT-PCR using specific primers flanking the insert used for silencing and grown for seed production. T1 seeds are collected, re-grown on agar plates and monitored exactly as T0 plantlets. Positive plants are grown in pots and cultivated in the greenhouse. At harvest time (10 week old plants), one leaf at mid stalk position is sampled and subjected to nitrate determination using either a nitrate colorimetric assay kit (Cayman, US) or Skalar. All remaining leaves are cured plant by plant in a small experimental air-curing barn for two months using standard methods that are known in the art. After curing, leaves of each plant are assembled and subjected to TSNA analyses.

Example 5: Silencing of NtCLCe Expression in *N. tabacum*

A DNA fragment (SEQ ID NO: 9) identified in the coding sequence of NtCLCe is cloned to silence both NtCLCe copies using a RNAi approach. The corresponding DNA fragment is then inserted into the Gateway vector pB7GWIWG2(II) via an entry vector, exactly as detailed by the manufacturer (Invitrogen). This vector contains a promoter for constitutive expression (the cauliflower mosaic virus CaMV 35S promoter) of the transgene in all tissues of the plant and the kan gene for kanamycin antibiotic resistance. The construct is then inserted in the genome of the Burley tobacco Kentucky 14 (KY14) via *Agrobacterium tumefasciens* using a classical leaf disk procedure. From calli, individual lines are regenerated. The selection on agar plates is performed by PCR on isolated genomic DNA from plantlets. RNAi silencing T0 lines is then monitored by RT-PCR using specific primers flanking the insert used for silencing and grown for seed production. T1 seeds are collected, re-grown on agar plates and monitored exactly as T0 plantlets. Positive plants are grown on pots and cultivated in the greenhouse. At harvest time (10 weeks old plants), one leaf at mid stalk position is sampled and subjected to nitrate determination using either a nitrate colorimetric assay kit (Cayman, US) or Skalar. The rest of the leaves are cured plant by plant in a small experimental air-curing barn for two months using standard methods that are known in the art. After curing, leaves of each plant are assembled and subjected to TSNA analyses.

Example 6: TSNA Analysis in CLC-NT2-RNAi and NtCLCe-RNAi Plants

Figure 2:
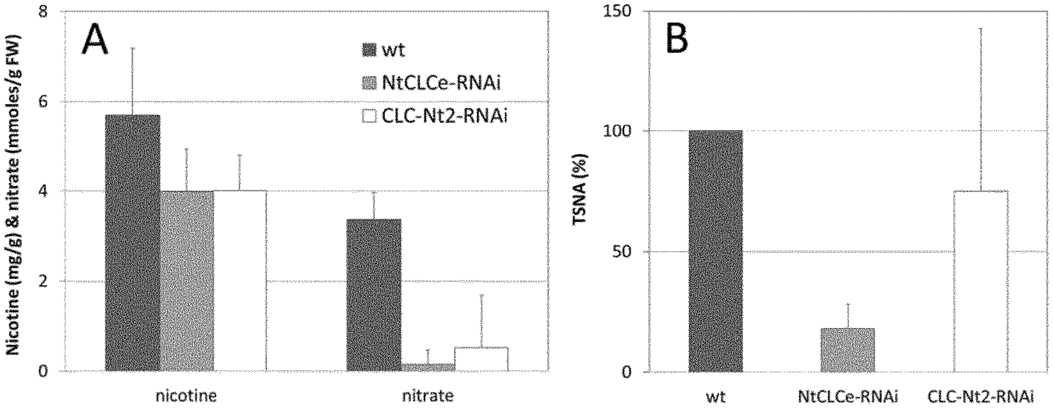
FIG. 2: Nicotine and nitrate analyses in green leaves of wt (n=11), NtCLCe-RNAi (n=5) and CLC-Nt2-RNAi (n=5) plants (A); total TSNA content in the corresponding leaves following air-curing process. In this experiment, plants were cultivated in 3 liter pots and the highest total TSNA value corresponds to 200 ng/g.

The selection of CLC-NT2-RNAi and NtCLCe-RNAi plants using PCR on genomic DNA to identify transgenic inserts followed by RT-PCR on cDNA (obtained from isolated total RNA) is performed. As shown in FIG. 1 (semi-quantitative RT-PCR analyses), CLC-Nt2 or NtCLCe genes are found to be fully or partially silenced in green leaves of CLC-Nt2-RNAi and NtCLCe-RNAi T1 plants compared to wild-type plants (three representative plants are shown). Interestingly, in both RNAi plants, NtCLCe and CLC-Nt2 genes are silenced independently of the construct used, thereby suggesting possible cross-talk regulation between these two genes in leaves. In a first experiment, T1 plantlets are grown in small pots (3 liter pots) after germination. At harvest time (10 weeks after transplanting), nitrate reduction is observed in both CLC-Nt2-RNAi and NtCLCe-RNAi green leaves (mid-stalk position), however the reduction of nitrate is significantly (P<0.01) more effective in NtCLCe-RNAi plants (~95%) compared to CLC-Nt2 plants (about seq id no:5%, see FIG. 2A). Nicotine reduction is also seen in both transgenic plants when compared to wt plants (~35%). This nicotine reduction suggests that NtCLCe and CLC-Nt2 affect nitrate redistribution in roots under certain growth conditions which influences nicotine synthesis. Total TSNA (NNN, NNK, NAT (N9-nitrosoanatabine) and NAB (N9-nitrosoanabasine) is determined in both CLC-RNAi plants after curing (see FIG. 2B). NNK, NNN, NAB and NAT are available commercially which can be of use as reference standards. Standard methods for the analysis of NNK, NNN, NAB and NAT are known in the art (see, for example, Nicotine & Tobacco Research (2006) 2:309-313). Ultra performance liquid chromatography-tandem mass spectrometry (UPLC-MS/MS) can be used. Methods for measuring nicotine are also known in the art (see, for example, International Journal of Cancer (2005); 116:16-19). The data indicate that the strong reduction of nitrate levels prevents the formation of TSNA in cured leaves, which may be because nitrate is the main source of nitrosating agent in leaves contributing to the formation of TSNA. The reduction in nitrate found in CLC-Nt2-RNAi plants does not result in such a strong TSNA effect when compared to NtCLCe-RNAi plants.

Figure 3:
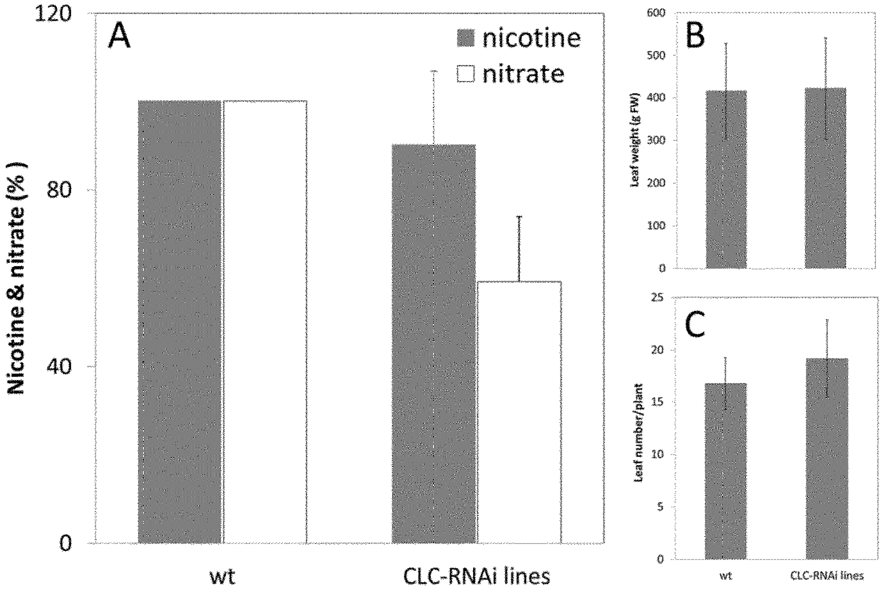
FIG. 3: Nicotine, nitrate analyses in green leaves (A), leaf weight (B) and leaf number (C) of wt (n=4), NtCLCe-RNAi and CLC-Nt2-RNAi plants (n=8) lacking both CLC-Nt2 and NtCLCe transcripts (CLC-RNAi lines). Leaves were harvested after 10 weeks growth in 10 liter pots under controlled greenhouse conditions. In this experiment, the maximum values for nicotine and nitrate were of 29.6 and 6.4 mg/g, respectively.

To prevent any stress conditions for root growth, the previous experiment is repeated using 10 liter pots. Under such conditions, wild-type tobacco plants accumulate about five times more nicotine when compared to the previous experiment. NtCLCe-RNAi and CLC-Nt2-RNAi plants showing reduced gene expression were selected exactly as described before. Since most of the transgenic plants from both constructs exhibited reduced expression for NtCLCe and CLC-Nt2 (see FIG. 1), the RNAi plants showing reduced expression for both CLCs were grouped together (CLC-RNAi plants) and subjected to nicotine and nitrate analyses (see FIG. 3A). The reduction of nicotine observed in the first experiments for CLC-RNAi plants was not found in this experiment, thereby confirming that confining root development by using small pots may trigger additional reduction of nicotine in both NtCLCe-RNAi and CLC-Nt2-RNAi plants compared to wild type plants (compare FIGS. 2A and 3A). However, nitrate was still significantly reduced (>40%) in both CLC-RNAi plants compared to wild type plants, thus confirming that reducing expression of NtCLCe and CLC-Nt2 leads to a nitrate content decrease in tobacco leaves. Under such growth conditions, transgenic plants did not show any phenotypic differences compared to wt plants, as can be seen by comparing total leaf weight and leaf numbers (see FIGS. 3B and 3C).

Figure 4:
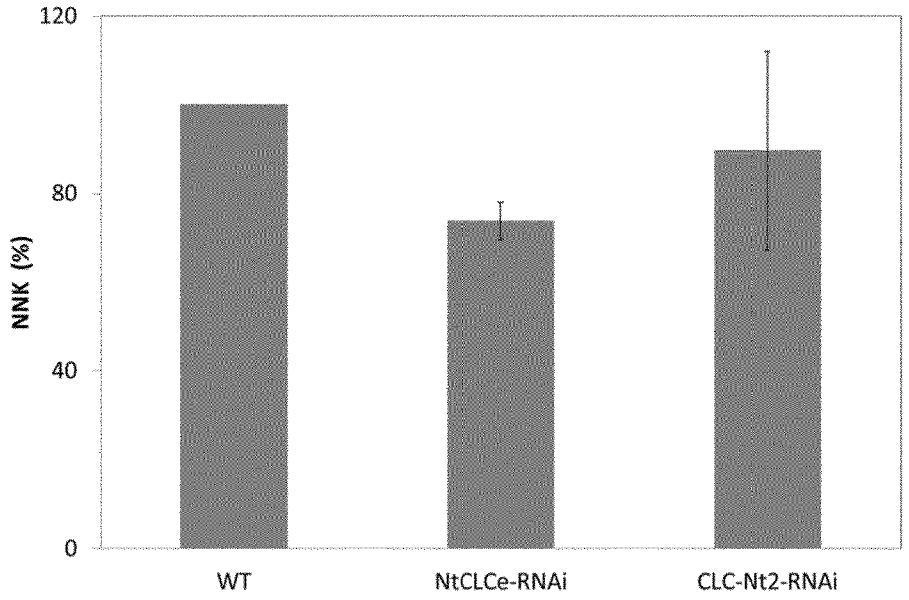
FIG. 4: Percentage of NNK in air-cured leaves of wt, NtCLCe-RNAi and CLC-Nt2-RNAi plants, after cultivation in 10 liter pots as shown in FIG. 3. In this experiment, the highest NNK value corresponds to 108 ng/g.

The analyses of TSNA in these plants showed that NNN was not reduced in air-cured leaves compared to wild type plants. However, 24 and 10% NNK reduction is seen in both NtCLCe-RNAi and CLC-Nt2-RNAi plants compared to wild type plants (see FIG. 4). The NNK reduction is more significant in NtCLCe-RNAi (P<0.01) than in CLC-Nt2-RNAi plants, thereby confirming the data obtained in the first experiment for total TSNA (see FIG. 2).

Although transgenic and wild type plants are not grown under a field environment and not cured in classical barns for air-curing tobacco, our data show that limiting the expression of NtCLCe (NtCLCe-s) and CLC-Nt2 (s and t copies) contributes to efficiently reduce nitrate in tobacco leaves. After curing, TSNA (NNK) is found to be reduced in the leaves, indicating that reducing the nitrate content in green leaves as a provider for nitrosating agents during curing will effectively contribute to reducing the formation of TSNA in the corresponding cured leaves. This reduction can correspond to an at least 20% reduction in NNK.

Example 7: Ethyl-methanesulfonate mutagensis of CLC-Nt2-s, CLC-Nt2-t, NtCLCe-s or NtCLCe-t in *N. tabacum*

M0 seeds of *Nicotiana tabacum* AA37 are treated with ethyl-methanesulfonate (EMS) at different concentrations and exposure times, in order to generate a population of plants with random point mutations. A kill-curve is estimated at M1 generation for each treatment, together with lethality, fertility and rate of chimerism. M1 plants are self fertilized to generate M2 families of seeds, to allow recessive alleles to be recovered as homozygous and lethal alleles to be recovered as heterozygous. Genomic DNA from 8 M2 plants per each family of the EMS mutagenised population is extracted and screened for mutants, while M2 plant material and M3 seeds are collected and stored for future analyses. To identify and characterise the mutant variants, genomic DNA samples from M2 plants are pooled in groups and screened by sequencing of targeted gene fragments. Target gene fragments are amplified using the primers shown in Table 2. Mutations in the target genes are retrieved by sequencing the individual DNA fragments. The various mutants are shown in Table 1.

Figure 5:
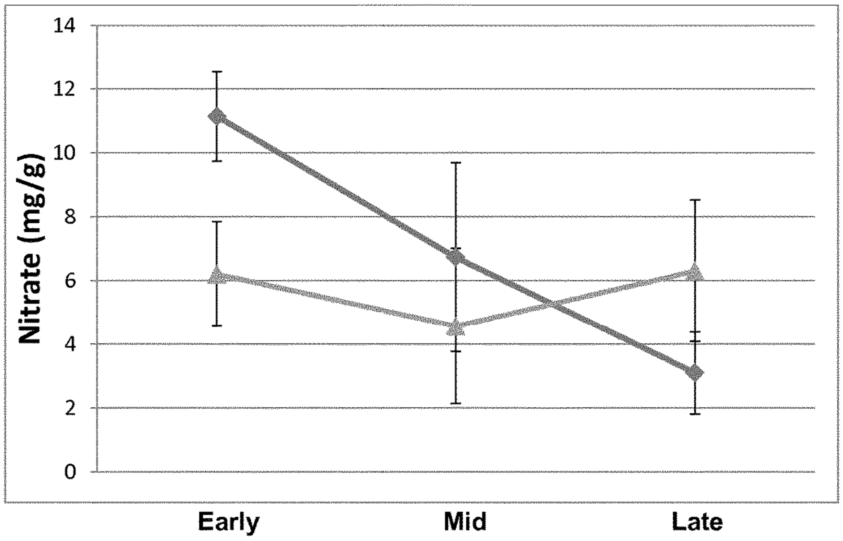
FIG. 5: Time course of nitrate and nicotine levels in green leaves of field grown CLCNt2-s G163R mutant plants. Entire leaves are harvested at mid-stalk position from field gorwn CLCNt2-s G163R homozygous plants (triangle) and out-segregant wild type (diamond) plants growing under Burley regime. Samples are harvested at three different times during the morning (early, mid and late) and freeze-dried. Powdered lamina material is analyzed for nitrate and nicotine content. N=4 to 8 individual plants. Standard deviation is indicated in the Figure. Early=8:00 am-9:00 am; Mid=9:30 am-10:30 am; Late=11:00 am-12:00 pm.
Figure 5:
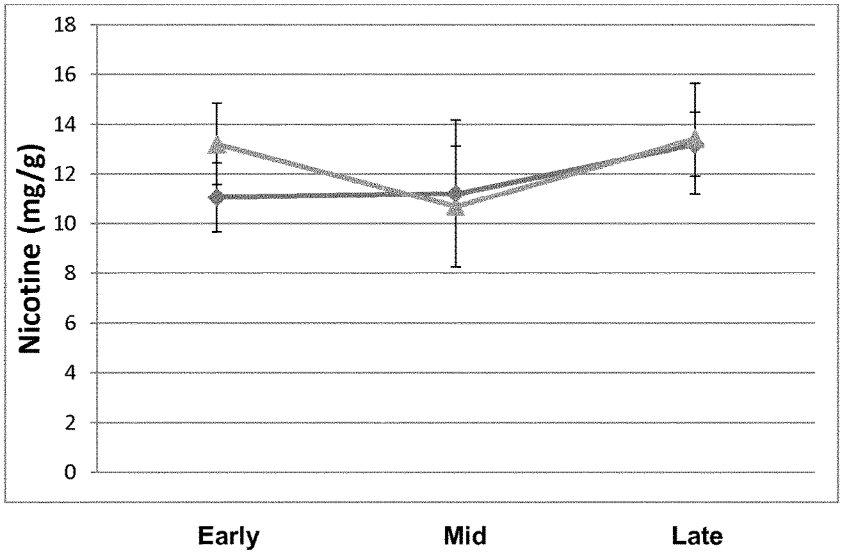

Example 8: Analysis of Field Grown CLCNt2-s G163R Homozygous Mutant Tobacco Plant The time course of nitrate and nicotine levels in green leaves of field grown CLCNt2-s G163R mutant tobacco plants is shown in FIG. 5. Entire leaves are harvested at mid-stalk position from CLCNt2-s G163R homozygous mutant tobacco plants (triangle) and out-segregant wild type (diamond) tobacco plants grow in field under Burley regime. Samples are harvested at three different times during the morning (early, mid and late) and freeze-dried. Powdered lamina material is analyzed for nitrate and nicotine content. N=4 to 8 individual plants. Standard deviation is indicated in the figures.

The results of this experiment show that the CLCNt2-s G163R homozygous mutant tobacco plant has a reduced level of nitrate in the early morning as compared to the control plant. The level of nitrate is reduced from about 11 mg/g in the control plant to about 6 mg/g in the mutant plant. The nitrate level continues to decrease in the mid-morning. The level of nitrate is reduced from about 7 mg/g in the control plant to about 4.5 mg/g in the mutant plant. By the late morning the nitrate level has increased in the mutant plant as compared to the mid-morning and reaches the nitrate level present in the early morning. For the control, the nitrate level in the control plant continues to decrease. By late morning, the level of nitrate increases to about 6 mg/g in the mutant plant and decreases to about 3 mg/g in the control plant. The level of nicotine is somewhat similar during the morning. The level of nicotine varies between about 13 mg/g and about 11 mg/g for the mutant plant and about 9 mg/g and 13 mg/g for the control plant. The nicotine result indicates that the metabolism of the mutant plant is normal. The biomass levels for the mutant and the control plant are also comparable.

Figure 6:
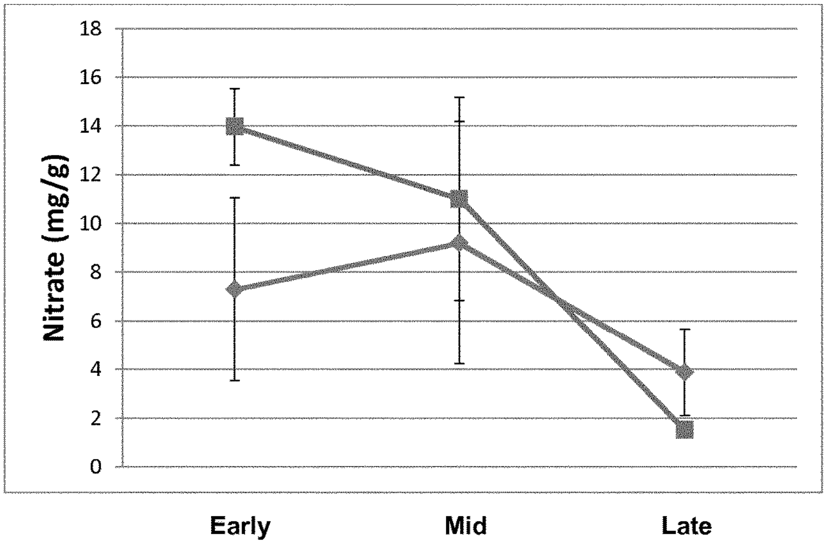
FIG. 6: Time course of nitrate and nicotine levels in green leaves of field grown NtCLCe-t P143L mutant plants. Entire leaves are harvested at mid-stalk position from field grown NtCLCe-t P143L homozygous (square) and out-segregant wild type (diamond) plants growing under Burley regime. Samples are harvested at three different times during the morning (early, mid and late) and freeze-dried. Powdered lamina material is analyzed for nitrate and nicotine content. N=4 to 8 individual plants. Standard deviation is indicated in the Figure. Early=8:00 am-9:00 am; Mid=9:30 am-10:30 am; Late=11:00 am-12:00 pm.
Figure 6:
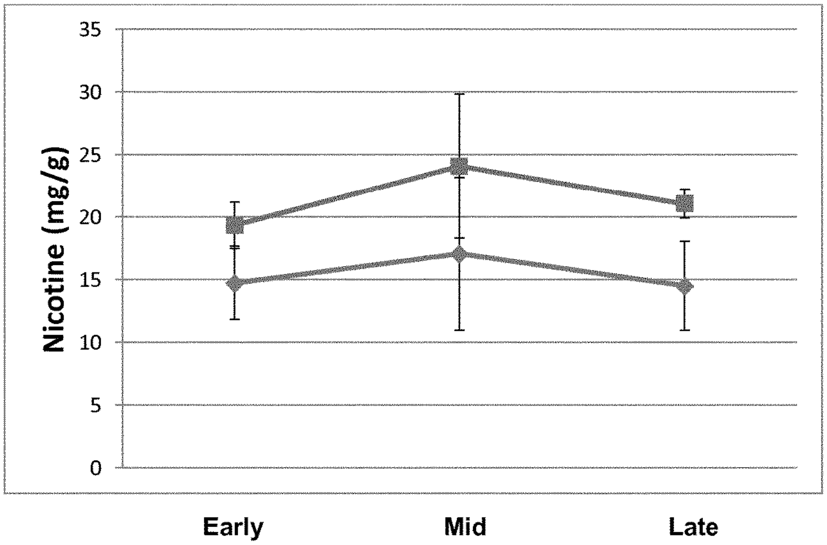

Example 9: Analysis of Field Grown NtCLCe-t P143L Homozygous Mutant Tobacco Plant The time course of nitrate and nicotine levels in green leaves of field grown NtCLCe-t P143L mutant plants is shown in FIG. 6. Entire leaves are harvested at mid-stalk position from field grown NtCLCe-t P143L homozygous (square) and out-segregant wild type (diamond) plants growing under Burley regime. Samples are harvested at three different times during the morning (early, mid and late) and freeze-dried. Powdered lamina material is analyzed for nitrate and nicotine content. N=4 to 8 individual plants. Standard deviation is indicated in the Figure.

The results of this experiment show that the NtCLCe-t P143L homozygous mutant tobacco plant has an increased level of nitrate in the early morning as compared to the control plant. The level of nitrate is increased from about 7 mg/g in the control plant to about 14 mg/g in the mutant plant. The nitrate level decreases in the mid-morning in the mutant plant and increases slightly in the control plant. The level of nitrate in the mutant plant is reduced to about 9 mg/g and the level of nitrate in the control plant increases to about 9 mg/g. By the late morning the nitrate level has continued to decrease in the mutant plant as compared to the mid-morning. For the control, the nitrate level in the control plant decreases. By late morning, the level of nitrate decreases to about 2 mg/g in the mutant plant and decreases to about 4 mg/g in the control plant. The level of nicotine is somewhat similar during the morning for each of the mutant and control plants. The level of nicotine varies between about 20 mg/g and about 24 mg/g for the mutant plant and about 15 mg/g and 17 mg/g for the control plant. The nicotine result indicates that the metabolism of the mutant plant is normal. The biomass levels for the mutant and the control plant are also comparable.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular, molecular and plant biology or related fields are intended to be within the scope of the following claims.

Sequences

SEQ ID NO: 1

(DNA sequence of CLC-Nt2 from *Nicotiana tabacum*; sequence originating from the ancestor *N. sylvestris*)

```
atggaggagccaactcgattagtagaagaagcaacgattaataacatggacggacaacagaatgaagaagaaagagatcc

agagagcaattcactgcatcagcctcttctcaagagaaacagaacactatcatccagtccatttgccttggttggagcta

aggtctcccacatcgaaagtttggattatgagtaagaacaactaataatcttatcatagatcaagtatagcttttcttta

cttgtgcattaaaagggccaacagaaattggatgtcctaattgtgtgtgtctgttttaggatcaacgagaatgatctctt

caagcatgactggagaaggagatctagagttcaagtattacagtatgtgttcttgaaatggacactggcatttttggtcg

gcctgcttacaggagttacagccaccctcatcaatcttgcaatcgaaaacatggctggttacaaacttcgagctgttgtg

aactatatcgaggatagaaggtaggtgatgttttccctatgatcaacaattcataaatgcttccagaagtcttactactg

attcttcaatacgataccactagctaatgactaagaacaagaccaaagatcacttatttgacttgaattatgttattgat

ttattcataattgagattgtaacaatggttacaggtaccttatgggatttgcatattttgcgggtgctaattttgtgctc

actttgatagctgcccttctctgcgtgtgctttgcacctactgctgcagggcctggaattcctgaaatcaaagcttatct

caacggtgtagatactcccaatatgtatggagcaaccacactttttgtcaaggtgcgtcacacacccaattttatcagtg

ctggcaattcagatagcaggcagattataacgccatcagtatagtattgagattctgtcgaaccagatgtataaatagat

agaatagcagcaaataacacattttttatcttagtcgtgatggcacctaatccgacccgctagataagccaaatacaatca

acacatatttatggaattcaatctcatttgggaagtgatctctatctttcagtaatcagataggaagtggtttaagaata

aaaagagaattttagaatcgaatgcactcatccagcgaggaagatccatcagtggtatctaatttactcttgaacttcca

gcagttcaatcctttggtaccgtcactgtaacttgtttttttcaatctttgtgactaacatggaagggaggaaaatcctg
```

-continued actttcagtgatttcctcgcttacagtgaaagtcaggatatagcttcggtgagactcagcttatatgtcttaattgaat atgctatttgttgactaacatggatttgccctatcatgaaaatgaaggaagcgccaaaaatacatatacttaaacagggg cggacccaagtggtgagaagtgggttcaactgaacccgcttcgtcaaaaaaatactgtgtatatgtataaattatggcta aagcaaggtaaattttgtatagaaataagcttatgttagttatggacttctcctgggtccgctactgtacttaaaagcac atacgaagagatacacaaactaagggcaaaggttcataatttaaggcagttgtgtccagaagaacaaattttgcttgcat gttgcagtgtgaatttaacaataaaagaattatgatcgcaaatttccacttgtaattgtactataagattctaaattttg agagatttgacatgtttgctttccctttgactgaatcgtaaaagtgaaagtgaagttcatcagaagtagattatgatact taccaacccctttttcccttaaacaatctttaatctgttcactcacagatcattggaagcattgcagcagtttctgctag cttagaccttggaaaagaagggccattggttcacattggcgcttgctttgcttccttactaggtcaaggtggtccagata attaccggctcaggtggcgttggctccgttacttcaacaacgatcgggacaggcgagatcttatcacatgtgggtcatca tcaggtgtgtgtgctgctttccgttctccagtaggtggtgtcctatttgctttagaggaagtggcaacatggtggagaag tgcactcctctggagaactttcttcagcacggcagttgtggtggtgatactgagggccttcattgaatactgcaaatctg gcaactgtggactttttggaagaggagggcttatcatgtttgatgtgagtggtgtcagtgttagctaccatgttgtggac atcatccctgttgtagtgattggaatcataggcggacttttgggaagcctctacaatcatgtcctccacaaaattctgag gctctacaatctgatcaacgagtaagcacctactcttccacattcccaactggatcatcaaacattcagttggttctcta tattttaaaggcaatgcatatccacacaaaaatgagcttacttggattagaatcatcttgagacattgatccaactgtct tgcatctttttaagtttaaatcctaattcctatccaaacatggccttcttatcacatttaactgccaaaaaaaaagggaa aactatagatgcaaaatcctgactttcaatctttgatcctttttatcttgcaggaagggaaaactacataaggttcttc tcgctctgagtgtctcccttttcacctccatttgcatgtatggacttcctttttggccaaatgcaagccttgtgatcca tcacttcccgggtcttgtcctggtactggagggacaggaaacttcaagcagttcaactgcccagacggctattacaatga tcttgctactcttctccttacaaccaacgatgatgcagtccgaaacattttctccataaacactcccggtgaattccaag ttatgtctcttattatctacttcgttctgtattgcatattgggactcatcacttttgggattgctgtgccatctggtctc ttccttccaatcatcctcatgggttcagcttatggtcgcttgcttgccattgccatgggatcttatacaaaaattgatcc agggctgtatgcggttctcggagcagcttcccttatggctggttcaatgagaatgactgtttctctttgcgtcatatttc ttgagctaacaaacaatcttctccttctgccaataacaatgctggttcttctaattgccaaaagtgtaggagactgcttc aacctaagtatttatgaaataatattggagctgaaaggtctacctttcctggatgccaacccggagccatggatgagaaa tatcactgctggtgagcttgctgatgtaaagccaccagtagttacactctgtggagttgagaaggtgggacgtatcgtag aggccttgaagaacaccacatataacggattccctgtcgtcgatgaaggagtagtgccaccggtgggtctgccagttggg gcaactgaattgcacggtcttgtcctaagaactcaccttcttttggttctcaagaaaaagtggttccttcatgaaagacg gaggacagaggagtgggaagtgagagagaaattcacctggattgatttagctgagaggggcggtaagatcgaagatgtgt tagttacaaaggatgaaatggagatgtatgtcgatttgcatcccctgactaacacaaccccttatactgtggtagaaagc ttgtcagtggctaaggcaatggtgcttttcaggcaggtggggctccgccacatgctcattgtacccaaataccaagcagc aggggtgagattataagcaaatttcagttatttttcttatgcaaatatctccctcctatcatagtataaagatgcacaga aatagtcatatggtaatataagcacttgtttagaataattataggtggcaaagttattttacattagaagtgataaaagc attacttacatcacacttgtgctccttttgtaggtatctcctgtggtgggaatcttgaccaggcaagacttgagagccca caacattttgagtgtcttccctcatctggagaagtcaaaaagcggtaaaaaggggaactga

SEQ ID NO: 2

(DNA sequence of CLC-Nt2 from *Nicotiana tabacum*; sequence originating from the ancestor *N. tomentosiformis*)

atggaggagccaactcgattagtagaagaagcaacgattaataacatggacagacaacagaatgaagaagaaagagatcc agagagcaattcactgcatcagcctctcctcaagagaaacagaacactatcatccagtccatttgccttggttggagcta aggtctcccatattgaaagtttagactatgagtaagaacaactaataatcttatctttagatcaagtatagcttttcttt -continued ataaatgggccaacagaaattggatgtcctaattttgtgtatctgctttaggatcaacgagaatgatctcttcaagcatg actggagaagaagatccagagttcaagtattacagtatgtattcttgaaatggacactggcatttttggtcgggcttctt acaggagtgacagcctcccttatcaatcttgcaatcgaaaacattgctggctacaaacttagagctgttgtgaactatat cgaggatagaaggttggtgatgttttccctatgatcagcaattcataaaggctactataattcttcaatatgattccact agctaatgactaagaacaagatcaaagatcacttatttgacttgaattatgttattgatttgttcataattgagattgta acaatggttacaggtaccttgtgggatttgcatattttgcgggtgctaattttgtgctcactttgatagctgcccttctc tgcgtgtgttttgcgcctactgctgcagggcctggaattcctgaaatcaaagcttatctcaacggtgtagatactcccaa catgtacggagcaaccacactttttgtcaaggtgcgtcacgcacccaattttatcagtgctggcaattcaggtagcaggc agattataacgccatcagtatagtattgagatcctgttgacctagatgtataaatagaaagaatagcagcaaataacaca tttttagcctacatatttatggaattcaatctcatttgggaagtgatatctatctttcagtaatcagataggaagttgtt taagaataaaaagagaattttatcgaatgcactcatccagcaaggaagatccatcagtggtatctaatctactcttgaac ttccagtagttcaatcctttggtactgtcactgtaacttgttttctcatccaccattaaaatacaatagcttccatgaga ctcagcttatatgtctcaattgaatatgctatttggtgactaacatgaatttgccctatcatgaaaataaatggaagtga caaaaatacatatacttaaaagcacatatgtagagacacgcagactaagggcaaaggttcacaattttaaggcagttgtg tccagaagaacaaatgaagaattatgatcacaaatttccacttgtaattgtactataaaatttttaattttgagagattc tgacatgtttgctttccctttgattgaatcgtaaaagtgaaagtgaagttcatcagaagtagattatgatacttaccaac tcctttttcccccctaaacaatctttaatctcttcacttacagatcattggaagcattgcagcagtttctgctagcttaga ccttggaaaagaagggccgttggttcacattggcgcttgttttgcttccttactaggtcaaggtggtccagataattacc ggctcaaatggcgctggctccgttacttcaacaacgatcgggacaggcgagatctcatcacatgtgggtcatcatcaggt gtgtgtgctgctttccgttctccagtaggtggtgtcctatttgctttagaggaagtggcaacatggtggagaagtgcact cctctggagaactttcttcagcacggcagttgtggtggtgatactgagggccttcatagaatactgcaaatctggctact gtggactttttggaagaggagggcttatcatgtttgatgtgagtggtgtcagtgttagctaccatgttgtggacatcatc cctgttgttgtgattggaatcataggcggacttttgggaagcctctacaattgtgtcctccacaaagttctgaggctcta caatctcatcaacgagtaagcaccaactcttccacattcccaactggatcatcaaacattcagttggttctctatattta aaaggcaatgcatatccacacaaaaatgagcttacttggattagaatcatcttgagacattgatccaactgccttgcatc tttttaagtttgaatcccaattcctatccaaacatggtctttttatcacatttaactgccaaaaaaagttactctataga tgtaaaatcctgactttcaaactttgatcctttttttatcttgcaggaagggaaaactacataaggttcttctcgctctga gcgtctcccttttcacctccatttgcatgtatggacttcctttttttggccaaatgcaagccttgtgattcatcacttcaa gggtcttgtcctggcactggaggtacaggaaacttcaagcagttcaactgccctgacggctattacaatgatctcgctac tcttctccttacaaccaacgatgatgcagtccgaaacattttctccataaacactcccggtgaattccatgttacgtctc ttattatctacttcgttctgtattgtatcttgggactcatcacttttgggattgctgtgccatctggtctcttccttcca atcatcctcatgggttcagcttatggtcgcttgcttgccattgccatgggatcttatacaaaaattgatccagggctgta tgccgttctgggagcagcttcccttatggctggttcaatgagaatgactgtttctctttgcgtcatatttcttgagctaa caaacaatcttctccttctgccaataacaatgctggttcttctaattgccaaaagtgtaggagactgctttaacctaagt atttatgaaataatattggaactgaaaggtctacctttcctggatgccaacccggagccatggatgagaaatatcactgc tggtgagcttgctgatgtaaagccaccagtagttacactttgtggagttgagaaggtgggacgtatcgtcgaggtcttga agaacaccacatataacggattccctgtcgtcgatgaaggagtggtgccaccggtgggtctgccagttggggcaactgaa ttgcacggtcttgtcctaagaactcaccttcttttggttctcaagaaaaagtggttccttaatgaaagacgaaggacaga ggagtgggaagtgagagagaaattcacctggattgatttagctgagaggggcggtaagatcgaagatgtggtagttacga aggatgaaatggagatgtatgtcgatttgcatcccctgactaacacaaccccttatactgtggtagaaagcttgtcagtg -continued gctaaggcaatggtgcttttcaggcaggtggggctccgccacatgctcattgtacccaaataccaagcagcaggggtgag attataagcaaatttcagttattattcttatgcaaatatctccctcctatcatagtattaagatgcacagaaatagtcat atcgtggcaaagttattttacgttagtaagtgataaaagcattacttacatcacacttgtgctccttttgtaggtatctc cggtggtgggaatcttgaccaggcaagacttgagagcccacaacattttgagtgtcttccctcatctggagaagtcaaaa agcggtaaaaaggggaactga

SEQ ID NO: 3

(DNA sequence of NtCLCe from *Nicotiana tabacum*; sequence originating from the ancestor *N. sylvestris*; one start codon)

atgaatcacggaagttgttgggtcgt catccaaattgctggccttgggctcgacgaccatctcttcctccgggacgttcctctgac ggaaacattgaaaaagaacaagatatgtgcgacagcagcaaagtcgatagtgatagtggc atccagataggatctctgctcgaggaagttatcccacaaggcaataataccgctataatc tcggcttgctttgttggcctcttcaccggtatcagtgtcgtgcttttcaacgctgcggta cgtgcgctataggtctttcatttctcttttcatgtactattcctccttacttacttggcc tcagtcaatcagccccctgcctactttaaattattgtacattttatcagaggagtgtcct atacatcaaattcacataacttagtaaaatatgctgatattctgaattttaaacttacca gcttagaacatccaggttagttcagaaacagataatctaaattggtctcatttataagtc attttgttattcaagacatacaatttggctcttgataaaagattatgcagcgcccgatga ttacctaatatttatcagcaacccatgtaatttaacaatattgtcaccatataaagaga actgaagagaatgttcaatttgtggtcatataacggatatctcccttggttaggttcatg aaatacgtgatctttgttgggatggaattccatatcgagctgcctcagaggagcccattg gagtacattggcaacgtgtaatcttagtaccagcttgtggcggtttggtagtcagctttt tgaatgccttccgagccactctggaggtttcaactgaaggaagttggacatcatctgtta aatctgtattggaaccagttttgaagacaatggccgcttgtgtcacattaggaactggga attccttaggaccagaaggccctagtgttgaaattggcacatctgttgccaagggagttg gagctctgcttgataaaggtggtcgtagaaagctgtcactcaaggctgctggatcagctg ctggaatcgcttctggtttgttccccatattattcttggttctgaaccatacatggtaca ttttccttataattacatgtagcctgttgtatgctttcctctttcccgggaagcctttttt gtaaatacaagtgtgtttgcactcaaaccaataaactgtaaaaaaggtgaactccttaag caagcaaaagcattagaaatgtaaactagacatatttctcagattgagagtctgagagat tagaacacgagtgtttccattagagagagaaaagagacttctagatatttctattatctc tgtaagagtgaatccgttcctatacaaaaaataggccttcattaaatacaagcttgggct gggtactactgggccaaagtaaaaaataaaaagaatcacccactatcaaatgggcctagt ctaacaaccccccttcaagctggagggtgacacaacccctagcttgcgaatatgaaaatga tgagcaggcccaagtaacactttggtaagaacatcaaccacttgagaagcactggagttg tgaaatagactgatcaggccattcccaagcttgccacaaacaaaatgacagtccagctta atgtgtttagtgcgttcatggaaaacttggtttttttgcaatgtggacttcctgattatca caaaataaaggaacaggtaaagaaggagaaactccaatatcagacaataatttggtgagc caagacacctctgcaacagccttactcatggacctatactcagcttcaattgatgatagt gagacaacaggttgcttctttgatttccagctcaccaagctgcccccccaagaaaaataca aaaaccagtgacagacctgcggctgtctgggcaagaagcccaatcactgcacaataaagc tgcaaagacaagtctggagagttattgcggaagattccaaagtcaaaagtgcccttgagg -continued

```
tatcttagcaagtgcagggcagcctgcatgttaggaacacagggagactgcataaactga
ctcagatgctgaacaacaaaactaaggtcaggccttgtgcgtatcaaaaagtttagcttg
tgcattagactcctgtactcttcaggcctgggcaaaggagtgccaatcttagcttttaac
ttcacattcaattcaagggggcaagtgacagaagagcaattcgaggaatgaaaatcagcc
agcaaatcatgaatgaactttttctgatgaagaagaaccccagaatcagtgtataaaacc
tcaatgctaaggaagtaattaagagagcccatgtccttaatcttgaactggtcactgaga
aaggacttcaaagcagccaattcagctagatcacacctagtcaatatgatatcattcaca
tagacaaccaagatgaccaaggaatccctagaacccttggtaaaaatagagaaatcattc
aaggaacgagagaagccattagagcacaaggcttgagataatttagcatactattgtctt
gaagccagtcttaaaccataaagagacttctggagtttgcatactaaaggagcagaagaa
gagtgaggaacagttaggcccggtggcagcttcatgaatacctcctcatcaaggtcccca
tgtaagaagacattattcacatctagttgaaagaggggccagtgttgtttaacagctaca
acaataagagttttgacaatagacatattgaccacaggagaaaaagtttcattaaagtca
ataccctcaacttgagtgacctagctttatatctctcaatactttcattagccctatatt
taaccttgtatacccacttacaactagtaggtttcttgccaggaggcaattcaacaatgt
cccaagttctgttggcatccaaggcctcaaattcacatctcatggctgcctgccattcag
gaacagctgcaacctgagagtaagaataaggctcaggaacatgaagttgactaagagaag
gagcattagaaatagatctggagggaggaggagaagaagtggaggtgcagacataactct
tgagatagttggttggattgtgtggcacggaagatcttctcaaagcaggaggaggtacaa
gagagttagaataatgagaaggagaagagatggaagtgggaacagagaagattgagaagc
agtagaaggagaaagtgaaggagatgaaggagaggaagaagacggaaaggaacattcatc
aaaacaagcagaaaagggaaaggggaagacttgaggtactacatgagaggattgaaagaa
aggaaaaatggtgttcataaaaaatgacatcttttgatacaaaacaggtgttattctgaa
gattaaggcgcttgtagcccttttggcaaaagggtagccaatgaaaacacaaggaaggg
acctaggatgaaatttgttttgtgaggggtggtgacagttgagtaacagaggcacccaaa
agctctaaggtggtgataagtagggtggaagaatgaagcaattcatagggacttttgtga
ttaagaagaggaaaaggaaatctgttaattaaatatgtggcagttaaaaagcagtcaccc
caaaatttaagtggtagatgagactgaaacataagtgacctagcagtctctagtaaattt
ctgtgttctctttctacaataccattttattggggggtgtgaggacaggaggtttggtgt
actatccctttttctgaaaagaaaaggcaaccagaagaactagatcccagttccaaagca
ttatcactcctaacagtttgaactttagattggaattgggtttcaaccatagcaatgaaa
accttgagcaaatcaaaggcattgcggcacccattaaatgtgtccaagtagccctagagt
agtcatctacaatggttaaaaaatacctagaaccattataggtaggagtagaatagggtc
accaagtatttatgtgtattagctgaaaaggctgggtggagtgaatagaactatcaggga
aggacaacctggtctgcctcgctaaaggacaaaccggactagtgaatgaccgtttggaag
acagtttgcaattaagaccagaaatgcatttcattttatagaagggaatatggccaagtt
tgtaatgccaaacaacatcatctttattcacattatgcaaagcagtactagtatttacaa
ttggagtatcatcaggtacagaaataggagcagaaactgaattaagcaaacaagaaataa
ggaaattagaaagaggtaaaggagatgatgttggaggcctggcattctgaaatagtttgt
agagtccattgtccaatctaccaagaaccactggcttcctcactgaagggccctgtaggg
tacaagtagccttggtaaattgtacaatatcatcatcatgggaaagtaatttgtacacaa
```

-continued

```
agatgagattatattgaaaactaggaatatagagcacattataaagaatcaagtcaggga
acaaggctaaggaaccaatattagtgaccttaaccttatacccattaggaagggagacaa
ggtatggtacaggaagtgtttgaacattaaaaaaacaaatgtttaagggaggtcatgtgg
tcagatgcccagggtctattactcaaactacactatctatcatagtcagcataaatgcac
cataagacaacccttgtgaggtaataactcaccagcaaagttggtagaagcaagatagtt
ggttgaagaagtagatgatgctgatgaagacagttgagattgttgaagtaacattagctg
agaatattggttcttggtaagaccaggaactggataggactgttcaggagcagaggtacc
ttcaggaccagctgacattgcagaaccaccagaggtatccacctcagcatgggcaacaga
ccttctgggaggaagagatctatttgacttgaaatttggaggaaagccattgagcttata
gcacttatcaatgctatgtccgggtttcttacaatagtagacatgtgaagctcaaaagat
cccttagaggtagtaccggacctttgaggttcaaaatttattttaggagagggaggaggc
ctggatacaccaacactgaaagaagcagaatttgaggcatattgagttctagcaaaaatt
tgtctttgcttctcatcagatagcaaaatcccatatacattaccaatggaaggtaagggc
ttcatcatgatgatgttgcttcttgtttggacataagtatcattcagtcccataaagaac
tggtagaccttttgttccctgtcttcagcagatttacccccacaagtacacattcaaact
ctcccggcagacaaagatgcaatatcatcccatagtcgtttaattttgttgaaatatgat
gctatgtccatggacccttgggaaatatgagccagttccttctttagctcaaagatccta
gtacctctcttctaactcagtccaaatattcttagcaaactcagagtattcaacactctt
ggatatttccttgtacatagagttagtcaaccaagagaccacaaggtcattgcaacgtta
ccactgtctggctagaggagaaccttcaggaggtctgtgagaagtaccattaatgaaatc
tagcttgttacgaatagacaaggcaactaggacattacgtctccaattgccataacagct
tccatcaaaaggaccggaaactaaggaagttcccagcacgtctgatggatggacatataa
ggggcgacagggatgggtataatcatcttcatggaaaattaggcgtaagggagtagaaga
agtcgcatcagcactggtgttattatcatttgccatttttttcaacagattgtcaatcaa
ccaacacaatacagatacacatatatagattgtgagaaagcacgagagaaaaatctatat
tattgatattctatttaattataatacaatgagccctatttatacaatacatatcatact
cctattctatgtgggactaggactaattcatattatgtacataactatctaacactcccc
ctcaagccggtgcatacaaatcatatgtaccgaacttgttacatatgtaactaatacaag
gaccagtaaggaacttggtgaaaatatctgcaaactgatcatttgacttcacaaactttg
tagcaatatctcatgagagtatcttttctctgacgaaatgacaattaatctcaatgtgtt
tagttctctcatgaaacaccggatttgatgctatatgaatggcagcttggttatcacaca
tcagttccatcttgctgacctcaccaaatttcaactaattaagtaaatgtttgatccaaa
ctagctcacaagttgtcacagccattgctcgatattctgcttctgcactagaccgagcaa
ccacattttgtttcttgctcttccaagacacctaattacctcctactaaaacacaatatc
cagacgtagaacatctgtcaaaaggtgatcctgcctagccagcatttgagtacccaacaa
tttgctcatggcctcgatcttcaaacaataatctgttacctggagctgattttatatatc
gaagaatgcagacaactgcatcccaatgactatcacaaggagaatccaagaactgactta
ccacactcactggaaaggaaatatcaggtctaatcactgtgaggtaatttaatttaccaa
ccagccgcctatatctagcaggatcgctaagcggctccccctgtcctggtagaagtttag
aattccgatccataggagtgtcaataggtctacaacgtgtcattcctgtctcctcaagaa
```

-continued

```
tgtctaaggcatacttcctttgtgagataacaatacatgtgctagactaagcgacctcaa

tacctagaaaatactttaatctgcccagatccttagtctgaaagtgctgaaagagatgtt

gtttcaacttagtaataccatcttgatcattgccggtaataacaatattatcaacataaa

ccaccagataaatactaagatttgaagaagaatgccgataaaacacagagtgatcagctt

cactacgagtcatgccgaactcttgaataactgtgctgaacttaccaaaccaggctcgag

gagactgttttagaccatagagggaccgacgcaaccgacatacaaggccactagactccc

cctgagcaacaaaaccaggtggttgctccatataaacttcacctcaaggtcaccacgaag

aaaagcattcttaatgtccaactgatagagaggccaatggagaacaacaaccatggatag

aaaaaggcggactgatgctattttagccacaggagagaaagtatcactgtaatcaagccc

aaatatctgagtataccctttggcaacaagacgagccttaagtcgatcaacctggccatc

tggaccaactttgactgcatacacccaacgacaaccaacaataaatttacccgaaggaag

aggaacaaactcccaagtaccactcgtatgtaaagcagacatctcgtcaatcatagcctg

tcaccaccctagatgagacagtgcttcacctggatggaaatagaggacaaagatgataca

aatgcacaatagggtgatgacagacgatggtaacttaaaccgacataatggggattagca

tttagtgtagaccgttcacctttccggagtgcaatcaattgactaagaggagacaagtcc

gcagtattagcaggatcaggtgcaggacgtgaatcagctgggcctgatgctgggcgcgga

cgacgatgataagttaggagtggtagagctgtagaaggttgaactggactaggcagtgga

actgaagctatatgtggtggaactggagctataggtggtggagctggagctgtaggtgaa

gatgaatgggagatagtgactgaatctccaaaagatggaactggtagcacctcagatata

tctaagtgattacctggactggtgaagtatgattgggtttcaaagaaggtaacatcagca

gacataaggtaccacctgaggtcaggagaatagcatcgatatcccttttgtgttctcgag

taacccaaaaatacgcacttaagagcacgaggagctaatttatcttttcttggagtaagg

ttatgaacaaaacacgtgctcccaaaggcacggggtggaagagagaacaaaggtaagtgg

ggaaacaagacagagaatggaacttgattctggatagctgaagatggcatacgattaata

agatagcaagatgtaagaactgcatccccccaaaaacgcaacggaacgtgagattgtatg

agtaaggtacgagcagtttcaataagatgtctattctttctttcagctacccgattttgt

tgggatgtgtatggacaagatgttttatgaataatcccatgagagttcataaactgttga

aatgggaaagacaaatactctaaggcattatcactacgaaatatgcggatagaaacccca

aattgattttgaatttcagcgtggaaggtctggaaagtagaaaacaactcagatcgattt

tttatcaaaaatatccaagtgcacctgtaataatcatcaatgaaactgacaaagtagcgg

aatcccaaggtagaactgacctgactaggaccccaaacatctgaatggactaaagtaaaa

ggtgactgactctgctcgattatcaagacggcgagggaaatgggagcacgtatgcttacc

gagctgacatgactcacactctagagtggacaagtgagataaaccagataccatttttttg

aagttttgacaaactgggatgtcccaaccgtttatgtaatagatctggtgaatcagtaac

aggacaagttgttgaagaaagacaagatgtaagtccatgtgattttgcaagaataaggta

gtaaaatccatttaattcacgcccggtaccaatgatccgccctgtactgcgttcctgtat

aaaaacaaggtcatcaagaaataaaacagagcatttaagtgatttggctaagcgactaac

ggctatgagattaaaaagactaacgagaacataaagaactgaatctaaaggtaaggaagg

aagtggacttacttggcttattccagttgccatggtttgagactcgttatccattgtgac

tgttgggagtgattgagaatatgaaatagtaatgaaaagagatttgttaccaaaaatatg

atcagatgcacctgaatcaatgacccaagactcagaggttgaagattgggagacacaagt
```

-continued cacactactatctgtttgagcaacggaagctatccctgaagatgtttgtttacatgtttt
gaactgaaggaactcaatataatccggtagagaaaccatccaactcttcgtagtattgga
ttccattttgctacaaccaatttctcaaattcttgattacaacttgtgtggttaaccttg
gaatgccaaatcagaacacccctttttttttttggaaaacattgttcactcgctggaaa
ataaaaaaggttgccggaatttgatgaaacttgaatagaccgactcggaataatgtccta
agaaggctgtccaaaaggagttttgtcagaaactgaccagaaggaggtccacgcaccggc
gcgtggacagatctcgccgaaaaaaaaatcactttggttggcgcgtgatggcgcgtggg
tggggtttttccggtcgggttttgtggggtttgctcccccggagatggagaacactgtgg
tggtgttggtttatgcacaacactggtaaaaagtggttttgatgcgaacagctactcagg
tcaccaaaaaattgcacggtgacgactgatttcttcccggatgtcgttggaatgacgcac
aacgataattatctcaccaatgctctgataccatgtgagaaagtacgggagaaaaatcta
tattattgatattctatttaattataatacaatgagccctatttataagactaggattaa
ttcatattatgtacataactatctaacatagatcaaataggcatgcaattcacaataatg
gtgaataaaatgatacgaagttacccagctcttttcgcgatcgaaaaggagaaaatagcc
ttcaatcacaaacgagaaagaagaatctccggcttgacagtagacgacttcgaaacccta
gctcgagatgaaaaccacaaaatccccaaatcacattaccaaccaaacaatttgagatca
caaatgttgaatatgtgagaatccgactaagaaatcaacaaaaaatcaatagaaatggtt
gaagaataccgacttgaaccctaaatgagtcagacatcacctagaatgaaatacaccttc
gaaattgacgaaaacaggaccggttgaaagcggagaacgtgccatagaaggatctacgct
ctgataccatgtaaacttgacatacttctcagattgagagtctgagagattagaaaacga
gtgtttccattagaaagagagaaaagagacttctagatatttcgattatctgtgtaaaaa
tgaatccgttcctatacaaaaattaggccttcattaaatacaagattcggccgggtatta
ctggcccaaagtaaaatataaaaagaatcacccactatcaaatgggcctagtctaacaag
aaaaccaacaaatagtccccccccccccccccaaaagataccactgaaatgacaccgggt
gcccaaaaataaagcagcttacttcttgactttgagaggaactgcaatccttatcggttt
gagaggaactgcaatcagctataagtagcttattaatttccagtgcctgcattctgccaa
gtactatgatatatttctgaagctttgtttccccagttcctttttcagacgtttgctgtc
aataaagttgagccagccaacttggctcccacaagctactaattttgtccaagcttactc
tatgggagaagttaaatttcccaaattccttgagcggaaaatgaaaaatggactcaaagt
gtcatattatgcaactatctaaagaaaaatactcaattgaagtttagataagaaaagtga
atgtatattgatgtagtctccgttaggtgagaagcgtatcacttacccagcaacatatgg
acctaacattttactagtgaagttttcacattgtatcaaaagctcaacaaacggaaaggt
gactaatcctaaaatgttatttcacatatatgggcacacggtttgtcaaccttctcatac
gtgcattatttgttctctatctttctatttcatccgatataaccaatcgttattgtaaat
tctataatgcctgtggttacttttgtctttagtgacaaatgacatttaggataaccatgt
agttattgacttatttcacttgaggtctcttccaattatgtagtagtagagtgttgagat
atggatatgttaccttctaaaaaaaagagtgtagagatgcggatagtttgctagctggct
tttgtctcccttcaagttgaattagcaaaagcttgtctcataagttggatagctagacaa
gaaaaactccaaattactttatgtagagtattcttaagcttgagtcgcgagttggaaact
ggaattatgtaaaaaaacctggaattatttggttgagcctgctttttagttttgtcaata -continued tttccagtatctaacccaacatgtttagagtgattcccggagagcctcagtacaaggcat ttgcagagtctttatgagagtccaggaaggggcacacattctgtagaggtatagtcttgt ccttattttcagggttgaactagttctttagaagttacctaggcttcctaatttccaaat ttctgccaggtcctttttttggtgaagtacttgaagtttaataaatcaaattttaatttct aacatatcctgagaaatttattcacaaattcaactggtgacttctgatgcagaaacataa gcaactgcttatgggttcatatgttcctgcaattttattgttgacatggattggcttcat atggttttgttcctgcaattttatcgctgacactaatcctttcatatggttttatgtgga gtgttaaatagaggttaagagacaagaagaggctgaaaaaggtgggcagttcatttgtta gtagactactctatttactaagagatatgatgtcccatacattactcgaattggctccga atccagattccacttctttgccgagtttccttattgtacatagttcgactcgtcaaggga aattcacttcctttgactgaataatgctagtttgagtagtaccttacattaaatggacca tttagttctatctacttgatagaatagactggtcatcaactagttgcaaatacaatgaca actttgccatgtttgcagagtcacctgatgaagaagtacctcaattagtagaacatttct tgaatgttctacagtattctctatgcctacatgaccacatcacttttccttttgcgttgt gagaacttgaacttggtgagcggggggttccccaggaatggcatcttgatggcagatgacc attctgtccttgtcttagctaatgcttcttgcattgcctcactagatttattatacctttt aaaaaatgtttgccattgttctgccataatagaaggatgtacccagctggtgcttcaaaa ctaatgaaatgctttacaattgtcgagtcctaaaggatgatttgtggaatcagatctcaa acaattctttttgaggaagaaaaataccaaaggtttttttctgtttgttggaagattaaaa atcctttaaatggtaaagatttatgaacttaattcagcgtttttgtggccattgctggaa aagagaaaaaacaatggcacttcttcgagtttgcttatccaaaaaaaagaagaagagaat gtcacgtaatgcaatttcatcttaggaaactttgcaggagaaaagcaagagtgataaaac agaactatttgtttttttaacaagttgttgtgacctatttcttgtcattcttatttgct aataagctaatgtactatagttcctgtactatggtttgttttgacttaatacggggatgt tcaatgagcattttcttgtttttctgctttcagcatctgctgccttacaggaattcatt ttctggaaatttacttcttgttctgctaacattttcctgttatatcttgtcagtcatttt ctctccatggttatactgtttgtgtcactttaaactctccttgttttctactttaaagga tttaatgctgctgtcgggggctgtttctttgctgtggaatctgtgttatggccatcacct gcagagtcctccttgtccttaacaaatacgacttcaatggttattctcagtgctgttata gcttctgtagtctcagaaattggtcttggctctgaacctgcatttgcggtcccaggatat gattttcgtacacctactggtaattttggacttctttctcgagtttgattcttaaataca attgtacccgtcacttacagcaacaactacatttcaacagctagttggggttggctacac agatcatcactatccatttcaattcatttagtcccatttctttcgaatattgagtacttt gggattctataatatcaaggttctttatatttctactttgacgtacaaatctctaaata gattaaagaagactcctagagacactggcctaatgcaaatgtaccaccatgaataaactt taatctgaaatagctggtatcttatataaggacccttagctttaattgtgttctatattg atcttttgggacaacttccttccaatattatgtcttacttatacagttatacttatcctt aagccttactctttagagtggttatccctaattcaagcttttgttggcaccatagctagt ttggttctaagtaaaaagttactctttagagtggtaactttttgtcaattttcttagtga aaatataacctctgtgacaaatctaccaagtataaatccaatttggttctatgtcatcct tgtagtttatccaagtcaatgctccatcactcttacaaaggttcatcgtatgactaatct -continued tttttggagaaaggtaacagtttgtattgataataagatcagcgccaggttggtcattag tgctaatagctgtacgtacaactccaaaagagcaaaagacaagcacctgatgtaaggtaa attacaagctgcctataaaatctatcaggtgtcctatctcactaaacatttcttgtttac accaaaaaaataaaacaaggaaagacaatccatcttaatcttctgaatggagtttctttt tccttcaaaacatctggagttccttccgttccatgcaatccaccatatacaagctgggat gattttccatttgtctttatccatttcttctaccaattcccttccaattgattagaagtt ccaatgtggttctagatatgacccaattaactcccaacagataaaagaagatgtgccacg gatttgtagtgattctgcaatgtaggaacaagtgagcattactttctacttcctgtccac aaagaaaacatcttgagcaaatctggaaacctcttctttgtaagttatcatgtgttaaac atgccttttttcaccaccaaccagacaaaacatgatactttgggaggagttttaaccctcc aaatgtgtttccaaggccacacctcagttgttgaaacattaggatgtagagtccagtatg ctcttttactgaaaatgcaccttttctattcagcttttaaactactttatctatggtctg tgatgtacccttgaaaggttcaagagtttggaggaagatagaaactctgtttatctccca atcatccaaagatcttctaaagttccagctccatccttgtgagctccagactgacttacc aatgcttggctttgaagacttagagagaataagtcaggaaaatatctttcaaccttcctt gccctatccggtgatcttcccaaaaagatgtctgcaacccattgccaatattgatcttga tattgctactgaaagatttcttttggtggcaggattactctcattaacaatgtacttgac aatctccatacatactaatgtctctttaccctcttgccattaaggttgtaaagagacttg tcaaattaagaaaaggtttcctatggaactgtttcaaggaaggaacctcctttcctttgg tcaagtggagttaagtcatataatctaggaagtggaggcttgggtatgaaatagctgcaa atacagaaaaggagcatcttatttaaatgatcacggaaatgtgcccaaaactttaaatat ctgcacagcatatggttgtagcaaaatttgaatcttcctgtcaatggtgctcatgtccag tgaatacccctgatggtgaaagtgtcctgaagggaagcaggaacttattggaagaattgg catctaacactcagcttttcggtgggtcatagcccattgaaaattgagtgcccagattta tatagttttgctctaaactgacgatgcagttgcacaacatacgacaaactaaggtgggac atcatcttcttcggaaggaattttgaggattaagagatagagtggttgattcagttgcaa atgaagcttcaagggttcaatatcatccaggagacaccggattctgatagataaaacaac agaaagatgagcactactttgttaggcttgttacaagttgctatcgtctttcttatctcg gtacacaatttagatttgggaacttagttggaaaagcagagtggttgtttttgtgaatag catcagacaaagcttctgagctggtacgacagaaaactcaacagggagaatagaagactg tggttcacaatttctgcatgcatcttgtaggttatttggtgggtaaattatttaatgttt tgaagggaaggtagaacatgttcataggcttagattcaaatgtttgtatttttttggctc tttggtgagagatgctgaacgtaaatgacataggcagctgactataatttctcagctcct tgctttttaaattgacaggcactgatatgtacatgtgaacatccaacacttttgtggtgc cgttccgatgaataaagaacattaatcacttactgatcaggagtaatagtttaggagttc tagaattttttgtacataaaatgaaccaaaaagaagatcggaatgagaacatgtttctttt tttgtttttttctttttcgtgaaaacttcaataacacttctgatagaatagctaggtccat ttgaattcctttggagacccttacacaaccaatgaatgacaagtatagcatttctaactc cctcccacacgtataacccagattttagggtttagatgtggatctgatttgaccttattg ccttttttttgtttttgttctttttgaagtagagagtgaggaggctcaacaattaattcgg -continued ctcaacgggctaatgattggacttacatgctacgacaatgttaggagagagagagagaga gagaagcccagagcagttacatgagttaagaaagagaagtccaaagcgatagaatatgaa gagagaaagcggttgtgctaacaggctccctgaagtttggctctgagcatccaactcaaa accttaaggcaatgagtagagtagcccaggaccatttaaattgctgttgaaaaccttaca caaccaataagggaacaagtgtaacattctcttacaaccctaccgtcttataagtcagtg ctctaatttagcataaaatcaaagtgaggcgatctacaatgaaatgaagtaaataactga taaatacaaagaatgttaattctccaatatagcctgaatgttcccagaacaaaataaact agtctcaggatttatcattaacatgatgttcctcttattttgagtgattaggaaggttaa tcaaggtataaattctttctaatttgtatcgtctagaattatttatctaacaaattttca gattaccggttcaaaagaggaatatatttgcatacaacgttaccataccttacaaaagg gagatgaacatttttttattttattattgtcctttttttcaattagggattatgcagtct tcctccacgtgatattactcttagaatcacgtttttgtcattgctattacttaatgtggt aagtacaaatgtgttttgaactctttttggtatgtaatattgagttaatttttggtttcc atttcagagctgccgctttatcttctgctgggcatcttttgtggcttagtttcagtggca ttatcaagttgtacatcatttatgctgcaaatagtggaaaatattcaaacgaccagcggc atgccaaaagcagcttttcctgtcctgggtggtcttctggttgggctggtagctttagca tatcctgaaatcctttaccagggttttgagaatgttaatatttgctagaatctcgccca ctagtgaaaggcctctccgctgatctgttgctccagcttgtagctgtcaaaatagtaaca acttcattatgtcgagcctctggattggttggaggctactatgcaccatctctattcatc ggtgctgctactggaactgcatatgggaaaattgttagctacattatctctcatgctgat ccaatctttcatctttccatcttggaagttgcatccccacaagcatatggcctggtatga atttgtcttttgttagaagtagcattacatatctggataagtgagtttttttattattgaa aagtaataacaggagagcaagagaatatagcacccaaatctacttctttcctctcttcta ttcttctgaaattcaaggtcctttaactcctccacggcctgtctagttattgatcctgta gacttaattcacataggtttaggacattcaagtttatccaaacttcgtgaaaaggtttct aattttttacattacagtatgagtcgtgtctacttgagaaacatatcactccatgtttc tatagagtctgttttctcctcagtttattttgatatatggggtcctattaagacagttca accttggattttcattatttttgttgtttcattgataattattcaagatgtacttggatt ttcttaacaagagatagttctcagttgtttttttgtgttcctaagtttttgtgctgcaata caaaattagtttgatgtctctatttgcatttttcccaatgataatgccttagaatatttt cttctcggtttcagtagcttatgatttctttagaaactctctatcagaaatctcaactga gatagatgagaggaagaataagcatatcattgagacggctcgtacccttctcattcagtc ccctgtcaagcttagtttcttgggcgatgcagtttcacgtcctttgattagattaattgg atgcctcatctgctatccaaaatcagattcaactttcgatattgtttcctcgcttacctt tatactctctttccctcgagtctttgggagcacatgttttgttcaataacatagctcctg gaaagtgaccagcgcaaccgacaagcaaggccttcttaatatagaaggagggcatatgct attctagccacgagggagaaagtaatattgtaatcaaacccaaatatctgagtataacct ttggcaatggcgatcaatttgattatatggaccaactttgcctacatatacccaccgata gatttacggggaggtagagaaataagctcccaagtaccactaatatgtaaagcagacatc tctttgatcatagcctgtccttgtggacatagggatagaaattgaggactaagatgacac aaaagcataatgctgtgatgataaacgatgataactcaaatcaatatgatggggatggga -continued

```
attaagagtggattgaatatctttgcggaatgtgattggtagactaggaggagacaagtc
cgcaataggtaaaagatccagtacatggaatgaatcttctggacatgatgttggactgac
gtcaatgataagtcaagagtggtggagttgcagaacatggaactggagctgtaggtgaca
taatcgaagttgtagggggtggagctatagaggaaggtgaaggagagatagtgactgaat
ctccaaaatatgaaaccggtaatacctcaaaaaatgtctaagagatcatttggacctatg
aagtatggttgcgttttaaagaaggtaacatcagcagacataaggtaccgcggaaagtca
ggtgaataacattgatatccttgttgcgtcctcgagtaacttagaaatacatatttgaga
gcacggggagctaacttatcttttctggagtaaggttataaaaaaacacatgctcccata
gacacgaggtggaagagagaaaggtgagtggggaaacaagacagagtatgaaacttgatt
cttgatagttgaagatggcatacaattaataagacaataggatgtgagaactgtatcccc
acgtaaacacaacagaacatgagattgtacgagttgggtatgagcagtctcaatgagata
cctattcttcctttcagctatcccattttattgagatgtgtatggacaaaatatttgatg
tatgatcctatgagagttcatgaactgctgaaatggagaagacaaatactctggggcatt
atcactatgaaatgtgcggttagaaaccccaaattgattttggatttcagagtgaaaggt
ctgaaaaatagagaccaactcagattgatttttcatgagaaatatccaagtggacttgga
ataatcatcaatgaaactgacaaagtagcagaattccaaggtagaactaactcgacaagg
acctcaaacatctgaatggactaaagtgaaaggtgactctattcgattatcaagacaccg
aggaaaatgagagcgagtatgccttctgagcggatatgactgacgctctagagtggacaa
gtgagacaaaccaggtaccattttctgaagttctgataaattgggatgtcctaaccgttt
atgtaataaatctggtggatcagtaaaaggacaagctgtaaggggacaaaaataccaaat
atttccagaagatggcaaactacaacagaagaagcaactacattaacaggctcaggatat
gtgatgaaatgaggacaaagagttgatcaagaaggagattctggaattctaccagaactt
atatagtgaaaatgaaccgtggaggcccagtgcaaattttgaaggcatctcctcactaag
catagaagagaagaactagttggaagctccatttgaagaaatagaggtgcttgaagcttt
gaaatcatgtgcccctgataaagcaccaggtccagacggcttcaccatggctttctttca
gaaaaattgggatactcttaaaatggacatcatggccgcacttaatcactttcaccagag
ctgtcacatggttagggcttgcaatgccaccttcatcgccttaattccaaagaaaaaggg
tgctatggagctcagagactacagatctattgacaaactagtctcgggggaacaaaatgc
tttcatcaagaacaggcacatcactgatgcttccttgattgccagtgaagtgctggattg
gagaatgaaaagtggaaaaccaggcgtgttgtgcaaactggacattgaaaaggcttttga
tcaattaagatggtcttacctcatgagtatcttgaggcagatggctttggggagaaatgg
ataagatggataaactattgcatttcaactgtcaagaactctgttttggtgaatagtggc
ccgaccggtttttctcctgccaaaagggcctaaggcaggggatctcctctcccctttcc
tattcattttggcgatggaaggactcactaaaatgttggagaaggctaagcaactacaat
ggatacaaggctttcaggtgggaaggaatcctgccagctcagttacagtatcccatctac
tctttgcggatgatactcttatttttgtggtactgagagatcacaagcacgaaatctca
acctgacgctgatgatcttcgaggcactatcaggactccacaacaatatgataaagagca
tcatataccctgtgaatgcagtccccaacatacaggagctagcagacatcctatgctgca
aaacagatactttcccaacatatcttggacttcccttgggagctaaattcaaatcaaaag
aagtttggaatggagtcctagagaagtttgaaaagaggcttgcgacttggcgaatgcaat
```

-continued acctctccatcggtggcaagttaactttaatcaatagtgtactggacagtcttcctacat accacatgtctttgttcccaattccaatctcagtcctaaagcagatggacaaactcagaa ggaagttcttacgggaaggatgcagcaaaacacacaaatttccactagtgaaatgactca aggtaactcaaccaaaattcaaaggaggcttgagcatcagggatctacaagcacacaaca aagctatgctcttaaaatggctctggagatatggacaggaggaatctaggctatggaagg acatcatagttgctaaatatggagcacacaatcactggtgttccaagaaaacaaacactc cttatggagttggtctgtggaagaacatcagcaaccactgggatgaattcttccaaaatg taactttcaaagttgggaatggaactcgtattaagttttggaaggatagatggctcggaa atacacctttgaaagacatgtttcccggtatgtatcagattgccttgaccaaagactcca ctgttgctcaaaatagagacaatggcacttggtgcccattttcagaagaaatttgcagga ttgggaggtcaacagcctactcacaatgttaagctccctagaaggtcataatatcgaaga tcaacagcctgacaaacttatttggggaaattctgagagaggcaagtacacagtcaaaga atgatacattcacctctgtgaccagaatccaataatagataactagccatggaaacacat ctggagaactgaagtgcctaccaaggtgacttgcttcacatggttgactctaaatggggc atgtctcactcaagacaacttaatcaagaggaatatcatactagttaatagatgctacat gtgccaacaacagtcagaaagtgtaaaccacctattcctccactgctcagttgcaaaaga catttggaacttcttctacactacctttggtctgaaatgggttatgccacaatcaacaaa gcaagcttttgaaagttggtatttttggagagttgacaaatccatcaaaaaaatctggaa aacggtgccggctgcatttttttggtgtatttggaaagaaaggaaccgaagatgttttga tgacatattaactccactctactccctcaaggctgcgtgtttagttaacttatttagttt tgtggattttattagctccctgatagtagcataggcttttgtaaatggagctaattatcc tatctcttttgtactctttgcatcttcttgatgccttttaatgaatctaatttacttcat aaaaaataaaaggacaagttgttgaaggaggaaaagatgtgagtccatgtgatttagcaa ggataaggtactaaagtccatttgattcacgcccggtaccaatgatccatcccgcattgc attcctgtattaaaacagagtcatcaagaaataaaatagagcaaataagtgattggccaa acgactagtggatatgagattaaaaggactatcgggaacataaagaactgaattcaaagg taaggaaggaagtggactagcttaacctattccagttgccatggtttgagaatagttggc cattgtgactgttggaagtgattgagagtaagaaatagtagtgaaaagagatttgttacc agaaatataatcagatgcaactgaatcaataacctaagagtcggaaaaagaaacacaagt catgttattacctgtttgaacaatagaagttatctccgaagaggattatttacatgtttt gtactgatggaactcaatataagccgataaagaaaccatccggatattcaaagtattgga tcaacagcttataagccaaaagcatccgatacgagtgccattataatggatcaagagaga tcaaacaacaaatcaccaaatatcataaacaaccaagaatctcgctggaatgtgaacaaa gattgaaaaacaacaatgtagctcgccaaaaatgtgcaaagtgatcgaaaaatattgaat cgtgagtggagagaaataggagcttcaatcgacccacacagtaccaaaaaatccaaaaac ggttgtcggagctcaagaaagttgtcaaaaagtatattgtatgcttcgaaagtagccgaa aaaggttggaagtgggatgtgtcaactccgaattatgatacgagcaccacagaagatcaa tttgtgtcaaaactaccgaaaaaaatacttcacaccccgacgcgtggagtactcgctcgt tggaacccttgctgccaacgtcgcatgtaggatcagttttcgaagaatcttattggggtt tggtcgccggacgatgtcggatcttgtggtgccgttggaattcgcacaaccctgaaggaa aagaaggttacacaaatcagatctgaaagtcaccgaaaagacacatggcgattgactttt -continued ttgtctcagatgtttctcaccgtcgctctgataccagttgttgggctcaactcgtttgaa gatactcttaacatagtgtgatattgtcccttttggaatgtgagtcatcttagctcggta agcatactcgctcttccaactagcccgaagatacttttaacagagtgtaatattatctgc tttgagccaagctggcgcggttttcatcaaaagacctcatactattaaaagatccataca ccttatatgtaggcttctaagttgctcggacacgggtgcgagtacccgacacaggtgcaa atctagaggtcagatcctttaaaatgtaaattctaagatttggggatacgaatcctagta cggatacgggtgcgaggatccgattaaaaataattcaaaaaaataagaaaataaaaaagt ctctaaattatgtgaaattttgtggaataactacgtatagcttgtaaagtgtggatttat tttttattctcaagttgtagataagtaaatgattgatttcctagataaggtatgttattt tcttcaaatttaccctagtttggttcgaatttcgggaaattgtatcttgtctcgaatttt tccttctgtcctgattaaactactcaaaatcgtctgaccagatccggtacggatcccata cccacatccacactagtgtcgtgtggacaagggtgcggcacctaaacttccgtgtaggag caatttaggtaggctcctaatcttttcagctattaatgtgggacttttacgcacctctat caaattccccaataaactaagtttcacgtggtccatcatcgcaatccacgggtctcttcc tctagttaagtcccacatggcccattaccatgatccacgggtcaattttcgtgattcatc gtgtgccacccacatcgttagtatttatggtaactaaagtacgcaactagcttttgcttg tgagcgtgtctccaagctcgtaaaggtaagaaaaccgagccgcatattccatcactctat catcaccatactcgtcccgcgaaacttgtaagataaaggtggctggttggtcagttgaac tacctcagagtgacttggtatagtatttcctttcttgtgaatatttaactcaattatgga ctctctgtgtgatagtcattgagagccattttctatatagccggtgcacacaaatcatat gtaccaagcttgttatatatgtaactaatacgaggaccagtgaaggactcggtgaaaata tctgcaatctggtcattcgacatacaaggccaatagactccccagcaataaaatcagggg gttgctgataaatagaattggccgaaatgttgccagaaaaaatttgaaaatagtgagacta agccgaattctacactacaaaataggttttaaaacacaaccagaaaacaaaaactttttt ggaaattactgttcacatcgaaaaaataaaagttgtcagaatttgatgtaatttatatgg ataggctcgtaatcactggacgagtaagttgtcctgaagaagttttgtcaaaaggtggcc ggaatggctcacacatgccggaaaacttattgtagctcgccggaaccctagttctggcgg tgcgtagaggcgtgtgactttctgccagactgattgactgtggtttgtcgcctgactttt cctaacaagatggtagtattggttttcgcacaacaattaccgatgaggagataacgcaaa tcaatcttgagtcgtcaatcggaaagacgcacggtggctgactttctatttagatgggac tggaatttctggagtttaatcgcacaagcgttttggatctgatggtaatactggtatgca cagtaccactgtagcagtgatgaaccctcaaaataagacaaagttgccagaaaattgcac ggcgatgagatctttcttccggatgtcaccggaatgacgcacaacgataatttctcactg aagctctgacaccatgtgagaatacacgggagaaaaatctatttttattaacaatgatac aatgagccctatatataatacatattctactctactacatatgggaatagggcatatttt actcctactacatatgagactaggactatttacacataactatctaacaagggctatatc tcagatttatgagaatatctacccaacgacccagagagacgagcctaatcattttgcagt ggcacagactataacaacaaaaaacctactcataatggttaaaccaactgattaagatgc ttacaggactatcttgagaaatgtacatattatatagatgcttgagttgcgtcccaatcc taaatagaagcttttattcgtaagcaagaagggaagcagctttacttgagccaatagctt -continued tcaaggtgcatgttgtcacaccaaggacatccagaatttgattttatagtgggaatatcg tttaaagataaaaaagatagcgtgcagaagattgcatacattagagatgcaaaatacgga atacccatactcccagataatgcagtatgccttttgcatgacctactggttgaatggaag cacctggtgaatttactaggtgtgttagtgatttctgctgcttccttcccctttctaaac tgcatactatctaaaatgttagggggggcagaagcccagtcaatctgactaggtgatgtta gtggtttccgcttcttcctcccacttctaaatgcgtactttctcaaatttaggagcatag aaacttaagcagctgcctacctgaggagttgcatgggaacataagagaatagactttacc tgtcatattttccataccttagttaattacagtgttatcctgataatgatctgttttctg gatctaggctgaatcgagattcaatcgcttttggttgaaaggatgctgctacagatcctt agtttacatcatttggttcttattctataagtacttcccctatcaactacttccttctt ttttcttaggttatttgcctctttaggttgtttggaaggaaaggaacagtagatgttttg atggaatagcaactccaaaccacttccttaaggctaatatcctgattggccaagtttctc caaagtccaaaacactttttttttccttcaaaaaagtacctttttttttcaaagttgagg tgtttggccaagcttttggaaggaaaaaaagtgtttttgagtagaagcagatgctcttga gaagcagaagaagtagcttcttcccggaagcacttttgagaaaaataaatttagaaacac tttttaaaagcttggccaaacactaattgctgcttaaaagtattttcagatttattagac aaacacaaactgcttctcaccaaaaatactttttttgaaaagtactttcaaacaaagcac ttttcaaaataagtttttagaagcttggctaaacaggctataaatgtcttttattttta cagctggagtaccctaacacctgtaaattcccctatacattttttcgactttggtagct cattaaccctagtataggactctttgttttggagctagcaaactcttttgttttcctatt tttgcatcttcttggtgccatttataatatctcttcaccaaaaaaaaaaaagttcccaaac tatgactaccttgagttggtcaaagcataaccaaagcatgggcacaccagtgtttgcgtg aattttatggatgttccttacctttatccttctgtgcttatgtagcatctgtcttggtca atcttttctgaagtctatattgtatttctgtgttgcaacatgagtttactgttaatctta ctgtttgacctcaattttgggttctttttgattttggaagacatcgtttaacaggttggc atggctgctactcttgctggtgtctgtcaggtgcctctcactgcggttttgcttctcttt gaactgacacaggattatcggatagttctgcccctcttgggagctgtggggttgtcttct tgggttacatctggacaaacaaggaaaagtgtagtgaaggatagagaaaaactaaaagat gcaagagcccacatgatgcagcgacaaggaacttctttctccaacatttctagtttaact tattcttcaggttcaccttcacagaaagagagtaacctctgcaaacttgagagttccctc tgtctttatgaatctgatgatgaagaaaatgatttggcaaggacaattctagtttcacag gcaatgagaacacgatatgtgacagttctaatgagcaccttgctaatggagaccatatcc ctcatgctagctgagaagcaatcttgtgcaataatagttgatgaaaataattttctcatt ggtctgctgacacttggtgatatccagaattacagcaagttgccaagaacagagggcaat ttccaggaggtagcttcttggtacatttcaatattcttaactgatgaaaaaataagggaa attgatctagcatgaaatgaagctaattataagttttacacagtagaactggtaaaacag ggttggctggatatttctttgttgaatttttaggattatatatattgttttagttttgta ggttgttttctgatgtgcttttttgactcggcagaatcttaagatgaaatggaaggttgta tcatcaaatgttaaataagggaatatgtgactttcaaagttaagcacggagtattttgga gtcaatagttacttcctgaatcttttaggatggaggagacagtttctataggaataggaa aaggggacctgatttcattatttgtgtgtatatacatttgttatctgaattcgcattact -continued ttctaacaaccaacaaaaggaaagtggacattcaatttgagccggagggagaaaatttaa
ctagaaaatgacctggccgtgaaataaaattattgatccgtcctttaactagttttcatg
gattgcctccttgcggatgatttttccaaccggtagaactactgttagtcgtccaaattc
tgacccccctactatgaataaaaatgtattagtaagtttagtgggtaatctccttgagaaa
taaaggaacaggagaaatattttattgatatatgctaagtgttttacaatagccctattt
atatacaatgtttacataaacctaaagccttctatataaatgtgggacactatacatgaa
ctaactctaacactatccctcaagctagtgcatataaattatatatatgcttgttacata
tataattaatttctctactttttggtatacttcttgtatacgggagttatctccctttttg
attaatacaatttaccttatcaaaaaaaaattaatacgaggaccagtgagggacttggtg
aaaatatctgcaagttgatcatttgacttctcaaactttgtaacaatatctcctgagaat
cttctctctcgtgaagtgacagtcaatctcagtgtgtttggtcctctcatggaacactgg
atttgatgcaatatgaaggacaacttgattatcacacacaagttccatctgactgattgc
tccaaattttaattatttgagcaattgtttgatccaaactagctcacatggtgcaagagt
catgactcgatattcggcttctgcgctagatcgagcaactacattctgtttcttgctttt
ccgagagacaaattacctcctattaaaacacaatatccagatacgtaacgtctatcagaa
ggtgaccctgcccaattagcatctgtgcgtccaacaatatgctcatggcatcgatcttcg
aatattagtcatttgtctggagctgattttatataacgaacaatgcgaacaactgcatcc
caatgactatcgcaaggaaattccataaactgacttacaacactcacaggaaataaaata
tcaggtctagtaattatgaggtaattcaattttccaaccaggcgcctatattttgcagga
ttgctaagaggctccccccctatcctggcagaagcttagcattcggattcataagagtatc
aatagttctgcagcccattattcatgtctcctcaagaatgtctaaagcatacttcctttg
cgaaataacaacctgaactagaccgagcgacctcaatacctacaaagtacttcaatctgc
taaggtcgttagtctggaagtgttgaaagtgatgttgtttcaaattagtaataccatcct
gatcattgcgagtaataacaatatcatcaacataaaccaccagataaatacagagattag
gagcagaatgccgataaaatacagagtgatcagcttcactattagtcatgccaaattccc
gaataattgtcctgaacttacgaaactaggctcgacgagattgttttaaaccatagagac
ttgcataagtgacatacaatacctctagactccccttgagcaacaaaaccaagtggttgc
tccatattaactttatcctcaagatcaccatggagaaaggcattctttatgtccaactga
taaagaggccaatgatgaacaatagccatggacaggaaaaggcgaacagatacgacttta
gccacgggagaaaagtgtcattattatcaagcccaaatagctgagtatatccttttgcaa
tcagacgagccttgagccaatcaacctggccatccaggtagactttgactgcataaaccc
aacgacaaccaacagtagacttacttgaaggaagagaacaaactcccatgtaccactcac
tcacatgtaaagcaaacatctcgtcaatcatagcctgtcgccatcctggatgagatagtg
cctcacctgtaaacttaggaatggaaacagtggacaaagatgatacaaaatcataatagg
gtgatgagatgcggtgataacttaaaccaacataatggggactaggattaagtttggatc
atacaccctttcgaagtgcaatcagtggactaggaggagccaagtccgcactagacgtgg
atgacaatgataagtcaagagtggtggcctcgtggttggagatgtaggatgagcaactgt
agactcctcagaagtcggtataggtaggagtacctgtgatgttgatgtggatttaagagg
aggaacaatagattcctcacaagtagatacaggtaagacctcagatatatcaagatgatt
agatgaagtaaagtaaggttgagactcaaaaaatgtgacatcgactgacataagatatct -continued acgaagatcaggtgagtagcagcgataccccttttgaacccgagaatagccaagaaagac acacctgagaacacaaggagctattttatctttttcaggagctaagttatgaacaaatgt actccttaaaacactaggaggaaagagtataaagatgacctagggaacaatactgagtgt ggaaactgattctagatggaagatgaaggcatccgattaattaagtaacaggttgtaaga actgcatcgtcccaaaaacgttgtggaacataggactgaatgagaagtgtgcgagcagtt ttaatgagatacctattctttctctctactaccctataatgttgaggagtatacagacat aggataatattttgagaagtcataaactattgaaactaagagaatacatattttaaggca ttatcactacgaaaagcgaataaaaacaccaagcggagttttaatttcagcataaaaact ctagaatattgaaaacaactcaaaacgatctttcatttggaaaatccaaatacatcttga gtaatcattaatgaaactaacaaaatccaaatcttaaggttgtgactctactaagacccc atatatcataatgaactaaagacaaaacagactctacacgactcttagcacgacgtgaaa atgtagctcgaatatatttcccaagttgacacgaatcacaatctaatgtggacaaaccag acaccatcttctgaagcttggataaactcggatgtcctaaacgtttgtgaattaggtcta gaggatctgtagttggacatgttgtagagggattgagtgagttaagatagtcaaggtctt gtgattcacgccatgtgccaatcgtctgtaccgtactgcggtcctgcatagtaaaagaat catcaataaaatatatatcacaatggaattcacgagtcaaatgactaacagatgcgagat taaaggacaaccggggacataaaaaatagaatctaaagtgacagaggacatgtgattagc ttgtccaactccttttgcttttgtttagacttcatttgctaaagtatcattgggaagaga ttgtgaataaacaattatttgacaaaagtgacatattaccactggggtatcaagttgctt agtcatactaagaatgtttgggagagggtggtggaagtgagggtaaggaggacagtgtct ctatccgagaaccagttcggattcatgcatgatcgttcaactgcggaagctatccgtctt attaggaggctggtggaacagtacaaggataggaagaaggatttgcacatgatgtttacc tagagtaagcgtatgacaaggtccctaaggaggttccttggagatgtcagaaggttaaag gtgttccggtagcatatactagggtgatgaaggacatgtatgatggagctaagactcggg ttaggacaatggaaagagactctaagcattgtttggttgttatggggttacagtaaggat ctacgctcaaaccgttcttatttgccttggcgatggacgcattaacgtaccatattcagg gagatgtgccatggtgtatgttattcgcggatgatatagttctgattgatgagacgcgag gcggtgttaacgagaggttgggggtttggagacagacccttgaatttaaaggtttcaagt tgagcaggactaagacagaatacttggaatgtaagttcagcgacgtgacggaggaagctg acatggacgcgaggcttgattcataagtcatccccaagagaggaagtttcaagtatcttg agtcagttatacagggagaagatggggagattgacaaggatgtcacgcaccgtattaagg gcggggtggatgaaatggaggttagcattcggtatcttttgtcacaagaatgtgccacca aaacttaaaggtaagttctatagagcggtggttagaccaaccatgttgtatggggcagag tgttggccagtcaagaattctcatatctagaagatgaaagtagcagaaatgagaatgttg agacggatatgcgggcatactacgttggaagattaagaatgaaaatatttgggtgaaggt gggcgtggccccatggaagttgtgcccaccattaaagactgctatctgaaaactaattct ttgggcccaaacattctggcccaaagtacctcgtgaataataatattgagctcatgtctg acatgttggaagaggagttactagcaaacacttatacacctatgttggtaacacaattga agaactacgaaaaacactcttctgcaaaggaaaatgagaagaagaagaagaagaagacga agaagaaggatgatgcaatgatcattgaagaaaaaggagagcaggaggacccatctaaac ttacaaagtctagaggaagaggaggacccagagtttgatgcttccctctgggtacaccaa -continued aacatcgtcaaacttaggcaaggagtttggggtaaacattcaggggtgtgagaaggaagc tttggagcttttcgtaaaattacaactagaggcataaaaaaaaaaaaggcaatccaggca tggaggtgacaaccttcgaaaagaaagggattcaaagaactgaaagggctggattttgg agtaacttcaagagtaatagaacaagaagtagggggttgcattattatcaaagatcaatg aagattaacattgaagaagtgggaaatccaaaaagactccaccgagaaggatgatgcaat gatcattgaagaaaaaggagagcatgagaaaaaacccgtagaaattgacagcactcacac acaataagacgagataataaagtagtgagttggccaattgaagaagctttacctcttaac ttacaaagtctagaggaagaggaggacccagagtttgatgcttccctctgggtacaccaa aacatcgtcaaacttaggcaaggagtttggggtaaactttcaggggtgtgagaaggatgt tttggagcttttcataaaattataacaagaggcatgggaaaaaaaaggaaatccaggcat gcaggtgacaaaaccttccaaaagaaagggactggaagaactgaaagggctggattttg gcgtaacttcaagagtaataggacaagaagtacgggattgcattattatcaaagatcaat gaagattaacattgtatcatggaatgtcaggggggttaaatcgacatagaaaaagaatgtt gattaggagtttaattcataggtggaaagcagatgttttctgtttccaagattcaaaatt aaaaggggacattagggagtttataagagaactatgggcaaataggtggtttaaatatgc acagttggaggctagtgggcctagagggggtattattgtcttatgggatagtaaaattgg ggagggggagatcagcagcctgagctcctattctgttacttgtaaatttataggtaaaac tcaggagtatacttggaatttatccactgtatacgctccaaatgatagggaggaaaggaa agaagtatggtgggaattagcaggtgccaggggaatttttatggaccttgggtaatttct ggggatttcaatactgtgaggtacccaccagagaaaaagaattacagcaaaatcactaga gcaataaatgaattctcataatttattgaagatatggaactggtggatctacaacttgca ggaggaagttacacttggaggacaggagatagacatgtgataacagctagactggatagg ttcttggtttttatggattggaatgagagcatcagaaacaccaagcaatcagttctccat tgaattacctctgaccattcccctgtgatgcttcaatgtggtaaccggtaccctgtcaaa tcctattacaagtttgagaattggtggctggaaacagagggcttcaaagaaaggattaaa gtctggtggagctcttttgcttgtgaaggaagacgtgactttattctggctttcaaactt aaagcatcgaaggaaaaaattgaagaaatggagtaaatctattcaaggaaacttggagat gcagaaattgagtattcttagtcaacttgcagaactagaagagacacatgatcaaaggag ccttactgaagaagaaatacacactaaatatgcagtctatggagtttggggagattgcaa aacatgaggaggtggcttggagacaaagatctagggctctttggttgaaagaagggacaa aaacatcaatttttttcctcaaaattgcaagtgcacataggaaatacaataacatagacca actgttacttgaaggaaaatttgtggcgaatccaacatacataacaaataatattggtac attttatcaaaaactatatataaagattgctagaggacaatcttatgttgcaaagtcttt tcgaagcttaggaaatttgggatagtgtcaggcatgtgaaagggataaagcacctggacc tgagaactgggaggtgataaacacggatatgatagctgcagttctttgttcatggaatgt ttgaggaaagctttaatgttacctttgtggtattgattcctaagaagatggaagctaagg aatagaaggactttaggcctattatgataggcaatgtgtacaagatcttgatagaaagac ttaagaaattggtgaacaagttggtgaagggtcaacggatgacttttattaaaggtagac agataatggatgttgttctaattgccaaatgaatgtgtagatgcaagaacaaaggcgaga aacctacaatactatgcaaactagatattgagaaggcatatgaccatctaaattggaact -continued ttctattggaatcgctgatgaggatgggctttggtgtaagatgggtcagctggatcaaat tctgcatcagcacaatgaaattctcaattttgataaatgtttcaccagtaggtttcttcc cttctcagagggatttgagacagggtgatccactatctccttttattattcattagtgct atgggaggcttaaatgatatgttaaagactactcaagataacaactgcatacggggtttt aaggtgaagtccagggcagacagtactattgagatttttcatcttcgatatgcagatgac gcacttatgttctgtgaggttgacaatgaacaattgaaagtgctgaaggtgatcttcatt ctgtttgaagccacatctgtattacaaattaactggaatgaaagctttatctatctagtt aatgaggtaactaagatccacttttggttggaatcctagaaggtaaaattggggaattg cctacagttatttggggatgccatgggggccaagagcaattttaaggggatttggactag ggtcgtagagatatgtgaaaaaattttaacaaactggaagagttagtatttatccttaag ggacaaactaatactaatcaattctatacttgatgattttcctacttacatgatgttcct cttctcaatccatgtgaatgttgtgaagagaatatataccccttagaaggaacttcctatg gggaggaaactatgacaaggaaagatctatttggtcaaatggaagtctctcacagtcagc aagaagtaagagtgttttggaatcaagaattggagaattcagaaccaaagtttgatgatg aagtggctatggagatttactacagaagaacattgtttgtggaaagaggtgatcatggag aagtatggcatagaagataaacggataacaaagtctgtaaatagatcttatggagttagt cgatggaaatccatcagggacctatagcttcagctcttgaataagtccaaattctgaata ggaaatggattgaaaatatctttttggaaggataattggctaaccaaggaactttgaaac aactctttcttgacatttacattccaaatcaacagcataaagcaataatagtagaattat gggctaatcaaggttggaatctcacatacagaagactatcaaaagacccggagattggca ggtcaacagagttcaaaggcactttggaacaatttaaagaggtctatacttctatagact atttgacttggcaagggaagtttattgttaattcagcctataaggaattcaacttctcag ctaactggattggttgttggccatagaagttgatttggaaagttaaaattccttatagag ttgcttgtttctcttggcttttggctaaagaggcagttctgacgcatgataatctaacca agagagattaccatttatgttcaagatgttatttatgtgaagagcaggcagagacaacca atccactttttttgcattgtaagttcactgcagttatggaggattttcattagtttaaa gggtatcatgtgggctatgcgtagaagtatacctgaagttctagcatactggaaaaaaga aagaaatctttccaattataaaaagagatggaggattatcctagcttgcatctggtggac catttgggaagaaagaaatcaaagatgcttcaaagataaatcagtcatattcagataatt aaaatgaagtggctagtcttgttttatttttggtgttaagtgttagatagttatgtatta tgtataagttgtctagtcccacattggaacgggagtaatatgtactatgtagagtatagc tataaataggacttcttgtactttattgtagagaatatattaataatatatttttcccgt gttgtctcacatggtatcagagaaaccgtgagatatcagtcgttgtgaaaaataccagcg gcttcgggaagaaaaaaatcaatcaactgctaggtatattagtcttcggcgaccgatcca ttaaatttctctggcaaagaaccactcatgggccctcacgcgcccaccgaaagaaatatt tccggcgaggttccaatttcatgcgcccgcgcgtgaggcagtttccggtcaaattttgac aaaggtcctttttgacagtttgttcaccctgtaattcccagtctatccatcattttttt atttcgatcacttcgcaatttctcgggcagctacagtgatttttccggcagaagcggtgt ttcctttgcctgcttcagcgagatacagttgattatttctattatttgtttctagacctc tctccaatccaacgatgtctttggaatttgatgtatttggttctgaaaacacgagttcta gaaagtcaagcttcatgattactttagagccattaatggggagttcaaactatttagctt -continued gggtttcctctgttgaattgtggtgtaaaggtcaaggtgttcgagatcacttaatcaaaa aggctagtgagggctgtgaaaaggtcaatttaagcagtttatgacgtctgtataccactc agcagaataggatagcaaagaaagaatatgcacatcattgagactgctcgcacacttctc attgagtctcacgttctgctacattttctgagcgatgcagttctaacggcttgttatttg attaatcggatgcctttatcttccatccagaatcagattctgcagttagtattgttttct cagtcacccttatactttttcgtcctcgtgcttttgggagcatgtgtttgttcataact tagctcccgaaaaaaataagttagctcctcgtgctctcaagtgtgtcttccttggatatt cccgagtttaaaagtgatattgttgctactcacctgatcgtaggtaccttatgtcagttg atgttgcatttttgagtctagaccttactttacctcttctgaccaccttgatatatata tgaggtcttacctataccgactcttgaggggtttactatagctcctcctctacatactga gccacagaaatcttactcatacctaccattggggaatctagtgttgctcctcctagatcc ccagctacaggaacacttttaacttatcgtcgtcgtccgcgcccagcatcatgtccagct gattcacgttctgcacctgctcctactgcggactagtctcatcctaatctaccaattgca cttcggaaaggtatatagtccacacttaatcctaatccatattatgtcggtttgagttat catcgtgtcatcacctcattatgcttttataacttctttgtccactgtttcaattcataa gtttacaggtgaagcactgtcacatccaggatggcaacatgctatgattgacgagatgtc tgctttacatacgagtagtacttgtgaacttgttcctcttccttcaggcaaatctactgt tggttatcgttgggtttatgccgtcaaagttggtccagatgaccagattgccaaagggta tagtcaaatatttggggcttggttacagtgatatttctctcccgtggctaaaataccat cagttcatctctttatatccatggttgttgttcgtcattggcatctctatcagtttgaca ttaagaatgtttttcttcacagtgagattgaggatgaagtttatatgaattaaccaccta attttgttgcttagggggagtctagtggctttgtatgttggttgcctcagacgctctatg gtctaaagtaatctcctcgagccttgtttagtaagttgagcacagttattcgggaatttg gccaactcgtagtgaagcttatcactttgtgctttattggcattttacttcaaatctctg tatttatttggtggtttatgttgacgatattgttattaccggcaatgaacaggatggtat tactgagttgaagcaacatctctttcagcacttttagactaaggatctgagtagattgaa gtatttttaggtattgtgattgctcagtctagcttaggttttgttatttcacattggaa gtagaaaaacttcaatcatttttctttatttgaaaggaagaaaaaaaaggtaatatctag acctaaatattaatctgaagacaagtgaggcttgctcagttggtaaaagcacctccacct acgatcgttaggtcctgggttcgagtcaccatggaggggaagtgtggaaacactatagat cctcctaatttgggagggggaaaaaaatattaatctgaattgacatgaatctcaatgaca atgaccaacgatttcctgcaattcttttcagtatggaatgaataaaaaatcaagctacaa gtctctattaaacgaaatgcactaacagggatcactctcaagaaaggaagtggttttggt tgttgttattccaggttggataaatcactttctttataaatatcataaaagacaagggct ttcttgcttcagcacatgtgggaaatgccgggggcttggctggtaccaagctcgagcgg tctttctatctttttggattgcatgcccaaggcaatgctttttgtagattgggatggatt gatcttcgcagaagtatgctttagacattcttgaggagacaggaatgacggattgtagac ccattgacacacctatggatccaaatgccacacttctaccaggatagggggagcctctta gtgatcctgcaagatataggcggctggttggcaagttgaattacctcacagtaactagac cttatatatcctttcctgtgagtgttgtaagtcagtttatggactctccttgtgatagtc -continued attgggatgtggttttccgaattcttcgatataaaatcagctccaagcaaagaactgttg ttcgaggatcgaggcccatgagcagatgttgattgggcacgatcaccttctaatagacat tctatatctggatattgtatgttaataggagttaatttggtgtcttggaagatcaagacg taaaatgtagttgatcggtctagtgcggaagcaaataatcgagcaattgttatggtaaca cgtgagctagtttggatcaaacaactgctcaaagaattgaaatttggagaaattgatgga accagtgtgtaataatcaagcagctcttcatattgcgtcaaatccggtgttccatgacag aattaaacacattgagattgactctcactttgccggagaaaagatactctcaggagatac cgttacaaagattgtgaagtcgaatgatcagcttagagatatttttaccaagtcccttgc tggtcctcgtattagttatatttgtagcaaactcggtatatatgatttatatgcaccaac ttaagggagagtgtgagatagttatgtacaacaaaatacccggtataatcccacaagtgg ggtatggagggtagtgtatacgtagagcttacccttaccctgtgaaggtagagaagctgt ttccaaataccctcggctccagtacaaatgaaaaggagcagtagcaacaagcagtaacaa caatgatatagtaaaataactgaagaaagaaataacatgtagacatataactccactaac aaacatgcaaggttaatactattgccacgagaatggcaaaggaatgttagatagttatgt attatatgtatattaatagtctagtctcacgttggaataggagtaatatgtactatgtag agtatagctataactaggacttcttgtaatatattgcatagagatatcaataatatattt ttcctgtgctttctcacgtaaaggaatgtaatgtacttagaagatcatgaatctatcttt gatgttttagacacctcgtgagaacacaaaggtttaggaactttattgtgttctttgtaa ttatgggtgactgccaatatgttaccttttcataaaaatgattatttggccattggatta gtttcaacagcctctctgcccctccgggtaggggtaaggtctgcgtacatattaccctct ccagaccccacttgtgggattatactgggttgttgttgttgttgttgtggattagtttca acaattttgatagttcttttatttgaatcaaactactcattcacatggattttgtatcgt atcattgagttaaaaaaattggttttgctaatttatcctcatgtataacaactacctatt tttcaatatattggattcaggagcttgtagtagctggagtttgctcttcaaagggcaata agtgccgggtatcatgcacagtgactccaaatacagatctcctttctgctctaactctta tggagaaacatgatctaagtcagctacctgttatactaggggacgtggaggatgaaggca tccatcctgtgggcattttggacagagaatgcatcaatgtagcttgcaggtttttgacat tcaacttttacttcaaagatataatgctttctggaaccattgatgataaaatatgcaaga aacttgtgcagaagtcgcactttactatcgattaccagataaagttacttatcaagaagt caaatatattgaacatatttctctaaaacactttgactggactgtaagcagaaacttact aaagtaggtcgtaagaaatggtttgatagggaaatcaccatctacacttaaaagagttgt gtgaatttgaattcttaaagcatgtgaaagttataaaaacttgttattatctaagcatct gaagcattttggccatccaaaggatcaaaaataggaaataatttcatttgtacaatgaac tccctgcacaaattctcacactaggtgtattctctattcatcactagcactacatgtgtc actacgaatcatatacaataaatctttgtaacataaaagacgacacataatatggaagta agccgagtatacaagggaagtttcatcattacggtgagctttttataagataatcaagtt ttactggaaaagggcaaaaactctcccgtatagaagtataccaaaaagtagaatacctta caaaaatatgattttctatgaacaacaccctatcttctatacttgtagggatctcatcgg ggcaccaaaaagagataaagggataagaggcttttcctcaaatgtacaaaatccttctct attccttcaaaagctctcctatttctctctctgcacactgtccacataagttcaatggag caacatccacgccctgtgtcttcttttccgtcttctataggtccagctgaacatggcttc -continued tttgactgagtgtggcatcaacgttgaagaccaaaccatcccagtacttccaaccacaaa cgagacactatatgacaatttagaagaagatgattcacatcttctcccgaacatttacac ataaaacaccagctgatacatgtaatcttcctcttcctcaaattatcagccgtcaggatc acccgtctcgtagctaactaggtgaagaagcacacctttctcgaaaacctcaggatccat acagagagatatggaaaagctgattcctccatgcccagaagcttctcataataagactta acaaagaaacaccactacttcccccccccccaaaaaaaaaaaaatctccatacatcgact ttcatgtgtaattcttgttcgtgaaacgacccaatcaacctttggcacaaatctcccagt cttgcgagttcctcctaaacttcaaatcacaatgaacttctccaccttgtagcctccgtg tcccttggactggcaactcctttggcatgaaactttgtacatattaggagatgtgatact caaagtgttgttcctgcaccaattgtacccccaaaaaacttaccatgctcccatcaccta acattgaatgatacgttccaaaatcttcgcactccttcaagaaacttttccgtaggcccc acccataagggagtgtgatttttttgctctccatcccctctccaagaatccattcccta aaccactgcaggacactttaacaatcactatgtcactttttctactagttctacattgag tgatatcttgatgtcattgaaatgcctctggaaaatcttcttctcatctaaaagaacact tgtttgccttttgaatccccctctaacattttctatgtttcattcatctttggtggaaca gagcattagcaactagagaacagctttgctag

SEQ ID NO: 4

(DNA sequence of NtCLCe from *Nicotiana tabacum*; sequence originating from the ancestor *N. tomentosiformis*; one start codon)

<u>atg</u>aatcacgaaagttgttgggtcgt catccaaattgctggccttgggctcgacgaccatctcttcctccgggacgttcctgtgac ggaaacattgaaaaagaacaagatatgtgcgacagcagcaaagacgatagtgatagtgat agtggtatccagataggatctctgctcgaggaagttatcccacaaggcaataataccgct ataatctcggcttgctttgttggcctcttcaccggtatcagtgtcgtgcttttcaacgct gcggtaagtgcgctataggtctttcatttctcttttcatctactattctcccttacttac ttggcctcagtcaatcagcccccctgcctactttaaattattgtacaatttatcagaggag tatcctatacatcaaattcacataacttagtaaaatatgctgacattctgaattttaacc ttaccagcttagaacatccaggctagttcagaaacagataatctaaattggcctcattta taagtcattttgttaatcaagacatacaatttggctcttgataaaagattatgcagcgcc cgatgataacctaatatttatcagcaacccatatgtcactttcttttgtttaaatgctct cccatgtaatttaacaatattgtcaccatacaaaagagaactgaagtgaatgttccattt gtggtcatataacggatatctcccttggttaggttcatgaaatacgtgatctttgttggg atggaattccatatcgagctgcctcagaggagcccattggagtacattggcaacgtgtaa tcttagtaccagcttgtggcggtttggtagtcagctttttgaatgccttccgagccactc tggaggtttcaactgaagaaagttggacatcatctgttaaatctgtgttggggccagttt tgaagacaatggccgcttgtgtcacattaggaactgggaattccttaggaccagaaggcc ctagtgttgaaattggtacatctgttgccaagggagttggagctctgcttgataaaggtg gtcgtagaaagctgtcactcaaggctgctggatcagctgctggaatcgcttctggtttgt tccccatattattcttggttctgaaccatacatggtacattttccttataattacatgta gcctgttgtatgctttcctctttcctgggaagcctttctgtaaatgcaaatgtgtttgca ctcaaaccaataaactgtaaaaacagtgaaccccttgagcaagcaaaagcactagaaaac caacaaatagatccccccccaagataccagtgaaatgacaccgggtgacccaaaaataa -continued agcagcttacatcttgactttgagaggaactgcaatcagctataagtaggttattaattt ccagtgcctgcattctgcccaagtactatgatatatttctgaagctttgtttccccagtt cctttttcagacgtttgctgtcaataaagttgagccagccaacttggttcccacaagcta ctaattttgtccaagcttactctatgggagaagttaaatttcccaaattccttgagcaga aaatgaaaaatgaactcaaagtgtcatattaggcaactatctaaagaaaaatacttaatt gaagtttagataagaaaagtgaatatatattgatgtagtctccgttaggtgagaagcgca tcacttacccagcaacatatggacctaaaatttactagtgaacttttcacattgtatcaa aagctcaacaaacagaaagatgactagtcctaaaatgttatttcacatcaaccttatcat acgtgcattatttgttctctatatttctatttcatccgatataaccaatcgtcattgtaa attctataatgcctgtggttacttttgtctttagtgacaaatgacatttaggctaaccat gtagttattgactgatttcgcttgacgtctcttccaattatgtagtagtagagtgttgag atatggatatgttaccttctaaaaaaaaagagtgttgagatgcggatggtttgctagctg gcttttgtctcccttcaagttgaattagcaaaagcaatgtctcataagttggatagctag acaagaaaaactccaaattactttatgtagagtattcttaagcttgagtcgcgagttgga aattggaattatgtaaaaaaacctggaattatttggttgagcctgctttttatttttgtc aatatttccagtatctaacccaacatgtttagagcaattcccagagagcctcaatacgag gcatttgcagagtctttatgagagtccaggaaggggcacacactgtagaggtatagtgtt gtccttattttttttttttgataaggtaagattttattaaaaggtaccaagatggtgca aaattacaaacatccaaactaatacaacaaagcaactacattcctcctagctcctctaga aaattcatatattgttccatatttttcattacatgtcttttacaccagaaatacaagttt aataagcatctgtttttaatcctggatacatgctgcctttccccttcaaagcaaatcctg tttctttccaaccatattgtccagaacacacatagaggaattgttcttcatactatctgt tgactctttgccactttttgttgttgccatgtctccaacaaactttacactggcaggcat tgcccacttgacatcatatatatttaggaagagctaccaacactgctttgccactttgaa atggatgattagatggttgactgtttctgcctcttcttcacacatgtaacaccggttaca tagagcaaaacctctcttctgcaagttctcctgagttagaaaagcttcctttgctccaat ccaaccaaaacgggctactttaataagtgcttttgacttccatattgctttccatggcca atttgactgataaagcccttgtagtttttgtaacaagctataacaactgctgactgtgaa aataccatcattacttgctgcccagattaatgagtctctcctgttttcctccaatctaac attattcaataactgcatcaattgggaaaattcatcaacttcccagtcattgaggcccct cttgaagattagctgccagccggtgcttgaatagaagtctaacactcttccatttttgtt aatagagcagctatatagaccaggaaactttgatctaagacttccattttccaaccacat atcagaccaaaacagggtattattaccatttccaagtttcagtttcacaaactgactata tttattccaaagattactaattgtgctccaaactcccccttttgaagaagattgaattga acgaggagcccacatgtccttcataccatacttggcatctatcaccttttttccataatct attcccatcataattatatctccatagccatttaaataaaagacttttgttatgcatctt tagattcctcactcctaatccccctctttctttttttttcatcacctcttgccatttgac caagtgaaatttcttgttatcattattaccttcccacaaaaatttattcctcatagtatt caatttttttctccactgatgttggcattttaacgagagatattagataagtaggtatacc atccatcacactattgaccagtgtaagcctaccaccaagagataaatattgtcttttcca -continued tgacaccagtttactgctacatctatccaagaccccctgccacatctttgcatcattctt
ttttgctccaagtggtaggcccagataggtggatggtagctgctccactttacaacccaa
aacatctgccagatcatcaatacaatgctcggcattaatactaaacacattactctttgc
caagttcactttcaatcccgagacagcttcaaaagctagtagtactcctatgaggtgtaa
gagttgctctttttcagcttcacataatatcaatgtatcatcagcatagagtatgtgtga
gaaatacagttcttccccctctctttttctaattttcaatcctctaatccaccctaactt
ttctgcttttaaaagcattctgctaaagatttccatcaccaacaaaaataaatagggggga
tattggatcccccctgtcttaacccccctctgagaattaaagtatctatgtggactcccatt
aattaaaactgagaagctaattgaggatatgcagaattttatccacccaatccatctttc
cccaaaattcgtatgtttcatcagatttaacagacatgaccaatttacatgatcataagc
cttttccacgtcaagtttgcaggccaccccctttaatcttcctcttgaatagatattcaag
acactcattagctaccatagcagcatcaataaattgccttcctcttacaaaggcattctg
attatctaatatcaattttcctatcaccatctttaatctttcagctatcgactttgcaat
tattttatagacactgcccaacaagctgataggtctaaaatctttcacttccgctgcccc
ctttttcttaggaataagagcaatgaaaattgagtttaggctcttagtcttgtccttatt
ttcagggttgaactagttctttagaagtttcctaggcttcctaatttccaaagttctgcc
aggtccttttctagtgaagtacttgaagtttaataaatcaaattttaatttctaacatat
cccgagaaattcattcacaaattcaactggtgacttctgatgcagaaacataagcaactg
cttatgggttcatatgttcctgcaattttattgttgacatggattggcttcatatggttt
tgttcctgcaattttatcgctgacactaatcctttcatatggttttatgtggggtggtaa
atagaggttaagagacaagaagaggctggaaaaggtgggcagttcatttgttagtagact
actctatttactaagagatatgatgtcccatacattactcgaattggctccaaatacaga
ttccacttctttgtcgagtttccttattgtacagagttcgactcgtcaagggaaattcac
ttcctttgactgaataatgctagtttgagtagtaccttaaattaaatggaccatttaatt
ctatctacttgatagaatagactggtcatcaactagttgcaaatataatgacaactccgc
catgtttgcagagtcacctgatgaagaagtacctcaattagtagaccatttcttgaatgt
tctacagtattctctatgcctacatgaccacatcacttttcctttttgcgttgtgagaact
tgaacttggtgagcgggggttccccaggaatggcatcttggtggcagatgaccattctgt
ccttatcttagctaatgcttcttggattgcctcactagatttattataccttttaataaat
gtttgccattgttctgccataatagagggatgtacctagctggtgcttcacatcacatag
tccaaaactaatgaaatgctttacaattgtcgagtactaaaggatgatttgtggaatcag
atctcaaacaatttattttgaggaagaaaaaataccaaaggttttttctgtttgttggaag
attaaaaatcctttaaaaggtaaagatttatgaacttaattcagcatttttgtggccatt
gctgaaaaagagaaaacaatggcacttattcgagtttgcttatccaaaaaaaaagaagaa
gagaatgtcacgtaatgcaatttcatcttaggaaactttgcaggagaaaagcaagagtga
taaaacagaactatttgtttttttgataagttgttgtgacctatttctttgtcattctta
tttgctaataagctaatgtaccctgtactatggttgttttgacttaatccggggatgttc
agtgagcattttcttgtttttttctgctgtcagcatctgctgccttacaggaattcatttt
ctggaaatttacttcttgttctgctaacattttcctgttatatcttgtcagtcattttct
ctccatggttatactgtttgtgtcactttgaaactctccttgttttctactttaaaggat
ttaatgctgctgtcgggggctgtttctttgctgtggaatctgtgttatggccatcacctg -continued cagagtcctccttgtacttgacaaatacgacttcaatggttattctcagtgctgttatag cttctgtagtctcagaaattggtcttggctctgaacctgcatttgcagttccaggatatg atttccgtacacctactggtaattttggacttctttctcgagtttgattcttaaatacaa ttgtacccgtcacttacagcaacaacaactacatttcaacagctagttggggttggctac acagatcatcactatccatttcaatttctttagtcccatttctttcgaatattcagtact ttgggattctctattatcagaggttctctttattttctactttgacgtacaaatctctaa atagattaaagaagactcctagagacactggcctaatgcaaatgtaccaccatgaataaa ccttaatctgaaatagctggtatcgtatataagaacctttagctttaattgtgttctata ttgatcttttgggacaacttccgtccaataatattatgtcttacttatacagttatactt atccttaaactttactctttagagtggttatccgtagttcaagcttttgttggcaccata gctagtttggttcttagtaaaaagttactctttagagtggtaactttttgtcaattttct tagtgaaaatataacctctgtgacaaatctaccaagtataaatccaatatggttctgtgt catacttgtagtttatccaagtctatgctccatcactcttacaaaggctcatcgtatgac taatttttttttgagaaaggtaacagtttgtattgataataagatcagcgccaggttagtc attagtgctaatagctgtatgtacaactccaaaagagcaaaagacaagcacctggtgtaa cgtaaattacaagctgcctataaaatctatcaggtctcctacctcactaaacatttcttg tttacaccaaaaaaataaaacaaggaaagacaatccatcttaatcttctgaatggagttt cttttgccttcaaacatctcgagttcctttcgttccatgcaatccaccatatacaagctg ggatgcttttccatttgtctttatccatttttttctaccaattcccttccaattgactaga agttccaatgtggttctagatatgacccaattaactcccaacatataaaagaacatgttc cacggatttgtagtgattctgcaatgtaggaacaagtgagcattactttctacttcctgt ccacaaagaaaacatcttgagcaaatctggaaacctcttctttgtaagttatcatgtgtt aaacatgctttttaccactaaccagacaaaacatgatactttgggaggagttttaaccc tccaaatgtgtttccaaggccacacctcagtcattgaaacattatgatttagagtccagt atgcatcttttactgaaaatgcacctttgctattcagcttccaaactattttatctatgg tcttgttagtttacagctatgtatatagtgtagtcttgtcccacattggaataggagtag tatgtccttgtatagtatagctataaataaggacctcttgtattgtattgaacatccaat atcaataacatattttctcccgtgctttctcacatggtatcagagcaattgtgagagatt tatcgctgcgcataaattccagcgactccgggaagagaaatcagtcaccggaagtctttt tccgacgactctttcaaggttgtttgcgtttgctttataaatccaacactaccacaagag taatcactgtccggcgaccaaaccccagtaaaaatctccggcagcagcctcctcacgcca ccagaagctcacgcgccggcgcgtacgaccacttccgtccatttttttgaaaaacttcctt cagaacagttgggtcgcctggtaattcctatcctacccctactgttttcatttcattccg accactttgagttttttccggctgctacagtactattccggcagctatagtactattccg acaactacagtaagattccggctgctacagtatttcattattctgtttttgtgtttcctt actctgtttcagtggattacaattgattctttctcttatttggtaataatttgcaacaat gtctatgggatttgatgtttttgggtctagaaacatgagttctggaagctctagtgttat tattacctcagaaccttaaatgggaggttcaaactacttagcttgggcttcatctgtcga gttgtggtgtagaggccaaggtgttcaagatcatctaatcaaaccgtctagcgaaggaga tgaaaaggcaataacactttggacaaaaatcgatgctcagttatgtagcatcttgtggcg -continued atctattgattccaagttgatgcccttgtttcgtccattcctgacatgttatttggtttg ggcaaaggcacacaccttatacactaatgacatatctcgcttctatgatgtgatatcgcg gatgacaaactgaaagaagcaagaattagatatgtctacttacttgggtcaagtacaagc aatcatgggggaatttgagaagttgatgccagtttctgctagtgttgaaaaacaacaaga gcagcgacaaaagatgtttctcgctcttaccctcgctgaacttcctaatgatcttgattc agtacgcgaccatattttagctagtccgactgtcccgacagttgatgaattattctctcg attactccgccttgctgtagcaccaagtcacccagtgatctcatcacagatacttgattc ctctgttcttgcatcccagacaatggatgttcgggcatctcaaactatggagcatagacg aggaggaggtcgttttggaagatctagacccaagtgttcttattgtcacaaacttggaca cactcgtgaaatgtgttattccttacatggtcgtccacccaaaaatgcttacattgctca gaccgagactccaggtaaccagggattttctttatctaaagaagaatataatgaactcct tcagtatcgaacaagtaagcagacatctccacaagtagcctcagttgcttagactgatac ttcttttactggtaatttttttgcttgtgtttcccagtctagcactcttggcccatgggt catggactcaggcgcttctgatcacatctctggtaatatatcacttttgttaaatattgt atattcatagtctcttcccattgttactttagccaatggatgtcaaattacggcaaaagg agttggacaagctaatcccttgtcttctatcaccctagattctgttctttatgtccctgg ctgtctttttcgtcttgcatctgttagtcgtttgactcgtgccctccattgtggtatata ttttattgacgattcttttattatgcaggactgcagtacgggacagacaattggtggagg acgtgaatcagaaggcctttactaccttaactcacccagtccttccacaacatgtctggt tacagatcctccagatctaatccacagacgtttaggacatccgagtttatccaaacttca gaagatggtgcctagtttatctagtttgtctacattagattgtgagtcgtgtcagcttgg gaaacatacccgagcctccttttcgcgtagtgttgagagtcttgcatagtctgccttctc cttagttcattctgatatatggggtcctagtagagtaagttcaaccttgggatttcgtta ttttgttagtttcattgatgattattcaagatgtacttggcttttcttaatgaaagaccg ttctgagttattttctatattccagagtttctgtgctgaaatgaaaaaccaatttggtgt ttctattcgcatttttcgcagtgataatgccttagaatatttatcttttcaatttcagca gtttatgacttctcaaggaattattcatcagacatcttgtccttatacccctcaacaaaa tggggttgctgagagaaagaataggcaccttattgagattgctcgcacacttctaattga atctcgtgttccgttgcgtttttggggcgatgcagtgctcacaacttgttatttgattaa tcggatgccttcatctcccatcaaggatcagattccacattcagtattgtttccccagtc acccttatactctcttccaccccgtatttttggaagcacgtgttttgttcataacttagc ccctgggaaagataagttagctcttcgtgctctcaagtgtgtcttccttggttattctcg tgttcagaagggatatcgttattattctccagatcttcgtaggtaccttatgtcagctga cgtcacatttttttgagtctaaacctttctttacttttgctgaccaccatgatatatctga ggtcttacctataccgacctttgaggagtttactatagctcctcctccaccttcgaccac agaggtttcatccataccagccgttgaggagtctagtgttgttcctcgtagttccccagc cacaggaacaccactcttgacttatcatcatcgttcgcgccctacatcgggcccaactgg ttctcgtcctgcacctgacccttctcctgctgcggaccctgctcctagtacactgattgc acttcggaaaggtatacgaaccatacttaaccctaatcctcattatgtcggtttgagtta tcatcgtctgtcatttccccattatgcttttatatcttctttgaactcggtttccatccc taagtctacaggtgaaacgttgtctcacccaggatggcgacaggctatgagtgacgagat -continued gtctgctttacatacaagtggtacttgggagcttgttcctcttccctcaggtaaatctac tgttggttgtcgttgggtttatgcagtcaaagttggtcccgatggccagattgatcgact taaggcccgtcttgttgccaaaggatatactcagatatttgggctcgattacagtgatac cttctctcccgtggctaaagtggcttcagtccgtctttttctatccatggctgcggttcg tcattggcccctctatcagctgaacactaagaatgcctttttttcacggtgatcttgagga tgaggtttatatagagcaaccacctggttttgttgctcaggagggggtctcgtggccttg tatgtcgcttgcgtcggtcactttatggtctaaagcagtctcctagagcctggtttggta agttcagcacggttatccaggagtttggcatgactcgtagtgaagctgatcactctgtgt tttatcggcaccctgttgacattccgatggatccgaattctaaacttatgccaggacagg gggagccgcttagcgatcctgcaagctataggcggctggttggaaaattaaattatctca cagtgactagacccgatatttcttatcctgtaagtgttgtgagtcgatttatgaattctc cctgtgatagtcattgggttgcagttgtccgcattattcggtatataaaatcggctccag gcaaagggttactgtttgaggatcaaggtcatgagcagatcgttggatactcagatgctg attgggcaggatcaccttctgatagacgttctacgtctggatgttgtgttttagtaggag gcaatttggtgtcttggaagagcaagaaacagaatgtagttgctcggtctagtgcagaag cagaatatcgagcaatggctatggcaacatatgagctagtctcgaccaaacaattgctca aggagttgaaatttggtgaaatcaatcggatggaacttgtgtgcgataatcaagctgccc ttcatattgcatcaaatccggtgttccatgagagaactaaacacattgagattgattgtc acttcgtcagagaaaagatactttcaggagagattgctacaaagtttgtgaggtcgaatg atcaacttgcagatattttcaccaagtctctcactggtcctcgtattggttatatatgta acaagctcggtacatatgatttgtatgcaccggcttgagggggagtgttagtttacagct atgtatatagtgtagtcttgtctcacattggaataggagtagtatgtccttgtatagtat agctataaataagacagtactaacgtcccttttgccgggggttctgcatctttaaataga tgcacgtggttccatagcagaccgtgttgatcacagatcgtgctgcatcctcttcccagc ggactcggtgagcccctcttgtattgtattgaacatccaatatcaataacatattttctc tcgtgctttctcacaggtctgtgatgtacccttgaaaggttcaagagtttggaggaagat agaaactctgtttatctcccaatcatccaaagatcttctaaagttccagttccatccttg tgagctccagactgacttaccaatgcttggctttgaagacttagagagaataagtcagga aaaatctttcaaccttccttgccctatccggtgatcttcccaaaaagatgtcttcaaccc attgccaacattgatcctgatattgctactgaaagatttcttttggtggcaggattactc tcattaacaatgtacttgacaatctccatacatacgaatgtctctttaccctcttgccat taaggttgtaaagagacttgtcaaattaagaagaggtttcctatggaactgtttcaagga aggaacctcctttcctttggtcaagtggagttaagtcatataatctaggaagtggagact tgggtataaaatagctgcaactacagaaaaggagcatcttatttaaatgatcacgcaaat gtgcccaaaactttaaatatctgcggagcatatggttgtagcaaaatttgaatcttccgg tcaatgttgctcatgtccagtgaatacccctgatggtgaaagtgtcctgaagggaagcag gaacttattggaggaattggcatttaacactcagcatttcgttaggtcatagcccgctga aaattgagtgcccagatttatatagttttgctctaaactgacgatgcagttgcacaacat acgacaaactaaggtgggacatcttcttcggaaggaattttgaggattaagagatagagt ggttgattcagttgcaaatgaagcttcaagggttcaatatcatccaggagacaccggatt -continued

```
ctgatagataaaacaacagaaagatgaacactactttgttaggcttgttacaagttgcta

tcgtctttcttatctcggcacacaatttagatttgggaacttatttggaaaatagagtgg

ttgtttttgtgaatagcatcagacaaagcttctgagctggtacgacagaaaactcaacag

ggagaataaaagactgtggttcacgatttctgcatgcatcttgtaggttatttggtgggt

aaaatatttaatgttttgaagggaaggtagaacatgttcataggcttagattcaaatgtt

tgtatttttttggctctttggtgagagatgctgaatgtaaatgacataggcagctgacta

taatttctcagctccttgcttttaaattggcaggcactgatatgtacatgtgaacatcc

aacacttttgtggtgccgttccgatgaataaagcacattaatcacttactgatcaggagt

aatagtttaggagttctagaattttgtacataaaatgaaccaaaaagaatatcggaatg

agaacatgtttctttttttgtttcttctttttcgtacaaatttcaataacacttctgata

gaatagctaggtccatttgaattcctttggagacccttacacaaccaatgaatggcaagt

atagcattttctaacaccctcccacatgtataatccagtttttagggtttagatgtggat

ttgatttgaccttattgcctttttttgtttttgttctttttgaagtagagagtgaggagg

ctcacaacgacgggctacgtagagcgagattaattcggctcaacgggctaatgattggac

ttacatgctacaacaatgttaggagaaagagagagagagagagagaagcccagagcagtt

ccacgagttaagaaagagaagtccaaagcgattgaatatgaagagagaaagcggttgtgc

taacaggctccctcaagtttggctctgagcatccaactcaaaaccttaaggcaatgagta

gagtagcccaggaccatttaaactcctgttgaaaaccttacacaaccaataagggaacaa

gtgtaacattctcttacaaccctaccgtcttataagtcagggctctaatttagcataaaa

tcaaagtgaggcgatctactatgaaatgaagaaaataactgataaatataaagaatgtta

attctcccatatagcctgaatgttcccagaacaaaataaattagtctcatgatttatcat

taacatgatgttcctcttattttgagtgattaggaaggttaatcaaggagtaaattcttt

ctaatttgtatcgtctagaattatttgtctaacaaattttcagattaccggtgatcaaaa

gaggaaaatattttgcatacaacgttaccataccttacaaaagggcgatgaacattttt

tattttattattgtcctttttttcaattaggggttatgcagtcttcctccacgtgatatt

actcttagaatcacgtttttgtcattgctattacttactgtggtaagtacaaatgtgttt

tgaactctttttggtatgtattattgagttaatttttcgtttccatttcagagctgccgc

tttatcttctgctgggcatcttttgtggcttagtttcagtggcattatcaagttgtacat

catttatgctgcaaatagtggaaaatattcaaatgaccagcggcatgccaaaagcagctt

ttcctgtcctgggcggtcttctggttgggctggtagctttagcatatcctgaaatccttt

accagggttttgagaatgttaatattctgctagaatctcgcccactagtgaaaggcctct

ccgctgatctgttgctccagcttgtagctgtcaaaatagtaacaacttcattatgccgag

cctctggattggttggaggctactatgcgccatctctattcatcggtgctgctactggaa

ctgcatatgggaaaattgttagctacattatctctcatgctgatccaatctttcatcttt

ccatcttggaagttgcatccccacaagcttatggcctggtatgaatttgtcttttgttag

aagtagcattacatatctggataagtgagtttttattattgaaaagtaataacaggaga

acaagagaatatatcacccaaatctacttctttcctctcttctattcttctgaaattcaa

ggtcctttaactcctccacagtctgtctagttattgatcctgtagacttaattcacatag

gtttaggacattcgagtttatccaaacttcatgaaaaggtttctaatttttttacattac

attatgagtcgtgtctacttgagaaacatatcactccatgtttctatagtctgttttctc

cttagtttattctgatatgtggggtcctattaagtcagttcaaccttgtattttcattat
```

-continued

```
ttttgcagtatcattgataattattcaagatgtacttggattttctttacaagagatagt
tctcagttgtttttgtgttcctaagtttttatgctgcaatacaaaattggtttgatgtc
tctatttgcatttttcccaatgataatgccttagaatattttcttttccgtttcagtagc
ttattatttctttaggaactctttatcagaaatctcaactgagatagatgagaggaagaa
taagcatatcattggtctcattcagtcccctgtcaagcttagtttcttgagcgatgcggt
ttcacgtccttttattagattaattggatgcctcatctgctatccaaaatcagttaactt
tcgatattgtttcctcgcttacctttatactctctttccctcgagtctttgggagcacat
gttttgttcaataacatagctcctggaaagtgaccagcgcaaccgacaaacaaggccttc
ttaatgtagaaggtggacatatgctattctagccacgggaaagaaagtaatattgtaatc
aaacccaaatatctgagtataacctttggcaatggcgatcaatttgattatatggaccaa
ctttgcctgcatatacccaccgacaaccaataatagatttaccgggaggtagagaaacaa
gctcccaaataccactaatatgtaaagcagatatatctctgatcatagcttgtccttgtg
gacatagggatagaaattaaggacaaagatgacacaaaagcataatgcggtgatgataaa
cgatgataactcaaatcaatataatggggatggggattgagagtggatcgaatatctttg
cggaatgcgattggtagactaggaggagagaagtctgtggacatgatgttggactgagat
caataataagtcaagaatggtggagctacagaacatggaactggagctgtaggtgacata
atcggagctgtaggaggtggagctatagaggaaggtgaaggagagatagcgactgaatct
ccaaaagatgaaaccggtaatacctcaaaaaatgtctaagagatcatttggacctatgaa
gtatgattgcgtttttaaaaaggtaacatcataaggtcaggtgaataacattgatatccc
cgttgcatcctcgagtaacttagaaatatacatttgagagcacggagagctaacttatct
tttctggagcaaggttgtaaacaaaacacgtgctcccaaagacacgaggtggaagagaga
aaggtgagtggggaaacaagacagaggatgaaacttgactcttgatagttgaagatgaca
tacaattaataagacaataggatgtgagatccaatgacagttctcatgaactgctgaaat
ggagaagacaaatactctggggcgttatcactacgaaatgtgcagttagaaaccccaaat
tgattttggatttcagtgtggaaggtctaaaaaatagagaacaactcagattgatttttc
atcaagaatatccaagtggacttggaataatcatcaatgaaactgacaaagtagcggaat
tccaaggtagaactaacccgacaaggaccccaaacatctgaatggactaaagtgaaaggt
aactctacccgattatcaggatgtcgagggaaatgagagtgagtatgccttctgagcgga
tatgactcacgctctagagtggacaagtgagacaaacgaggtactattttctaaagttct
gataaattgggatgtcctaactgtatatgtaataaatctggtggatcagtaaaaggacaa
gctgtaggggggaaaaaaataccaaatatttccagaagatggcaaactacaacagaagatg
caactgcattaacatgctcaggataggtgatgaaatcattgaggacaaagagttgatcaa
gaaggagattctggaattttaccagaacttatatagtgaaaatgaaccctggaggcgcag
tgcaaatttcgaagacatctcctcactaagcatagaagagaagaactggttggaagctcc
atttgtagaaatagaggtgcttgaagctttgaaatcatgtgccccttataaagcaccagg
tccagaaggcttcactatggatttctttcagaaaaattgggatactcttaaaacagacat
catggctgcacttaatcattttcaccagagctgtcacatggttagggcttgcaatgccac
cttcattgccctaattccaaagaaaaatggtgctatggagctcagagactacagacctat
tagcttgacaggtattgtatacaaattggtttcaaagattttagcagagaggctcaagaa
ggtaattgacaaactagtctcgggggaacaaaatgctttcatcaagaacaggcagatcac
```

-continued tgatgcttccttgattgccaatgaagtgctggattggagaatgaaaagtggagaaccagg cgtgttgtgcaaactggacattaaaaaggcttttgatcaattaagctggtcttacctcat gagtatcttgaggcagatgggctttggggagaaatggagaagatggataaactattgcat ttcaactgtcaagtactctgttttggtgaatagggacccaatcggtttttttctcccccca aaagggcctaaggcaggggggatcccctctccccccttcctattcattctggcgatggaagg actcactaaaatgttggagaaggctaagcaactgcaatggatacaaggctttcaggtggg aaggaatcctgccagctcagttacagtatctcatctactctttgcggatgatactcttat tttctgtggtactgagagatcacaagcacgaaatctcaacctgacactgatgatcttcga ggcactatcaggactccacatcaatatgataaagagcatcatataccctgtgaatgcagt ccccaacatacaagagctagcagacatcctatgccgcaaaacagacactttcccaaccac atatcttggacttcccttgggagctaaattcaaatcaaaagaagtttggaatggagtcct agagaagtttgaaaagaggcttgcgacttggcaaatgcaatacctccccatgggtggcag gttaactttaatcaatagtgtactggacagtcttcccacataccacatatctttgttccc aattccaatctcagtcctaaagcagatggacaaactcagaaggaagttcttatgggaagg atgcagcaaaacacacaaatttccactagtgaaatggctgaaggtaactcaaccaaaatt caaaggagtcttgggaatcagggatgctatgctcttaaaatggctctggagatatggaca ggaggaatctaggctatggaaggacatcatatttgctaaatatggagcacacaaccactg gtgttccaagaaaacaaactctccttatggagttggtctgtggaagaacatcagcaacca ctgggatgaattcttccaaaatgtaactttcaaagttgggaatgtaactcgtataagttt tggaaggatagatggcttggaaatacacctttgaaagacatgtttcccagtatgtatcag attgccgtgaccaaagactccactgttgctcataatagaaacaatgacacttggtaccca cttttcagaagaaatttgcaggattgggaggtcaacaacctactcacaatgttaagctcc ctagaatgtcataacattgaagatcaacaacctgacaaacttatttgggaaaattctaag agaggcaagtacacagtcaaagaatgatacattcacctctgtgaccagaatccaatatat aactggccatggaaacatatctggagaactaaagtgcctaccaagatgacttgcttcaca tgattgtctctaaatggggcctgtctcactcaagacaacttaatcaagaggaacatcata taagttaatagatgctacatgtgccaacaacagtcagaaagtgtaaagcacttattcctt cactgctcagttgcaaaagaaatttggaacttcttctacactacctttggtctaaaatgg gttatgccacaatcaactaagcaagcttttgaaagttggtatttttggagagttgataaa tccattagaaaaatctggaaaatggtgtcggccgcaagtttttggtgtatttggaaagaa aggaactgaagatgttttgatggcatatcaactccactcaaggctgcgtgtttagttaac ttattttgctggaactatctcacccctgttaatagtgctgatacttctgtggatttcatt agccccctgatagtagcataggcttttgtaaatggagctaattatcctttctcttttgta ctctttgcatcttcttgatgccttttaatgaatctaatttacttcatcaaaaagaaaatg acaagttgttgaaggaggaaaagatgtgagtccatgtgatttagcaaggataaggtacta aagtccatttgattcacgtccggtaccaatgatccgtctcgtgctgcattcctgtattaa aacagagtcatcaagaaataaaatagagcaaataagtgattggccaagcgactagtggat atgagattaaaaggactatggggaacataaaaaaactgaattcaaaggtaaggaaggaagt ggactagcttaacctattctagttgccatggtttgagaatcgttggccattgtgactatt ggaagtgattgagagtaagaaatagtagtgaaaggagatttgttacccgaaatataatta gatgcacctgaatcaatgacccaaaagtcggaagaagaggaaacacaagtcacgctatta -continued cctgtttgaacaatagagattagtttggatcaaatagttgtatagagaactgaaatttgg agaaatcaatcatatagaacttgtatgtgattattgttgccctttatattgcgtcaaatc ctaaaacacattgagattaactgccacttatcacagaaaagatattctctagagacattg ttacaatttcatgaagtcaagtaattagcttgaacatatcttcagcaagtccctcgtcag tcctcatattagttacatttgtaacaatgtcggtacataagacttataagcaccagtttg aggaggagtggtagagagttgatgtacatagttaaagtagatatacttacacttagtgtt atgtaaagagtggatataaaaagggatcagcataagacaattgtcttcgcgcgtcttaac atttttttcctgtctttatttctctcatggtatcagataacctatctctatcttggttta cccaatggttggcccccatattgtattagccatgctccagttgactaggcttggacgggc agaggtgttaaattatcccatattggttgaaagaatgagctattgtctccttatatggtc ttagacaattctccaactcatgagatattttgttttggctgagttagccctaaggtttat tttttgtcatattctttaaccttatggcaatgcttgtacacggaaaaaccggagtgcaag acttaaattaggagaaggaaactattgaaggtgaggaacttaaagggttgtgagaataca cgggagaaaaaaatcttaatactatctagtggccttgtatatcaaatgatcagcttgcaa atattttcaccaagtccctcactggtcctcgtattagttacatatgtaacaagttcggta tatatgatttgtatgcaccggcttgaggttatgcatattctattcctcctactatatatg tgactaggaaatattttactcctactgcatatgggactaggactatttacacataactat ctaacattcccctcaagccagtgcacacaagtcatatgtaccgagcttgttacatatgta actaatacgaggaccagtgagggatttagtaaaaatatctgcaagctggtcattcgacat acaaggccactagactcccccccgagcaacaaaaccaggtggttgctgataaacagaaact ggccgaaaagttgccggaaaaaatttgaaaatagtgagactaagccgaattctacactaca aaataggttctaaaacaccaccagaaaacaaaaactttctagaaattactcttcacacc ggaaaaaataaaagttgtcagaatttgatgtaatttatatagataggttcggaatcactg gaggagtaagttgtcccgaagaagttttgtcaaaaagtggccggaatggctcacatgcgc cggaaaacttactgtagctcgcaggaaccctagttctggcggtgcgtggaggcgcgtgac ttaagattaagatgcttacaggactatcttgagaaatatacatattatatagacgcttga gttgcttcccaatcctaaatagaagcttttattcgtaggcaagaagggaagcagctttac ttgagccaatagctttcaaggtgcacgttgtcacaccaaggacatccagaatttgatttt atagggggtgtgagaaagcacgggagaaaatatgttattgatatttggataataaataca atacaagaggtccctatttatagctatacactacaaggagatattactcctcttccaatg tgggacaagaatacactatacatatctgtaaactaacactccccctcaagtcggtgcata cacatcatatgtaccgatcttgttacacatgtagctaatacgagaaccaataagagactt agtgaaaatatctgctagttgatcattcgactttacaaactttgtaacaatatctcctga aagtatttttttctctgacaaagtgacagtcgatctcaatgtgtttagtcctctcatggaa caccggatttgacacaatatgaagagtagcttggttatcacacattagttccatcttgct gatttctccgaattttaactccttgagcaactgcttgacccaaaataactcacacgtcgt catagccatggcccgatattcggcttcggcgctagatcgagcaactacattctgtttctt gctcttccacgagaccaaattacctcctactagaacacaatatccagacatagaacgtct atcaaaaggtgatcttgcccaatcagcatctgtgtacccaacaatctgctcgtggccttg atcctcgaatagtaatcctttgcccggagctgactttatataccgaagaatgcgaacaac -continued tgcatcccagtgactatcacagggagaatccataaactgacttacaacactcaccggaaa agaaatgtcaggtctagtcactgtgaggtaattcaatttgccaaccaacctcctatatct cgtagggtctctaagaggctccccctgtccaggcagaagcttagcattcagatccatagg agagtcaataggtctgcaacccatcattccagtctcctcaagaatgtctaagacatactt ccgctgtgaaataacaatacctgagctagactgagcgacctcaatacctaaaaaatactt caatctgcccagatccttagtctggaagtgctgaaagagatgttgcttcagattagtaat accatcctgatcattgccagtaataacaatatcatcaacataaatcactagataaataca cagattaggagcagaatgccgataaaacacagagtgatcagcctcactacgagtcatacc gaactcctgaataattgtgctgaacttaccaaaccaagctcgaggggactgtttcaaacc atatagtgacctgcgcaatctgcacacacaaccattaaactcccctaagcaacaaaacca ggtggttgctccatataaacttcttcctcaagatcactgtggagaaaagcattcttaatg tctaactgataaagaggccaatgacgtacaacagccatggacaaaaagagacgaacagat gctactttagccacgggagagaacatatcactataatcaagcccaaaaatctgagtatat ccttttgcaacaagacgagccttaaaccgatcaacctggccatccggaccgactttgact gcataaacccaacgacaaccaacagtagacttacctgcaggaagaggaacaagctcccaa gtgcaactcgcatgtaaagcagacatctcgtcaatcatagcatgtcgccatcctggatga gatagtgcctcacctgtagacttagggatagaaacagtggacaaagaagatataaaagca taatgaggtgacgacagacgatgataacttaaaccgacatagtggggattaggattaagt gtggatcatacacctttgcggagtgcaattggttgactaagaggagacaagtccgcagta ggtgcagaatctgatgcggggcgtgaatcacctgggcctgatgctggatatggacgacga tgataagtcaagagtggtggagctgccgaaggttgaactggattatgtggaggaactgga gctataggtggtggagctacaactggagctgtaggtggtggaactagagtaactgaatct ccaaaagatgaaactggtagtacctcagaaatatctaagtgatgacctgaacctgtgaag tatgattgggtttcaaagaaggtaacatcagcagacataaggtactgctggaggttagga gagtagcatcgataccccttttgtgttctcgagaaacctagaaatacgcacttaagagca cgaggagctaacttatccgttcctggaataaggttatgcacaaaacaagtgcttccaaag atacgaggtggaagagagagaacaaaggtaagtggtaaaacatgacagagaatggaacttgg ttctggatagctgatgatgtcatacgattaataagatagcaagatgtaagaactgtatcc cccaaaaaacgcaacggagcatgagattgtatgagtagggtacgagcagtttcaataaaat gtctattctttctttcagctaccccattttgttgagatgtgtacagacaagatgtttgat gaataatcccatgagatttcataaactgctgaaatggggaagacaaatactctcgggcat tatcactacgaaatgtgcgaatagaaaccccaaattgattttgaatttcagcgtggaagg tctggaaaatagaaaacagctcagatcgatttttttatcaaaaatatccaagtgcacctgg aataatcatcaatgaaactgacaaaatagcagaatcccaaggtggaactgacccgactag gaccccaaacatctgaatggactaaagtaaaaggtgactctgctcgattatcaagacgcc taaggaaatgggagcgagtatgcttaccgagctgacatgactcacactctagagctgaca agtgagataaaccagataccattttctgaagttttgacaaactgggatgtcccaaccgtt tatgtaataaatctggtgaatcagtaacaggacatattgtagatggaagacaagatgcga gtccatgtatttagcaaggataaggtaataaagtccgtttgattcacgcccggtaccaat gatccgccccgtactgcgttcttgtataaaaacatggtcatcaagaaataaaataacgca tttaagtgatttggctaagcgactaacaactatgagattaaaaggactattgcgaacata -continued aaggactgaatctaaaggtaaggaagaaagtgggcttgcttgacctattgcagttgccat
ggtttgagacccattggctattgtgacttttggaaaagattgagaatacgaaatagtagt
gaaaagagatttgttaccagaaatatgatctgatgcacctgaatcaatgacccaagactc
agaggatgaagattgggaaaaacaagtcacgctattacctgtttgaacaacagaagctat
ctcagaagatgtctgcttacatgctttgtactaaaggaactcaatataatctgctaaaga
aaccatccgactattcaaagcatcggttcccatgtcgctacaatttgtagtagtagggtt
aacttgaaatagtggaaataagtaactccggtgagaaaactgaagaaatagcttgaaaac
actgtttacaacagtaaaaacagaacactgttctgcgccggaatctactgtagctgacgg
aaaaactcaaagtagtcggaatgaaacgaaaaacagtaggggtaggatcggaattaccag
gcgacccaactattctgaaggaagtttttcaaaaaatggccggaagtggtcgtacgtgtc
ggcgcgtgagctcacgcgcgtgagcttctggtggcgcgtggaggcgcgtgaggaggctgc
tgccggagattttcactggggtttggtcgccggacagtgactactcttgtggtagtgttg
gattttgcacaacactgacggagataaagcagacgcaaacagccttgaaaaagtcgccgg
aaaagacttccggtgactgatttctcttcctggaatcgctggaatttatgcacagcgata
aatctctcacaattgctctgataccatgtgagaaagcatgggagaaaatatgttattgat
atttggataataaatacaatacaagaggtccctatttatagctatacactacaaggagat
attacttctcttccaatgtgggacaaaaatacactatacatatctgtaaactaacaaggg
gaatatcgtttaaagataaaaaagatagcgtgcagaagattgcatacattagagatgcaa
aatacagaatacccatactcccagataatgcagtatgccttttgcatgacccactggttg
aatggaagcacctggtcaatttactaggtgtgttagtgatttttgctgcttccttcccct
ttctaaactacatactatctaaaatgttaggggggacagaagcccagtcaatctgactagg
tgatgttagtggtttccgcttctttctcccacttctaaatgcgtactttctcaaatttag
gagcatagaaacttaagcagctgcctacctgaggaggtgcatgggaacataagagaatag
actttacctgtcatattttccataccttagttaattacagtgttatcctgataatgatct
gttttctgtatctaggctgaatcgagattcaatcgcttttggctgaaaggatgctgctac
agatccttagtttacatcattgtggttcttattctataagtacttcccctatcaactact
tccttctttttttcttaggttatttgcctcttaggttgtttgcaaggaaaggaacaataga
tgttttgatggaatagcaactccaaaccacttccttaaggctaatatactgtttggccaa
gcttcttcaaagtccaaagccctttttttgtcttcaaaaaagtatcttttttttcccaaagt
tgaggtgtttggccaaacttttggaaggaaaaaaaaagtgcttttgagtaaagcagaagct
cttgagaagtagaaaaagtagtttttttcccggaagcattttttttgaaaagcacttttgag
aaaaataaacttagaaacactttttaaaagtttggccaaacactaattgctgcttaaaag
tgtttttcagatttattagccaaacacaaactgcttctcaccaaaagtactttttttgaaa
aatactttttttgaaaagtgattttcaaacaaagcacttttcaaaataagtttattttaga
agcttgtcaaccggctataaatgtcttttattttttacagctagagtaccctaacacctgt
aaattcccctagacatttttttttcgactttgttagctcattaaccctagtataggactctt
tgttttggagctagcaaactcttttgttttcctatttttgcatcttcttggtgccattta
taatatctcttacttcaccaaaaaaaaataagttcccaaaatatgactaccttgagttggc
caaagcataaccaaagcttgggcacaccagtgtttgcgtgaattttatggatgttcctta
cctttatccttctgtgcttatgtagcatctgtcttggttaatcttttctgaagtctatag -continued tgtatttctgtgttgcaacatgagtttactgtcaatcttactgtttgacctcaattttgg gttctttttgattttgaaagacatcgtttaacaggttggcatggctgctactcttgctgg tgtctgtcaggtgcctctcactgctgttttgcttctctttgaactgacacagaattatcg gatagttctgcccctcttgggagctgtggggttgtcttcttgggttacatctggacaaac aaggaaaagtgtagtgaaggatagagaaagactaaaagatgcaagagcccacatgatgca gcgacaaggaacttctttctccaacatttctagtttaacttattcttcaggtgtgaaacc ttcacagaaagagagtaacctatgcaaacttgagagttccctctgtctttatgaatctga tgatgaagaaaatgatttggcaaggacaattctagtttcacaggcaatgagaacacgata tgtgacagttctaatgagcaccttgctaacggagaccatatccctcatgctagctgagaa gcaatcttgtgcaataatagttgatgaaaataattttctcattggtctgctgacacttag tgatatccagaattacagcaagttgccaagagcagagggcaatttccaggaggtagcttc ttggtacatttcaatattcttaactgatgaaaaaataagggaaattgatctagcatgaaa ttaagctaattataagttttacactgtagaactggtaaaacagggttggctggatatttc tttgttgaatttttaggattatatgtattgttttagttttgtaggttgttttctgatgtg ctttttgacttggcagaatcttaagatgaaatggaaggtgtttaaccaaaaaatagaatt ttcagtcaaagcctatatttagaagaaaacgggttattgataaccaagttttactttact tccccaacaatctatttggtaaatagcaaaagtaatgcgtatgtgagaaagcacgggaga aaatatattattgatattagatattcaatataatacaagaggtcctacacatcatatagc tatagtctacaaactacatattactctcattccaatgtgggactacacataactaacact ccccctcaagccggtgcatacatatcatatgtaccgagcttgttacacatgtaactaata cgagaaccagtaagagacttagtgaaaatatctgctagttgatcatttgactttacaaac tttgtaaaaatatctcctgaaagtatttttctctgacaaagtaacagtcgatctcaatg tgtttagtcctctcatggaatagcggatttgacgcaatatgaagagcagcttggttatca cacaccagttccatcttgctgatttctccaaactttaactccttgagcaactgcttgacc caaactaactctcacgttgccatagccattgcccgatattcgacgtcggcgccagatcga gcaactacattctgtttcttgctcttccacgagaccaaattacctcctactagaacacaa tatccaggcgtagaacgtctatcaaaaggtgatcctgcccaatcagcatttgtgtaccca acaatttgctcgtggcctcgatcctcgagtagtaatcctttgcttggagatgactttata taccgaagaatgcgaacaactgcatcccagtgactatcacagggagaatccataaactga cttacaacactcaccggaaaagaaatgtcaggtctagtcactgtgaggtaattcaatttg ccaaccaacctcctatatctcgtagggtctctaagaggctccccgtgtctaggcagaagc ttagcattcggatccataagagagtcaataggtctgtaacccatcattccagtctcctca aaaatgtctaaggcataattccgctgtgaaataacaatacctgagctagactgaggcact gagcaacctcaatacctagaaaatacttcaatctgcccagatccttagtctggaagtgct gaaagagatgttgcttcagattagtaatatcatcctgatcattgccagtaataacaatat catcaacataaaccactagataaatacacagattaggagtaaagtgccgataaaacacag agagatcagcctcactacgagtcatggcgaactcctgaataattatgctgaacttaccaa accaagctcgaggggactgtttcaaaccatataatgacctgcacaatctacacacacaac cattaaactccccctgagcaacaaaaccaggtggttactccatataaacttcttcctcaa gatcaccgtggagaaaagcattcttaatgtctaactgataaagaggccaatgacgtacaa cagccatggacaaaaagagacgaacaaatgctattttagccacgggagagaaagtatcac -continued tataatcaagcccaaaaatctgagtatatccttttgcaacaagacgagccttaagccgat caacctggccatccgggccgactttgaccgcataaacctaatgacaaccaacattagact tacctgcaggaagaggaacaagctcccaagtgccactcgcatgtaaagcagacatctcgt caatcatagcatgtcgccatcctggatgagatagtgcctcacctgtagacttagggatag aaacagtggacaaagaagatataaaagcataatgaggtgatgacacacgatgatgactta aaccgacatagtggggattaggattacgtgtggatcgtacgcctttgcggagtgcaattg gttgactaagaggagacaagatcgtagtaggtgcagaatctgatgcagggcgtgaatcac ttgggcatgatgttggatgtggacgacgatgataagtcaagagtggtggagctgcagaag gttgaactggattatgtggaggaactggaggtggagctacaactggagctgtaggtggtg gaactggagctataagtggtggagctacaactggagctggagatgtagaggaagatgaat gagagatagtgactgaatctccaaaaaataaaattggtagtacctcagaaatatctaagt gatgacatgaacctgtgaagtatgattgagtttcaaagaaggtaacatcagcggacataa ggtaccgctgaaggtcaagagagtagcatcgataccccttttgtgttctcgagtaaccta gaaatacgcacttaagagcacgaggagctaacttatctgttcctggagtaaggttatgga caaaacaagtgattccaaagatacagggtggaagagagaacaaaggtaagtggggaaaca tgacaaagaatggaacttggttttggataactgaagatggcatacgattaataagatagc aagatataagaactgcatcccccccaaaaacgaaacggagcatgagattgtatgagtaggg tacgagcaatttcaataagatgtctatttttttctttcagctaccccattttgttgagatg tgtacagacaagatgtttgatgaataatcccatgagatttcataaactgctgaaatgggg aagacaaatactctcgggcattatcactaggaaatgtgcgaatagaaaccccaaattgat tttgaatttttagcgtggaaggtctggaaaaatagaaaacaactcagatcgatttttat caaaaatatccaagtgcaccttgaataatcatcaattattcaataaaactgacaaagtag cagaatcccaaggtggaactgacccgactaggaccccaaacatttgagaatggactaaag taaaaggtgactctgcttgattatcaagacgccgagggaaatggaagcgagtatgcttat cgaactgacatgactcacactctagagctgacaagtgagataaaccagataccattttat gaagttttgacaaattgggatgtcccgaccgtttatgtaataaatttggtgtattagtaa caggacaagttgttgaaggaagacaagatgtgagtccgtgtgatttagcaaggataaggt aataaagtccgtttgattcacgtccggtaccaataattcgtcccgtactgcgttcctgta taaaaacatggtcatcaagaaataaaacaacgcatttaagtgatttggctaagcgactaa tagttatgagattaaaaggactattgggaacataaatgactgaatataaaggtaaggaag gaagtgagcttgcttgacttattgttgttgccattgtttgagacctattggccattgtga ctcttgaaagagattgaaaatacgaaatagtagtgaaaagagatttgttaccagaaatat gatctgatgcacctgaatcaatgacccaaaactcagatgatgaagattgggagaaacaag tcacgctattacctgtttaaacaacagaagctatcacagaagatgtctgcttacatgctt tgtaccgaaggaactcaatataatctgctaaagaaaccatccgactattcaaagtatcgg ttcccatgtcgctacaatttgtagtaataggatggatagactcggaaaattgtaaagtta tcggaatttgtcgtaaccaggatcgagcaagctgtcttgaagaaatggtttcaaaaaatg tccggaaaggtcacttttacgccggaaaaatataaaaatggtcgaaatttgatttgaatt agatgggtaggctcggaattgtgaggagagcagactgtcctgaagaagcttaatgaaaaa atggccggaaagtggccggaaccctcgccgtaaaagttgttaccggcgcgtgaaggcgcg -continued tggcatttttctgccagataaattttcaggggttggtcgtcggagggtgatcccttgtg
gtggtgttggtttttgcacaataccgacaggccttaggtcacccgaaaatttgcacgatg
actaagttctttcttcccggttaacgctggaatgacgcacatcgatcttttctcactaat
gctatgataccatgtgagaaagcacgggagaaaatatattattgatattagatactcaat
ataatacaagaggtcatatttatagctatagtctacaaagtacatattactctcattcaa
atgtgggactacacataactaacaacgtaaattaacaaagagaaataaggaatgtaacaa
cagtcaatccctaaaatcaaggtagaaaactttgataaagcagagaattatagaatgtat
ttcagtagtacttggaacttgtccttacaaataaaaattctttatccttatataggggcgt
acaatcataacatttttcgcacttaattcgaattcattatgagcattaattgtattgatt
gcccgttatcatagataaccataactgacgtatttgtaactataaatgccttataacggc
tctgattccccttccttatttacttctggtttgtgtatctttccttctttttagccttta
ttcattcagttctcgcctcttctttgacaactgtcaagcccgatcctctgttctgtactg
tctcgtgggtgtttcccccgtaccttccttatattcttaattctgttaattgagagtgtc
acttgtcactatgccattgttccacgcgtcatgtttcatccacgtgtaatatctttttc
caccaatacagataatcccccactttctgaatattctcaactgaatattcgggtaagttt
ttatggcgggaattctttgccgtcgtttttcgagtatcatcgtgtcatcttcagaaccga
tgtgacgtacgtcacgtctatttaatgcctatgccaggtggcttctatcgattggctctg
cagtttttttagcgctttttagggtttttcagcggctgcgtcagtcacgaagtgacggttc
cattatgacgcttcataatgactaactttaatgatggtcgtgtcttcttattaatacttc
attcctttttgatctcttggagtcttccttcttcagtatccaccacattacttctttgta
tttctgcatcttctctttgatattcctttggacaatcatgtcttcttctacaccagaccc
ccgtaaggttgtgattgttgacgaacttgatctttctactgctcctactagaagtaggag
aggtggtagacttcgtagtcttggttcactatctaatcgtggttcttcttcccagggtag
tgctgctaagccatcttcttctagacctagggctcctttaaccccctagatcttcttctag
gaatagagatttaaatgatccagtgcgcgaacctacagttgcagagattgttcctcaaga
attttcttttgtaactgaccgtgaaaccataaggaatcaaatttcttctatagcctccct
caataccgctaacctttatccaagtttaatcagtaatggtcttctctcccgggttcgaag
agaatattactgaaaccagatttcccaattttagtccctggtgccaaccagagaattact
ccataccatgttggtttttcctttgtttacacctacccttttactttagggttcaaacca
cctattgaaccagtaatcattgaattctgtcgttatttcaacgtgtgtcttggccagatt
gaccacatagtatggagggctgttcatgccttcgttatttatcagatttggtttccatgc
ctttcacttttcagcacttgcttcatctctactcccctaaattgtttcgtgaagtagttt
ttactctcgtggctagaagtaagagagtgttggttagccttgaagacgattgggaccgtg
gctggtacgctcgttttgttgctgctcccactagtgcattagtgggtgaagaaaatatgc
ctttcccggagaaatggaactttgcacgtaagctttcttctcctctttttttttgtctta
aaaaaactccatgtaatcatatacccacttcttcagcaactatggaagtttttatgctt
gggtagaaaagatgttaactgctgcgcctatggagaaaagatcctggaaatacttttctc
aaagatttggttggaaagtgaagacgcacggtactttttaccttcattgtttttcctttt
ctcttccttgtttgttcaatgatttctcatccttcccttttttttactagggtttccga
ttcgtggtattagtcccgcgtctgttccatcaactaggctttccgtgattcttgttcagg
aaagaattttaagtgcttcttcttcaaaaaggaaaactgacggagcccgtggctctgatg -continued acgaagaagaaacagaggagggttctttggtgcgaaggtcacgcgtcaggagacgcgtgg tttctgatgatgaaactactccttctcatgaccctctatctagttcaatccccttttagac tcacggatgagctagagagtaccccttttagtgatttcttatgatgatgctgttgatcccc ctccaagttctgttgatagattgtttgctcatggcttcgagggtgatgaagttttgggcc tgtttctgaagaattgccccttgcttcccttccagtttcagttttcattaacccttccgt gtccttacctgatgatactcctgttgttattctcgtggctgcttctactccgtcatctat tcccgtgactgcttctcatgcagaggccaaaccttctagcagcagaagggcaatgaaaag agttgttgttgaggttcctgaaggtgagaacttattaagaaaatccggtcaagccgacgt gtagttgaaacctatgctcggccccgtagagaagaagaagttagaaagccatagctcact cactttaatgaatgatatcgttcattcttccttgaaagtacaagcttaattatatttcct ttcttttctctttcttattcataactcttcctcctttttttgcagatcaacttgattggca cagagcttatgaaaagagtttctcaggcggaccggcaagttatagatttgcgcaccgagg ctgataactggaaggaacaattcgaaggtcttcaattggaaaaagaggttccggcggaag agaagaatgctttggaacaacagatgagagtgattgcctctgaattagcagttgaaaaag cttcctcgagccaggttggaaaggataagtatatacttgaatcctcctttgctgaacaac tttccaaggcaactgaagaaataaggagtttgaaggaactccttaatcaaaaagaggttt atgcgagagaattggttcaaacacttactcaagttcaggaagatctccgtgcctctactt ataagattcagttcttggaaagttctctcgcttctttgaagacagcttacgatgcctctg aagcagaaaaagaagagctgagagctgagatttaccagtgggagaaggattatgagattc tcgaggataatctatcgttggatgtaagttgggctttcttaaacactcgtctcgagactc tagttgaagccaaccatgagggttttgaccttaatgctgagattgctaaggctaaagaag caattgataaaactcagcaacgtcaaatcttttcctcacctgaagacgaaggtcccgaag gtgatggagattga

SEQ ID NO: 5

(Protein sequence of CLC-Nt2 from *Nicotiana tabacum*, translated from SEQ ID NO: 1)

MEEPTRLVEEATINNMDGQQNEEERDPESNSLHQPLLKRNRTLSSSPFALVGAKVSHIES

LDYEINENDLFKHDWRRRSRVQVLQYVFLKWTLAFLVGLLTGVTATLINLAIENMAGYKL

RAVVNYIEDRRYLMGFAYFAGANFVLTLIAALLCVCFAPTAAGPGIPEIKAYLNGVDTPN

MYGATTLFVKIIGSIAAVSASLDLGKEGPLVHIGACFASLLGQGGPDNYRLRWRWLRYFN

NDRDRRDLITCGSSSGVCAAFRSPVGGVLFALEEVATWWRSALLWRTFFSTAVVVVILRA

FIEYCKSGNCGLFGRGGLIMFDVSGVSVSYHVVDIIPVVVIGIIGGLLGSLYNHVLHKIL

RLYNLINEKGKLHKVLLALSVSLFTSICMYGLPFLAKCKPCDPSLPGSCPGTGGTGNFKQ

FNCPDGYYNDLATLLLTTNDDAVRNIFSINTPGEFQVMSLIIYFVLYCILGLITFGIAVP

SGLFLPIILMGSAYGRLLAIAMGSYTKIDPGLYAVLGAASLMAGSMRMTVSLCVIFLELT

NNLLLLPITMLVLLIAKSVGDCFNLSIYEIILELKGLPFLDANPEPWMRNITAGELADVK

PPVVTLCGVEKVGRIVEALKNTTYNGFPVVDEGVVPPVGLPVGATELHGLVLRTHLLLVL

KKKWFLHERRRTEEWEVREKFTWIDLAERGGKIEDVLVTKDEMEMYVDLHPLTNTTPYTV

VESLSVAKAMVLFRQVGLRHMLIVPKYQAAGVSPVVGILTRQDLRAHNILSVFPHLEKSK

SGKKGN

-continued

SEQ ID NO: 6

(Protein sequence of CLC-Nt2 from *Nicotiana tabacum*, translated from SEQ ID NO: 2)

MEEPTRLVEEATINNMDRQQNEEERDPESNSLHQPLLKRNRTLSSSPFALVGAKVSHIES

LDYEINENDLFKHDWRRRSRVQVLQYVFLKWTLAFLVGLLTGVTASLINLAIENIAGYKL

RAVVNYIEDRRYLVGFAYFAGANFVLTLIAALLCVCFAPTAAGPGIPEIKAYLNGVDTPN

MYGATTLFVKIIGSIAAVSASLDLGKEGPLVHIGACFASLLGQGGPDNYRLKWRWLRYFN

NDRDRRDLITCGSSSGVCAAFRSPVGGVLFALEEVATWWRSALLWRTFFSTAVVVVILRA

FIEYCKSGYCGLFGRGGLIMFDVSGVSVSYHVVDIIPVVVIGIIGGLLGSLYNCVLHKVL

RLYNLINEKGKLHKVLLALSVSLFTSICMYGLPFLAKCKPCDSSLQGSCPGTGGTGNFKQ

FNCPDGYYNDLATLLLTTNDDAVRNIFSINTPGEFHVTSLIIYFVLYCILGLITFGIAVP

SGLFLPIILMGSAYGRLLAIAMGSYTKIDPGLYAVLGAASLMAGSMRMTVSLCVIFLELT

NNLLLLPITMLVLLIAKSVGDCFNLSIYEIILELKGLPFLDANPEPWMRNITAGELADVK

PPVVTLCGVEKVGRIVEVLKNTTYNGFPVVDEGVVPPVGLPVGATELHGLVLRTHLLLVL

KKKWFLNERRRTEEWEVREKFTWIDLAERGGKIEDVVVTKDEMEMYVDLHPLTNTTPYTV

VESLSVAKAMVLFRQVGLRHMLIVPKYQAAGVSPVVGILTRQDLRAHNILSVFPHLEKSK

SGKKGN

SEQ ID NO: 7

(Protein sequence of NtCLCe from *Nicotiana tabacum*; sequence originating from the ancestor *N. sylvestris*; one start codon, translated from SEQ ID NO: 3)

MCDSSKVDSDSGIQIGSLLEEVIPQGNNTAIISACFVGLFTGISVVLFNAAVHEIRDLCWDG

IPYRAASEEPIGVHWQRVILVPACGGLVVSFLNAFRATLEVSTEGSWTSS

VKSVLEPVLKTMAACVTLGTGNSLGPEGPSVEIGTSVAKGVGALLDKGGR

RKLSLKAAGSAAGIASGFNAAVGGCFFAVESVLWPSPAESSLSLTNTTSM

VILSAVIASVVSEIGLGSEPAFAVPGYDFRTPTELPLYLLLGIFCGLVSV

ALSSCTSFMLQIVENIQTTSGMPKAAFPVLGGLLVGLVALAYPEILYQGF

ENVNILLESRPLVKGLSADLLLQLVAVKIVTTSLCRASGLVGGYYAPSLF

IGAATGTAYGKIVSYIISHADPIFHLSILEVASPQAYGLVGMAATLAGVC

QVPLTAVLLLFELTQDYRIVLPLLGAVGLSSWVTSGQTRKSVVKDREKLK

DARAHMMQRQGTSFSNISSLTYSSGSPSQKESNLCKLESSLCLYESDDEE

NDLARTILVSQAMRTRYVTVLMSTLLMETISLMLAEKQSCAIIVDENNFL

IGLLTLGDIQNYSKLPRTEGNFQEELVVAGVCSSKGNKCRVSCTVTPNTD

LLSALTLMEKHDLSQLPVILGDVEDEGIHPVGILDRECINVACRALATRE

QLC

SEQ ID NO: 8

(RNAi sequence used to silence CLC-Nt2)

gtcatcatcaggtgtgtgtgctgctttccgttctccagtaggtggtgtcctatttgctttagaggaagtggcaacatggtggagaa gtgcactcctctggagaactttcttcagcacggcagttgtggtggtgatactgagggccttcattgaatactgcaaatctggcaac tgtggactttttggaagaggagggcttatcatgtttgatgtgagtggtgtcagtgttagctaccatgttgtggacatcatccctgt tgtagtgattggaatcataggcggacttttgggaagcctctacaatcatgtcctccacaaaattctgaggctctacaatctgatca acgagaagggaaaactacataaggttcttctcgctctgagtgtctcccttttcacctccatttg

SEQ ID NO: 9

(RNAi sequence used to silence CLCe)

gaaatcctttaccagggttttgagaatgttaatattctgctagaatctcgcccactagtgaaaggcctctccgctgatctgttgct ccagcttgtagctgtcaaaatagtaacaacttcattatgccgagcctctggattggttggaggctactatgcgccatctctattca -continued tcggtgctgctactggaactgcatatgggaaaattgttagctacattatctctcatgctgatccaatctttcatctttccatcttg gaagttgcatccccacaagcttat

SEQ ID NO: 10

(DNA sequence of NtCLCe from *Nicotiana tabacum*; sequence originating from the ancestor *N. sylvestris*; two start codons)

atgattagcggccaaaacactgtgctgcacaatcctcctaattcgctcttcaattcctta tctcctcgccatatctgtatatctttctgtaacgacaaagctttaaaaaagtcagtcacg cactccgcccctcggtttgctcgtctgttaaacaatgaatcacggaagttgttgggtcgt catccaaattgctggccttgggctcgacgaccatctcttcctccgggacgttcctctgac ggaaacattgaaaaagaacaagatatgtgcgacagcagcaaagtcgatagtgatagtggc atccagataggatctctgctcgaggaagttatcccacaaggcaataataccgctataatc tcggcttgctttgttggcctcttcaccggtatcagtgtcgtgcttttcaacgctgcggta cgtgcgctataggtctttcatttctcttttcatgtactattcctccttacttacttggcc tcagtcaatcagcccccctgcctactttaaattattgtacattttatcagaggagtgtcct atacatcaaattcacataacttagtaaaatatgctgatattctgaattttaaacttacca gcttagaacatccaggttagttcagaaacagataatctaaattggtctcatttataagtc attttgttattcaagacatacaatttggctcttgataaaagattatgcagcgcccgatga ttacctaatatttatcagcaacccatgtaatttaacaatattgtcaccatataaaagaga actgaagagaatgttcaatttgtggtcatataacggatatctcccttggttaggttcatg aaatacgtgatctttgttgggatggaattccatatcgagctgcctcagaggagcccattg gagtacattggcaacgtgtaatcttagtaccagcttgtggcggtttggtagtcagctttt tgaatgccttccgagccactctggaggtttcaactgaaggaagttggacatcatctgtta aatctgtattggaaccagttttgaagacaatggccgcttgtgtcacattaggaactggga attccttaggaccagaaggccctagtgttgaaattggcacatctgttgccaagggagttg gagctctgcttgataaaggtggtcgtagaaagctgtcactcaaggctgctggatcagctg ctggaatcgcttctggtttgttccccatattattcttggttctgaaccatacatggtaca ttttccttataattacatgtagcctgttgtatgctttcctctttcccgggaagcctttt gtaaatacaagtgtgtttgcactcaaaccaataaactgtaaaaaaggtgaactccttaag caagcaaaagcattagaaatgtaaactagacatatttctcagattgagagtctgagagat tagaacacgagtgtttccattagagagagaaaagagacttctagatatttctattatctc tgtaagagtgaatccgttcctatacaaaaaataggccttcattaaatacaagcttgggct gggtactactgggccaaagtaaaaaataaaaagaatcacccactatcaaatgggcctagt ctaacaaccccccttcaagctggagggtgacacaacccctagcttgcgaatatgaaaatga tgagcaggcccaagtaacactttggtaagaacatcaaccacttgagaagcactggagttg tgaaatagactgatcaggccattcccaagcttgccacaaacaaaatgacagtccagctta atgtgtttagtgcgttcatggaaaacttggtttttttgcaatgtggacttcctgattatca caaaataaaggaacaggtaaagaaggagaaactccaatatcagacaataatttggtgagc caagacacctctgcaacagccttactcatggacctatactcagcttcaattgatgatagt gagacaacaggttgcttctttgatttccagctcaccaagctgcccccccaagaaaaataca aaaaccagtgacagacctgcggctgtctgggcaagaagcccaatcactgcacaataaagc tgcaaagacaagtctggagagttattgcggaagattccaaagtcaaaagtgcccttgagg tatcttagcaagtgcagggcagcctgcatgttaggaacacagggagactgcataaactga -continued ctcagatgctgaacaacaaaactaaggtcaggccttgtgcgtatcaaaaagtttagcttg tgcattagactcctgtactcttcaggcctgggcaaaggagtgccaatcttagcttttaac ttcacattcaattcaaggggggcaagtgacagaagagcaattcgaggaatgaaaatcagcc agcaaatcatgaatgaactttttctgatgaagaagaaccccagaatcagtgtataaaacc tcaatgctaaggaagtaattaagagagcccatgtccttaatcttgaactggtcactgaga aaggacttcaaagcagccaattcagctagatcacacctagtcaatatgatatcattcaca tagacaaccaagatgaccaaggaatccctagaacccttggtaaaaatagagaaatcattc aaggaacgagagaagccattagagcacaaggcttgagataatttagcatactattgtctt gaagccagtcttaaaccataaagagacttctggagtttgcatactaaaggagcagaagaa gagtgaggaacagttaggcccggtggcagcttcatgaatacctcctcatcaaggtcccca tgtaagaagacattattcacatctagttgaaagaggggccagtgttgtttaacagctaca acaataagagttttgacaatagacatattgaccacaggagaaaaagtttcattaaagtca ataccctcaacttgagtgacctagctttatatctctcaatactttcattagccctatatt taaccttgtatacccacttacaactagtaggtttcttgccaggaggcaattcaacaatgt cccaagttctgttggcatccaaggcctcaaattcacatctcatggctgcctgccattcag gaacagctgcaacctgagagtaagaataaggctcaggaacatgaagttgactaagagaag gagcattagaaatagatctggagggaggaggagaagaagtggaggtgcagacataactct tgagatagttggttggattgtgtggcacggaagatcttctcaaagcaggaggaggtacaa gagagttagaataatgagaaggagaagagatggaagtgggaacagagaagattgagaagc agtagaaggagaaagtgaaggagatgaaggagaggaagaagacggaaaggaacattcatc aaaacaagcagaaaagggaaaggggaagacttgaggtactacatgagaggattgaaagaa aggaaaaatggtgttcataaaaaatgacatcttttgatacaaaacaggtgttattctgaa gattaaggcgcttgtagcccttttggcaaaagggtagccaatgaaaacacaaggaaggg acctaggatgaaatttgttttgtgaggggtggtgacagttgagtaacagaggcacccaaa agctctaaggtggtgataagtagggtggaagaatgaagcaattcatagggacttttgtga ttaagaagaggaaaaggaaatctgttaattaaatatgtggcagttaaaaagcagtcaccc caaaatttaagtggtagatgagactgaaacataagtgacctagcagtctctagtaaattt ctgtgttctctttctacaataccattttattggggggtgtgaggacaggaggtttggtgt actatcccttttctgaaaagaaaaggcaaccagaagaactagatcccagttccaaagca ttatcactcctaacagtttgaactttagattggaattgggtttcaaccatagcaatgaaa accttgagcaaatcaaaggcattgcggcacccattaaatgtgtccaagtagccctagagt agtcatctacaatggttaaaaaaatacctagaaccattataggtaggagtagaatagggtc accaagtatttatgtgtattagctgaaaaggctgggtggagtgaatagaactatcaggga aggacaacctggtctgcctcgctaaaggacaaaccggactagtgaatgaccgtttggaag acagtttgcaattaagaccagaaatgcatttcattttatagaagggaatatggccaagtt tgtaatgccaaacaacatcatctttattcacattatgcaaagcagtactagtatttacaa ttggagtatcatcaggtacagaaataggagcagaaactgaattaagcaaacaagaaataa ggaaattagaaagaggtaaaggagatgatgttggaggcctggcattctgaaatagtttgt agagtccattgtccaatctaccaagaaccactggcttcctcactgaagggccctgtaggg tacaagtagccttggtaaattgtacaatatcatcatcatgggaaagtaatttgtacacaa -continued agatgagattatattgaaaactaggaatatagagcacattataaagaatcaagtcaggga acaaggctaaggaaccaatattagtgaccttaaccttatacccattaggaagggagacaa ggtatggtacaggaagtgtttgaacattaaaaaaacaaatgtttaagggaggtcatgtgg tcagatgcccagggtctattactcaaactacactatctatcatagtcagcataaatgcac cataagacaacccttgtgaggtaataactcaccagcaaagttggtagaagcaagatagtt ggttgaagaagtagatgatgctgatgaagacagttgagattgttgaagtaacattagctg agaatattggttcttggtaagaccaggaactggataggactgttcaggagcagaggtacc ttcaggaccagctgacattgcagaaccaccagaggtatccacctcagcatgggcaacaga ccttctgggaggaagagatctatttgacttgaaatttggaggaaagccattgagcttata gcacttatcaatgctatgtccgggtttcttacaatagtagacatgtgaagctcaaaagat cccttagaggtagtaccggacctttgaggttcaaaatttattttaggagagggaggaggc ctggatacaccaacactgaaagaagcagaatttgaggcatattgagttctagcaaaaatt tgtctttgcttctcatcagatagcaaaatcccatatacattaccaatggaaggtaagggc ttcatcatgatgatgttgcttcttgtttggacataagtatcattcagtcccataaagaac tggtagaccttttgttccctgtcttcagcagatttacccccacaagtacacattcaaact ctcccggcagacaaagatgcaatatcatcccatagtcgtttaattttgttgaaatatgat gctatgtccatggacccttgggaaatatgagccagttccttctttagctcaaagatccta gtacctctcttctaactcagtccaaatattcttagcaaactcagagtattcaacactctt ggatatttccttgtacatagagttagtcaaccaagagaccacaaggtcattgcaacgtta ccactgtctggctagaggagaaccttcaggaggtctgtgagaagtaccattaatgaaatc tagcttgttacgaatagacaaggcaactaggacattacgtctccaattgccataacagct tccatcaaaaggaccggaaactaaggaagttcccagcacgtctgatggatggacatataa ggggcgacagggatgggtataatcatcttcatggaaaattaggcgtaagggagtagaaga agtcgcatcagcactggtgttattatcatttgccatttttttcaacagattgtcaatcaa ccaacacaatacagatacacatatatagattgtgagaaagcacgagagaaaaatctatat tattgatattctatttaattataatacaatgagccctatttatacaatacatatcatact cctattctatgtgggactaggactaattcatattatgtacataactatctaacactcccc ctcaagccggtgcatacaaatcatatgtaccgaacttgttacatatgtaactaatacaag gaccagtaaggaacttggtgaaaatatctgcaaactgatcatttgacttcacaaactttg tagcaatatctcatgagagtatcttttctctgacgaaatgacaattaatctcaatgtgtt tagttctctcatgaaacaccggatttgatgctatatgaatggcagcttggttatcacaca tcagttccatcttgctgacctcaccaaatttcaactaattaagtaaatgtttgatccaaa ctagctcacaagttgtcacagccattgctcgatattctgcttctgcactagaccgagcaa ccacattttgtttcttgctcttccaagacacctaattacctcctactaaaacacaatatc cagacgtagaacatctgtcaaaaggtgatcctgcctagccagcatttgagtacccaacaa tttgctcatggcctcgatcttcaaacaataatctgttacctggagctgattttatatatc gaagaatgcagacaactgcatcccaatgactatcacaaggagaatccaagaactgactta ccacactcactggaaaggaaatatcaggtctaatcactgtgaggtaatttaatttaccaa ccagccgcctatatctagcaggatcgctaagcggctccccctgtcctggtagaagtttag aattccgatccataggagtgtcaataggtctacaacgtgtcattcctgtctcctcaagaa tgtctaaggcatacttcctttgtgagataacaatacatgtgctagactaagcgacctcaa -continued tacctagaaaatactttaatctgcccagatccttagtctgaaagtgctgaaagagatgtt
gtttcaacttagtaataccatcttgatcattgccggtaataacaatattatcaacataaa
ccaccagataaatactaagatttgaagaagaatgccgataaaacacagagtgatcagctt
cactacgagtcatgccgaactcttgaataactgtgctgaacttaccaaaccaggctcgag
gagactgttttagaccatagagggaccgacgcaaccgacatacaaggccactagactccc
cctgagcaacaaaaccaggtggttgctccatataaacttcacctcaaggtcaccacgaag
aaaagcattcttaatgtccaactgatagagaggccaatggagaacaacaaccatggatag
aaaaaggcggactgatgctattttagccacaggagagaaagtatcactgtaatcaagccc
aaatatctgagtataccctttggcaacaagacgagccttaagtcgatcaacctggccatc
tggaccaactttgactgcatacacccaacgacaaccaacaataaatttacccgaaggaag
aggaacaaactcccaagtaccactcgtatgtaaagcagacatctcgtcaatcatagcctg
tcaccaccctagatgagacagtgcttcacctggatggaaatagaggacaaagatgataca
aatgcacaatagggtgatgacagacgatggtaacttaaaccgacataatggggattagca
tttagtgtagaccgttcacctttccggagtgcaatcaattgactaagaggagacaagtcc
gcagtattagcaggatcaggtgcaggacgtgaatcagctgggcctgatgctgggcgcgga
cgacgatgataagttaggagtggtagagctgtagaaggttgaactggactaggcagtgga
actgaagctatatgtggtggaactggagctataggtggtggagctggagctgtaggtgaa
gatgaatgggagatagtgactgaatctccaaaagatggaactggtagcacctcagatata
tctaagtgattacctggactggtgaagtatgattgggtttcaaagaaggtaacatcagca
gacataaggtaccacctgaggtcaggagaatagcatcgatatcccttttgtgttctcgag
taacccaaaaatacgcacttaagagcacgaggagctaatttatcttttcttggagtaagg
ttatgaacaaaacacgtgctcccaaaggcacggggtggaagagagaacaaaggtaagtgg
ggaaacaagacagagaatggaacttgattctggatagctgaagatggcatacgattaata
agatagcaagatgtaagaactgcatcccccccaaaaacgcaacggaacgtgagattgtatg
agtaaggtacgagcagtttcaataagatgtctattctttctttcagctacccgattttgt
tgggatgtgtatggacaagatgttttatgaataatcccatgagagttcataaactgttga
aatgggaaagacaaatactctaaggcattatcactacgaaatatgcggatagaaacccca
aattgattttgaatttcagcgtggaaggtctggaaagtagaaaacaactcagatcgattt
tttatcaaaaatatccaagtgcacctgtaataatcatcaatgaaactgacaaagtagcgg
aatcccaaggtagaactgacctgactaggaccccaaacatctgaatggactaaagtaaaa
ggtgactgactctgctcgattatcaagacggcgagggaaatgggagcacgtatgcttacc
gagctgacatgactcacactctagagtggacaagtgagataaaccagataccatttttg
aagttttgacaaactgggatgtcccaaccgtttatgtaatagatctggtgaatcagtaac
aggacaagttgttgaagaaagacaagatgtaagtccatgtgattttgcaagaataaggta
gtaaaatccatttaattcacgcccggtaccaatgatccgccctgtactgcgttcctgtat
aaaaacaaggtcatcaagaaataaaacagagcatttaagtgatttggctaagcgactaac
ggctatgagattaaaaagactaacgagaacataaagaactgaatctaaaggtaaggaagg
aagtggacttacttggcttattccagttgccatggtttgagactcgttatccattgtgac
tgttgggagtgattgagaatatgaaatagtaatgaaaagagatttgttaccaaaaatatg
atcagatgcacctgaatcaatgacccaagactcagaggttgaagattgggagacacaagt -continued

```
cacactactatctgtttgagcaacggaagctatccctgaagatgtttgtttacatgtttt
gaactgaaggaactcaatataatccggtagagaaaccatccaactcttcgtagtattgga
ttccattttgctacaaccaatttctcaaattcttgattacaacttgtgtggttaaccttg
gaatgccaaatcagaacacccctttttttttttggaaaacattgttcactcgctggaaa
ataaaaaaggttgccggaatttgatgaaacttgaatagaccgactcggaataatgtccta
agaaggctgtccaaaaggagttttgtcagaaactgaccagaaggaggtccacgcaccggc
gcgtggacagatctcgccgaaaaaaaaaatcactttggttggcgcgtgatggcgcgtggg
tggggtttttccggtcgggttttgtggggtttgctcccccggagatggagaacactgtgg
tggtgttggtttatgcacaacactggtaaaaagtggttttgatgcgaacagctactcagg
tcaccaaaaaattgcacggtgacgactgatttcttcccggatgtcgttggaatgacgcac
aacgataattatctcaccaatgctctgataccatgtgagaaagtacgggagaaaaatcta
tattattgatattctatttaattataatacaatgagccctatttataagactaggattaa
ttcatattatgtacataactatctaacatagatcaaataggcatgcaattcacaataatg
gtgaataaaatgatacgaagttacccagctcttttcgcgatcgaaaaggagaaaatagcc
ttcaatcacaaacgagaaagaagaatctccggcttgacagtagacgacttcgaaacccta
gctcgagatgaaaaccacaaaatccccaaatcacattaccaaccaaacaatttgagatca
caaatgttgaatatgtgagaatccgactaagaaatcaacaaaaaatcaatagaaatggtt
gaagaataccgacttgaaccctaaatgagtcagacatcacctagaatgaaatacaccttc
gaaattgacgaaaacaggaccggttgaaagcggagaacgtgccatagaaggatctacgct
ctgataccatgtaaacttgacatacttctcagattgagagtctgagagattagaaaacga
gtgtttccattagaaagagagaaaagagacttctagatatttcgattatctgtgtaaaaa
tgaatccgttcctatacaaaaattaggccttcattaaatacaagattcggccgggtatta
ctggcccaaagtaaaatataaaaagaatcacccactatcaaatgggcctagtctaacaag
aaaaccaacaaatagtccccccccccccccccaaaagataccactgaaatgacaccgggt
gcccaaaaataaagcagcttacttcttgactttgagaggaactgcaatccttatcggttt
gagaggaactgcaatcagctataagtagcttattaatttccagtgcctgcattctgccaa
gtactatgatatatttctgaagctttgtttccccagttcctttttcagacgtttgctgtc
aataaagttgagccagccaacttggctcccacaagctactaattttgtccaagcttactc
tatgggagaagttaaatttcccaaattccttgagcggaaaatgaaaaatggactcaaagt
gtcatattatgcaactatctaaagaaaaatactcaattgaagtttagataagaaaagtga
atgtatattgatgtagtctccgttaggtgagaagcgtatcacttacccagcaacatatgg
acctaacattttactagtgaagttttcacattgtatcaaaagctcaacaaacggaaaggt
gactaatcctaaaatgttatttcacatatatgggcacacggtttgtcaaccttctcatac
gtgcattatttgttctctatctttctatttcatccgatataaccaatcgttattgtaaat
tctataatgcctgtggttacttttgtctttagtgacaaatgacatttaggataaccatgt
agttattgacttatttcacttgaggtctcttccaattatgtagtagtagagtgttgagat
atggatatgttaccttctaaaaaaaagagtgtagagatgcggatagtttgctagctggct
tttgtctcccttcaagttgaattagcaaaagcttgtctcataagttggatagctagacaa
gaaaaactccaaattactttatgtagagtattcttaagcttgagtcgcgagttggaaact
ggaattatgtaaaaaaacctggaattatttggttgagcctgctttttagttttgtcaata
tttccagtatctaacccaacatgtttagagtgattcccggagagcctcagtacaaggcat
```

-continued ttgcagagtctttatgagagtccaggaaggggcacacattctgtagaggtatagtcttgt ccttattttcagggttgaactagttctttagaagttacctaggcttcctaatttccaaat ttctgccaggtcctttttttggtgaagtacttgaagtttaataaatcaaattttaatttct aacatatcctgagaaatttattcacaaattcaactggtgacttctgatgcagaaacataa gcaactgcttatgggttcatatgttcctgcaattttattgttgacatggattggcttcat atggttttgttcctgcaattttatcgctgacactaatcctttcatatggttttatgtgga gtgttaaatagaggttaagagacaagaagaggctgaaaaaggtgggcagttcatttgtta gtagactactctatttactaagagatatgatgtcccatacattactcgaattggctccga atccagattccacttctttgccgagtttccttattgtacatagttcgactcgtcaaggga aattcacttcctttgactgaataatgctagtttgagtagtaccttacattaaatggacca tttagttctatctacttgatagaatagactggtcatcaactagttgcaaatacaatgaca actttgccatgtttgcagagtcacctgatgaagaagtacctcaattagtagaacatttct tgaatgttctacagtattctctatgcctacatgaccacatcacttttccttttgcgttgt gagaacttgaacttggtgagcgggggttccccaggaatggcatcttgatggcagatgacc attctgtccttgtcttagctaatgcttcttgcattgcctcactagatttattataccttt aaaaaatgtttgccattgttctgccataatagaaggatgtacccagctggtgcttcaaaa ctaatgaaatgctttacaattgtcgagtcctaaaggatgatttgtggaatcagatctcaa acaattctttttgaggaagaaaaataccaaaggtttttttctgtttgttggaagattaaaa atcctttaaatggtaaagatttatgaacttaattcagcgtttttgtggccattgctggaa aagagaaaaaacaatggcacttcttcgagtttgcttatccaaaaaaaagaagaagagaat gtcacgtaatgcaatttcatcttaggaaactttgcaggagaaaagcaagagtgataaaac agaactatttgttttttttaacaagttgttgtgacctatttcttgtcattcttatttgct aataagctaatgtactatagttcctgtactatggtttgttttgacttaatacggggatgt tcaatgagcattttcttgtttttttctgctttcagcatctgctgccttacaggaattcatt ttctggaaatttacttcttgttctgctaacattttcctgttatatcttgtcagtcatttt ctctccatggttatactgtttgtgtcactttaaactctccttgttttctactttaaagga tttaatgctgctgtcgggggctgtttctttgctgtggaatctgtgttatggccatcacct gcagagtcctccttgtccttaacaaatacgacttcaatggttattctcagtgctgttata gcttctgtagtctcagaaattggtcttggctctgaacctgcatttgcggtcccaggatat gattttcgtacacctactggtaattttggacttctttctcgagtttgattcttaaataca attgtacccgtcacttacagcaacaactacatttcaacagctagttggggttggctacac agatcatcactatccatttcaattcatttagtcccatttctttcgaatattgagtacttt gggattctataatatcaaggttctttatattttctactttgacgtacaaatctctaaata gattaaagaagactcctagagacactggcctaatgcaaatgtaccaccatgaataaactt taatctgaaatagctggtatcttatataaggacccttagctttaattgtgttctatattg atcttttgggacaacttccttccaatattatgtcttacttatacagttatacttatcctt aagccttactctttagagtggttatccctaattcaagcttttgttggcaccatagctagt ttggttctaagtaaaaagttactctttagagtggtaacttttttgtcaattttcttagtga aaatataacctctgtgacaaatctaccaagtataaatccaatttggttctatgtcatcct tgtagtttatccaagtcaatgctccatcactcttacaaaggttcatcgtatgactaatct -continued tttttggagaaaggtaacagtttgtattgataataagatcagcgccaggttggtcattag tgctaatagctgtacgtacaactccaaaagagcaaaagacaagcacctgatgtaaggtaa attacaagctgcctataaaatctatcaggtgtcctatctcactaaacatttcttgtttac accaaaaaaataaaacaaggaaagacaatccatcttaatcttctgaatggagtttctttt tccttcaaaacatctggagttccttccgttccatgcaatccaccatatacaagctgggat gattttccatttgtctttatccatttcttctaccaattcccttccaattgattagaagtt ccaatgtggttctagatatgacccaattaactcccaacagataaaagaagatgtgccacg gatttgtagtgattctgcaatgtaggaacaagtgagcattactttctacttcctgtccac aaagaaaacatcttgagcaaatctggaaacctcttctttgtaagttatcatgtgttaaac atgccttttcaccaccaaccagacaaaacatgatactttgggaggagttttaaccctcc aaatgtgtttccaaggccacacctcagttgttgaaacattaggatgtagagtccagtatg ctcttttactgaaaatgcaccttttctattcagcttttaaactactttatctatggtctg tgatgtacccttgaaaggttcaagagtttggaggaagatagaaactctgtttatctccca atcatccaaagatcttctaaagttccagctccatccttgtgagctccagactgacttacc aatgcttggctttgaagacttagagagaataagtcaggaaaatatctttcaaccttcctt gccctatccggtgatcttcccaaaaagatgtctgcaacccattgccaatattgatcttga tattgctactgaaagatttcttttggtggcaggattactctcattaacaatgtacttgac aatctccatacatactaatgtctctttaccctcttgccattaaggttgtaaagagacttg tcaaattaagaaaaggtttcctatggaactgtttcaaggaaggaacctcctttcctttgg tcaagtggagttaagtcatataatctaggaagtggaggcttgggtatgaaatagctgcaa atacagaaaaggagcatcttatttaaatgatcacggaaatgtgcccaaaactttaaatat ctgcacagcatatggttgtagcaaaatttgaatcttcctgtcaatggtgctcatgtccag tgaatacccctgatggtgaaagtgtcctgaagggaagcaggaacttattggaagaattgg catctaacactcagcttttcggtgggtcatagcccattgaaaattgagtgcccagattta tatagttttgctctaaactgacgatgcagttgcacaacatacgacaaactaaggtgggac atcatcttcttcggaaggaattttgaggattaagagatagagtggttgattcagttgcaa atgaagcttcaagggttcaatatcatccaggagacaccggattctgatagataaaacaac agaaagatgagcactactttgttaggcttgttacaagttgctatcgtctttcttatctcg gtacacaatttagatttgggaacttagttggaaaagcagagtggttgtttttgtgaatag catcagacaaagcttctgagctggtacgacagaaaactcaacagggagaatagaagactg tggttcacaatttctgcatgcatcttgtaggttatttggtgggtaaattatttaatgttt tgaagggaaggtagaacatgttcataggcttagattcaaatgtttgtattttttggctc tttggtgagagatgctgaacgtaaatgacataggcagctgactataatttctcagctcct tgctttttaaattgacaggcactgatatgtacatgtgaacatccaacacttttgtggtgc cgttccgatgaataaagaacattaatcacttactgatcaggagtaatagtttaggagttc tagaatttttgtacataaaatgaaccaaaaagaagatcggaatgagaacatgtttctttt tttgtttttttctttttcgtgaaaacttcaataacacttctgatagaatagctaggtccat ttgaattcctttggagacccttacacaaccaatgaatgacaagtatagcatttctaactc cctcccacacgtataacccagattttagggtttagatgtggatctgatttgaccttattg ccttttttttgtttttgttctttttgaagtagagagtgaggaggctcaacaattaattcgg ctcaacgggctaatgattggacttacatgctacgacaatgttaggagagagagagagaga -continued gagaagcccagagcagttacatgagttaagaaagagaagtccaaagcgatagaatatgaa
gagagaaagcggttgtgctaacaggctccctgaagtttggctctgagcatccaactcaaa
accttaaggcaatgagtagagtagcccaggaccatttaaattgctgttgaaaaccttaca
caaccaataagggaacaagtgtaacattctcttacaaccctaccgtcttataagtcagtg
ctctaatttagcataaaatcaaagtgaggcgatctacaatgaaatgaagtaaataactga
taaatacaaagaatgttaattctccaatatagcctgaatgttcccagaacaaaataaact
agtctcaggatttatcattaacatgatgttcctcttattttgagtgattaggaaggttaa
tcaaggtataaattctttctaatttgtatcgtctagaattatttatctaacaaattttca
gattaccggttcaaaagaggaatatattttgcatacaacgttaccataccttacaaaagg
gagatgaacatttttttatttattattgtcctttttttcaattagggattatgcagtct
tcctccacgtgatattactcttagaatcacgtttttgtcattgctattacttaatgtggt
aagtacaaatgtgttttgaactctttttggtatgtaatattgagttaatttttggtttcc
atttcagagctgccgctttatcttctgctgggcatcttttgtggcttagtttcagtggca
ttatcaagttgtacatcatttatgctgcaaatagtggaaaatattcaaacgaccagcggc
atgccaaaagcagcttttcctgtcctgggtggtcttctggttgggctggtagctttagca
tatcctgaaatcctttaccagggttttgagaatgttaatattttgctagaatctcgccca
ctagtgaaaggcctctccgctgatctgttgctccagcttgtagctgtcaaaatagtaaca
acttcattatgtcgagcctctggattggttggaggctactatgcaccatctctattcatc
ggtgctgctactggaactgcatatgggaaaattgttagctacattatctctcatgctgat
ccaatctttcatctttccatcttggaagttgcatccccacaagcatatggcctggtatga
atttgtcttttgttagaagtagcattacatatctggataagtgagtttttttattattgaa
aagtaataacaggagagcaagagaatatagcacccaaatctacttctttcctctcttcta
ttcttctgaaattcaaggtcctttaactcctccacggcctgtctagttattgatcctgta
gacttaattcacataggtttaggacattcaagtttatccaaacttcgtgaaaaggtttct
aattttttttacattacagtatgagtcgtgtctacttgagaaacatatcactccatgtttc
tatagagtctgttttctcctcagtttattttgatatatggggtcctattaagacagttca
accttggattttcattatttttgttgtttcattgataattattcaagatgtacttggatt
ttcttaacaagagatagttctcagttgtttttttgtgttcctaagtttttgtgctgcaata
caaaattagtttgatgtctctatttgcatttttcccaatgataatgccttagaatatttt
cttctcggtttcagtagcttatgatttctttagaaactctctatcagaaatctcaactga
gatagatgagaggaagaataagcatatcattgagacggctcgtacccttctcattcagtc
ccctgtcaagcttagtttcttgggcgatgcagtttcacgtcctttgattagattaattgg
atgcctcatctgctatccaaaatcagattcaactttcgatattgtttcctcgcttacctt
tatactctctttccctcgagtctttgggagcacatgttttgttcaataacatagctcctg
gaaagtgaccagcgcaaccgacaagcaaggccttcttaatatagaaggagggcatatgct
attctagccacgagggagaaagtaatattgtaatcaaacccaaatatctgagtataacct
ttggcaatggcgatcaatttgattatatggaccaactttgcctacatatacccaccgata
gatttacggggaggtagagaaataagctcccaagtaccactaatatgtaaagcagacatc
tctttgatcatagcctgtccttgtggacatagggatagaaattgaggactaagatgacac
aaaagcataatgctgtgatgataaacgatgataactcaaatcaatatgatggggatggga -continued attaagagtggattgaatatctttgcggaatgtgattggtagactaggaggagacaagtc
cgcaataggtaaaagatccagtacatggaatgaatcttctggacatgatgttggactgac
gtcaatgataagtcaagagtggtggagttgcagaacatggaactggagctgtaggtgaca
taatcgaagttgtagggggtggagctatagaggaaggtgaaggagagatagtgactgaat
ctccaaaatatgaaaccggtaatacctcaaaaaatgtctaagagatcatttggacctatg
aagtatggttgcgttttaaagaaggtaacatcagcagacataaggtaccgcggaaagtca
ggtgaataacattgatatccttgttgcgtcctcgagtaacttagaaatacatatttgaga
gcacggggagctaacttatcttttctggagtaaggttataaaaaaacacatgctcccata
gacacgaggtggaagagagaaaggtgagtggggaaacaagacagagtatgaaacttgatt
cttgatagttgaagatggcatacaattaataagacaataggatgtgagaactgtatcccc
acgtaaacacaacagaacatgagattgtacgagttgggtatgagcagtctcaatgagata
cctattcttcctttcagctatcccattttattgagatgtgtatggacaaaatatttgatg
tatgatcctatgagagttcatgaactgctgaaatggagaagacaaatactctggggcatt
atcactatgaaatgtgcggttagaaaccccaaattgattttggatttcagagtgaaaggt
ctgaaaaatagagaccaactcagattgatttttcatgagaaatatccaagtggacttgga
ataatcatcaatgaaactgacaaagtagcagaattccaaggtagaactaactcgacaagg
acctcaaacatctgaatggactaaagtgaaaggtgactctattcgattatcaagacaccg
aggaaaatgagagcgagtatgccttctgagcggatatgactgacgctctagagtggacaa
gtgagacaaaccaggtaccattttctgaagttctgataaattgggatgtcctaaccgttt
atgtaataaatctggtggatcagtaaaaggacaagctgtaaggggacaaaaataccaaat
atttccagaagatggcaaactacaacagaagaagcaactacattaacaggctcaggatat
gtgatgaaatgaggacaaagagttgatcaagaaggagattctggaattctaccagaactt
atatagtgaaaatgaaccgtggaggcccagtgcaaattttgaaggcatctcctcactaag
catagaagagaagaactagttggaagctccatttgaagaaatagaggtgcttgaagcttt
gaaatcatgtgcccctgataaagcaccaggtccagacggcttcaccatggctttctttca
gaaaaattgggatactcttaaaatggacatcatggccgcacttaatcactttcaccagag
ctgtcacatggttagggcttgcaatgccaccttcatcgccttaattccaaagaaaaaggg
tgctatggagctcagagactacagatctattgacaaactagtctcgggggaacaaaatgc
tttcatcaagaacaggcacatcactgatgcttccttgattgccagtgaagtgctggattg
gagaatgaaaagtggaaaaccaggcgtgttgtgcaaactggacattgaaaaggcttttga
tcaattaagatggtcttacctcatgagtatcttgaggcagatggctttggggagaaatgg
ataagatggataaactattgcatttcaactgtcaagaactctgttttggtgaatagtggc
ccgaccggtttttctcctgccaaaagggcctaaggcaggggatctcctctcccctttcc
tattcattttggcgatggaaggactcactaaaatgttggagaaggctaagcaactacaat
ggatacaaggctttcaggtgggaaggaatcctgccagctcagttacagtatcccatctac
tctttgcggatgatactcttatttttgtggtactgagagatcacaagcacgaaatctca
acctgacgctgatgatcttcgaggcactatcaggactccacaacaatatgataaagagca
tcatataccctgtgaatgcagtccccaacatacaggagctagcagacatcctatgctgca
aaacagatactttcccaacatatcttggacttcccttgggagctaaattcaaatcaaaag
aagtttggaatggagtcctagagaagtttgaaaagaggcttgcgacttggcgaatgcaat
acctctccatcggtggcaagttaactttaatcaatagtgtactggacagtcttcctacat -continued accacatgtctttgttcccaattccaatctcagtcctaaagcagatggacaaactcagaa ggaagttcttacgggaaggatgcagcaaaacacacaaatttccactagtgaaatgactca aggtaactcaaccaaaattcaaaggaggcttgagcatcagggatctacaagcacacaaca aagctatgctcttaaaatggctctggagatatggacaggaggaatctaggctatggaagg acatcatagttgctaaatatggagcacacaatcactggtgttccaagaaaacaaacactc cttatggagttggtctgtggaagaacatcagcaaccactgggatgaattcttccaaaatg taactttcaaagttgggaatggaactcgtattaagttttggaaggatagatggctcggaa atacacctttgaaagacatgtttcccggtatgtatcagattgccttgaccaaagactcca ctgttgctcaaaatagagacaatggcacttggtgcccattttcagaagaaatttgcagga ttgggaggtcaacagcctactcacaatgttaagctccctagaaggtcataatatcgaaga tcaacagcctgacaaacttatttggggaaattctgagagaggcaagtacacagtcaaaga atgatacattcacctctgtgaccagaatccaataatagataactagccatggaaacacat ctggagaactgaagtgcctaccaaggtgacttgcttcacatggttgactctaaatggggc atgtctcactcaagacaacttaatcaagaggaatatcatactagttaatagatgctacat gtgccaacaacagtcagaaagtgtaaaccacctattcctccactgctcagttgcaaaaga catttggaacttcttctacactacctttggtctgaaatgggttatgccacaatcaacaaa gcaagcttttgaaagttggtatttttggagagttgacaaatccatcaaaaaaatctggaa aacggtgccggctgcatttttttggtgtatttggaaagaaaggaaccgaagatgttttga tgacatattaactccactctactccctcaaggctgcgtgtttagttaacttatttagttt tgtggattttattagctccctgatagtagcataggcttttgtaaatggagctaattatcc tatctcttttgtactctttgcatcttcttgatgccttttaatgaatctaatttacttcat aaaaaataaaaggacaagttgttgaaggaggaaaagatgtgagtccatgtgatttagcaa ggataaggtactaaagtccatttgattcacgcccggtaccaatgatccatcccgcattgc attcctgtattaaaacagagtcatcaagaaataaaatagagcaaataagtgattggccaa acgactagtggatatgagattaaaaggactatcgggaacataaagaactgaattcaaagg taaggaaggaagtggactagcttaacctattccagttgccatggtttgagaatagttggc cattgtgactgttggaagtgattgagagtaagaaatagtagtgaaaagagatttgttacc agaaatataatcagatgcaactgaatcaataacctaagagtcggaaaaagaaacacaagt catgttattacctgtttgaacaatagaagttatctccgaagaggattatttacatgtttt gtactgatggaactcaatataagccgataaagaaaccatccggatattcaaagtattgga tcaacagcttataagccaaaagcatccgatacgagtgccattataatggatcaagagaga tcaaacaacaaatcaccaaatatcataaacaaccaagaatctcgctggaatgtgaacaaa gattgaaaaacaacaatgtagctcgccaaaaatgtgcaaagtgatcgaaaaatattgaat cgtgagtggagagaaataggagcttcaatcgacccacacagtaccaaaaaatccaaaaac ggttgtcggagctcaagaaagttgtcaaaaagtatattgtatgcttcgaaagtagccgaa aaaggttggaagtgggatgtgtcaactccgaattatgatacgagcaccacagaagatcaa tttgtgtcaaaactaccgaaaaaaatacttcacaccccgacgcgtggagtactcgctcgt tggaacccttgctgccaacgtcgcatgtaggatcagttttcgaagaatcttattggggtt tggtcgccggacgatgtcggatcttgtggtgccgttggaattcgcacaaccctgaaggaa aagaaggttacacaaatcagatctgaaagtcaccgaaaagacacatggcgattgactttt -continued ttgtctcagatgtttctcaccgtcgctctgataccagttgttgggctcaactcgtttgaa gatactcttaacatagtgtgatattgtcccttttggaatgtgagtcatcttagctcggta agcatactcgctcttccaactagcccgaagatacttttaacagagtgtaatattatctgc tttgagccaagctggcgcggttttcatcaaaagacctcatactattaaaagatccataca ccttatatgtaggcttctaagttgctcggacacgggtgcgagtacccgacacaggtgcaa atctagaggtcagatcctttaaaatgtaaattctaagatttggggatacgaatcctagta cggatacgggtgcgaggatccgattaaaaataattcaaaaaaataagaaaataaaaaagt ctctaaattatgtgaaattttgtggaataactacgtatagcttgtaaagtgtggatttat tttttattctcaagttgtagataagtaaatgattgatttcctagataaggtatgttattt tcttcaaatttaccctagtttggttcgaatttcgggaaattgtatcttgtctcgaatttt tccttctgtcctgattaaactactcaaaatcgtctgaccagatccggtacggatcccata cccacatccacactagtgtcgtgtggacaagggtgcggcacctaaacttccgtgtaggag caatttaggtaggctcctaatcttttcagctattaatgtgggacttttacgcacctctat caaattccccaataaactaagtttcacgtggtccatcatcgcaatccacgggtctcttcc tctagttaagtcccacatggcccattaccatgatccacgggtcaattttcgtgattcatc gtgtgccacccacatcgttagtatttatggtaactaaagtacgcaactagcttttgcttg tgagcgtgtctccaagctcgtaaaggtaagaaaaccgagccgcatattccatcactctat catcaccatactcgtcccgcgaaacttgtaagataaaggtggctggttggtcagttgaac tacctcagagtgacttggtatagtatttcctttcttgtgaatatttaactcaattatgga ctctctgtgtgatagtcattgagagccatttttctatatagccggtgcacacaaatcatat gtaccaagcttgttatatatgtaactaatacgaggaccagtgaaggactcggtgaaaata tctgcaatctggtcattcgacatacaaggccaatagactccccagcaataaaatcagggg gttgctgataaatagaattggccgaaatgttgccagaaaaatttgaaaatagtgagacta agccgaattctacactacaaaataggttttaaaacacaaccagaaaacaaaaactttttt ggaaattactgttcacatcgaaaaaataaaagttgtcagaatttgatgtaatttatatgg ataggctcgtaatcactggacgagtaagttgtcctgaagaagttttgtcaaaaggtggcc ggaatggctcacacatgccggaaaacttattgtagctcgccggaaccctagttctggcgg tgcgtagaggcgtgtgactttctgccagactgattgactgtggtttgtcgcctgactttt cctaacaagatggtagtattggttttcgcacaacaattaccgatgaggagataacgcaaa tcaatcttgagtcgtcaatcggaaagacgcacggtggctgactttctatttagatgggac tggaatttctggagtttaatcgcacaagcgttttggatctgatggtaatactggtatgca cagtaccactgtagcagtgatgaaccctcaaaataagacaaagttgccagaaaattgcac ggcgatgagatctttcttccggatgtcaccggaatgacgcacaacgataatttctcactg aagctctgacaccatgtgagaatacacgggagaaaaatctatttttattaacaatgatac aatgagccctatatataatacatattctactctactacatatgggaatagggcatatttt actcctactacatatgagactaggactatttacacataactatctaacaagggctatatc tcagatttatgagaatatctacccaacgacccagagagacgagcctaatcattttgcagt ggcacagactataacaacaaaaaacctactcataatggttaaaccaactgattaagatgc ttacaggactatcttgagaaatgtacatattatatagatgcttgagttgcgtcccaatcc taaatagaagcttttattcgtaagcaagaagggaagcagctttacttgagccaatagctt tcaaggtgcatgttgtcacaccaaggacatccagaatttgattttatagtgggaatatcg -continued tttaaagataaaaaagatagcgtgcagaagattgcatacattagagatgcaaaatacgga atacccatactcccagataatgcagtatgccttttgcatgacctactggttgaatggaag cacctggtgaatttactaggtgtgttagtgatttctgctgcttccttcccctttctaaac tgcatactatctaaaatgttagggggcagaagcccagtcaatctgactaggtgatgtta gtggtttccgcttcttcctcccacttctaaatgcgtactttctcaaatttaggagcatag aaacttaagcagctgcctacctgaggagttgcatgggaacataagagaatagactttacc tgtcatattttccataccttagttaattacagtgttatcctgataatgatctgttttctg gatctaggctgaatcgagattcaatcgcttttggttgaaaggatgctgctacagatcctt agtttacatcatttggttcttattctataagtacttcccctatcaactacttccttctt ttttcttaggttatttgcctctttaggttgtttggaaggaaaggaacagtagatgttttg atggaatagcaactccaaaccacttccttaaggctaatatcctgattggccaagtttctc caaagtccaaaacactttttttttccttcaaaaaagtacctttttttttcaaagttgagg tgtttggccaagcttttggaaggaaaaaaagtgtttttgagtagaagcagatgctcttga gaagcagaagaagtagcttcttcccggaagcacttttgagaaaaataaatttagaaacac tttttaaaagcttggccaaacactaattgctgcttaaaagtattttcagatttattagac aaacacaaactgcttctcaccaaaaatactttttttgaaaagtacttttcaaacaaagcac ttttcaaaataagtttttagaagcttggctaaacaggctataaatgtcttttattttta cagctggagtaccctaacacctgtaaattcccctatacattttttcgactttggtagct cattaaccctagtataggactctttgttttggagctagcaaactcttttgttttcctatt tttgcatcttcttggtgccatttataatatctcttcaccaaaaaaaaaaagttcccaaac tatgactaccttgagttggtcaaagcataaccaaagcatgggcacaccagtgtttgcgtg aattttatggatgttccttacctttatccttctgtgcttatgtagcatctgtcttggtca atcttttctgaagtctatattgtatttctgtgttgcaacatgagtttactgttaatctta ctgtttgacctcaattttgggttctttttgattttggaagacatcgtttaacaggttggc atggctgctactcttgctggtgtctgtcaggtgcctctcactgcggttttgcttctcttt gaactgacacaggattatcggatagttctgcccctcttgggagctgtggggttgtcttct tgggttacatctggacaaacaaggaaaagtgtagtgaaggatagagaaaaactaaaagat gcaagagcccacatgatgcagcgacaaggaacttctttctccaacatttctagtttaact tattcttcaggttcaccttcacagaaagagagtaacctctgcaaacttgagagttccctc tgtctttatgaatctgatgatgaagaaaatgatttggcaaggacaattctagtttcacag gcaatgagaacacgatatgtgacagttctaatgagcaccttgctaatggagaccatatcc ctcatgctagctgagaagcaatcttgtgcaataatagttgatgaaaataattttctcatt ggtctgctgacacttggtgatatccagaattacagcaagttgccaagaacagagggcaat ttccaggaggtagcttcttggtacatttcaatattcttaactgatgaaaaaataagggaa attgatctagcatgaaatgaagctaattataagttttacacagtagaactggtaaaacag ggttggctggatatttctttgttgaatttttaggattatatatattgttttagttttgta ggttgttttctgatgtgcttttttgactcggcagaatcttaagatgaaatggaaggttgta tcatcaaatgttaaataagggaatatgtgactttcaaagttaagcacggagtattttgga gtcaatagttacttcctgaatcttttaggatggaggagacagtttctataggaataggaa aaggggacctgatttcattatttgtgtgtatatacatttgttatctgaattcgcattact -continued ttctaacaaccaacaaaaggaaagtggacattcaatttgagccggagggagaaaatttaa ctagaaaatgacctggccgtgaaataaaattattgatccgtcctttaactagttttcatg gattgcctccttgcggatgatttttccaaccggtagaactactgttagtcgtccaaattc tgacccccctactatgaataaaaatgtattagtaagtttagtgggtaatctccttgagaaa taaaggaacaggagaaatattttattgatatatgctaagtgttttacaatagccctattt atatacaatgtttacataaacctaaagccttctatataaatgtgggacactatacatgaa ctaactctaacactatccctcaagctagtgcatataaattatatatatgcttgttacata tataattaatttctctacttttttggtatacttcttgtatacgggagttatctcccttttg attaatacaatttaccttatcaaaaaaaaattaatacgaggaccagtgagggacttggtg aaaatatctgcaagttgatcatttgacttctcaaactttgtaacaatatctcctgagaat cttctctctcgtgaagtgacagtcaatctcagtgtgtttggtcctctcatggaacactgg atttgatgcaatatgaaggacaacttgattatcacacacaagttccatctgactgattgc tccaaattttaattatttgagcaattgtttgatccaaactagctcacatggtgcaagagt catgactcgatattcggcttctgcgctagatcgagcaactacattctgtttcttgctttt ccgagagacaaattacctcctattaaaacacaatatccagatacgtaacgtctatcagaa ggtgaccctgcccaattagcatctgtgcgtccaacaatatgctcatggcatcgatcttcg aatattagtcatttgtctggagctgattttatataacgaacaatgcgaacaactgcatcc caatgactatcgcaaggaaattccataaactgacttacaacactcacaggaaataaaata tcaggtctagtaattatgaggtaattcaattttccaaccaggcgcctatattttgcagga ttgctaagaggctccccccctatcctggcagaagcttagcattcggattcataagagtatc aatagttctgcagcccattattcatgtctcctcaagaatgtctaaagcatacttcctttg cgaaataacaacctgaactagaccgagcgacctcaatacctacaaagtacttcaatctgc taaggtcgttagtctggaagtgttgaaagtgatgttgtttcaaattagtaataccatcct gatcattgcgagtaataacaatatcatcaacataaaccaccagataaatacagagattag gagcagaatgccgataaaatacagagtgatcagcttcactattagtcatgccaaattccc gaataattgtcctgaacttacgaaactaggctcgacgagattgttttaaaccatagagac ttgcataagtgacatacaatacctctagactccccttgagcaacaaaaccaagtggttgc tccatattaactttatcctcaagatcaccatggagaaaggcattctttatgtccaactga taaagaggccaatgatgaacaatagccatggacaggaaaaggcgaacagatacgacttta gccacgggagaaaagtgtcattattatcaagcccaaatagctgagtatatcctttttgcaa tcagacgagccttgagccaatcaacctggccatccaggtagactttgactgcataaaccc aacgacaaccaacagtagacttacttgaaggaagagaacaaactcccatgtaccactcac tcacatgtaaagcaaacatctcgtcaatcatagcctgtcgccatcctggatgagatagtg cctcacctgtaaacttaggaatggaaacagtggacaaagatgatacaaaatcataatagg gtgatgagatgcggtgataacttaaaccaacataatggggactaggattaagtttggatc atacaccctttcgaagtgcaatcagtggactaggaggagccaagtccgcactagacgtgg atgacaatgataagtcaagagtggtggcctcgtggttggagatgtaggatgagcaactgt agactcctcagaagtcggtataggtaggagtacctgtgatgttgatgtggatttaagagg aggaacaatagattcctcacaagtagatacaggtaagacctcagatatatcaagatgatt agatgaagtaaagtaaggttgagactcaaaaaatgtgacatcgactgacataagatatct acgaagatcaggtgagtagcagcgatacccctttttgaacccgagaatagccaagaaagac -continued acacctgagaacacaaggagctattttatctttttcaggagctaagttatgaacaaatgt
actccttaaaacactaggaggaaagagtataaagatgacctagggaacaatactgagtgt
ggaaactgattctagatggaagatgaaggcatccgattaattaagtaacaggttgtaaga
actgcatcgtcccaaaaacgttgtggaacataggactgaatgagaagtgtgcgagcagtt
ttaatgagatacctattctttctctctactaccctataatgttgaggagtatacagacat
aggataatattttgagaagtcataaactattgaaactaagagaatacatattttaaggca
ttatcactacgaaaagcgaataaaaacaccaagcggagttttaatttcagcataaaaact
ctagaatattgaaaacaactcaaaacgatctttcatttggaaaatccaaatacatcttga
gtaatcattaatgaaactaacaaaatccaaatcttaaggttgtgactctactaagacccc
atatatcataatgaactaaagacaaaacagactctacacgactcttagcacgacgtgaaa
atgtagctcgaatatatttcccaagttgacacgaatcacaatctaatgtggacaaaccag
acaccatcttctgaagcttggataaactcggatgtcctaaacgtttgtgaattaggtcta
gaggatctgtagttggacatgttgtagagggattgagtgagttaagatagtcaaggtctt
gtgattcacgccatgtgccaatcgtctgtaccgtactgcggtcctgcatagtaaaagaat
catcaataaaatatatatcacaatggaattcacgagtcaaatgactaacagatgcgagat
taaaggacaaccggggacataaaaaatagaatctaaagtgacagaggacatgtgattagc
ttgtccaactccttttgcttttgtttagacttcatttgctaaagtatcattgggaagaga
ttgtgaataaacaattatttgacaaaagtgacatattaccactggggtatcaagttgctt
agtcatactaagaatgtttgggagagggtggtggaagtgagggtaaggaggacagtgtct
ctatccgagaaccagttcggattcatgcatgatcgttcaactgcggaagctatccgtctt
attaggaggctggtggaacagtacaaggataggaagaaggatttgcacatgatgtttacc
tagagtaagcgtatgacaaggtccctaaggaggttccttggagatgtcagaaggttaaag
gtgttccggtagcatatactagggtgatgaaggacatgtatgatggagctaagactcggg
ttaggacaatggaaagagactctaagcattgtttggttgttatggggttacagtaaggat
ctacgctcaaaccgttcttatttgccttggcgatggacgcattaacgtaccatattcagg
gagatgtgccatggtgtatgttattcgcggatgatatagttctgattgatgagacgcgag
gcggtgttaacgagaggttgggggtttggagacagacccttgaatttaaaggtttcaagt
tgagcaggactaagacagaatacttggaatgtaagttcagcgacgtgacggaggaagctg
acatggacgcgaggcttgattcataagtcatccccaagagaggaagtttcaagtatcttg
agtcagttatacagggagaagatggggagattgacaaggatgtcacgcaccgtattaagg
gcggggtggatgaaatggaggttagcattcggtatcttttgtcacaagaatgtgccacca
aaacttaaaggtaagttctatagagcggtggttagaccaaccatgttgtatggggcagag
tgttggccagtcaagaattctcatatctagaagatgaaagtagcagaaatgagaatgttg
agacggatatgcgggcatactacgttggaagattaagaatgaaaatatttgggtgaaggt
gggcgtggccccatggaagttgtgcccaccattaaagactgctatctgaaaactaattct
ttgggcccaaacattctggcccaaagtacctcgtgaataataatattgagctcatgtctg
acatgttggaagaggagttactagcaaacacttatacacctatgttggtaacacaattga
agaactacgaaaaacactcttctgcaaaggaaaatgagaagaagaagaagaagaagacga
agaagaaggatgatgcaatgatcattgaagaaaaaggagagcaggaggacccatctaaac
ttacaaagtctagaggaagaggaggacccagagtttgatgcttccctctgggtacaccaa -continued

```
aacatcgtcaaacttaggcaaggagtttggggtaaacattcaggggtgtgagaaggaagc

tttggagcttttcgtaaaattacaactagaggcataaaaaaaaaaaaggcaatccaggca

tggaggtgacaaccttcgaaaagaaagggattcaaagaactgaaagggctggatttttgg

agtaacttcaagagtaatagaacaagaagtagggggttgcattattatcaaagatcaatg

aagattaacattgaagaagtgggaaatccaaaaagactccaccgagaaggatgatgcaat

gatcattgaagaaaaaggagagcatgagaaaaaacccgtagaaattgacagcactcacac

acaataagacgagataataaagtagtgagttggccaattgaagaagctttacctcttaac

ttacaaagtctagaggaagaggaggacccagagtttgatgcttccctctgggtacaccaa

aacatcgtcaaacttaggcaaggagtttggggtaaactttcaggggtgtgagaaggatgt

tttggagcttttcataaaattataacaagaggcatgggaaaaaaaaggaaatccaggcat

gcaggtgacaaaaccttccaaaagaaagggactggaagaactgaaagggctggattttg

gcgtaacttcaagagtaataggacaagaagtacgggattgcattattatcaaagatcaat

gaagattaacattgtatcatggaatgtcaggggggttaaatcgacatagaaaaagaatgtt

gattaggagtttaattcataggtggaaagcagatgttttctgtttccaagattcaaaatt

aaaaggggacattagggagtttataagagaactatgggcaaataggtggtttaaatatgc

acagttggaggctagtgggcctagagggggtattattgtcttatgggatagtaaaattgg

ggagggggagatcagcagcctgagctcctattctgttacttgtaaatttataggtaaaac

tcaggagtatacttggaatttatccactgtatacgctccaaatgatagggaggaaaggaa

agaagtatggtgggaattagcaggtgccaggggaatttttatggaccttgggtaatttct

ggggatttcaatactgtgaggtacccaccagagaaaaagaattacagcaaaatcactaga

gcaataaatgaattctcataatttattgaagatatggaactggtggatctacaacttgca

ggaggaagttacacttggaggacaggagatagacatgtgataacagctagactggatagg

ttcttggtttttatggattggaatgagagcatcagaaacaccaagcaatcagttctccat

tgaattacctctgaccattcccctgtgatgcttcaatgtggtaaccggtaccctgtcaaa

tcctattacaagtttgagaattggtggctggaaacagagggcttcaaagaaaggattaaa

gtctggtggagctcttttgcttgtgaaggaagacgtgactttattctggctttcaaactt

aaagcatcgaaggaaaaaattgaagaaatggagtaaatctattcaaggaaacttggagat

gcagaaattgagtattcttagtcaacttgcagaactagaagagacacatgatcaaaggag

ccttactgaagaagaaatacacactaaatatgcagtctatggagtttggggagattgcaa

aacatgaggaggtggcttggagacaaagatctagggctctttggttgaaagaagggacaa

aaacatcaatttttttcctcaaaattgcaagtgcacataggaaatacaataacatagacca

actgttacttgaaggaaaatttgtggcgaatccaacatacataacaaataatattggtac

attttatcaaaaactatatataaagattgctagaggacaatcttatgttgcaaagtcttt

tcgaagcttaggaaatttgggatagtgtcaggcatgtgaaagggataaagcacctggacc

tgagaactgggaggtgataaacacggatatgatagctgcagttctttgttcatggaatgt

ttgaggaaagctttaatgttacctttgtggtattgattcctaagaagatggaagctaagg

aatagaaggactttaggcctattatgataggcaatgtgtacaagatcttgatagaaagac

ttaagaaattggtgaacaagttggtgaagggtcaacggatgacttttattaaaggtagac

agataatggatgttgttctaattgccaaatgaatgtgtagatgcaagaacaaaggcgaga

aacctacaatactatgcaaactagatattgagaaggcatatgaccatctaaattggaact

ttctattggaatcgctgatgaggatgggctttggtgtaagatgggtcagctggatcaaat
```

-continued tctgcatcagcacaatgaaattctcaattttgataaatgtttcaccagtaggtttcttcc
cttctcagagggatttgagacagggtgatccactatctccttttattattcattagtgct
atgggaggcttaaatgatatgttaaagactactcaagataacaactgcatacggggtttt
aaggtgaagtccagggcagacagtactattgagatttttcatcttcgatatgcagatgac
gcacttatgttctgtgaggttgacaatgaacaattgaaagtgctgaaggtgatcttcatt
ctgtttgaagccacatctgtattacaaattaactggaatgaaagctttatctatctagtt
aatgaggtaactaagatccactttttggttggaatcctagaaggtaaaattggggaattg
cctacagttatttggggatgccatgggggccaagagcaattttaaggggatttggactag
ggtcgtagagatatgtgaaaaaattttaacaaactggaagagttagtatttatccttaag
ggacaaactaatactaatcaattctatacttgatgattttcctacttacatgatgttcct
cttctcaatccatgtgaatgttgtgaagagaatatataccccttagaaggaacttcctatg
gggaggaaactatgacaaggaaagatctatttggtcaaatggaagtctctcacagtcagc
aagaagtaagagtgttttggaatcaagaattggagaattcagaaccaaagtttgatgatg
aagtggctatggagatttactacagaagaacattgtttgtggaaagaggtgatcatggag
aagtatggcatagaagataaacggataacaaagtctgtaaatagatcttatggagttagt
cgatggaaatccatcagggacctatagcttcagctcttgaataagtccaaattctgaata
ggaaatggattgaaaatatctttttggaaggataattggctaaccaaggaactttgaaac
aactctttcttgacatttacattccaaatcaacagcataaagcaataatagtagaattat
gggctaatcaaggttggaatctcacatacagaagactatcaaaagacccggagattggca
ggtcaacagagttcaaaggcactttggaacaatttaaagaggtctatacttctatagact
atttgacttggcaagggaagtttattgttaattcagcctataaggaattcaacttctcag
ctaactggattggttgttggccatagaagttgatttggaaagttaaaattccttatagag
ttgcttgtttctcttggcttttggctaaagaggcagttctgacgcatgataatctaacca
agagagattaccatttatgttcaagatgttatttatgtgaagagcaggcagagacaacca
atccactttttttgcattgtaagttcactgcagttatggaggattttcattagtttaaa
gggtatcatgtgggctatgcgtagaagtatacctgaagttctagcatactggaaaaaaga
aagaaatctttccaattataaaaagagatggaggattatcctagcttgcatctggtggac
catttgggaagaaagaaatcaaagatgcttcaaagataaatcagtcatattcagataatt
aaaatgaagtggctagtcttgttttatttttggtgttaagtgttagatagttatgtatta
tgtataagttgtctagtcccacattggaacgggagtaatatgtactatgtagagtatagc
tataaataggacttcttgtactttattgtagagaatatattaataatatatttttcccgt
gttgtctcacatggtatcagagaaaccgtgagatatcagtcgttgtgaaaaataccagcg
gcttcgggaagaaaaaaatcaatcaactgctaggtatattagtcttcggcgaccgatcca
ttaaatttctctggcaaagaaccactcatgggccctcacgcgcccaccgaaagaaatatt
tccggcgaggttccaatttcatgcgcccgcgcgtgaggcagtttccggtcaaattttgac
aaaggtccttttttgacagtttgttcaccctgtaattcccagtctatccatcattttttt
atttcgatcacttcgcaatttctcgggcagctacagtgatttttccggcagaagcggtgt
ttcctttgcctgcttcagcgagatacagttgattatttctattatttgtttctagacctc
tctccaatccaacgatgtctttggaatttgatgtatttggttctgaaaacacgagttcta
gaaagtcaagcttcatgattactttagagccattaatggggagttcaaactatttagctt -continued gggtttcctctgttgaattgtggtgtaaaggtcaaggtgttcgagatcacttaatcaaaa aggctagtgagggctgtgaaaaggtcaatttaagcagtttatgacgtctgtataccactc agcagaataggatagcaaagaaagaatatgcacatcattgagactgctcgcacacttctc attgagtctcacgttctgctacattttctgagcgatgcagttctaacggcttgttatttg attaatcggatgcctttatcttccatccagaatcagattctgcagttagtattgttttct cagtcacccttatactttttcgtcctcgtgcttttgggagcatgtgtttgttcataact tagctcccgaaaaaaataagttagctcctcgtgctctcaagtgtgtcttccttggatatt cccgagtttaaaagtgatattgttgctactcacctgatcgtaggtaccttatgtcagttg atgttgcatttttgagtctagaccttactttacctcttctgaccaccttgatatatata tgaggtcttacctataccgactcttgaggggtttactatagctcctcctctacatactga gccacagaaatcttactcatacctaccattggggaatctagtgttgctcctcctagatcc ccagctacaggaacacttttaacttatcgtcgtcgtccgcgcccagcatcatgtccagct gattcacgttctgcacctgctcctactgcggactagtctcatcctaatctaccaattgca cttcggaaaggtatatagtccacacttaatcctaatccatattatgtcggtttgagttat catcgtgtcatcacctcattatgcttttataacttctttgtccactgtttcaattcataa gtttacaggtgaagcactgtcacatccaggatggcaacatgctatgattgacgagatgtc tgctttacatacgagtagtacttgtgaacttgttcctcttccttcaggcaaatctactgt tggttatcgttgggtttatgccgtcaaagttggtccagatgaccagattgccaaagggta tagtcaaatatttggggcttggttacagtgatattttctctcccgtggctaaaataccat cagttcatctctttatatccatggttgttgttcgtcattggcatctctatcagtttgaca ttaagaatgtttttcttcacagtgagattgaggatgaagtttatatgaattaaccaccta attttgttgcttagggggagtctagtggctttgtatgttggttgcctcagacgctctatg gtctaaagtaatctcctcgagccttgtttagtaagttgagcacagttattcgggaatttg gccaactcgtagtgaagcttatcactttgtgctttattggcattttacttcaaatctctg tatttatttggtggtttatgttgacgatattgttattaccggcaatgaacaggatggtat tactgagttgaagcaacatctctttcagcacttttagactaaggatctgagtagattgaa gtattttttaggtattgtgattgctcagtctagcttaggttttgttatttcacattggaa gtagaaaaacttcaatcatttttctttatttgaaaggaagaaaaaaaaggtaatatctag acctaaatattaatctgaagacaagtgaggcttgctcagttggtaaaagcacctccacct acgatcgttaggtcctgggttcgagtcaccatggaggggaagtgtggaaacactatagat cctcctaatttgggaggggggaaaaaaatattaatctgaattgacatgaatctcaatgaca atgaccaacgatttcctgcaattcttttcagtatggaatgaataaaaaatcaagctacaa gtctctattaaacgaaatgcactaacagggatcactctcaagaaaggaagtggttttggt tgttgttattccaggttggataaatcactttctttataaatatcataaaagacaagggct ttcttgcttcagcacatgtgggaaatgccggggggcttggctggtaccaagctcgagcgg tctttctatctttttggattgcatgcccaaggcaatgctttttgtagattgggatggatt gatcttcgcagaagtatgctttagacattcttgaggagacaggaatgacggattgtagac ccattgacacacctatggatccaaatgccacacttctaccaggatagggggagcctctta gtgatcctgcaagatataggcggctggttggcaagttgaattacctcacagtaactagac cttatatatcctttcctgtgagtgttgtaagtcagtttatggactctccttgtgatagtc attgggatgtggttttccgaattcttcgatataaaatcagctccaagcaaagaactgttg -continued ttcgaggatcgaggcccatgagcagatgttgattgggcacgatcaccttctaatagacat tctatatctggatattgtatgttaataggagttaatttggtgtcttggaagatcaagacg taaaatgtagttgatcggtctagtgcggaagcaaataatcgagcaattgttatggtaaca cgtgagctagtttggatcaaacaactgctcaaagaattgaaatttggagaaattgatgga accagtgtgtaataatcaagcagctcttcatattgcgtcaaatccggtgttccatgacag aattaaacacattgagattgactctcactttgccggagaaaagatactctcaggagatac cgttacaaagattgtgaagtcgaatgatcagcttagagatatttttaccaagtcccttgc tggtcctcgtattagttatatttgtagcaaactcggtatatatgatttatatgcaccaac ttaagggagagtgtgagatagttatgtacaacaaaatacccggtataatcccacaagtgg ggtatggagggtagtgtatacgtagagcttacccttaccctgtgaaggtagagaagctgt ttccaaataccctcggctccagtacaaatgaaaaggagcagtagcaacaagcagtaacaa caatgatatagtaaaataactgaagaaagaaataacatgtagacatataactccactaac aaacatgcaaggttaatactattgccacgagaatggcaaaggaatgttagatagttatgt attatatgtatattaatagtctagtctcacgttggaataggagtaatatgtactatgtag agtatagctataactaggacttcttgtaatatattgcatagagatatcaataatatattt ttcctgtgctttctcacgtaaaggaatgtaatgtacttagaagatcatgaatctatcttt gatgttttagacacctcgtgagaacacaaaggtttaggaactttattgtgttctttgtaa ttatgggtgactgccaatatgttaccttttcataaaaatgattatttggccattggatta gtttcaacagcctctctgcccctccgggtaggggtaaggtctgcgtacatattaccctct ccagaccccacttgtgggattatactgggttgttgttgttgttgttgtggattagtttca acaattttgatagttcttttatttgaatcaaactactcattcacatggattttgtatcgt atcattgagttaaaaaaattggttttgctaatttatcctcatgtataacaactacctatt tttcaatatattggattcaggagcttgtagtagctggagtttgctcttcaaagggcaata agtgccgggtatcatgcacagtgactccaaatacagatctcctttctgctctaactctta tggagaaacatgatctaagtcagctacctgttatactaggggacgtggaggatgaaggca tccatcctgtgggcattttggacagagaatgcatcaatgtagcttgcaggtttttgacat tcaacttttacttcaaagatataatgctttctggaaccattgatgataaaatatgcaaga aacttgtgcagaagtcgcactttactatcgattaccagataaagttacttatcaagaagt caaatatattgaacatatttctctaaaacactttgactggactgtaagcagaaacttact aaagtaggtcgtaagaaatggtttgatagggaaatcaccatctacacttaaaagagttgt gtgaatttgaattcttaaagcatgtgaaagttataaaaacttgttattatctaagcatct gaagcattttggccatccaaaggatcaaaaataggaaataatttcatttgtacaatgaac tccctgcacaaattctcacactaggtgtattctctattcatcactagcactacatgtgtc actacgaatcatatacaataaatctttgtaacataaaagacgacacataatatggaagta agccgagtatacaagggaagtttcatcattacggtgagctttttataagataatcaagtt ttactggaaaagggcaaaaactctcccgtatagaagtataccaaaaagtagaataccttta caaaaatatgattttctatgaacaacaccctatcttctatacttgtagggatctcatcgg ggcaccaaaaagagataaagggataagaggcttttcctcaaatgtacaaaatccttctct attccttcaaaagctctcctatttctctctctgcacactgtccacataagttcaatggag caacatccacgccctgtgtcttcttttccgtcttctataggtccagctgaacatggcttc -continued tttgactgagtgtggcatcaacgttgaagaccaaaccatcccagtacttccaaccacaaa cgagacactatatgacaatttagaagaagatgattcacatcttctcccgaacatttacac ataaaacaccagctgatacatgtaatcttcctcttcctcaaattatcagccgtcaggatc acccgtctcgtagctaactaggtgaagaagcacacctttctcgaaaacctcaggatccat acagagagatatggaaaagctgattcctccatgcccagaagcttctcataataagactta acaaagaaacaccactacttccccccccccccaaaaaaaaaaaatctccatacatcgact ttcatgtgtaattcttgttcgtgaaacgacccaatcaacctttggcacaaatctcccagt cttgcgagttcctcctaaacttcaaatcacaatgaacttctccaccttgtagcctccgtg tcccttggactggcaactcctttggcatgaaactttgtacatattaggagatgtgatact caaagtgttgttcctgcaccaattgtacccccaaaaaacttaccatgctcccatcaccta acattgaatgatacgttccaaaatcttcgcactccttcaagaaacttttccgtaggcccc acccataagggagtgtgattttttttgctctccatcccctctccaagaatccattcccta aaccactgcaggacactttaacaatcactatgtcactttttctactagttctacattgag tgatatcttgatgtcattgaaatgcctctggaaaatcttcttctcatctaaaagaacact tgtttgccttttgaatccccctctaacattttctatgtttcattcatctttggtggaaca gagcattagcaactagagaacagctttgctag

SEQ ID NO: 11

(DNA sequence of NtCLCe from *Nicotiana tabacum*; sequence originating from the ancestor *N. tomentosiformis*; two start codons)

<u>atg</u>attagcggccaaaacaccgtgctgcaccatcctcctaattcgctcttcaattcctta tctcctcgccatatctgtgtatctttctgtaacgacaaagctttaaaaaagtcagtcacg cactccgcccctcggtttgctcgtctgttaaacaatgaatcacgaaagttgttgggtcgt catccaaattgctggccttgggctcgacgaccatctcttcctccgggacgttcctgtgac ggaaacattgaaaaagaacaagatatgtgcgacagcagcaaagacgatagtgatagtgat agtggtatccagataggatctctgctcgaggaagttatcccacaaggcaataataccgct ataatctcggcttgctttgttggcctcttcaccggtatcagtgtcgtgcttttcaacgct gcggtaagtgcgctataggtctttcatttctcttttcatctactattctcccttacttac ttggcctcagtcaatcagcccccctgcctactttaaattattgtacaatttatcagaggag tatcctatacatcaaattcacataacttagtaaaatatgctgacattctgaattttaacc ttaccagcttagaacatccaggctagttcagaaacagataatctaaattggcctcattta taagtcattttgttaatcaagacatacaatttggctcttgataaaagattatgcagcgcc cgatgataacctaatatttatcagcaacccatatgtcactttcttttgtttaaatgctct cccatgtaatttaacaatattgtcaccatacaaaagagaactgaagtgaatgttccattt gtggtcatataacggatatctcccttggttaggttcatgaaatacgtgatctttgttggg atggaattccatatcgagctgcctcagaggagcccattggagtacattggcaacgtgtaa tcttagtaccagcttgtggcggtttggtagtcagctttttgaatgccttccgagccactc tggaggtttcaactgaagaaagttggacatcatctgttaaatctgtgttggggccagttt tgaagacaatggccgcttgtgtcacattaggaactgggaattccttaggaccagaaggcc ctagtgttgaaattggtacatctgttgccaagggagttggagctctgcttgataaaggtg gtcgtagaaagctgtcactcaaggctgctggatcagctgctggaatcgcttctggtttgt tccccatattattcttggttctgaaccatacatggtacattttccttataattacatgta gcctgttgtatgctttcctctttcctgggaagcctttctgtaaatgcaaatgtgtttgca -continued ctcaaaccaataaactgtaaaaacagtgaaccccttgagcaagcaaaagcactagaaaac caacaaatagatcccccccccaagataccagtgaaatgacaccgggtgacccaaaaataa agcagcttacatcttgactttgagaggaactgcaatcagctataagtaggttattaattt ccagtgcctgcattctgcccaagtactatgatatatttctgaagctttgtttccccagtt cctttttcagacgtttgctgtcaataaagttgagccagccaacttggttcccacaagcta ctaattttgtccaagcttactctatgggagaagttaaatttcccaaattccttgagcaga aaatgaaaaatgaactcaaagtgtcatattaggcaactatctaaagaaaaatacttaatt gaagtttagataagaaaagtgaatatatattgatgtagtctccgttaggtgagaagcgca tcacttacccagcaacatatggacctaaaatttactagtgaacttttcacattgtatcaa aagctcaacaaacagaaagatgactagtcctaaaatgttatttcacatcaaccttatcat acgtgcattatttgttctctatatttctatttcatccgatataaccaatcgtcattgtaa attctataatgcctgtggttacttttgtctttagtgacaaatgacatttaggctaaccat gtagttattgactgatttcgcttgacgtctcttccaattatgtagtagtagagtgttgag atatggatatgttaccttctaaaaaaaaagagtgttgagatgcggatggtttgctagctg gcttttgtctcccttcaagttgaattagcaaaagcaatgtctcataagttggatagctag acaagaaaaactccaaattactttatgtagagtattcttaagcttgagtcgcgagttgga aattggaattatgtaaaaaaacctggaattatttggttgagcctgctttttatttttgtc aatatttccagtatctaacccaacatgtttagagcaattcccagagagcctcaatacgag gcatttgcagagtctttatgagagtccaggaaggggcacacactgtagaggtatagtgtt gtccttatttttttttttttgataaggtaagattttattaaaaggtaccaagatggtgca aaattacaaacatccaaactaatacaacaaagcaactacattcctcctagctcctctaga aaattcatatattgttccatatttttcattacatgtcttttacaccagaaatacaagttt aataagcatctgtttttaatcctggatacatgctgcctttccccttcaaagcaaatcctg tttctttccaaccatattgtccagaacacacatagaggaattgttcttcatactatctgt tgactctttgccactttttgttgttgccatgtctccaacaaactttacactggcaggcat tgcccacttgacatcatatatatttaggaagagctaccaacactgctttgccactttgaa atggatgattagatggttgactgtttctgcctcttcttcacacatgtaacaccggttaca tagagcaaaacctctcttctgcaagttctcctgagttagaaaagcttcctttgctccaat ccaaccaaaacgggctactttaataagtgcttttgacttccatattgctttccatggcca atttgactgataaagcccttgtagtttttgtaacaagctataacaactgctgactgtgaa aataccatcattacttgctgcccagattaatgagtctctcctgttttcctccaatctaac attattcaataactgcatcaattgggaaaattcatcaacttcccagtcattgaggcccct cttgaagattagctgccagccggtgcttgaatagaagtctaacactcttccatttttgtt aatagagcagctatatagaccaggaaactttgatctaagacttccattttccaaccacat atcagaccaaaacagggtattattaccatttccaagtttcagtttcacaaactgactata tttattccaaagattactaattgtgctccaaactccccctttgaagaagattgaattga acgaggagcccacatgtccttcataccatacttggcatctatcacctttttccataatct attcccatcataattatatctccatagccatttaaataaaagacttttgttatgcatctt tagattcctcactcctaatccccctctttctttttttttcatcacctcttgccatttgac caagtgaaatttcttgttatcattattaccttcccacaaaaatttattcctcatagtatt caatttttttctccactgatgttggcattttaacgagagatattagataagtaggtatacc -continued atccatcacactattgaccagtgtaagcctaccaccaagagataaatattgtcttttcca tgacaccagtttactgctacatctatccaagacccccctgccacatctttgcatcattctt ttttgctccaagtggtaggcccagataggtggatggtagctgctccactttacaacccaa aacatctgccagatcatcaatacaatgctcggcattaatactaaacacattactctttgc caagttcactttcaatcccgagacagcttcaaaagctagtagtactcctatgaggtgtaa gagttgctctttttcagcttcacataatatcaatgtatcatcagcatagagtatgtgtga gaaatacagttcttcccccctctctttttctaattttcaatcctctaatccaccctaactt ttctgcttttaaaagcattctgctaaagatttccatcaccaacaaaaataaatagggggga tattggatcccccctgtcttaacccccctctgagaattaaagtatctatgtggactcccatt aattaaaactgagaagctaattgaggatatgcagaattttatccacccaatccatctttc cccaaaattcgtatgtttcatcagatttaacagacatgaccaatttacatgatcataagc cttttccacgtcaagtttgcaggccacccctttaatcttcctcttgaatagatattcaag acactcattagctaccatagcagcatcaataaattgccttcctcttacaaaggcattctg attatctaatatcaattttcctatcaccatctttaatctttcagctatcgactttgcaat tattttatagacactgcccaacaagctgataggtctaaaatctttcacttccgctgcccc ctttttcttaggaataagagcaatgaaaattgagtttaggctcttagtcttgtccttatt ttcagggttgaactagttctttagaagtttcctaggcttcctaatttccaaagttctgcc aggtccttttctagtgaagtacttgaagtttaataaatcaaattttaatttctaacatat cccgagaaattcattcacaaattcaactggtgacttctgatgcagaaacataagcaactg cttatgggttcatatgttcctgcaattttattgttgacatggattggcttcatatggttt tgttcctgcaattttatcgctgacactaatcctttcatatggttttatgtggggtggtaa atagaggttaagagacaagaagaggctggaaaaggtgggcagttcatttgttagtagact actctatttactaagagatatgatgtcccatacattactcgaattggctccaaatacaga ttccacttctttgtcgagtttccttattgtacagagttcgactcgtcaagggaaattcac ttcctttgactgaataatgctagtttgagtagtaccttaaattaaatggaccatttaatt ctatctacttgatagaatagactggtcatcaactagttgcaaatataatgacaactccgc catgtttgcagagtcacctgatgaagaagtacctcaattagtagaccatttcttgaatgt tctacagtattctctatgcctacatgaccacatcacttttccttttgcgttgtgagaact tgaacttggtgagcgggggttccccaggaatggcatcttggtggcagatgaccattctgt ccttatcttagctaatgcttcttggattgcctcactagatttattatacctttaataaat gtttgccattgttctgccataatagagggatgtacctagctggtgcttcacatcacatag tccaaaactaatgaaatgctttacaattgtcgagtactaaaggatgatttgtggaatcag atctcaaacaatttattttgaggaagaaaaataccaaaggtttttttctgtttgttggaag attaaaaatcctttaaaaggtaaagatttatgaacttaattcagcatttttgtggccatt gctgaaaaagagaaaacaatggcacttattcgagtttgcttatccaaaaaaaaaagaagaa gagaatgtcacgtaatgcaatttcatcttaggaaactttgcaggagaaaagcaagagtga taaaacagaactatttgtttttttgataagttgttgtgacctatttctttgtcattctta tttgctaataagctaatgtaccctgtactatggttgttttgacttaatccggggatgttc agtgagcattttcttgtttttttctgctgtcagcatctgctgccttacaggaattcatttt ctggaaatttacttcttgttctgctaacattttcctgttatatcttgtcagtcattttct -continued

```
ctccatggttatactgtttgtgtcactttgaaactctccttgttttctactttaaaggat

ttaatgctgctgtcgggggctgtttctttgctgtggaatctgtgttatggccatcacctg

cagagtcctccttgtacttgacaaatacgacttcaatggttattctcagtgctgttatag

cttctgtagtctcagaaattggtcttggctctgaacctgcatttgcagttccaggatatg

atttccgtacacctactggtaattttggacttctttctcgagtttgattcttaaatacaa

ttgtacccgtcacttacagcaacaacaactacatttcaacagctagttggggttggctac

acagatcatcactatccatttcaatttctttagtcccatttctttcgaatattcagtact

ttgggattctctattatcagaggttctctttattttctactttgacgtacaaatctctaa

atagattaaagaagactcctagagacactggcctaatgcaaatgtaccaccatgaataaa

ccttaatctgaaatagctggtatcgtatataagaacctttagctttaattgtgttctata

ttgatcttttgggacaacttccgtccaataatattatgtcttacttatacagttatactt

atccttaaactttactctttagagtggttatccgtagttcaagcttttgttggcaccata

gctagtttggttcttagtaaaaagttactctttagagtggtaactttttgtcaattttct

tagtgaaaatataacctctgtgacaaatctaccaagtataaatccaatatggttctgtgt

catacttgtagtttatccaagtctatgctccatcactcttacaaaggctcatcgtatgac

taatttttttttgagaaaggtaacagtttgtattgataataagatcagcgccaggttagtc

attagtgctaatagctgtatgtacaactccaaaagagcaaaagacaagcacctggtgtaa

cgtaaattacaagctgcctataaaatctatcaggtctcctacctcactaaacatttcttg

tttacaccaaaaaaataaaacaaggaaagacaatccatcttaatcttctgaatggagttt

cttttgccttcaaacatctcgagttcctttcgttccatgcaatccaccatatacaagctg

ggatgcttttccatttgtctttatccatttttctaccaattcccttccaattgactaga

agttccaatgtggttctagatatgacccaattaactcccaacatataaaagaacatgttc

cacggatttgtagtgattctgcaatgtaggaacaagtgagcattactttctacttcctgt

ccacaaagaaaacatcttgagcaaatctggaaacctcttctttgtaagttatcatgtgtt

aaacatgctttttttaccactaaccagacaaaacatgatactttgggaggagttttaaccc

tccaaatgtgtttccaaggccacacctcagtcattgaaacattatgatttagagtccagt

atgcatcttttactgaaaatgcacctttgctattcagcttccaaactattttatctatgg

tcttgttagtttacagctatgtatatagtgtagtcttgtcccacattggaataggagtag

tatgtccttgtatagtatagctataaataaggacctcttgtattgtattgaacatccaat

atcaataacatattttctcccgtgctttctcacatggtatcagagcaattgtgagagatt

tatcgctgcgcataaattccagcgactccgggaagagaaatcagtcaccggaagtctttt

tccgacgactctttcaaggttgtttgcgtttgctttataaatccaacactaccacaagag

taatcactgtccggcgaccaaaccccagtaaaaatctccggcagcagcctcctcacgcca

ccagaagctcacgcgccggcgcgtacgaccacttccgtccatttttttgaaaaacttcctt

cagaacagttgggtcgcctggtaattcctatcctacccctactgttttcatttcattccg

accactttgagtttttttccggctgctacagtactattccggcagctatagtactattccg

acaactacagtaagattccggctgctacagtatttcattattctgtttttgtgtttcctt

actctgtttcagtggattacaattgattctttctcttatttggtaataatttgcaacaat

gtctatgggatttgatgtttttgggtctagaaacatgagttctggaagctctagtgttat

tattacctcagaaccttaaatgggaggttcaaactacttagcttgggcttcatctgtcga

gttgtggtgtagaggccaaggtgttcaagatcatctaatcaaaccgtctagcgaaggaga
```

-continued tgaaaaggcaataacactttggacaaaaatcgatgctcagttatgtagcatcttgtggcg atctattgattccaagttgatgcccttgtttcgtccattcctgacatgttatttggtttg ggcaaaggcacacaccttatacactaatgacatatctcgcttctatgatgtgatatcgcg gatgacaaactgaaagaagcaagaattagatatgtctacttacttgggtcaagtacaagc aatcatgggggaatttgagaagttgatgccagtttctgctagtgttgaaaaacaacaaga gcagcgacaaaagatgtttctcgctcttaccctcgctgaacttcctaatgatcttgattc agtacgcgaccatattttagctagtccgactgtcccgacagttgatgaattattctctcg attactccgccttgctgtagcaccaagtcacccagtgatctcatcacagatacttgattc ctctgttcttgcatcccagacaatggatgttcgggcatctcaaactatggagcatagacg aggaggaggtcgttttggaagatctagacccaagtgttcttattgtcacaaacttggaca cactcgtgaaatgtgttattccttacatggtcgtccacccaaaaatgcttacattgctca gaccgagactccaggtaaccagggattttctttatctaaagaagaatataatgaactcct tcagtatcgaacaagtaagcagacatctccacaagtagcctcagttgcttagactgatac ttcttttactggtaatttttttgcttgtgtttcccagtctagcactcttggcccatgggt catggactcaggcgcttctgatcacatctctggtaatatatcacttttgttaaatattgt atattcatagtctcttcccattgttactttagccaatggatgtcaaattacggcaaaagg agttggacaagctaatcccttgtcttctatcaccctagattctgttctttatgtccctgg ctgtctttttcgtcttgcatctgttagtcgtttgactcgtgccctccattgtggtatata ttttattgacgattcttttattatgcaggactgcagtacgggacagacaattggtggagg acgtgaatcagaaggcctttactaccttaactcacccagtccttccacaacatgtctggt tacagatcctccagatctaatccacagacgtttaggacatccgagtttatccaaacttca gaagatggtgcctagtttatctagtttgtctacattagattgtgagtcgtgtcagcttgg gaaacatacccgagcctccttttcgcgtagtgttgagagtcttgcatagtctgccttctc cttagttcattctgatatatggggtcctagtagagtaagttcaaccttgggatttcgtta ttttgttagtttcattgatgattattcaagatgtacttggcttttcttaatgaaagaccg ttctgagttattttctatattccagagtttctgtgctgaaatgaaaaaccaatttggtgt ttctattcgcatttttcgcagtgataatgccttagaatatttatcttttcaatttcagca gtttatgacttctcaaggaattattcatcagacatcttgtccttataccccctcaacaaaa tggggttgctgagagaaagaataggcaccttattgagattgctcgcacacttctaattga atctcgtgttccgttgcgtttttggggcgatgcagtgctcacaacttgttatttgattaa tcggatgccttcatctcccatcaaggatcagattccacattcagtattgtttccccagtc acccttatactctcttccaccccgtatttttggaagcacgtgttttgttcataacttagc ccctgggaaagataagttagctcttcgtgctctcaagtgtgtcttccttggttattctcg tgttcagaagggatatcgttattattctccagatcttcgtaggtaccttatgtcagctga cgtcacatttttgagtctaaacctttctttacttttgctgaccaccatgatatatctga ggtcttacctataccgacctttgaggagtttactatagctcctcctccaccttcgaccac agaggtttcatccataccagccgttgaggagtctagtgttgttcctcgtagttccccagc cacaggaacaccactcttgacttatcatcatcgttcgcgccctacatcgggcccaactgg ttctcgtcctgcacctgacccttctcctgctgcggaccctgctcctagtacactgattgc acttcggaaaggtatacgaaccatacttaaccctaatcctcattatgtcggtttgagtta -continued tcatcgtctgtcatttccccattatgcttttatatcttctttgaactcggtttccatccc taagtctacaggtgaaacgttgtctcacccaggatggcgacaggctatgagtgacgagat gtctgctttacatacaagtggtacttgggagcttgttcctcttccctcaggtaaatctac tgttggttgtcgttgggtttatgcagtcaaagttggtcccgatggccagattgatcgact taaggcccgtcttgttgccaaaggatatactcagatatttgggctcgattacagtgatac cttctctcccgtggctaaagtggcttcagtccgtctttttctatccatggctgcggttcg tcattggcccctctatcagctgaacactaagaatgcctttttttcacggtgatcttgagga tgaggtttatatagagcaaccacctggttttgttgctcaggagggggtctcgtggccttg tatgtcgcttgcgtcggtcactttatggtctaaagcagtctcctagagcctggtttggta agttcagcacggttatccaggagtttggcatgactcgtagtgaagctgatcactctgtgt tttatcggcaccctgttgacattccgatggatccgaattctaaacttatgccaggacagg gggagccgcttagcgatcctgcaagctataggcggctggttggaaaattaaattatctca cagtgactagacccgatatttcttatcctgtaagtgttgtgagtcgatttatgaattctc cctgtgatagtcattgggttgcagttgtccgcattattcggtatataaaatcggctccag gcaaagggttactgtttgaggatcaaggtcatgagcagatcgttggatactcagatgctg attgggcaggatcaccttctgatagacgttctacgtctggatgttgtgttttagtaggag gcaatttggtgtcttggaagagcaagaaacagaatgtagttgctcggtctagtgcagaag cagaatatcgagcaatggctatggcaacatatgagctagtctcgaccaaacaattgctca aggagttgaaatttggtgaaatcaatcggatggaacttgtgtgcgataatcaagctgccc ttcatattgcatcaaatccggtgttccatgagagaactaaacacattgagattgattgtc acttcgtcagagaaaagatactttcaggagagattgctacaaagtttgtgaggtcgaatg atcaacttgcagatattttcaccaagtctctcactggtcctcgtattggttatatatgta acaagctcggtacatatgatttgtatgcaccggcttgagggggagtgttagtttacagct atgtatatagtgtagtcttgtctcacattggaataggagtagtatgtccttgtatagtat agctataaataagacagtactaacgtcccttttgccgggggttctgcatctttaaataga tgcacgtggttccatagcagaccgtgttgatcacagatcgtgctgcatcctcttcccagc ggactcggtgagcccctcttgtattgtattgaacatccaatatcaataacatattttctc tcgtgctttctcacaggtctgtgatgtacccttgaaaggttcaagagtttggaggaagat agaaactctgtttatctcccaatcatccaaagatcttctaaagttccagttccatccttg tgagctccagactgacttaccaatgcttggctttgaagacttagagagaataagtcagga aaaatctttcaaccttccttgccctatccggtgatcttcccaaaaagatgtcttcaaccc attgccaacattgatcctgatattgctactgaaagatttcttttggtggcaggattactc tcattaacaatgtacttgacaatctccatacatacgaatgtctctttaccctcttgccat taaggttgtaaagagacttgtcaaattaagaagaggtttcctatggaactgtttcaagga aggaacctcctttcctttggtcaagtggagttaagtcatataatctaggaagtggagact tgggtataaaatagctgcaactacagaaaaggagcatcttatttaaatgatcacgcaaat gtgcccaaaactttaaatatctgcggagcatatggttgtagcaaaatttgaatcttccgg tcaatgttgctcatgtccagtgaatacccctgatggtgaaagtgtcctgaagggaagcag gaacttattggaggaattggcatttaacactcagcatttcgttaggtcatagcccgctga aaattgagtgcccagatttatatagttttgctctaaactgacgatgcagttgcacaacat acgacaaactaaggtgggacatcttcttcggaaggaattttgaggattaagagatagagt -continued ggttgattcagttgcaaatgaagcttcaagggttcaatatcatccaggagacaccggatt ctgatagataaaacaacagaaagatgaacactactttgttaggcttgttacaagttgcta tcgtctttcttatctcggcacacaatttagatttgggaacttatttggaaaatagagtgg ttgtttttgtgaatagcatcagacaaagcttctgagctggtacgacagaaaactcaacag ggagaataaaagactgtggttcacgatttctgcatgcatcttgtaggttatttggtgggt aaaatatttaatgttttgaagggaaggtagaacatgttcataggcttagattcaaatgtt tgtatttttttggctctttggtgagagatgctgaatgtaaatgacataggcagctgacta taatttctcagctccttgctttttaaattggcaggcactgatatgtacatgtgaacatcc aacacttttgtggtgccgttccgatgaataaagcacattaatcacttactgatcaggagt aatagtttaggagttctagaatttttgtacataaaatgaaccaaaaagaatatcggaatg agaacatgtttctttttttgtttcttctttttcgtacaaatttcaataacacttctgata gaatagctaggtccatttgaattcctttggagacccttacacaaccaatgaatggcaagt atagcattttctaacaccctcccacatgtataatccagtttttagggtttagatgtggat ttgatttgaccttattgcctttttttgtttttgttctttttgaagtagagagtgaggagg ctcacaacgacgggctacgtagagcgagattaattcggctcaacgggctaatgattggac ttacatgctacaacaatgttaggagaaagagagagagagagagagaagcccagagcagtt ccacgagttaagaaagagaagtccaaagcgattgaatatgaagagagaaagcggttgtgc taacaggctccctcaagtttggctctgagcatccaactcaaaaccttaaggcaatgagta gagtagcccaggaccatttaaactcctgttgaaaaccttacacaaccaataagggaacaa gtgtaacattctcttacaaccctaccgtcttataagtcagggctctaatttagcataaaa tcaaagtgaggcgatctactatgaaatgaagaaaataactgataaatataaagaatgtta attctcccatatagcctgaatgttcccagaacaaaataaattagtctcatgatttatcat taacatgatgttcctcttattttgagtgattaggaaggttaatcaaggagtaaattcttt ctaatttgtatcgtctagaattatttgtctaacaaattttcagattaccggtgatcaaaa gaggaaaatattttgcatacaacgttaccataccttacaaaagggcgatgaacatttttt tattttattattgtcctttttttcaattaggggttatgcagtcttcctccacgtgatatt actcttagaatcacgtttttgtcattgctattacttactgtggtaagtacaaatgtgttt tgaactctttttggtatgtattattgagttaatttttcgtttccatttcagagctgccgc tttatcttctgctgggcatcttttgtggcttagtttcagtggcattatcaagttgtacat catttatgctgcaaatagtggaaaatattcaaatgaccagcggcatgccaaaagcagctt ttcctgtcctgggcggtcttctggttgggctggtagctttagcatatcctgaaatccttt accagggttttgagaatgttaatattctgctagaatctcgcccactagtgaaaggcctct ccgctgatctgttgctccagcttgtagctgtcaaaatagtaacaacttcattatgccgag cctctggattggttggaggctactatgcgccatctctattcatcggtgctgctactggaa ctgcatatgggaaaattgttagctacattatctctcatgctgatccaatctttcatcttt ccatcttggaagttgcatccccacaagcttatggcctggtatgaatttgtcttttgttag aagtagcattacatatctggataagtgagtttttattattgaaaagtaataacaggaga acaagagaatatatcacccaaatctacttctttcctctcttctattcttctgaaattcaa ggtcctttaactcctccacagtctgtctagttattgatcctgtagacttaattcacatag gtttaggacattcgagtttatccaaacttcatgaaaaggtttctaatttttttacattac -continued attatgagtcgtgtctacttgagaaacatatcactccatgtttctatagtctgttttctc cttagtttattctgatatgtggggtcctattaagtcagttcaaccttgtattttcattat ttttgcagtatcattgataattattcaagatgtacttggatttctttacaagagatagt tctcagttgtttttttgtgttcctaagtttttatgctgcaatacaaaattggtttgatgtc tctatttgcatttttcccaatgataatgccttagaatatttttcttttccgtttcagtagc ttattatttctttaggaactctttatcagaaatctcaactgagatagatgagaggaagaa taagcatatcattggtctcattcagtcccctgtcaagcttagtttcttgagcgatgcggt ttcacgtccttttattagattaattggatgcctcatctgctatccaaaatcagttaactt tcgatattgtttcctcgcttacctttatactctctttccctcgagtctttgggagcacat gttttgttcaataacatagctcctggaaagtgaccagcgcaaccgacaaacaaggccttc ttaatgtagaaggtggacatatgctattctagccacgggaaagaaagtaatattgtaatc aaacccaaatatctgagtataacctttggcaatggcgatcaatttgattatatggaccaa ctttgcctgcatatacccaccgacaaccaataatagatttaccgggaggtagagaaacaa gctcccaaataccactaatatgtaaagcagatatatctctgatcatagcttgtccttgtg gacatagggatagaaattaaggacaaagatgacacaaaagcataatgcggtgatgataaa cgatgataactcaaatcaatataatggggatggggattgagagtggatcgaatatctttg cggaatgcgattggtagactaggaggagagaagtctgtggacatgatgttggactgagat caataataagtcaagaatggtggagctacagaacatggaactggagctgtaggtgacata atcggagctgtaggaggtggagctatagaggaaggtgaaggagagatagcgactgaatct ccaaaagatgaaaccggtaatacctcaaaaaatgtctaagagatcatttggacctatgaa gtatgattgcgtttttaaaaaggtaacatcataaggtcaggtgaataacattgatatccc cgttgcatcctcgagtaacttagaaatatacatttgagagcacggagagctaacttatct tttctggagcaaggttgtaaacaaaacacgtgctcccaaagacacgaggtggaagagaga aaggtgagtggggaaacaagacagaggatgaaacttgactcttgatagttgaagatgaca tacaattaataagacaataggatgtgagatccaatgacagttctcatgaactgctgaaat ggagaagacaaatactctggggcgttatcactacgaaatgtgcagttagaaaccccaaat tgattttggatttcagtgtggaaggtctaaaaaatagagaacaactcagattgatttttc atcaagaatatccaagtggacttggaataatcatcaatgaaactgacaaagtagcggaat tccaaggtagaactaacccgacaaggaccccaaacatctgaatggactaaagtgaaaggt aactctacccgattatcaggatgtcgagggaaatgagagtgagtatgccttctgagcgga tatgactcacgctctagagtggacaagtgagacaaacgaggtactattttctaaagttct gataaattgggatgtcctaactgtatatgtaataaatctggtggatcagtaaaaggacaa gctgtagggggaaaaaaataccaaatatttccagaagatggcaaactacaacagaagatg caactgcattaacatgctcaggataggtgatgaaatcattgaggacaaagagttgatcaa gaaggagattctggaattttaccagaacttatatagtgaaaatgaaccctggaggcgcag tgcaaatttcgaagacatctcctcactaagcatagaagagaagaactggttggaagctcc atttgtagaaatagaggtgcttgaagctttgaaatcatgtgccccttataaagcaccagg tccagaaggcttcactatggatttctttcagaaaaattgggatactcttaaaacagacat catggctgcacttaatcattttcaccagagctgtcacatggttagggcttgcaatgccac cttcattgccctaattccaaagaaaaatggtgctatggagctcagagactacagacctat tagcttgacaggtattgtatacaaattggtttcaaagattttagcagagaggctcaagaa -continued ggtaattgacaaactagtctcggggggaacaaaatgctttcatcaagaacaggcagatcac tgatgcttccttgattgccaatgaagtgctggattggagaatgaaaagtggagaaccagg cgtgttgtgcaaactggacattaaaaaggcttttgatcaattaagctggtcttacctcat gagtatcttgaggcagatgggctttggggagaaatggagaagatggataaactattgcat ttcaactgtcaagtactctgttttggtgaataggacccaatcggtttttctcccccca aaagggcctaaggcaggggggatcccctctccccttcctattcattctggcgatggaagg actcactaaaatgttggagaaggctaagcaactgcaatggatacaaggctttcaggtggg aaggaatcctgccagctcagttacagtatctcatctactctttgcggatgatactcttat tttctgtggtactgagagatcacaagcacgaaatctcaacctgacactgatgatcttcga ggcactatcaggactccacatcaatatgataaagagcatcatataccctgtgaatgcagt ccccaacatacaagagctagcagacatcctatgccgcaaaacagacactttcccaaccac atatcttggacttcccttgggagctaaattcaaatcaaaagaagtttggaatggagtcct agagaagtttgaaaagaggcttgcgacttggcaaatgcaatacctccccatgggtggcag gttaactttaatcaatagtgtactggacagtcttcccacataccacatatctttgttccc aattccaatctcagtcctaaagcagatggacaaactcagaaggaagttcttatgggaagg atgcagcaaaacacacaaatttccactagtgaaatggctgaaggtaactcaaccaaaatt caaaggagtcttgggaatcagggatgctatgctcttaaaatggctctggagatatggaca ggaggaatctaggctatggaaggacatcatatttgctaaatatggagcacacaaccactg gtgttccaagaaaacaaactctccttatggagttggtctgtggaagaacatcagcaacca ctgggatgaattcttccaaaatgtaactttcaaagttgggaatgtaactcgtataagttt tggaaggatagatggcttggaaatacacctttgaaagacatgtttcccagtatgtatcag attgccgtgaccaaagactccactgttgctcataatagaaacaatgacacttggtaccca cttttcagaagaaatttgcaggattgggaggtcaacaacctactcacaatgttaagctcc ctagaatgtcataacattgaagatcaacaacctgacaaacttatttgggaaaattctaag agaggcaagtacacagtcaaagaatgatacattcacctctgtgaccagaatccaatatat aactggccatggaaacatatctggagaactaaagtgcctaccaagatgacttgcttcaca tgattgtctctaaatggggcctgtctcactcaagacaacttaatcaagaggaacatcata taagttaatagatgctacatgtgccaacaacagtcagaaagtgtaaagcacttattcctt cactgctcagttgcaaaagaaatttggaacttcttctacactacctttggtctaaaatgg gttatgccacaatcaactaagcaagcttttgaaagttggtatttttggagagttgataaa tccattagaaaaatctggaaaatggtgtcggccgcaagtttttggtgtatttggaaagaa aggaactgaagatgttttgatggcatatcaactccactcaaggctgcgtgtttagttaac ttattttgctggaactatctcacccctgttaatagtgctgatacttctgtggatttcatt agccccctgatagtagcataggcttttgtaaatggagctaattatcctttctcttttgta ctctttgcatcttcttgatgccttttaatgaatctaatttacttcatcaaaaagaaaatg acaagttgttgaaggaggaaaagatgtgagtccatgtgatttagcaaggataaggtacta aagtccatttgattcacgtccggtaccaatgatccgtctcgtgctgcattcctgtattaa aacagagtcatcaagaaataaaatagagcaaataagtgattggccaagcgactagtggat atgagattaaaaggactatggggaacataaaaaaactgaattcaaaggtaaggaaggaagt ggactagcttaacctattctagttgccatggtttgagaatcgttggccattgtgactatt -continued ggaagtgattgagagtaagaaatagtagtgaaaggagatttgttacccgaaatataatta gatgcacctgaatcaatgacccaaaagtcggaagaagaggaaacacaagtcacgctatta cctgtttgaacaatagagattagtttggatcaaatagttgtatagagaactgaaatttgg agaaatcaatcatatagaacttgtatgtgattattgttgccctttatattgcgtcaaatc ctaaaacacattgagattaactgccacttatcacagaaaagatattctctagagacattg ttacaatttcatgaagtcaagtaattagcttgaacatatcttcagcaagtccctcgtcag tcctcatattagttacatttgtaacaatgtcggtacataagacttataagcaccagtttg aggaggagtggtagagagttgatgtacatagttaaagtagatatacttacacttagtgtt atgtaaagagtggatataaaaagggatcagcataagacaattgtcttcgcgcgtcttaac atttttttcctgtctttatttctctcatggtatcagataacctatctctatcttggttta cccaatggttggcccccatattgtattagccatgctccagttgactaggcttggacgggc agaggtgttaaattatcccatattggttgaaagaatgagctattgtctccttatatggtc ttagacaattctccaactcatgagatattttgttttggctgagttagccctaaggtttat tttttgtcatattctttaaccttatggcaatgcttgtacacggaaaaaccggagtgcaag acttaaattaggagaaggaaactattgaaggtgaggaacttaaagggttgtgagaataca cgggagaaaaaaatcttaatactatctagtggccttgtatatcaaatgatcagcttgcaa atattttcaccaagtccctcactggtcctcgtattagttacatatgtaacaagttcggta tatatgatttgtatgcaccggcttgaggttatgcatattctattcctcctactatatatg tgactaggaaatattttactcctactgcatatgggactaggactatttacacataactat ctaacattcccctcaagccagtgcacacaagtcatatgtaccgagcttgttacatatgta actaatacgaggaccagtgagggatttagtaaaaatatctgcaagctggtcattcgacat acaaggccactagactcccccgagcaacaaaaccaggtggttgctgataaacagaaact ggccgaaaagttgccggaaaaatttgaaaatagtgagactaagccgaattctacactaca aaataggttctaaaacaccaccagaaaacaaaaactttttctagaaattactcttcacacc ggaaaaaataaaagttgtcagaatttgatgtaatttatatagataggttcggaatcactg gaggagtaagttgtcccgaagaagttttgtcaaaaagtggccggaatggctcacatgcgc cggaaaacttactgtagctcgcaggaaccctagttctggcggtgcgtggaggcgcgtgac ttaagattaagatgcttacaggactatcttgagaaatatacatattatatagacgcttga gttgcttcccaatcctaaatagaagcttttattcgtaggcaagaagggaagcagctttac ttgagccaatagctttcaaggtgcacgttgtcacaccaaggacatccagaatttgatttt ataggggggtgtgagaaagcacgggagaaaatatgttattgatatttggataataaataca atacaagaggtccctatttatagctatacactacaaggagatattactcctcttccaatg tgggacaagaatacactatacatatctgtaaactaacactccccctcaagtcggtgcata cacatcatatgtaccgatcttgttacacatgtagctaatacgagaaccaataagagactt agtgaaaatatctgctagttgatcattcgactttacaaactttgtaacaatatctcctga aagtatttttttctctgacaaagtgacagtcgatctcaatgtgtttagtcctctcatggaa caccggatttgacacaatatgaagagtagcttggttatcacacattagttccatcttgct gatttctccgaattttaactccttgagcaactgcttgacccaaaataactcacacgtcgt catagccatggcccgatattcggcttcggcgctagatcgagcaactacattctgtttctt gctcttccacgagaccaaattacctcctactagaacacaatatccagacatagaacgtct atcaaaaggtgatcttgcccaatcagcatctgtgtacccaacaatctgctcgtggccttg -continued atcctcgaatagtaatcctttgcccggagctgactttatataccgaagaatgcgaacaac tgcatcccagtgactatcacagggagaatccataaactgacttacaacactcaccggaaa agaaatgtcaggtctagtcactgtgaggtaattcaatttgccaaccaacctcctatatct cgtagggtctctaagaggctcccccctgtccaggcagaagcttagcattcagatccatagg agagtcaataggtctgcaacccatcattccagtctcctcaagaatgtctaagacatactt ccgctgtgaaataacaatacctgagctagactgagcgacctcaatacctaaaaaatactt caatctgcccagatccttagtctggaagtgctgaaagagatgttgcttcagattagtaat accatcctgatcattgccagtaataacaatatcatcaacataaatcactagataaataca cagattaggagcagaatgccgataaaacacagagtgatcagcctcactacgagtcatacc gaactcctgaataattgtgctgaacttaccaaaccaagctcgaggggactgtttcaaacc atatagtgacctgcgcaatctgcacacacaaccattaaactcccctaagcaacaaaacca ggtggttgctccatataaacttcttcctcaagatcactgtggagaaaagcattcttaatg tctaactgataaagaggccaatgacgtacaacagccatggacaaaaagagacgaacagat gctactttagccacgggagagaacatatcactataatcaagcccaaaaatctgagtatat ccttttgcaacaagacgagccttaaaccgatcaacctggccatccggaccgactttgact gcataaacccaacgacaaccaacagtagacttacctgcaggaagaggaacaagctcccaa gtgcaactcgcatgtaaagcagacatctcgtcaatcatagcatgtcgccatcctggatga gatagtgcctcacctgtagacttagggatagaaacagtggacaaagaagatataaaagca taatgaggtgacgacagacgatgataacttaaaccgacatagtggggattaggattaagt gtggatcatacacctttgcggagtgcaattggttgactaagaggagacaagtccgcagta ggtgcagaatctgatgcggggcgtgaatcacctgggcctgatgctggatatggacgacga tgataagtcaagagtggtggagctgccgaaggttgaactggattatgtggaggaactgga gctataggtggtggagctacaactggagctgtaggtggtggaactagagtaactgaatct ccaaaagatgaaactggtagtacctcagaaatatctaagtgatgacctgaacctgtgaag tatgattgggtttcaaagaaggtaacatcagcagacataaggtactgctggaggttagga gagtagcatcgatacccctttttgtgttctcgagaaacctagaaatacgcacttaagagca cgaggagctaacttatccgttcctggaataaggttatgcacaaaacaagtgcttccaaag atacgaggtggaagagagaacaaaggtaagtggtaaaacatgacagagaatggaacttgg ttctggatagctgatgatgtcatacgattaataagatagcaagatgtaagaactgtatcc cccaaaaacgcaacggagcatgagattgtatgagtagggtacgagcagtttcaataaaat gtctattctttctttcagctaccccattttgttgagatgtgtacagacaagatgtttgat gaataatcccatgagatttcataaactgctgaaatggggaagacaaatactctcgggcat tatcactacgaaatgtgcgaatagaaaccccaaattgattttgaatttcagcgtggaagg tctggaaaatagaaaacagctcagatcgatttttttatcaaaaatatccaagtgcacctgg aataatcatcaatgaaactgacaaaatagcagaatcccaaggtggaactgacccgactag gaccccaaacatctgaatggactaaagtaaaaggtgactctgctcgattatcaagacgcc taaggaaatgggagcgagtatgcttaccgagctgacatgactcacactctagagctgaca agtgagataaaccagataccattttctgaagttttgacaaactgggatgtcccaaccgtt tatgtaataaatctggtgaatcagtaacaggacatattgtagatggaagacaagatgcga gtccatgtatttagcaaggataaggtaataaagtccgtttgattcacgcccggtaccaat -continued gatccgccccgtactgcgttcttgtataaaaacatggtcatcaagaaataaaataacgca tttaagtgatttggctaagcgactaacaactatgagattaaaggactattgcgaacata aaggactgaatctaaaggtaaggaagaaagtgggcttgcttgacctattgcagttgccat ggtttgagacccattggctattgtgacttttggaaaagattgagaatacgaaatagtagt gaaaagagatttgttaccagaaatatgatctgatgcacctgaatcaatgacccaagactc agaggatgaagattgggaaaaacaagtcacgctattacctgtttgaacaacagaagctat ctcagaagatgtctgcttacatgctttgtactaaaggaactcaatataatctgctaaaga aaccatccgactattcaaagcatcggttcccatgtcgctacaatttgtagtagtagggtt aacttgaaatagtggaaataagtaactccggtgagaaaactgaagaaatagcttgaaaac actgtttacaacagtaaaaacagaacactgttctgcgccggaatctactgtagctgacgg aaaaactcaaagtagtcggaatgaaacgaaaaacagtaggggtaggatcggaattaccag gcgacccaactattctgaaggaagtttttcaaaaaatggccggaagtggtcgtacgtgtc ggcgcgtgagctcacgcgcgtgagcttctggtggcgcgtggaggcgcgtgaggaggctgc tgccggagattttcactggggtttggtcgccggacagtgactactcttgtggtagtgttg gattttgcacaacactgacggagataaagcagacgcaaacagccttgaaaaagtcgccgg aaaagacttccggtgactgatttctcttcctggaatcgctggaatttatgcacagcgata aatctctcacaattgctctgataccatgtgagaaagcatgggagaaaatatgttattgat atttggataataaatacaatacaagaggtccctatttatagctatacactacaaggagat attacttctcttccaatgtgggacaaaaatacactatacatatctgtaaactaacaaggg gaatatcgtttaaagataaaaaagatagcgtgcagaagattgcatacattagagatgcaa aatacagaatacccatactcccagataatgcagtatgccttttgcatgacccactggttg aatggaagcacctggtcaatttactaggtgtgttagtgatttttgctgcttccttcccct ttctaaactacatactatctaaaatgttaggggacagaagcccagtcaatctgactagg tgatgttagtggtttccgcttctttctcccacttctaaatgcgtactttctcaaatttag gagcatagaaacttaagcagctgcctacctgaggaggtgcatgggaacataagagaatag actttacctgtcatattttccataccttagttaattacagtgttatcctgataatgatct gttttctgtatctaggctgaatcgagattcaatcgcttttggctgaaaggatgctgctac agatccttagtttacatcattgtggttcttattctataagtacttcccctatcaactact tccttctttttttcttaggttatttgcctcttaggttgtttgcaaggaaaggaacaataga tgttttgatggaatagcaactccaaaccacttccttaaggctaatatactgtttggccaa gcttcttcaaagtccaaagccctttttttgtcttcaaaaaagtatcttttttttcccaaagt tgaggtgtttggccaaacttttggaaggaaaaaaaagtgcttttgagtaaagcagaagct cttgagaagtagaaaaagtagtttttttcccggaagcatttttttgaaaagcacttttgag aaaaataaacttagaaacactttttaaaagtttggccaaacactaattgctgcttaaaag tgtttttcagatttattagccaaacacaaactgcttctcaccaaaagtactttttttgaaa aatactttttttgaaaagtgattttcaaacaaagcacttttcaaaataagtttattttaga agcttgtcaaccggctataaatgtcttttatttttacagctagagtaccctaacacctgt aaattcccctagacatttttttcgactttgttagctcattaaccctagtataggactctt tgttttggagctagcaaactcttttgttttcctatttttgcatcttcttggtgccattta taatatctcttacttcaccaaaaaaaataagttcccaaaatatgactaccttgagttggc caaagcataaccaaagcttgggcacaccagtgtttgcgtgaattttatggatgttcctta -continued cctttatccttctgtgcttatgtagcatctgtcttggttaatcttttctgaagtctatag
tgtatttctgtgttgcaacatgagtttactgtcaatcttactgtttgacctcaattttgg
gttctttttgattttgaaagacatcgtttaacaggttggcatggctgctactcttgctgg
tgtctgtcaggtgcctctcactgctgttttgcttctctttgaactgacacagaattatcg
gatagttctgcccctcttgggagctgtggggttgtcttcttgggttacatctggacaaac
aaggaaaagtgtagtgaaggatagagaaagactaaaagatgcaagagcccacatgatgca
gcgacaaggaacttctttctccaacatttctagtttaacttattcttcaggtgtgaaacc
ttcacagaaagagagtaacctatgcaaacttgagagttccctctgtctttatgaatctga
tgatgaagaaaatgatttggcaaggacaattctagtttcacaggcaatgagaacacgata
tgtgacagttctaatgagcaccttgctaacggagaccatatccctcatgctagctgagaa
gcaatcttgtgcaataatagttgatgaaaataattttctcattggtctgctgacacttag
tgatatccagaattacagcaagttgccaagagcagagggcaatttccaggaggtagcttc
ttggtacatttcaatattcttaactgatgaaaaaataagggaaattgatctagcatgaaa
ttaagctaattataagttttacactgtagaactggtaaaacagggttggctggatatttc
tttgttgaatttttaggattatatgtattgttttagttttgtaggttgttttctgatgtg
ctttttgacttggcagaatcttaagatgaaatggaaggtgtttaaccaaaaaatagaatt
ttcagtcaaagcctatatttagaagaaaacgggttattgataaccaagttttactttact
tccccaacaatctatttggtaaatagcaaaagtaatgcgtatgtgagaaagcacgggaga
aaatatattattgatattagatattcaatataatacaagaggtcctacacatcatatagc
tatagtctacaaactacatattactctcattccaatgtgggactacacataactaacact
ccccctcaagccggtgcatacatatcatatgtaccgagcttgttacacatgtaactaata
cgagaaccagtaagagacttagtgaaaatatctgctagttgatcatttgactttacaaac
tttgtaaaaatatctcctgaaagtatttttctctgacaaagtaacagtcgatctcaatg
tgtttagtcctctcatggaatagcggatttgacgcaatatgaagagcagcttggttatca
cacaccagttccatcttgctgatttctccaaactttaactccttgagcaactgcttgacc
caaactaactctcacgttgccatagccattgcccgatattcgacgtcggcgccagatcga
gcaactacattctgtttcttgctcttccacgagaccaaattacctcctactagaacacaa
tatccaggcgtagaacgtctatcaaaaggtgatcctgcccaatcagcatttgtgtaccca
acaatttgctcgtggcctcgatcctcgagtagtaatcctttgcttggagatgactttata
taccgaagaatgcgaacaactgcatcccagtgactatcacagggagaatccataaactga
cttacaacactcaccggaaaagaaatgtcaggtctagtcactgtgaggtaattcaatttg
ccaaccaacctcctatatctcgtagggtctctaagaggctccccgtgtctaggcagaagc
ttagcattcggatccataagagagtcaataggtctgtaacccatcattccagtctcctca
aaaatgtctaaggcataattccgctgtgaaataacaatacctgagctagactgaggcact
gagcaacctcaatacctagaaaatacttcaatctgcccagatccttagtctggaagtgct
gaaagagatgttgcttcagattagtaatatcatcctgatcattgccagtaataacaatat
catcaacataaaccactagataaatacacagattaggagtaaagtgccgataaaacacag
agagatcagcctcactacgagtcatggcgaactcctgaataattatgctgaacttaccaa
accaagctcgaggggactgtttcaaaccatataatgacctgcacaatctacacacacaac
cattaaactcccccctgagcaacaaaaccaggtggttactccatataaacttcttcctcaa -continued gatcaccgtggagaaaagcattcttaatgtctaactgataaagaggccaatgacgtacaa cagccatggacaaaaagagacgaacaaatgctattttagccacgggagagaaagtatcac tataatcaagcccaaaaatctgagtatatccttttgcaacaagacgagccttaagccgat caacctggccatccgggccgactttgaccgcataaacctaatgacaaccaacattagact tacctgcaggaagaggaacaagctcccaagtgccactcgcatgtaaagcagacatctcgt caatcatagcatgtcgccatcctggatgagatagtgcctcacctgtagacttagggatag aaacagtggacaaagaagatataaaagcataatgaggtgatgacacacgatgatgactta aaccgacatagtggggattaggattacgtgtggatcgtacgcctttgcggagtgcaattg gttgactaagaggagacaagatcgtagtaggtgcagaatctgatgcagggcgtgaatcac ttgggcatgatgttggatgtggacgacgatgataagtcaagagtggtggagctgcagaag gttgaactggattatgtggaggaactggaggtggagctacaactggagctgtaggtggtg gaactggagctataagtggtggagctacaactggagctggagatgtagaggaagatgaat gagagatagtgactgaatctccaaaaaataaaattggtagtacctcagaaatatctaagt gatgacatgaacctgtgaagtatgattgagtttcaaagaaggtaacatcagcggacataa ggtaccgctgaaggtcaagagagtagcatcgataccccttttgtgttctcgagtaaccta gaaatacgcacttaagagcacgaggagctaacttatctgttcctggagtaaggttatgga caaaacaagtgattccaaagatacagggtggaagagagaacaaaggtaagtggggaaaca tgacaaagaatggaacttggttttggataactgaagatggcatacgattaataagatagc aagatataagaactgcatcccccccaaaaacgaaacggagcatgagattgtatgagtaggg tacgagcaatttcaataagatgtctatttttttctttcagctaccccattttgttgagatg tgtacagacaagatgtttgatgaataatcccatgagatttcataaactgctgaaatgggg aagacaaatactctcgggcattatcactaggaaatgtgcgaatagaaaccccaaattgat tttgaatttttagcgtggaaggtctggaaaaatagaaaacaactcagatcgatttttttat caaaaatatccaagtgcaccttgaataatcatcaattattcaataaaactgacaaagtag cagaatcccaaggtggaactgacccgactaggaccccaaacatttgagaatggactaaag taaaaggtgactctgcttgattatcaagacgccgagggaaatggaagcgagtatgcttat cgaactgacatgactcacactctagagctgacaagtgagataaaccagataccattttat gaagttttgacaaattgggatgtcccgaccgtttatgtaataaatttggtgtattagtaa caggacaagttgttgaaggaagacaagatgtgagtccgtgtgatttagcaaggataaggt aataaagtccgtttgattcacgtccggtaccaataattcgtcccgtactgcgttcctgta taaaaacatggtcatcaagaaataaaacaacgcatttaagtgatttggctaagcgactaa tagttatgagattaaaaggactattgggaacataaatgactgaatataaaggtaaggaag gaagtgagcttgcttgacttattgttgttgccattgtttgagacctattggccattgtga ctcttgaaagagattgaaaatacgaaatagtagtgaaaagagatttgttaccagaaatat gatctgatgcacctgaatcaatgacccaaaactcagatgatgaagattgggagaaacaag tcacgctattacctgtttaaacaacagaagctatcacagaagatgtctgcttacatgctt tgtaccgaaggaactcaatataatctgctaaagaaaccatccgactattcaaagtatcgg ttcccatgtcgctacaatttgtagtaataggatggatagactcggaaaattgtaaagtta tcggaatttgtcgtaaccaggatcgagcaagctgtcttgaagaaatggtttcaaaaaatg tccggaaaggtcacttttacgccggaaaaatataaaaatggtcgaaatttgatttgaatt agatgggtaggctcggaattgtgaggagagcagactgtcctgaagaagcttaatgaaaaa -continued atggccggaaagtggccggaaccctcgccgtaaaagttgttaccggcgcgtgaaggcgcg
tggcatttttttctgccagataaattttcaggggttggtcgtcggagggtgatcccttgtg
gtggtgttggtttttgcacaataccgacaggccttaggtcacccgaaaatttgcacgatg
actaagttctttcttcccggttaacgctggaatgacgcacatcgatcttttctcactaat
gctatgataccatgtgagaaagcacgggagaaaatatattattgatattagatactcaat
ataatacaagaggtcatatttatagctatagtctacaaagtacatattactctcattcaa
atgtgggactacacataactaacaacgtaaattaacaaagagaaataaggaatgtaacaa
cagtcaatccctaaaatcaaggtagaaaactttgataaagcagagaattatagaatgtat
ttcagtagtacttggaacttgtccttacaaataaaattctttatccttatatagggggcgt
acaatcataacatttttcgcacttaattcgaattcattatgagcattaattgtattgatt
gcccgttatcatagataaccataactgacgtatttgtaactataaatgccttataacggc
tctgattccccttccttatttacttctggtttgtgtatctttccttctttttagccttta
ttcattcagttctcgcctcttctttgacaactgtcaagcccgatcctctgttctgtactg
tctcgtgggtgtttcccccgtaccttccttatattcttaattctgttaattgagagtgtc
acttgtcactatgccattgttccacgcgtcatgtttcatccacgtgtaatatctttttttc
caccaatacagataatcccccactttctgaatattctcaactgaatattcgggtaagttt
ttatggcgggaattctttgccgtcgtttttcgagtatcatcgtgtcatcttcagaaccga
tgtgacgtacgtcacgtctatttaatgcctatgccaggtggcttctatcgattggctctg
cagtttttttagcgctttttagggtttttcagcggctgcgtcagtcacgaagtgacggttc
cattatgacgcttcataatgactaactttaatgatggtcgtgtcttcttattaatacttc
attccttttgatctcttggagtcttccttcttcagtatccaccacattacttctttgta
tttctgcatcttctctttgatattcctttggacaatcatgtcttcttctacaccagaccc
ccgtaaggttgtgattgttgacgaacttgatctttctactgctcctactagaagtaggag
aggtggtagacttcgtagtcttggttcactatctaatcgtggttcttcttcccagggtag
tgctgctaagccatcttcttctagacctagggctcctttaacccctagatcttcttctag
gaatagagatttaaatgatccagtgcgcgaacctacagttgcagagattgttcctcaaga
attttcttttgtaactgaccgtgaaaccataaggaatcaaatttcttctatagcctccct
caataccgctaacctttatccaagtttaatcagtaatggtcttctctcccgggttcgaag
agaatattactgaaaccagatttcccaattttagtccctggtgccaaccagagaattact
ccataccatgttggtttttcctttgtttacacctacccttttactttagggttcaaacca
cctattgaaccagtaatcattgaattctgtcgttatttcaacgtgtgtcttggccagatt
gaccacatagtatggagggctgttcatgccttcgttatttatcagatttggtttccatgc
ctttcacttttcagcacttgcttcatctctactcccctaaattgtttcgtgaagtagttt
ttactctcgtggctagaagtaagagagtgttggttagccttgaagacgattgggaccgtg
gctggtacgctcgttttgttgctgctcccactagtgcattagtgggtgaagaaaatatgc
ctttcccggagaaatggaactttgcacgtaagctttcttctcctcttttttttttgtctta
aaaaaactccatgtaatcatatacccacttcttcagcaactatggaagtttttttatgctt
gggtagaaaagatgttaactgctgcgcctatggagaaaagatcctggaaatacttttctc
aaagatttggttggaaagtgaagacgcacggtactttttaccttcattgtttttcctttt
ctcttccttgtttgttcaatgatttctcatccttccctttttttttactagggtttccga -continued ttcgtggtattagtcccgcgtctgttccatcaactaggctttccgtgattcttgttcagg aaagaattttaagtgcttcttcttcaaaaaggaaaactgacggagcccgtggctctgatg acgaagaagaaacagaggagggttctttggtgcgaaggtcacgcgtcaggagacgcgtgg tttctgatgatgaaactactccttctcatgaccctctatctagttcaatcccttttagac tcacggatgagctagagagtacccctttagtgatttcttatgatgatgctgttgatcccc ctccaagttctgttgatagattgtttgctcatggcttcgagggtgatgaagttttgggcc tgtttctgaagaattgccccttgcttcccttccagtttcagttttcattaacccttccgt gtccttacctgatgatactcctgttgttattctcgtggctgcttctactccgtcatctat tcccgtgactgcttctcatgcagaggccaaaccttctagcagcagaagggcaatgaaaag agttgttgttgaggttcctgaaggtgagaacttattaagaaaatccggtcaagccgacgt gtagttgaaacctatgctcggccccgtagagaagaagaagttagaaagccatagctcact cactttaatgaatgatatcgttcattcttccttgaaagtacaagcttaattatatttcct ttcttttctctttcttattcataactcttcctcctttttttgcagatcaacttgattggca cagagcttatgaaaagagtttctcaggcggaccggcaagttatagatttgcgcaccgagg ctgataactggaaggaacaattcgaaggtcttcaattggaaaaagaggttccggcggaag agaagaatgctttggaacaacagatgagagtgattgcctctgaattagcagttgaaaaag cttcctcgagccaggttggaaaggataagtatatacttgaatcctcctttgctgaacaac tttccaaggcaactgaagaaataaggagtttgaaggaactccttaatcaaaaagaggttt atgcgagagaattggttcaaacacttactcaagttcaggaagatctccgtgcctctactt ataagattcagttcttggaaagttctctcgcttctttgaagacagcttacgatgcctctg aagcagaaaaagaagagctgagagctgagatttaccagtgggagaaggattatgagattc tcgaggataatctatcgttggatgtaagttgggctttcttaaacactcgtctcgagactc tagttgaagccaaccatgagggttttgaccttaatgctgagattgctaaggctaaagaag caattgataaaactcagcaacgtcaaatcttttcctcacctgaagacgaaggtcccgaag gtgatggagattga

SEQ ID NO: 12

(Protein sequence of NtCLCe from *Nicotiana tabacum*; sequence originating from the ancestor *N. sylvestris*; two start codons, translated from SEQ ID NO: 10)

MISGQNTVLHNPPNSLFNSLSPRHICISFCNDKALKKSVTHSAPRFARLL

NNESRKLLGRHPNCWPWARRPSLPPGRSSDGNIEKEQDMCDSSKVDSDSG

IQIGSLLEEVIPQGNNTAIISACFVGLFTGISVVLFNAAVHEIRDLCWDG

IPYRAASEEPIGVHWQRVILVPACGGLVVSFLNAFRATLEVSTEGSWTSS

VKSVLEPVLKTMAACVTLGTGNSLGPEGPSVEIGTSVAKGVGALLDKGGR

RKLSLKAAGSAAGIASGFNAAVGGCFFAVESVLWPSPAESSLSLTNTTSM

VILSAVIASVVSEIGLGSEPAFAVPGYDFRTPTELPLYLLLGIFCGLVSV

ALSSCTSFMLQIVENIQTTSGMPKAAFPVLGGLLVGLVALAYPEILYQGF

ENVNILLESRPLVKGLSADLLLQLVAVKIVTTSLCRASGLVGGYYAPSLF

IGAATGTAYGKIVSYIISHADPIFHLSILEVASPQAYGLVGMAATLAGVC

QVPLTAVLLLFELTQDYRIVLPLLGAVGLSSWVTSGQTRKSVVKDREKLK

DARAHMMQRQGTSFSNISSLTYSSGSPSQKESNLCKLESSLCLYESDDEE

NDLARTILVSQAMRTRYVTVLMSTLLMETISLMLAEKQSCAIIVDENNFL

IGLLTLGDIQNYSKLPRTEGNFQEELVVAGVCSSKGNKCRVSCTVTPNTD

-continued

LLSALTLMEKHDLSQLPVILGDVEDEGIHPVGILDRECINVACRALATRE

QLC

SEQ ID NO: 13

(Protein sequence of NtCLCe from *Nicotiana tabacum*; sequence originating from the ancestor *N. tomentosiformis*; one start codon, translated from SEQ ID NO: 4)

MCDSSKDDSDSDSGIQIGSLLEEVIPQGNNTAIISACFVGLFTGISVVLFNAAVHEIRDLCW

DGIPYRAASEEPIGVHWQRVILVPACGGLVVSFLNAFRATLEVSTEESWT

SSVKSVLGPVLKTMAACVTLGTGNSLGPEGPSVEIGTSVAKGVGALLDKG

GRRKLSLKAAGSAAGIASGFNAAVGGCFFAVESVLWPSPAESSLYLTNTT

SMVILSAVIASVVSEIGLGSEPAFAVPGYDFRTPTELPLYLLLGIFCGLV

SVALSSCTSFMLQIVENIQMTSGMPKAAFPVLGGLLVGLVALAYPEILYQ

GFENVNILLESRPLVKGLSADLLLQLVAVKIVTTSLCRASGLVGGYYAPS

LEIGAATGTAYGKIVSYIISHADPIFHLSILEVASPQAYGLVGMAATLAG

VCQVPLTAVLLLFELTQNYRIVLPLLGAVGLSSWVTSGQTRKSVVKDRER

LKDARAHMMQRQGTSFSNISSLTYSSGVKPSQKESNLCKLESSLCLYESD

DEENDLARTILVSQAMRTRYVTVLMSTLLTETISLMLAEKQSCAIIVDEN

NFLIGLLTLSDIQNYSKLPRAEGNFQEINLIGTELMKRVSQADRQVIDLR

TEADNWKEQFEGLQLEKEVPAEEKNALEQQMRVIASELAVEKASSSQVGK

DKYILESSFAEQLSKATEEIRSLKELLNQKEVYARELVQTLTQVQEDLRA

STYKIQFLESSLASLKTAYDASEAEKEELRAEIYQWEKDYEILEDNLSLD

VSWAFLNTRLETLVEANHEGFDLNAEIAKAKEAIDKTQQRQIFSSPEDEG

PEGDGD

SEQ ID NO: 14

(Protein sequence of NtCLCe from *Nicotiana tabacum*; sequence originating from the ancestor *N. tomentosiformis*; two start codons, translated from SEQ ID NO: 11)

MISGQNTVLHHPPNSLFNSLSPRHICVSFCNDKALKKSVTHSAPRFARLL

NNESRKLLGRHPNCWPWARRPSLPPGRSCDGNIEKEQDMCDSSKDDSDSD

SGIQIGSLLEEVIPQGNNTAIISACFVGLFTGISVVLFNAAVHEIRDLCW

DGIPYRAASEEPIGVHWQRVILVPACGGLVVSFLNAFRATLEVSTEESWT

SSVKSVLGPVLKTMAACVTLGTGNSLGPEGPSVEIGTSVAKGVGALLDKG

GRRKLSLKAAGSAAGIASGFNAAVGGCFFAVESVLWPSPAESSLYLTNTT

SMVILSAVIASVVSEIGLGSEPAFAVPGYDFRTPTELPLYLLLGIFCGLV

SVALSSCTSFMLQIVENIQMTSGMPKAAFPVLGGLLVGLVALAYPEILYQ

GFENVNILLESRPLVKGLSADLLLQLVAVKIVTTSLCRASGLVGGYYAPS

LEIGAATGTAYGKIVSYIISHADPIFHLSILEVASPQAYGLVGMAATLAG

VCQVPLTAVLLLFELTQNYRIVLPLLGAVGLSSWVTSGQTRKSVVKDRER

LKDARAHMMQRQGTSFSNISSLTYSSGVKPSQKESNLCKLESSLCLYESD

DEENDLARTILVSQAMRTRYVTVLMSTLLTETISLMLAEKQSCAIIVDEN

NFLIGLLTLSDIQNYSKLPRAEGNFQEINLIGTELMKRVSQADRQVIDLR

TEADNWKEQFEGLQLEKEVPAEEKNALEQQMRVIASELAVEKASSSQVGK

DKYILESSFAEQLSKATEEIRSLKELLNQKEVYARELVQTLTQVQEDLRA

STYKIQFLESSLASLKTAYDASEAEKEELRAEIYQWEKDYEILEDNLSLD

-continued

VSWAFLNTRLETLVEANHEGFDLNAEIAKAKEAIDKTQQRQIFSSPEDEG

PEGDGD

TABLE 1

| Gene | Mutation | Sequence 5' of SNP | Sequence 3' of SNP | Original codon | Original amino acid | Mutant codon | Mutant amino acid |
|---|---|---|---|---|---|---|---|
| CLCe-S | E21K | ctctgctcgag | aagttatccca | gaa | glu | aaa | lys |
| CLCe-S | L58F | aatacgtgat | tttgttggga | ctt | leu | ttt | phe |
| CLCe-S | P141S | accagaaggc | ctagtgttga | cct | pro | tct | ser |
| CLCe-S | G175E | cagctgctg | aatcgcttct | ctc | leu | ttc | phe |
| CLCe-S | S5N | tgcgacagca | caaagtcgata | agc | ser | aac | asn |
| CLCe-S | A34V | tataatctcgg | ttgctttgtt | gct | ala | gtt | val |
| CLCe-S | M124I | tgaagacaat | gccgcttgtg | atg | met | ata | ile |
| CLCe-S | L40F | gctttgttggc | tcttcaccgg | ctc | leu | ttc | phe |
| CLCe-S | D8N | agatatgtgc | acagcagcaa | gac | asp | aac | asn |
| CLCe-S | C35Y | aatctcggctt | ctttgttggcc | tgc | cys | tac | tyr |
| CLCe-S | A30V | caataataccg | tataatctcgg | gct | ala | gtt | val |
| CLCe-S | A177V | gctggaatcg | ttctggtttgt | gct | ala | gtt | val |
| CLCe-S | G42D | ctcttcaccg | tatcagtgtc | ggt | gly | gat | asp |
| CLCe-S | G88D | ccagcttgtg | cggtttggtag | ggc | gly | gac | asp |
| CLCe-S | G155R | ccaagggagtt | gagctctgct | gga | gly | aga | arg |
| CLCe-S | D158N | agctctgctt | ataaaggtggt | gat | asp | aat | asn |
| CLCe-S | A170V | ctcaaggctg | tggatcagctg | gct | ala | gat | asp |
| CLCe-S | A174V | tggatcagctg | tggaatcgctt | gct | ala | gtt | val |
| CLCe-S | A126V | gacaatggccg | ttgtgtcaca | gct | ala | gtt | val |
| CLCe-S | G131R | gtgtcacatta | gaactgggaa | gga | gly | aga | arg |
| CLCe-T | P184S | ctggtttgttc | ccatattattc | ccc | pro | tcc | ser |
| CLCe-T | G89D | accagcttgtg | cggtttggtag | ggc | gly | gac | asp |
| CLCe-T | K166N | ggtcgtagaaa | ctgtcactcaa | aag | lys | aaa | gin |
| CLCe-T | G18R | gtatccagata | gatctctgct | gga | gly | aga | arg |
| CLCe-T | G76R | ggagcccatt | gagtacattgg | gga | gly | aga | arg |
| CLCe-T | G173R | tcaaggctgct | gatcagctgc | gga | gly | aga | arg |
| CLCe-T | P143L | accagaaggcc | tagtgttgaaat | cct | pro | ctt | leu |
| CLCe-T | M1I | aacaagatat | tgcgacagcag | atg | met | ata | ile |
| CLCe-T | S4N | atgtgcgaca | cagcaaagacga | agc | ser | aac | asn |
| CLCe-T | V154I | cccttggttag | ttcatgaaata | gtt | val | att | ile |
| CLCe-T | G89D | cagcttgtg | cggtttggta | ggc | gly | gac | asp |
| CLCe-T | A128V | gacaatggccg | ttgtgtcacat | gct | ala | gtt | val |
| CLCe-T | S137F | aactgggaatt | cttaggacca | tcc | ser | ttc | phe |
| CLCe-T | G181S | gaatcgcttct | gtttgttccc | ggt | gly | agt | ser |
| CLCNt2-S | G503E | cattgccatgg | atcttataca | gga | gly | gaa | glu |

TABLE 1-continued

| Gene | Mutation | Sequence 5' of SNP | Sequence 3' of SNP | Original codon | Original amino acid | Mutant codon | Mutant amino acid |
|---|---|---|---|---|---|---|---|
| CLCNt2-S | G471R | attgcatattg | gactcatcact | gga | gly | aga | arg |
| CLCNt2-S | V659I | ccttcttttg | ttctcaagaaa | gtt | val | att | ile |
| CLCNt2-S | S566N | cttcaacctaa | tatttatgaa | agt | ser | aat | asn |
| CLCNt2-S | P637S | gagtagtgcca | cggtgggtct | ccg | pro | tcg | ser |
| CLCNt2-S | A597T | ctggtgagctt | ctgatgtaaag | gct | ala | act | thr |
| CLCNt2-S | P711L | gatttgcatc | cctgactaac | ccc | pro | ctc | leu |
| CLCNt2-S | G135R | gtaccttatg | gatttgcata | gga | gly | aga | arg |
| CLCNt2-S | A151V | tttgatagctg | ccttctctgcg | gcc | ala | gtc | val |
| CLCNt2-S | G690D | agctgagaggg | cggtaagatc | ggc | gly | gac | asp |
| CLCNt2-S | G737R | tcaggcaggtg | ggctccgcca | ggg | gly | agg | arg |
| CLCNt2-S | G135R | gtaccttatg | gatttgcata | gga | gly | aga | arg |
| CLCNt2-S | G163R | ctactgctgca | ggcctggaatt | ggg | gly | agg | arg |
| CLCNt2-S | P480S | gattgctgtg | catctggtctc | cca | pro | tca | ser |
| CLCNt2-S | S520F | cggagcagctt | ccttatggct | tcc | ser | ttc | phe |
| CLCNt2-S | A514T | cagggctgtat | cggttctcgg | gcg | ala | acg | thr |
| CLCNt2-S | A518V | ggttctcggag | agcttccctta | gca | ala | gta | val |
| CLCNt2-S | G476E | catcactttg | gattgctg | ggg | gly | gag | glu |
| CLCNt2-S | R739S | gtggggctcc | ccacatgctc | cgc | arg | cac | ser |
| CLCNt2-S | G517E | tgcggttctcg | agcagcttcc | gga | gly | gaa | glu |
| CLCNt2-S | E585K | atgccaacccg | agccatggatg | gag | glu | aag | lys |
| CLCNt2-S | V677I | aggagtgggaa | tgagagagaaa | gta | val | ata | ile |
| CLCNt2-T | A514T | cagggctgtat | ccgttctggga | gcc | ala | acc | thr |
| CLCNt2-T | L537F | gcgtcatattt | ttgagctaaca | ctt | leu | ttt | phe |
| CLCNt2-T | R593I | gccatggatga | aaatatcact | aga | arg | ata | ile |
| CLCNt2-T | A749T | caaataccaa | cagcaggggtg | gca | ala | aca | thr |
| CLCNt2-T | G524D | cttatggctg | ttcaatgagaa | ggt | gly | gat | asp |
| CLCNt2-T | S408F | cacttcaagggt | ttgtcctggca | tct | ser | ttt | phe |
| CLCNt2-T | G503R | cattgccatg | gatcttataca | gga | gly | aga | arg |
| CLCNt2-T | P547S | ttctccttctg | caataacaatgc | cca | pro | tca | ser |
| CLCNt2-T | G691D | gctgagaggg | cggtaagatcga | ggc | gly | gac | asp |
| CLCNt2-T | A478V | tttgggattg | tgtgccatctg | gct | ala | gtt | val |
| CLCNt2-T | A749V | ctccgccacatg | tcattgtacc | gct | ala | gtt | val |
| CLCNt2-T | T713I | gcatcccctga | taacacaaccc | act | thr | att | ile |
| CLCNt2-T | M550I | caataacaat | ctggttcttc | atg | met | ata | ile |
| CLCNt2-T | P586S | gccaacccggag | catggatgaga | cca | pro | tca | ser |
| CLCNt2-T | R670K | ccttaatgaaa | acgaaggaca | aga | arg | aaa | lys |
| CLCNt2-T | R678K | gtgggaagtga | agagaaattc | aga | arg | aaa | lys |
| CLCNt2-T | D631N | tccctgtcgtc | atgaaggagtg | gat | asp | aat | asn |
| CLCNt2-T | L657F | gaactcacctt | ttttggttctc | ctt | leu | ttt | phe |

TABLE 1-continued

| Gene | Mutation | Sequence 5' of SNP | Sequence 3' of SNP | Original codon | Original amino acid | Mutant codon | Mutant amino acid |
|---|---|---|---|---|---|---|---|
| CLCNt2-T | G737R | caggcaggtg | ggctccgccac | ggg | gly | agg | arg |
| CLCNt2-T | S525L | atggctggtt | aatgagaatga | tca | ser | tta | leu |
| CLCNt2-T | A597T | tggtgagctt | ctgatgtaaag | gct | ala | act | thr |
| CLCNt2-T | E674K | aaggacagag | agtgggaagtg | gag | glu | aag | lys |

CLC-Nt2-s corresponds to the polypeptide sequence shown in SEQ ID NO. 5 that is encoded by SEQ ID NO: 1
CLC-Nt2-t corresponds to the sequence shown in SEQ ID NO. 6 that is encoded by SEQ ID NO: 2
NtCLCe-s corresponds to the sequence shown in SEQ ID NO. 7 that is encoded by SEQ ID NO: 3
NtCLCe-t corresponds to the sequence shown in SEQ ID NO. 13 that is encoded by SEQ ID NO: 4

TABLE 2

| Target gene | Forward primer (5' to 3') | Reverse primer (5' to 3') |
|---|---|---|
| CLCe-s | TATCTCCTCGCCATATCTGTA | GTGCAAACACACTTGTATTTAC |
| CLCe-t | ACCATCTCTTCCTCCGGGA | TATAGGATACTCCTCTGATAAAT |
| CLCe-t | TTGTACAATTTATCAGAGGAGTA | TTGGTTTGAGTGCAAACACA |
| CLCNt2-s | ACTATATCGAGGATAGAAGGTA | TATCTATTTATACATCTGGTTCG |
| CLCNt2-s | CTTGTGATCCATCACTTCCC | TATGACTATTTCTGTGCATCTTT |
| CLCNt2-s | GCCTTGTGATTCATCACTTCAA | TATGACTATTTCTGTGCATCTTA |
| CLCNt2-t | GGTTCTTCTCGCTCTGAGC | AACGTAAAATAACTTTGCCACG |

The invention claimed is:

1. A mutant, non-naturally occurring or transgenic tobacco plant cell comprising one or more mutations in:

(i) a polynucleotide comprising a sequence encoding a member of the CLC family of chloride channels and having at least 99% sequence identity to SEQ ID NO: 1;

(ii) a polypeptide encoded by the polynucleotide set forth in (i); or (iii) a polypeptide comprising a sequence encoding a member of the CLC family of chloride channels and having at least 99% sequence identity to SEQ ID NO: 5 and wherein the one or more mutations comprises a substitution mutation at position G163 of SEQ ID NO: 5; the expression or activity of the polynucleotide or the polypeptide is reduced as compared to a control tobacco plant containing a control tobacco plant cell; and nitrate levels in a mutant, non-naturally occurring or transgenic tobacco plant containing the mutant, non-naturally occurring or transgenic tobacco plant cell are decreased as compared to the control tobacco plant containing the control tobacco plant cell.

2. A mutant, non-naturally occurring or transgenic tobacco plant or component thereof comprising the mutant, non-naturally occurring or transgenic tobacco plant cell according to claim 1.

3. A method for modulating at least the total tobacco specific nitrosamine levels of a tobacco plant or a component thereof, comprising the steps of:

introducing into the genome of the tobacco plant one or more mutations within at least one allele of a member of the CLS family of chloride channels comprising:

(i) a polynucleotide comprising a sequence having at least 99% sequence identity to SEQ ID NO:1;

(ii) a polypeptide encoded by the polynucleotide set forth in (i); or (iii) a polypeptide comprising a sequence having at least 99% sequence identity to SEQ ID NO:5;

and wherein the one or mutations comprises a substitution mutation at position G163 of SEQ ID NO: 5.

4. The method according to claim 3, wherein the 4-(methylnitrosamino)-1-(3-pyridyl)-1-butanone (NNK) content and/or the nictotine content is modulated in the tobacco plant; and/or wherein at least the N-nitrosonicotine (NNN) content is the same as the control tobacco plant.

5. The method according to claim 3, wherein the component of the tobacco plant is a leaf.

6. A mutant, non-naturally occurring, or transgenic tobacco plant or a component thereof that is obtained or obtainable by the method according to claim 3.

7. A mutant, non-naturally occurring or transgenic tobacco plant according to claim 2, wherein the NNK content is about 110 ng/g or less on a dry weight basis, optionally, wherein the nitrate content is about 7 mg/g or less on a dry weight basis.

8. Tobacco plant material including biomass, seed, stem or leaves from the tobacco plant of claim 2.

9. A method for producing cured tobacco plant material with reduced levels of at least NNK therein comprising:

curing the tobacco plant material of claim 8 for a period of time sufficient for the levels of at least NNK therein to decrease.

10. A mutant, non-naturally occurring or transgenic tobacco plant cell comprising a polypeptide having at least 99% sequence identity to SEQ ID NO:5 and wherein the polypeptide comprises a substitution mutation at position G163 of SEQ ID NO:5.

11. A mutant, non-naturally occurring or transgenic tobacco plant cell comprising a polypeptide of the CLC family of chloride channels, wherein the polypeptide comprises a substitution mutation at a position corresponding to G163 of SEQ ID NO:5.

* * * * *